US011970493B2

(12) United States Patent
Choi et al.

(10) Patent No.: US 11,970,493 B2
(45) Date of Patent: Apr. 30, 2024

(54) AUTOTAXIN INHIBITOR COMPOUNDS

(71) Applicant: ILDONG PHARMACEUTICAL CO., LTD., Seoul (KR)

(72) Inventors: Sung-Ku Choi, Hwaseong-si (KR); Yoon-Suk Lee, Hwaseong-si (KR); Sung-Wook Kwon, Hwaseong-si (KR); Kyung-Sun Kim, Hwaseong-si (KR); Jeong-Geun Kim, Hwaseong-si (KR); Jeong-Ah Kim, Hwaseong-si (KR); An-Na Moon, Hwaseong-si (KR); Sun-Young Park, Hwaseong-si (KR); Jun-Su Ban, Hwaseong-si (KR); Dong-Keun Song, Hwaseong-si (KR); Kyu-Sic Jang, Hwaseong-si (KR); Ju-Young Jung, Hwaseong-si (KR); Soo-Jin Lee, Hwaseong-si (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 10 days.

(21) Appl. No.: 17/493,456

(22) Filed: Oct. 4, 2021

(65) Prior Publication Data

US 2022/0106311 A1   Apr. 7, 2022

Related U.S. Application Data

(60) Provisional application No. 63/088,219, filed on Oct. 6, 2020.

(51) Int. Cl.
C07D 471/04   (2006.01)
(52) U.S. Cl.
CPC ................... *C07D 471/04* (2013.01)
(58) Field of Classification Search
CPC .................................... C07D 471/04
USPC .................................. 514/210.21
See application file for complete search history.

(56) References Cited

U.S. PATENT DOCUMENTS

| | | |
|---|---|---|
| 8,993,590 B2 | 3/2015 | Desroy et al. |
| 9,249,141 B2 | 2/2016 | Desroy et al. |
| 9,309,243 B2 | 4/2016 | Bentley et al. |
| 9,670,204 B2 | 6/2017 | Desroy et al. |
| 10,125,132 B2 | 11/2018 | Desroy et al. |
| 10,526,329 B2 | 1/2020 | Desroy et al. |
| 11,072,611 B2 | 7/2021 | Desroy et al. |
| 2015/0203486 A1 | 7/2015 | Bentley et al. |
| 2018/0127425 A1 | 5/2018 | Desroy et al. |

FOREIGN PATENT DOCUMENTS

| | | |
|---|---|---|
| CN | 109384803 A | 2/2019 |
| CN | 111004235 A | 4/2020 |
| EP | 2872508 A1 | 5/2015 |
| EP | 4180430 A1 | 5/2023 |
| WO | WO 2012/026765 A2 | 3/2012 |
| WO | WO 2014/009295 A1 | 1/2014 |
| WO | WO 2014/139882 A1 | 9/2014 |
| WO | WO 2014/202458 A1 | 12/2014 |
| WO | WO 2017/192931 A1 | 11/2017 |
| WO | WO 2019/029620 A1 | 2/2019 |
| WO | WO 2019/030275 A1 | 2/2019 |
| WO | WO 2019/158107 A1 | 8/2019 |
| WO | WO 2019/223721 A1 | 11/2019 |
| WO | WO 2019/228403 A1 | 12/2019 |
| WO | WO 2020/030669 A1 | 2/2020 |
| WO | WO 2021/143753 A1 | 7/2021 |
| WO | WO 2022/007882 A1 | 1/2022 |

OTHER PUBLICATIONS

Joncour et al., Journal of Medicinal Chemistry (2017), 60(17), 7371-7392.*
Banerjee, S. et al. "Molecular Modelling Guided Design, Synthesis and QSAR Analysis of New Small Molecule Non-Lipid Autotaxin Inhibitors." Bioorganic Chemistry, Author Manuscript, vol. 103, Oct. 2020, pp. 1-28.
PCT International Search Report and Written Opinion, PCT Application No. PCT/IB2021/000693, dated Mar. 30, 2022, 14 pages.
Desroy, N. et al. "Discovery of 2-[[2-Ethyl-6[4-[2-(3-hydroxyazetidin-1-yl)-2-oxoethyl]piperzin-1-yl]-8-methylimidazo[1,2-a]pyridine-3-yl]methylamino]-4-(4-fluorophenyl)thiazole-5-carbonitrile (GLPG1690), a First-in-Class Autotaxin Inhibitor Undergoing Clinical Evaluation for the Treatment of Idiopathic Pulmonary Fibrosis." Journal of Medical Chemistry, vol. 60, Apr. 17, 2017, pp. 3580-3590.
Joncour, A. et al. "Discovery, Structure-Activity Relationship, and Binding Mode of an Imidazo[1,2-a]pyridine Series of Autotaxin Inhibitors." Journal of Medical Chemistry, vol. 60, Jul. 21, 2017, pp. 7371-7392.
Lei, H. et al. "Catalyst-Free Cyclization- and Curtius Rearrangement-Induced Functional Group Transformation: An Improved Synthetic Strategy of First-in-Class ATX Inhibitor Ziritaxestat (GLPG-1690)." vol. 24, No. 6, 2020, pp. 997-1005.
Nikitopoulou, I. et al. "Increased Autotaxin Levels in Severe COVID-19, Correlating with IL-6 Levels, Endothelial Dysfunction Biomarkers, and Impaired Functions of Dendritic Cells." International Journal of Molecular Sciences, vol. 22, Sep. 16, 2021, pp. 1-18.
Tan, Z. et al. "An Updated Patent Review of Autotaxin Inhibitors (2017-Present)." Expert Opinion on Therapeutic Patents, vol. 31, No. 5, Jan. 12, 2021, pp. 421-434.

(Continued)

*Primary Examiner* — Niloofar Rahmani
(74) *Attorney, Agent, or Firm* — Glenn J. Foulds; Fenwick & West LLP

(57) ABSTRACT

The present disclosure provides autotaxin (ATX) inhibitor compounds and compositions including said compounds. The present disclosure also provides methods of using said compounds and compositions for inhibiting ATX. Also provided are methods of preparing said compounds and compositions, and synthetic precursors of said compounds.

51 Claims, No Drawings

(56) References Cited

OTHER PUBLICATIONS

Zhang, X. et al. "The Expression Regulation and Biological Function of Autotaxin." Cells, vol. 10, No. 4, Apr. 19, 2021, pp. 1-13.

* cited by examiner

AUTOTAXIN INHIBITOR COMPOUNDS

1. CROSS REFERENCE TO RELATED APPLICATIONS

This application claims the benefit of U.S. Provisional Application No. 63/088,219, filed Oct. 6, 2020, which is hereby incorporated in its entirety by reference.

2. BACKGROUND

Autotaxin (ATX), also known as ectonucleotide pyrophosphatase/phosphodiesterase 2 (ENPP-2) or lysophospholipase D, is a protein that belongs to the ENPP family of enzymes. As the only member of the ENPP family of enzymes with lysophospholipase D (lysoPLD) activity, ATX is responsible for the hydrolysis of lysophosphatidyl choline (LPC) into lysophosphatidic acid (LPA). LPA is a family of bioactive lipids of varying fatty acyl chain length that signals LPA receptors to modulate various cellular events. LPA and LPA receptor activities are attributed to a broad range of physiological actions, such as blood pressure regulation, platelet activation, cell growth, and smooth muscle contraction. LPA and LPA receptor activities have also been associated with various other physiological conditions, disorders, and diseases, such as proliferative diseases, cancer, inflammation, autoimmune disease, and fibrosis.

3. SUMMARY OF THE INVENTION

The present disclosure provides autotaxin (ATX) inhibitor compounds and compositions including said compounds. The present disclosure also provides methods of using said compounds and compositions for inhibiting ATX. Also provided are methods of preparing said compounds and compositions, and synthetic precursors of said compounds.

In a first aspect, the ATX inhibitor compound is of formula (I):

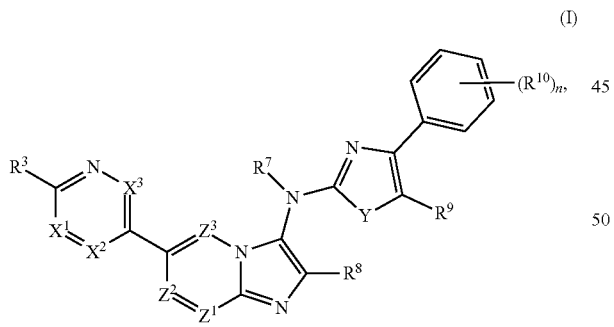

(I)

or a pharmaceutically acceptable salt thereof,
wherein:
  $X^1$, $X^2$, and $X^3$ are independently selected from $C-R^1$ and N;
  $Z^1$, $Z^2$, and $Z^3$ are independently selected from $C-R^1$ and N;
  each $R^1$ is independently selected from —H, -halogen, optionally substituted —$(C_1-C_6)$alkyl and optionally substituted —$(C_1-C_6)$alkoxy;
  Y is selected from S, O, and $N-R^2$, wherein $R^2$ is selected from —H, and optionally substituted —$(C_1-C_6)$alkyl;
  $R^3$ is selected from optionally substituted $R^4$—C(O)—$(C_1-C_3)$alkyl-, $R^4$C(O)—, optionally substituted monocyclic or bicyclic carbocycle, optionally substituted monocyclic or bicyclic heterocycle, $R^5R^6$HC—, and $R^5R^6$N—;
  $R^4$ is selected from $H_2N$—, HO—, $R^5R^6N$—, optionally substituted $(C_1-C_{10})$alkyl-, optionally substituted $(C_1-C_{10})$alkoxy-, optionally substituted monocyclic or bicyclic carbocycle, optionally substituted monocyclic or bicyclic heterocycle, optionally substituted cycloalkyl-$(C_1-C_6)$alkylene-, and optionally substituted heterocycle-$(C_1-C_6)$alkylene-;
  $R^5$ and $R^6$ are independently selected from H—, $H_2N$—, HO—, optionally substituted $(C_1-C_{10})$alkyl-, optionally substituted monocyclic or bicyclic carbocycle (e.g., saturated monocyclic carbocycle, e.g., cycloalkyl), optionally substituted monocyclic or bicyclic heterocycle (e.g., saturated monocyclic heterocycle, e.g., azetidine, pyrrolidine or piperidine), optionally substituted $R^4$C(O)—$(C_1-C_{10})$alkyl-, $R^4$C(O)—, $R^4$—, and substituted amino;
  or R and $R^6$ together with the nitrogen or carbon atom to which they are attached are cyclically linked to form an optionally substituted carbocycle or an optionally substituted heterocycle (e.g., azetidine, morpholine, pieridine or piperazine);
  $R^7$ is selected from H—, and optionally substituted $(C_1-C_6)$alkyl-;
  $R^8$ is selected from —H, -halogen, and optionally substituted —$(C_1-C_6)$alkyl;
  $R^9$ and each $R^{10}$ are independently selected from —H, -halogen, —CN, —OH, optionally substituted —$(C_1-C_6)$alkoxy, —$NH_2$, substituted amino, optionally substituted —$(C_1-C_6)$alkyl-$NH_2$ (e.g., —$CH_2NH_2$) and optionally substituted —$(C_1-C_6)$alkyl; and
  n is 0, 1, 2, 3, 4, or 5.

In some embodiments, the compound of formula (I) is a compound of formula (Ia).

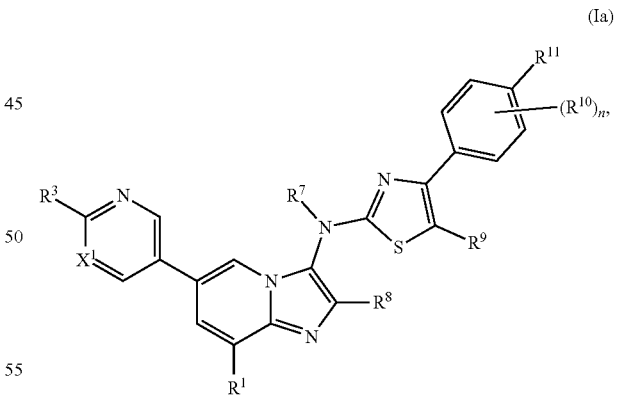

(Ia)

wherein:
  $R^1$ is selected from —H, -halogen, optionally substituted —$(C_1-C_6)$alkyl and optionally substituted —$(C_1-C_6)$alkoxy;
  $R^3$ is selected from $R^4$C(O)—, $R^4$C(O)$CH_2$—, $R^5R^6N$—, and $R^5R^6$HC—;
  $R^{11}$ is —H, -halogen, —CN, —OH, optionally substituted —$(C_1-C_6)$alkoxy, —$NH_2$, —$NR^5R^6$, —$CH_2NH_2$ and optionally substituted —$(C_1-C_6)$alkyl; and
  n is 0, 1, 2, or 3.

In some embodiments, the compound of formula (I) is a compound of formula (Ib):

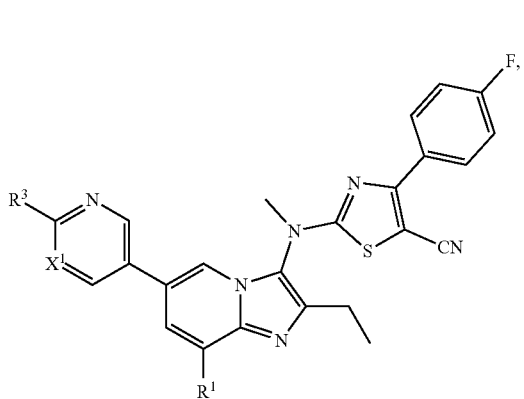
(Ib)

wherein:

X₁ is C—H or N; and

R¹ is selected from —H, -halogen, optionally substituted —(C₁-C₆)alkyl and optionally substituted —(C₁-C₆) alkoxy.

In some embodiments of formula (I)-(Ib), a) R³ is

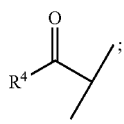;

b) R³ is

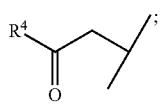;

c) R³ is

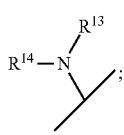;

d) R³ is

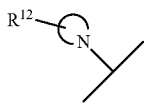

that is an optionally substituted monocyclic or bicyclic (C₂-C₉)heterocycle- (e.g., (C₂-C₅)heterocycloalkyl-); or e) R³ is

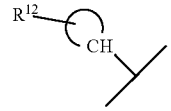

that is an optionally substituted monocyclic or bicyclic (C₃-C₈)carbocycle- (e.g., (C₃-C₆)cycloalkyl-), or an optionally substituted monocyclic or bicyclic (C₂-C₉)heterocycle- (e.g., (C₂-C₅)heterocycloalkyl-);

wherein:

R⁴ is selected from HO—, H₂N—, R¹⁵R¹⁶N—, optionally substituted (C₁-C₅)alkyl-, optionally substituted monocyclic or bicyclic carbocycle, and optionally substituted monocyclic or bicyclic heterocycle;

R¹² is selected from —H, —NH₂, —OH, —CH₂C(O)R⁴, —C(O)R⁴, —CHR¹⁵R¹⁶, —NR¹⁵R¹⁶, optionally substituted —(C₁-C₅)alkyl, optionally substituted monocyclic or bicyclic —(C₃-C₈)carbocycle (e.g., —(C₃-C₆)cycloalkyl), and an optionally substituted monocyclic or bicyclic —(C₂-C₉)heterocycle (e.g., —(C₂-C₅)heterocycloalkyl);

R¹³ and R¹⁴ are independently selected from —H, —CH₂C(O)R¹⁷, —CH₂R¹⁷, —C(O)R¹⁷, —R¹⁸C(O)R¹⁷, —CH₂R¹⁸C(O)R¹⁷, optionally substituted —(C₁-C₅)alkyl, optionally substituted monocyclic or bicyclic —(C₃-C₈)carbocycle (e.g., —(C₃-C₆)cycloalkyl), and an optionally substituted monocyclic or bicyclic —(C₂-C₄)heterocycle (e.g., —(C₂-C₅)heterocycloalkyl), wherein R¹⁷ and R¹⁸ are independently selected from optionally substituted —(C₁-C₅)alkyl, optionally substituted monocyclic or bicyclic —(C₃-C₈)carbocycle (e.g., —(C₃-C₆)cycloalkyl), and an optionally substituted monocyclic or bicyclic —(C₂-C₉)heterocycle (e.g., —(C₂-C₅)heterocycloalkyl); and R¹⁵ and R¹⁶ are independently selected from H—, optionally substituted (C₂-C₅)heterocycloalkyl-C(O)—, optionally substituted (C₃-C₆)cycloalkyl-C(O)—, optionally substituted (C₁-C₅)alkyl-, optionally substituted 3- to 10-membered saturated monocyclic heterocycle or carbocycle, and optionally substituted 3- to 10-membered saturated bicyclic heterocycle or carbocycle, wherein the optional substituents are selected from hydroxy, HOCH₂—, cyano, halogen, substituted amino (e.g., (C₁-C₅)alkyl-substituted amino), and (C₁-C₅)alkyl; or R¹⁵ and R¹⁶ are cyclically linked to form a 3- to 6-membered monocyclic saturated heterocycle, optionally substituted with hydroxy, HOCH₂—, cyano, halogen, substituted amino (e.g., (C₁-C₅)alkyl-substituted amino), or (C₁-C₅)alkyl.

In some embodiments of formula (I)-(Ib),

R³ is

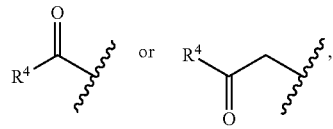

R⁴ is selected from R³²—, R³²HN—, R³²N(R³³)—, and R³²HN—R³⁶—;

$R^{32}$ and $R^{33}$ are independently selected from H—, optionally substituted —($C_1$-$C_3$)alkyl, optionally substituted cycloalkyl (e.g., cyclopropyl, cyclobutyl, cyclopentyl, or cyclohexyl), and optionally substituted saturated heterocycle (e.g., azetidine, pyrrolidine, piperidine, morpholine, piperazine, morpholine-3-one, or piperidine-2-one);

$R^{36}$ is selected from optionally substituted ($C_1$-$C_3$)alkyl, optionally substituted cycloalkyl (e.g., cyclopropyl, cyclobutyl, cyclopentyl, or cyclohexyl), and optionally substituted saturated heterocycle (e.g., azetidine, pyrrolidine, piperidine); and the optional substituents of the $R^{32}$, $R^{33}$ and $R^{36}$ groups are independently selected from —CN, —OH, —$CH_2OH$, —($C_1$-$C_3$)alkyl (e.g., —$CH_3$), —($C_1$-$C_3$)alkoxy, —($C_3$-$C_6$)cycloalkyl, ($C_2$-$C_5$)heterocycloalkyl (e.g., azetidine), and —N($R^{37}$)$R^{38}$, wherein $R^{37}$ and $R^{38}$ are independently selected from H, ($C_1$-$C_3$)alkyl, ($C_3$-$C_6$)cycloalkyl (e.g., cyclopropyl or cyclobutyl), and ($C_2$-$C_5$)heterocycloalkyl (e.g., azetidine).

In some embodiments of formula (I)-(Ib),
$R^3$ is

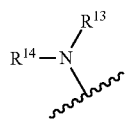

$R^4$ is selected from $R^{34}$—, $R^{31}CH_2$—, $R^{34}C(O)R^{35}$—, and $R^{34}C(O)R^{35}CH_2$—;

each $R^{34}$ and $R^{35}$ are independently selected from optionally substituted —($C_1$-$C_3$)alkyl, optionally substituted cycloalkyl, and optionally substituted saturated heterocycle (e.g., azetidine, pyrrolidine, piperidine, morpholine, piperazine); and the optional substituents of the $R^{34}$ and $R^{35}$ groups are independently selected from —CN, —OH, —$CH_2OH$, —($C_1$-$C_3$)alkyl (e.g., —$CH_3$), —($C_1$-$C_3$)alkoxy, and —($C_1$-$C_3$)alkyl; and $R^{13}$ is —H.

In some embodiments of formula (I)-(Ib), $R^3$ is

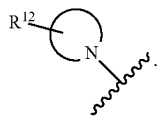

In some embodiments, $R^3$ is selected from:

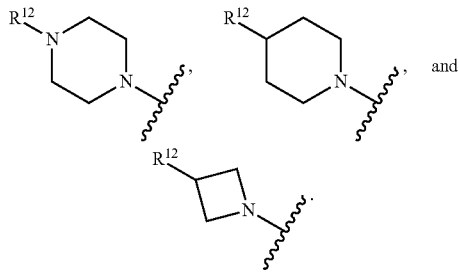

In certain embodiments,
$R^{12}$ is selected from H—, $H_2N$—, $R^{31}$—C(O)—, $R^{31}$—C(O)$CH_2$—, $R^{31}$—NHC(O)—, $R^{31}$—C(O)NH—, $R^{31}$—NH—, $R^{31}$—N($CH_3$)C(O)—, $R^{31}$—C(O)N($CH_3$)—, $R^{31}$—N($CH_3$)—, and $R^{31}$—O—;

$R^{31}$ is selected from optionally substituted cycloalkyl (e.g., cyclopropyl, cyclobutyl, cyclopentyl, or cyclohexyl), and optionally substituted saturated heterocycle (e.g., azetidine, pyrrolidine, piperidine, morpholine, piperazine, morpholine-3-one, or piperidine-2-one); and the optional substituents of the $R^{31}$ group are selected from NC—, HO—, $HOCH_2$—, ($C_1$-$C_3$)alkyl- (e.g., $H_3C$—), ($C_1$-$C_3$)alkoxy-, substituted ($C_1$-$C_3$)alkyl-, and ($C_3$-$C_6$)cycloalkyl- (e.g., cyclopropyl), and ($C_2$-$C_5$) heterocycloalkyl- (e.g., azetidine, pyrrolidine, piperidine, morpholine, piperazine, morpholine-3-one, or piperidine-2-one).

In some embodiments of formula (I)-(Ib), $R^3$ is

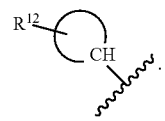

In another embodiments, $R^3$ is

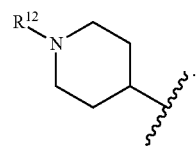

In another embodiments,
$R^{12}$ is selected from H—, $R^{31}$—C(O)—, $R^{31}$—C(O)$CH_2$—, $R^{31}$—NHC(O)—, $R^{31}$—C(O)NH—, $R^{31}$—N($CH_3$)C(O)—, and $R^{31}$—C(O)N($CH_3$)—;

$R^{31}$ is selected from optionally substituted ($C_1$-$C_3$)alkyl-, optionally substituted cycloalkyl- (e.g., cyclopropyl, cyclobutyl, cyclopentyl, or cyclohexyl-), and optionally substituted saturated heterocycle (e.g., azetidine, pyrrolidine, piperidine); and the optional substituents of the $R^{31}$ group are selected from NC—, HO—, $HOCH_2$—, ($C_1$-$C_3$)alkyl- (e.g., $H_3C$—), ($C_1$-$C_3$)alkoxy- and substituted ($C_1$-$C_3$)alkyl.

In some embodiments of formula (I), the compound is of formula (Ic):

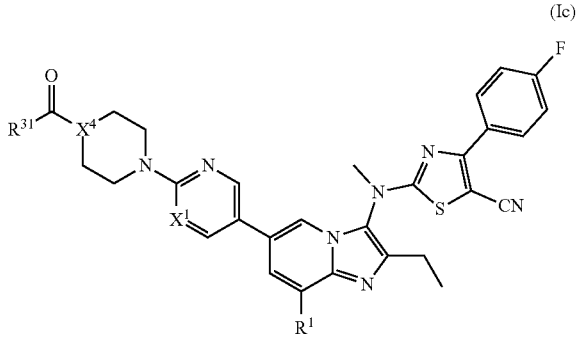

(Ic)

wherein:
X¹ and X⁴ are independently N or C—R¹;
R¹ is selected from H, halogen, optionally substituted —($C_1$-$C_6$)alkyl, and optionally substituted —($C_1$-$C_6$)alkoxy; and
$R^{31}$ is selected from optionally substituted ($C_2$-$C_5$)heterocycloalkyl-, and optionally substituted ($C_3$-$C_7$)cycloalkyl-. In some embodiments of formula (Ic), $R^{31}$ is optionally substituted ($C_3$-$C_5$)heterocycloalkyl.

In some embodiments of formula (Ic), the compound is of formula (Id):

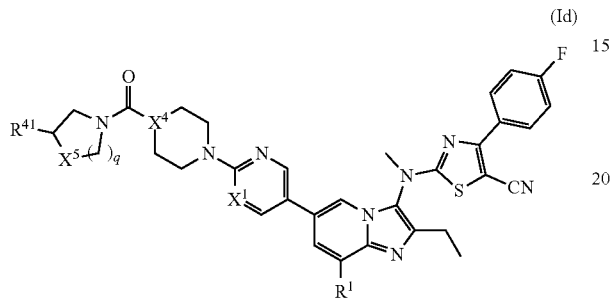

(Id)

wherein:
X¹ and X⁴ are independently N or CH; and
$R^{41}$ is H—, or HO—; and
q is 0, 1 or 2; wherein
when q is 0 or 1, X⁵ is $CH_2$; and
when q is 2, X is NH, O, or CH(OH).

In some embodiments of formula (I), the compound is of formula (Ie):

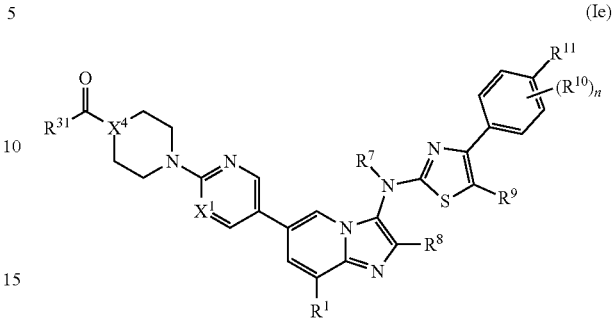

(Ie)

wherein:
$X_1$ and X⁴ are independently N or C—R¹;
R¹ is selected from H, halogen, optionally substituted —($C_1$-$C_6$)alkyl, and optionally substituted —($C_1$-$C_6$)alkoxy;
$R^{31}$ is selected from optionally substituted ($C_2$-$C_5$)heterocycloalkyl, and optionally substituted ($C_3$-$C_7$)cycloalkyl-;
$R^{11}$ is —H, -halogen, —CN, —OH, optionally substituted —($C_1$-$C_6$)alkoxy, —$NH_2$, —$NR^5R^6$, —$CH_2NH_2$ and optionally substituted —($C_1$-$C_6$)alkyl; and
n is 0, 1, 2, or 3.

In some embodiments of formula (Ie), the compound is of formula (If):

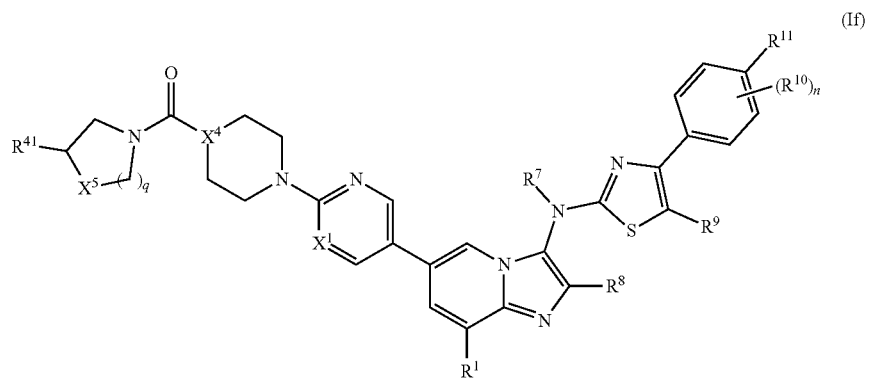

(If)

wherein:
X$^1$ and X$^4$ are independently N or CH;
R$^{41}$ is H—, or HO—; and
q is 0, 1 or 2; wherein
when q is 0 or 1, X$^5$ is CH$_2$; and
when q is 2, X$^5$ is NH, O, or CH(OH).

In a second aspect, the present disclosure provides for a pharmaceutical composition comprising an ATX inhibitor compound, or a pharmaceutically acceptable salt thereof, as described herein (e.g., a compound of formula (I)-(If)), and a pharmaceutically acceptable excipient.

In a third aspect, the present disclosure provides a method of inhibiting ATX using said compounds and compositions. In some embodiments, the method includes contacting a sample comprising ATX with an effective amount of an ATX inhibitor compound, or a pharmaceutically acceptable salt thereof, as described herein (e.g., a compound of formula (I)-(If)) to inhibit the ATX.

4. DETAILED DESCRIPTION OF THE INVENTION

4.1. ATX Inhibitor Compounds

As summarized above, the present disclosure provides compounds and compositions for use in inhibiting autotaxin (ATX). The compounds can include a fused bicyclic structure including a five membered imidazole ring fused (e.g., a imidazole ring fused at 1,2 positions) to a six membered heterocycle ring such as a pyridine (e.g., where the imidazo N1 atom is part of the pyridine ring), pyridiazine, pyrazine or pyrimidine ring. In some embodiments the fused bicyclic structure is an imidazo[1,2-a]pyridine, imidazo[1,2-b]pyridazine, imidazo[1,2-a]pyrimidine, or imidazo[1,2-a]pyrazine. The fused bicyclic structure is substituted at the 3-position with an amino group substituted with a five membered heterocycle such as a 2-substituted thiazole, oxazole or imidazole ring that itself is further substituted at the 4-position with an optionally substituted phenyl ring.

In the ATX inhibitor compounds of this disclosure, the fused bicyclic structure can be substituted at the 6 position with a six membered heterocycle such as a pyridin-3-yl, pyrimidin-5-yl, pyridazin-3-yl or pyrazin-2-yl that is itself further substituted at the para position with various para substituents (e.g., as described herein).

More specifically, in a first aspect, the present disclosure provides a compound of formula (I):

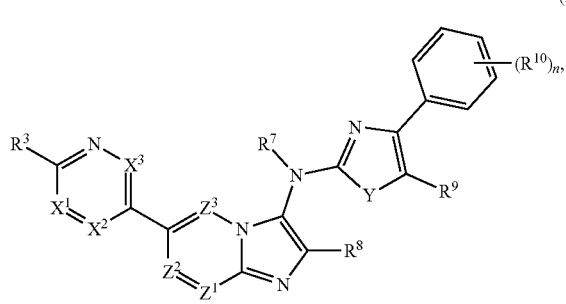

(I)

or a pharmaceutically acceptable salt thereof.
wherein:
X$^1$, X$^2$, and X$^3$ are independently selected from C—R$^1$ and N;

Z$^1$, Z$^2$, and Z$^3$ are independently selected from C—R$^1$ and N;
each R$^1$ is independently selected from —H, -halogen, optionally substituted —(C$_1$-C$_6$)alkyl and optionally substituted —(C$_1$-C$_6$)alkoxy;
Y is selected from S, O, and N—R$^2$, wherein R$^2$ is selected from —H, and optionally substituted —(C$_1$-C$_6$)alkyl;
R$^3$ is selected from optionally substituted R$^4$—C(O)—(C$_1$-C$_3$)alkyl-, R$^4$C(O)—, optionally substituted monocyclic or bicyclic carbocycle, optionally substituted monocyclic or bicyclic heterocycle, R$^5$R$^6$HC—, and R$^5$R$^6$N—;
R$^4$ is selected from H$_2$N—, HO—, R$^5$R$^6$N—, optionally substituted (C$_1$-C$_{10}$)alkyl-, optionally substituted (C$_1$-C$_{10}$)alkoxy-, optionally substituted monocyclic or bicyclic carbocycle, optionally substituted monocyclic or bicyclic heterocycle, optionally substituted cycloalkyl-(C$_1$-C$_6$)alkylene-, and optionally substituted heterocycle-(C$_1$-C$_6$)alkylene-;
R$^5$ and R$^6$ are independently selected from H—, H$_2$N—, HO—, optionally substituted (C$_1$-C$_{10}$)alkyl-, optionally substituted monocyclic or bicyclic carbocycle (e.g., saturated monocyclic carbocycle, e.g., cycloalkyl), optionally substituted monocyclic or bicyclic heterocycle (e.g., saturated monocyclic heterocycle, e.g., azetidine, pyrrolidine or piperidine), optionally substituted R$^4$C(O)—(C$_1$-C$_{10}$)alkyl-, R$^4$C(O)—, R$^4$—, and substituted amino;
or R$^5$ and R$^6$ together with the nitrogen or carbon atom to which they are attached are cyclically linked to form an optionally substituted carbocycle or an optionally substituted heterocycle (e.g., azetidine, morpholine, pieridine or piperazine);
R$^7$ is selected from H—, and optionally substituted (C$_1$-C$_6$)alkyl-;
R$^8$ is selected from —H, -halogen, and optionally substituted —(C$_1$-C$_6$)alkyl;
R$^9$ and each R$^{10}$ are independently selected from —H, -halogen, —CN, —OH, optionally substituted —(C$_1$-C$_6$)alkoxy, —NH$_2$, substituted amino, optionally substituted —(C$_1$-C$_6$)alkyl-NH$_2$ (e.g., —CH$_2$NH$_2$) and optionally substituted —(C$_1$-C$_6$)alkyl; and
n is 0, 1, 2, 3, 4, or 5.

In some embodiments of formula (I), X$^1$ is N. In some embodiments of formula (I), X$^2$ is N. In some embodiments of formula (I), X$^3$ is N.

In some embodiments of formula (I), X$^1$ is N, X$^2$ is C—H, and X$^3$ is C—H.

In some embodiments of formula (I), X$^1$ is C—H, X$^2$ is C—H, and X$^3$ is C—H.

In some embodiments of formula (I), Y is S. In some embodiments, Y is O. In some embodiments, Y is NH.

In some embodiments of formula (I), Z$^1$ is N. In some embodiments of formula (I), Z$^2$ is N. In some embodiments of formula (I), Z$^3$ is N. In some embodiments of formula (I), one and only one of Z$^1$ to Z$^3$ is N.

In some embodiments of formula (I), Z$^1$ is C—H, Z$^2$ is C—H, and Z$^3$ is C—H.

In some embodiments of formula (I), n is 0. In some embodiments of formula (I), n is 1. In some embodiments of formula (I), n is 1 and the R$^{10}$ substituent is located at the para position. In some embodiments of formula (I), n is 2.

In some embodiments, the compound of formula (I) is a compound of formula (Ia):

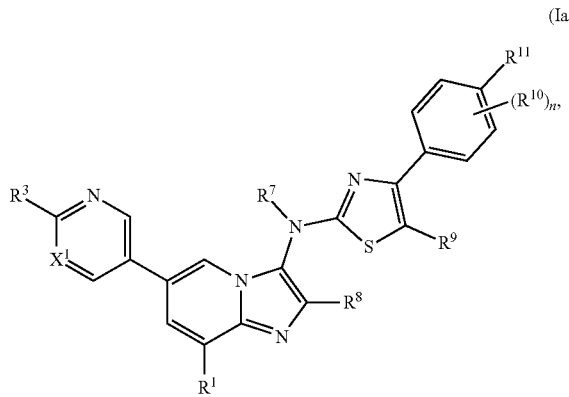

(Ia)

wherein:
R$^1$ is selected from —H, -halogen, optionally substituted —(C$_1$-C$_6$)alkyl and optionally substituted —(C$_1$-C$_6$)alkoxy;
R$^3$ is selected from R$^4$C(O)—, R$^4$C(O)CH$_2$—, R$^5$R$^6$N—, and R$^5$R$^6$HC—;
R$^{11}$ is —H, -halogen, —CN, —OH, optionally substituted —(C$_1$-C$_6$)alkoxy, —NH$_2$, —NR$^5$R$^6$, —CH$_2$NH$_2$ and optionally substituted —(C$_1$-C$_6$)alkyl; and
n is 0, 1, 2, or 3.

In some embodiments of formula (I)-(Ia), X$^1$ is N. In some other embodiment of formula (I)-(Ia), X$^1$ is C—H.

In some embodiments of formula (I)-(Ia), R$^1$ is H. In some embodiments of formula (I)-(Ia), R$^1$ is substituted —(C$_1$-C$_3$)alkyl. In some embodiments of formula (I)-(Ia), R$^1$ is methyl. In some embodiments of formula (I)-(Ia), R$^1$ is a halogen. In certain embodiments of formula (I)-(Ia), R$^1$ is F. In some embodiments of formula (I)-(Ia), R$^1$ is substituted —(C$_1$-C$_3$)alkoxy. In some embodiments of formula (I)-(Ia), R$^1$ is methoxy.

In some embodiments of formula (I)-(Ia), R$^7$ is optionally substituted (C$_1$-C$_6$)alkyl-. In some embodiments of formula (I)-(Ia), R$^7$ is (C$_1$-C$_3$)alkyl-. In some embodiments of formula (I)-(Ia), R$^7$ is H$_3$CH$_2$C—. In some embodiments of formula (I)-(Ia), R$^7$ is H$_3$C—.

In some embodiments of formula (I)-(Ia), R$^8$ is optionally substituted —(C$_1$-C$_6$)alkyl. In some embodiments of formula (I)-(Ia), R$^8$ is (C$_1$-C$_3$)alkyl-. In another embodiment of formula (I)-(Ia), R$^8$ is —CH$_2$CH$_3$. In another embodiment of formula (I)-(Ia), R$^8$ is —CH$_3$.

In some embodiments of formula (I)-(Ia), R$^9$ is selected from -halogen, —CN, —OH, —(C$_1$-C$_6$)alkoxy, —NH$_2$, substituted amino, —(C$_1$-C$_6$)alkyl-NH$_2$ (e.g., —CH$_2$NH$_2$) and —(C$_1$-C$_6$)alkyl. In some embodiments of formula (I)-(Ia), R$^9$ is halogen. In certain cases, the halogen is F or Cl. In some embodiments of formula (I)-(Ia), R$^9$ is —OH. In some embodiments of formula (I)-(Ia), R$^9$ is —OCH$_3$. In some embodiments of formula (I)-(Ia), R$^9$ is amino or substituted amino. In some embodiments of formula (I)-(Ia), R$^9$ is —(C$_1$-C$_6$)alkyl-NH$_2$. In certain cases of formula (I)-(Ia), R$^9$ is —CH$_2$NH$_2$. In some embodiments of formula (I)-(Ia), R$^9$ is —(C$_1$-C$_6$)alkyl. In some embodiments of formula (I)-(Ia), R$^9$ is CH$_3$. In some embodiments of formula (I)-(Ia), R$^9$ is —CH$_2$CH$_3$. In some embodiments of formula (I)-(Ia), R$^9$ is H. In some embodiments of formula (I)-(Ia), R$^9$ is —CN.

In some embodiments of formula (Ia), R$^{11}$ is -halogen. In another embodiment of formula (Ia), R$^{11}$ is —F. In some embodiments of formula (Ia), R$^{11}$ is —CN. In some embodiments of formula (Ia), R$^{11}$ is —OH. In some embodiments of formula (Ia), R$^{11}$ is —(C$_1$-C$_6$)alkoxy. In some embodiments of formula (Ia), R$^{11}$ is —NH$_2$ or —NR$^5$R$^6$. In some embodiments of formula (Ia), R$^{11}$ is —CH$_2$NH$_2$. In some embodiments of formula (Ia), R$^{11}$ is —(C$_1$-C$_6$)alkyl. In some embodiments of formula (Ia), R$^{11}$ is —CH$_3$. In some embodiments of formula (Ia), R$^{11}$ is —CH$_2$CH$_3$.

In some embodiments, the compound of formula (I) is a compound of formula (Ib):

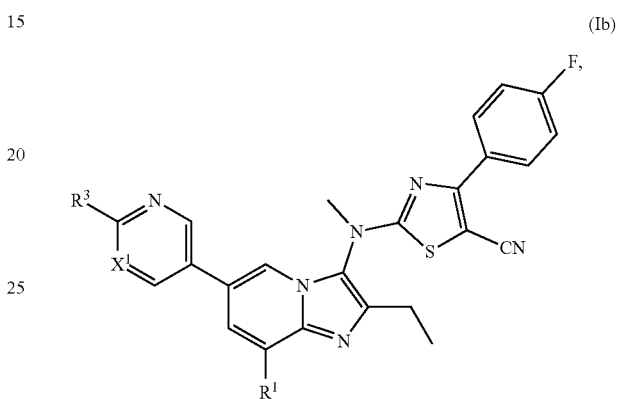

(Ib)

wherein:
X$^1$ is C—H or N; and
R$^1$ is selected from —H, -halogen, optionally substituted —(C$_1$-C$_6$)alkyl, and optionally substituted —(C$_1$-C$_6$)alkoxy.

In some embodiments of formula (Ib), X$^1$ is N. In some other embodiment of formula (Ib), X$^1$ is C—H.

In some embodiments of formula (Ib), R$^1$ is H. In some embodiments of formula (Tb), R$^1$ is substituted —(C$_1$-C$_3$)alkyl. In some embodiments of formula (Ib), R$^1$ is methyl. In some embodiments of formula (Ib), R$^1$ is a halogen. In certain embodiments of formula (Ib), R$^1$ is F. In some embodiments of formula (Ib), R$^1$ is substituted —(C$_1$-C$_3$)alkoxy. In some embodiments of formula (Ib), R$^1$ is methoxy.

In some embodiments of the compound of formula (I)-(Ib), (a) R$^3$ is

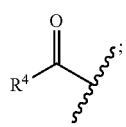

;

(b) R$^3$ is

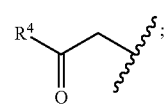

;

(c) R³ is

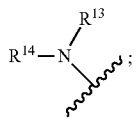

(d) R³ is

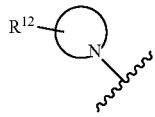

that is an optionally substituted monocyclic or bicyclic (C₂-C₉)heterocycle- (e.g., (C₂-C₅)heterocycloalkyl); or (e) R³ is

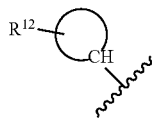

that is an optionally substituted monocyclic or bicyclic (C₃-C₈)carbocycle- (e.g., (C₃-C₆)cycloalkyl-), or an optionally substituted monocyclic or bicyclic (C₂-C₉)heterocycle- (e.g., (C₂-C₅)heterocycloalkyl-);
wherein:
R⁴ is selected from HO—, H₂N—, R¹⁵R¹⁶N—, optionally substituted (C₁-C₅)alkyl-, optionally substituted monocyclic or bicyclic carbocycle, and optionally substituted monocyclic or bicyclic heterocycle;
R¹² is selected from —H, —NH₂, —OH, —CH₂C(O)R⁴, —C(O)R⁴, —CHR¹⁵R¹⁶, —NR¹⁵R¹⁶, optionally substituted —(C₁-C₅)alkyl, optionally substituted monocyclic or bicyclic —(C₃-C₈)carbocycle (e.g., —(C₃-C₆)cycloalkyl), and an optionally substituted monocyclic or bicyclic —(C₂-C₉)heterocycle (e.g., —(C₂-C₅)heterocycloalkyl;
R¹³ and R¹⁴ are independently selected from —H, —CH₂C(O)R¹⁷, —CH₂R¹⁷, —C(O)R¹⁷, —R¹⁸C(O)R¹⁷, —CH₂R¹⁸C(O)R¹⁷, optionally substituted —(C₁-C₅)alkyl, optionally substituted monocyclic or bicyclic —(C₃-C₈)carbocycle (e.g., —(C₃-C₆)Cycloalkyl), and an optionally substituted monocyclic or bicyclic —(C₂-C₉)heterocycle (e.g., —(C₂-C₅)heterocycloalkyl), wherein R¹⁷ and R¹⁸ are independently selected from optionally substituted —(C₁-C₅)alkyl, optionally substituted monocyclic or bicyclic —(C₃-C₈)carbocycle (e.g., —(C₃-C₆)cycloalkyl), and an optionally substituted monocyclic or bicyclic —(C₂-C₉)heterocycle (e.g., —(C₂-C₅)heterocycloalkyl); and
R¹⁵ and R¹⁶ are independently selected from H—, optionally substituted (C₂-C₅)heterocycloalkyl-C(O)—, optionally substituted (C₃-C₆)cycloalkyl-C(O)—, optionally substituted (C₁-C₅)alkyl-, optionally substituted 3- to 10-membered saturated monocyclic heterocycle or carbocycle, and optionally substituted 3- to 10-membered saturated bicyclic heterocycle or carbocycle, wherein the optional substituents are selected from hydroxy, HOCH₂—, cyano, halogen, substituted amino (e.g., (C₁-C₅)alkyl-substituted amino), and (C₁-C₅)alkyl; or R¹⁵ and R¹⁶ are cyclically linked to form a 3- to 6-membered monocyclic saturated heterocycle, optionally substituted with hydroxy, HOCH₂—, cyano, halogen, substituted amino (e.g., (C₁-C₅)alkyl-substituted amino), or (C₁-C₅)alkyl.

In some embodiments of the compound of formula (I)-(Ib),
R³ is

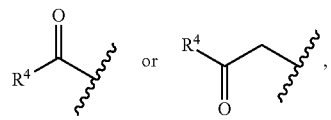

R⁴ is selected from R¹², R³²HN—, R³²N(R³³)—, and R³²HN—R³⁶—;
R³² and R³³ are independently selected from H—, optionally substituted —(C₁-C₃)alkyl, optionally substituted cycloalkyl, and optionally substituted saturated heterocycle; and
R³⁶ is selected from optionally substituted (C₁-C₃)alkyl, optionally substituted cycloalkyl (e.g., cyclopropyl, cyclobutyl, cyclopentyl, or cyclohexyl), and optionally substituted saturated heterocycle (e.g., azetidine, pyrrolidine, piperidine); and
the optional substituents of the R³², R³³ and R³⁶ groups are independently selected from —CN, —OH, —CH₂OH, —(C₁-C₃)alkyl (e.g., —CH₃), —(C₁-C₆)alkoxy, —(C₃-C₆)cycloalkyl, —(C₂-C₅)heterocycloalkyl (e.g., azetidine), and —N(R³⁷)R³⁸, wherein R³⁷ and R³⁸ are independently selected from H, (C₁-C₃)alkyl, (C₃-C₆)cycloalkyl (e.g., cyclopropyl or cyclobutyl), and (C₂-C₅)heterocycloalkyl (e.g., azetidine).

In some embodiments, R³³ is —(C₁-C₃)alkyl and R² is optionally substituted cycloalkyl, or optionally substituted saturated heterocycle. In some embodiments, R³² is optionally substituted cycloalkyl that is optionally substituted cyclopropyl, cyclobutyl, cyclopentyl, or cyclohexyl. In some embodiments, R³² is optionally substituted heterocycle that is optionally substituted azetidine, pyrrolidine, piperidine, morpholine, piperazine, morpholine-3-one, or piperidine-2-one.

In some embodiments, R⁴ is an azetidine, pyrrolidine or piperidine ring that is substituted (e.g., at the 3-position) with —OH. In some embodiments, R⁴ is R³²HN—R³⁶— where R³⁶ is azetidine and R³² is selected from azetidine, cyclobutyl, cyclopropyl, ethyl and methyl. In some embodiments, R⁴ is R³²HN—, where R³² is selected from H, —(C₁-C₃)alkyl (e.g., methyl), azetidine, pyrrolidine, piperidine, cyclopentyl, cyclobutyl, and cyclopropyl, and R³² is optionally substituted, e.g., with —CN or —OH.

In some embodiments, R⁴ is selected from:

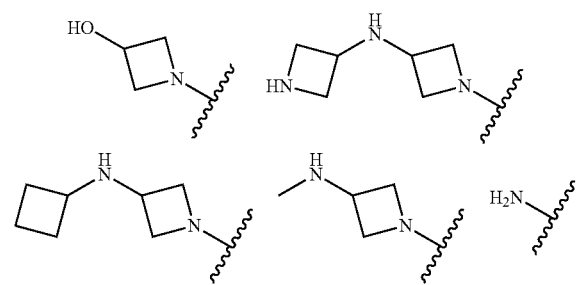

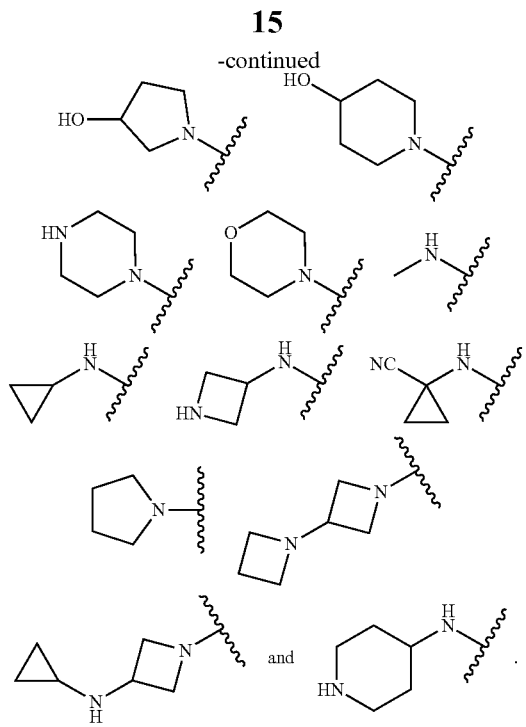

In some embodiments of formula (Ib), the compound is selected from compounds 11-16, 47-65 and 87 of Table 1.

In some embodiments of the compound of formula (I)-(Ib), $R^3$ is

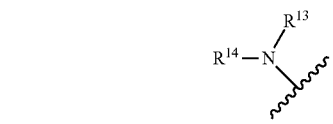

$R^{14}$ is selected from $R^{34}$—, $R^{34}CH_2$—, $R^{34}C(O)R^{35}$—, and $R^{34}C(O)R^{35}CH_2$—;

each $R^{34}$ and $R^{35}$ are independently selected from optionally substituted —$(C_1$-$C_3)$alkyl, optionally substituted cycloalkyl, and optionally substituted saturated heterocycle;

the optional substituents of the $R^{34}$ and $R^{35}$ groups are independently selected from —CN, —OH, —CH$_2$OH, —$(C_1$-$C_3)$alkyl (e.g., —CH$_3$), —$(C_1$-$C_3)$alkoxy, and —$(C_1$-$C_3)$alkyl; and $R^{13}$ is —H. In some embodiments, the optionally substituted cycloalkyl is optionally substituted cyclopropyl, cyclobutyl, cyclopentyl, or cyclohexyl. In some embodiments, the optionally substituted heterocycle is optionally substituted azetidine, pyrrolidine, piperidine, morpholine, piperazine, morpholine-3-one, or piperidine-2-one.

In some embodiments, $R^{14}$ is selected from:

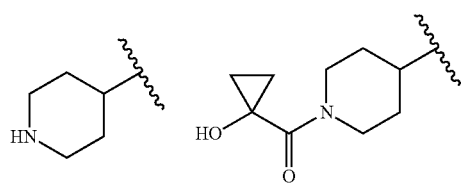

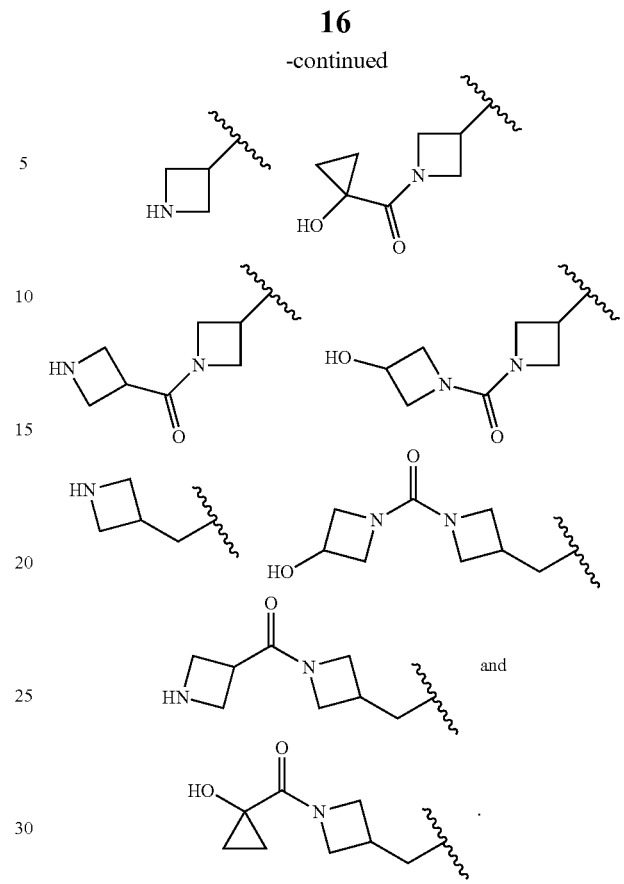

In some embodiments of formula (Ib), the compound is selected from compounds 21, 22, and 34-41 of Table 1.

In some embodiments of the compound of formula (I)-(Ib), $R^3$ is

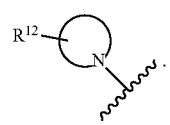

In another embodiment, $R^3$ is selected from:

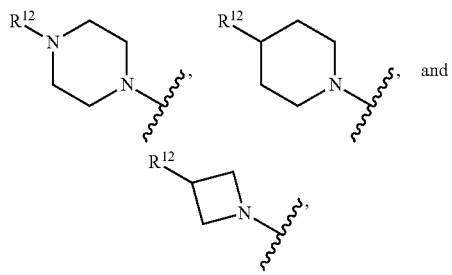

wherein:
$R^{12}$ is selected from H—, $H_2N$—, $R^{31}$—C(O)—, $R^{31}$—C(O)CH$_2$—, $R^{31}$—NHC(O)—, $R^{31}$—C(O)NH—, $R^{31}$—NH—, $R^{31}$—N(CH$_3$)C(O)—, $R^{31}$—C(O)N(CH$_3$)—, $R^{31}$—N(CH$_3$)—, and $R^{31}$—O—;

$R^{31}$ is selected from optionally substituted cycloalkyl, optionally substituted saturated heterocycle; and the optional substituents of the R³¹ group are selected from NC—, HO—, HOCH₂—, (C₁-C₃)alkyl- (e.g., H₃C—), (C₁-C₃)alkoxy-, substituted (C₁-C₃)alkyl-, and (C₃-C₆)cycloalkyl- (e.g., cyclopropyl), and (C₂-C₅) heterocycloalkyl- (e.g., azetidine, pyrrolidine, piperidine, morpholine, piperazine, morpholine-3-one, or piperidine-2-one). In some embodiments, the optionally substituted cycloalkyl is optionally substituted cyclopropyl, cyclobutyl, cyclopentyl, or cyclohexyl. In some embodiments, the optionally substituted saturated heterocycle is optionally substituted azetidine, pyrrolidine, piperidine, morpholine, piperazine, morpholine-3-one, or piperidine-2-one.

In some embodiments, R¹² is selected from:

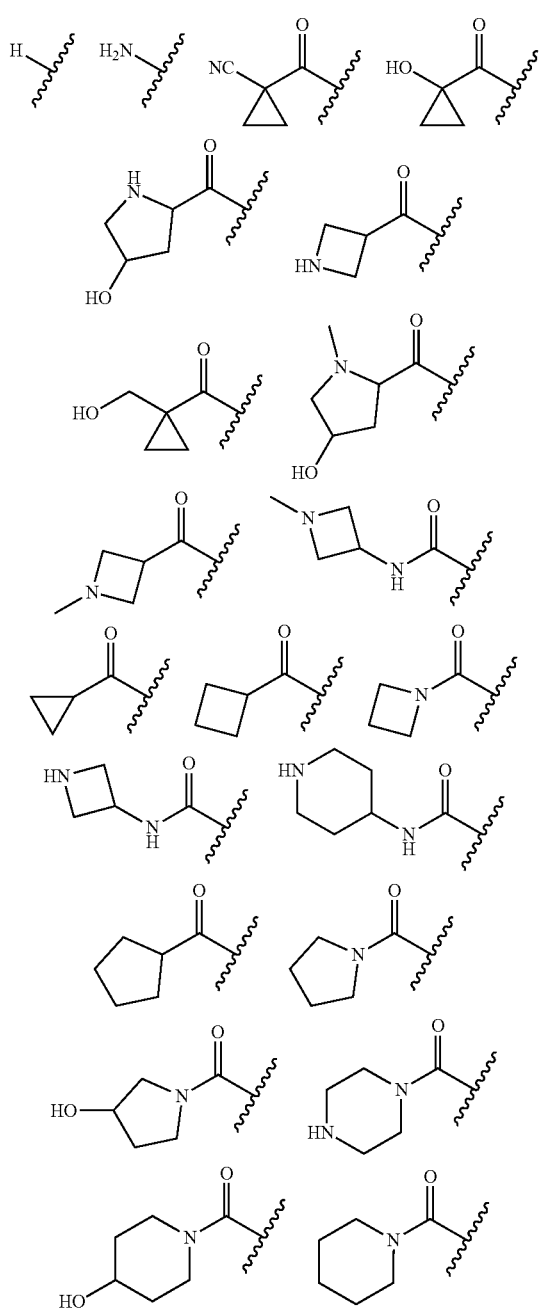

-continued

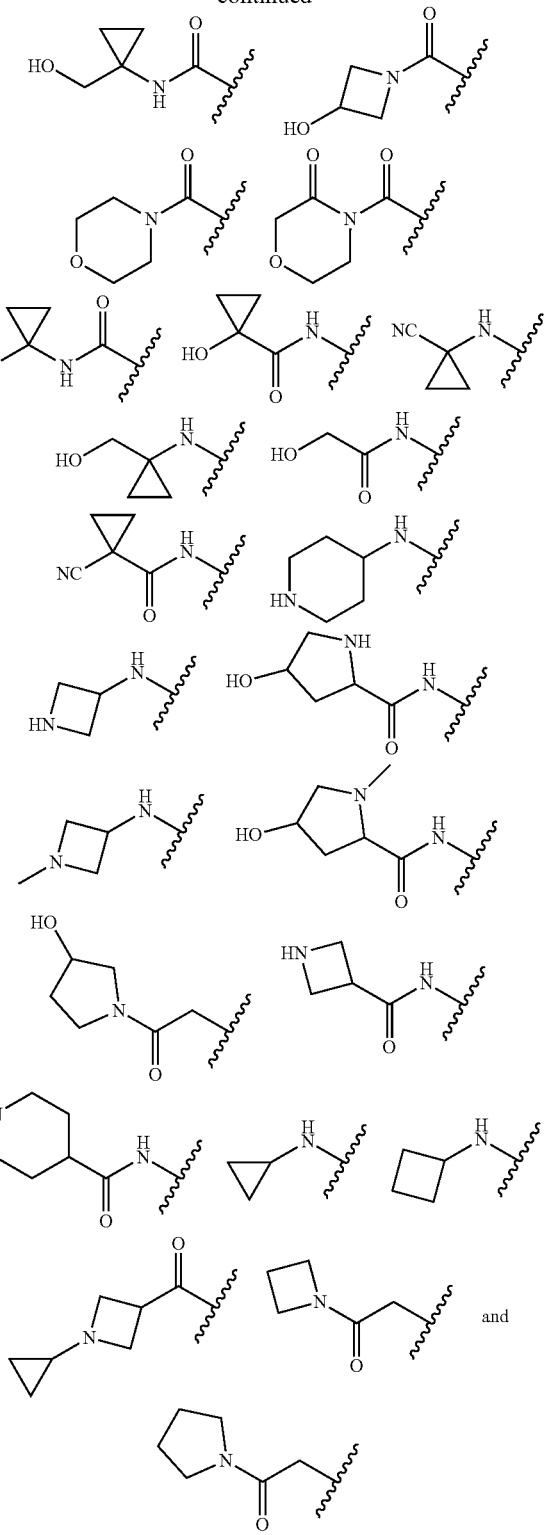

In some embodiments of formula (Ib), the compound is selected from compounds 1-10, 17-20, 23-33, 42-46, 66-80 and of Table 1.

In some embodiments of formula (Ib), the compound is selected from compounds 81-86, 88-98, 105-115, and 118-127 of Table 1.

In some embodiments of the compound of formula (I)-(Ib), $R^3$ is

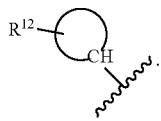

In another embodiment, $R^3$ is

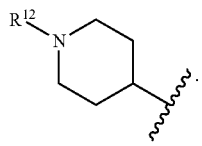

In another embodiment, $R^{12}$ is selected from H—, $R^{31}$—C(O)—, $R^{31}$—C(O)CH$_2$—, $R^{31}$—NHC(O)—, $R^{31}$—C(O)NH—, $R^{31}$—N(CH$_3$)C(O)—, and $R^{31}$—C(O)N(CH$_3$)—;

$R^{31}$ is selected from optionally substituted (C$_1$-C$_3$)alkyl-, optionally substituted cycloalkyl-, and optionally substituted saturated heterocycle; and the optional substituents of the $R^{31}$ group are selected from NC—, HO—, HOCH$_2$—, (C$_1$-C$_3$)alkyl- (e.g., H$_3$C—), (C$_1$-C$_3$)alkoxy- and substituted (C$_1$-C$_3$)alkyl-. In some embodiments, the optionally substituted cycloalkyl is optionally substituted cyclopropyl, cyclobutyl, cyclopentyl, or cyclohexyl. In some embodiments, the optionally substituted heterocycle is optionally substituted azetidine, optionally substituted pyrrolidine, or optionally substituted piperidine.

In another embodiment, $R^2$ is selected from:

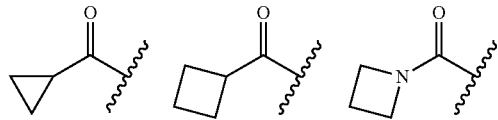

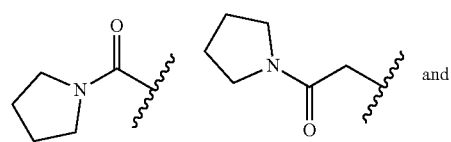

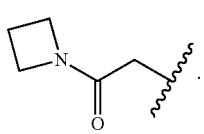

In some embodiments of formula (Ib), the compound is selected from compounds 99-104 of Table 1.

In some embodiments of formula (I)-(Ia), the compound is of formula (Ie):

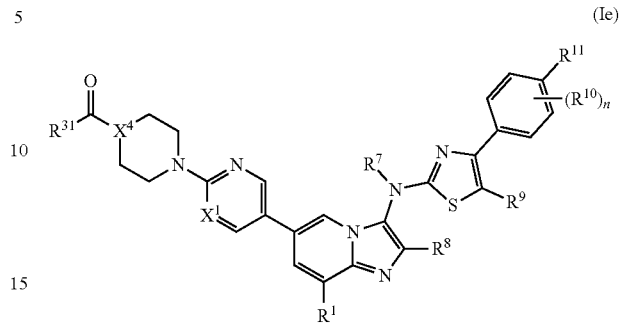

wherein:

$X^1$ and $X^4$ are independently N or C—R$^1$;

$R^1$ is selected from H, halogen, optionally substituted —(C$_1$-C$_6$)alkyl, and optionally substituted —(C$_1$-C$_6$)alkoxy; and $R^{31}$ is selected from optionally substituted (C$_2$-C$_5$)heterocycloalkyl, and optionally substituted (C$_3$-C$_7$)cycloalkyl-;

$R^{11}$ is —H, -halogen, —CN, —OH, optionally substituted —(C$_1$-C$_6$)alkoxy, —NH$_2$, —NR$^5$R$^6$, —CH$_2$NH$_2$ and optionally substituted —(C$_1$-C$_6$)alkyl; and n is 0, 1, 2, or 3.

In some embodiments of the compound of formula (Ie), the optional substituents of the $R^{31}$ group are selected from NC—, HO—, HOCH$_2$—, (C$_1$-C$_3$)alkyl- (e.g., H$_3$C—), (C$_1$-C$_3$)alkoxy-, substituted (C$_1$-C$_3$)alkyl-, and (C$_3$-C$_6$)cycloalkyl- (e.g., cyclopropyl).

In some embodiments of formula (Ie), the compound is of formula (If):

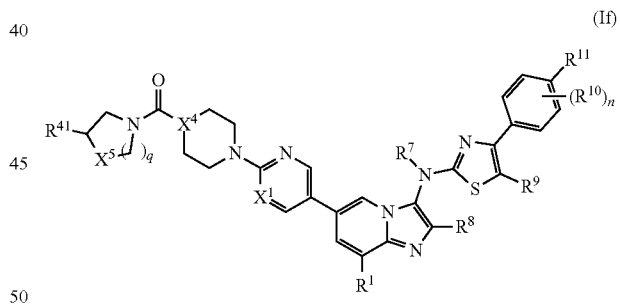

wherein:

$X_1$ and $X^4$ are independently N or CH, $R^{41}$ is H—, or HO—; and q is 0, 1 or 2; wherein when q is 0 or 1, $X^5$ is CH$_2$; and when q is 2, $X^5$ is NH, O, or CH(OH).

In some embodiments of formula (Ie)-(If), $R^7$ is optionally substituted (C$_1$-C$_6$)alkyl-. In some embodiments of formula (Ie)-(If), $R^7$ is (C$_1$-C$_3$)alkyl-. In some embodiments of formula (Ie)-(If), $R^7$ is H$_3$CH$_2$C—. In some embodiments of formula (Ie)-(If), $R^7$ is H$_3$C—.

In some embodiments of formula (Ie)-(If), $R^8$ is optionally substituted —(C$_1$-C$_6$)alkyl. In some embodiments of formula (Ie)-(If), $R^8$ is (C$_1$-C$_3$)alkyl-. In some embodiments of formula (Ie)-(If), $R^8$ is —CH$_2$CH$_3$. In some embodiments of formula (Ie)-(If), $R^8$ is —CH$_3$.

In some embodiments of formula (Ie)-(If), $R^9$ is selected from -halogen, —CN, —OH, —($C_1$-$C_6$)alkoxy, —$NH_2$, substituted amino, —($C_1$-$C_6$)alkyl-$NH_2$ (e.g., —$CH_2NH_2$) and —($C_1$-$C_6$)alkyl. In some embodiments of formula (Ie)-(If), $R^9$ is halogen. In certain cases, the halogen is F or Cl. In some embodiments of formula (Ie)-(If), $R^9$ is —OH. In some embodiments of formula (Ie)-(If), $R^9$ is —$OCH_3$. In some embodiments of formula (Ie)-(If), $R^9$ is amino or substituted amino. In some embodiments of formula (Ie)-(If), $R^9$ is —($C_1$-$C_6$)alkyl-$NH_2$. In certain cases, $R^9$ is —$CH_2NH_2$. In some embodiments of formula (Ie)-(If), $R^9$ is —($C_1$-$C_6$)alkyl. In some embodiments of formula (Ie)-(If), $R^9$ is $CH_3$. In some embodiments of formula (Ie)-(If), $R^9$ is —$CH_2CH_3$. In some embodiments of formula (Ie)-(If), $R^9$ is H. In some embodiments of formula (Ie)-(If), $R^9$ is —CN.

In some embodiments of formula (Ie)-(If), $R^{11}$ is -halogen. In another embodiment of formula (Ie)-(If), $R^{11}$ is —F. In some embodiments of formula (Ie)-(If), $R^{11}$ is —CN. In some embodiments of formula (Ie)-(If), $R^{11}$ is —OH. In some embodiments of formula (Ie)-(If), $R^{11}$ is —($C_1$-$C_6$) alkoxy. In some embodiments of formula (Ie)-(If), $R^{11}$ is —$NH_2$ or —$NR^5R^6$. In some embodiments of formula (Ie)-(If), $R^{11}$ is —$CH_2NH_2$. In some embodiments of formula (Ie)-(If), $R^{11}$ is —($C_1$-$C_6$)alkyl. In some embodiments of formula (Ie)-(If), $R^{11}$ is —$CH_3$. In some embodiments of formula (Ie)-(If), $R^{11}$ is —$CH_2CH_3$.

In some embodiments of formula (I)-(Ib), the compound is of formula (Ic):

(Ic)

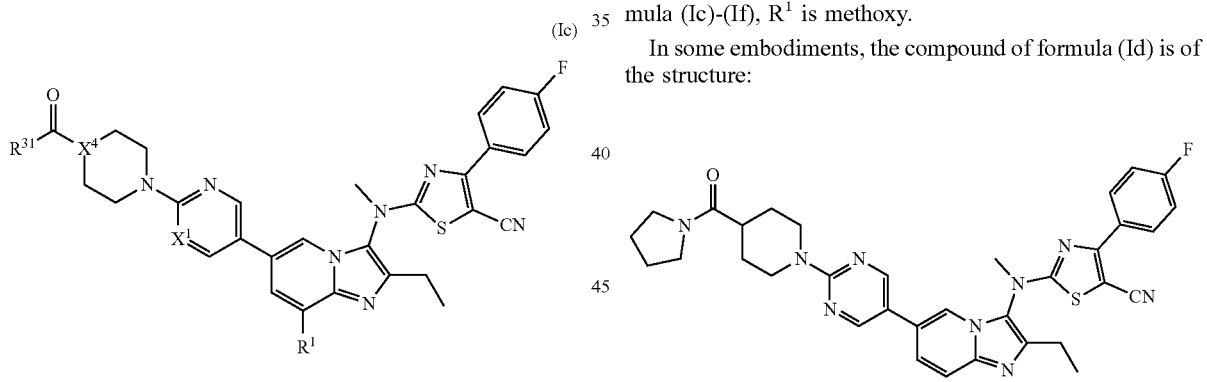

wherein:

$X_1$ and $X^4$ are independently N or C—$R^1$;

$R^1$ is selected from H, halogen, optionally substituted —($C_1$-$C_6$)alkyl, and optionally substituted —($C_1$-$C_6$)alkoxy; and $R^{31}$ is optionally substituted ($C_2$-$C_5$)heterocycloalkyl-, or optionally substituted ($C_3$-$C_7$)cycloalkyl. In some embodiments of formula (Ic), the optional substituents of the $R^{31}$ group are selected from NC—, HO—, $HOCH_2$—, ($C_1$-$C_3$)alkyl- (e.g., $H_3C$—), ($C_1$-$C_3$) alkoxy-, substituted ($C_1$-$C_3$)alkyl-, ($C_3$-$C_6$)cycloalkyl- (e.g., cyclopropyl), and ($C_2$-$C_5$)heterocycloalkyl- (e.g., azetidine, pyrrolidine, piperidine, morpholine, piperazine, morpholine-3-one, or piperidine-2-one).

In some embodiments of formula (Ic), the compound is of formula (Id):

(Id)

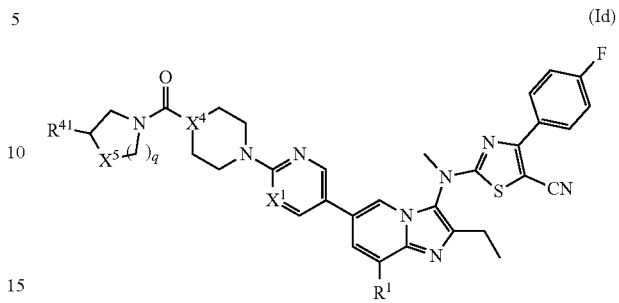

wherein:

$X^1$ and $X^4$ are independently N or CH;

$R^{41}$ is H—, or HO—; and q is 0, 1 or 2; wherein when q is 0 or 1, $X^5$ is $CH_2$; and when q is 2, $X^5$ is NH, O, or CH(OH).

In some embodiments of formula (Ic)-(If), $X^1$ is N. In some other embodiment of formula (Ic)-(If), $X^1$ is C—H.

In some embodiments of formula (Ic)-(If), $R^1$ is H. In some embodiments of formula (Ic)-(If), $R^1$ is substituted —($C_1$-$C_3$)alkyl. In some embodiments of formula (Ic)-(If), $R^1$ is methyl. In some embodiments of formula (Ic)-(If), $R^1$ is a halogen. In certain embodiments of formula (Ic)-(if), $R^1$ is F. In some embodiments of formula (Ic)-(If), $R^1$ is substituted —($C_1$-$C_3$)alkoxy. In some embodiments of formula (Ic)-(If), $R^1$ is methoxy.

In some embodiments, the compound of formula (Id) is of the structure:

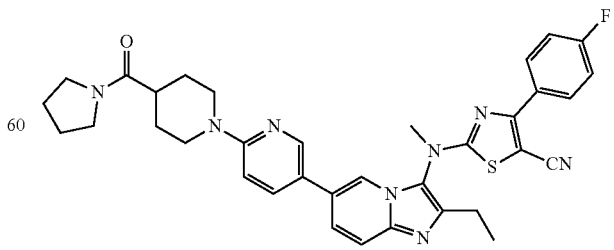

or a salt thereof.

In some embodiments, the compound of formula (Id) is of the structure:

or a salt thereof.

In some embodiments, the compound of formula (Id) is of the structure:

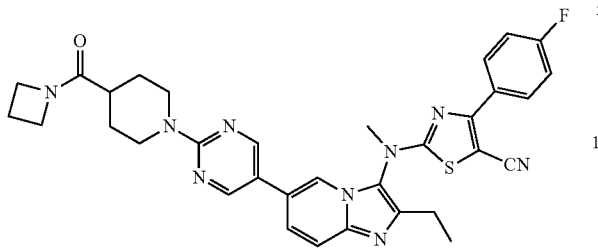

or a salt thereof.

In some embodiments, the compound of formula (Id) is of the structure:

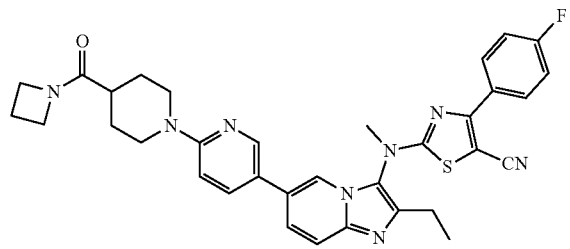 [SMILES: CCc1nc2ccc(-c3cnc(N4CCC(C(=O)N5CCC5)CC4)nc3)cn2c1N(C)c1nc(-c2ccc(F)cc2)c(C#N)s1]

or a salt thereof.

In some embodiments the compound of formula Id is of the structure:

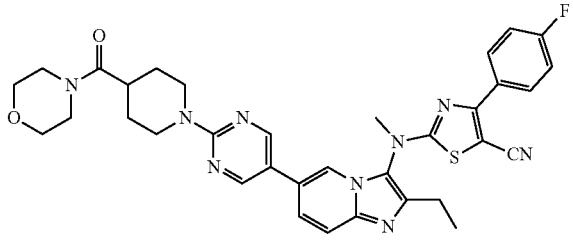 [SMILES: CCc1nc2ccc(-c3cnc(N4CCC(C(=O)N5CCOCC5)CC4)nc3)cn2c1N(C)c1nc(-c2ccc(F)cc2)c(C#N)s1]

or a salt thereof.

In some embodiments, the compound of formula (Id) is of the structure:

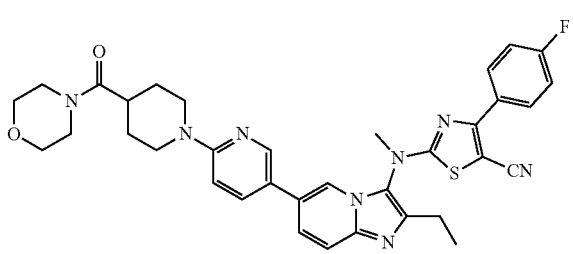 [SMILES: CCc1nc2ccc(-c3ccc(N4CCC(C(=O)N5CCOCC5)CC4)nc3)cn2c1N(C)c1nc(-c2ccc(F)cc2)c(C#N)s1]

or a salt thereof.

In some embodiments, the compound of formula (Id) is of the structure:

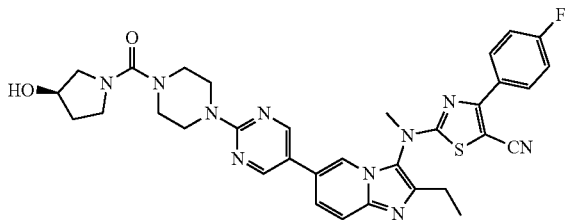 [SMILES: CCc1nc2ccc(-c3cnc(N4CCN(C(=O)N5CC[C@@H](O)C5)CC4)nc3)cn2c1N(C)c1nc(-c2ccc(F)cc2)c(C#N)s1]

or a salt thereof.

In some embodiments, the compound of formula (Id) is of the structure:

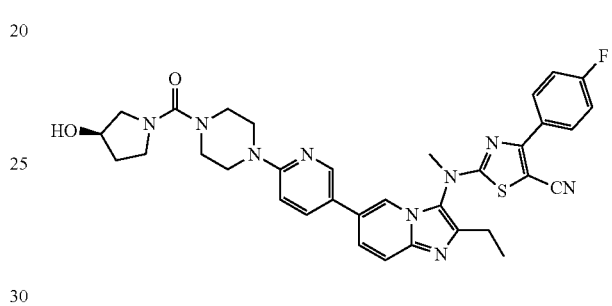

or a salt thereof.

In some embodiments, the compound of formula (Id) is of the structure:

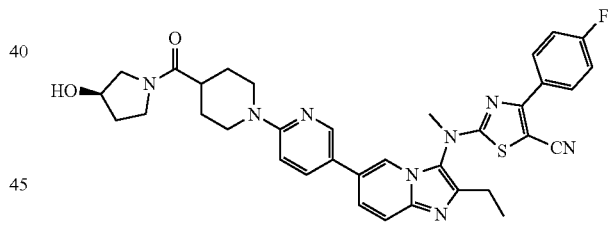

or a salt thereof.

In some embodiments, the compound of formula (Id) is of the structure:

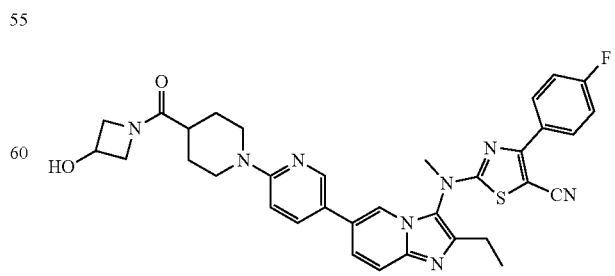

or a salt thereof.

In some embodiments, the compound of formula (Id) is of the structure:

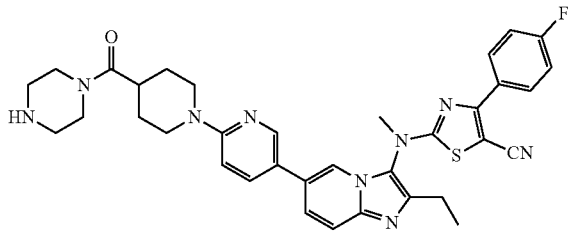 [SMILES: CCc1nc2ccc(-c3ccc(N4CCC(C(=O)N5CCNCC5)CC4)nc3)cn2c1N(C)c1nc(-c2ccc(F)cc2)c(C#N)s1]

or a salt thereof.

In some embodiments, the compound of formula (Id) is of the structure:

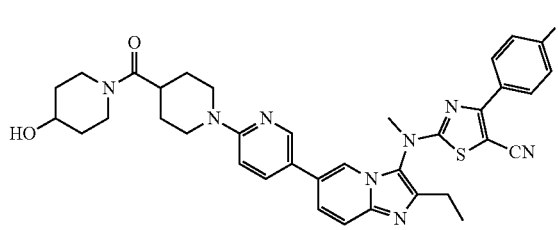

or a salt thereof.

ATX inhibitor compounds of the present disclosure (e.g., of any one of formula (I)-(If)) may have a structure selected from any of those listed in Table 1 or a pharmaceutically acceptable salt thereof.

Also disclosed herein are compounds of formula (II):

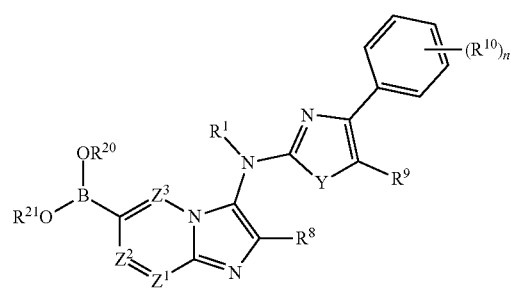

or a pharmaceutically acceptable salt or isomer thereof, wherein:

$Z^1$, $Z^2$, and $Z^3$ are independently selected from C—$R^1$ and N;

$R^{20}$ and $R^{21}$ are each independently selected from H, and optionally substituted —($C_1$-$C_6$)alkyl;

or $R^{20}$ and $R^{21}$ together with the boron atom to which they are attached from an optionally substituted heterocycle;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^7$ is selected from H—, and optionally substituted ($C_1$-$C_6$)alkyl-;

$R^8$ is selected from —H, -halogen, and optionally substituted —($C_1$-$C_6$)alkyl;

$R^9$ and each $R^{10}$ are independently selected from —H, -halogen, —CN, —OH, optionally substituted —($C_1$-$C_6$)alkoxy, —$NH_2$, substituted amino, optionally substituted —($C_1$-$C_6$)alkyl-$NH_2$ and optionally substituted —($C_1$-$C_6$)alkyl; and n is 0, 1, 2, 3, 4, or 5.

In certain embodiments, the compound of formula (II) is:

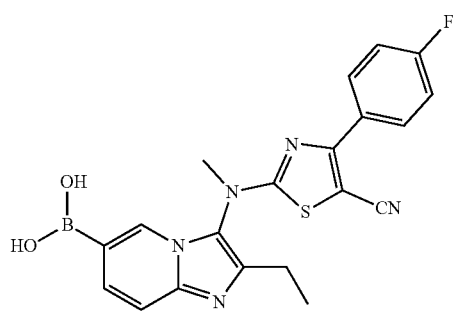 [SMILES: CCc1nc2ccc(B(O)O)cn2c1N(C)c1nc(-c2ccc(F)cc2)c(C#N)s1]

Also disclosed herein are compound of formula (III):

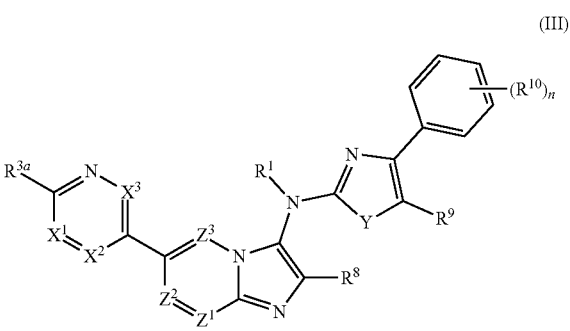

or a pharmaceutically acceptable salt or isomer thereof. wherein:

$X^1$, $X^2$, and $X^3$ are independently selected from C—$R^1$ and N;

$Z^1$, $Z^2$, and $Z^3$ are independently selected from C—$R^1$ and N;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^{3a}$ is selected from optionally substituted $R^4$—C(O)—($C_1$-$C_3$)alkyl-, $R^4$C(O)—, halogen, optionally substituted monocyclic or bicyclic carbocycle, optionally substituted monocyclic or bicyclic heterocycle, $R^5R^6$HC—, and $R^5R^6$N—;

$R^4$ is selected from $H_2$N—, HO—, $R^5R^6$N—, optionally substituted ($C_1$-$C_{10}$)alkyl-, optionally substituted ($C_1$-$C_{10}$)alkoxy-, optionally substituted monocyclic or bicyclic carbocycle, optionally substituted monocyclic or bicyclic heterocycle, optionally substituted cycloalkyl-($C_1$-$C_6$)alkylene-, and optionally substituted heterocycle-($C_1$-$C_6$)alkylene-;

$R^5$ and $R^6$ are independently selected from H—, $H_2$N—, HO—, optionally substituted ($C_1$-$C_{10}$)alkyl-, optionally substituted monocyclic or bicyclic carbocycle, optionally substituted monocyclic or bicyclic heterocycle, optionally substituted R⁴C(O)—(C₁-C₁₀)alkyl-, R⁴C(O)—, R⁴—, and substituted amino;

or R and R⁶ together with the nitrogen or carbon atom to which they are attached are cyclically linked to form an optionally substituted carbocycle or an optionally substituted heterocycle;

R⁷ is selected from H—, and optionally substituted (C₁-C₆)alkyl-;

R⁸ is selected from —H, -halogen, and optionally substituted —(C₁-C₆)alkyl;

R⁹ and each R¹⁰ are independently selected from —H, -halogen, —CN, —OH, optionally substituted —(C₁-C₆)alkoxy, —NH₂, substituted amino, optionally substituted —(C₁-C₆)alkyl-NH₂ and optionally substituted —(C₁-C₆)alkyl; and n is 0, 1, 2, 3, 4, or 5.

In certain embodiments, the compound of formula (III) is one of the following compounds:

(128)
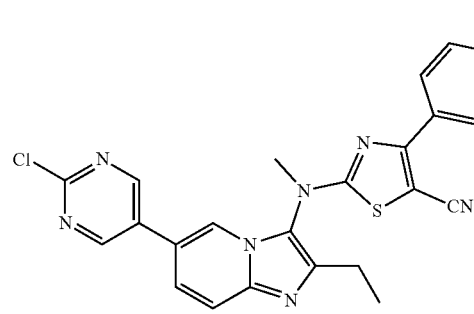

(129)
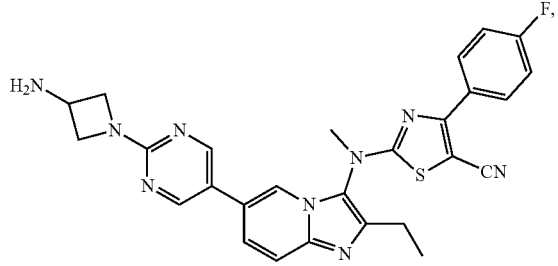

(130)
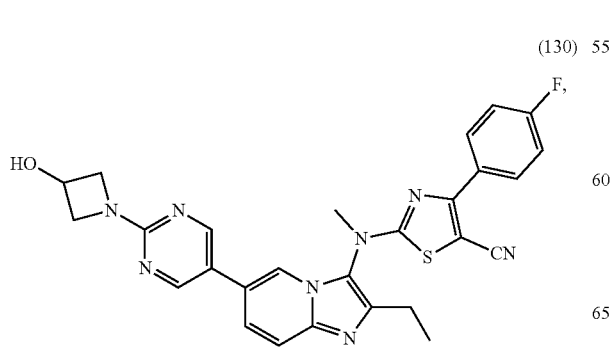

(131)
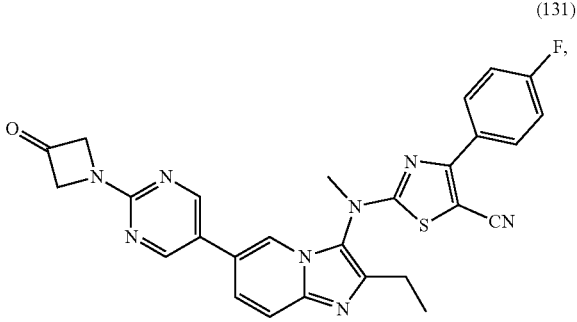

(132)
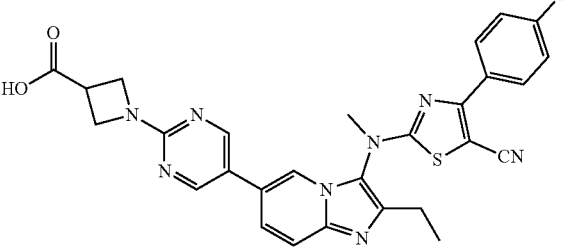

(134)
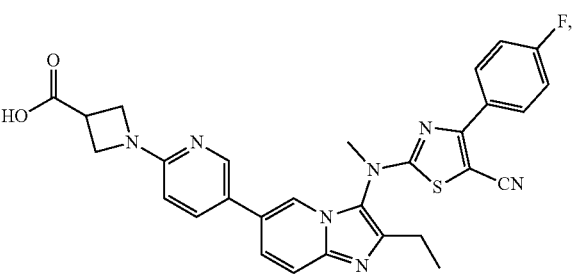

(135)
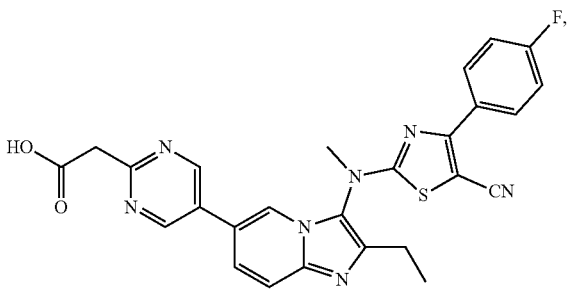

(136)
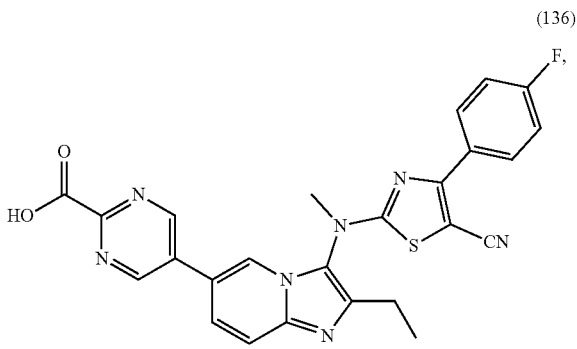

-continued
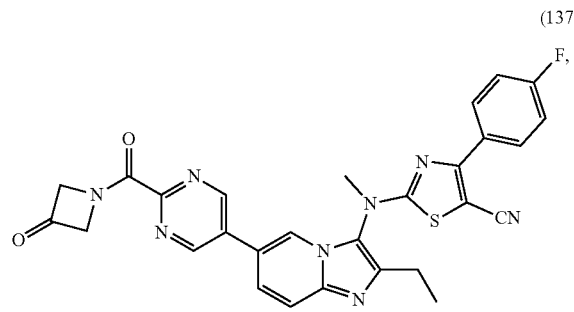 (137)
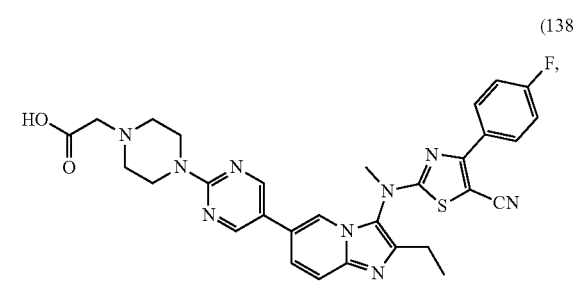 (138)
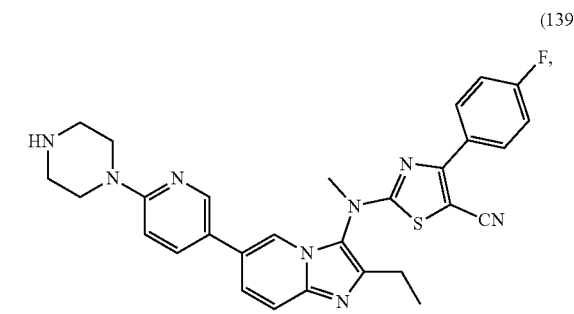 (139)
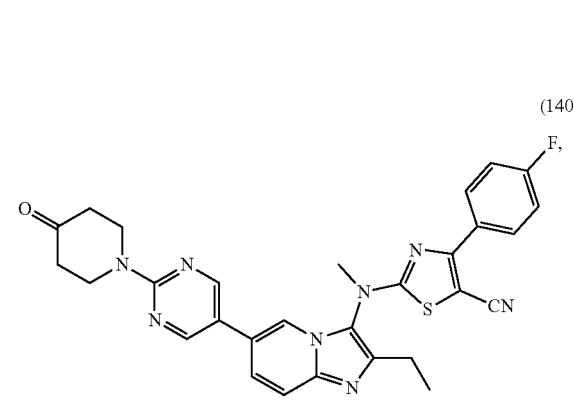 (140)
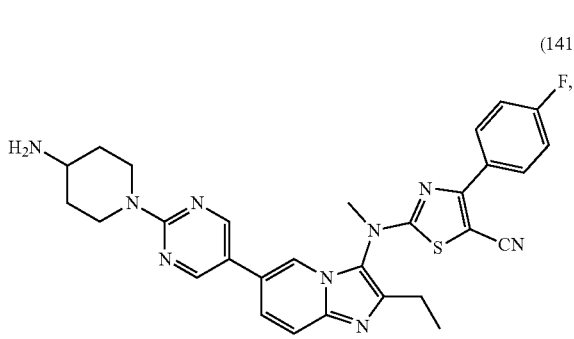 (141)
-continued
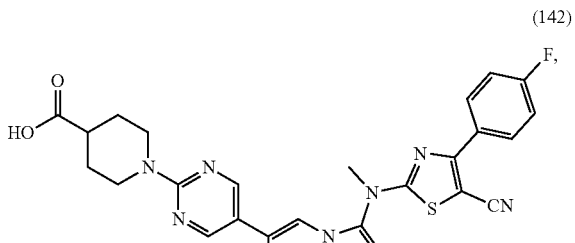 (142)
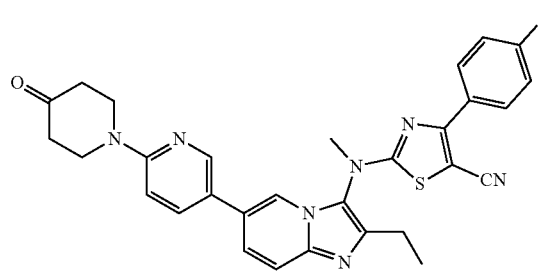 (143)
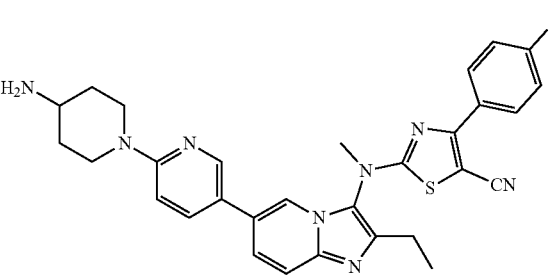 (144)
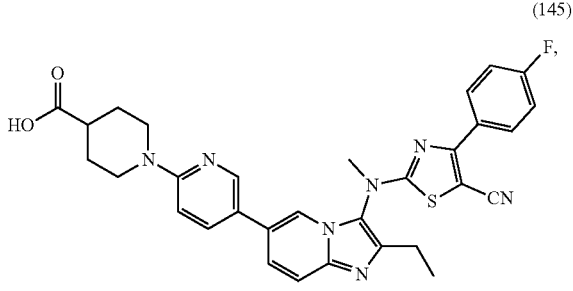 (145)
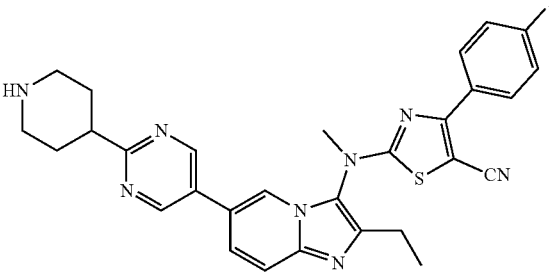 (146)

-continued

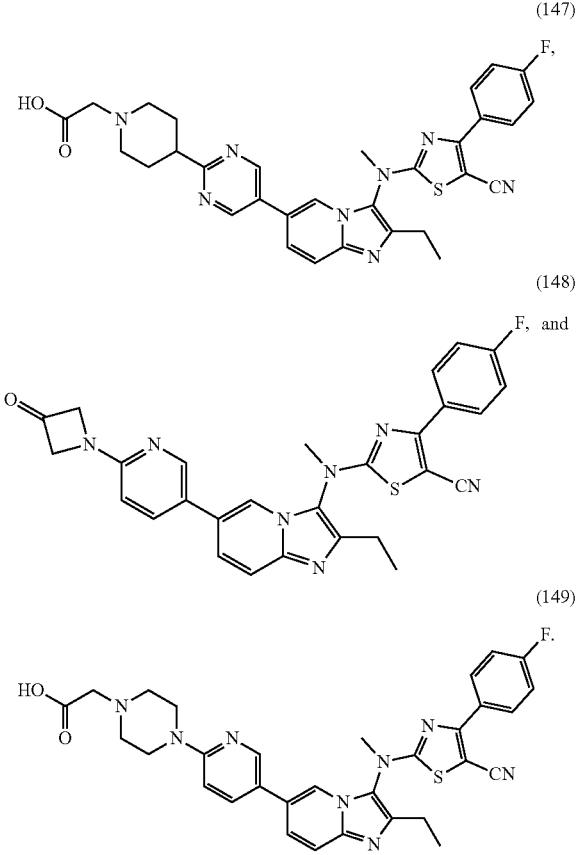

(147)

(148)

(149)

In certain embodiments, compounds of the present disclosure (e.g., of any one of formula (II)-(III)) may have a structure selected from any of those listed in Table 1A or a pharmaceutically acceptable salt thereof.

4.1.1. Isotopically Labelled Analogs

The present disclosure also encompasses isotopically-labeled compounds which are identical to those compounds as described herein, except that one or more atoms are replaced by an atom having an atomic mass or mass number different from the atomic mass or mass number usually found in nature ("isotopologues"). The compounds of the present disclosure may also contain unnatural proportions of atomic isotopes at one or more atoms that constituted such compounds. Examples of isotopes that can be incorporated into compounds described herein include isotopes of hydrogen, carbon, nitrogen, oxygen, phosphorus, fluorine and chlorine, such as $^2$H ("D"), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound described herein can have one or more H atoms replaced with deuterium.

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P and $^{35}$S are thus within the scope of the present technology. Procedures for inserting such labels into the compounds of the present technology will be readily apparent to those skilled in the art based on the disclosure herein.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

In some embodiments, certain isotopically-labeled compounds, such as those labeled with $^3$H and $^{14}$C, can be useful in compound and/or substrate tissue distribution assays. Tritiated ($^3$H) and carbon-14 ($^{14}$C) isotopes can be particularly preferred for their ease of preparation and detectability. Further, substitution with heavier isotopes such as deuterium can afford certain therapeutic advantages resulting from greater metabolic stability, such as increased in vivo half-life or reduced dosage requirements, and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

In some embodiments, the compounds disclosed in the present disclosure are deuterated analogs of any of the compounds, or a salt thereof, as described herein. A deuterated analog of a compound of formula (I)-(If) is a compound where one or more hydrogen atoms are substituted with a deuterium. In some embodiments, the deuterated analog is a compound of formula (I) that includes a deuterated $R^1$, $R^2$, $R^3$, $R^4$, $R^5$, $R^6$, $R^7$, $R^8$, $R^9$, or $R^{10}$ group. In certain embodiments of a deuterated analog of a compound of formula (I), $R^1$, $R^2$, $R^3$, $R^4$, $R^5$, $R^6$, $R^7$, $R^8$, $R^9$, and $R^{10}$ are independently selected from optionally substituted ($C_1$-$C_6$) alkyl, optionally substituted ($C_1$-$C_6$)alkoxy, optionally substituted ($C_1$-$C_6$)alkylene-heterocycloalkyl, optionally substituted monocyclic or bicyclic carbocycle, and optionally substituted monocyclic or bicyclic heterocycle including at least one deuterium atom. In certain embodiments of the deuterated analog of a compound of formula (I), $R^1$, $R^7$, $R^8$, $R^9$, and $R^{10}$ are independently selected from an optionally substituted ($C_1$-$C_3$) alkyl, an optionally substituted ($C_1$-$C_3$) alkoxy, and an optionally substituted ($C_1$-$C_3$)-alkylene-heterocycle (e.g. —$(CH_2)_m$-morpholine, —$(CH_2)_m$-piperazine, and —$(CH_2)_m$-piperidine). In some embodiments of a deuterated analog of formula (I), $R^1$, $R^7$, $R^8$, $R^9$ and $R^{10}$ are independently —$CD_3$. In some embodiments of a deuterated analog of formula (I), $R^1$, $R^7$, $R^8$, $R^9$ and $R^{10}$ are independently —$CD_2$-$CD_3$. In some embodiments of a deuterated analog of a compound of formula (I), wherein the optional substituent is an optionally substituted heterocycloalkyl including at least one deuterium atom

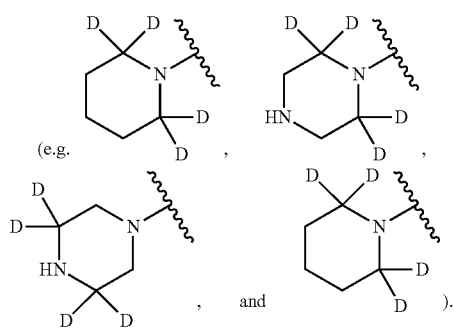

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

4.1.2. Fluorinated Analogs

In some embodiments, the compounds disclosed in the present disclosure are fluorinated analogs of any of the compounds, or a salt thereof, as described herein. A fluorinated analog of a compound of formula (I)-(If) is a compound where one or more hydrogen atoms or substituents are substituted with a fluorine atom. In some embodiments, the fluorinated analog is a compound of formula (I) that includes a fluorinated $R^1$, $R^2$, $R^3$, $R^4$, $R^5$, $R^6$, $R^7$, $R^8$, $R^9$, or $R^{10}$ group. In some embodiments of a fluorinated analog of a compound of formula (I), $R^1$, $R^2$, $R^3$, $R^4$, $R^5$, $R^6$, $R^7$, $R^8$, $R^9$, and $R^{10}$ are independently selected from optionally substituted ($C_1$-$C_6$)alkyl, optionally substituted ($C_1$-$C_6$) alkoxy, optionally substituted ($C_1$-$C_6$)alkylene-heterocycloalkyl, optionally substituted monocyclic or bicyclic carbocycle, optionally substituted monocyclic or bicyclic heterocycle, optionally substituted aryl, and optionally substituted heteroaryl including at least one fluorine atom. In some embodiments of a fluorinated analog of a compound of formula (I), the hydrogen atom of an aliphatic or an aromatic C—H bond is replaced by a fluorine atom. In some embodiments of a fluorinated analog of a compound of formula (I), at least one hydrogen of an optionally substituted aryl or an optionally substituted heteroaryl is replaced by a fluorine atom. In some embodiments of a fluorinated analog of a compound of formula (I), a hydroxyl substituent (—OH) or an amino substituent (—$NH_2$) is replaced by a fluorine atom. In some embodiments of a fluorinated analog of a compound of formula (I), $R^1$, $R^2$, $R^3$, $R^4$, $R^5$, $R^6$, $R^7$, $R^8$, $R^9$, and $R^{10}$ are independently selected from F, $CF_3$, $CF_2CF_3$, $CHF_2$, $OCF_3$, $OCHF_2$, and $OCF_2CF_3$.

4.1.3. Isomers

The term "compound", as used herein, is meant to include all stereoisomers, geometric isomers, tautomers, and isotopes of the structures depicted.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. In some embodiments, the compounds described herein have one or more chiral centers. It is understood that if an absolute stereochemistry is not expressly indicated, then each chiral center may independently be of the R-configuration or the S-configuration or a mixture thereof. Thus, compounds described herein include enriched or resolved optical isomers at any or all asymmetric atoms as are apparent from the depictions. Racemic mixtures of R-enantiomer and S-enantiomer, and enantio-enriched stereomeric mixtures comprising of R- and S-enantiomers, as well as the individual optical isomers can be isolated or synthesized so as to be substantially free of their enantiomeric or diastereomeric partners, and these stereoisomers are all within the scope of the present technology.

Compounds of the present disclosure containing an asymmetrically substituted atom may be isolated in optically active or racemic forms. It is well known in the art how to prepare optically active forms, such as by resolution of racemic forms, by synthesis from optically active starting materials, or through use of chiral auxiliaries.

Geometric isomers, resulting from the arrangement of substituents around a carbon-carbon double bond or arrangement of substituents around a cycloalkyl or heterocyclic ring, can also exist in the compounds of the present disclosure. Geometric isomers of olefins, C=N double bonds, or other types of double bonds may be present in the compounds described herein, and all such stable isomers are included in the present disclosure. Specifically, cis and trans geometric isomers of the compounds of the present disclosure may also exist and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

4.1.4. Salts and Other Forms

In some embodiments, the compounds described herein are present in a salt form. In some embodiments, the compounds are provided in the form of pharmaceutically acceptable salts.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

Compounds containing an amine functional group or a nitrogen-containing heteroaryl group may be basic in nature and may react with any number of inorganic and organic acids to from the corresponding pharmaceutically acceptable salts. Inorganic acids commonly employed to form such salts include hydrochloric, hydrobromic, hydroiodic, sulfuric, and phosphoric acids, and related inorganic acids.

Organic acids commonly employed to form such salts include para-toluenesulfonic, methanesulfonic, oxalic, para-bromophenylsulfonic, fumaric, maleic, carbonic, succinic, citric, benzoic and acetic acid, and related organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the related salts.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like.

Other examples of salts include anions of the compounds of the present disclosure compounded with a suitable cation such as $N^+$, $NH_4^+$, and $NW_4^+$ (where W can be a $C_1$-$C_8$ alkyl group), and the like. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Compounds that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The compounds described herein can be present in various forms including crystalline, powder and amorphous forms of those compounds, pharmaceutically acceptable salts, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

In some embodiments, the compounds described herein are present in a solvate form. In some embodiments, the compounds described herein are present in a hydrate form when the solvent component of the solvate is water.

4.1.5. Prodrugs

Aspects of this disclosure include prodrug derivatives of any of the ATX inhibitor compounds. In some embodiments, the compounds described herein are present in a prodrug form. Any convenient prodrug forms of the subject compounds can be prepared, for example, according to the strategies and methods described by Rautio et al. ("Prodrugs: design and clinical applications", Nature Reviews Drug Discovery 7, 255-270 (February 2008)).

It is understood that all variations of salts, solvates, hydrates, prodrugs and/or stereoisomers of the compounds described herein and shown in Table 1 are meant to be encompassed by the present disclosure.

In some embodiments, the compound is represented by the structure of one of the compounds in Table 1. The present disclosure is meant to encompass, a compound of Table 1, or a salt, a single stereoisomer, a mixture of stereoisomers and/or an isotopically labelled form thereof.

TABLE 1

| Compounds | |
|---|---|
| Cmpd | Structure |
| 1 |  |

TABLE 1-continued
Compounds
| Cmpd | Structure |
|---|---|
| 2 | 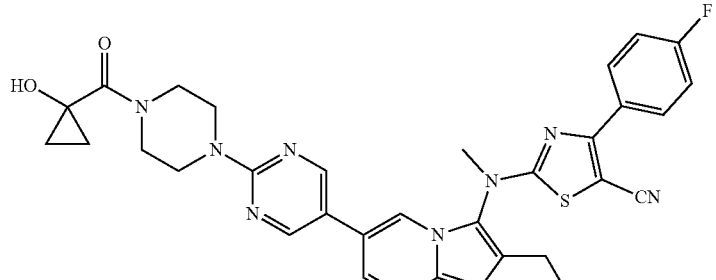 |
| 3 | 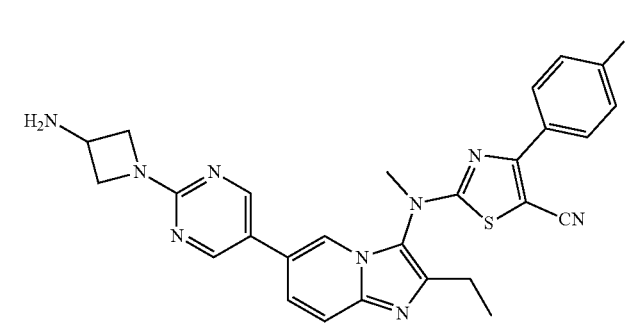 |
| 4 | 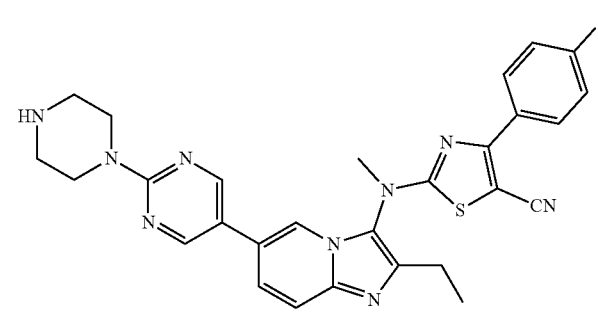 |
| 5 | 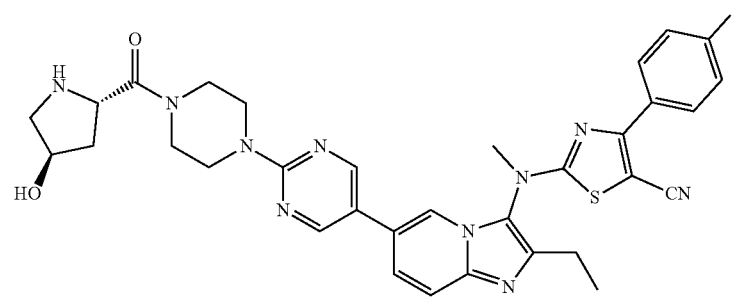 |
| 6 | 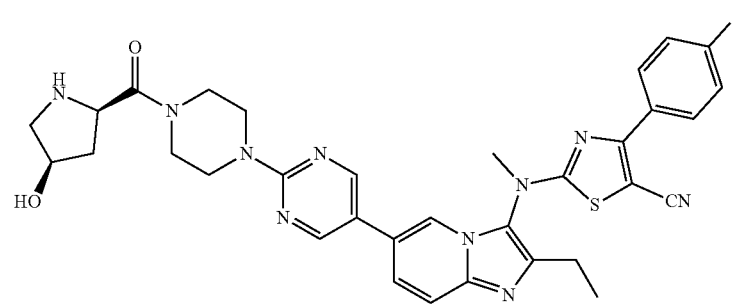 |

TABLE 1-continued

| Cmpd | Structure |
|---|---|
| 7 | 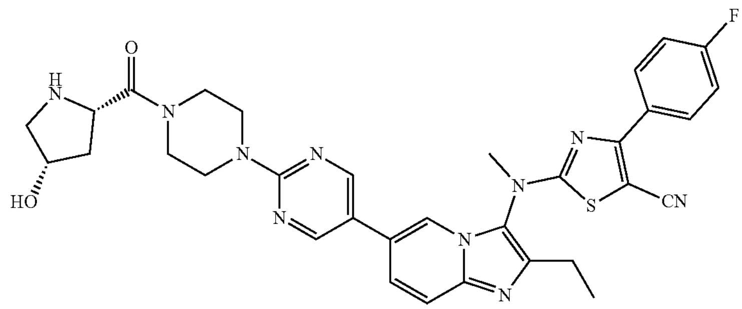 [SMILES: CCc1nc2ccc(-c3cnc(N4CCN(C(=O)[C@@H]5C[C@H](O)CN5)CC4)nc3)cn2c1N(C)c1nc(-c2ccc(F)cc2)c(C#N)s1] |
| 8 | 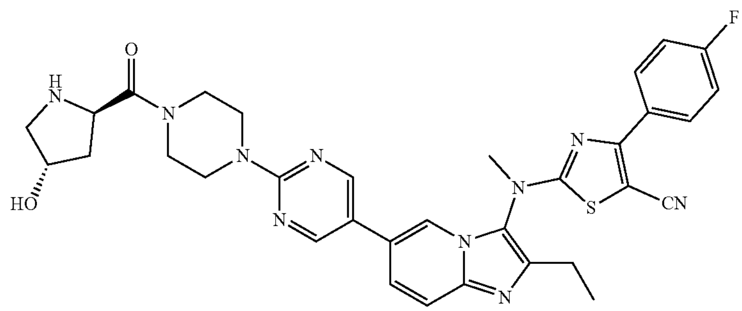 [SMILES: CCc1nc2ccc(-c3cnc(N4CCN(C(=O)[C@H]5C[C@H](O)CN5)CC4)nc3)cn2c1N(C)c1nc(-c2ccc(F)cc2)c(C#N)s1] |
| 9 | 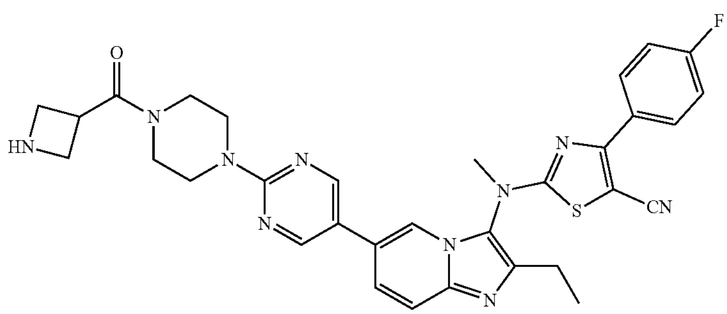 [SMILES: CCc1nc2ccc(-c3cnc(N4CCN(C(=O)C5CNC5)CC4)nc3)cn2c1N(C)c1nc(-c2ccc(F)cc2)c(C#N)s1] |
| 10 | 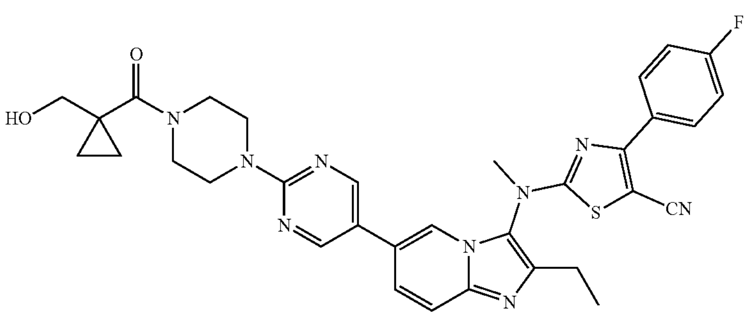 |
| 11 | 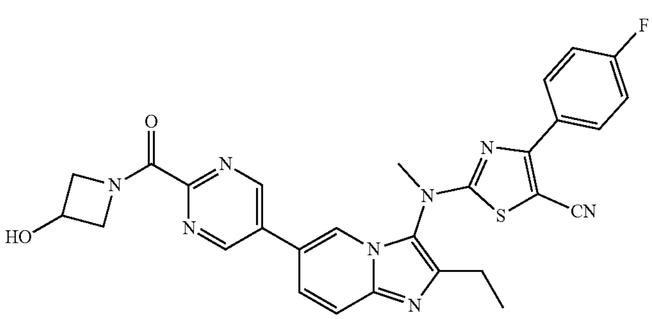 [SMILES: CCc1nc2ccc(-c3cnc(C(=O)N4CC(O)C4)nc3)cn2c1N(C)c1nc(-c2ccc(F)cc2)c(C#N)s1] |

TABLE 1-continued
Compounds
| Cmpd | Structure |
|---|---|
| 12 | 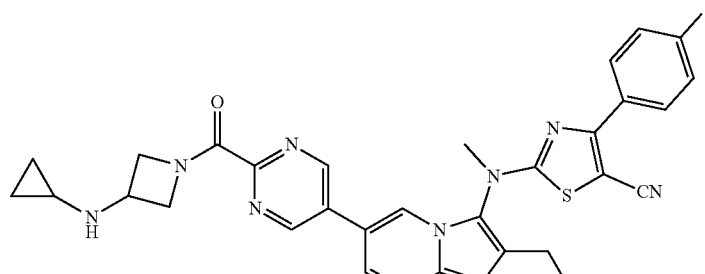 |
| 13 | 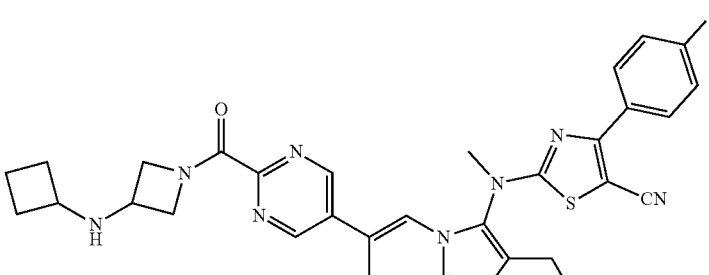 |
| 14 | 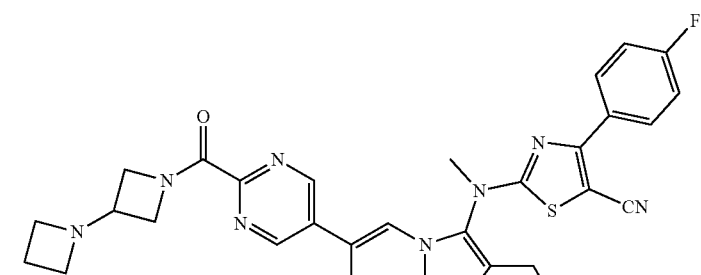 |
| 15 | 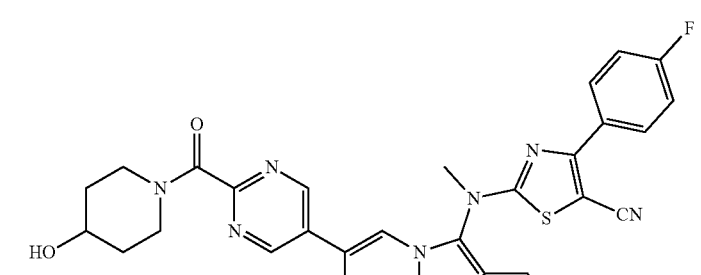 |
| 16 | 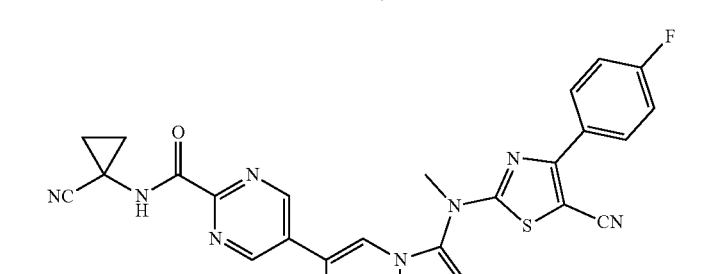 |

TABLE 1-continued
Compounds
| Cmpd | Structure |
|---|---|
| 17 | 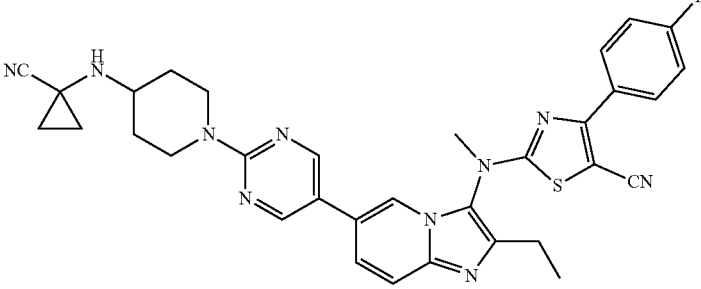 |
| 18 | 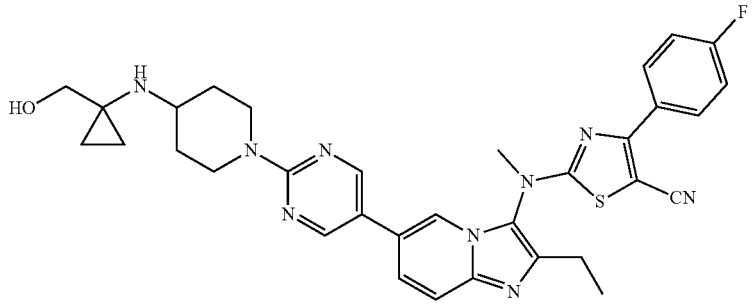 |
| 19 | 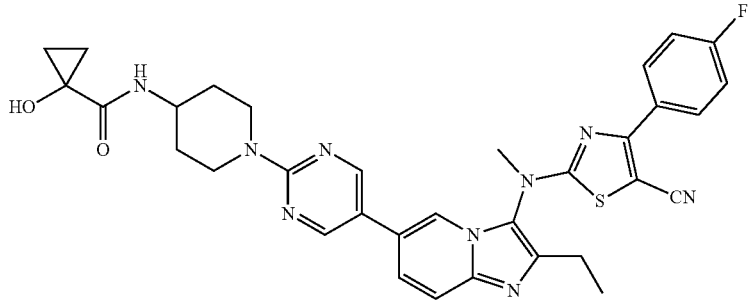 [SMILES: CCc1nc2ccc(-c3cnc(N4CCC(NC(=O)C5(C#N)CC5)CC4)nc3)cn2c1N(C)c1nc(-c2ccc(F)cc2)c(C#N)s1] |
| 20 | 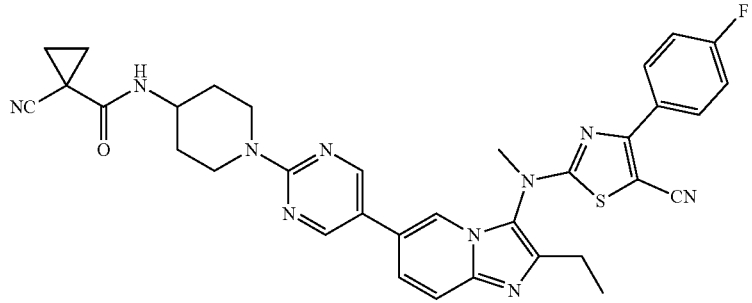 |
| 21 | 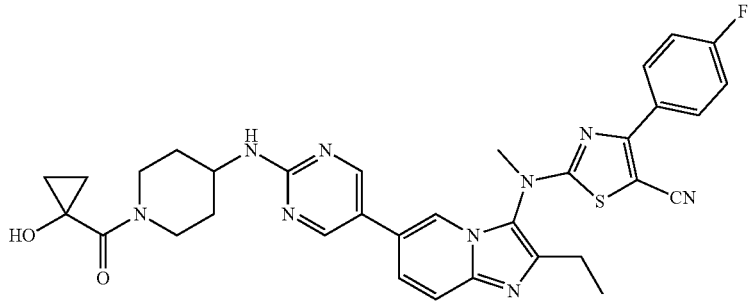 [SMILES: CCc1nc2ccc(-c3cnc(NC4CCN(C(=O)C5(O)CC5)CC4)nc3)cn2c1N(C)c1nc(-c2ccc(F)cc2)c(C#N)s1] |

TABLE 1-continued

Compounds

| Cmpd | Structure |
|---|---|
| 22 | (chemical structure) |
| 23 | (chemical structure) |
| 24 | (chemical structure) |
| 25 | (chemical structure) |
| 26 | (chemical structure) |

TABLE 1-continued

| Cmpd | Structure |
|---|---|
| 27 | 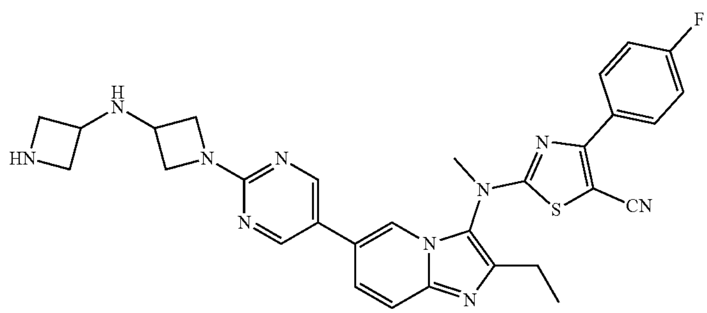 [SMILES: CCc1nc2ccc(-c3cnc(N4CC(NC5CNC5)C4)nc3)cn2c1N(C)c1nc(-c2ccc(F)cc2)c(C#N)s1] |
| 28 | 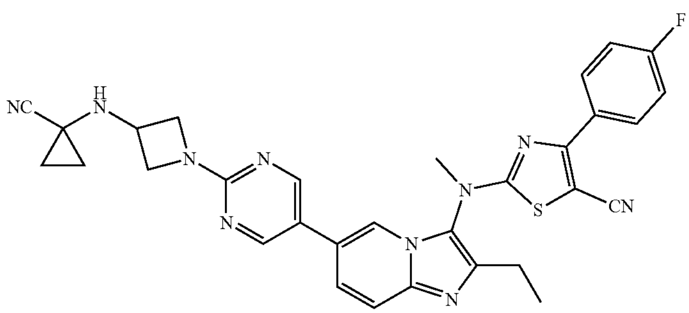 [SMILES: CCc1nc2ccc(-c3cnc(N4CC(NC5(C#N)CC5)C4)nc3)cn2c1N(C)c1nc(-c2ccc(F)cc2)c(C#N)s1] |
| 29 | 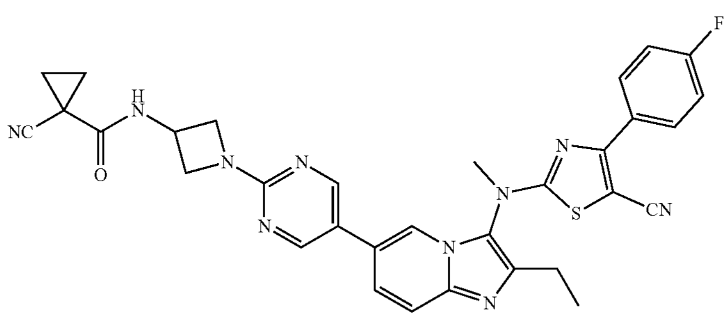 [SMILES: CCc1nc2ccc(-c3cnc(N4CC(NC(=O)C5(C#N)CC5)C4)nc3)cn2c1N(C)c1nc(-c2ccc(F)cc2)c(C#N)s1] |
| 30 | 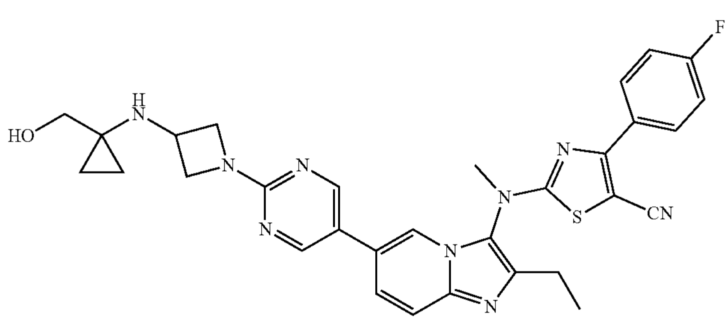 [SMILES: CCc1nc2ccc(-c3cnc(N4CC(NC5(CO)CC5)C4)nc3)cn2c1N(C)c1nc(-c2ccc(F)cc2)c(C#N)s1] |

TABLE 1-continued

Compounds

| Cmpd | Structure |
|---|---|
| 31 | 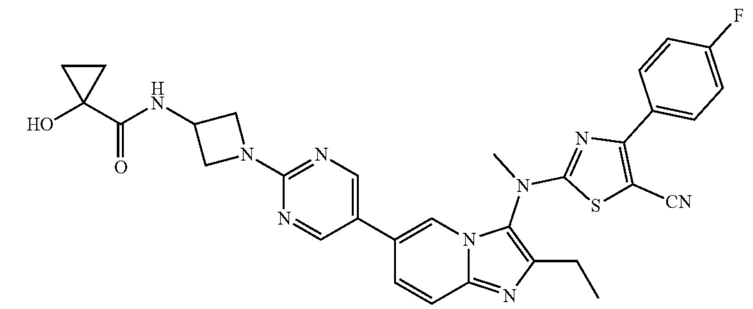 |
| 32 | 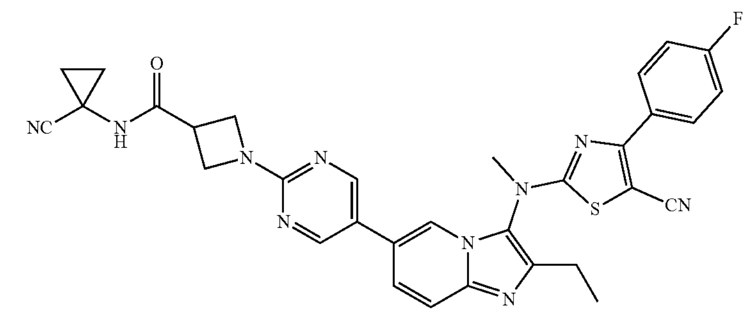 [SMILES: CCc1nc2ccc(-c3cnc(N4CC(C(=O)NC5(C#N)CC5)C4)nc3)cn2c1N(C)c1nc(-c2ccc(F)cc2)c(C#N)s1] |
| 33 | 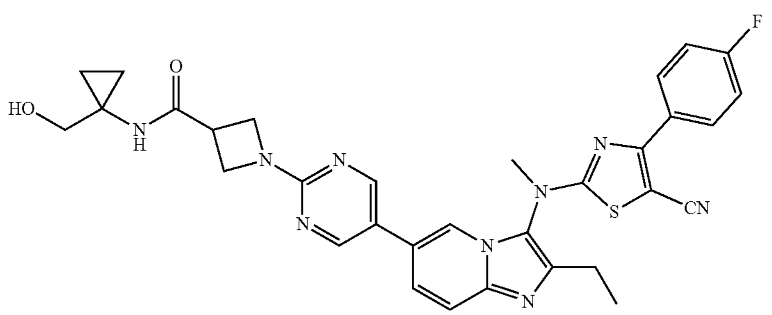 |
| 34 | 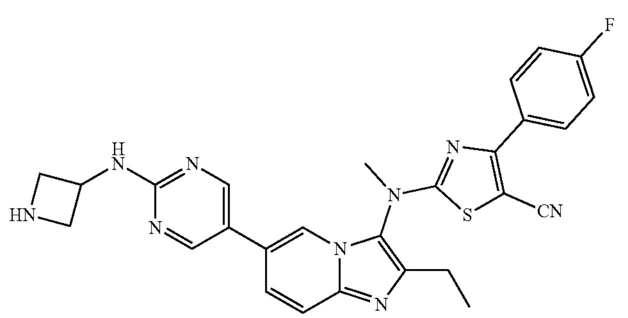 [SMILES: CCc1nc2ccc(-c3cnc(NC4CNC4)nc3)cn2c1N(C)c1nc(-c2ccc(F)cc2)c(C#N)s1] |
| 35 | 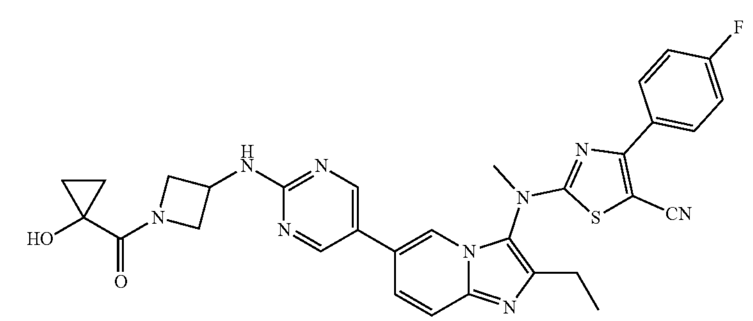 [SMILES: CCc1nc2ccc(-c3cnc(NC4CN(C(=O)C5(O)CC5)C4)nc3)cn2c1N(C)c1nc(-c2ccc(F)cc2)c(C#N)s1] |

TABLE 1-continued

Compounds

| Cmpd | Structure |
|---|---|
| 36 | 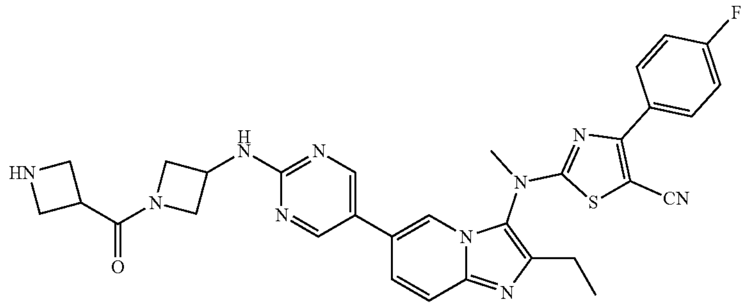 [SMILES: CCc1nc2ccc(-c3cnc(NC4CN(C(=O)C5CNC5)C4)nc3)cn2c1N(C)c1nc(-c2ccc(F)cc2)c(C#N)s1] |
| 37 | 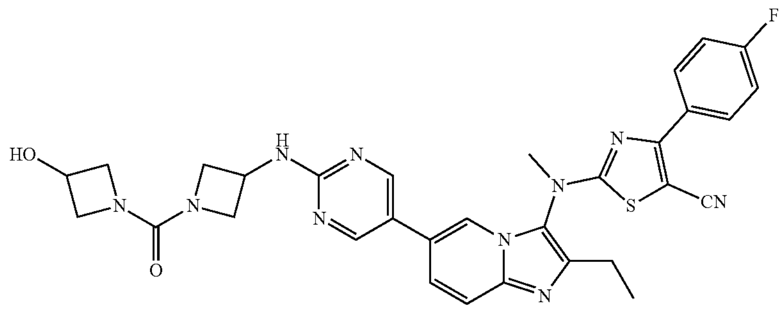 [SMILES: CCc1nc2ccc(-c3cnc(NC4CN(C(=O)N5CC(O)C5)C4)nc3)cn2c1N(C)c1nc(-c2ccc(F)cc2)c(C#N)s1] |
| 38 | 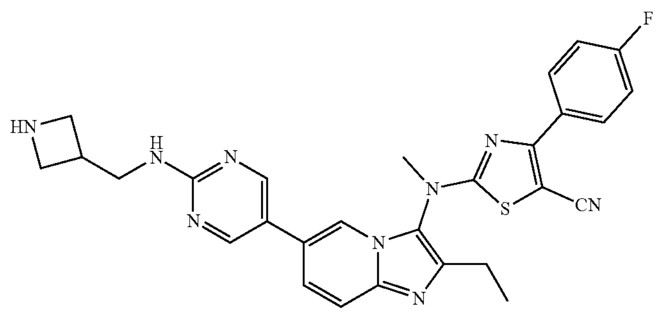 [SMILES: CCc1nc2ccc(-c3cnc(NCC4CNC4)nc3)cn2c1N(C)c1nc(-c2ccc(F)cc2)c(C#N)s1] |
| 39 | 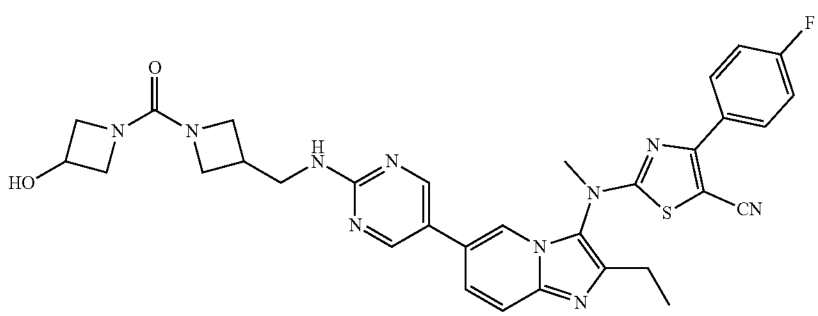 [SMILES: CCc1nc2ccc(-c3cnc(NCC4CN(C(=O)N5CC(O)C5)C4)nc3)cn2c1N(C)c1nc(-c2ccc(F)cc2)c(C#N)s1] |
| 40 | 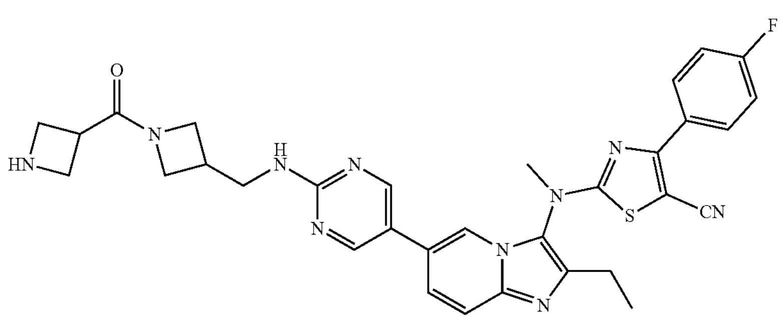 [SMILES: CCc1nc2ccc(-c3cnc(NCC4CN(C(=O)C5CNC5)C4)nc3)cn2c1N(C)c1nc(-c2ccc(F)cc2)c(C#N)s1] |

TABLE 1-continued

Compounds

| Cmpd | Structure |
|---|---|
| 41 | 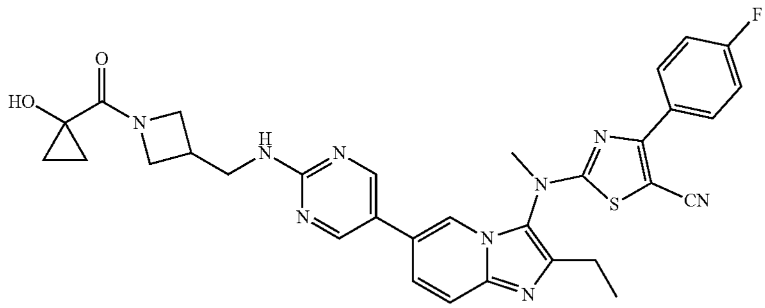 [SMILES: CCc1nc2ccc(-c3cnc(NCC4CN(C(=O)C5(O)CC5)C4)nc3)cn2c1N(C)c1nc(-c2ccc(F)cc2)c(C#N)s1] |
| 42 | 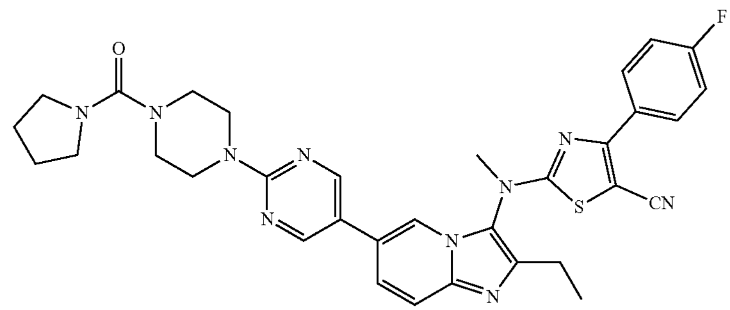 [SMILES: CCc1nc2ccc(-c3cnc(N4CCN(C(=O)N5CCCC5)CC4)nc3)cn2c1N(C)c1nc(-c2ccc(F)cc2)c(C#N)s1] |
| 43 | 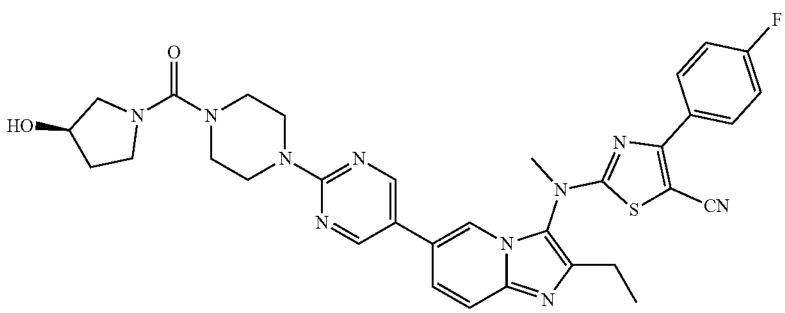 [SMILES: CCc1nc2ccc(-c3cnc(N4CCN(C(=O)N5CC[C@@H](O)C5)CC4)nc3)cn2c1N(C)c1nc(-c2ccc(F)cc2)c(C#N)s1] |
| 44 | 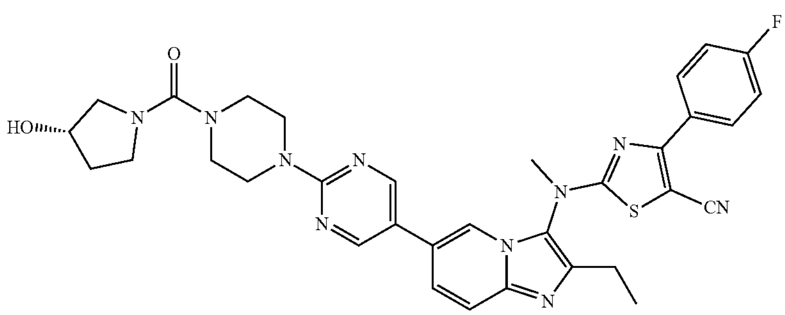 [SMILES: CCc1nc2ccc(-c3cnc(N4CCN(C(=O)N5CC[C@H](O)C5)CC4)nc3)cn2c1N(C)c1nc(-c2ccc(F)cc2)c(C#N)s1] |
| 45 | 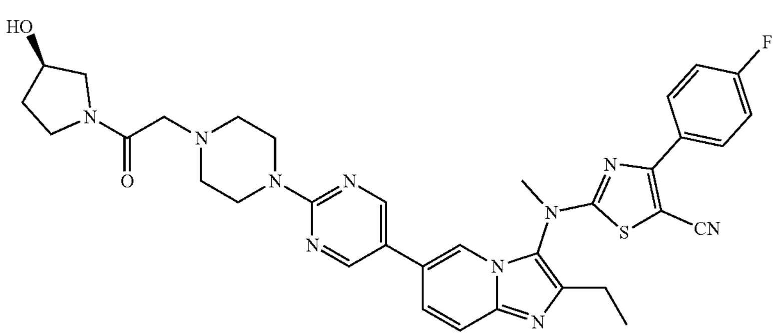 [SMILES: CCc1nc2ccc(-c3cnc(N4CCN(CC(=O)N5CC[C@@H](O)C5)CC4)nc3)cn2c1N(C)c1nc(-c2ccc(F)cc2)c(C#N)s1] |

TABLE 1-continued

| Cmpd | Structure |
|---|---|
| 46 | 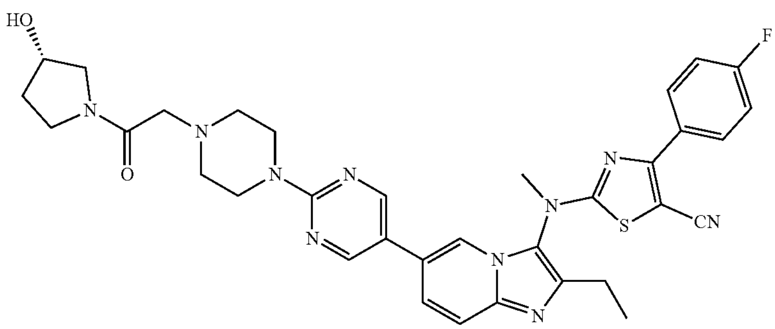 [SMILES: CCc1nc2ccc(-c3cnc(N4CCN(CC(=O)N5CC[C@H](O)C5)CC4)nc3)cn2c1N(C)c1nc(-c2ccc(F)cc2)c(C#N)s1] |
| 47 | 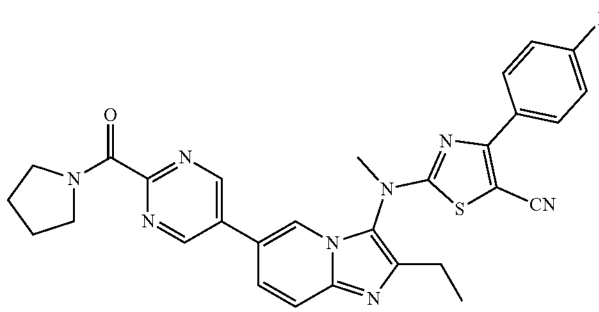 |
| 48 | 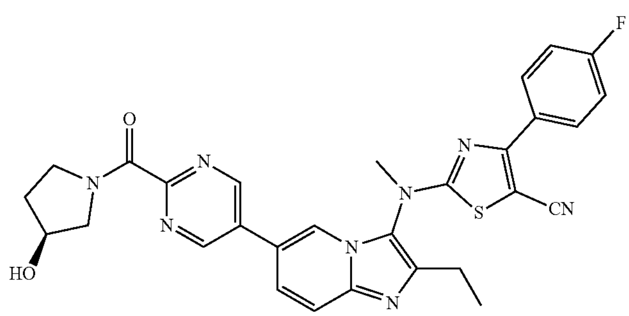 [SMILES: CCc1nc2ccc(-c3cnc(C(=O)N4CC[C@H](O)C4)nc3)cn2c1N(C)c1nc(-c2ccc(F)cc2)c(C#N)s1] |
| 49 | 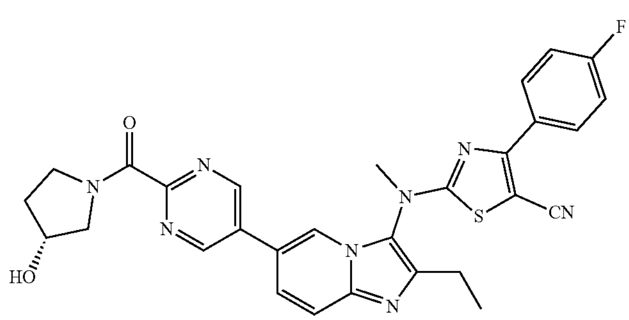 [SMILES: CCc1nc2ccc(-c3cnc(C(=O)N4CC[C@@H](O)C4)nc3)cn2c1N(C)c1nc(-c2ccc(F)cc2)c(C#N)s1] |

TABLE 1-continued
Compounds
| Cmpd | Structure |
|---|---|
| 50 | 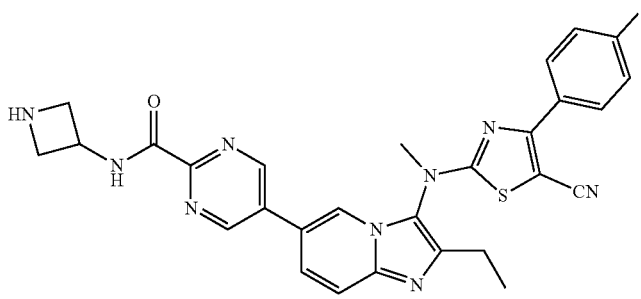 |
| 51 | 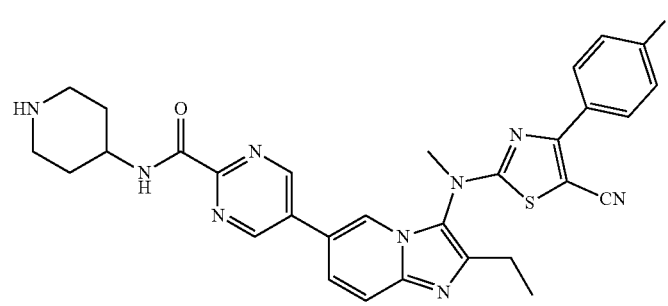 |
| 52 | 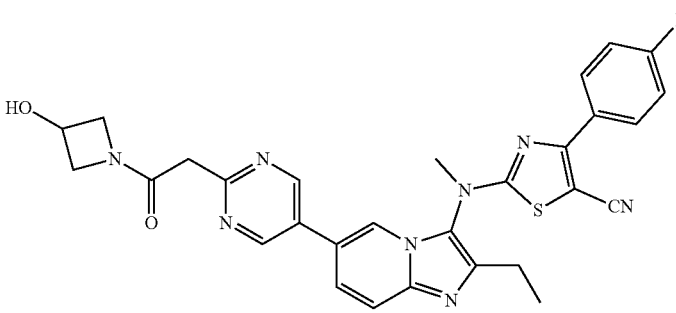 |
| 53 | 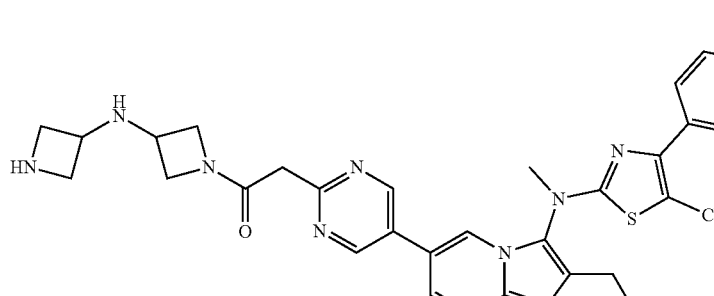 |
| 54 | 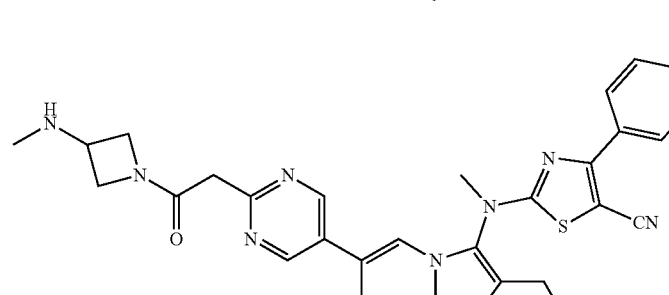 |

TABLE 1-continued

| Cmpd | Structure |
|---|---|
| 55 | 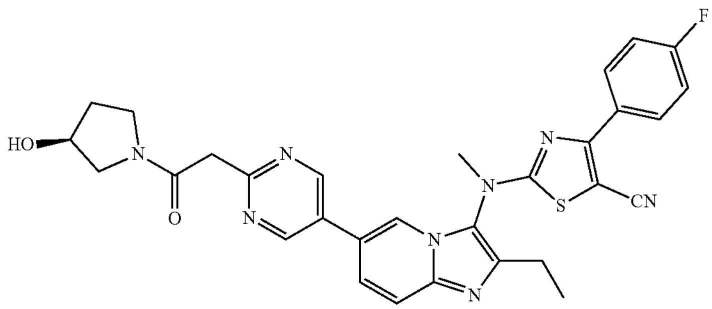 [SMILES: CCc1nc2ccc(-c3cnc(CC(=O)N4CC[C@H](O)C4)nc3)cn2c1N(C)c1nc(-c2ccc(F)cc2)c(C#N)s1] |
| 56 | 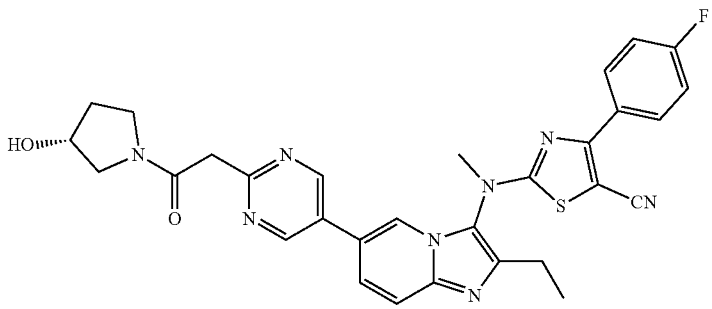 [SMILES: CCc1nc2ccc(-c3cnc(CC(=O)N4CC[C@@H](O)C4)nc3)cn2c1N(C)c1nc(-c2ccc(F)cc2)c(C#N)s1] |
| 57 | 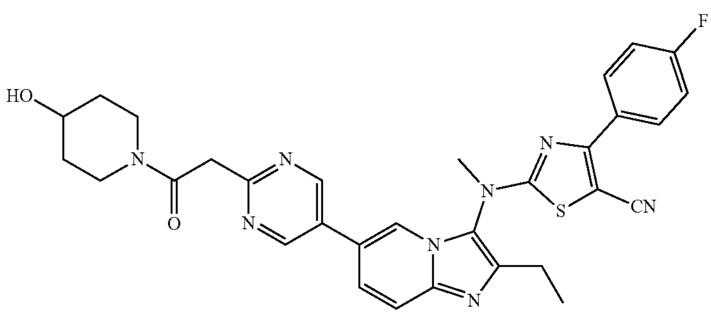 [SMILES: CCc1nc2ccc(-c3cnc(CC(=O)N4CCC(O)CC4)nc3)cn2c1N(C)c1nc(-c2ccc(F)cc2)c(C#N)s1] |
| 58 | 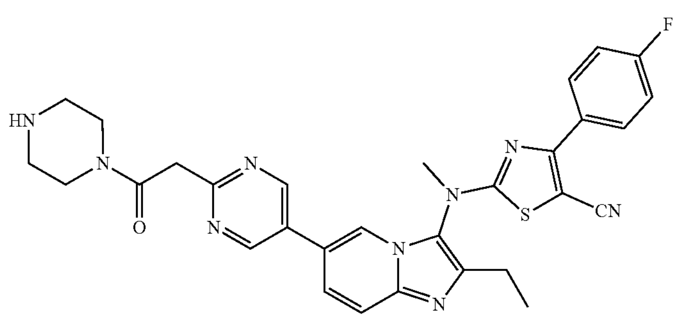 [SMILES: CCc1nc2ccc(-c3cnc(CC(=O)N4CCNCC4)nc3)cn2c1N(C)c1nc(-c2ccc(F)cc2)c(C#N)s1] |
| 59 | 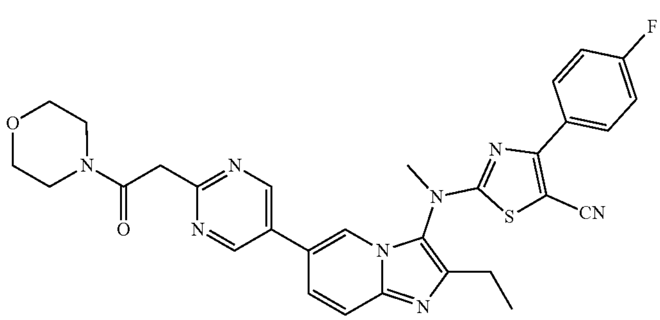 [SMILES: CCc1nc2ccc(-c3cnc(CC(=O)N4CCOCC4)nc3)cn2c1N(C)c1nc(-c2ccc(F)cc2)c(C#N)s1] |

TABLE 1-continued

Compounds

| Cmpd | Structure |
|---|---|
| 60 | 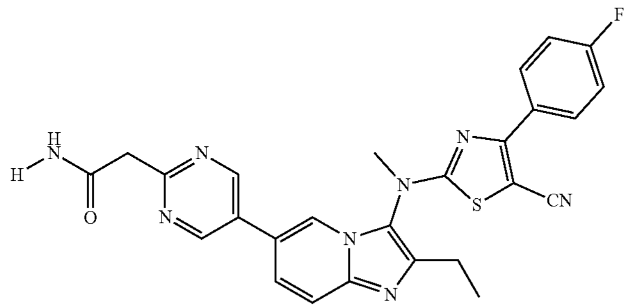 [SMILES: CCc1nc2ccc(-c3cnc(CC(N)=O)nc3)cn2c1N(C)c1nc(-c2ccc(F)cc2)c(C#N)s1] |
| 61 | 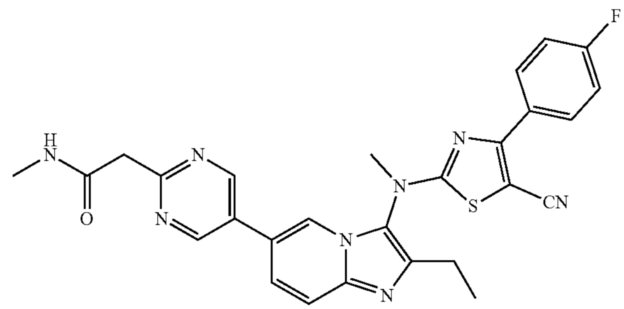 [SMILES: CCc1nc2ccc(-c3cnc(CC(=O)NC)nc3)cn2c1N(C)c1nc(-c2ccc(F)cc2)c(C#N)s1] |
| 62 | 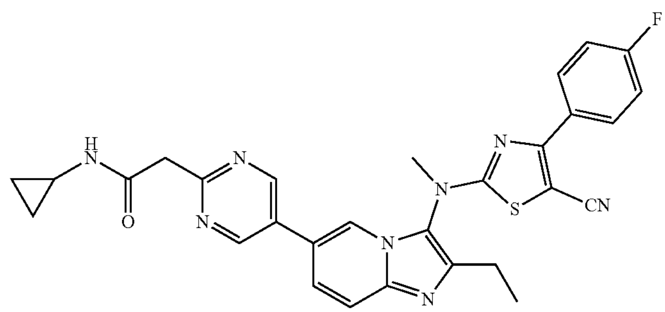 [SMILES: CCc1nc2ccc(-c3cnc(CC(=O)NC4CC4)nc3)cn2c1N(C)c1nc(-c2ccc(F)cc2)c(C#N)s1] |
| 63 | 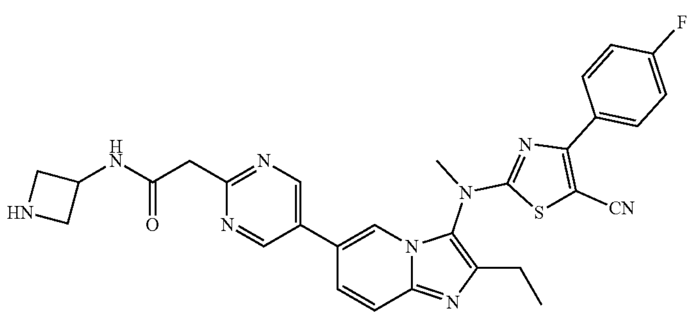 [SMILES: CCc1nc2ccc(-c3cnc(CC(=O)NC4CNC4)nc3)cn2c1N(C)c1nc(-c2ccc(F)cc2)c(C#N)s1] |
| 64 | 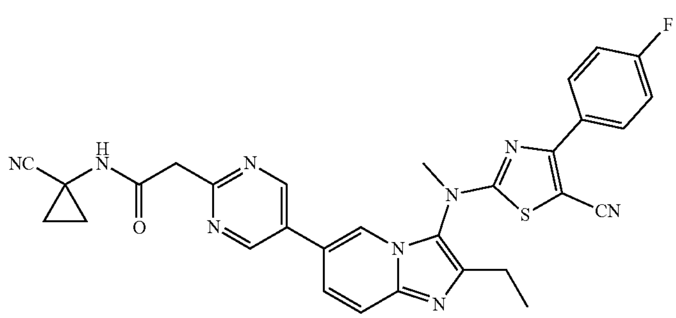 [SMILES: CCc1nc2ccc(-c3cnc(CC(=O)NC4(C#N)CC4)nc3)cn2c1N(C)c1nc(-c2ccc(F)cc2)c(C#N)s1] |

TABLE 1-continued
Compounds
| Cmpd | Structure |
|---|---|
| 65 | 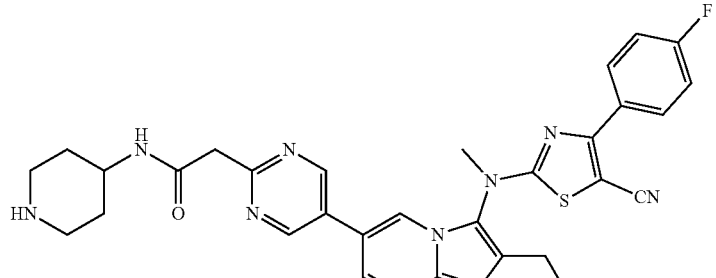 |
| 66 | 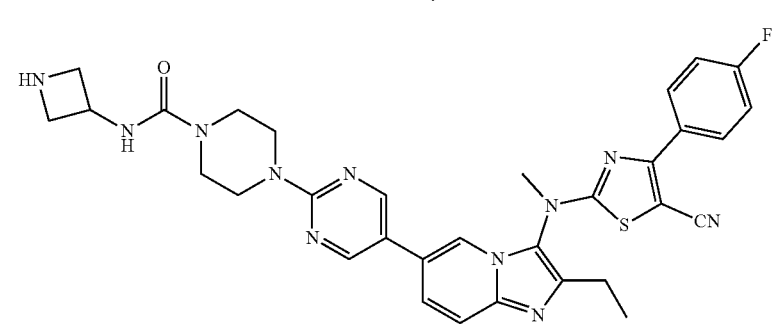 |
| 67 | 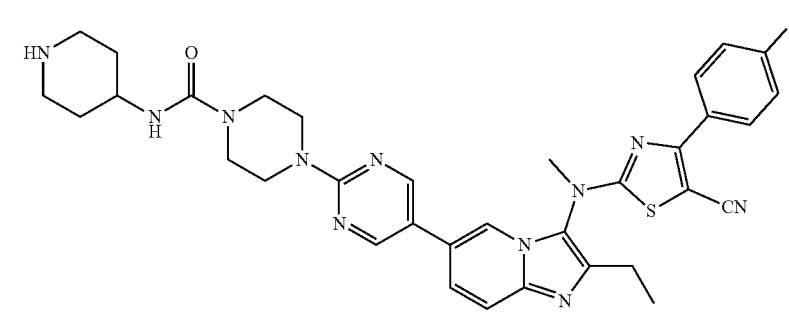 |
| 68 | 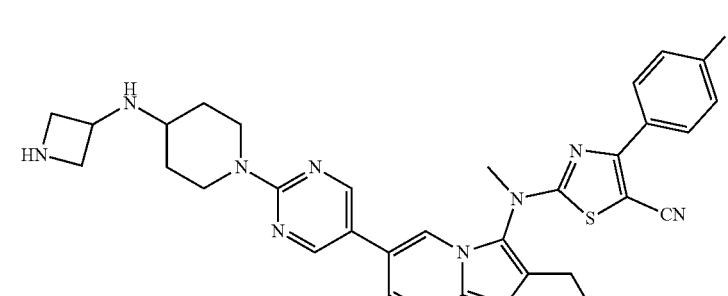 |
| 69 | 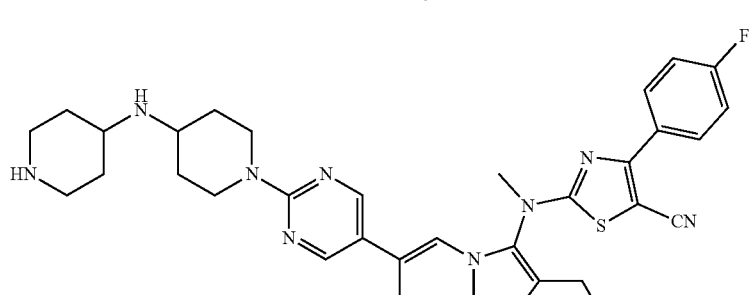 |

TABLE 1-continued
Compounds
| Cmpd | Structure |
|------|-----------|
| 70 | 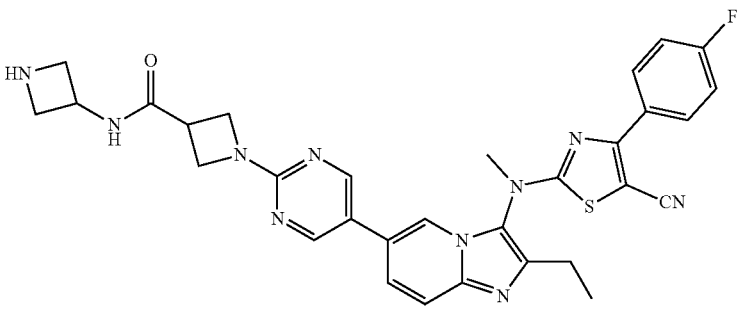 [SMILES: CCc1nc2ccc(-c3cnc(N4CC(C(=O)NC5CNC5)C4)nc3)cn2c1N(C)c1nc(-c2ccc(F)cc2)c(C#N)s1] |
| 71 | 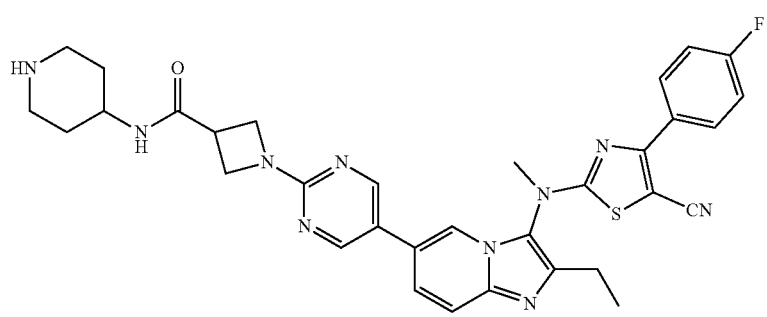 [SMILES: CCc1nc2ccc(-c3cnc(N4CC(C(=O)NC5CCNCC5)C4)nc3)cn2c1N(C)c1nc(-c2ccc(F)cc2)c(C#N)s1] |
| 72 | 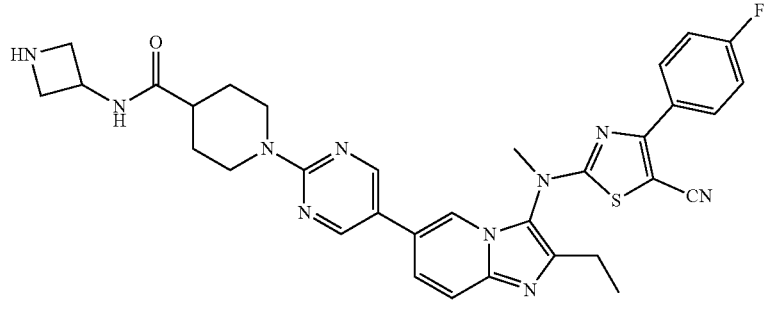 [SMILES: CCc1nc2ccc(-c3cnc(N4CCC(C(=O)NC5CNC5)CC4)nc3)cn2c1N(C)c1nc(-c2ccc(F)cc2)c(C#N)s1] |
| 73 | 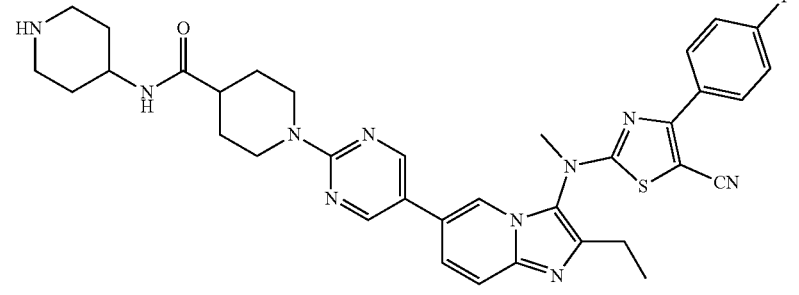 |
| 74 | 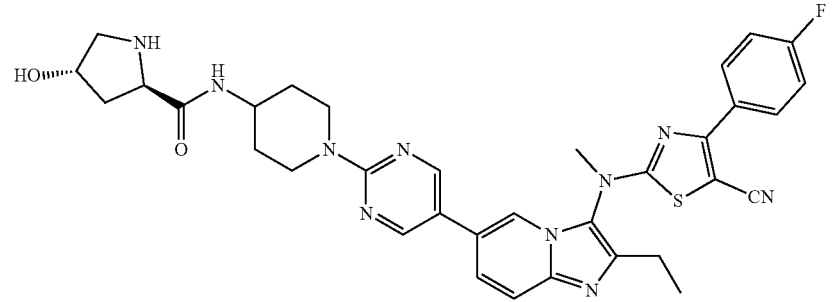 [SMILES: CCc1nc2ccc(-c3cnc(N4CCC(NC(=O)[C@H]5C[C@H](O)CN5)CC4)nc3)cn2c1N(C)c1nc(-c2ccc(F)cc2)c(C#N)s1] |

TABLE 1-continued

| Cmpd | Structure |
|---|---|
| 75 | 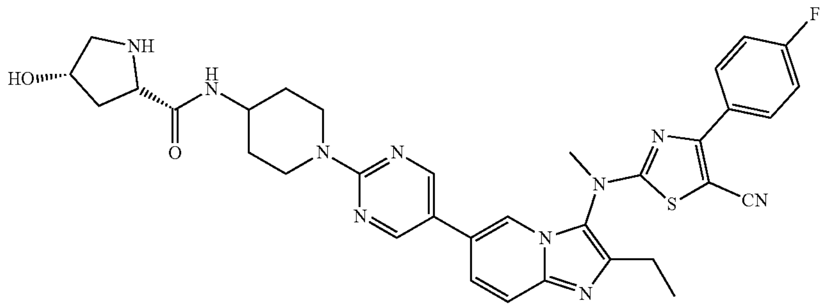 |
| 76 | 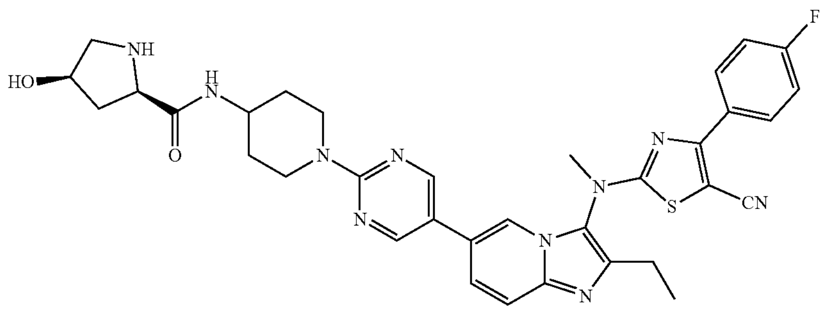 [SMILES: CCc1nc2ccc(-c3cnc(N4CCC(NC(=O)[C@H]5C[C@@H](O)CN5)CC4)nc3)cn2c1N(C)c1nc(-c2ccc(F)cc2)c(C#N)s1] |
| 77 | 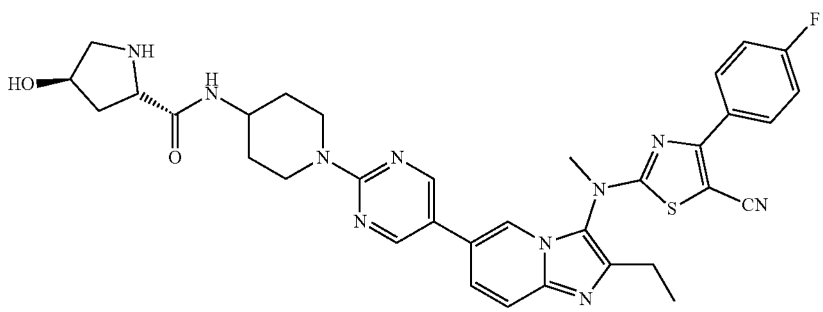 |
| 78 | 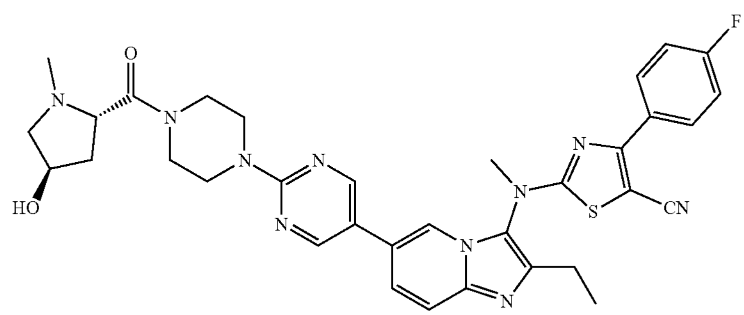 [SMILES: CCc1nc2ccc(-c3cnc(N4CCN(C(=O)[C@@H]5C[C@@H](O)CN5C)CC4)nc3)cn2c1N(C)c1nc(-c2ccc(F)cc2)c(C#N)s1] |
| 79 | 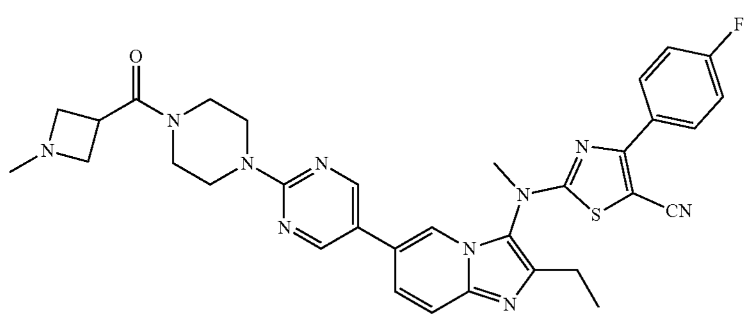 [SMILES: CCc1nc2ccc(-c3cnc(N4CCN(C(=O)C5CN(C)C5)CC4)nc3)cn2c1N(C)c1nc(-c2ccc(F)cc2)c(C#N)s1] |

TABLE 1-continued
Compounds
| Cmpd | Structure |
|---|---|
| 80 | 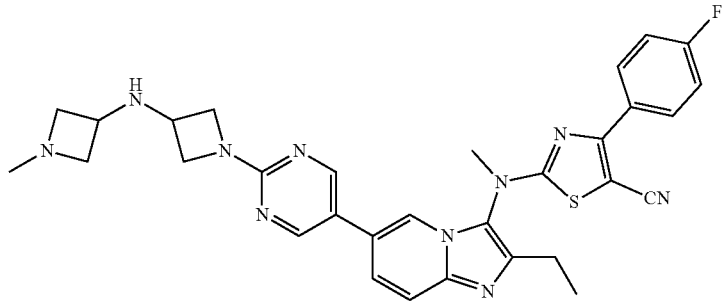 [SMILES: CCc1nc2ccc(-c3cnc(N4CC(NC5CN(C)C5)C4)nc3)cn2c1N(C)c1nc(-c2ccc(F)cc2)c(C#N)s1] |
| 81 | 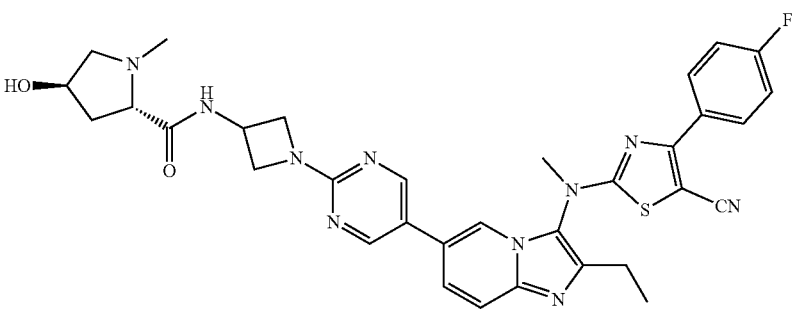 [SMILES: CCc1nc2ccc(-c3cnc(N4CC(NC(=O)[C@@H]5C[C@@H](O)CN5C)C4)nc3)cn2c1N(C)c1nc(-c2ccc(F)cc2)c(C#N)s1] |
| 82 | 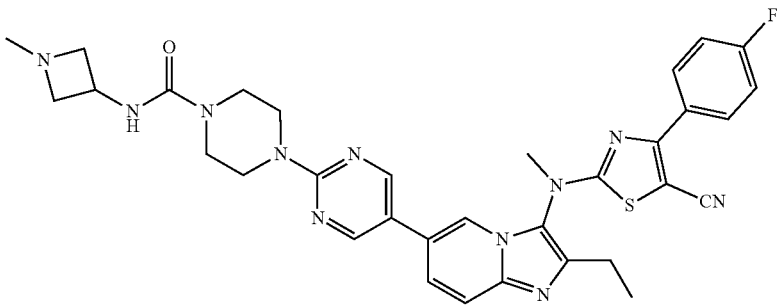 [SMILES: CCc1nc2ccc(-c3cnc(N4CCN(C(=O)NC5CN(C)C5)CC4)nc3)cn2c1N(C)c1nc(-c2ccc(F)cc2)c(C#N)s1] |
| 83 | 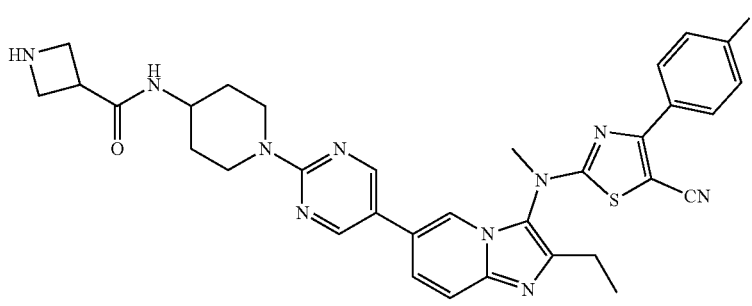 |
| 84 | 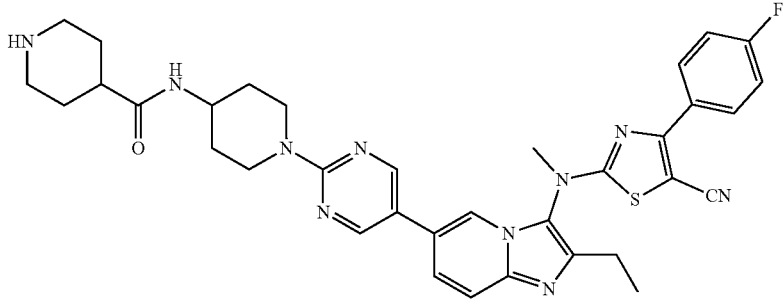 [SMILES: CCc1nc2ccc(-c3cnc(N4CCC(NC(=O)C5CCNCC5)CC4)nc3)cn2c1N(C)c1nc(-c2ccc(F)cc2)c(C#N)s1] |

TABLE 1-continued
| Cmpd | Structure |
|---|---|
| 85 | 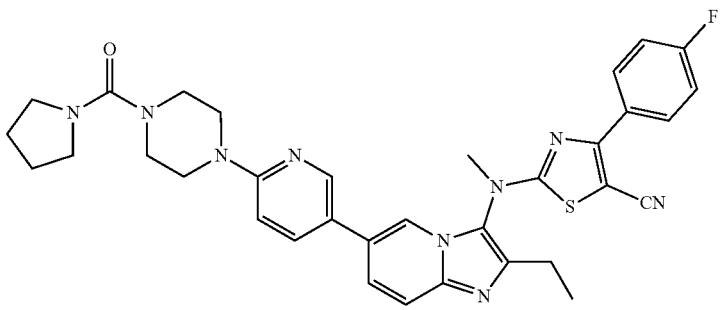 |
| 86 | 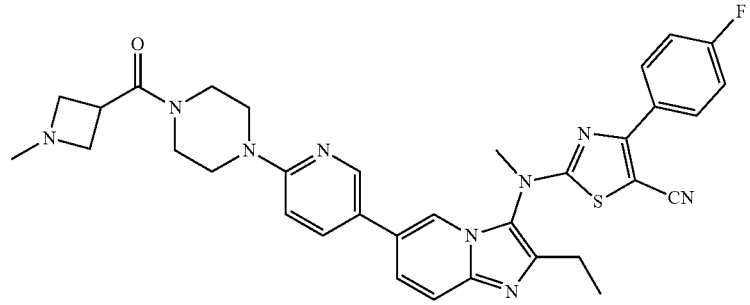 |
| 87 | 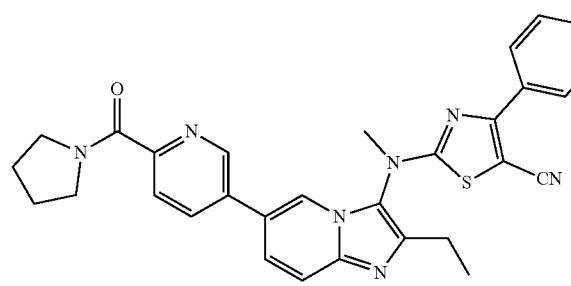 |
| 88 | 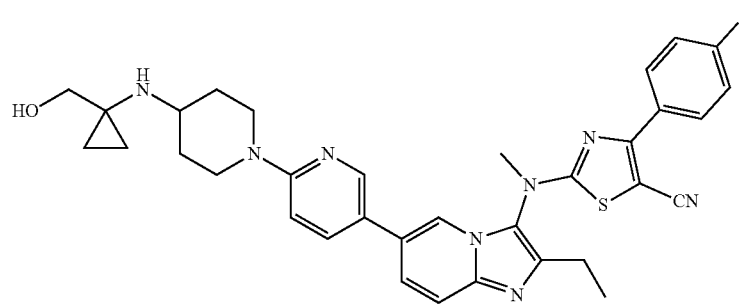 |
| 89 | 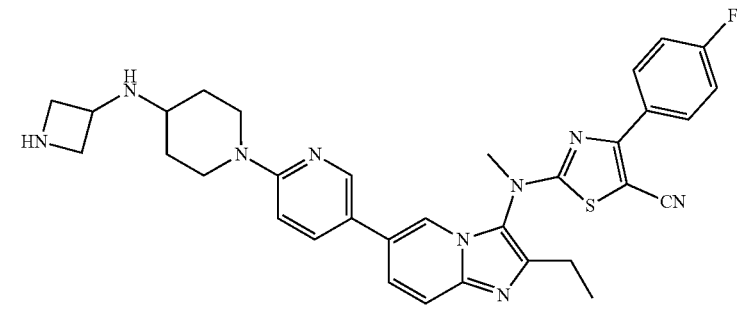 [SMILES: CCc1nc2ccc(-c3ccc(N4CCC(NC5CNC5)CC4)nc3)cn2c1N(C)c1nc(-c2ccc(F)cc2)c(C#N)s1] |

TABLE 1-continued

| Cmpd | Structure |
|------|-----------|
| 90 | 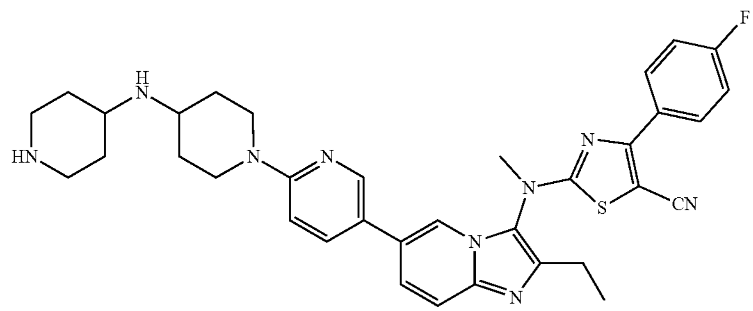 [SMILES: CCc1nc2ccc(-c3ccc(N4CCC(NC5CCNCC5)CC4)nc3)cn2c1N(C)c1nc(-c2ccc(F)cc2)c(C#N)s1] |
| 91 | 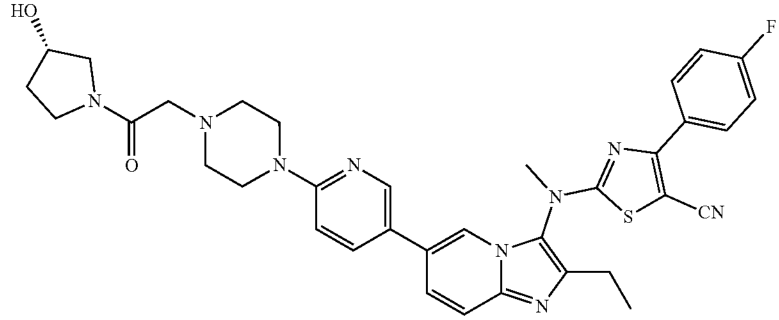 |
| 92 | 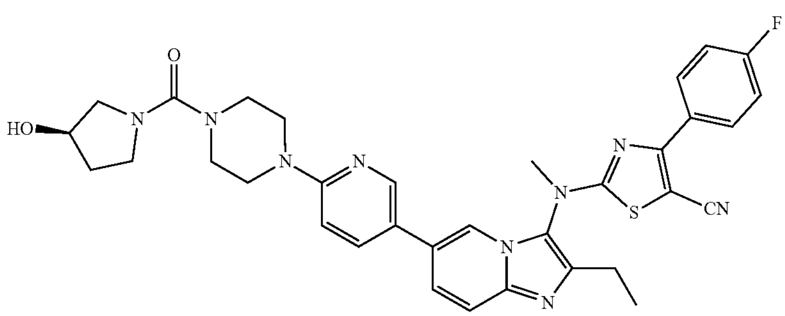 [SMILES: CCc1nc2ccc(-c3ccc(N4CCN(C(=O)N5CC[C@@H](O)C5)CC4)nc3)cn2c1N(C)c1nc(-c2ccc(F)cc2)c(C#N)s1] |
| 93 | 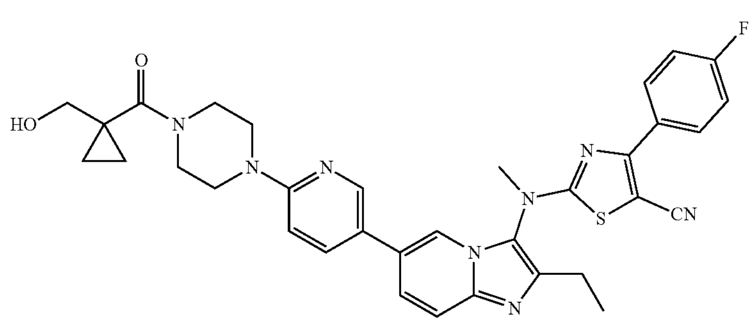 [SMILES: CCc1nc2ccc(-c3ccc(N4CCN(C(=O)C5(CO)CC5)CC4)nc3)cn2c1N(C)c1nc(-c2ccc(F)cc2)c(C#N)s1] |

TABLE 1-continued
Compounds
| Cmpd | Structure |
|---|---|
| 94 | 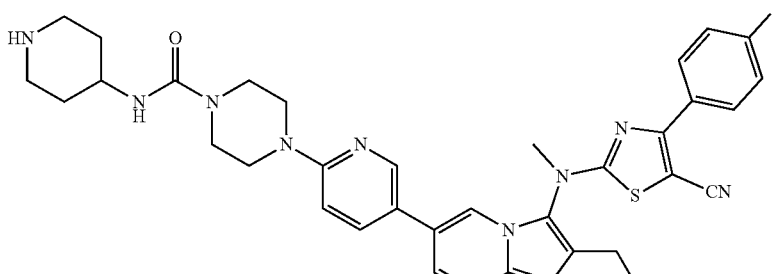 |
| 95 | 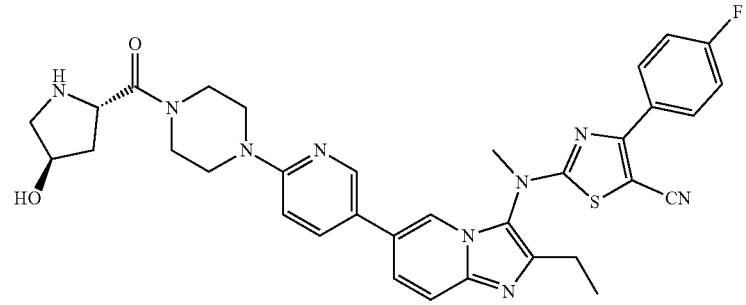 |
| 96 | 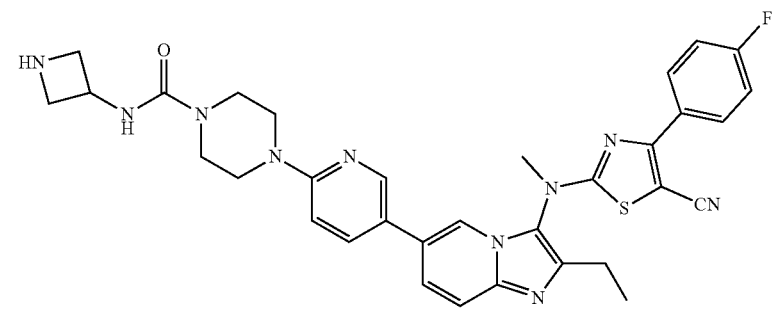 [SMILES: CCc1nc2ccc(-c3ccc(N4CCN(C(=O)NC5CNC5)CC4)nc3)cn2c1N(C)c1nc(-c2ccc(F)cc2)c(C#N)s1] |
| 97 | 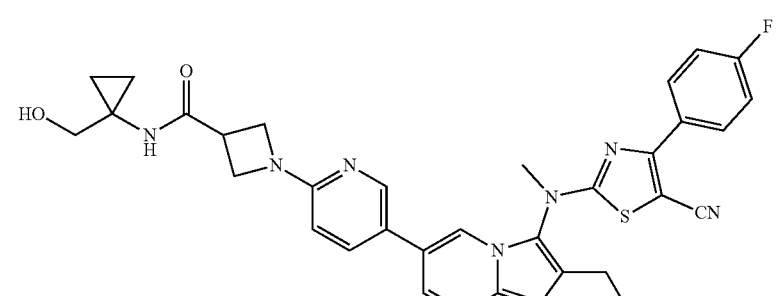 |
| 98 | 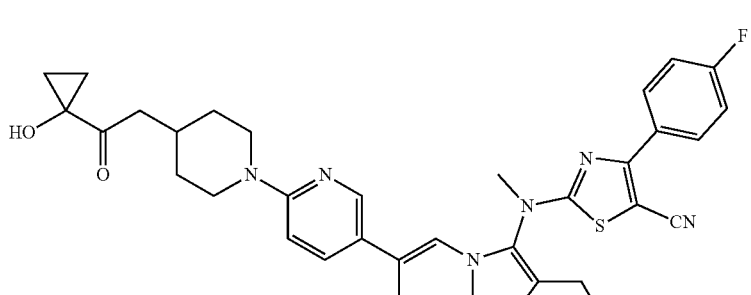 |

TABLE 1-continued
Compounds
| Cmpd | Structure |
|---|---|
| 99 | 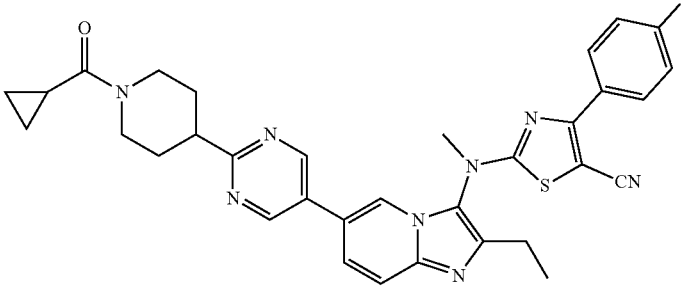 |
| 100 | 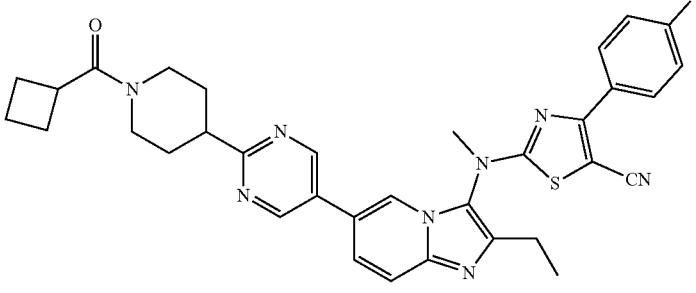 |
| 101 | 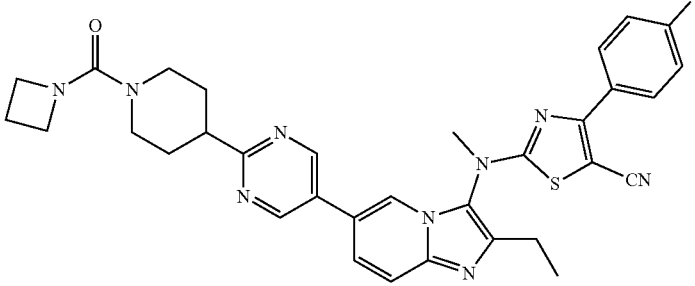 |
| 102 | 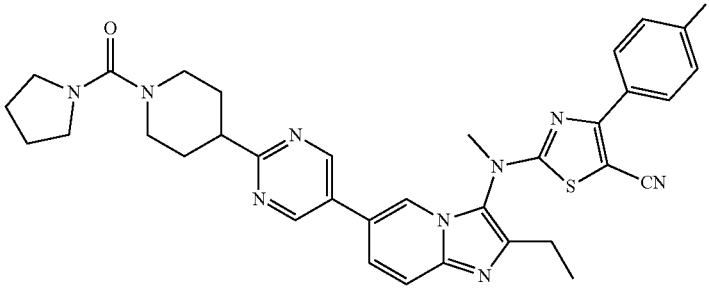 |
| 103 | 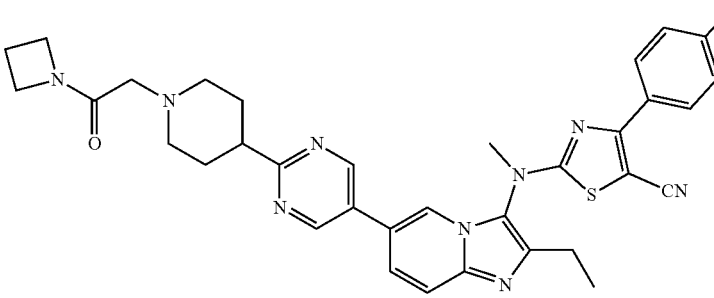 |

TABLE 1-continued
Compounds
| Cmpd | Structure |
|---|---|
| 104 | 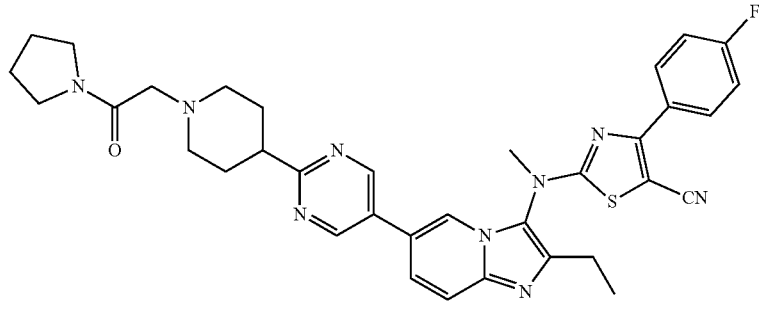 [SMILES: CCc1nc2ccc(-c3cnc(C4CCN(CC(=O)N5CCCC5)CC4)nc3)cn2c1N(C)c1nc(-c2ccc(F)cc2)c(C#N)s1] |
| 105 | 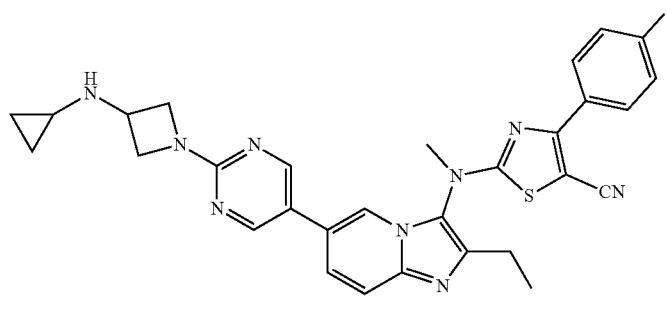 |
| 106 | 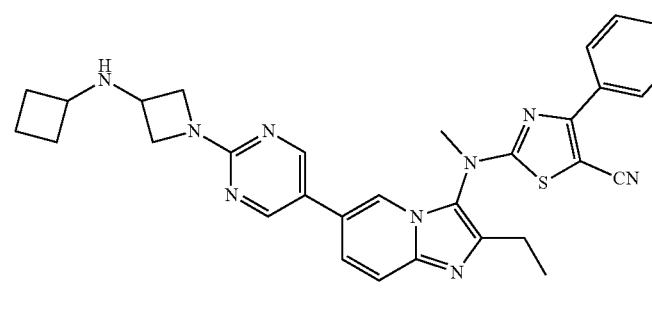 |
| 107 | 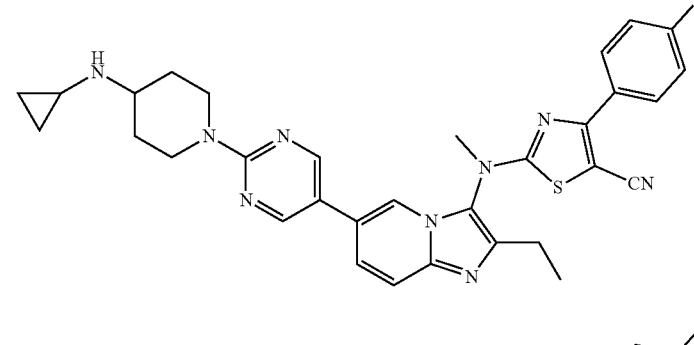 |
| 108 | 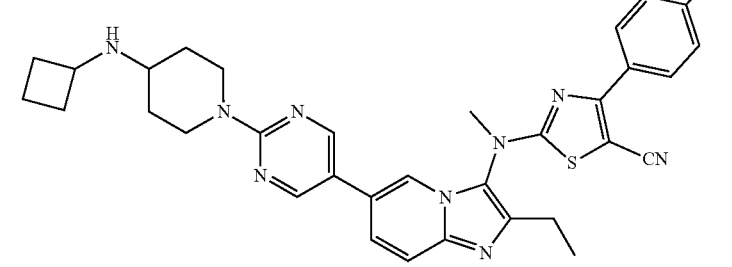 |

TABLE 1-continued

| Cmpd | Structure |
|---|---|
| 109 | 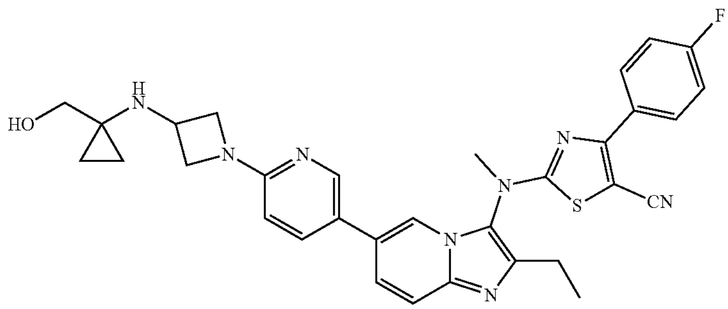 |
| 110 | 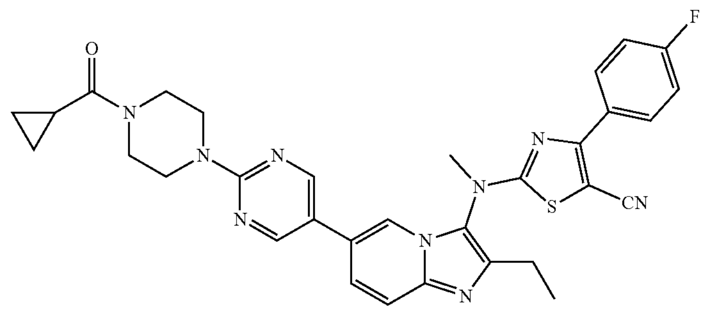 [SMILES: CCc1nc2ccc(-c3cnc(N4CCN(C(=O)C5CC5)CC4)nc3)cn2c1N(C)c1nc(-c2ccc(F)cc2)c(C#N)s1] |
| 111 | 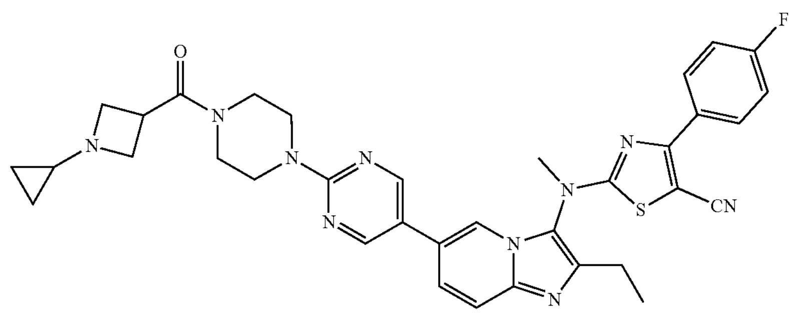 [SMILES: CCc1nc2ccc(-c3cnc(N4CCN(C(=O)C5CN(C6CC6)C5)CC4)nc3)cn2c1N(C)c1nc(-c2ccc(F)cc2)c(C#N)s1] |
| 112 | 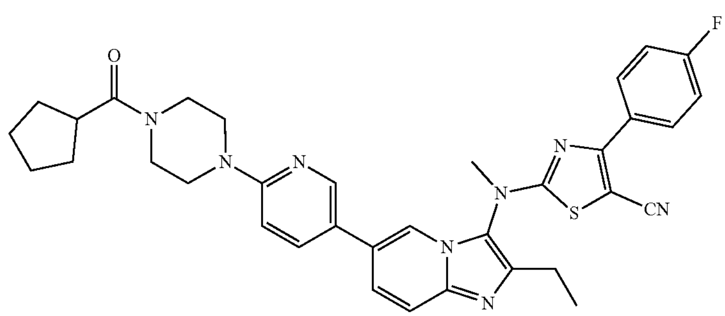 [SMILES: CCc1nc2ccc(-c3ccc(N4CCN(C(=O)C5CCCC5)CC4)nc3)cn2c1N(C)c1nc(-c2ccc(F)cc2)c(C#N)s1] |
| 113 | 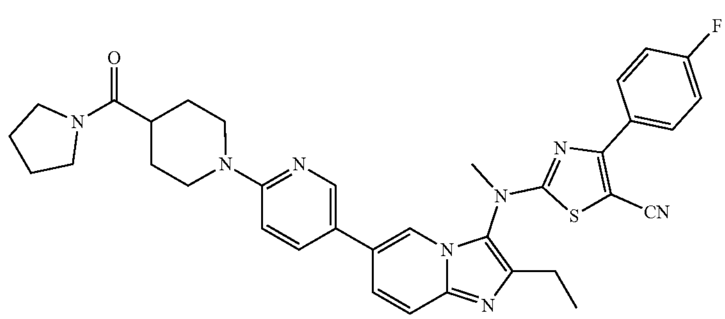 [SMILES: CCc1nc2ccc(-c3ccc(N4CCC(C(=O)N5CCCC5)CC4)nc3)cn2c1N(C)c1nc(-c2ccc(F)cc2)c(C#N)s1] |

TABLE 1-continued

| Cmpd | Structure |
|---|---|
| 114 | 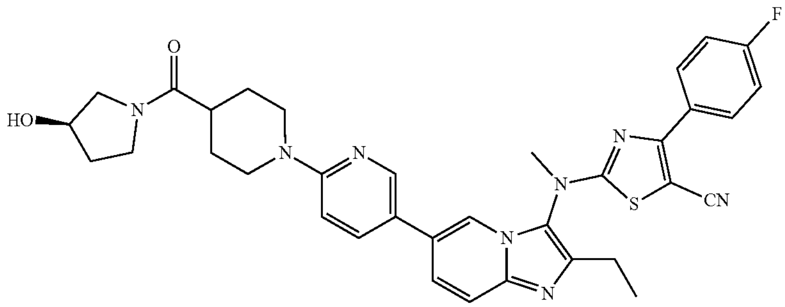 [SMILES: CCc1nc2ccc(-c3ccc(N4CCC(C(=O)N5CC[C@@H](O)C5)CC4)nc3)cn2c1N(C)c1nc(-c2ccc(F)cc2)c(C#N)s1] |
| 115 | 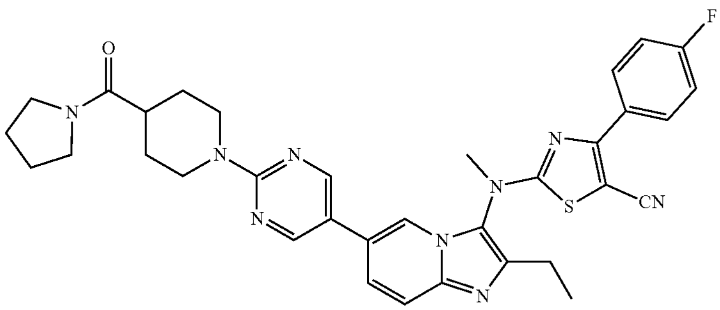 [SMILES: CCc1nc2ccc(-c3cnc(N4CCC(C(=O)N5CCCC5)CC4)nc3)cn2c1N(C)c1nc(-c2ccc(F)cc2)c(C#N)s1] |
| 118 | 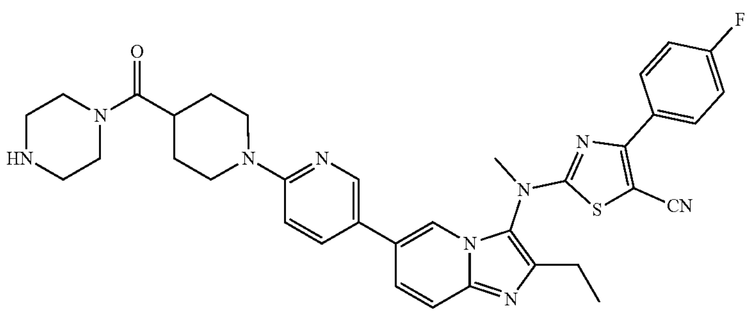 [SMILES: CCc1nc2ccc(-c3ccc(N4CCC(C(=O)N5CCNCC5)CC4)nc3)cn2c1N(C)c1nc(-c2ccc(F)cc2)c(C#N)s1] |
| 119 | 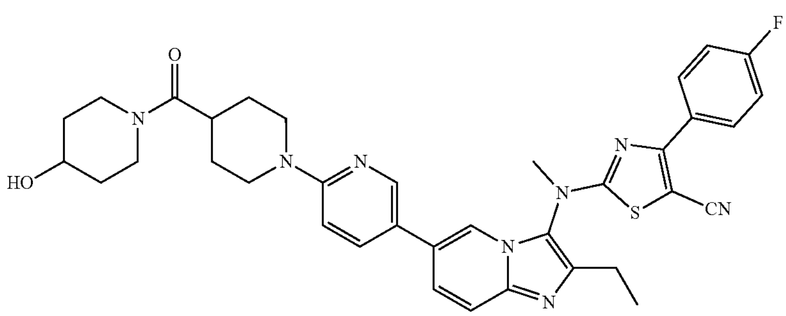 [SMILES: CCc1nc2ccc(-c3ccc(N4CCC(C(=O)N5CCC(O)CC5)CC4)nc3)cn2c1N(C)c1nc(-c2ccc(F)cc2)c(C#N)s1] |
| 120 | 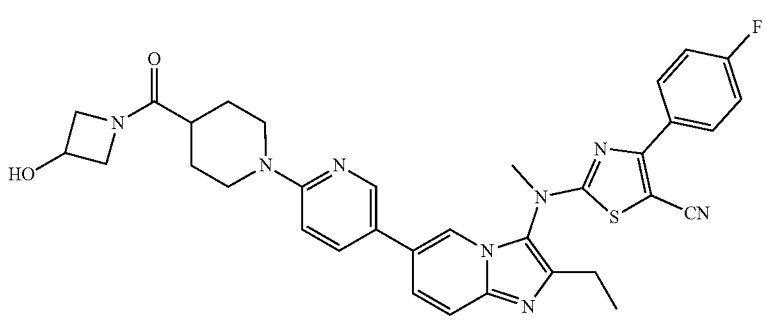 [SMILES: CCc1nc2ccc(-c3ccc(N4CCC(C(=O)N5CC(O)C5)CC4)nc3)cn2c1N(C)c1nc(-c2ccc(F)cc2)c(C#N)s1] |

TABLE 1-continued

Compounds

| Cmpd | Structure |
|------|-----------|
| 121 | 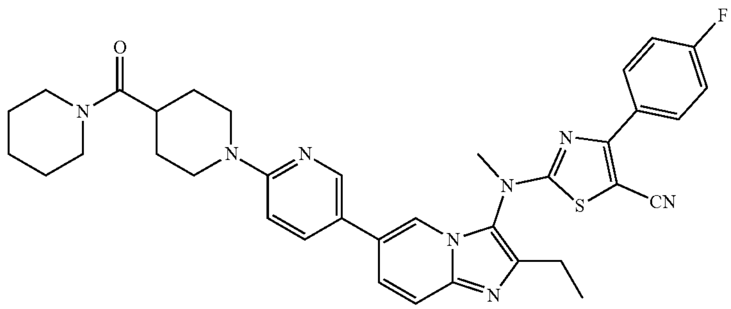 [SMILES: CCc1nc2ccc(-c3ccc(N4CCC(C(=O)N5CCCCC5)CC4)nc3)cn2c1N(C)c1nc(-c2ccc(F)cc2)c(C#N)s1] |
| 122 | 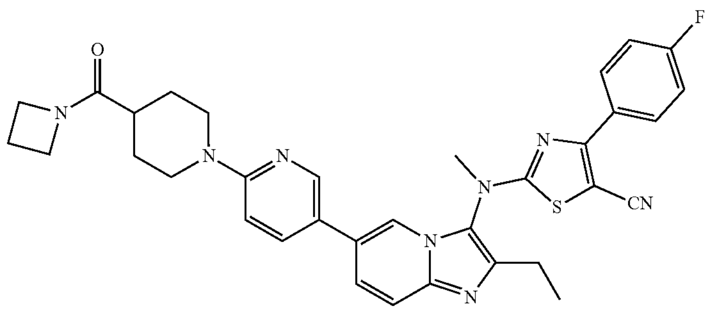 [SMILES: CCc1nc2ccc(-c3ccc(N4CCC(C(=O)N5CCC5)CC4)nc3)cn2c1N(C)c1nc(-c2ccc(F)cc2)c(C#N)s1] |
| 123 | 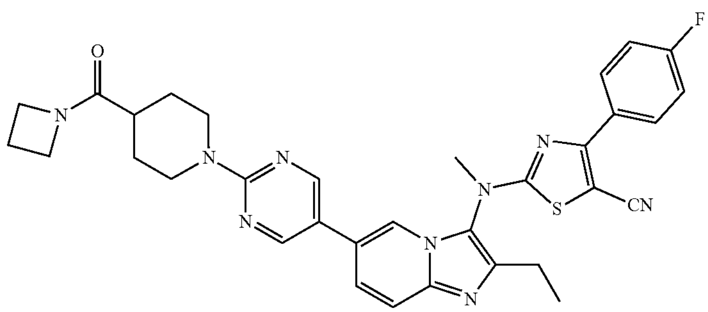 [SMILES: CCc1nc2ccc(-c3cnc(N4CCC(C(=O)N5CCC5)CC4)nc3)cn2c1N(C)c1nc(-c2ccc(F)cc2)c(C#N)s1] |
| 124 | 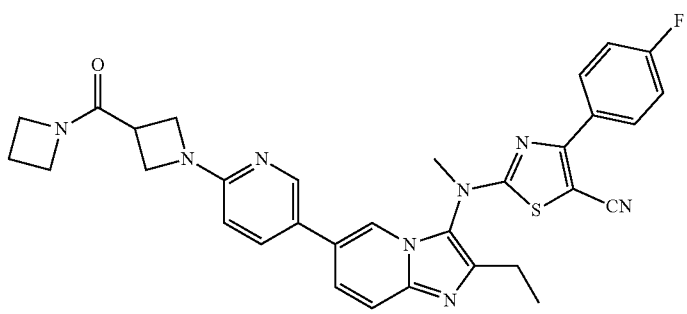 [SMILES: CCc1nc2ccc(-c3ccc(N4CC(C(=O)N5CCC5)C4)nc3)cn2c1N(C)c1nc(-c2ccc(F)cc2)c(C#N)s1] |
| 125 | 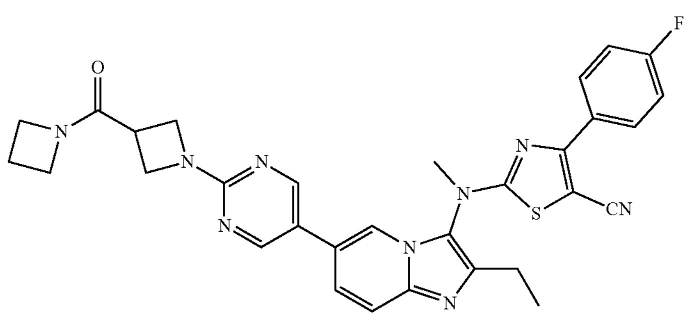 [SMILES: CCc1nc2ccc(-c3cnc(N4CC(C(=O)N5CCC5)C4)nc3)cn2c1N(C)c1nc(-c2ccc(F)cc2)c(C#N)s1] |

TABLE 1-continued

Compounds

| Cmpd | Structure |
|------|-----------|
| 126 | 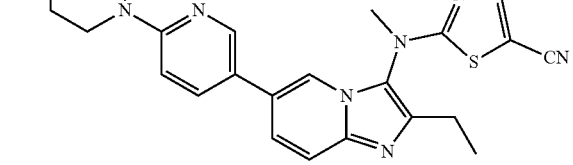 |
| 127 | 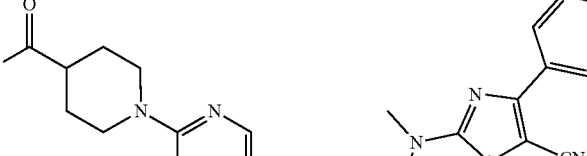 |

4.1.6. Compound Synthesis

Compounds of the present disclosure may be synthesized according to standard methods known in the art [see, e.g. Morrison and Boyd in "Organic Chemistry", 6$^{th}$ edition, Prentice Hall (1992)]. Some compounds and/or intermediates of the present disclosure may be commercially available, known in the literature, or readily obtainable by those skilled in the art using standard procedures. Some compounds of the present disclosure may be synthesized using schemes, examples, or intermediates described herein. Where the synthesis of a compound, intermediate or variant thereof is not fully described, those skilled in the art can recognize that the reaction time, number of equivalents of reagents and/or temperature may be modified from reactions described herein to prepare compounds presented or intermediates or variants thereof and that different work-up and/or purification techniques may be necessary or desirable to prepare such compounds, intermediates, or variants.

Synthesized compounds may be validated for proper structure by methods known to those skilled in the art, for example by nuclear magnetic resonance (NMR) spectroscopy and/or mass spectrometry. Thus, also provided by this disclosure are synthetic precursor or intermediate compounds. In some embodiments, the compound or precursor intermediate compound (e.g., a precursor in the synthesis of a compound listed in Table 1) is represented by the structure of one of the compounds in Table 1A, or a protected version thereof. The present disclosure is meant to encompass, a compound of Table 1A, or a salt, a single stereoisomer, a mixture of stereoisomers and/or an isotopically labelled form thereof.

TABLE 1A

Additional compounds and/or precursor intermediates

| Cmpd | Structure |
|------|-----------|
| 128 | 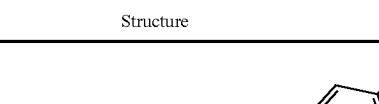 |

TABLE 1A-continued

Additional compounds and/or precursor intermediates

| Cmpd | Structure |
|---|---|
| 129 | 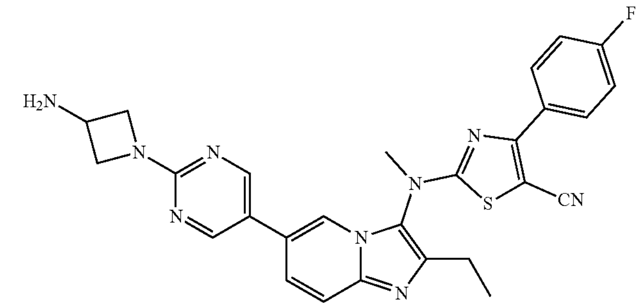 [SMILES: CCc1nc2ccc(-c3cnc(N4CC(N)C4)nc3)cn2c1N(C)c1nc(-c2ccc(F)cc2)c(C#N)s1] |
| 130 | 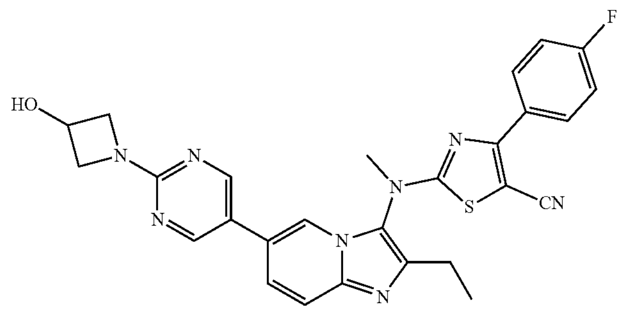 [SMILES: CCc1nc2ccc(-c3cnc(N4CC(O)C4)nc3)cn2c1N(C)c1nc(-c2ccc(F)cc2)c(C#N)s1] |
| 131 | 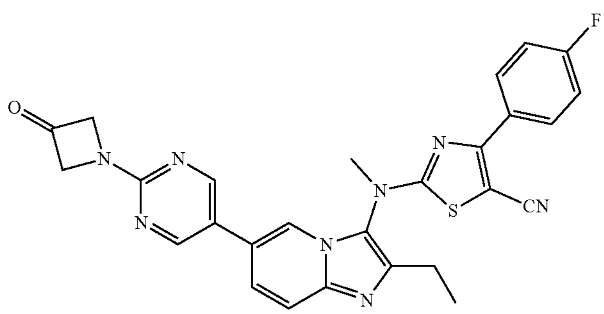 |
| 132 | 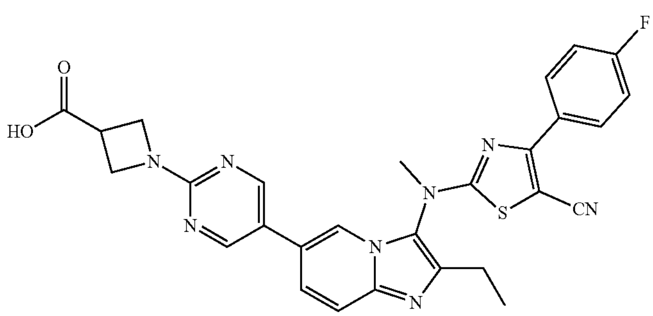 [SMILES: CCc1nc2ccc(-c3cnc(N4CC(C(=O)O)C4)nc3)cn2c1N(C)c1nc(-c2ccc(F)cc2)c(C#N)s1] |
| 133 | 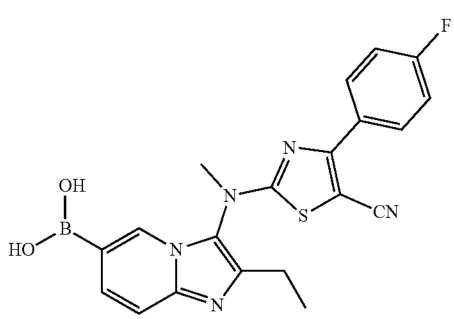 [SMILES: CCc1nc2ccc(B(O)O)cn2c1N(C)c1nc(-c2ccc(F)cc2)c(C#N)s1] |

TABLE 1A-continued

Additional compounds and/or precursor intermediates

| Cmpd | Structure |
|---|---|
| 134 | 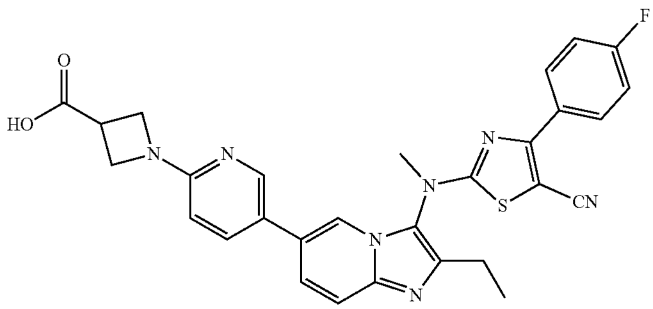 |
| 135 | 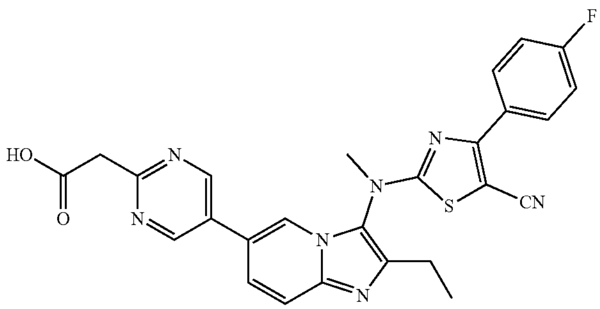 [SMILES: CCc1nc2ccc(-c3cnc(CC(=O)O)nc3)cn2c1N(C)c1nc(-c2ccc(F)cc2)c(C#N)s1] |
| 136 | 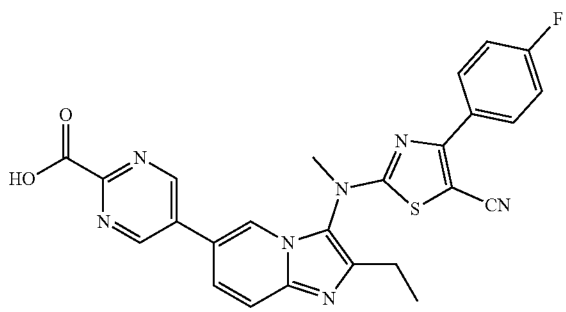 [SMILES: CCc1nc2ccc(-c3cnc(C(=O)O)nc3)cn2c1N(C)c1nc(-c2ccc(F)cc2)c(C#N)s1] |
| 137 | 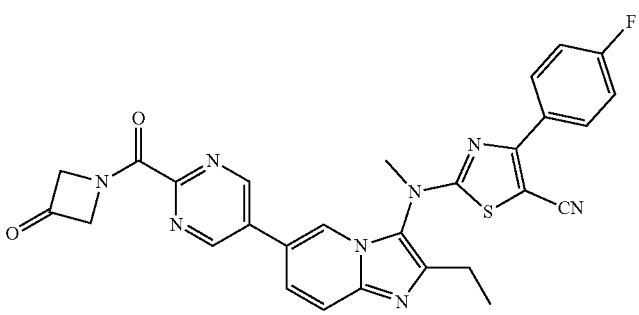 [SMILES: CCc1nc2ccc(-c3cnc(C(=O)N4CC(=O)C4)nc3)cn2c1N(C)c1nc(-c2ccc(F)cc2)c(C#N)s1] |
| 138 | 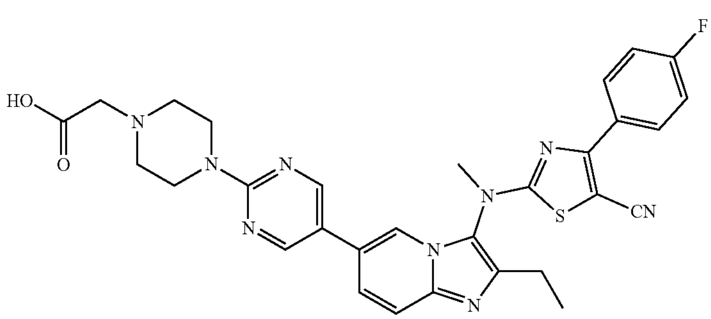 [SMILES: CCc1nc2ccc(-c3cnc(N4CCN(CC(=O)O)CC4)nc3)cn2c1N(C)c1nc(-c2ccc(F)cc2)c(C#N)s1] |

TABLE 1A-continued

Additional compounds and/or precursor intermediates

| Cmpd | Structure |
|---|---|
| 139 | 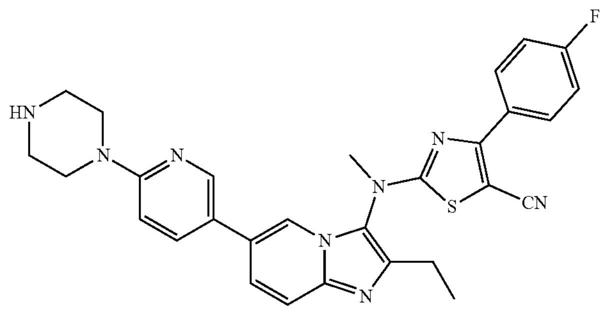 [SMILES: CCc1nc2ccc(-c3ccc(N4CCNCC4)nc3)cn2c1N(C)c1nc(-c2ccc(F)cc2)c(C#N)s1] |
| 140 | 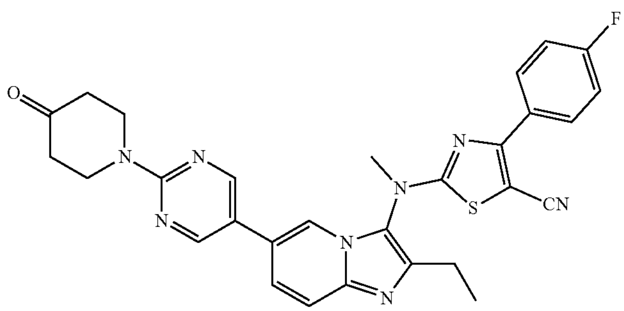 [SMILES: CCc1nc2ccc(-c3cnc(N4CCC(=O)CC4)nc3)cn2c1N(C)c1nc(-c2ccc(F)cc2)c(C#N)s1] |
| 141 | 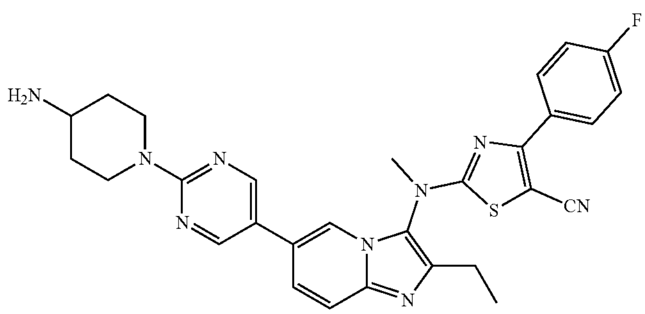 [SMILES: CCc1nc2ccc(-c3cnc(N4CCC(N)CC4)nc3)cn2c1N(C)c1nc(-c2ccc(F)cc2)c(C#N)s1] |
| 142 | 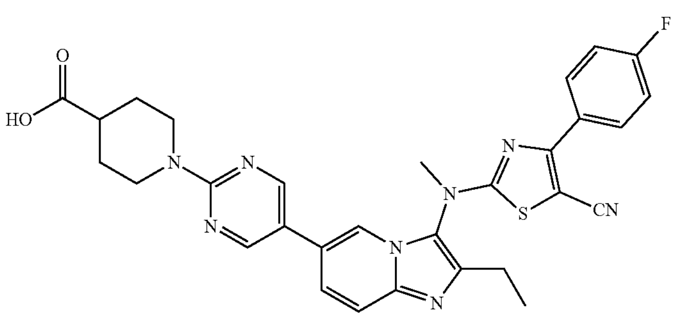 [SMILES: CCc1nc2ccc(-c3cnc(N4CCC(C(=O)O)CC4)nc3)cn2c1N(C)c1nc(-c2ccc(F)cc2)c(C#N)s1] |
| 143 | 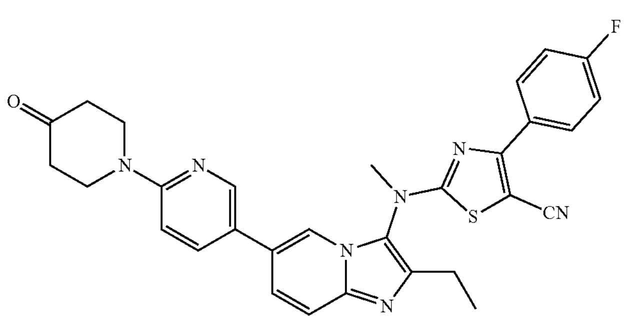 [SMILES: CCc1nc2ccc(-c3ccc(N4CCC(=O)CC4)nc3)cn2c1N(C)c1nc(-c2ccc(F)cc2)c(C#N)s1] |

TABLE 1A-continued

Additional compounds and/or precursor intermediates

| Cmpd | Structure |
|---|---|
| 144 | 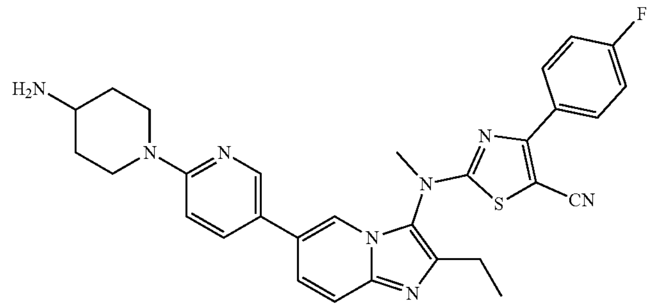 [SMILES: CCc1nc2ccc(-c3ccc(N4CCC(N)CC4)nc3)cn2c1N(C)c1nc(-c2ccc(F)cc2)c(C#N)s1] |
| 145 | 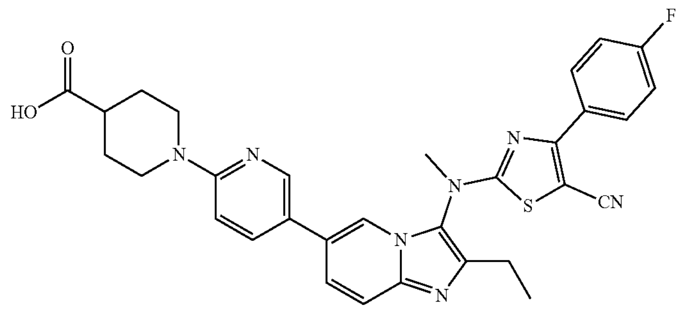 [SMILES: CCc1nc2ccc(-c3ccc(N4CCC(C(=O)O)CC4)nc3)cn2c1N(C)c1nc(-c2ccc(F)cc2)c(C#N)s1] |
| 146 | 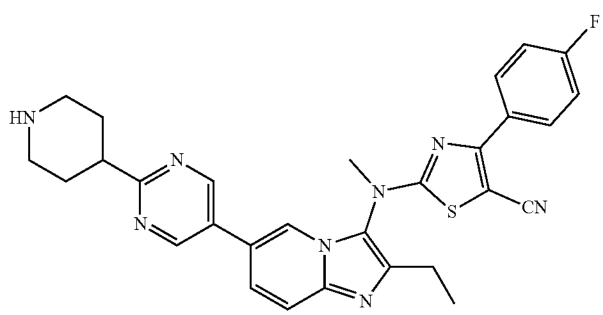 [SMILES: CCc1nc2ccc(-c3cnc(C4CCNCC4)nc3)cn2c1N(C)c1nc(-c2ccc(F)cc2)c(C#N)s1] |
| 147 | 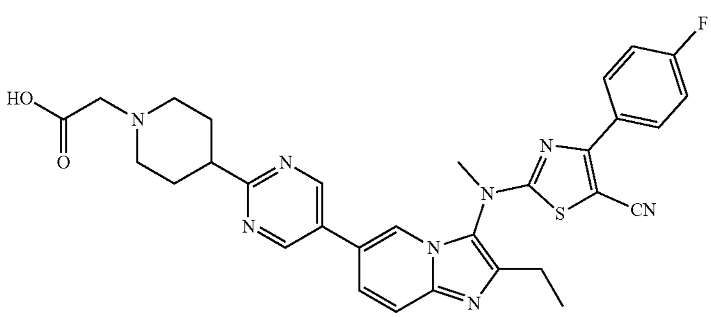 [SMILES: CCc1nc2ccc(-c3cnc(C4CCN(CC(=O)O)CC4)nc3)cn2c1N(C)c1nc(-c2ccc(F)cc2)c(C#N)s1] |
| 148 | 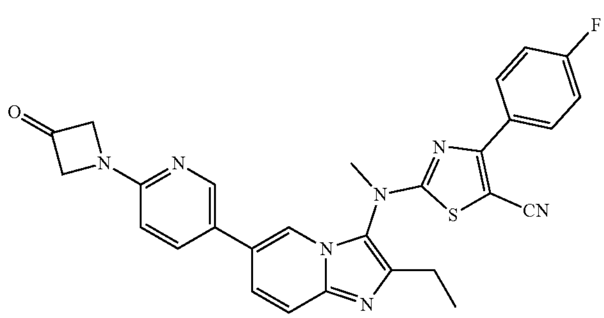 [SMILES: CCc1nc2ccc(-c3ccc(N4CC(=O)C4)nc3)cn2c1N(C)c1nc(-c2ccc(F)cc2)c(C#N)s1] |

TABLE 1A-continued

Additional compounds and/or precursor intermediates

| Cmpd | Structure |
|---|---|
| 149 | 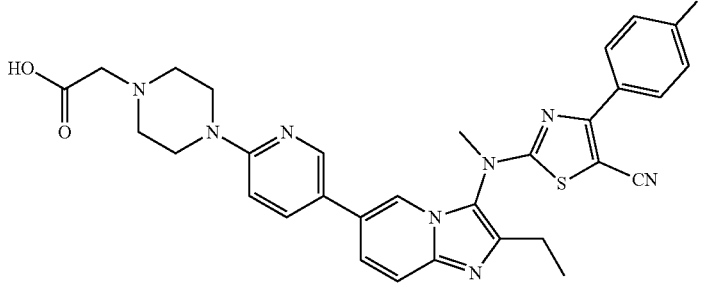 |

4.2. Compositions

Compounds of the present disclosure may be included in a composition that includes one or more compounds and at least one excipient (e.g., a pharmaceutically acceptable excipient). Such compositions may include an ATX inhibitor.

The compounds described herein can find use in pharmaceutical compositions for administration to a subject in need thereof in a variety of therapeutic applications where inhibition of ATX is desirable. In some embodiments, compounds of the present disclosure may be formulated as pharmaceutical compositions.

Accordingly, in a second aspect, the present disclosure provides pharmaceutical compositions comprising at least one compound described herein, a pharmaceutically acceptable salt thereof, or a prodrug thereof, and at least one pharmaceutically acceptable excipient. The phrase "pharmaceutically acceptable excipient," refers any ingredient other than the inventive compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, dispensing, or dispersing agents, sweeteners, and waters of hydration. In some embodiments, the pharmaceutical composition comprises a compound as described herein, a pharmaceutically acceptable salt thereof, or a prodrug thereof in a therapeutically effective amount.

In some embodiments, the pharmaceutical compositions are formulated for oral delivery. In some embodiments, the pharmaceutical compositions are formulated for parenteral administration to a subject in need thereof. In some parenteral embodiments, the pharmaceutical compositions are formulated for intravenous administration to a subject in need thereof. In some parenteral embodiments, the pharmaceutical compositions are formulated for subcutaneous administration to a subject in need thereof.

4.3. Methods of Inhibiting ATX

Aspects of the present disclosure include methods of inhibiting ATX using ATX inhibitor compounds described herein. Such methods may include methods of modulating (e.g., inhibiting) ATX in biological systems by contacting such systems with ATX inhibiting compounds (e.g., ATX inhibitor compounds having structures according to any of those of Table 1 or Table 1A, or a pharmaceutically acceptable salt thereof). Biological systems may include, but are not limited to, cells, tissues, organs, bodily fluids, organisms, non-mammalian subjects, and mammalian subjects (e.g., humans).

In some embodiments, the method of inhibiting ATX comprises contacting a biological system or sample comprising ATX with an effective amount of any of the compounds or a pharmaceutically acceptable salt thereof as described herein, or a pharmaceutical composition as described herein to inhibit ATX. In certain embodiments, the biological system or sample is in vitro. In another embodiment, the biological system or sample is in vivo.

The ATX inhibitors may inhibit the enzymatic activity of ATX in a sample, e.g., as assessed by a hATX/ENPP2 inhibition assay described in Example 12. ATX inhibitors according to such methods may have $IC_{50}$ values for ATX inhibition (e.g., as assessed by the assay of Example 12) of less than 1000 nM, such as 200 nM or less, or 20 nM or less. Biological systems may include subjects (e.g., human subjects).

In some embodiments, the present disclosure provides methods of inhibiting ATX activity in a subject in need thereof. In some cases, the percentage of ATX activity inhibited in a subject may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%. In some cases, this level of inhibition and/or maximum inhibition of ATX activity may be achieved by from about 1 hour after administration to about 3 hours after administration, from about 2 hours after administration to about 4 hours after administration, from about 3 hours after administration to about 10 hours after administration, from about 5 hours after administration to about 20 hours after administration, or from about 12 hours after administration to about 24 hours after administration. Inhibition of ATX activity may continue throughout a period of at least 1 day, of at least 2 days, of at least 3 days, of at least 4 days, of at least 5 days, of at least 6 days, of at least 7 days, of at least 2 weeks, of at least 3 weeks, of at least 4 weeks, of at least 8 weeks, of at least 3 months, of at least 6 months, or at least 1 year. In some cases, this level of inhibition may be achieved through daily administration. Such daily administration may include administration for at least 2 days, for at least 3 days, for at least 4 days, for at least 5 days, for at least 6 days, for at least 7 days, for at least 2 weeks, for at least 3 weeks, for at least 4 weeks, for at least 2 months, for at least 4 months, for at least 6 months, for at least 1 year, or for at least 5 years. In some cases, subjects may be administered compounds or compositions of the present disclosure for the life of such subjects.

In some embodiments, the present disclosure provides methods of modulating LPA or a LPA-associated activity in a subject. In some cases, the percentage of LPA or a LPA-associated activity modulated in a subject may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%.

In some embodiments, compounds of the present disclosure may be used in assays used to assess ATX inhibition and/or modulation of LPA or LPA-associated biological activity. Some assays may include diagnostic assays. In some cases, compounds may be included in methods of drug discovery. In some embodiments, methods of the present disclosure include use of ATX-inhibiting compounds of the present disclosure to assess ATX inhibition by other compounds. Such methods may include conjugating ATX inhibiting compounds with one or more detectable labels (e.g., fluorescent dyes) and measuring ATX dissociation (via detectable label detection) in the presence of the other compounds. The detectable labels may include fluorescent compounds.

4.3.1. Therapeutic Indications

In some embodiments, methods of the present disclosure include methods of treating therapeutic indications using compounds and/or compositions disclosed herein. The term "therapeutic indication" refers to any symptom, condition, disorder, or disease that may be alleviated, stabilized, improved, cured, or otherwise addressed by some form of treatment or other therapeutic intervention (e.g., through ATX inhibitor administration). Therapeutic indications of interest may include, but are not limited to, inflammatory indications, autoimmune indications, proliferative diseases, cancer, and fibrosis. In certain embodiments, the fibrosis occurs in the liver, e.g., liver fibrosis. Therapeutic indications associated with ATX and/or LPA biological activity and/or dysfunction are referred to herein as "ATX-related indications." In some embodiments, methods of the present disclosure may include treating ATX-related indications by administering compounds and/or compositions disclosed herein (e.g., ATX inhibitor compounds).

The terms "treat," "treatment," and the like, refer to relief from or alleviation of pathological processes. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

4.4. Definitions

Unless defined otherwise, all technical and scientific terms used herein have the same meaning as commonly understood by one of ordinary skill in the art to which this disclosure pertains.

It is understood that the definitions provided herein are not intended to be mutually exclusive. Accordingly, some chemical moieties may fall within the definition of more than one term.

The symbol " ~~~~~ " refers to a covalent bond that is a single or a double bond.

The term "$C_x$-$C_y$" when used in conjunction with a chemical moiety, such as alkyl, alkenyl, or alkynyl is meant to include groups that contain from x to y carbons in the chain. For example, the term "$C_1$-$C_6$ alkyl" refers to substituted or unsubstituted saturated hydrocarbon groups, including straight-chain alkyl and branched-chain alkyl groups that contain from 1 to 6 carbons. In some embodiments, the term "($C_x$-$C_y$)alkylene" refers to a substituted or unsubstituted alkylene chain with from x to y carbons in the alkylene chain. For example "($C_x$-$C_y$)alkylene may be selected from methylene, ethylene, propylene, butylene, pentylene, and hexylene, any one of which is optionally substituted.

The term "alkyl" refers to an unbranched or branched saturated hydrocarbon chain. In some embodiments, alkyl as used herein has 1 to 20 carbon atoms (($C_1$-$C_{20}$)alkyl), 1 to 10 carbon atoms (($C_1$-$C_{10}$)alkyl), 1 to 8 carbon atoms (($C_1$-$C_5$)alkyl), 1 to 6 carbon atoms (($C_1$-$C_6$)alkyl), 1 to 5 carbon atoms (($C_1$-$C_5$)alkyl) or 1 to 3 carbon atoms (($C_1$-$C_5$)alkyl). Examples include, but are not limited to, methyl, ethyl, n-propyl, isopropyl, n-butyl, sec-butyl, tert-butyl, n-pentyl, 2-pentyl, isopentyl, neopentyl, n-hexyl, 2-hexyl, 3-hexyl, and 3-methyl pentyl. When an alkyl residue having a specific number of carbons is named, all geometric isomers having that number of carbons may be encompassed. For example, "butyl" can include n-butyl, sec-butyl, isobutyl and t-butyl, and "propyl" can include n-propyl and isopropyl. Unless stated otherwise specifically in the specification, an alkyl chain is optionally substituted by one or more substituents such as those substituents described herein.

The term "alkylene" refers to a straight divalent hydrocarbon chain linking the rest of the molecule to a radical group, consisting solely of carbon and hydrogen, containing no unsaturation, and preferably having from 1 to 20 carbon atoms (($C_1$-$C_{20}$)alkylene), 1 to 10 carbon atoms (($C_1$-$C_{10}$) alkylene), 1 to 6 carbon atoms (($C_1$-$C_6$)alkylene), or 1 to 5 carbon atoms (($C_1$-$C_5$)alkylene). Examples include, but are not limited to, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. Unless stated otherwise specifically in the specification, an alkylene chain is optionally substituted by one or more substituents such as those substituents described herein. Examples include, methylene (—$CH_2$—), ethylene (—$CH_2CH_2$—), propylene (—$CH_2CH_2CH_2$—), 2-methylpropylene (—$CH_2$—CH($CH_3$)—$CH_2$—), hexylene (—($CH_2$)$_6$—) and the like.

The term "alkenyl" refers to an aliphatic hydrocarbon group containing at least one carbon-carbon double bond including straight-chain, branched-chain and cyclic alkenyl groups. In some embodiments, the alkenyl group has 2-10 carbon atoms (a $C_{2-10}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl. An alkylalkenyl is an alkyl group as defined herein bonded to an alkenyl group as defined herein.

The alkenyl group can be unsubstituted or substituted through available carbon atoms with one or more groups defined hereinabove for alkyl The term "alkynyl" refers to straight or branched monovalent hydrocarbyl groups having from 2 to 6 carbon atoms and preferably 2 to 3 carbon atoms and having at least 1 and preferably from 1 to 2 sites of acetylenic (C≡C—) unsaturation. Examples of such alkynyl groups include, but are not limited to, acetylenyl (C≡CH), and propargyl (CH$_2$C≡CH).

The term "aryl" refers to a monocyclic or polycyclic group having at least one hydrocarbon aromatic ring, wherein all of the ring atoms of the at least one hydrocarbon aromatic ring are carbon. Aryl may include groups with a single aromatic ring (e.g., phenyl) and multiple fused aromatic rings (e.g., naphthyl, anthryl). Aryl may further include groups with one or more aromatic hydrocarbon rings fused to one or more non-aromatic hydrocarbon rings (e.g., fluorenyl; 2,3-dihydro-1H-indene; 1,2,3,4-tetrahydronaphthalene). In certain embodiments, aryl includes groups with an aromatic hydrocarbon ring fused to a non-aromatic ring, wherein the non-aromatic ring comprises at least one ring heteroatom independently selected from the group consisting of N, O, and S. For example, in some embodiments, aryl includes groups with a phenyl ring fused to a non-aromatic ring, wherein the non-aromatic ring comprises at least one ring heteroatom independently selected from the group consisting of N, O, and S (e.g., chromane; thiochromane; 2,3-dihydrobenzofuran; indoline). In some embodiments, aryl as used herein has from 6 to 14 carbon atoms (($C_6$-$C_{14}$) aryl), or 6 to 10 carbon atoms (($C_6$-$C_{10}$)aryl). Where the aryl includes fused rings, the aryl may connect to one or more substituents or moieties of the formulae described herein through any atom of the fused ring for which valency permits.

The term "cycloalkyl" refers to a monocyclic or polycyclic saturated hydrocarbon. In some embodiments, cycloalkyl has 3 to 20 carbon atoms (($C_3$-$C_{20}$)cycloalkyl), 3 to 8 carbon atoms (($C_3$-$C_8$)cycloalkyl), 3 to 6 carbon atoms (($C_3$-$C_6$)cycloalkyl), or 3 to 5 carbon atoms (($C_3$-$C_5$)cycloalkyl). In some embodiments, cycloalkyl has 3 to 8 carbon atoms having single or multiple cyclic rings including fused, bridged, and spiro ring systems. Examples of suitable cycloalkyl groups include, but are not limited to, adamantyl, cyclopropyl, cyclobutyl, cyclopentyl, cyclooctyl, octahydropentalenyl, octahydro-1H-indene, decahydronaphthalene, cubane, bicyclo[3.1.0]hexane, and bicyclo[1.1.1]pentane, and the like.

The term "carbocycle" refers to a saturated, unsaturated or aromatic ring system in which each atom of the ring system is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl.

The term "heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems.

The term "heteroaryl" refers to an aromatic group of from 4 to 10 carbon atoms and 1 to 4 heteroatoms selected from the group consisting of oxygen, nitrogen and sulfur within the ring. Such heteroaryl groups can have a single ring (i.e., pyridinyl or furyl) or multiple condensed rings (i.e., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Preferred heteroaryls include 5 or 6 membered heteroaryls such as pyridinyl, pyrrolyl, indolyl, thiophenyl, and furanyl.

The term "heteroalkyl" refers to an alkyl substituent in which one or more of the carbon atoms and any attached hydrogen atoms are independently replaced with the same or different heteroatomic group. For example, 1, 2, or 3 carbon atoms may be independently replaced with the same or different heteroatomic substituent.

The term "substituted" refers to moieties having substituents replacing a hydrogen on one or more carbons or substitutable heteroatoms, e.g., NH or NH$_2$, of a compound. It will be understood that "substitution" or "substituted with" includes the implicit proviso that such substitution is in accordance with permitted valence of the substituted atom and the substituent, and that the substitution results in a stable compound. For example, stable compounds include, but is not limited to, compounds which do not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. The term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants, unless specified otherwise.

When referring to compound features, the phrase "optionally substituted" may be used interchangeably with the phrase "unsubstituted or substituted" and refers to when a non-hydrogen substituent may or may not be present on a given atom or group, and, thus, the description includes structures where a non-hydrogen substituent is present and structures where a non-hydrogen substituent is not present. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible and/or inherently unstable.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$N (R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2). In another exemplary embodiment, substituents include alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo, thioxo, cyano, nitro, imino, oximo, hydrazine, —R$^b$OR$^a$, —R$^b$—OC(O)—R$^a$, —R$^b$—OC(O)—OR$^a$, —R$^b$—OC(O)—N(R a)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N (R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^a$, R$^b$, and R$^c$ are independently selected from hydrogen, alkyl, cycloalkyl, cycloalkylalkyl, aryl, aralkyl, heterocycloalkyl, heterocycloalkylalkyl, heteroaryl, and heteroarylalkyl; and wherein each R$^a$, R$^b$, and R$^c$, valence permitting, may be optionally substituted with alkyl, alkenyl, alkynyl, halogen, haloalkyl, haloalkenyl, haloalkynyl, oxo, thioxo, cyano, nitro, imino, oximo, hydrazine, —R$^b$OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N (R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2).

The term "isomers" refers to two or more compounds comprising the same numbers and types of atoms, groups or components, but with different structural arrangement and connectivity of the atoms.

The term "tautomer" refers to one of two or more structural isomers which readily convert from one isomeric form to another and which exist in equilibrium.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their respective enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, Classics in Stereoselective Synthesis, Wiley-VCH: Weinheim, 2009.

The symbol=denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituent on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compound wherein the substituents are disposed on both the same and opposite sides of the plane of the ring are designated "cis/trans."

Singular articles such as "a," "an" and "the" and similar referents in the context of describing the elements are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (i.e., "such as") provided herein, is intended merely to better illuminate the embodiments and does not pose a limitation on the scope of the claims unless otherwise stated.

In some embodiments, where the use of the term "about" is before a quantitative value, the present disclosure also includes the specific quantitative value itself, unless specifically stated otherwise. As used herein, the term "about" refers to a ±10% variation from the nominal value unless otherwise indicated or inferred. Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

A dash ("-") symbol that is not between two letters or symbols refers to a point of bonding or attachment for a substituent. For example, —$NH_2$ is attached through the nitrogen atom.

The term "pharmaceutically acceptable salt" refers to a salt which is acceptable for administration to a subject. It is understood that such salts, with counter ions, will have acceptable mammalian safety for a given dosage regime. Such salts can also be derived from pharmaceutically acceptable inorganic or organic bases and from pharmaceutically acceptable inorganic or organic acids, and may comprise organic and inorganic counter ions. The neutral forms of the compounds described herein may be converted to the corresponding salt forms by contacting the compound with a base or acid and isolating the resulting salts.

The terms "pharmaceutically acceptable excipient," "pharmaceutically acceptable diluent," "pharmaceutically acceptable carrier," and "pharmaceutically acceptable adjuvant" are used interchangeably and refer to an excipient, diluent, carrier, or adjuvant that is useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. The phrase "pharmaceutically acceptable excipient" includes both one and more than one such excipient, diluent, carrier, and/or adjuvant.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (i.e., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

4.5. Additional Embodiments

Aspects of this disclosure are further described in the following numbered clauses:

Clause 1. A compound of formula (I):

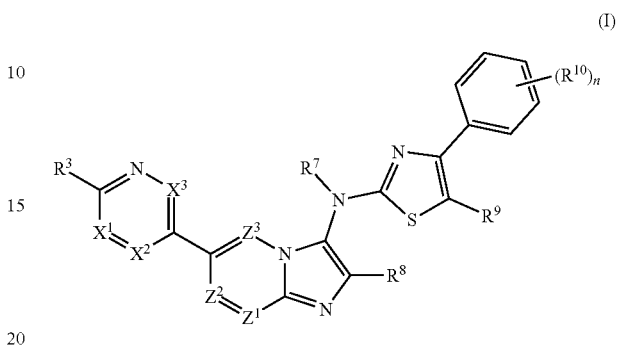

or a pharmaceutically acceptable salt or isomer thereof, wherein:

$X^1$, $X^2$, and $X^3$ are independently selected from C—$R^1$ and N;

$Z^1$, $Z^2$, and $Z^3$ are independently selected from C—$R^1$ and N;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^3$ is selected from optionally substituted $R^4$—C(O)—($C_1$-$C_3$)alkyl-, $R^4$C(O)—, optionally substituted monocyclic or bicyclic carbocycle, optionally substituted monocyclic or bicyclic heterocycle, $R^5R^6$HC—, and $R^5R^6$N—;

$R^4$ is selected from $H_2$N—, HO—, $R^5R^6$N—, optionally substituted ($C_1$-$C_{10}$)alkyl-, optionally substituted ($C_1$-$C_{10}$)alkoxy-, optionally substituted monocyclic or bicyclic carbocycle, optionally substituted monocyclic or bicyclic heterocycle, optionally substituted cycloalkyl-($C_1$-$C_6$)alkylene-, and optionally substituted heterocycle-($C_1$-$C_6$)alkylene-;

$R^5$ and $R^6$ are independently selected from H—, $H_2$N—, HO—, optionally substituted ($C_1$-$C_{10}$)alkyl-, optionally substituted monocyclic or bicyclic carbocycle, optionally substituted monocyclic or bicyclic heterocycle, optionally substituted $R^4$C(O)—($C_1$-$C_{10}$)alkyl-, $R^4$C(O)—, $R^4$—, and substituted amino:

or $R^5$ and $R^6$ together with the nitrogen or carbon atom to which they are attached are cyclically linked to form an optionally substituted carbocycle or an optionally substituted heterocycle;

$R^7$ is selected from H—, and optionally substituted ($C_1$-$C_6$)alkyl-;

$R^8$ is selected from —H, -halogen, and optionally substituted —($C_1$-$C_6$)alkyl;

$R^9$ and each $R^{10}$ are independently selected from —H, -halogen, —CN, —OH, optionally substituted —($C_1$-$C_6$)alkoxy, —$NH_2$, substituted amino, optionally substituted —($C_1$-$C_6$)alkyl-$NH_2$ and optionally substituted —($C_1$-$C_6$)alkyl; and n is 0, 1, 2, 3, 4, or 5.

Clause 2. The compound of clause 1, wherein $X^1$ is N, $X^2$ is C—H, and $X^3$ is C—H.

Clause 3. The compound of clause 1, wherein $X^1$ is C—H, $X^2$ is C—H, and X is C—H.

Clause 4. The compound of any one of clauses 1 to 3, wherein Y is S.

Clause 5. The compound of any one of clauses 1 to 4, wherein $Z^1$ is C—H, $Z^2$ is C—H, and $Z^3$ is C—H.

Clause 6. The compound of any one of clauses 1 to 5, wherein the compound is of formula (Ia):

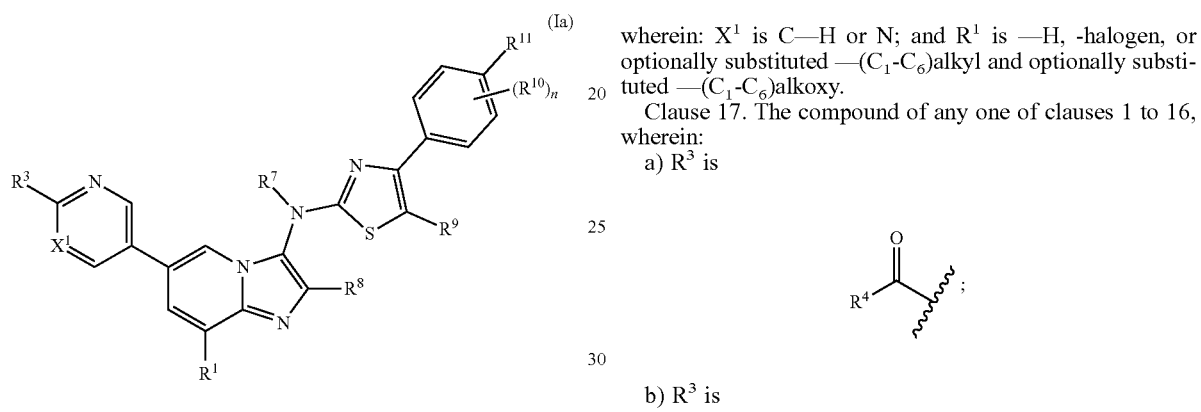

wherein:
- $R^1$ is selected from —H, -halogen, optionally substituted —($C_1$-$C_6$)alkyl and optionally substituted —($C_1$-$C_6$)alkoxy;
- $R^3$ is selected from $R^4C(O)$—, $R^4C(O)CH_2$—, $R^5R^6N$—, and $R^5R^6HC$—;
- $R^{11}$ is —H, -halogen, —CN, —OH, optionally substituted —($C_1$-$C_6$)alkoxy, —$NH_2$, —$NR^5R^6$, —$CH_2NH_2$ and optionally substituted —($C_1$-$C_6$)alkyl; and
- n is 0, 1, 2, or 3.

Clause 7. The compound of clause 6, wherein $X^1$ is N.

Clause 8. The compound of clause 6, wherein $X^1$ is C—H.

Clause 9. The compound of any one of clauses 1 to 8, wherein $R^7$ is optionally substituted ($C_1$-$C_6$)alkyl-.

Clause 10. The compound of clause 9, wherein $R^7$ is $H_3C$—.

Clause 11. The compound of any one of clauses 1 to 10, wherein $R^8$ is optionally substituted —($C_1$-$C_6$)alkyl.

Clause 12. The compound of clause 11, wherein $R^8$ is —$CH_2CH_3$.

Clause 13. The compound of any one of clauses 1 to 12, wherein $R^9$ is —CN.

Clause 14. The compound of any one of clauses 1 to 13, wherein $R^{11}$ is -halogen.

Clause 15. The compound of clause 14, wherein $R^{11}$ is —F.

Clause 16. The compound of any one of clauses 1 to 15, wherein the compound is of formula (Ib):

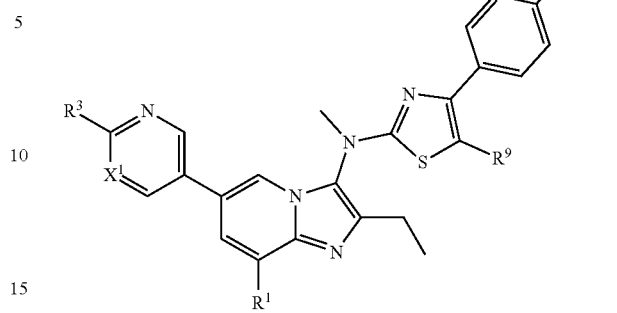

wherein: $X^1$ is C—H or N; and $R^1$ is —H, -halogen, or optionally substituted —($C_1$-$C_6$)alkyl and optionally substituted —($C_1$-$C_6$)alkoxy.

Clause 17. The compound of any one of clauses 1 to 16, wherein:

a) $R^3$ is

b) $R^3$ is

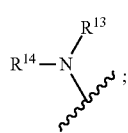

c) $R^3$ is

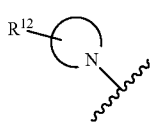

d) $R^3$ is

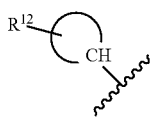

that is an optionally substituted monocyclic or bicyclic ($C_2$-$C_9$)heterocycle-; or e) $R^3$ is that is an optionally substituted monocyclic or bicyclic ($C_3$-$C_8$)carbocycle-, or an optionally substituted monocyclic or bicyclic ($C_2$-$C_9$)heterocycle-;
wherein:
$R^4$ is selected from HO—, $H_2N$—, $R^{15}R^{16}N$—, optionally substituted ($C_1$-$C_5$)alkyl-, optionally substituted monocyclic or bicyclic carbocycle, and optionally substituted monocyclic or bicyclic heterocycle;
$R^{12}$ is selected from —H, —$NH_2$, —OH—, —$CH_2C(O)R^4$, —$C(O)R^4$, —$CHR^{15}R^{16}$, —$NR^{15}R^{16}$, optionally substituted —($C_1$-$C_5$)alkyl, optionally substituted monocyclic or bicyclic —($C_3$-$C_8$)carbocycle, and an optionally substituted monocyclic or bicyclic —($C_2$-$C_9$)heterocycle; and
$R^{13}$ and $R^{14}$ are independently selected from —H, —$CH_2C(O)R^{17}$, —$CH_2R^{17}$, —$C(O)R^{17}$, —$R^{18}C(O)R^{17}$, —$CH_2R^{18}C(O)R^{17}$, optionally substituted —($C_1$-$C_5$)alkyl, optionally substituted monocyclic or bicyclic —($C_3$-$C_8$)carbocycle, and an optionally substituted monocyclic or bicyclic —($C_2$-$C_9$)heterocycle, wherein $R^{17}$ and $R^{18}$ are independently selected from optionally substituted —($C_1$-$C_5$)alkyl, optionally substituted monocyclic or bicyclic —($C_3$-$C_8$)carbocycle, and an optionally substituted monocyclic or bicyclic —($C_2$-$C_9$)heterocycle; and
$R^{15}$ and $R^{16}$ are independently selected from H—, optionally substituted ($C_2$-$C_5$)heterocycloalkyl-C(O)—, optionally substituted ($C_3$-$C_6$) cycloalkyl-C(O)—, optionally substituted ($C_1$-$C_5$)alkyl-, optionally substituted 3- to 10-membered saturated monocyclic heterocycle or carbocycle, and optionally substituted 3- to 10-membered saturated bicyclic heterocycle or carbocycle, wherein the optional substituents are selected from hydroxy, $HOCH_2$—, cyano, halogen, substituted amino, and ($C_1$-$C_5$)alkyl; or $R^{15}$ and $R^{16}$ are cyclically linked to form a 3- to 6-membered monocyclic saturated heterocycle, optionally substituted with hydroxy, $HOCH_2$—, cyano, halogen, substituted amino, or ($C_1$-$C_5$)alkyl.

Clause 18. The compound of any one of clauses 1 to 17, wherein:
$R^3$ is

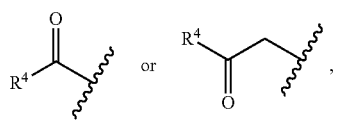

$R^4$ is selected from $R^{32}$, $R^{32}HN$—, $R^{32}N(R^{33})$—, and $R^{32}HN$—$R^{36}$—;
$R^{32}$ and $R^{33}$ are independently selected from H—, optionally substituted ($C_1$-$C_3$)alkyl, optionally substituted cycloalkyl, and optionally substituted saturated heterocycle;
$R^{36}$ is selected from optionally substituted ($C_1$-$C_3$)alkyl, optionally substituted cycloalkyl, and optionally substituted saturated heterocycle; and
the optional substituents of the $R^{32}$, $R^{33}$ and $R^{36}$ groups are independently selected from —CN, —OH, —$CH_2OH$, —($C_1$-$C_3$)alkyl, —($C_1$-$C_3$)alkoxy, —($C_3$-$C_6$)cycloalkyl, ($C_2$-$C_5$)heterocycloalkyl, and —$N(R^{37})R^{38}$, wherein $R^{37}$ and $R^{38}$ are independently selected from H, ($C_1$-$C_3$)alkyl, ($C_3$-$C_6$)cycloalkyl, and ($C_2$-$C_5$)heterocycloalkyl.

Clause 19. The compound of clause 18, wherein $R^4$ is selected from:

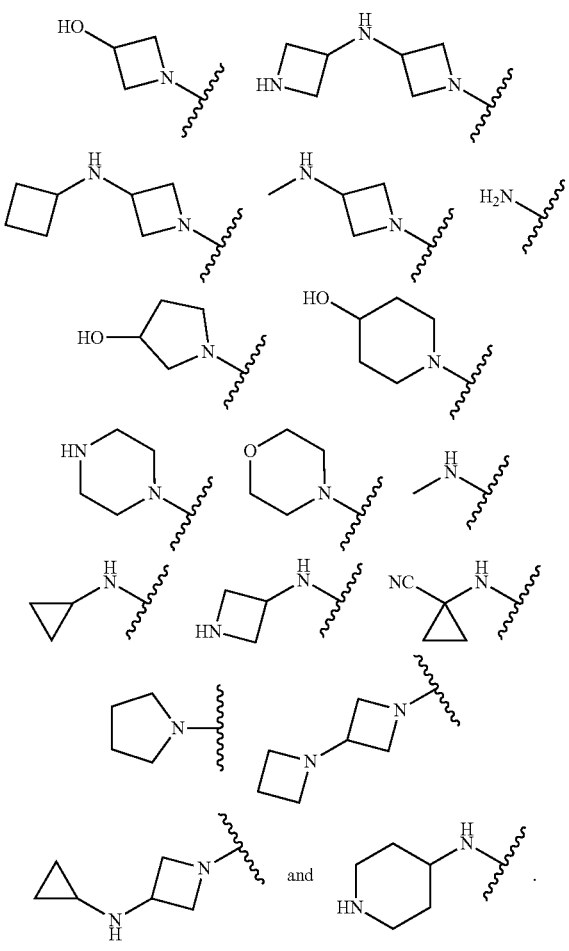

Clause 20. The compound of clause 19, wherein the compound is selected from compounds 11-16, 47-65 and 87 of Table 1.

Clause 21. The compound of any one of clauses 1 to 17, wherein:
$R^3$ is

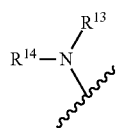

$R^{14}$ is selected from $R^{34}$—, $R^{34}CH_2$—, $R^{34}C(O)R^{35}$—, and $R^{34}C(O)R^{35}CH_2$—;
each $R^{34}$ and $R^{35}$ are independently selected from optionally substituted —($C_1$-$C_3$)alkyl, optionally substituted cycloalkyl, and optionally substituted saturated heterocycle;
the optional substituents of the $R^{34}$ and $R^{35}$ groups are independently selected from —CN, —OH, —$CH_2OH$, —($C_1$-$C_3$)alkyl, —($C_1$-$C_3$)alkoxy, and —($C_1$-$C_3$)alkyl; and
$R^3$ is —H.

Clause 22. The compound of clause 21, wherein $R^{14}$ is selected from:

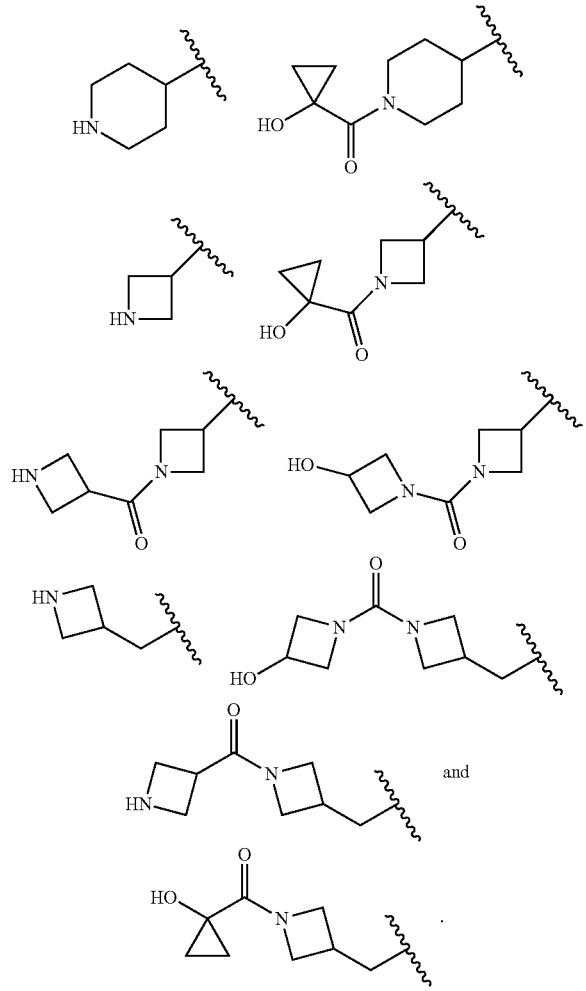

Clause 23. The compound of clause 22, wherein the compound is selected from compounds 21, 22, and 34-41 of Table 1.

Clause 24. The compound of any one of clauses 1 to 17, wherein $R^3$ is

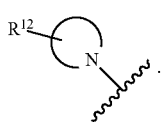

Clause 25. The compound of clause 24, wherein $R^3$ is selected from:

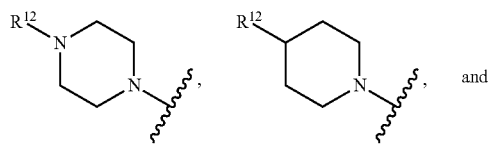

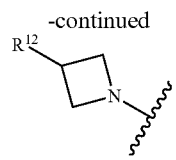

Clause 26. The compound of clause 24 or 25, wherein:

$R^{12}$ is selected from H—, $H_2N$—, $R^{31}$—C(O)—, $R^{31}$—C(O)CH_2—, $R^{31}$—NHC(O)—, $R^{31}$—C(O)NH—, $R^{31}$—NH—, $R^{31}$—N(CH_3)C(O)—, $R^{31}$—C(O)N(CH_3)—, $R^{31}$—N(CH_3)—, and $R^{31}$—O—;

$R^{31}$ is selected from optionally substituted cycloalkyl, and optionally substituted saturated heterocycle; and the optional substituents of the $R^{31}$ group are selected from NC—, HO—, HOCH_2—, ($C_1$-$C_3$)alkyl-, ($C_1$-$C_3$)alkoxy-, substituted ($C_1$-$C_3$)alkyl-, ($C_3$-$C_6$)cycloalkyl-, and ($C_2$-$C_5$)heterocycloalkyl-.

Clause 27. The compound of any one of clauses 24 to 26, wherein $R^{12}$ is selected from:

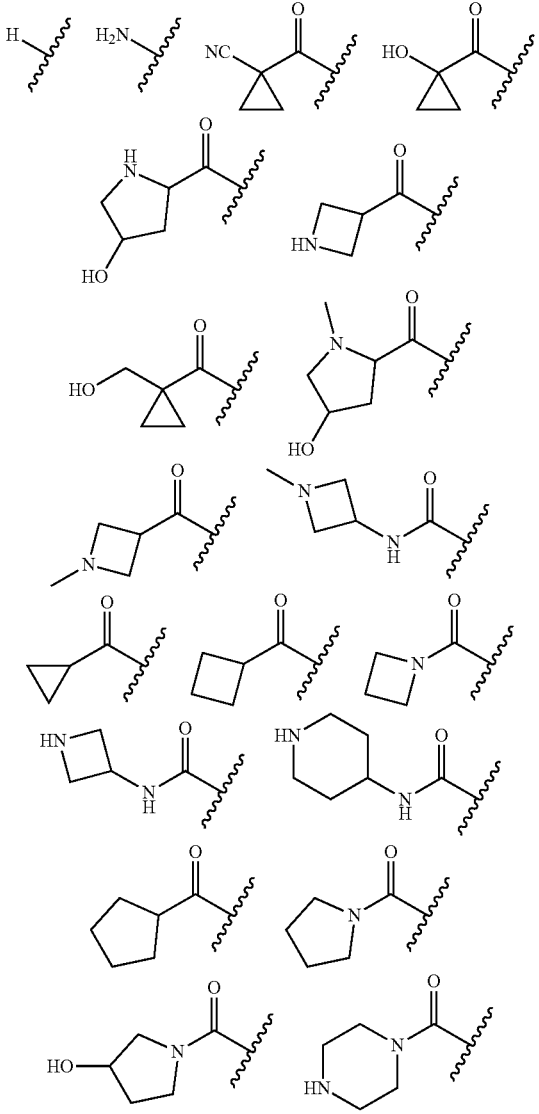

-continued

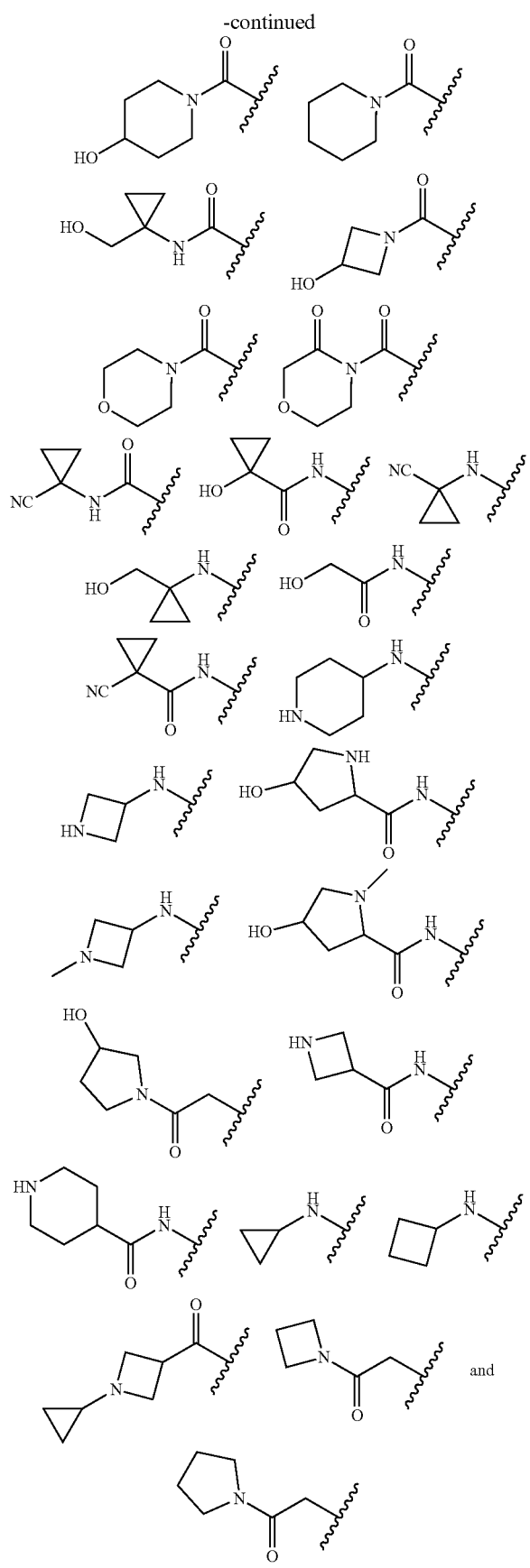

Clause 28. The compound of any one of clauses 24 to 27, wherein the compound is selected from compounds 1-10, 17-20, 23-33, 42-46, 66-86, 88-98, 105-115, and 118-127 of Table 1.

Clause 29. The compound of any one of clauses 1 to 5, wherein the compound is of formula (Ie):

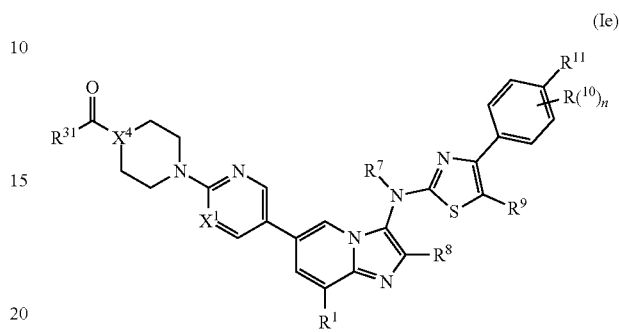

(Ie)

wherein:
- $X^1$ and $X^4$ are independently N or C—$R^1$;
- $R^1$ is selected from H, halogen, optionally substituted —($C_1$-$C_6$)alkyl, and optionally substituted —($C_1$-$C_6$)alkoxy; and
- $R^{31}$ is selected from optionally substituted ($C_2$-$C_5$)heterocycloalkyl, and optionally substituted ($C_3$-$C_7$)cycloalkyl-;
- $R^{11}$ is —H, -halogen, —CN, —OH, optionally substituted —($C_1$-$C_6$)alkoxy, —$NH_2$, —$NR^5R^6$, —$CH_2NH_2$ and optionally substituted —($C_1$-$C_6$)alkyl; and
- n is 0, 1, 2, or 3.

Clause 30. The compound of clause 29, wherein the optional substituents of the $R^{31}$ group are selected from NC—, HO—, $HOCH_2$—, ($C_1$-$C_3$)alkyl- (e.g., $H_3C$—), ($C_1$-$C_3$)alkoxy-, substituted ($C_1$-$C_3$)alkyl-, and ($C_3$-$C_6$)cycloalkyl- (e.g., cyclopropyl).

Clause 31. The compound of clause 29 or 30, wherein the compound is of formula (If).

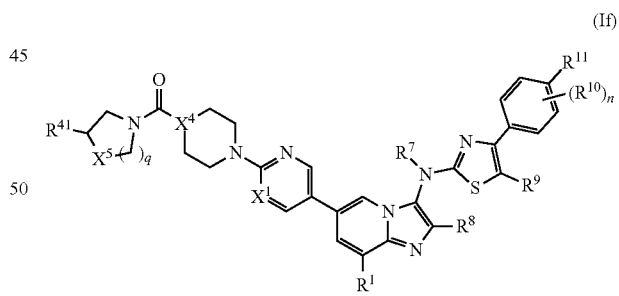

(If)

wherein:
- $X^1$ and $X^4$ are independently N or CH;
- $R^{41}$ is H—, or HO—; and
- q is 0, 1 or 2; wherein
- when q is 0 or 1, $X_5$ is $CH_2$; and
- when q is 2, $X^5$ is NH, O, or CH(OH).

Clause 32. The compound of any one of clauses 29 to 31, wherein $R^7$ is optionally substituted ($C_1$-$C_6$)alkyl-.

Clause 33. The compound of clause 32, wherein $R^7$ is $H_3C$—.

Clause 34. The compound of any one of clauses 29 to 33, wherein $R^8$ is optionally substituted —($C_1$-$C_6$)alkyl.

Clause 35. The compound of clause 34, wherein $R^8$ is —$CH_2CH_3$.

Clause 36. The compound of any one of clauses 29 to 35, wherein $R^9$ is —CN.

Clause 37. The compound of any one of clauses 29 to 36, wherein $R^{11}$ is -halogen.

Clause 38. The compound of clause 37, wherein $R^{11}$ is —F.

Clause 39. The compound of clause 24 or 29, wherein the compound is of formula (Ic):

(Ic)

wherein:
- $X^1$ and $X^4$ are independently N or C—$R^1$;
- $R^1$ is selected from H, halogen, optionally substituted —($C_1$-$C_6$)alkyl, and optionally substituted —($C_1$-$C_6$) alkoxy; and
- $R^{31}$ is selected from optionally substituted ($C_2$-$C_5$)heterocycloalkyl, and optionally substituted ($C_3$-$C_7$)cycloalkyl-.

Clause 40. The compound of clause 39, wherein the optional substituents of the $R^{31}$ group are selected from NC—, HO—, $HOCH_2$—, ($C_1$-$C_3$)alkyl- (e.g., $H_3C$—), ($C_1$-$C_3$)alkoxy-, substituted ($C_1$-$C_3$)alkyl-, and ($C_3$-$C_6$)cycloalkyl- (e.g., cyclopropyl).

Clause 41. The compound of clause 39 or 40, wherein the compound is of formula (Id):

(Id)

wherein:
- $X^1$ and $X^4$ are independently N or CH;
- $R^{41}$ is H—, or HO—; and
- q is 0, 1 or 2; wherein
  when q is 0 or 1, $X^5$ is $CH_2$; and
  when q is 2, $X^5$ is NH, O, or CH(OH).

Clause 42. The compound of any one of clauses 29 to 41, wherein $X^1$ is N.

Clause 43. The compound of any one of clauses 29 to 41, wherein $X^1$ is C—H.

Clause 44. The compound of any one of clauses 41 to 43, wherein the compound is selected from:

-continued


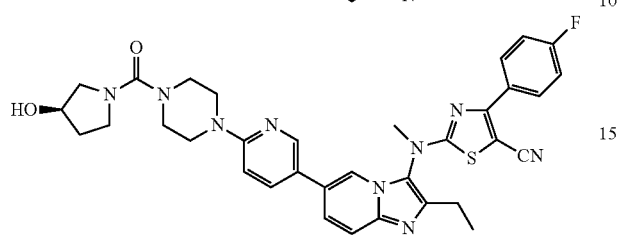

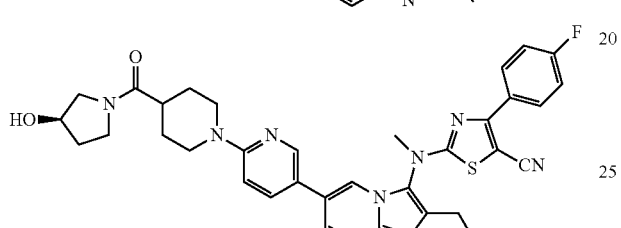

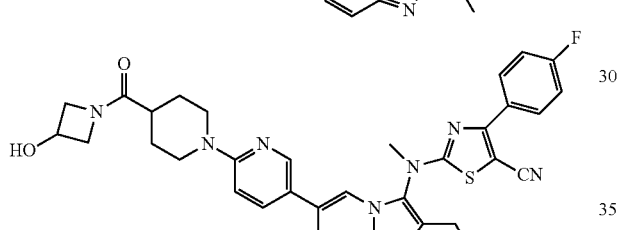

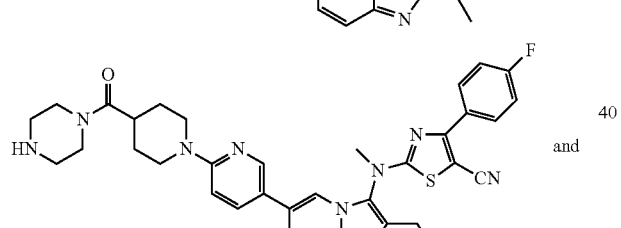

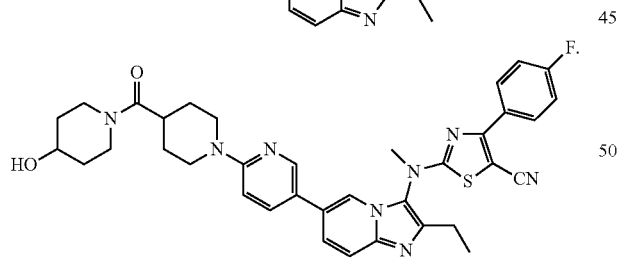

Clause 45. The compound of any one of clauses 1 to 17, wherein R³ is

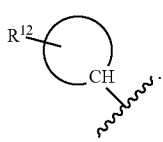

Clause 46. The compound of clause 45, wherein R³ is

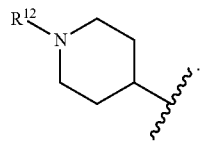

Clause 47. The compound of clause 45 or 46, wherein:
R¹² is selected from H—, R³¹—C(O)—, R³¹—C(O)CH₂—, R³¹—NHC(O)—, R³¹—C(O)NH—, R³¹—N(CH₃)C(O)—, and R³¹—C(O)N(CH₃)—;
R³¹ is selected from optionally substituted (C₁-C₃)alkyl-, optionally substituted cycloalkyl-, and optionally substituted saturated heterocycle; and
the optional substituents of the R³¹ group are selected from NC—, HO—, HOCH₂—, (C₁-C₃)alkyl-, (C₁-C₃)alkoxy- and substituted (C₁-C₃)alkyl-.

Clause 48. The compound of any one of clauses 46 to 47, wherein R¹² is selected from:

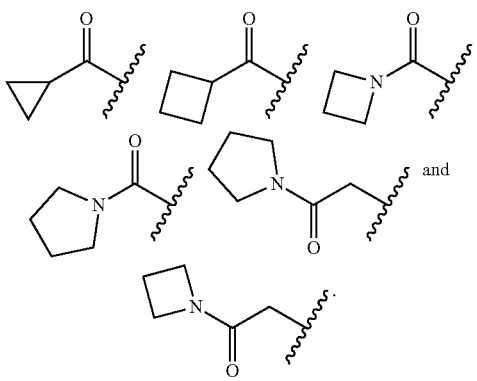

Clause 49. The compound of any one of clauses 45 to 48, wherein the compound is selected from compounds 99-104 of Table 1.

Clause 50. A pharmaceutical composition comprising: a compound or a pharmaceutically acceptable salt thereof according to any one of clauses 1 to 49; and a pharmaceutically acceptable excipient.

Clause 51. A compound for use in inhibiting autotaxin (ATX), wherein the compound is a compound or a pharmaceutically acceptable salt thereof according to any one of clauses 1 to 49.

Clause 52. A pharmaceutical composition for use in inhibiting autotaxin (ATX), wherein the pharmaceutical composition is according to clause 50.

Clause 53. Use of a compound for the manufacture of a medicament for inhibiting autotaxin (ATX), wherein the compound is a compound or a pharmaceutically acceptable salt thereof according to any one of clauses 1 to 49.

Clause 54. Use of a pharmaceutical composition for the manufacture of a medicament for in inhibiting autotaxin (ATX), wherein the pharmaceutical composition is according to clause 50.

Clause 55. A method of inhibiting autotaxin, the method comprising contacting a biological system comprising autotaxin with an effective amount of a compound or a pharmaceutically acceptable salt thereof according to any one of clauses 1 to 49 to inhibit autotaxin.

Clause 56. The method of clause 55, wherein the biological system is comprised in an in vitro sample.

Clause 57. The method of clause 55, wherein the biological system is in vivo.

Clause 58. A method of inhibiting autotaxin in a subject in need thereof, comprising administering to the subject a therapeutically effective amount of a compound or a pharmaceutically acceptable salt thereof according to any one of clauses 1 to 49, or a pharmaceutical composition according to clause 50.

Clause 59. A method of treating an ATX-related indication in a subject in need thereof, comprising administering to the subject a therapeutically effective amount of a compound or a pharmaceutically acceptable salt thereof according to any one of clauses 1 to 49, or a pharmaceutical composition according to clause 50.

Clause 60. The method of clause 59, wherein the ATX-related indication is selected from an inflammatory disease, autoimmune disease, proliferative disease, cancer, and fibrosis.

Clause 61. The method of clause 60, wherein the fibrosis occurs in the liver, e.g., the fibrosis is liver fibrosis.

Clause 62. A compound for use in inhibiting autotaxin (ATX), wherein the compound is a compound or a pharmaceutically acceptable salt thereof according to any one of clauses 1 to 49.

Clause 63. A pharmaceutical composition for use in inhibiting autotaxin (ATX), wherein the pharmaceutical composition is according to clause 50.

Clause 64. Use of a compound for the manufacture of a medicament for treating an ATX-related indication, wherein the compound is a compound or a pharmaceutically acceptable salt thereof according to any one of clauses 1 to 49.

Clause 65. Use of a pharmaceutical composition for the manufacture of a medicament treating an ATX-related indication, wherein the pharmaceutical composition is according to clause 50.

Clause 66. The use of clause 64 or 65, wherein the ATX-related indication is selected from an inflammatory disease, autoimmune disease, proliferative disease, cancer, and fibrosis.

Clause 67. The use of clause 66, wherein the fibrosis occurs in the liver, e.g., the fibrosis is liver fibrosis.

Clause 68. A compound of formula (II):

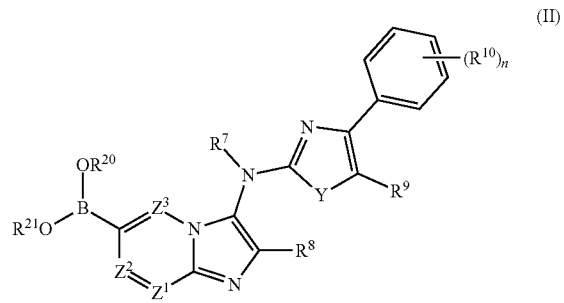

(II)

or a pharmaceutically acceptable salt or isomer thereof, wherein:

$Z^1$, $Z^2$, and $Z^3$ are independently selected from C—$R^1$ and N;

$R^{20}$ and $R^{21}$ are each independently selected from H, and optionally substituted —($C_1$-$C_6$)alkyl; or $R^{20}$ and $R^{21}$ together with the boron atom to which they are attached from an optionally substituted heterocycle;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^7$ is selected from H—, and optionally substituted ($C_1$-$C_6$)alkyl-;

$R^8$ is selected from —H, -halogen, and optionally substituted —($C_1$-$C_6$)alkyl;

$R^9$ and each $R^{10}$ are independently selected from —H, -halogen, —CN, —OH, optionally substituted —($C_1$-$C_6$)alkoxy, —$NH_2$, substituted amino, optionally substituted —($C_1$-$C_6$)alkyl-$NH_2$ and optionally substituted —($C_1$-$C_6$)alkyl; and n is 0, 1, 2, 3, 4, or 5.

Clause 69. The compound of clause 68, wherein the compound is:

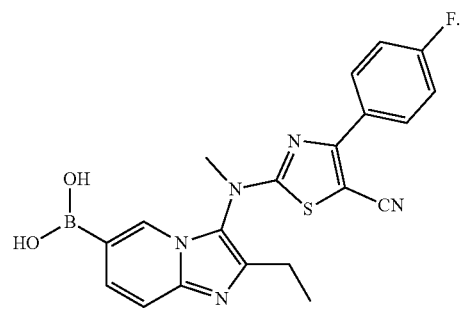 [SMILES: CCc1nc2ccc(B(O)O)cn2c1N(C)c1nc(-c2ccc(F)cc2)c(C#N)s1]

Clause 70. A compound of formula (III):

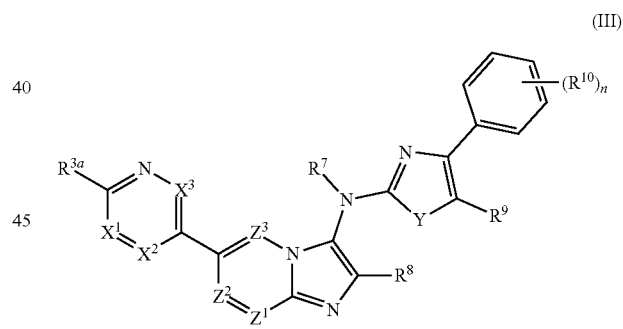

(III)

or a pharmaceutically acceptable salt or isomer thereof, wherein:

$X^1$, $X^2$, and $X^3$ are independently selected from C—$R^1$ and N;

$Z^1$, $Z^2$, and $Z^3$ are independently selected from C—$R^1$ and N;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^{3a}$ is selected from optionally substituted $R^4$—C(O)—($C_1$-$C_3$)alkyl-, $R^4$C(O)—, halogen, optionally substituted monocyclic or bicyclic carbocycle, optionally substituted monocyclic or bicyclic heterocycle, $R^5R^6$HC—, and $R^5R^6$N—;

$R^4$ is selected from $H_2N-$, $HO-$, $R^5R^6N-$, optionally substituted $(C_1-C_{10})$alkyl-, optionally substituted $(C_1-C_{10})$alkoxy-, optionally substituted monocyclic or bicyclic carbocycle, optionally substituted monocyclic or bicyclic heterocycle, optionally substituted cycloalkyl-$(C_1-C_6)$alkylene-, and optionally substituted heterocycle-$(C_1-C_6)$alkylene-;

$R^5$ and $R^6$ are independently selected from $H-$, $H_2N-$, $HO-$, optionally substituted $(C_1-C_{10})$alkyl-, optionally substituted monocyclic or bicyclic carbocycle, optionally substituted monocyclic or bicyclic heterocycle, optionally substituted $R^4C(O)-(C_1-C_{10})$alkyl-, $R^4C(O)-$, $R^4-$, and substituted amino;

or $R^5$ and $R^6$ together with the nitrogen or carbon atom to which they are attached are cyclically linked to form an optionally substituted carbocycle or an optionally substituted heterocycle;

$R^7$ is selected from $H-$, and optionally substituted $(C_1-C_6)$alkyl-;

$R^8$ is selected from $-H$, -halogen, and optionally substituted $-(C_1-C_6)$alkyl;

$R^9$ and each $R^{10}$ are independently selected from $-H$, -halogen, $-CN$, $-OH$, optionally substituted $-(C_1-C_6)$alkoxy, $-NH_2$, substituted amino, optionally substituted $-(C_1-C_6)$alkyl-$NH_2$ and optionally substituted $-(C_1-C_6)$alkyl; and n is 0, 1, 2, 3, 4, or 5.

Clause 71. The compound of clause 70, wherein the compound is selected from compounds 128-132, and 134-149 of Table 1A.

As described herein, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

5. EXAMPLES

The following examples are offered to illustrate the present disclosure and are not to be construed in any way as limiting the scope of the present technology. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

Unless otherwise stated, all temperatures are in degrees Celsius. Efforts have been made to ensure accuracy with respect to numbers used (e.g., amounts, temperatures, etc.), but some experimental errors and deviation should be allowed for.

All experiments conformed to the ethical guidelines for investigation in conscious animals and in full compliance with the central Israeli animal care commission.

In the examples below, if an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
$Cs_2CO_3$=cesium carbonate
NaH=sodium hydride
o/n=overnight
HATU=1-[Bis(dimethylamino)methylene]-1H-1,2,3-trIzolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
DIEA=diisopropylethylamine
equiv.=equivalent
EtOAc or EA=ethyl acetate
EtOH=ethanol
EDCI=1-ethyl-3-(3-dimethylaminopropyl)carbodiimide
g=gram
h=hours
HCl=hydrochloric acid
HPLC=high-performance liquid chromatography
HOAc=acetic acid
HOBT=hydroxybenzotriazole
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
ppm=parts per million
TFA=trifluoroacetic acid
TLC=thin layer chromatography
TsOH=p-Toluenesulfonic acid
UV=ultraviolet
wt %=weight percent
µM=micromolar

5.1. General Synthetic Methods

Compound Characterization

Final compounds were confirmed by HPLC/MS analysis and determined to be >90% pure by weight. $^1H$ and $^{13}C$ NMR spectra were recorded in $CDCl_3$ (residual internal standard $CHCl_3$=δ 7.26), DMSO-$d_6$ (residual internal standard $CD_3SOCD_2H$=δ 2.50), methanol-d4 (residual internal standard CD2HOD=δ 3.20), or acetone-d6 (residual internal standard $CD_3COCD_2H$=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

5.2. Example 1—Synthesis of Amino-Linked Pyrimidine-Type Compounds
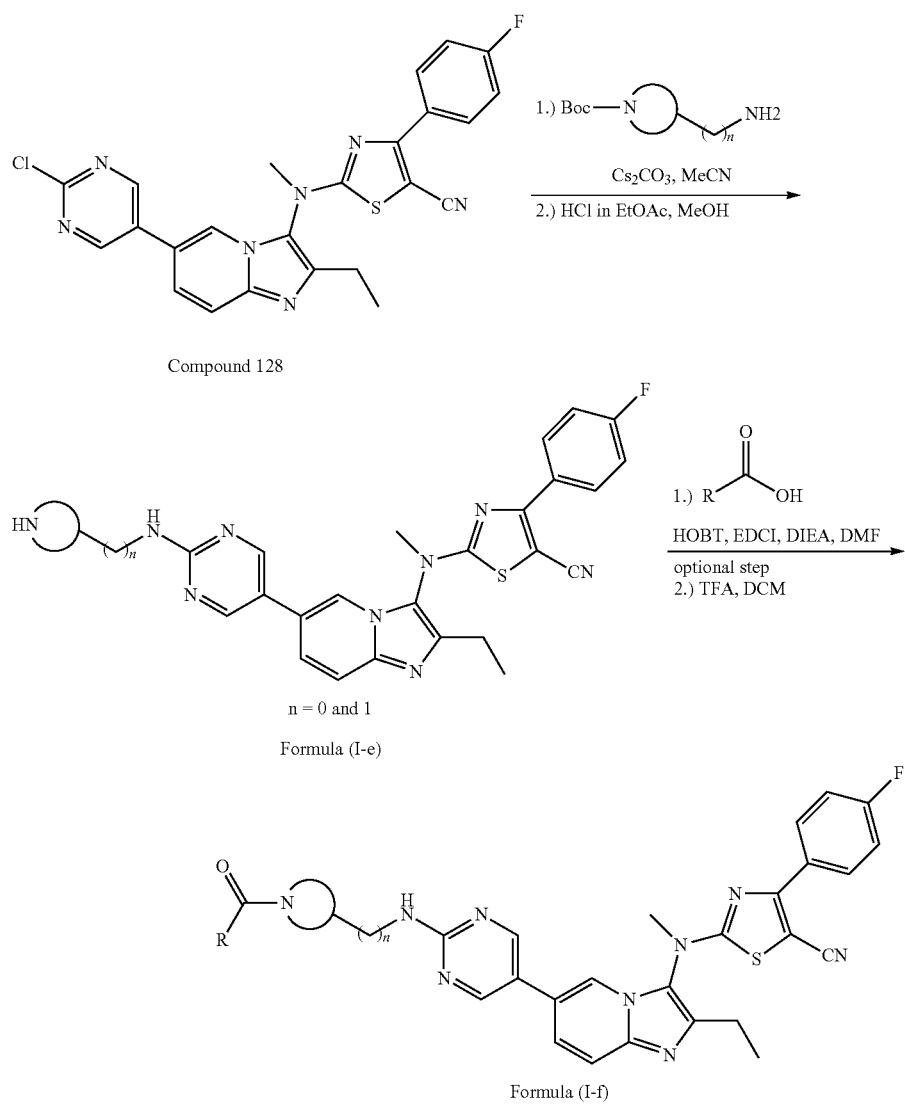
5.2.1. Synthesis of Compound 128
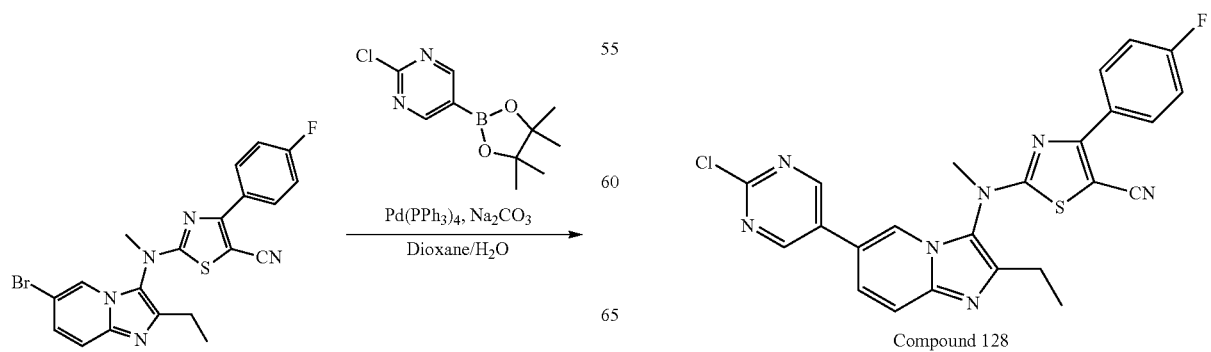

A mixture of 2-((6-bromo-2-ethylimidazo[1,2-a]pyridin-3-yl)(methyl)amino)-4-(4-fluorophenyl)thiazole-5-carbonitrile (2 g, 4.38 mmol), 2-chloro-5-(4,4,5,5-tetramethyl-1,3,2-dioxaborolan-2-yl)pyrimidine (1.16 g, 4.82 mmol), Pd(PPh$_3$)$_4$ (1.01 g, 876.55 umol), Na$_2$CO$_3$ (1.86 g, 17.53 mmol) was dissolved in dioxane (40 mL) and water (10 mL) and stirred at 80° C. under N$_2$ for 6 h. The mixture was cooled to room temperature, then diluted with water (100 mL), extracted with EA (50 mL×2). The organic layer was dried over Na$_2$SO$_4$ and evaporated, the residue was purified by silica gel (PE:EA=1:1) to afford compound 128, 2-((6-(2-chloropyrimidin-5-yl)-2-ethylimidazo[1,2-a]pyridin-3-yl)(methyl)amino)-4-(4-fluorophenyl)thiazole-5-carbonitrile (2 g, 88.29% yield) as a brown solid. MS: m/z=490.2 (M+1, ESI+).

5.2.2. Synthesis of Compound 21

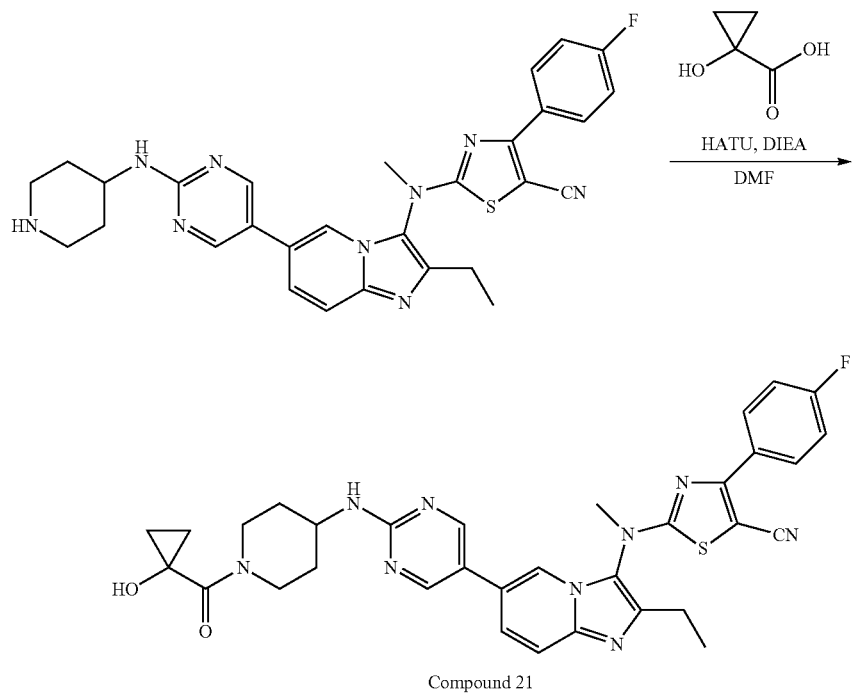

Compound 21

To a solution of 2-((2-ethyl-6-(2-(piperidin-4-ylamino)pyrimidin-5-yl)imidazo[1,2-a]pyridin-3-yl) (methyl)amino)-4-(4-fluorophenyl)thiazole-5-carbonitrile (150 mg, 270.93 umol) and 1-hydroxy cyclopropane-1-carboxylic acid (33.19 mg, 325.11 umol) in DMF (5 mL) was added HATU (153.32 mg, 406.39 umol) and DIEA (140.06 mg, 1.08 mmol), the reaction mixture was stirred at 25° C. for 6 h. The reaction mixture was poured into water (50 mL) and extracted with EA (10 mL×3). The combined organic layers were dried over Na$_2$SO$_4$ and concentrated under reduced pressure and purified by Prep-HPLC to afford compound 21 2-((2-ethyl-6-(2-((1-(1-hydroxycyclopropane-1-carbonyl)piperidin-4-yl)amino)pyrimidin-5-yl)imidazo[1,2-a]pyridin-3-yl)(methyl)amino)-4-(4-fluorophenyl) thiazole-5-carbonitrile (51 mg, 29.53% yield) as a white solid. $^1$H NMR (400 MHz, DMSO-d$_6$) δ 8.70 (s, 2H), 8.63 (s, 1H), 8.11-8.07 (t, 2H), 7.68 (s, 2H), 7.45-7.40 (m, 3H), 6.30 (s, 1H), 4.32 (s, 2H), 4.03-4.00 (m, 1H), 3.63 (s, 3H), 2.70-2.64 (dd, 2H), 1.91-1.88 (d, 2H), 1.42 (s, 2H), 1.28-1.17 (m, 5H), 0.90-0.87 (m, 2H), 0.76-0.73 (m, 2H); MS: m/z=638.2 (M+1, ESI+).

5.2.3. Synthesis of Compound 22

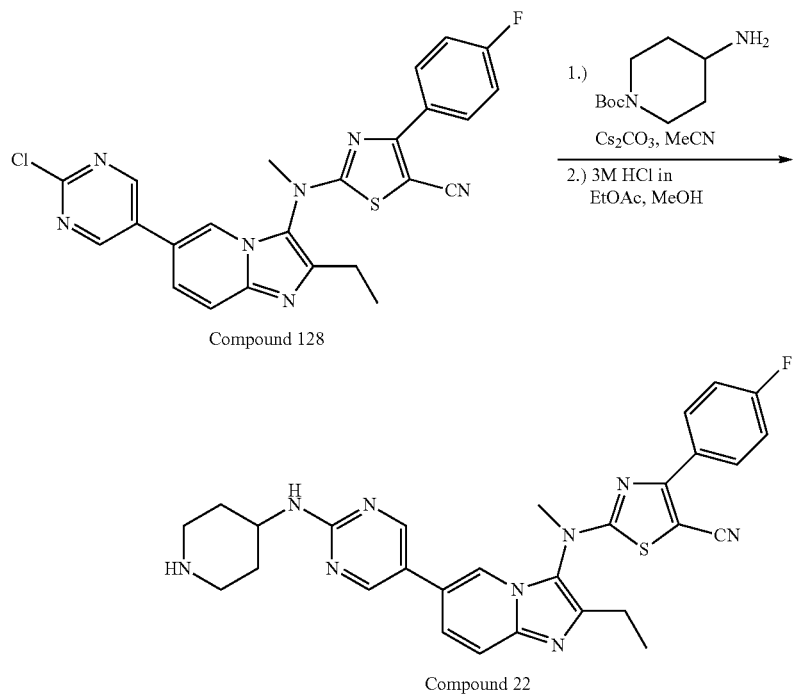

Step One:

To a solution of compound 128, 2-((6-(2-chloropyrimidin-5-yl)-2-ethylimidazo[1,2-a]pyridin-3-yl)(methyl)amino)-4-(4-fluoro phenyl)thiazole-5-carbonitrile (500 mg, 1.02 mmol) and tert-butyl 4-aminopiperidine-1-carboxylate (245.26 mg, 1.22 mmol) in MeCN (20 mL) was added $Cs_2CO_3$ (997.50 mg, 3.06 mmol), the reaction mixture was stirred at 90° C. for 16 h. The reaction mixture was concentrated under reduced pressure and the residue was purified by column chromatography to afford tert-butyl4-((5-(3-((5-cyano-4-(4-fluorophenyl)thiazol-2-yl)(methyl)amino)-2-ethylimidazo[1,2-a] pyridine-6-yl)pyrimidin-2-yl)amino) piperidine-1-carboxylate (550 mg, 82.44% yield) as a brown solid. MS: m/z=654.2 (M+1, ESI+).

Step Two:

To a solution of tert-butyl 4-((5-(3-((5-cyano-4-(4-fluorophenyl)thiazol-2-yl)(methyl)amino)-2-ethyl imidazo[1,2-a] pyridin-6-yl)pyrimidin-2-yl)amino)piperidine-1-carboxylate (300 mg, 458.88 umol) in MeOH (3 mL) was added 3M HCl in EA (3 M, 5 mL). The reaction mixture was stirred at 25° C. for 1 h. The excess of solvent was removed under reduced pressure. The residue was purified by Prep-HPLC to afford compound 22, 2-((2-ethyl-6-(2-(piperidin-4-ylamino)pyrimidin-5-yl)imidazo[1,2-a]pyridin-3-yl)(methyl)amino)-4-(4-fluorophenyl)thiazole-5-carbonitrile (20 mg, 7.87% yield) as a yellow solid. $^1$H NMR (400 MHz, DMSO-d6) δ 8.67 (s, 2H), 8.59 (s, 1H), 8.10-8.07 (m, 2H), 7.67 (s, 2H), 7.43-7.39 (t, 2H), 7.32-7.30 (d, 1H), 3.81-3.79 (m, 1H), 3.63 (s, 3H), 2.98-2.95 (d, 2H), 2.70-2.64 (dd, 2H), 2.55 (s, 1H), 1.86-1.80 (m, 4H), 1.39-1.36 (dd, 2H), 1.28-1.25 (t, 3H); MS: m/z=554.2 (M+1, ESI+).

5.2.4. Synthesis of Compound 34

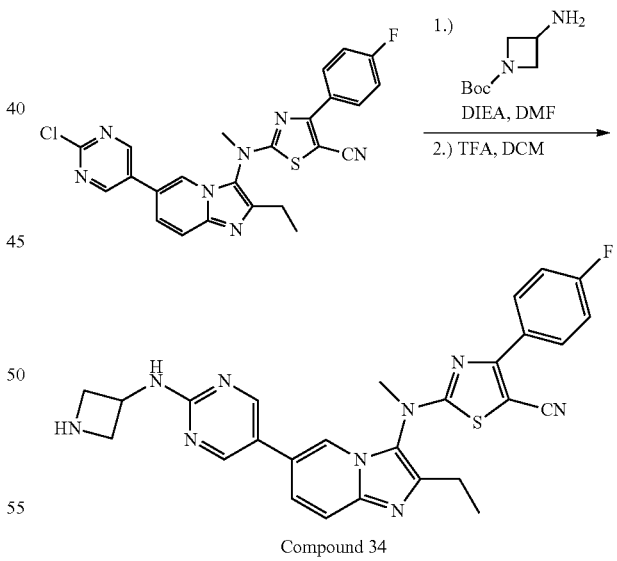

Step One:

To a solution of 2-((6-(2-chloropyrimidin-5-yl)-2-ethylimidazo[1,2-a]pyridin-3-yl)(methyl)amino)-4-(4-fluorophenyl) thiazole-5-carbonitrile (800 mg, 1.63 mmol) and tert-butyl 3-aminoazetidine-1-carboxylate (562.42 mg, 3.27 mmol) in DMF (5 mL) was added DIEA (633.09 mg, 4.9 mmol, the resulting mixture was stirred at 80° C. for 5 h. The reaction mixture was poured into water (50 mL) and extracted with DCM (10 mL×3). The combined organic layers were washed with water (50 mL×3) and brine (50 mL), dried over Na$_2$SO$_4$ and concentrated under reduced pressure and purified by column chromatography to afford tert-butyl 3-((5-(3-((5-cyano-4-(4-fluoro phenyl)thiazol-2-yl)(methyl)amino)-2-ethylimidazo[1,2-a]pyridin-6-yl)pyrimidin-2-yl)amino)azetidine-1-carboxylate (680 mg, 66.65% yield) as a yellow solid. MS: m/z=626.1 (M+1, ESI+).

Step Two:

To a solution of tert-butyl 3-((5-(3-((5-cyano-4-(4-fluorophenyl)thiazol-2-yl)(methyl)amino)-2-ethyl imidazo[1,2-a]pyridin-6-yl)pyrimidin-2-yl)amino)azetidine-1-carboxylate (680 mg, 1.09 mmol) in DCM (8 mL) was added TFA (3 g, 26.31 mmol). The reaction mixture was stirred at 25° C. for 3 h. The excess of solvent was removed under reduced pressure, the residue was purified by Prep-HPLC to afford compound 34, 2-((6-(2-(azetidin-3-ylamino) pyrimidin-5-yl)-2-ethylimidazo[1,2-a]pyridin-3-yl)(methyl)amino)-4-(4-fluorophenyl)thiazole-5-carbonitrile (400 mg, 70.03% yield) as a yellow solid. $^1$H NMR (400 MHz, DMSO-d$_6$) δ 8.77 (s, 2H), 8.67 (s, 1H), 8.15-8.08 (m, 3H), 7.70 (s, 2H), 7.44-7.40 (t, 2H), 4.81-4.74 (m, 1H), 4.15-4.10 (t, 2H), 3.98-3.94 (t, 2H), 3.63 (s, 3H), 2.70-2.64 (dd, 2H), 1.28-1.25 (t, 3H); MS: m/z=526.1 (M+1, ESI+).

5.2.5. Synthesis of Compound 35

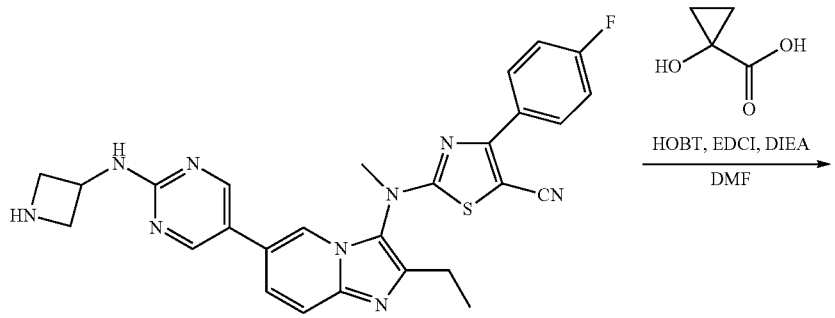

Compound 34

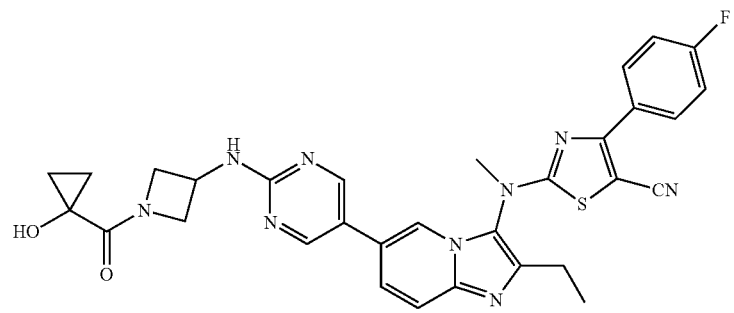

Compound 35

To a solution of compound 34, 2-((6-(2-(azetidin-3-ylamino)pyrimidin-5-yl)-2-ethylimidazo[1,2-a]pyridin-3-yl) (methyl)amino)-4-(4-fluorophenyl)thiazole-5-carbonitrile (120 mg, 228.31 umol) and 1-hydroxy cyclopropane-1-carboxylic acid (46.62 mg, 456.62 umol) in DCM (5 mL) was added HOBT (61.70 mg, 456.62 umol), EDCI (87.53 mg, 456.62 umol) and DIEA (118.03 mg, 913.24 umol), the resulting mixture was stirred at 25° C. for 1 h. The reaction mixture was poured into water (50 mL) and extracted with DCM (10 mL×3). The combined organic layers were dried over Na$_2$SO$_4$ and concentrated under reduced pressure and purified by Prep-HPLC to afford compound 35, 2-((2-ethyl-6-(2-((1-(1-hydroxycyclopropane-1-carbonyl)azetidin-3-yl)amino)pyrimidin-5-yl)imidazo[1,2-a]pyridin-3-yl) (methyl) amino)-4-(4-fluorophenyl)thiazole-5-carbonitrile (70 mg, 50.29% yield) as a white solid. $^1$H NMR (400 MHz, DMSO-d$_6$) δ 8.74 (s, 2H), 8.66 (s, 1H), 8.11-8.07 (m, 3H), 7.69 (s, 2H), 7.44-7.40 (t, 2H), 5.98 (s, 1H), 4.74-4.70 (t, 1H), 4.58-4.52 (m, 1H), 4.30 (s, 1H), 4.17-4.13 (t, 1H), 3.82 (s, 1H), 3.63 (s, 3H), 2.70-2.64 (dd, 2H), 1.28-1.25 (t, 3H), 1.03-1.00 (dd, 2H), 0.78-0.75 (dd, 2H); MS: m/z=610.1 (M+1, ESI+).

5.2.6. Synthesis of Compound 36

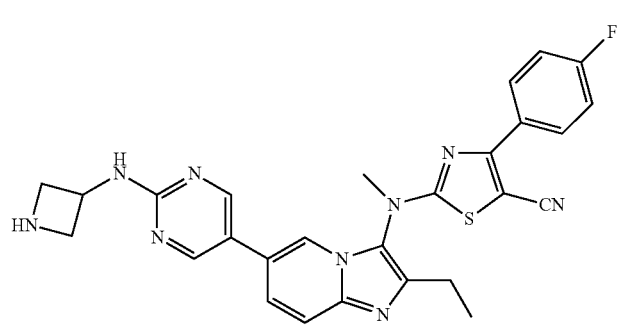

Compound 34

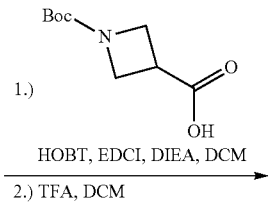

1.) HOBT, EDCI, DIEA, DCM
2.) TFA, DCM

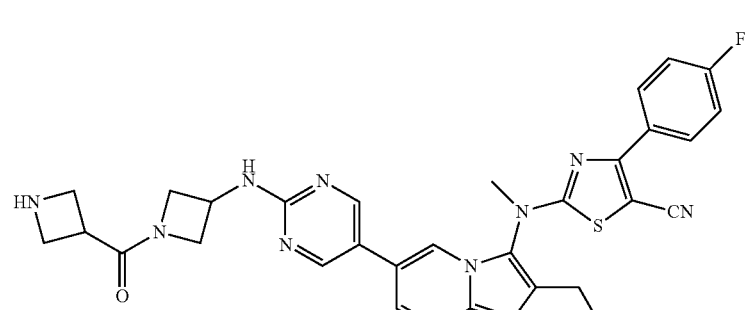

Compound 36

Step One:
To a solution of compound 34, 2-((6-(2-(azetidin-3-ylamino)pyrimidin-5-yl)-2-ethylimidazo[1,2-a]pyridin-3-yl) (methyl)amino)-4-(4-fluorophenyl)thiazole-5-carbonitrile (160 mg, 304.41 umol) and 1-(tert-butoxycarbonyl) azetidine-3-carboxylic acid (122.51 mg, 608.83 umol) in DCM (5 mL) was added HOBT (82.27 mg, 608.83 umol), EDCI (116.71 mg, 608.83 umol) and DIEA (157.37 mg, 1.22 mmol), the resulting mixture was stirred at 25° C. for 1 h. The reaction mixture was poured into water (50 mL) and extracted with DCM (10 mL×3). The combined organic layers were dried over Na$_2$SO$_4$ and concentrated under reduced pressure and purified by column chromatography to afford tert-butyl3-(3-((5-(3-((5-cyano-4-(4-fluorophenyl)thiazol-2-yl)(methyl)amino)-2-ethylimidazo[1,2-a]pyridin-6-yl) pyrimidin-2-yl)amino)azetidine-1-carbonyl)azetidine-1-carboxylate (180 mg, 83.42% yield) as a yellow solid. MS: m/z=709.2 (M+1, ESI+).

Step Two:
To a solution of tert-butyl 3-(3-((5-(3-((5-cyano-4-(4-fluorophenyl)thiazol-2-yl)(methyl)amino)-2-ethylimidazo[1,2-a]pyridin-6-yl)pyrimidin-2-yl)amino)azetidine-1-carbonyl)azetidine-1-carboxylate (150 mg, 211.62 umol) in DCM (4 mL) was added TFA (1.5 g, 13.15 mmol). The reaction mixture was stirred at 25° C. for 1 h. The excess of solvent was removed under reduced pressure, the residue was purified by Prep-HPLC to afford compound 36, 2-((6-(2-((1-(azetidine-3-carbonyl)azetidin-3-yl)amino)pyrimidin-5-yl)-2-ethylimidazo[1,2-a]pyridin-3-yl)(methyl) amino)-4-(4-fluorophenyl) thiazole-5-carbonitrile (68 mg, 52.79% yield) as a white solid. $^1$H NMR (400 MHz, DMSO-d$_6$) δ 8.75 (s, 2H), 8.66 (s, 1H), 8.34 (s, 1H), 8.11-8.07 (m, 3H), 7.69 (s, 2H), 7.44-7.40 (t, 2H), 4.60-4.56 (m, 1H), 4.35-4.31 (t, 1H), 4.18-4.14 (t, 1H), 3.93-3.73 (m, 6H), 3.63 (s, 3H), 3.56-3.50 (m, 1H), 2.70-2.64 (dd, 2H), 1.28-1.25 (t, 3H); MS: m/z=609.1 (M+1, ESI+).

5.2.7. Synthesis of Compound 37

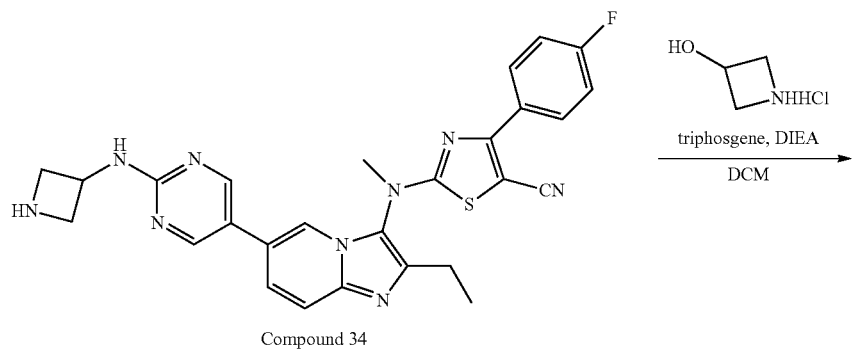

Compound 34

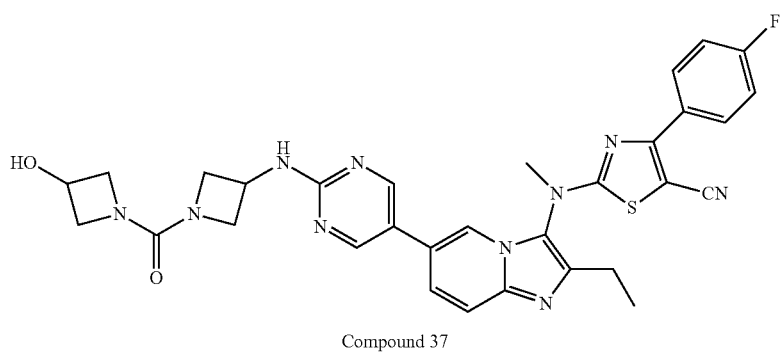

Compound 37

To a solution of compound 34, 2-((6-(2-(azetidin-3-ylamino)pyrimidin-5-yl)-2-ethylimidazo[1,2-a]pyridin-3-yl)(methyl)amino)-4-(4-fluorophenyl)thiazole-5-carbonitrile (200 mg, 380.52 umol) in DCM (5 mL) was added triphosgene (56.46 mg, 190.26 umol) and stirred at 0° C. for 0.5 h, then DIEA (147.54 mg, 1.14 mmol) was added and stirred at 0° C. for another 0.5 h. After that, azetidin-3-ol hydrochloride (55.63 mg, 761.03 umol) was added to the above reaction mixture and stirred at 25° C. for 0.5 h. Added water (50 mL) to the reaction mixture, then extracted with DCM (50 mL×2). The organic layer was washed with water (50 mL×2) and brine (50 mL), dried over $Na_2SO_4$ and concentrated. The residue was purified by Prep-HPLC to afford compound 37, 2-((2-ethyl-6-(2-((1-(3-hydroxyazetidine-1-carbonyl)azetidin-3-yl)amino)pyrimidin-5-yl)imidazo[1,2-a]pyridin-3-yl)(methyl)amino)-4-(4-fluorophenyl)thiazole-5-carbonitrile (105 mg, 44.17% yield) as a white solid. $^1$H NMR (400 MHz, DMSO-$d_6$) δ 8.73 (s, 2H), 8.66 (s, 1H), 8.09-8.03 (m, 3H), 7.69 (s, 2H), 7.44-7.40 (t, 2H), 5.60-5.58 (d, 1H), 4.56-4.53 (m, 1H), 4.39-4.35 (m, 1H), 4.10-4.07 (t, 2H), 3.99-3.95 (t, 2H), 3.76 (s, 2H), 3.63 (s, 3H), 3.59-3.55 (m, 2H), 2.69-2.64 (dd, 2H), 1.28-1.23 (t, 3H); MS: m/z=625.1 (M+1, ESI+).

5.2.8. Synthesis of Compound 38 Formate

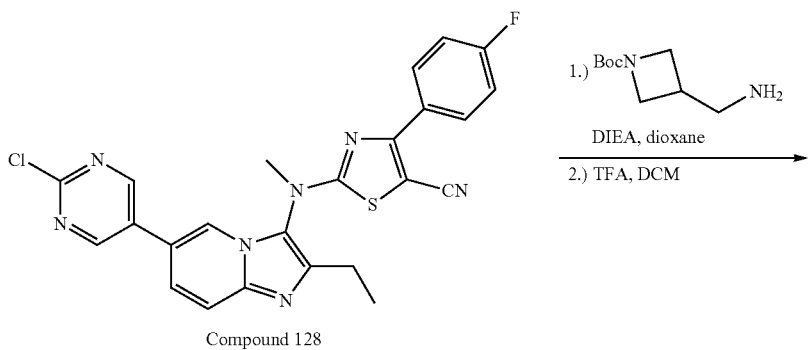

Compound 128

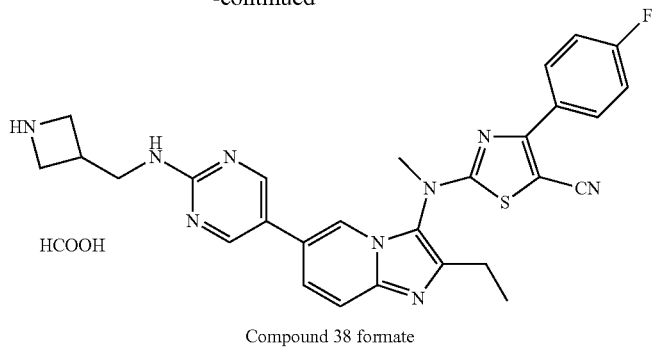

Compound 38 formate

Step One:

To a solution of compound 128, 2-((6-(2-chloropyrimidin-5-yl)-2-ethylimidazo[1,2-a]pyridin-3-yl)(methyl)amino)-4-(4-fluorophenyl) thiazole-5-carbonitrile (900 mg, 1.84 mmol) and tert-butyl 3-(aminomethyl) azetidine-1-carboxylate (411.24 mg, 2.21 mmol) in dioxane (15 mL) was added DIEA (951.23 mg, 7.36 mmol), the resulting mixture was stirred at 100° C. for 16 h. After cooled to room temperature, the reaction mixture was poured into water (150 mL) and extracted with EA (50 mL×3). The combined organic layers were dried over Na$_2$SO$_4$ and concentrated under reduce pressure and purified by column chromatography to afford tert-butyl 3-(((5-(3-((5-cyano-4-(4-fluoro phenyl)thiazol-2-yl)(methyl)amino)-2-ethylimidazo[1,2-a]pyridin-6-yl)pyrimidin-2-yl)amino)methyl)azetidine-1-carboxylate (820 mg, 69.66% yield) as a yellow solid. MS: m/z=640.3 (M+1, ESI+).

Step Two:

To a solution of tert-butyl 3-(((5-(3-((5-cyano-4-(4-fluorophenyl)thiazol-2-yl)(methyl)amino)-2-ethylimidazo[1,2-a]pyridin-6-yl)pyrimidin-2-yl)amino)methyl)azetidine-1-carboxylate (800 mg, 1.25 mmol) in DCM (15 mL) was added TFA (142.59 mg, 1.25 mmol). The reaction mixture was stirred at 25° C. for 1 h. The excess of solvent was removed under reduced pressure, the residue was purified by Prep-HPLC to afford compound 38 formate, 2-((6-(2-((azetidin-3-ylmethyl) amino)pyrimidin-5-yl)-2-ethyl imidazo[1,2-a]pyridin-3-yl)(methyl)amino)-4-(4-fluorophenyl)thiazole-5-carbonitrile formate (400 mg, 59.28% yield) as a yellow solid. $^1$H NMR (400 MHz, DMSO-d$_6$) δ 8.70 (s, 2H), 8.63 (s, 1H), 8.38 (s, 1H), 8.11-8.07 (t, 2H), 7.69 (s, 2H), 7.63-7.60 (t, 1H), 7.44-7.40 (t, 2H), 3.87-3.82 (t, 2H), 3.67-3.63 (m, 5H), 3.53-3.50 (t, 2H), 3.02-2.97 (m, 1H), 2.69-2.64 (dd, 3H), 1.28-1.25 (t, 3H); MS: m/z=540.2 (M+1, ESI+).

5.2.9. Synthesis of Compound 39

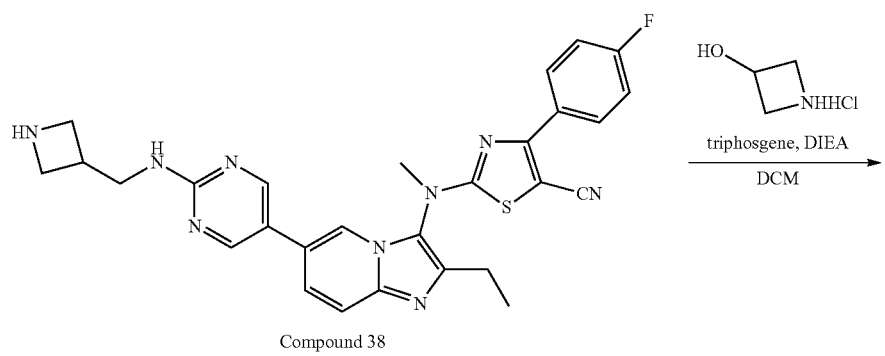

Compound 38

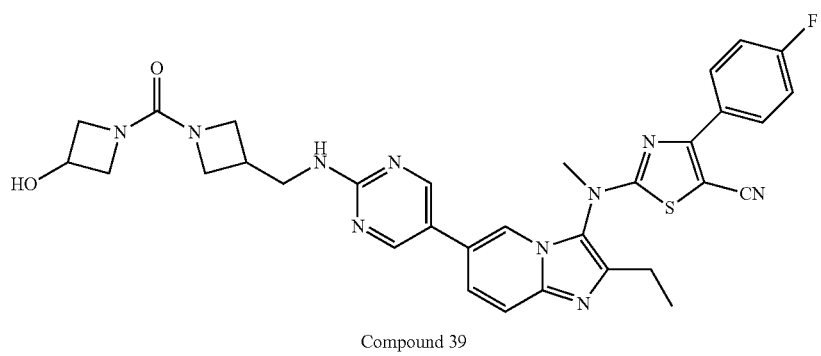

Compound 39

To a solution of compound 38, 2-((6-(2-((azetidin-3-ylmethyl)amino)pyrimidin-5-yl)-2-ethylimidazo[1,2-a]pyridin-3-yl)(methyl)amino)-4-(4-fluorophenyl)thiazole-5-carbonitrile (160 mg, 296.50 umol) in DCM (5 mL) was added triphosgene (54.99 mg, 185.31 umol) and stirred at 0° C. for 0.5 h, then DIEA (191.28 mg, 1.48 mmol) was added and stirred at 0° C. for another 0.5 h. After that, azetidin-3-ol hydrochloride (43.86 mg, 0.6 mmol) was added to the above reaction mixture and stirred at 25° C. for 0.5 h. Added water (50 mL) to the reaction mixture, then extracted with DCM (50 mL×2). The organic layer was washed with water (50 mL×2) and brine (50 mL), dried over $Na_2SO_4$ and concentrated. The residue was purified by Prep-HPLC to afford compound 39, 2-((2-ethyl-6-(2-(((1-(3-hydroxyazetidine-1-carbonyl)azetidin-3-yl)methyl)amino)pyrimidin-5-yl)imidazo[1,2-a]pyridin-3-yl)(methyl)amino)-4-(4-fluorophenyl)thiazole-5-carbonitrile (24 mg, 12.69% yield) as a white solid. $^1$H NMR (400 MHz, DMSO-$d_6$) δ 8.69 (s, 2H), 8.63 (s, 1H), 8.11-8.07 (t, 2H), 7.68 (s, 2H), 7.62-7.59 (t, 1H), 7.44-7.40 (t, 2H), 5.57 (s, 1H), 4.36 (s, 1H), 3.96-3.93 (t, 2H), 3.85-3.81 (t, 2H), 3.63 (s, 3H), 3.58-3.53 (m, 4H), 3.50-3.47 (t, 2H), 2.79-2.75 (m, 1H), 2.69-2.64 (dd, 2H), 1.28-1.24 (t, 3H); MS: m/z=639.2 (M+1, ESI+).

5.2.10. Synthesis of Compound 40

2.22 mmol), the resulting mixture was stirred at 25° C. for 3 h. The reaction mixture was poured into water (50 mL) and extracted with EA (10 mL×3). The combined organic layers were washed with water (50 mL×2) and brine (50 mL), dried over $Na_2SO_4$ and concentrated under reduced pressure and purified by column chromatography to afford tert-butyl 3-(3-(((5-(3-((5-cyano-4-(4-fluoro phenyl)thiazol-2-yl)(methyl)amino)-2-ethylimidazo[1,2-a]pyridin-6-yl)pyrimidin-2-yl)amino)methyl)azetidine-1-carbonyl)azetidine-1-carboxylate (350 mg, 87.28% yield) as a brown solid. MS: m/z=723.3 (M+1, ESI+).

Step Two:
To a solution of tert-butyl 3-(3-(((5-(3-((5-cyano-4-(4-fluorophenyl)thiazol-2-yl)(methyl)amino)-2-ethylimidazo[1,2-a]pyridin-6-yl)pyrimidin-2-yl)amino)methyl)azetidine-1-carbonyl)azetidine-1-carboxylate (350 mg, 484.21 umol) in DCM (4 mL) was added TFA (2 mL). The reaction mixture was stirred at 25° C. for 16 h. The excess of solvent was removed under reduced pressure, the residue was purified by Prep-HPLC to afford compound 40, 2-((6-(2-(((1-(azetidine-3-carbonyl)azetidin-3-yl)methyl)amino)pyrimidin-5-yl)-2-ethylimidazo[1,2-a]pyridin-3-yl)(methyl)amino)-4-(4-fluoro phenyl)thiazole-5-carbonitrile (30 mg, 9.95% yield) as a white solid. $^1$H NMR (400 MHz, DMSO-$d_6$) δ 8.69 (s, 2H), 8.63 (s, 1H), 8.09 (s, 2H), 7.68 (s, 2H), 7.64-7.62 (t, 1H), 7.44-7.40 (t, 2H), 4.06-4.02 (t, 1H), 3.89-3.74 (m, 3H), 3.69-3.54 (m, 6H), 3.50-3.41 (m, 5H), 2.81 (s, 1H), 2.69-2.64 (dd, 2H), 1.28-1.24 (t, 3H); MS: m/z=623.1 (M+1, ESI+).

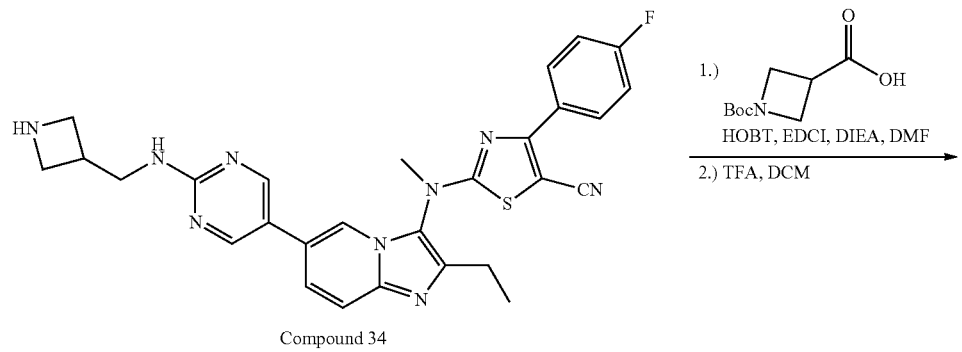

Compound 34

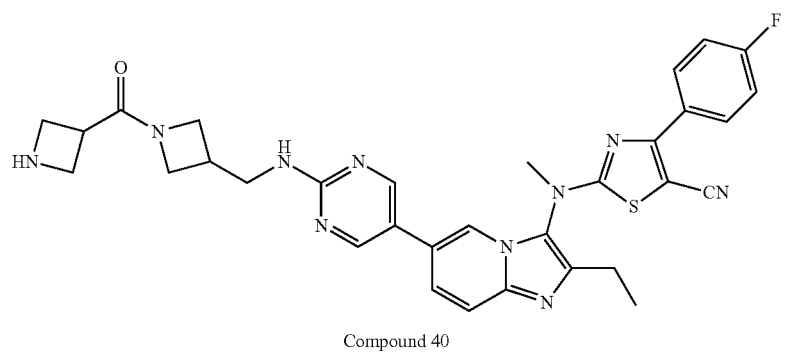

Compound 40

Step One:
To a solution of compound 34, 2-((6-(2-((azetidin-3-ylmethyl)amino)pyrimidin-5-yl)-2-ethylimidazo[1,2-a]pyridin-3-yl)(methyl)amino)-4-(4-fluorophenyl)thiazole-5-carbonitrile (300 mg, 555.94 umol) and 1-(tert-butoxycarbonyl)azetidine-3-carboxylic acid (123.05 mg, 611.53 umol) in DMF (6 mL) was added HOBT (90.14 mg, 667.13 umol), EDCI (127.89 mg, 667.13 umol) and DIEA (287.40 mg,

5.2.11. Synthesis of Compound 41

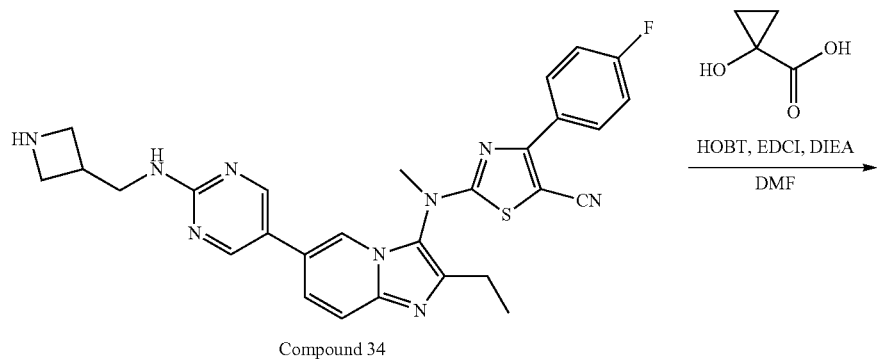
Compound 34

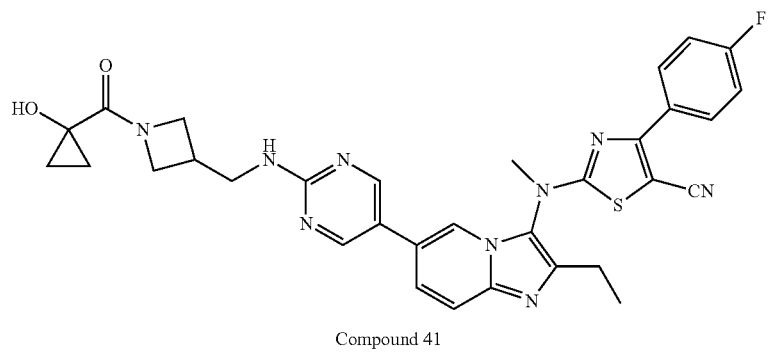
Compound 41

To a solution of compound 34, 2-((6-(2-((azetidin-3-ylmethyl)amino)pyrimidin-5-yl)-2-ethylimidazo[1,2-a]pyridin-3-yl)(methyl)amino)-4-(4-fluorophenyl)thiazole-5-carbonitrile (41.62 mg, 407.69 umol) in DMF (4 mL) was added HOBT (60.09 mg, 444.75 umol), EDCI (85.26 mg, 444.75 umol) and DIEA (191.60 mg, 1.48 mmol), the resulting mixture was stirred at 25° C. for 3 h. The reaction mixture was poured into water (50 mL) and extracted with EA (10 mL×3). The combined organic layers were washed with water (50 mL×2) and brine (50 mL), dried over Na$_2$SO$_4$ and concentrated under reduced pressure and purified by column chromatography to afford compound 41, 2-((2-ethyl-6-(2-(((1-(1-hydroxy cyclopropane-1-carbonyl)azetidin-3-yl)methyl)amino)pyrimidin-5-yl)imidazo[1,2-a]pyridin-3-yl)(methyl)amino)-4-(4-fluoro phenyl)thiazole-5-carbonitrile (70 mg, 30.28% yield) as a white solid. $^1$H NMR (400 MHz, DMSO-d$_6$) δ 8.70 (s, 2H), 8.64 (s, 1H), 8.11-8.07 (t, 2H), 7.68 (s, 2H), 7.66-7.64 (t, 1H), 7.44-7.40 (t, 2H), 5.94 (s, 1H), 4.48-4.44 (t, 1H), 4.18-4.15 (m, 1H), 3.90-3.86 (t, 1H), 3.63-3.60 (m, 4H), 3.54-3.51 (t, 2H), 2.85-2.78 (m, 1H), 2.69-2.64 (dd, 2H), 1.28-1.25 (t, 3H), 0.99-0.98 (d, 2H), 0.74-0.73 (d, 2H); MS: m/z=624.2 (M+1, ESI+).

5.3. Example 2—Synthesis of Azetidine-Linked Pyrimidine-Type Compounds

General Scheme 2

Route A

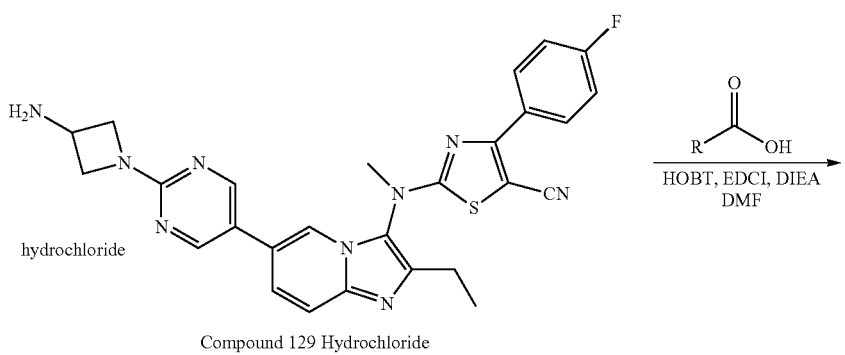
Compound 129 Hydrochloride

-continued
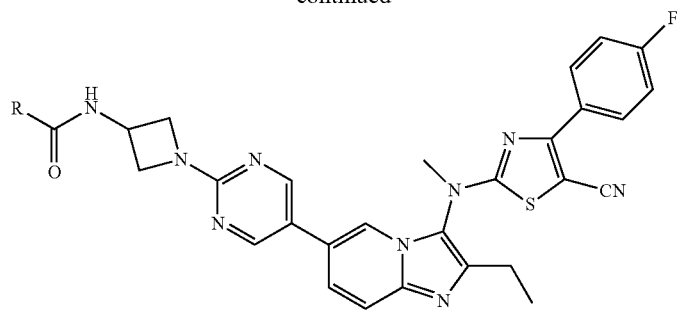
Formula (I-g)
Route B
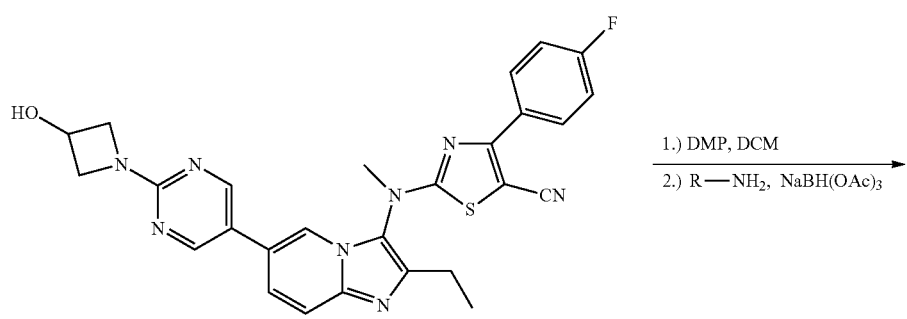
Compound 130
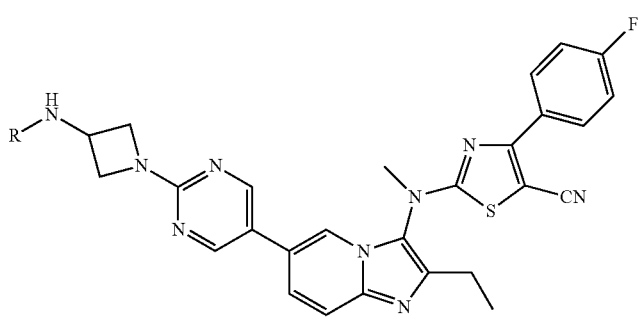
Formula (I-h)
Route C
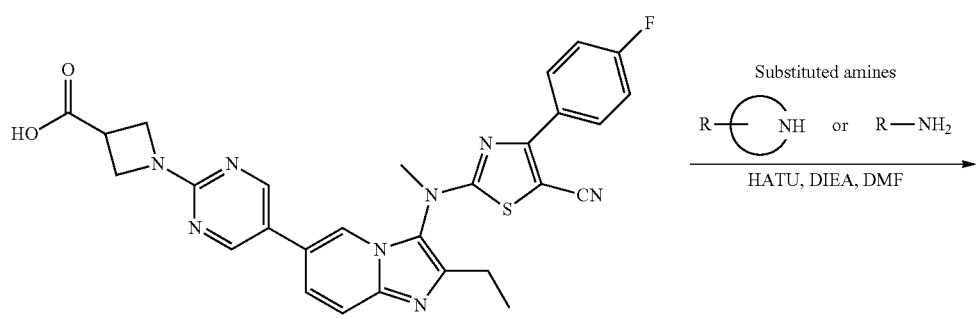
Compound 132

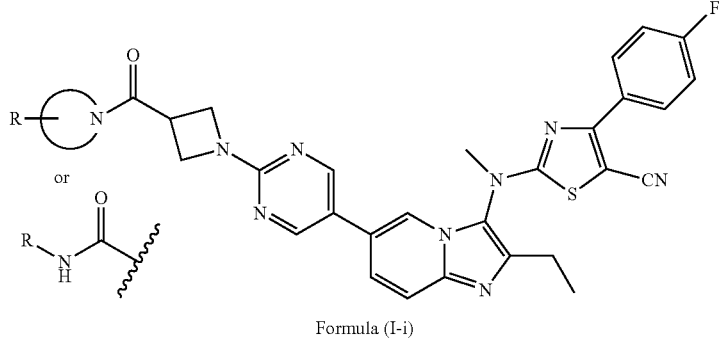

Formula (I-i)

5.3.1. Synthesis of Compound 129 Hydrochloride

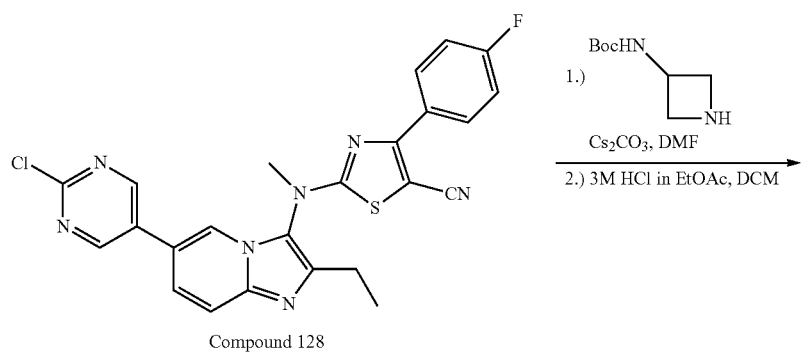

Compound 128

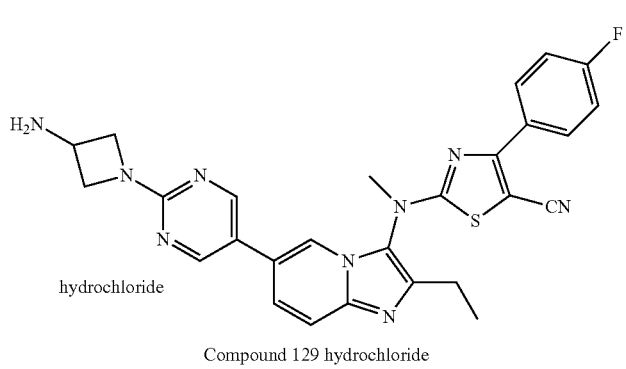

Compound 129 hydrochloride

Step One:

A mixture of compound 128, 2-((6-(2-chloropyrimidin-5-yl)-2-ethylimidazo[1,2-a]pyridin-3-yl)(methyl)amino)-4-(4-fluorophenyl) thiazole-5-carbonitrile (1 g, 2.04 mmol) and tert-butyl azetidin-3-ylcarbamate (386.66 mg, 2.25 mmol) in DMF (20 mL) was added $Cs_2CO_3$ (1.99 g, 6.12 mmol) and stirred at 25° C. for 3 h. The reaction mixture was diluted with water (100 mL), extracted with DCM (30 mL×3) and dried over $Na_2SO_4$. The organic layer was evaporated to afford tert-butyl (1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamate (1.1 g, 86.13% yield) as a brown solid. MS: m/z=626.3 (M+1, ESI+).

To a solution of tert-butyl (1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamate (1.2 g, 1.92 mmol) in DCM (20 mL) was added HCl (3 M in EA, 12.79 mL), the mixture was stirred at 25° C. for 3 h. Then concentrated, the residue was washed with EA (30 mL), the solid was collected to afford compound 129 hydrochloride, 2-((6-(2-(3-aminoazetidin-1-yl)pyrimidin-5-yl)-2-ethylimidazo[1,2-a]pyridin-3-yl)(methyl)amino)-4-(4-fluorophenyl) thiazole-5-carbonitrile hydrochloride (1 g, 99.00% yield) as a white solid. MS: m/z=526.3 (M+1, ESI+).

5.3.2. Synthesis of Compound 130

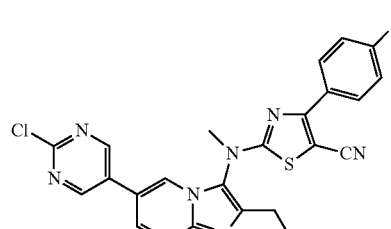
Compound 128

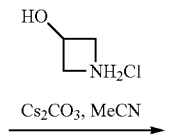

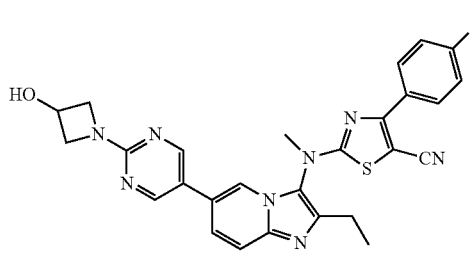
Compoudn 130

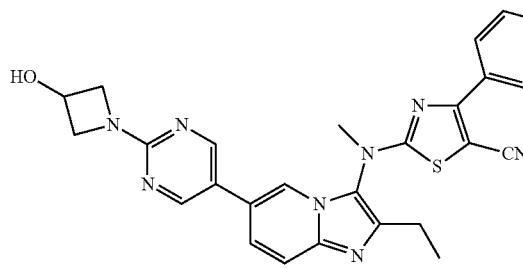
Compound 130

To a solution of compound 128, 2-((6-(2-chloropyrimidin-5-yl)-2-ethylimidazo[1,2-a]pyridin-3-yl)(methyl) amino)-4-(4-fluorophenyl) thiazole-5-carbonitrile (1.2 g, 2.45 mmol) and azetidin-3-ol hydrochloride (321.99 mg, 2.94 mmol) in MeCN (30 mL) was added $Cs_2CO_3$ (2.39 g, 7.35 mmol). The reaction mixture was stirred at 70° C. for 3 h. The reaction mixture was concentrated under reduced pressure and the residue was purified by column chromatography to afford compound 130, 2-((2-ethyl-6-(2-(3-hydroxyazetidin-1-yl)pyrimidin-5-yl)imidazo[1,2-a]pyridin-3-yl)(methyl)amino)-4-(4-fluorophenyl)thiazole-5-carbonitrile (850 mg, 65.91% yield) as a yellow solid. MS: m/z=527.1 (M+1, ESI+).

5.3.3. Synthesis of Compound 131

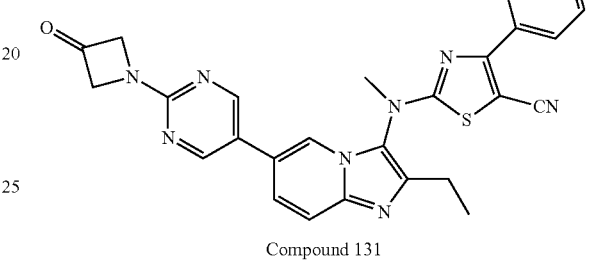
Compound 131

To a solution of compound 130, 2-((2-ethyl-6-(2-(3-hydroxyazetidin-1-yl)pyrimidin-5-yl)imidazo[1,2-a]pyridin-3-yl)(methyl)amino)-4-(4-fluorophenyl)thiazole-5-carbonitrile (800.00 mg, 1.52 mmol) in DCM (20 mL) was added Dess-Martin (1.29 g, 3.04 mmol). The reaction mixture was stirred at 25° C. for 3 h. The reaction mixture was concentrated under reduced pressure and the residue was purified by column chromatography to afford compound 131, 2-((2-ethyl-6-(2-(3-oxoazetidin-1-yl)pyrimidin-5-yl)imidazo[1,2-a]pyridin-3-yl)(methyl)amino)-4-(4-fluorophenyl)thiazole-5-carbonitrile (680 mg, 85.33% yield) as a yellow solid. MS: m/z=525.4 (M+1, ESI+).

5.3.4. Synthesis of Compound 132

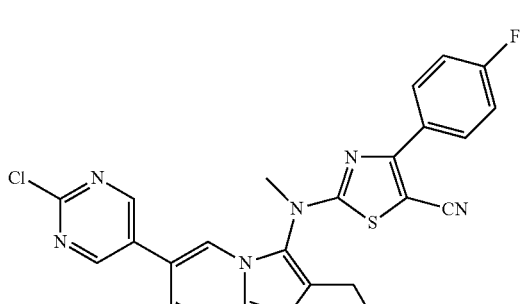
Compound 128

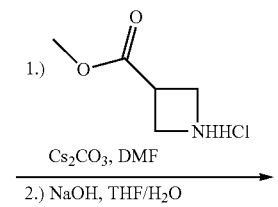

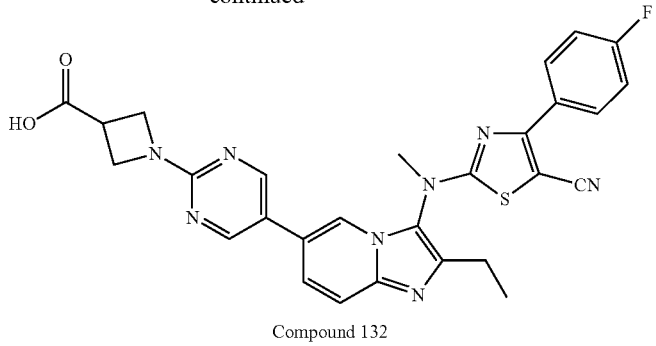

Compound 132

Step One:

To a solution of compound 128 2-((6-(2-chloropyrimidin-5-yl)-2-ethylimidazo[1,2-a]pyridin-3-yl)(methyl)amino)-4-(4-fluorophenyl) thiazole-5-carbonitrile (800 mg, 1.63 mmol) and methyl azetidine-3-carboxylate hydrochloride (369.79 mg, 2.45 mmol) in DMF (10 mL) was added $Cs_2CO_3$ (2.13 g, 6.53 mmol), the resulting mixture was stirred at 100° C. for 2 h. The reaction mixture was poured into water (100 mL) and extracted with EA (30 mL×3). The combined organic layers were washed with water (100 mL×3) and brine (100 mL), dried over $Na_2SO_4$ and concentrated under reduce pressure, the residue was purified by column chromatography to afford methyl 1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxylate (800 mg, 86.16% yield) as a brown solid. MS: m/z=569.1 (M+1, ESI+).

Step Two:

To a solution of methyl 1-(5-(3-((5-cyano-4-(4-fluorophenyl)thiazol-2-yl)(methyl)amino)-2-ethyl imidazo[1,2-a]pyridin-6-yl)pyrimidin-2-yl)azetidine-3-carboxylate (800 mg, 1.41 mmol) in THF (10 mL) and $H_2O$ (5 mL) was added NaOH (112.55 mg, 2.81 mmol) and stirred at 25° C. for 16 h. The reaction mixture was acidified to pH to 7 with 2 N HCl, extracted with EA (10 mL×3). The combined organic layers were washed with water (10 mL×3) and brine (10 mL), dried over $Na_2SO_4$ and concentrated under reduce pressure, the residue was purified by column chromatography to afford compound 132, 1-(5-(3-((5-cyano-4-(4-fluorophenyl)thiazol-2-yl)(methyl)amino)-2-ethyl imidazo[1,2-a] pyridine-6-yl)pyrimidin-2-yl)azetidine-3-carboxylic acid (440 mg, 56.41% yield) as a brown solid MS: m/z=555.2 (M+1, ESI+).

5.3.5. Synthesis of Compound 3

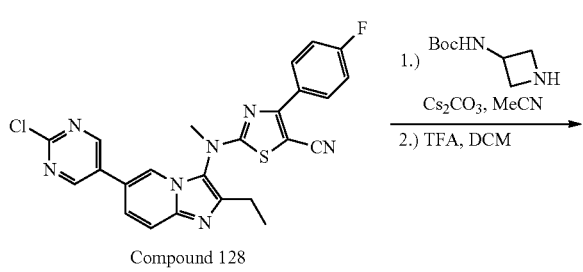

Compound 128

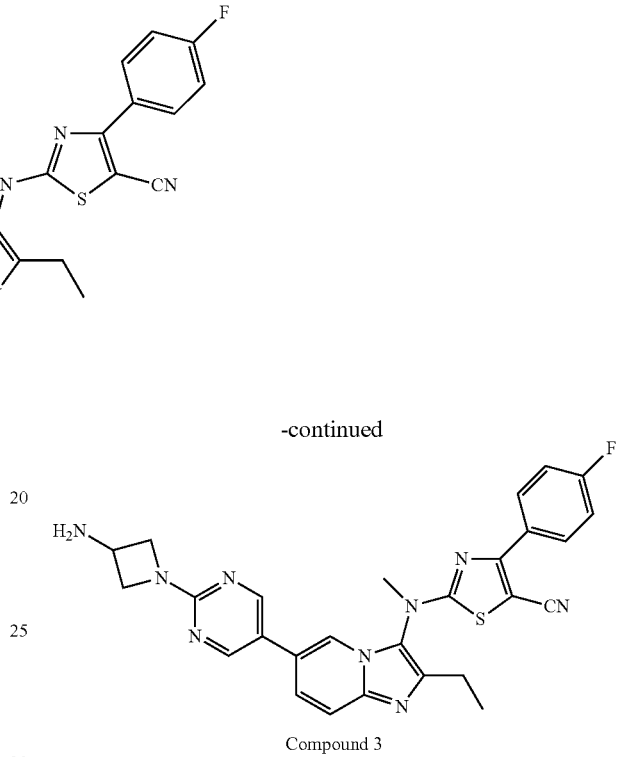

Compound 3

Step One:

To a solution of compound 128, 2-((6-(2-chloropyrimidin-5-yl)-2-ethylimidazo[1,2-a]pyridin-3-yl)(methyl) amino)-4-(4-fluorophenyl)thiazole-5-carbonitrile (300 mg, 612.3 umol) and tert-butyl azetidin-3-ylcarbamate (158.18 mg, 918.5 umol) in MeCN (20 mL) was added $Cs_2CO_3$ (598.49 mg, 183.7 umol), the reaction mixture was stirred at 80° C. for 2 h. Filtered and concentrated, the residue was purified by Prep-HPLC to afford tert-butyl (1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamate (210 mg, 54.81% yield) as a yellow solid. MS: m/z=626.2 (M+1, ESI+).

Step Two:

To a solution of tert-butyl (1-(5-(3-((5-cyano-4-(4-fluorophenyl)thiazol-2-yl)(methyl)amino)-2-ethyl imidazo[1,2-a]pyridin-6-yl)pyrimidin-2-yl)azetidin-3-yl)carbamate (210 mg, 335.6 umol) in DCM (20 mL) was added TFA (328.98 mg, 3.36 mmol), the reaction mixture was stirred at 25° C. for 4 h. Concentrated and the residue was purified by Prep-HPLC to afford compound 3, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile (80 mg, 45.35% yield) as a white solid. $^1H$ NMR (400 MHz, DMSO-$d_6$) δ 8.72 (s, 2H), 8.64 (s, 1H), 8.11-8.07 (t, 2H), 7.68 (s, 2H), 7.44-7.39 (t, 2H), 4.23-4.19 (t, 2H), 3.82-3.78 (m, 1H), 3.68-3.63 (m, 5H), 2.70-2.64 (dd, 2H), 2.17 (t, 2H), 1.29-1.25 (t, 3H); MS: m/z=526.1 (M+1, ESI+).

5.3.6. Synthesis of Compound 23

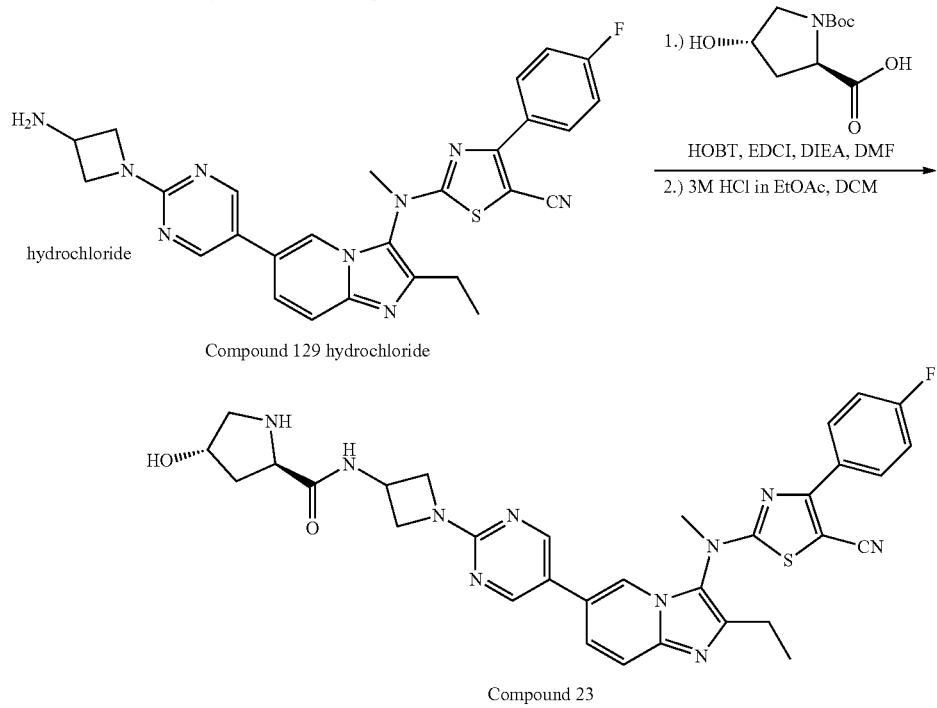

Compound 129 hydrochloride

Compound 23

Step One:

A mixture of compound 129 hydrochloride, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile hydrochloride (150 mg, 285.39 umol), (2R,4S)-1-(tert-butoxycarbonyl)-4-hydroxypyrrolidine-2-carboxylic acid (72.59 mg, 313.93 umol), HOBT (46.27 mg, 342.46 umol) and EDCI (65.65 mg, 342.46 umol) dissolved in DMF (3 mL) was added DIEA (147.53 mg, 1.14 mmol) and stirred at 25° C. for 2 h. The mixture was diluted with water (30 mL), extracted with EA (10 mL×3) and dried over $Na_2SO_4$. Then the organic layer was evaporated to afford tert-butyl (2R,4S)-2-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamoyl)-4-hydroxypyrrolidine-1-carboxylate (160 mg, 81.21% yield) as a brown oil. MS: m/z=739.2 (M+1, ESI+).

Step Two:

To a solution of tert-butyl (2R,4S)-2-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamoyl)-4-hydroxy pyrrolidine-1-carboxylate (160 mg, 216.56 umol) in DCM (3 mL) was added HCl (3 M in EA, 1.08 mL), the mixture was stirred at 25° C. for 2 h. After that, the reaction mixture was evaporated and the residue was purified by Prep-HPLC to afford compound 23, (2R, 4S)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)-4-hydroxypyrrolidine-2-carboxamide (10 mg, 7.24% yield) as a white solid. $^1$H NMR (400 MHz, DMSO-$d_6$) δ 8.76 (s, 2H), 8.65 (s, 1H), 8.62 (s, 1H), 8.10-8.07 (t, 2H), 7.69 (s, 2H), 7.44-7.40 (t, 2H), 4.70-4.58 (m, 2H), 4.30-4.26 (t, 2H), 4.16 (s, 1H), 3.97-3.95 (m, 2H), 3.75-3.68 (m, 1H), 3.63 (s, 3H), 2.88-2.84 (m, 1H), 2.74-2.64 (m, 3H), 2.02-1.90 (m, 2H), 1.71-1.64 (m, 1H), 1.28-1.24 (t, 3H); MS: m/z=639.4 (M+1, ESI+).

5.3.7. Synthesis of Compound 24

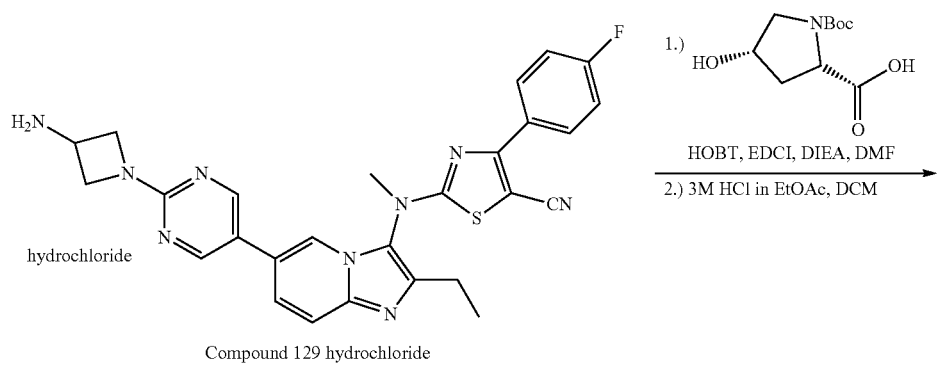

Compound 129 hydrochloride

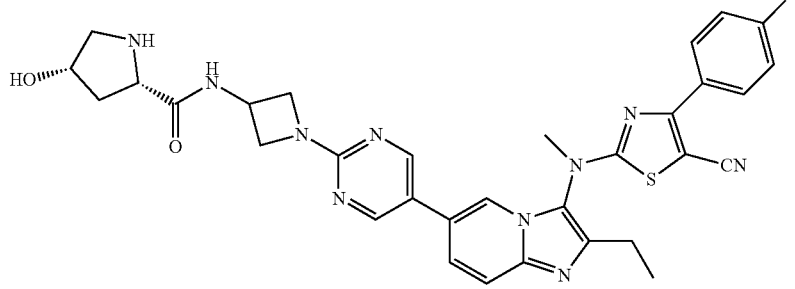

Compound 24

Step One:

A mixture of compound 129 hydrochloride, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile hydrochloride (150 mg, 285.39 umol), (2S,4S)-1-(tert-butoxycarbonyl)-4-hydroxypyrrolidine-2-carboxylic acid (72.59 mg, 313.93 umol), HOBT (46.27 mg, 342.46 umol) and EDCI (65.65 mg, 342.46 umol) dissolved in DMF (3 mL) was added DIEA (147.53 mg, 1.14 mmol) and stirred at 25° C. for 6 h. The mixture was diluted with water (30 mL), extracted with EA (10 mL×3) and dried over $Na_2SO_4$. Then the organic layer was evaporated to afford tert-butyl (2S,4S)-2-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamoyl)-4-hydroxypyrrolidine-1-carboxylate (150 mg, 71.14% yield) as a brown oil. MS: m/z=739.2 (M+1, ESI+).

Step Two:

To a solution of tert-butyl (2S,4S)-2-((1-(5-(3-((5-cyano-4-(4-fluorophenyl)thiazol-2-yl) (methyl) amino)-2-ethyl imidazo[1,2-a]pyridin-6-yl)pyrimidin-2-yl)azetidin-3-yl) carbamoyl)-4-hydroxy pyrrolidine-1-carboxylate (150 mg, 203.02 umol) in DCM (3 mL) was added HCl (3 M in EA, 1.02 mL), the mixture was stirred at 25° C. for 2 h. The resulting mixture was evaporated and the residue was purified by Prep-HPLC to afford compound 24, (2S,4S)—N-(1-(5-(3-((5-cyano-4-(4-fluorophenyl)thiazol-2-yl)(methyl) amino)-2-ethylimidazo[1,2-a]pyridin-6-yl)pyrimidin-2-yl) azetidin-3-yl)-4-hydroxy pyrrolidine-2-carboxamide (70 mg, 54.26% yield) as a white solid. $^1$H NMR (400 MHz, DMSO-$d_6$) δ 8.76 (s, 2H), 8.65 (s, 1H), 8.58-8.56 (d, 1H), 8.10-8.07 (t, 2H), 7.69 (s, 2H), 7.44-7.40 (t, 2H), 4.62-4.59 (m, 2H), 4.32-4.27 (m, 2H), 4.12-4.08 (m, 1H), 3.98-3.93 (m, 2H), 3.63 (s, 3H), 3.50-3.47 (dd, 1H), 2.88-2.84 (dd, 1H), 2.70-2.64 (m, 3H), 2.15-1.97 (m, 2H), 1.65-1.59 (m, 1H), 1.28-1.25 (t, 3H); MS: m/z=639.4 (M+1, ESI+).

5.3.8. Synthesis of Compound 25

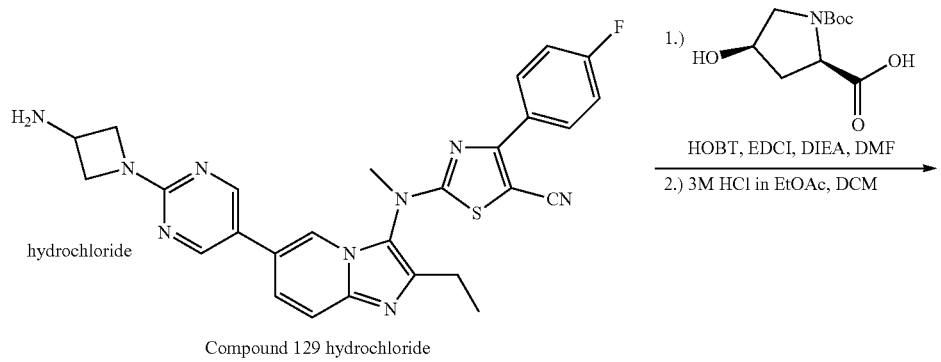

Compound 129 hydrochloride

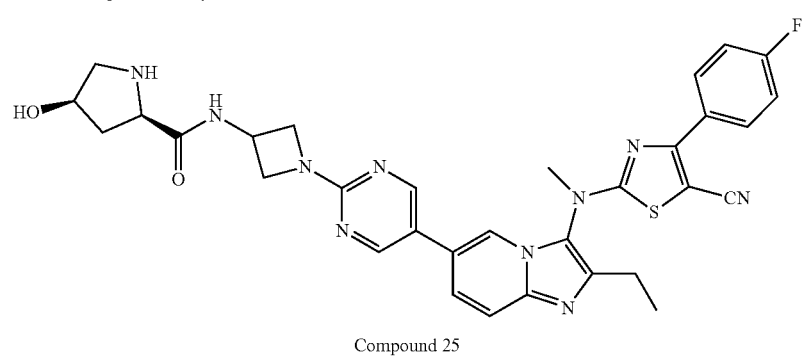

Compound 25

Step One:

A mixture of compound 129 hydrochloride, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile hydrochloride (150 mg, 285.39 umol), (2R,4R)-1-(tert-butoxycarbonyl)-4-hydroxypyrrolidine-2-carboxylic acid (72.59 mg, 313.93 umol), HOBT (46.27 mg, 342.46 umol) and EDCI (65.65 mg, 342.46 umol) dissolved in DMF (3 mL) was added DIEA (147.53 mg, 1.14 mmol) and stirred at 25° C. for 4 h. The mixture was diluted with water (30 mL), extracted with EA (10 mL-3) and dried over $Na_2SO_4$. Then the organic layer was evaporated to afford tert-butyl (2R,4R)-2-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamoyl)-4-hydroxypyrrolidine-1-carboxylate (155 mg, 73.51% yield) as a brown oil. MS: m/z=739.2 (M+1, ESI+).

Step Two:

To a solution of tert-butyl (2R,4R)-2-((1-(5-(3-((5-cyano-4-(4-fluorophenyl)thiazol-2-yl)(methyl)amino)-2-ethyl imidazo[1,2-a]pyridin-6-yl)pyrimidin-2-yl)azetidin-3-yl)carbamoyl)-4-hydroxy pyrrolidine-1-carboxylate (155 mg, 209.79 umol) in DCM (3 mL) was added HCl (3 M in EA, 1.05 mL), the reaction mixture was stirred at 25° C. for 2 h. The result mixture was evaporated and the residue was purified by Prep-HPLC to afford compound 25, (2R,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-yl) azetidin-3-yl)-4-hydroxypyrrolidine-2-carboxamide (24 mg, 17.91% yield) as a white solid. $^1$H NMR (400 MHz, DMSO-$d_6$) δ 8.76 (s, 2H), 8.66 (s, 1H), 8.59-8.57 (d, 1H), 8.10-8.07 (t, 2H), 7.69 (s, 2H), 7.44-7.40 (t, 2H), 4.63-4.58 (m, 2H), 4.32-4.27 (m, 2H), 4.12-4.08 (m, 1H), 3.98-3.93 (m, 2H), 3.63 (s, 3H), 3.52-3.48 (dd, 1H), 2.89-2.85 (dd, 1H), 2.70-2.64 (m, 3H), 2.15-1.95 (m, 2H), 1.66-1.60 (m, 1H), 1.28-1.24 (t, 3H); MS: m/z=639.4 (M+1, ESI+).

5.3.9. Synthesis of Compound 26

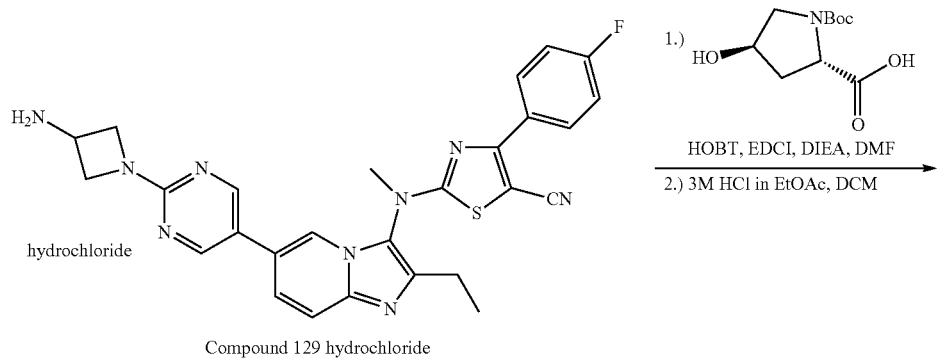

Compound 129 hydrochloride

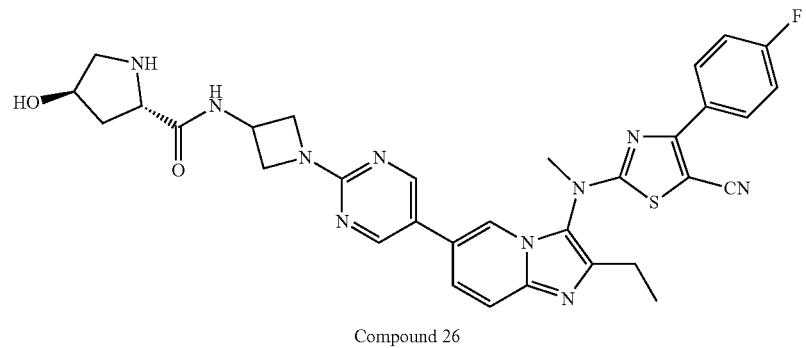

Compound 26

Step One:

A mixture of compound 129 hydrochloride, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile hydrochloride (150 mg, 285.39 umol), (2S,4R)-1-(tert-butoxycarbonyl)-4-hydroxypyrrolidine-2-carboxylic acid (72.59 mg, 313.93 umol), HOBT (46.27 mg, 342.46 umol) and EDCI (65.65 mg, 342.46 umol) dissolved in DMF (3 mL) was added DIEA (147.53 mg, 1.14 mmol) and stirred at 25° C. for 2 h. The mixture was diluted with water (30 mL), extracted with EA (10 mL×3) and dried over $Na_2SO_4$. Then the organic layer was evaporated to afford tert-butyl (2S,4R)-2-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)carbamoyl)-4-hydroxypyrrolidine-1-carboxylate (166 mg, 78.73% yield) as a brown oil. MS: m/z=739.2 (M+1, ESI+).

Step Two:

To a solution of tert-butyl (2S,4R)-2-((1-(5-(3-((5-cyano-4-(4-fluorophenyl)thiazol-2-yl)(methyl)amino)-2-ethyl imidazo[1,2-a]pyridin-6-yl)pyrimidin-2-yl)azetidin-3-yl)carbamoyl)-4-hydroxy pyrrolidine-1-carboxylate (166 mg, 224.68 umol) in DCM (3 mL) was added HCl (3 M in EA, 1.12 mL), the reaction mixture was stirred at 25° C. for 2 h. The result mixture was evaporated and the residue was purified by Prep-HPLC to afford compound 26, (2S,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)-4-hydroxypyrrolidine-2-carboxamide (70 mg, 46.14% yield) as a white solid. $^1$H NMR (400 MHz, DMSO-$d_6$) δ 8.75 (s, 2H), 8.65 (s, 1H), 8.57-8.55 (d, 1H), 8.10-8.07 (t, 2H), 7.69 (s, 2H), 7.44-7.40 (t, 2H), 4.63-4.60 (m, 2H), 4.29-4.26 (m, 2H), 4.15 (s, 1H), 3.98-3.93 (m, 2H), 3.70-3.63 (m, 4H), 2.84-2.80 (dd, 1H), 2.72-2.64 (m, 31H), 1.92-1.87 (m, 2H), 1.69-1.63 (m, 1H), 1.28-1.25 (t, 3H); MS: m/z=639.4 (M+1, ESI+).

5.3.10. Synthesis of Compound 27 Formate

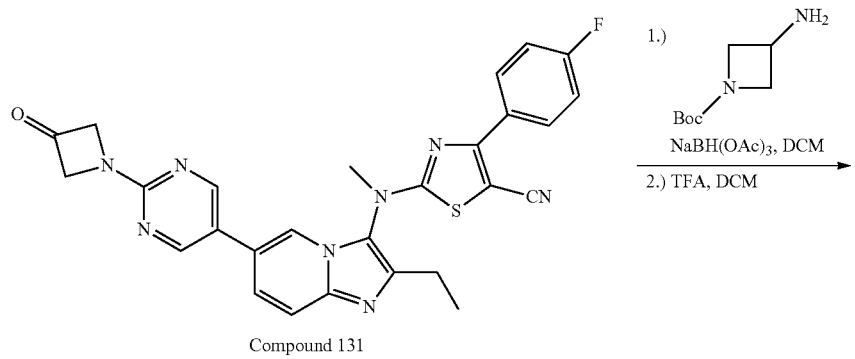

Compound 131

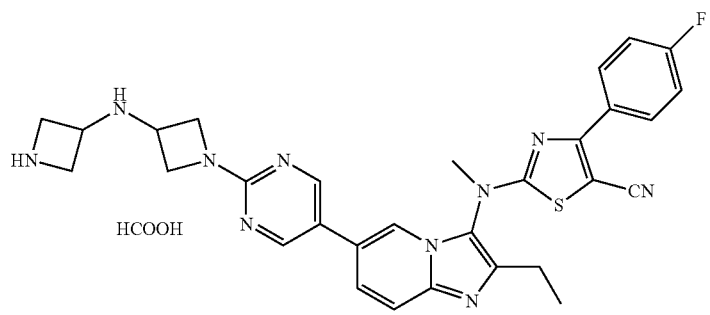

Compound 27 Formate

Step One:

To a solution of compound 131, 2-((2-ethyl-6-(2-(3-oxoazetidin-1-yl)pyrimidin-5-yl)imidazo[1,2-a]pyridin-3-yl) (methyl)amino)-4-(4-fluorophenyl)thiazole-5-carbonitrile (400 mg, 762.53 umol) and tert-butyl 3-aminoazetidine-1-carboxylate (157.59 mg, 915.03 umol) in DCM (10 mL) was added NaBH(OAc)$_3$ (323.22 mg, 1.53 mmol). The mixture was stirred at 25° C. for 24 h. The resulting solution was quenched by saturated NH$_4$Cl (30 mL) and extracted with DCM (30 mL×3), the combined organic layers were washed with water (30 mL) and brine (30 mL), dried over Na$_2$SO$_4$ and concentrated under reduced pressure. The residue was purified by column chromatography to afford tert-butyl 3-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)amino)azetidine-1-carboxylate (260 mg, 50.08% yield) as a yellow solid. MS: m/z=681.6 (M+1, ESI+).

Step Two:

To a solution of tert-butyl 3-((1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)amino) azetidine-1-carboxylate (260.00 mg, 381.91 umol) in DCM (10 mL) was added TFA (435.45 mg, 3.82 mmol). The reaction mixture was stirred at 25° C. for 3 h. The reaction mixture was concentrated under reduced pressure and the residue was purified by Prep-HPLC to afford compound 27 Formate, 2-((6-(2-(3-(azetidin-3-ylamino)azetidin-1-yl)pyrimidin-5-yl)-2-ethylimidazo[1,2-a]pyridin-3-yl)(methyl)amino)-4-(4-fluorophenyl)thiazole-5-carbonitrile formate (70 mg, 29.28% yield) as a white solid. $^1$H NMR (400 MHz, DMSO-d$_6$) δ 8.74 (s, 2H), 8.64 (s, 1H), 8.11-8.07 (t, 2H), 7.69 (s, 2H), 7.44-7.40 (t, 2H), 4.19-4.17 (m, 2H), 3.93 (s, 2H), 3.72-3.63 (m, 10H), 2.70-2.64 (dd, 2H), 1.28-1.25 (t, 3H); MS: m/z=581.2 (M+1, ESI+).

5.3.11. Synthesis of Compound 27

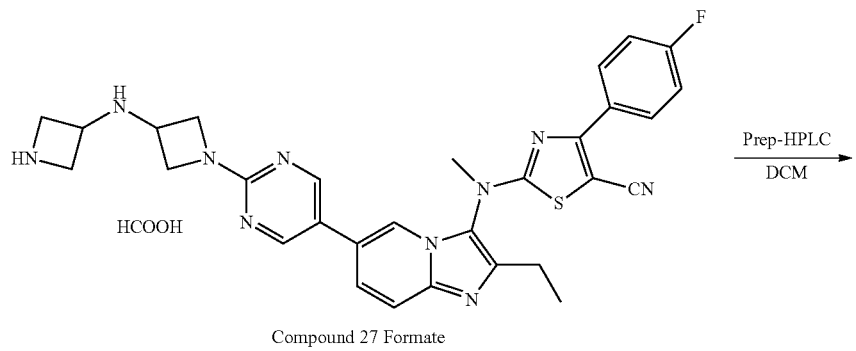

Compound 27 Formate

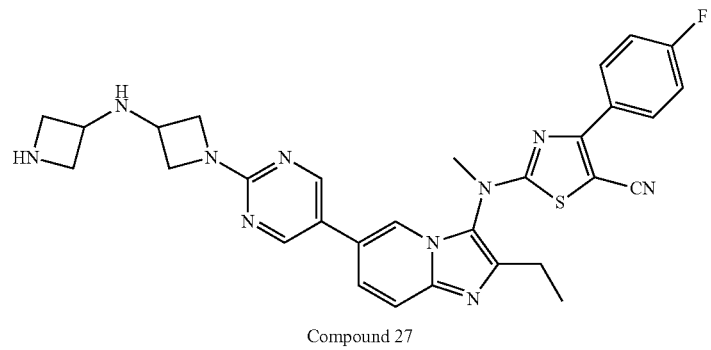

Compound 27

Compound 27 formate, 2-((6-(2-(3-(azetidin-3-ylamino)azetidin-1-yl)pyrimidin-5-yl)-2-ethylimidazo[1,2-a] pyridin-3-yl)(methyl)amino)-4-(4-fluorophenyl)thiazole-5-carbonitrile formate (34 mg, 0.054 mmol) was purified by Prep-HPLC to afford compound 27, 2-((6-(2-(3-(azetidin-3-ylamino)azetidin-1-yl)pyrimidin-5-yl)-2-ethylimidazo[1,2-a] pyridin-3-yl)(methyl)amino)-4-(4-fluorophenyl)thiazole-5-carbonitrile (13 mg, 41.26% yield) as a white solid. $^1$H NMR (400 MHz, DMSO-$d_6$) δ 8.73 (s, 2H), 8.64 (s, 1H), 8.11-8.07 (t, 2H), 7.68 (s, 2H), 7.44-7.40 (t, 2H), 4.18-4.14 (t, 2H), 3.72-3.38 (m, 13H), 2.69-2.64 (dd, 2H), 1.28-1.24 (t, 3H); MS: m/z=581.3 (M+1, ESI+).

5.3.12. Synthesis of Compound 28

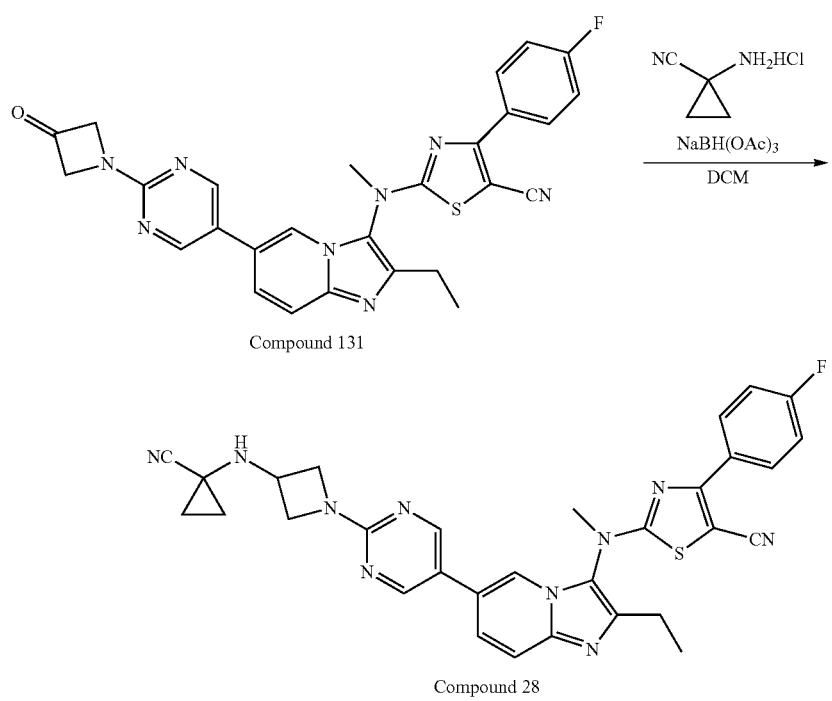

Compound 131

Compound 28

A mixture of compound 131, 2-((2-ethyl-6-(2-(3-oxoazetidin-1-yl)pyrimidin-5-yl)imidazo[1,2-a]pyridin-3-yl)(methyl)amino)-4-(4-fluorophenyl)thiazole-5-carbonitrile (159.39 mg, 303.84 umol) and 1-amino cyclopropane-1-carbonitrile hydrochloride (72.05 mg, 607.69 umol) in DCM (10 mL) was stirred at 25° C. for 1 h. Then NaBH(OAc)$_3$ (193.19 mg, 911.53 umol) was added to the above solution in portions. The reaction mixture was stirred at 25° C. for 16 h. The resulting solution was quenched by saturated NH$_4$Cl (30 mL) and extracted with DCM (30 mL×3), the combined organic layers were washed with water (30 mL) and brine (30 mL), dried over Na$_2$SO$_4$ and concentrated under reduced pressure. The residue was purified by Prep-HPLC to afford compound 28, 2-((6-(2-(3-((1-cyanocyclopropyl)amino)azetidin-1-yl)pyrimidin-5-yl)-2-ethylimidazo[1,2-a]pyridin-3-yl)(methyl)amino)-4-(4-fluorophenyl)thiazole-5-carbonitrile (72 mg, 40.12% yield) as a white solid. $^1$H NMR (400 MHz, DMSO-$d_6$) δ 8.75 (s, 2H), 8.66 (s, 1H), 8.11-8.07 (t, 2H), 7.69 (s, 2H), 7.44-7.40 (t, 2H), 4.30-4.27 (m, 2H), 4.21-4.18 (d, 1H), 3.91-3.88 (m, 3H), 3.63 (s, 3H), 2.70-2.64 (dd, 2H), 1.28-1.25 (t, 3H), 1.20-1.17 (dd, 2H), 1.01-0.98 (dd, 2H); MS: m/z=591.2 (M+1, ESI+).

5.3.13. Synthesis of Compound 29

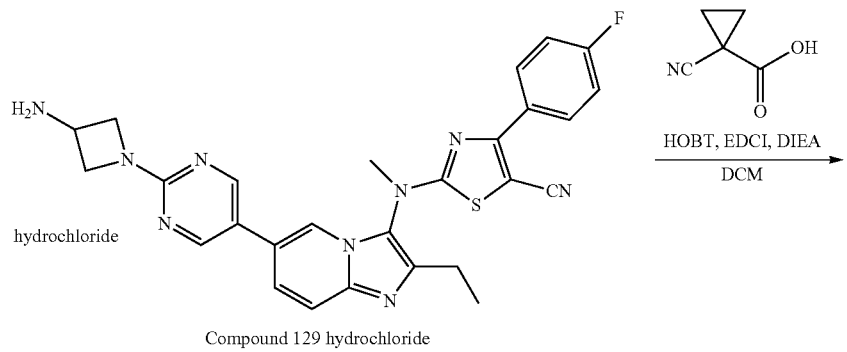

Compound 129 hydrochloride

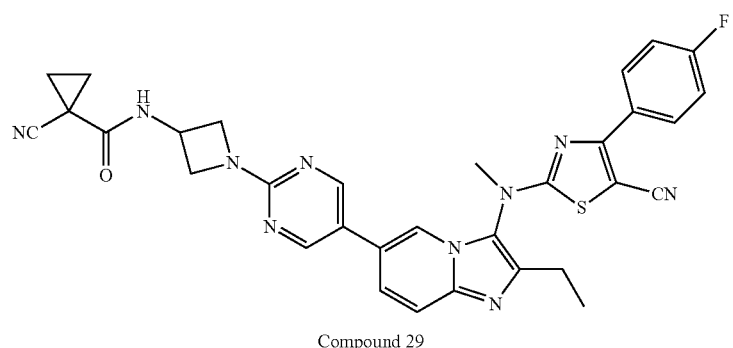

Compound 29

To a solution of compound 129 hydrochloride, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile hydrochloride (80 mg, 142.33 umol) and 1-cyanocyclopropane-1-carboxylic acid (23.72 mg, 213.50 umol) in DCM (5 mL) was added HOBT (29.06 mg, 213.50 umol), EDCI (40.93 mg, 213.50 umol) and DIEA (73.58 mg, 569.33 umol). The resulting mixture was stirred at 25° C. for 10 h. The reaction mixture was poured into water (20 mL) and extracted with DCM (10 mL×3). The combined organic layers were dried over $Na_2SO_4$ and concentrated under reduced pressure and purified by Prep-HPLC to afford compound 29, 1-cyano-N-(1-(5-(3-((5-cyano-4-(4-fluorophenyl)thiazol-2-yl)(methyl)amino)-2-ethylimidazo[1,2-a]pyridin-6-yl) pyrimidin-2-yl)azetidin-3-yl)cyclopropane-1-carboxamide (13 mg, 14.77% yield) as a white solid. $^1$H NMR (400 MHz, DMSO-$d_6$) δ 8.77-8.73 (m, 3H), 8.66 (s, 1H), 8.09 (s, 2H), 7.70 (s, 2H), 7.44-7.40 (t, 2H), 4.65 (s, 1H), 4.28 (s, 2H), 4.06 (s, 2H), 3.63 (s, 3H), 2.71-2.67 (m, 2H), 1.57-1.53 (m, 4H), 1.29-1.26 (t, 3H); MS: m/z=619.1 (M+1, ESI+).

5.3.14. Synthesis of Compound 30

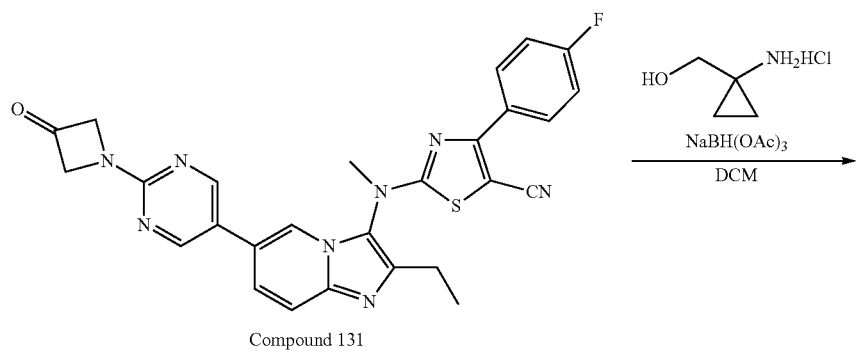

Compound 131

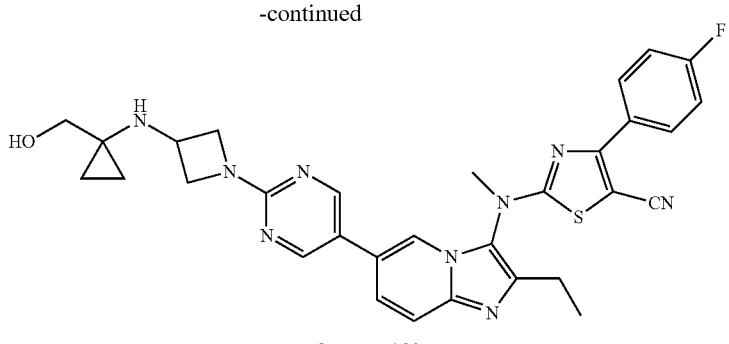

Compound 30

To a solution of compound 131, 2-((2-ethyl-6-(2-(3-oxoazetidin-1-yl)pyrimidin-5-yl)imidazo[1,2-a]pyridin-3-yl)(methyl)amino)-4-(4-fluorophenyl)thiazole-5-carbonitrile (180 mg, 343.14 umol) and (1-aminocyclopropyl) methanol hydrochloride (50.89 mg, 411.76 umol) in DCM (10 mL) was added NaBH(OAc)$_3$ (145.45 mg, 686.27 umol). The reaction mixture was stirred at 25° C. for 24 h. The resulting mixture was quenched by saturated NH$_4$Cl (30 mL) and extracted with DCM (10 mL×3), the combined organic layers were washed with brine (30 mL), dried over Na$_2$SO$_4$ and evaporated under reduce pressure. The residue was purified by Prep-HPLC to afford compound 30, 2-((2-ethyl-6-(2-(3-(((1-(hydroxymethyl)cyclopropyl)amino)azetidin-1-yl)pyrimidin-5-yl)imidazo[1,2-a]pyridin-3-yl)(methyl)amino)-4-(4-fluorophenyl)thiazole-5-carbonitrile (62 mg, 30.33% yield) as a white solid. $^1$H NMR (400 MHz, DMSO-d$_6$) δ 8.72 (s, 2H), 8.64 (s, 1H), 8.10-8.07 (t, 2H), 7.68 (s, 2H), 7.44-7.40 (t, 2H), 4.55-4.52 (t, 1H), 4.24-4.21 (t, 2H), 3.82-3.75 (m, 3H), 3.63 (s, 3H), 3.27-3.25 (d, 2H), 2.93 (bs, 1H), 2.69-2.64 (dd, 2H), 1.28-1.24 (t, 3H), 0.43-0.41 (d, 4H); MS: m/z=596.3 (M+1, ESI+).

5.3.15. Synthesis of Compound 31

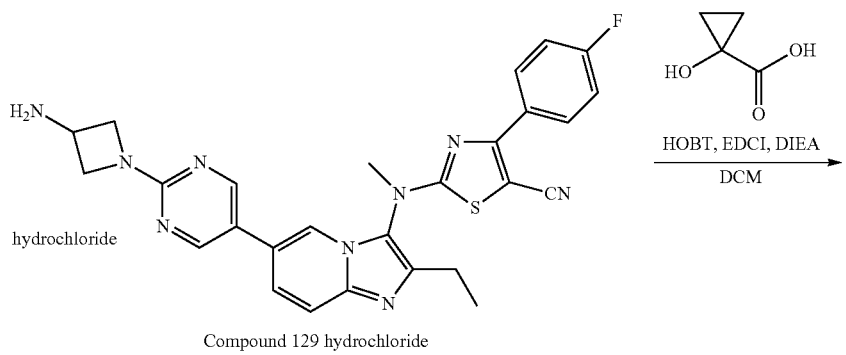

Compound 129 hydrochloride

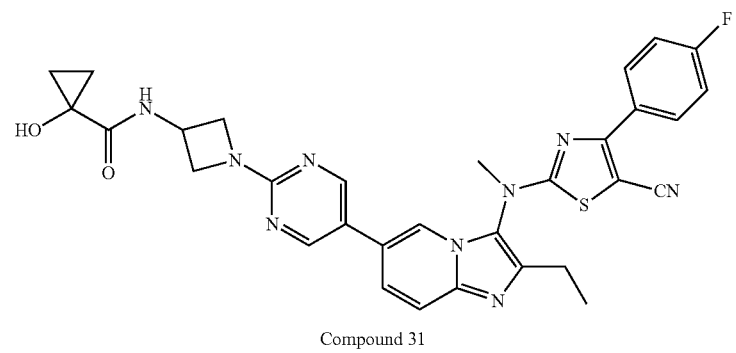

Compound 31

To a solution of compound 129 hydrochloride, 2-((6-(2-(3-aminoazetidin-1-yl)pyrimidin-5-yl)-2-ethylimidazo[1,2-a]pyridin-3-yl)methyl)amino)-4-(4-fluorophenyl)thiazole-5-carbonitrile hydrochloride (80 mg, 142.33 umol) and 1-hydroxycyclopropane-1-carboxylic acid (21.80 mg, 213.50 umol) in DCM (5 mL) was added HOBT (29.06 mg, 213.50 umol), EDCI (40.93 mg, 213.50 umol) and DIEA (73.58 mg, 569.33 umol). The resulting mixture was stirred at 25° C. for 1 h. The reaction mixture was poured into water (20 mL) and extracted with DCM (10 mL×3). The combined organic layers were dried over Na$_2$SO$_4$ and concentrated under reduced pressure and purified by Prep-HPLC to afford compound 31, N-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)-1-hydroxycyclopropane-1-carboxamide (15 mg, 17.24% yield) as a white solid. $^1$H NMR (400 MHz, DMSO-d$_6$) δ 8.75-8.73 (d, 2H), 8.63 (s, 2H), 8.07 (s, 2H), 7.67 (s, 2H), 7.42-7.38 (t, 2H), 6.19 (s, 1H), 4.70 (s, 1H), 4.28-4.24 (m, 2H), 4.07-4.06 (m, 2H), 3.63 (s, 3H), 2.68-2.62 (m, 2H), 1.27-1.23 (t, 3H), 1.00 (s, 2H), 0.82 (s, 2H); MS: m/z=610.1 (M+1, ESI+).

5.3.16. Synthesis of Compound 32

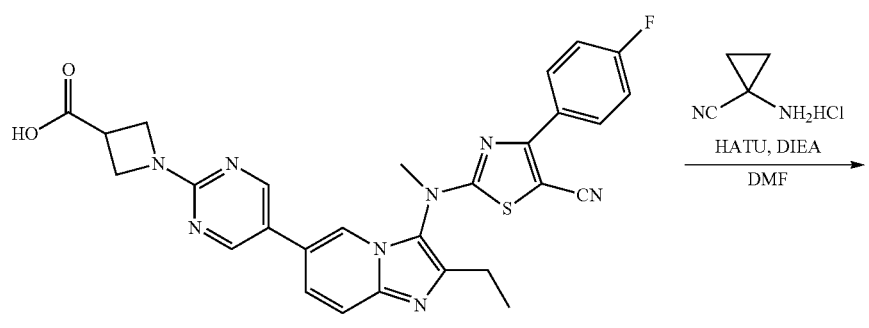

Compound 132

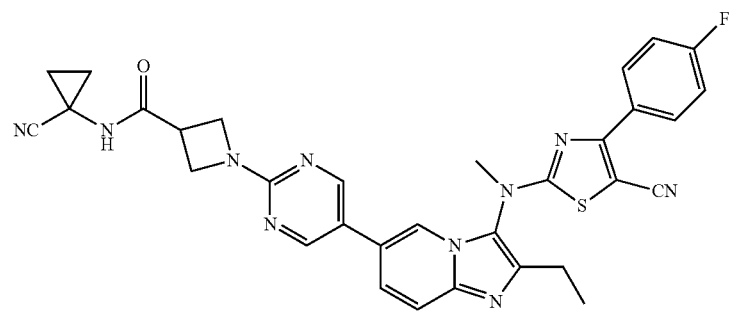

Compound 32

To a solution of compound 132, 1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxylic acid (200 mg, 360.62 umol) and 1-aminocyclopropane-1-carbonitrile hydrochloride (42.60 mg, 361.01 umol) in DMF (10 mL) was added HATU (204.08 mg, 540.93 umol) and DIEA (186.43 mg, 1.44 mmol) and stirred at 25° C. for 2 h. The reaction mixture was poured into water (100 mL), extracted with EA (30 mL×3). The combined organic layers were washed with water (100 mL×3) and brine (100 mL), dried over $Na_2SO_4$ and concentrated under reduce pressure, the residue was purified by Prep-HPLC to afford compound 32, 1-(5-(3-((5-cyano-4-(4-fluorophenyl)thiazol-2-yl)(methyl)amino)-2-ethylimidazo[1,2-a]pyridin-6-yl) pyrimidin-2-yl)-N-(1-cyanocyclopropyl)azetidine-3-carboxamide (46 mg, 20.62% yield) as a white solid. $^1$H NMR (400 MHz, DMSO-$d_6$) δ 8.97 (s, 1H), 8.76 (s, 2H), 8.66 (s, 1H), 8.10-8.07 (t, 2H), 7.69 (s, 2H), 7.44-7.40 (t, 2H), 4.20-4.16 (t, 2H), 4.08-4.05 (t, 2H), 3.63 (s, 3H), 3.45-3.40 (m, 1H), 2.70-2.64 (dd, 2H), 1.49-1.45 (dd, 2H), 1.28-1.25 (t, 3H), 1.17-1.14 (dd, 2H); MS: m/z=619.2 (M+1, ESI+).

5.3.17. Synthesis of Compound 33

To a solution of compound 132, 1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxylic acid (200 mg, 360.62 umol) and (1-amino cyclopropyl) methanol (31.42 mg, 360.62 umol) in DMF (10 mL) was added HATU (204.08 mg, 540.93 umol) and DIEA (186.43 mg, 1.44 mmol) and stirred at 25° C. for 16 h. The reaction mixture was poured into water (100 mL), extracted with EA (30 mL×3). The combined organic layers were washed with water (100 mL×3) and brine (100 mL), dried over $Na_2SO_4$ and concentrated under reduce pressure, the residue was purified by Prep-HPLC to afford compound 33, 1-(5-(3-((5-cyano-4-(4-fluoro phenyl)thiazol-2-yl)(methyl)amino)-2-ethylimidazo[1,2-a]pyridin-6-yl)pyrimidin-2-yl)-N-(1-(hydroxymethyl)cyclopropyl)azetidine-3-carboxamide (114 mg, 50.68% yield) as a white solid. $^1$H NMR (400 MHz, DMSO-$d_6$) δ 8.75 (s, 2H), 8.65 (s, 1H), 8.29 (s, 1H), 8.10-8.07 (t, 2H), 7.69 (s, 2H), 7.44-7.40 (t, 2H), 4.72-4.69 (t, 1H), 4.15-4.11 (t, 2H), 4.07-4.03 (t, 2H), 3.63 (s, 3H), 3.41-3.36 (m, 3H), 2.70-2.64 (dd, 2H), 1.28-1.25 (t, 3H), 0.67-0.64 (m, 2H), 0.57-0.54 (m, 2H); MS: m/z=624.2 (M+1, ESI+).

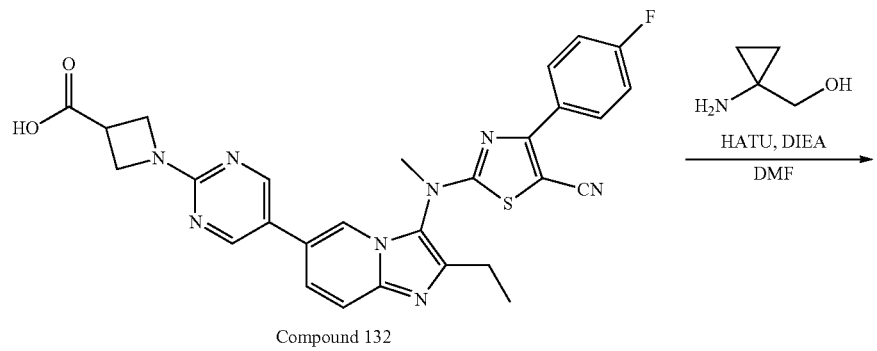

Compound 132

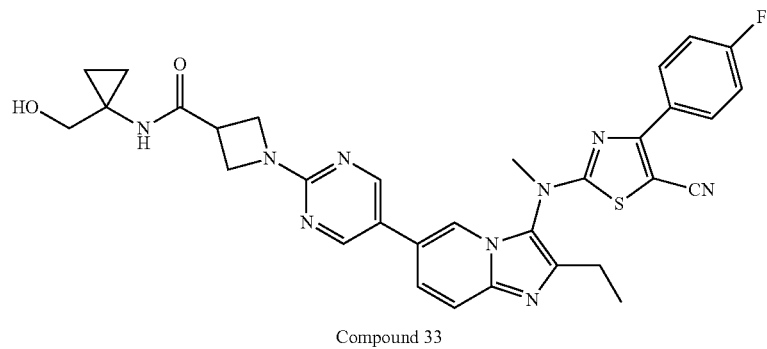

Compound 33

5.3.18. Synthesis of Compound 70 Hydrochloride

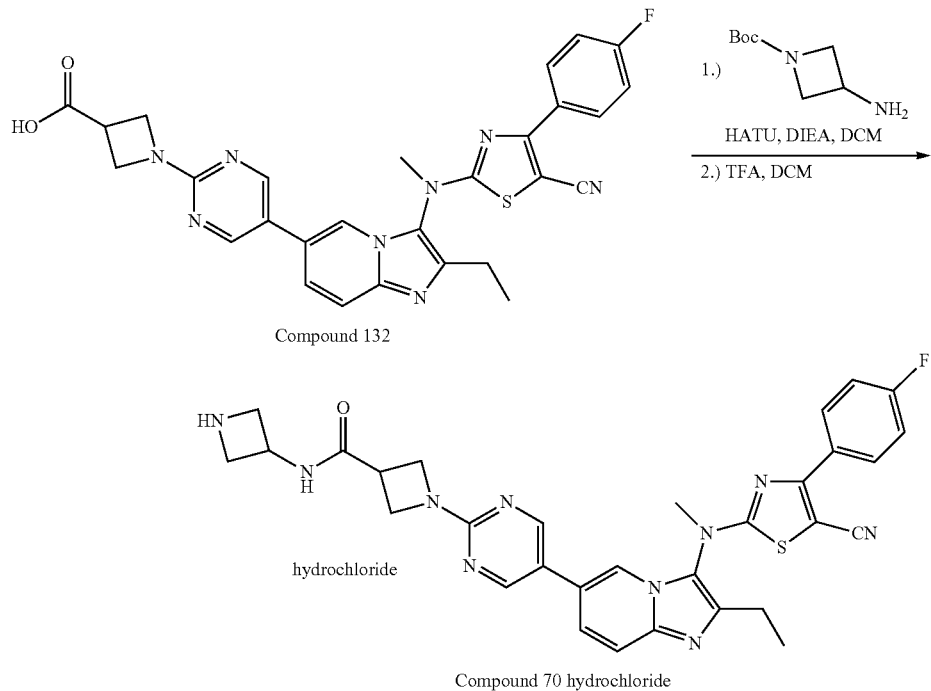

Step One:

To a solution of compound 132, 1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxylic acid (340 mg, 613.06 umol) and tert-butyl 3-aminoazetidine-1-carboxylate (184.17 mg, 1.07 mmol) in DCM (5 mL) was added HATU (346.93 mg, 919.58 umol) and DIEA (237.70 mg, 1.84 mmol), The resulting mixture was stirred at 25° C. for 2 h. The reaction mixture was poured into water (50 mL), extracted with DCM (10 mL×3). The combined organic layers were washed with water (30 mL×3) and brine (30 mL), dried over Na$_2$SO$_4$ and concentrated under reduce pressure, the residue was purified by column chromatography to afford tert-butyl 3-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxamido)azetidine-1-carboxylate (300 mg, 69.12% yield) as a yellow solid. MS: m/z=709.6 (M+1, ESI+).

Step Two:

To a solution of tert-butyl 3-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxamido)azetidine-1-carboxylate (300 mg, 423.25 umol) in DCM (8 mL) was added TFA (2 g, 17.54 mmol). The reaction mixture was stirred at 25° C. for 1 h. The reaction mixture was concentrated under reduced pressure and the residue was purified by Prep-HPLC to afford compound 70 hydrochloride, N-(azetidin-3-yl)-1-(5-(3-((5-cyano-4-(4-fluorophenyl)thiazol-2-yl)(methyl)amino)-2-ethylimidazo[1,2-a]pyridin-6-yl)pyrimidin-2-vl) azetidine-3-carboxamide hydrochloride (175 mg, 64.10% yield) as a pale yellow solid. $^1$H NMR (400 MHz, DMSO-d$_6$) δ 9.51 (s, 11H), 9.38 (s, 11H), 9.22-9.21 (d, 1H), 9.13 (s, 1H), 8.87 (s, 2H), 8.40-8.37 (d, 11H), 8.14-8.12 (d, 1H), 8.01 (s, 2H), 7.42-7.38 (t, 2H), 4.67-4.61 (m, 1H), 4.28-4.24 (t, 2H), 4.16-4.13 (t, 2H), 4.06-3.93 (m, 4H), 3.67 (s, 3H), 3.57-3.50 (m, 1H), 2.91-2.85 (dd, 2H), 1.36-1.33 (t, 3H); MS: m/z=609.1 (M+1, ESI+).

5.3.19. Synthesis of Compound 70

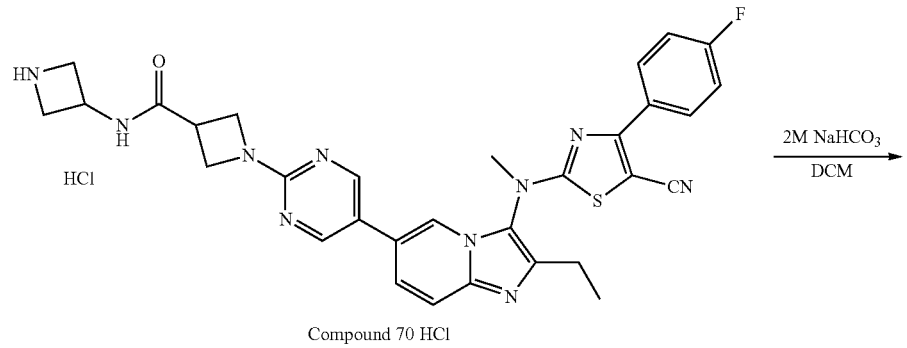

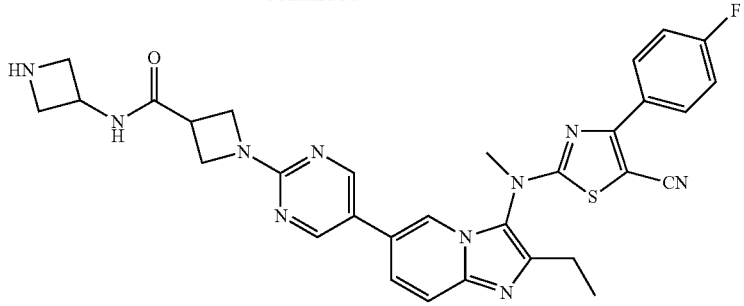

Compound 70

To a mixture of compound 70 hydrochloride, N-(azetidin-3-yl)-1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxamide hydrochloride (130 mg, 0.2 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 70, N-(azetidin-3-yl)-1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxamide (100 mg, 81.9% yield) as a white solid. $^1$H NMR (400 MHz, DMSO-d6) δ 9.08 (s, 1H), 8.76 (s, 2H), 8.66 (s, 1H), 8.08 (s, 2H), 7.69 (s, 2H), 7.44-7.40 (t, 2H), 7.22 (s, 1H), 4.63-4.58 (m, 1H), 4.23-4.05 (m, 4H), 3.87-3.69 (m, 2H), 3.63 (s, 3H), 3.50-3.48 (m, 2H), 2.70-2.64 (dd, 2H), 1.28-1.24 (t, 3H); MS: m/z=609.3 (M+1, ESI+).

5.3.20. Synthesis of Compound 71 Hydrochloride

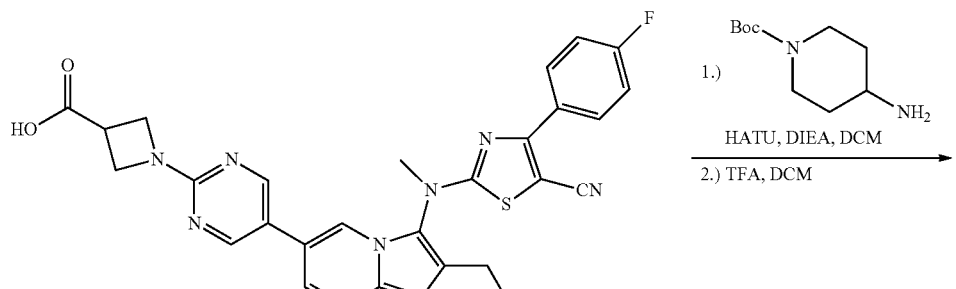

Compound 132

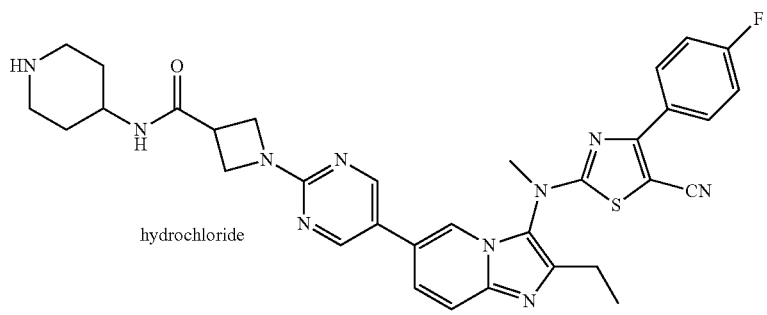

Compound 71 hydrochloride

Step One:

To a solution of compound 132, 1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxylic acid (340 mg, 613.06 umol) and tert-butyl 4-aminopiperidine-1-carboxylate (184.17 mg, 1.07 mmol) in DCM (6 mL) was added HATU (346.93 mg, 919.58 umol) and DIEA (237.70 mg, 1.84 mmol), The resulting mixture was stirred at 25° C. for 2 h. The reaction mixture was poured into water (50 mL), extracted with DCM (10 mL×3). The combined organic layers were washed with water (30 mL×3) and brine (30 mL), dried over $Na_2SO_4$ and concentrated under reduce pressure, the residue was purified by column chromatography to afford tert-butyl 4-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxamido)piperidine-1-carboxylate (300 mg, 69.04% yield) as a yellow solid. MS: m/z=737.2 (M+1, ESI+).

Step Two:

To a solution of tert-butyl 4-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxamido)piperidine-1-carboxylate (300 mg, 407.13 umol) in DCM (8 mL) was added TFA (2 g, 17.54 mmol). The reaction mixture was stirred at 25° C. for 1 h. The reaction mixture was concentrated under reduced pressure and the residue was purified by Prep-HPLC to afford compound 71 hydrochloride, 1-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl) azetidine-3-carboxamide hydrochloride (120 mg, 43.16% yield) as a pale yellow solid. $^1$H NMR (400 MHz, DMSO-$d_6$) δ 9.25 (s, 2H), 9.14 (s, 1H), 8.90 (s, 2H), 8.49-8.48 (d, 1H), 8.41-8.39 (d, 1H), 8.15-8.12 (d, 1H), 8.01 (s, 2H), 7.42-7.38 (t, 2H), 4.28-4.24 (t, 2H), 4.15-4.12 (t, 2H), 3.86 (s, 1H), 3.68 (s, 3H), 3.60-3.53 (m, 1H), 3.25-3.22 (d, 2H), 2.95-2.86 (m, 4H), 1.92-1.89 (d, 2H), 1.73-1.65 (m, 2H), 1.37-1.33 (t, 3H); MS: m/z=637.1 (M+1, ESI+).

5.3.21. Synthesis of Compound 71

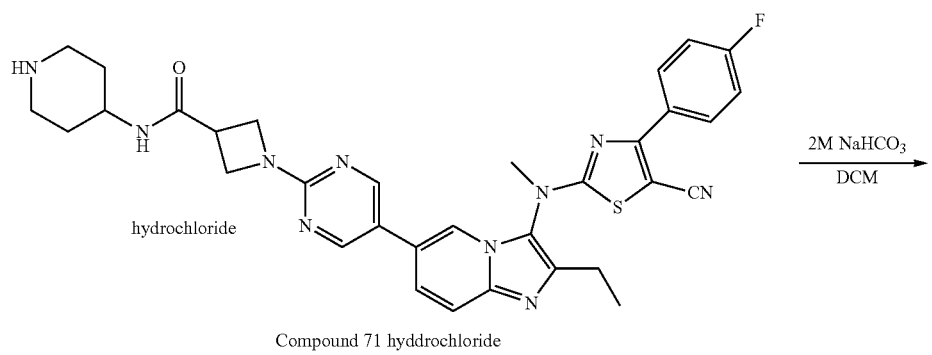

Compound 71 hyddrochloride

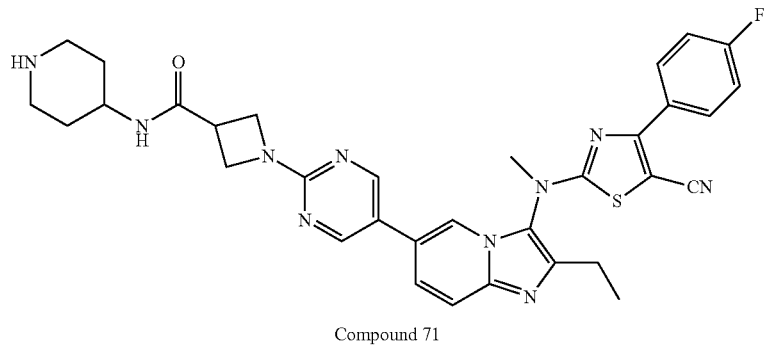

Compound 71

To a mixture of compound 71 hydrochloride, 1-(5-(3-((5-cyano-4-(4-fluorophenyl)thiazol-2-yl)(methyl)amino)-2-ethylimidazo [1,2-a]pyridin-6-yl)pyrimidin-2-yl)-N-(piperidin-4-yl)azetidine-3-carboxamide hydrochloride (80 mg, 0.12 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 71, 1-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl) azetidine-3-carboxamide (25 mg, 33% yield) as a white solid. $^1$H NMR (400 MHz, DMSO-d6) S 8.75 (s, 2H), 8.65 (s, 1H), 8.24-8.22 (d, 1H), 8.10-8.07 (t, 2H), 7.69 (s, 2H), 7.44-7.40 (t, 2H), 4.19-4.15 (t, 2H), 4.07-4.04 (t, 2H), 3.80 (s, 1H), 3.63 (s, 3H), 3.50-3.42 (m, 1H), 3.16-3.13 (d, 2H), 2.84-2.79 (t, 2H), 2.70-2.64 (dd, 2H), 1.84-1.82 (m, 2H), 1.55-1.52 (m, 2H), 1.28-1.24 (t, 3H); MS: m/z=637.3 (M+1, ESI+).

5.3.22. Synthesis of Compound 80 Hydrochloride

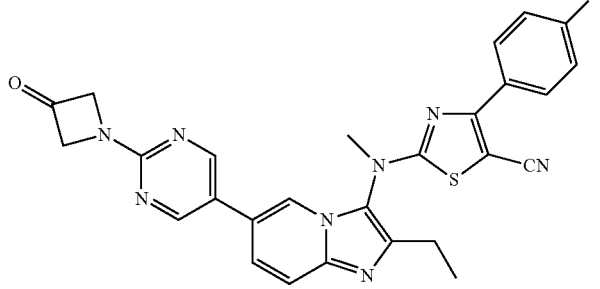

Compound 131

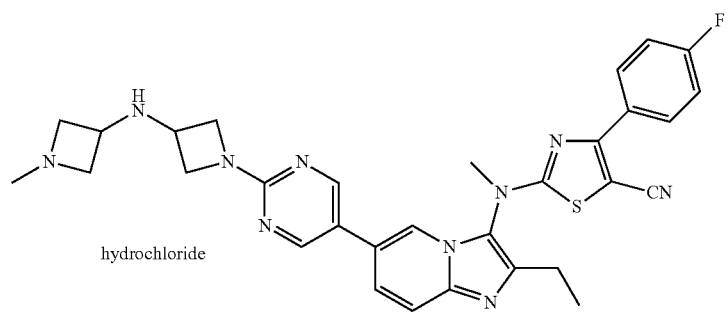

Compound 80 hydrochloride

To a solution of compound 131, 2-((2-ethyl-6-(2-(3-oxoazetidin-1-yl)pyrimidin-5-yl)imidazo[1,2-a]pyridin-3-yl) (methyl)amino)-4-(4-fluorophenyl)thiazole-5-carbonitrile (1 g, 1.91 mmol) and 1-methylazetidin-3-amine 2HCl (454.82 mg, 2.86 mmol) in DCE (10 mL) was added DIEA (385.80 mg, 3.81 mmol) and stirred at 25° C. for 0.5 h, then Ti(i-PrO)$_4$ (1.08 g, 3.81 mmol) was added in portions. The reaction mixture was stirred at 25° C. for 16 h and NaBH$_3$CN (359.392 mg, 5.72 mmol) was added to the above solution, the reaction mixture was stirred at 40° C. for another 3 h. Filtered and the filtrate was evaporated under reduce pressure, the residue was purified by Prep-HPLC to afford compound 80 hydrochloride, 2-((2-ethyl-6-(2-(3-((I-methylazetidin-3-yl)amino)azetidin-1-yl)pyrimidin-5-yl) imidazo[1,2-a] pyridin-3-yl)(methyl)amino)-4-(4-fluorophenyl)thiazole-5-carbonitrile hydrochloride (40 mg, 3.53% yield) as an off-white solid. $^1$H NMR (400 MHz, MeOD) δ 9.02 (s, 1H), 8.94 (s, 2H), 8.37-8.34 (d, 1H), 8.12-8.09 (d, 1H), 8.02-7.98 (t, 2H), 7.21-7.17 (t, 2H), 4.75-4.36 (m, 1H), 3.75 (s, 3H), 3.13 (s, 2H), 3.08 (s, 1H), 2.99-2.94 (dd, 2H), 1.44-1.40 (t, 3H); MS: m/z=595.3 (M+1, ESI+).

5.3.23. Synthesis of Compound 80

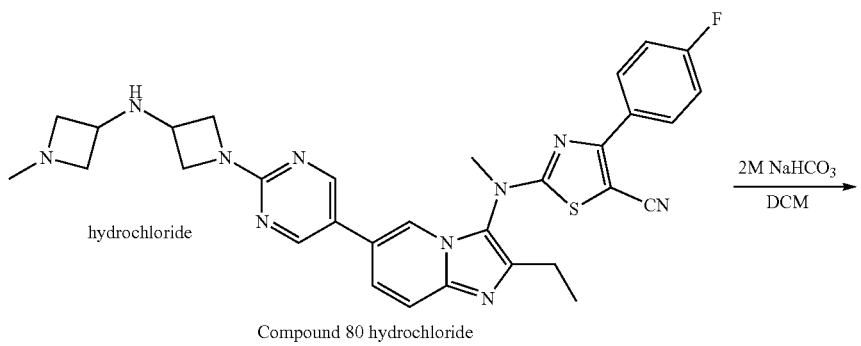

Compound 80 hydrochloride

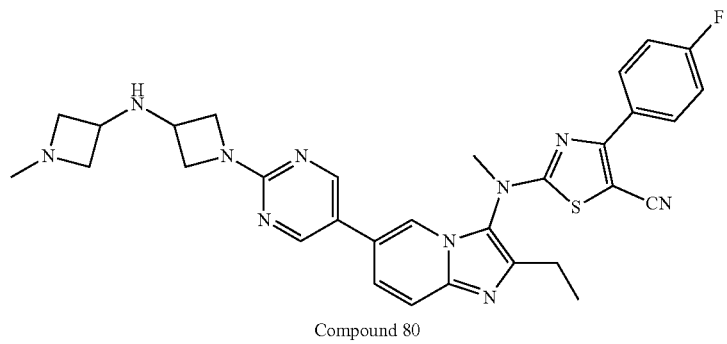

Compound 80

To a mixture of compound 80 hydrochloride, 2-((2-ethyl-6-(2-(3-((l-methylazetidin-3-yl)amino)azetidin-1-yl)pyrimidin-5-yl)imidazo[1,2-a]pyridin-3-yl)(methyl)amino)-4-(4-fluorophenyl)thiazole-5-carbonitrile hydrochloride (34 mg, 0.054 mmol) in $H_2O$ (3 mL) was added 2 M $NaHCO_3$ (1.05 mL, 2.1 mmol) at 0° C. and stirred for 0.5 h. Then extracted with DCM (5 mL×2). The organic layer was washed with water (5 mL) and brine (5 mL), dried over $Na_2SO_4$ and concentrated to afford compound 80, 2-((2-ethyl-6-(2-(3-((1-methylazetidin-3-yl)amino)azetidin-1-yl)pyrimidin-5-yl)imidazo[1,2-a]pyridin-3-yl) (methyl)amino)-4-(4-fluorophenyl)thiazole-5-carbonitrile (15 mg, 46.87% yield) as a white solid. $^1H$ NMR (400 MHz, DMSO-$d_6$) δ 8.81 (s, 2H), 8.67 (s, 1H), 8.10-8.07 (t, 2H), 7.71 (s, 2H), 7.44-7.40 (t, 2H), 3.77-3.74 (m, 4H), 3.63 (s, 3H), 3.54-3.48 (m, 5H), 3.16 (s, 2H), 2.70-2.64 (m, 2H), 2.20 (s, 3H), 1.28-1.25 (t, 3H); MS: m/z=596.0 (M+1, ESI+).

5.3.24. Synthesis of Compound 81 Hydrochloride

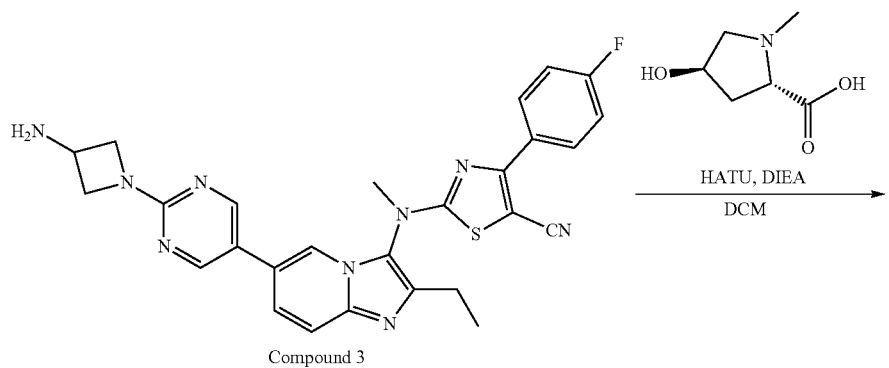

Compound 3

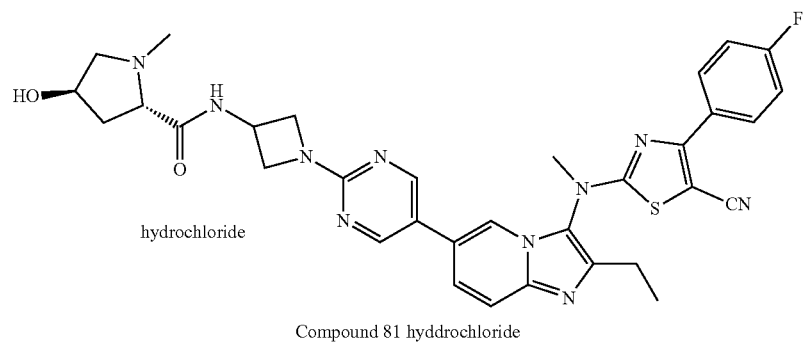

Compound 81 hyddrochloride

To a solution of compound 3, 2-((6-(2-(3-aminoazetidin-1-yl)pyrimidin-5-yl)-2-ethylimidazo[1,2-a]pyridin-3-yl)(methyl)amino)-4-(4-fluorophenyl)thiazole-5-carbonitrile (120 mg, 228.31 umol) and (2S,4R)-4-hydroxy-1-methylpyrrolidine-2-carboxylic acid (33.14 mg, 228.31 umol) in DCM (3 mL) was added HATU (129.20 mg, 342.46 umol) and DIEA (88.52 mg, 684.93 umol). The resulting mixture was stirred at 25° C. for 2 h. The reaction mixture was poured into water (20 mL) and extracted with DCM (10 mL×3). The combined organic layers were dried over $Na_2SO_4$ and concentrated under reduced pressure and purified by Prep-HPLC to afford compound 81 hydrochloride, (2S,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)-4-hydroxy-1-methyl pyrrolidine-2-carboxamide hydrochloride (55 mg, 35.03% yield) as a pale yellow solid. $^1$H NMR (400 MHz, DMSO-$d_6$) δ 10.02 (s, 1H), 9.96-9.95 (d, 1H), 9.16 (s, 1H), 8.91 (s, 2H), 8.42-8.40 (d, 1H), 8.15-8.12 (d, 1H), 8.01 (s, 2H), 7.42-7.38 (t, 2H), 4.68-4.66 (m, 1H), 4.42-4.40 (d, 4H), 4.17-4.12 (m, 2H), 3.82-3.79 (m, 1H), 3.68 (s, 3H), 3.08-3.05 (d, 1H), 2.91-2.86 (m, 5H), 2.48-2.43 (m, 11H), 2.10-2.02 (m, 1H), 1.37-1.34 (t, 3H); MS: m/z=653.1 (M+1, ESI+).

5.3.25. Synthesis of Compound 81

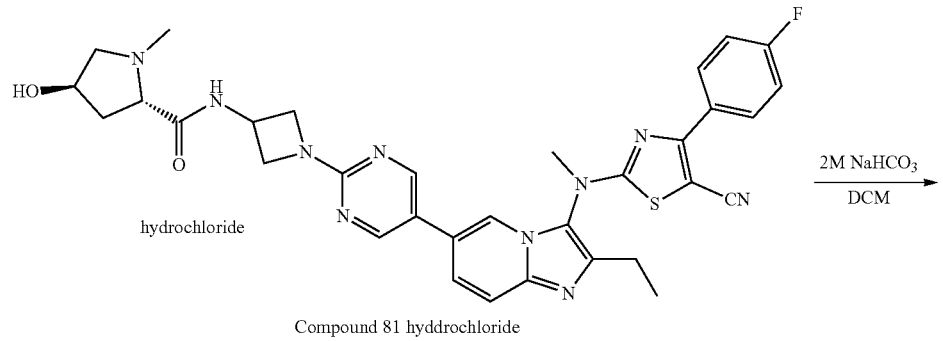

Compound 81 hyddrochloride

Compound 81

To a mixture of compound 81 hydrochloride, (2S,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)azetidin-3-yl)-4-hydroxy-1-methylpyrrolidine-2-carboxamide hydrochloride (19 mg, 0.027 mmol) in $H_2O$ (3 mL) was added 2 M $NaHCO_3$ (1.05 mL, 2.1 mmol) at 0° C. and stirred for 0.5 h. Then extracted with DCM (5 mL×2). The organic layer was washed with water (5 mL) and brine (5 mL), dried over $Na_2SO_4$ and concentrated to afford compound 81, (2S,4R)—N-(1-(5-(3-((5-cyano-4-(4-fluorophenyl)thiazol-2-yl)(methyl)amino)-2-ethylimidazo [1,2-a]pyridin-6-yl)pyrimidin-2-yl)azetidin-3-yl)-4-hydroxy-1-methylpyrrolidine-2-carboxamide (5 mg, 27.78% yield) as a white solid. $^1$H NMR (400 MHz, DMSO-d6) δ 8.73 (s, 2H), 8.65 (s, 1H), 8.43-8.41 (d, 1H), 8.10-8.07 (t, 2H), 7.69 (s, 2H), 7.44-7.40 (t, 2H), 4.85-4.841 (d, 1H), 4.66-4.60 (m, 1H), 4.30-4.25 (m, 2H), 4.20-4.16 (m, 1H), 3.99-3.96 (m, 2H), 3.63 (s, 3H), 3.26-3.22 (m, 1H), 2.96-2.92 (t, 1H), 2.70-2.64 (m, 2H), 2.24 (s, 3H), 2.19-2.15 (m, 1H), 1.87-1.85 (m, 2H), 1.28-1.24 (t, 3H); MS: m/z=653.0 (M+1, ESI+).

5.3.26. Synthesis of Compound 105

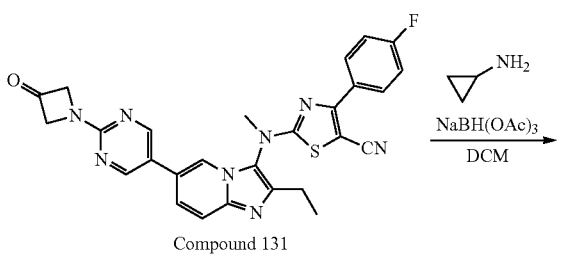

Compound 131

-continued

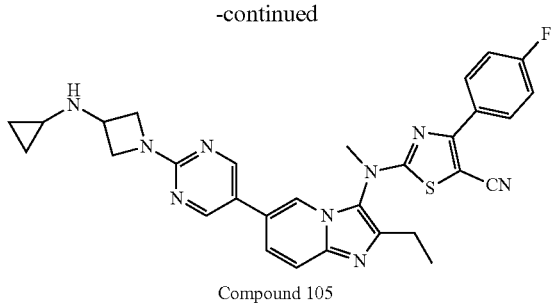

Compound 105

To a solution of compound 131, 2-((2-ethyl-6-(2-(3-oxoazetidin-1-yl)pyrimidin-5-yl)imidazo[1,2-a]pyridin-3- yl) (methyl)amino)-4-(4-fluorophenyl)thiazole-5-carbonitrile (250 mg, 476.58 umol) and cyclopropanamine (43.43 mg, 498.52 umol) in DCM (8 mL) was added NaBH(OAc)$_3$ (202.01 mg, 953.16 umol), the reaction mixture was stirred at 25° C. for 16 h. The mixture was poured into water (30 mL), extracted with DCM (10 mL×3). The organic was washed by brine (30 mL), then dried over Na$_2$SO$_4$ and concentrated. The residue was purified by Prep-HPLC to afford compound 105, 2-((6-(2-(3-(cyclopropylamino)azetidin-1-yl)pyrimidin-5-yl)-2-ethylimidazo[1,2-a]pyridin-3-yl)(methyl)amino)-4-(4-fluorophenyl)thiazole-5-carbonitrile (86 mg, 31.90% yield) as a white solid. $^1$H NMR (400 MHz, DMSO-d$_6$) δ 8.73 (s, 2H), 8.64 (s, 1H), 8.10-8.05 (m, 2H), 7.68 (s, 2H), 7.44-7.40 (t, 2H), 4.22-4.18 (t, 2H), 3.81-3.70 (m, 3H), 3.63 (s, 3H), 2.98 (bs, 1H), 2.69-2.63 (dd, 2H), 2.09-2.05 (m, 1H), 1.28-1.23 (t, 3H), 0.39-0.34 (m, 2H), 0.25-0.20 (m, 2H); MS: m/z=566.1 (M+1, ESI+); HRMS: 566.2247.

5.3.27. Synthesis of Compound 106

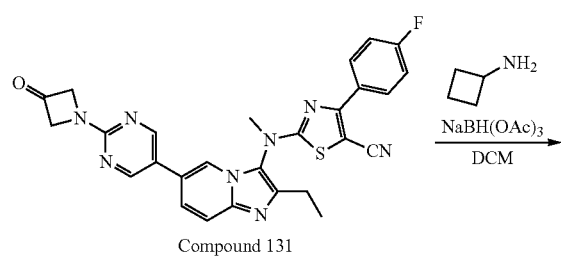

Compound 131

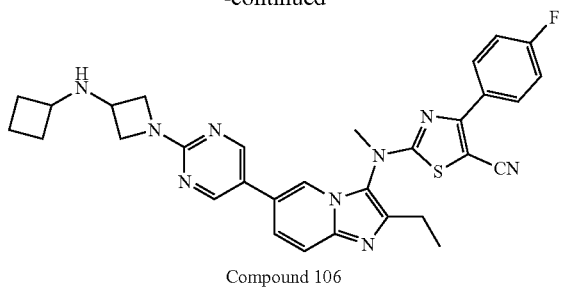

Compound 106

To a solution of compound 131, 2-((2-ethyl-6-(2-(3-oxoazetidin-1-yl)pyrimidin-5-yl)imidazo[1,2-a]pyridin-3-yl) (methyl)amino)-4-(4-fluorophenyl)thiazole-5-carbonitrile (250 mg, 476.58 umol) and cyclobutanamine (50.84 mg, 714.87 umol) in DCM (8 mL) was added NaBH(OAc)$_3$ (303.02 mg, 1.43 mmol), the reaction mixture was stirred at 25° C. for 16 h. The mixture was poured into water (30 mL), extracted with DCM (10 mL×3). The organic was washed by brine (30 mL), then dried over Na$_2$SO$_4$ and concentrated. The residue was purified by Prep-HPLC to afford compound 106, 2-((6-(2-(3-(cyclobutylamino)azetidin-1-yl)pyrimidin-5-yl)-2-ethylimidazo[1,2-a]pyridin-3-yl)(methyl)amino)-4-(4-fluorophenyl)thiazole-5-carbonitrile (92 mg, 33.30% yield) as a white solid. $^1$H NMR (400 MHz, DMSO-d$_6$) δ 8.72 (s, 2H), 8.64 (s, 1H), 8.09-8.07 (t, 2H), 7.68 (s, 2H), 7.43-7.39 (t, 2H), 4.18-4.14 (t, 2H), 3.74-3.63 (m, 6H), 3.18-3.14 (m, 1H), 2.70-2.64 (dd, 3H), 2.07-2.03 (m, 2H), 1.71-1.51 (m, 4H), 1.28-1.25 (t, 3H); MS: m/z=580.2 (M+1, ESI+); HRMS: 580.2404.

5.3.28. Synthesis of Compound 125

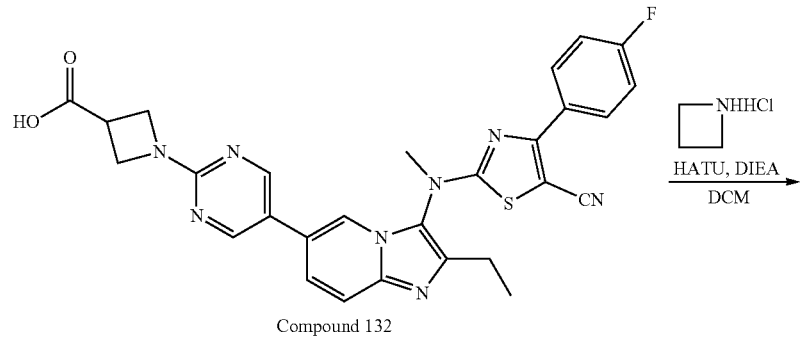

Compound 132

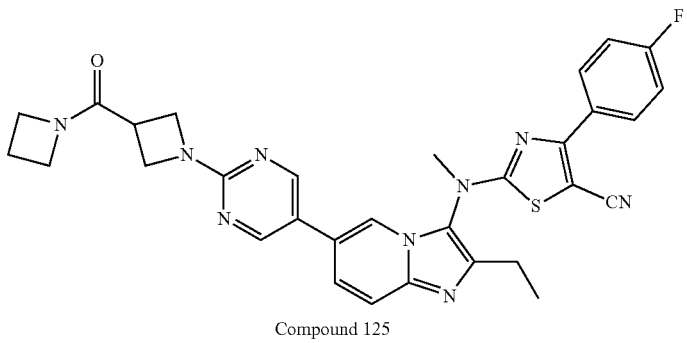

Compound 125

To a solution of compound 132, 1-(5-(3-((5-cyano-4-(4-fluorophenyl)thiazol-2-yl)(methyl)amino)-2-ethylimidazo[1,2-a]pyridin-6-yl)pyrimidin-2-yl)azetidine-3-carboxylic acid (380 mg, 685.18 umol) and azetidine hydrochloride (76.92 mg, 822.22 umol) in DMF (10 mL) was added HATU (387.75 mg, 1.03 mmol) and DIEA (265.66 mg, 2.06 mmol), the reaction mixture was stirred at 25° C. for 2 h. The mixture was poured into water (100 mL) and extracted with EA (30 mL×2), the organic layer was washed with brine (100 mL), then dried over $Na_2SO_4$ and concentrated. The residue was purified by Prep-HPLC to afford compound 125, 2-((6-(2-(3-(azetidine-1-carbonyl)azetidin-1-yl)pyrimidin-5-yl)-2-ethylimidazo[1,2-a]pyridin-3-yl)(methyl)amino)-4-(4-fluorophenyl)thiazole-5-carbonitrile (255 mg, 62.69% yield) as a white solid. $^1$H NMR (400 MHz, DMSO-$d_6$) δ 8.76 (s, 2H), 8.67 (s, 1H), 8.09 (s, 2H), 7.70 (s, 2H), 7.44-7.40 (t, 2H), 4.20-4.16 (m, 2H), 4.11-4.05 (m, 4H), 3.89-3.86 (t, 2H), 3.64 (s, 3H), 3.54-3.40 (m, 1H), 2.70-2.65 (dd, 2H), 2.22-2.18 (m, 2H), 1.29-1.25 (t, 3H); MS: m/z=594.1 (M+1, ESI+); HRMS: 594.2195.

5.4. Example 3—Synthesis of Azetidine-Linked Pyridine Compounds

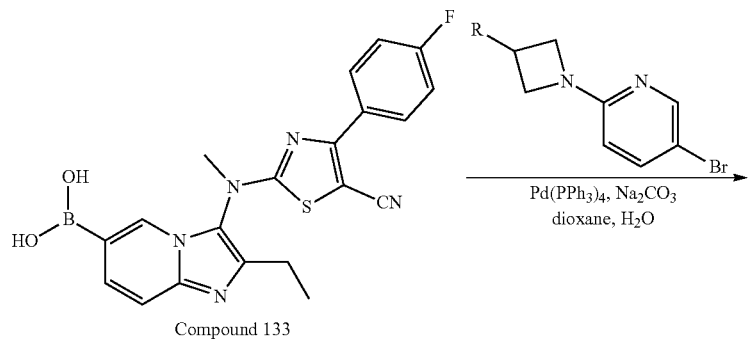

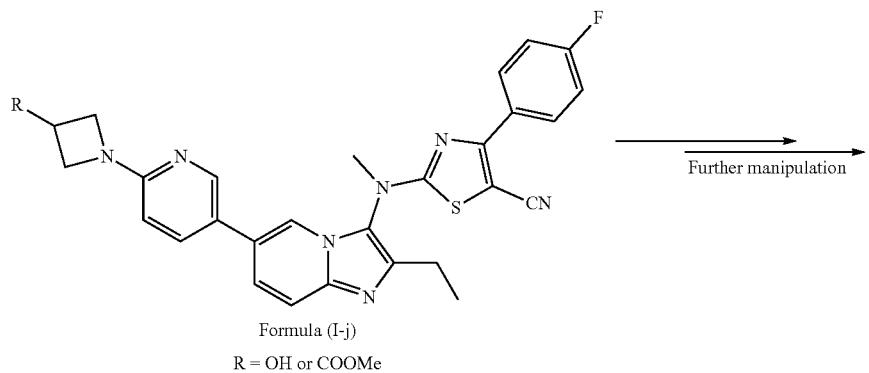

5.4.1. Synthesis of Compound 133

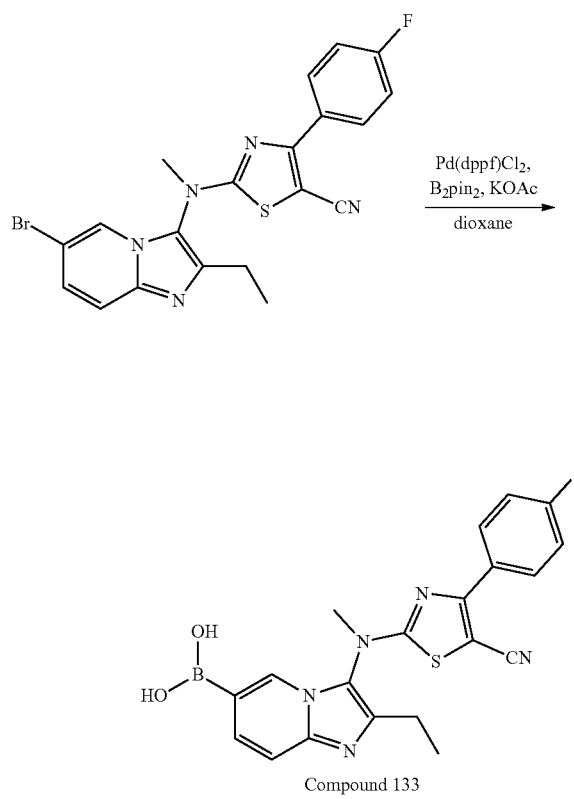

Compound 133

To a solution of 2-((6-bromo-2-ethylimidazo[1,2-a]pyridin-3-yl)(methyl)amino)-4-(4-fluorophenyl) thiazole-5-carbonitrile (12 g, 26.30 mmol) and B₂pin₂ (8.68 g, 34.19 mmol) in dioxane (200 mL) was added KOAc (7.74 g, 78.89 mmol) and Pd(dppf)Cl₂ (962.06 mg, 1.31 mmol), the reaction mixture was stirred at 90° C. for 6 h under N₂. The reaction mixture was cooled to room temperature and quenched by saturated NH₄Cl (200 mL), extracted with EA (100 mL×3) and the combined organic layers were washed with water (100 mL×3) and brine (100 mL), dried over Na₂SO₄ and concentrated. The residue was purified by reversed-phase column chromatography to afford compound 133, (3-((5-cyano-4-(4-fluorophenyl)thiazol-2-yl)(methyl)amino)-2-ethylimidazo[1,2-a] pyridine-6-yl)boronic acid (7.5 g, 67.70% yield) as a light-yellow solid. MS: m/z=422.1 (M+1, ESI+).

5.4.2. Synthesis of methyl 1-(5-bromopyridin-2-yl)azetidine-3-carboxylate

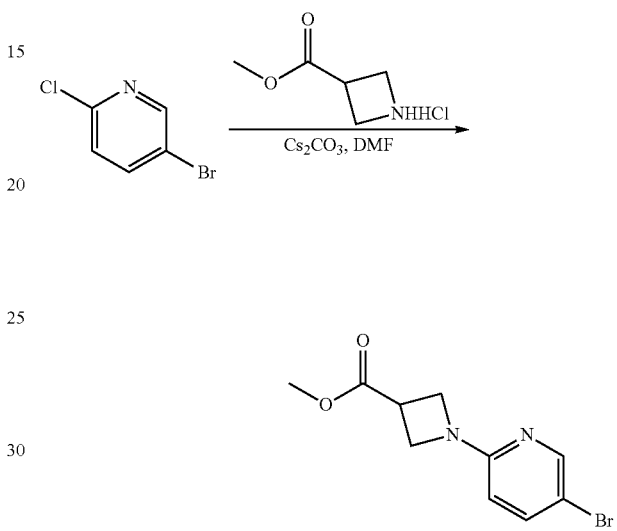

To a solution of 5-bromo-2-chloro-pyridine (1.3 g, 6.76 mmol) and methyl azetidine-3-carboxylate hydrochloride (1.54 g, 10.13 mmol) in DMF (20 mL) was added Cs₂CO₃ (6.60 g, 20.27 mmol), the reaction mixture was stirred at 140° C. for 5 h. The mixture was poured ino water (200 mL) and extracted with EA (40 mL×3), the organic layer was washed with brine (200 mL), then dried over Na₂SO₄ and concentrated. The residue was purified by column chromatography to afford methyl 1-(5-bromopyridin-2-yl)azetidine-3-carboxylate (300 mg, 16.38% yield) as yellow oil. MS: m/z=271.0 (M+1, ESI+).

5.4.3. Synthesis of Compound 134

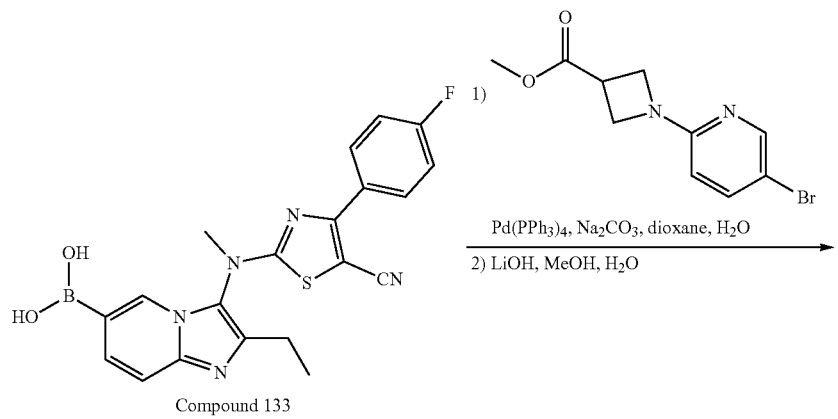

Compound 133

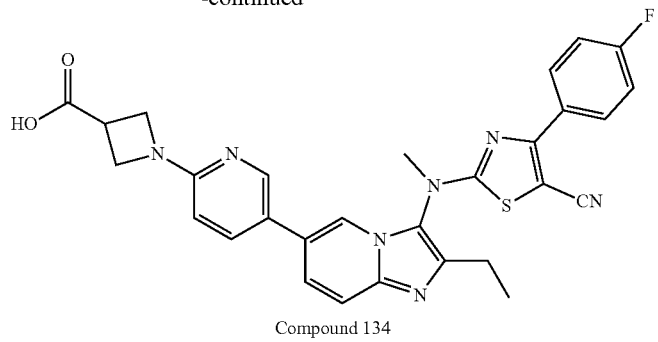

Compound 134

Step One:
To a mixture of methyl 1-(5-bromopyridin-2-yl)azetidine-3-carboxylate (300 mg, 1.11 mmol) and compound 133, (3-((5-cyano-4-(4-fluorophenyl)thiazol-2-yl)(methyl)amino)-2-ethylimidazo[1,2-a]pyridin-6-yl) boronic acid (466.14 mg, 1.11 mmol) in dioxane (20 mL) and water (4 mL) was added $Na_2CO_3$ (351.85 mg, 3.32 mmol) and $Pd(PPh_3)_4$ (127.87 mg, 110.66 umol), the reaction mixture was stirred at 100° C. for 2 h under $N_2$. The mixture was poured into water (60 mL) and extracted with EA (20 mL×2). The organic layer was washed by brine (100 mL), then dried over $Na_2SO_4$ and concentrated. The residue was purified by column chromatography to afford methyl 1-(5-(3-((5-cyano-4-(4-fluorophenyl)thiazol-2-yl)(methyl)amino)-2-ethylimidazo[1,2-a]pyridin-6-yl)pyridin-2-yl)azetidine-3-carboxylate (210 mg, 33.43% yield) as a yellow solid. MS: m/z=568.2 (M+1, ESI+).

Step Two:
To a solution of methyl 1-(5-(3-((5-cyano-4-(4-fluorophenyl)thiazol-2-yl)(methyl)amino)-2-ethyl imidazo[1,2-a]pyridin-6-yl)pyridin-2-yl)azetidine-3-carboxylate (210 mg, 369.96 umol) in MeOH (9 mL) and $H_2O$ (1 mL) was added LiOH (88.60 mg, 3.70 mmol), the reaction mixture was stirred at 25° C. for 5 h. The reaction mixture was concentrated under reduced pressure and the residue was poured into 2N HCl (20 mL) and extracted with EA (10 mL×2), the organic layer was washed by brine (20 mL), then dried over $Na_2SO_4$ and concentrated to afford compound 134, 1-(5-(3-((5-cyano-4-(4-fluorophenyl)thiazol-2-yl)(methyl)amino)-2-ethylimidazo[1,2-a]pyridin-6-yl)pyridin-2-yl) azetidine-3-carboxylic acid (195 mg, 95.21% yield) as a white solid. MS: m/z=554.1 (M+1, ESI+).

5.4.4. Synthesis of 1-(5-bromopyridin-2-yl)azetidin-3-ol

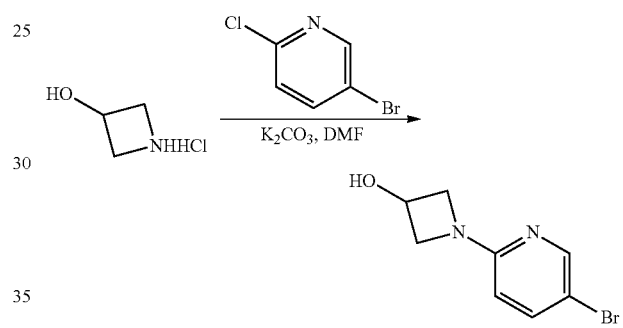

To a mixture of azetidin-3-ol hydrochloride (3.3 g, 45.15 mmol) and 5-bromo-2-chloro-pyridine (8.69 g, 45.15 mmol) in DMF (50 mL) was added $K_2CO_3$ (18.72 g, 135.44 mmol), the reaction mixture was stirred at 120° C. for 3 h. The mixture was poured into water (500 mL), extracted with EA (100 mL×3). The organic was washed by brine (300 mL), then dried over $Na_2SO_4$ and concentrated. The residue was purified by column chromatography to afford 1-(5-bromopyridin-2-yl)azetidin-3-ol (600 mg, 5.80% yield) as a yellow solid. MS: m/z=229.0 (M+1, ESI+).

5.4.5. Synthesis of Compound 148

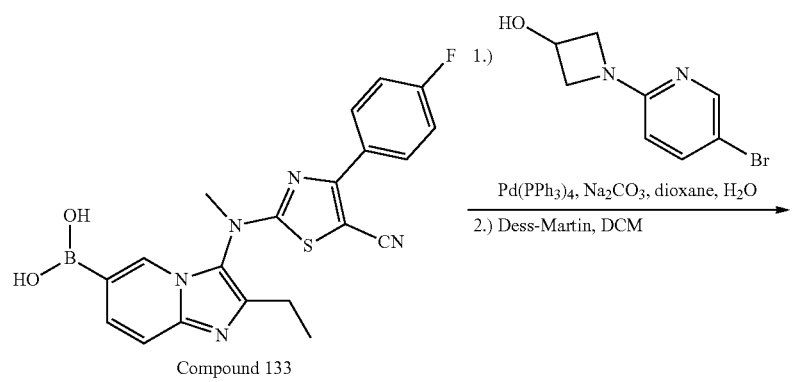

Compound 133

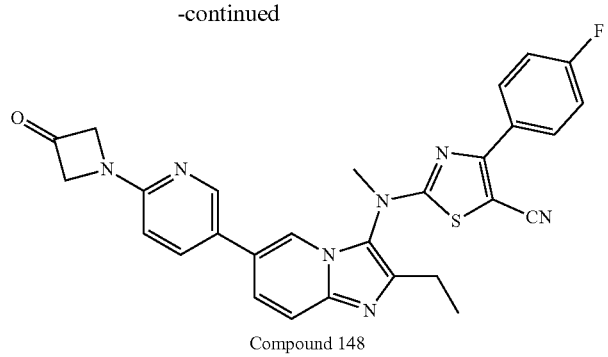

Compound 148

Step One:

To a mixture of 1-(5-bromopyridin-2-yl)azetidin-3-ol (600 mg, 2.62 mmol) and compound 133, (3-((5-cyano-4-(4-fluorophenyl)thiazol-2-yl)(methyl)amino)-2-ethylimidazo[1,2-a]pyridin-6-yl) boronic acid (1.10 g, 2.62 mmol) in dioxane (20 mL) and water (4 mL) was added $Na_2CO_3$ (832.83 mg, 7.86 mmol) and $Pd(PPh_3)_4$ (302.67 mg, 261.92 umol), the reaction mixture was stirred at 100° C. for 2 h under $N_2$. The mixture was poured into water (60 mL) and extracted with EA (20 mL×2). The organic layer was washed by brine (100 mL), then dried over $Na_2SO_4$ and concentrated. The residue was purified by column chromatography to afford 2-((2-ethyl-6-(6-(3-hydroxyazetidin-1-yl)pyridin-3-yl) imidazo[1,2-a]pyridin-3-yl)(methyl)amino)-4-(4-fluorophenyl)thiazole-5-carbonitrile (660 mg, 47.94% yield) as a yellow solid. MS: m/z=526.1 (M+1, ESI+).

Step Two:

To a solution of 2-((2-ethyl-6-(6-(3-hydroxyazetidin-1-yl) pyridin-3-yl)imidazo[1,2-a]pyridin-3-yl) (methyl)amino)-4-(4-fluorophenyl)thiazole-5-carbonitrile (660 mg, 1.26 mmol) in DCM (10 mL) was added Dess-Martin (1.07 g, 2.51 mmol), the reaction mixture was stirred at 25° C. for 3 h. The mixture was evaporate and purified by column chromatography to afford compound 148, 2-((2-ethyl-6-(6-(3-oxoazetidin-1-yl)pyridin-3-yl)imidazo[1,2-a]pyridin-3-yl)(methyl)amino)-4-(4-fluorophenyl) thiazole-5-carbonitrile (450 mg, 68.44% yield) as a yellow solid. MS: m/z=524.0 (M+1, ESI+).

5.4.6. Synthesis of Compound 97

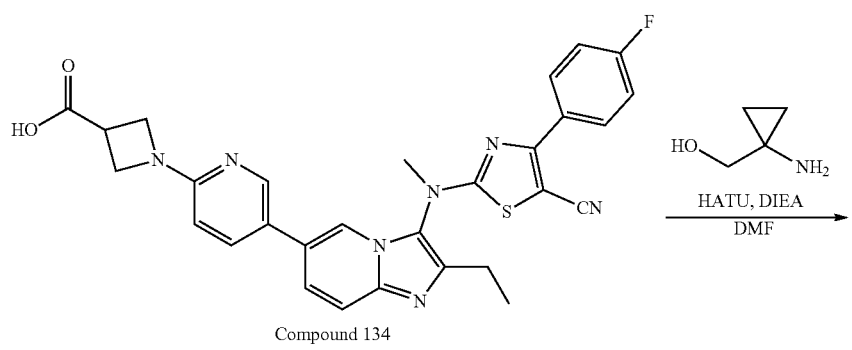

Compound 134

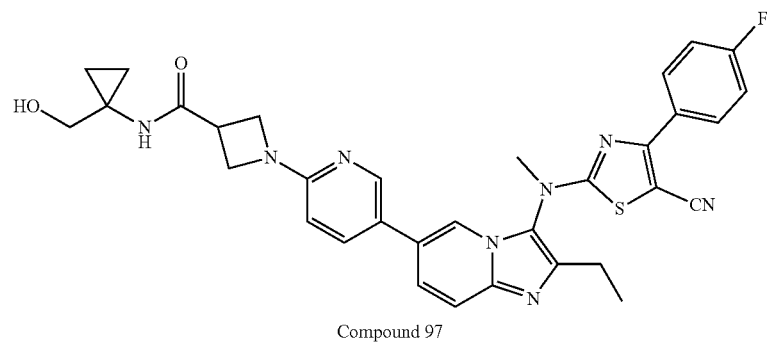

Compound 97

To a solution of compound 134, 1-(5-(3-((5-cyano-4-(4-fluorophenyl)thiazol-2-yl)(methyl)amino)-2-ethylimidazo[1,2-a]pyridin-6-yl)pyridin-2-yl)azetidine-3-carboxylic acid (195 mg, 352.23 umol) and (1-amino cyclopropyl)methanol (36.82 mg, 422.68 umol) in DMF (5 mL) was added HATU (199.33 mg, 528.35 umol) and DIEA (136.57 mg, 1.06 mmol), the reaction mixture was stirred at 25° C. for 2 h. The mixture was poured into water (50 mL) and extracted with EA (20 mL×2). The organic layer was washed with water (50 mL×2) and brine (50 mL), then dried over Na$_2$SO$_4$ and concentrated. The residue was purified by Prep-HPLC to afford compound 97, 1-(5-(3-((5-cyano-4-(4-fluorophenyl)thiazol-2-yl)(methyl)amino)-2-ethylimidazo[1,2-a]pyridin-6-yl)pyridin-2-yl)-N-(1-(hydroxymethyl) cyclopropyl)azetidine-3-carboxamide (95 mg, 43.31% yield) as a white solid. $^1$H NMR (400 MHz, DMSO-d) δ 8.55 (s, 1H), 8.47-8.46 (d, 1H), 8.27 (s, 1H), 8.10-8.07 (t, 2H), 7.94-7.91 (dd, 1H), 7.67 (s, 2H), 7.44-7.39 (t, 2H), 6.47-6.45 (d, 1H), 4.71-4.68 (t, 1H), 4.06-4.02 (t, 2H), 3.96-3.93 (t, 2H), 3.63 (s, 3H), 3.42-3.38 (m, 3H), 2.69-2.63 (dd, 2H), 1.28-1.24 (t, 3H), 0.67-0.53 (m, 4H); MS: m/z=623.2 (M+1, ESI+); HRMS: 623.2351.

5.4.7. Synthesis of Compound 124

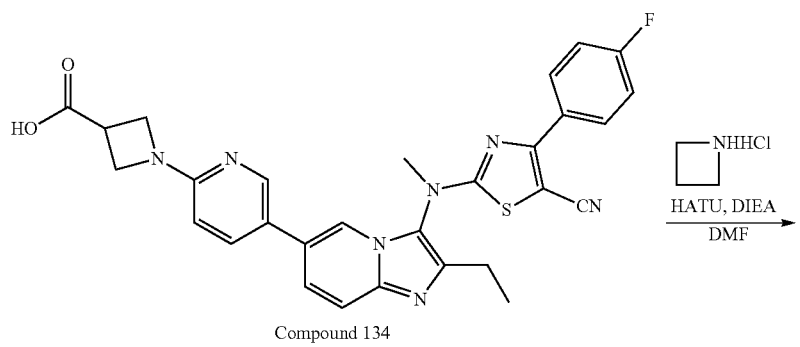

Compound 134

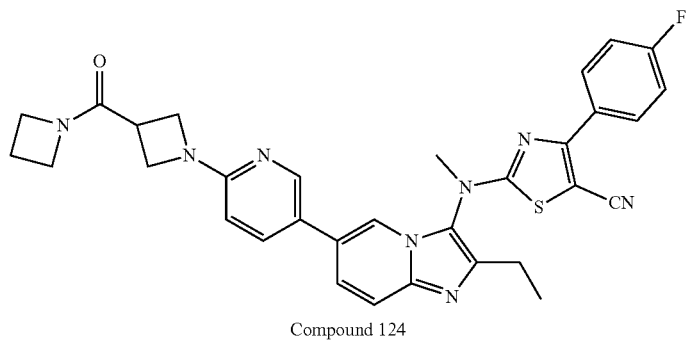

Compound 124

To a solution of compound 134, 1-(5-(3-((5-cyano-4-(4-fluorophenyl)thiazol-2-yl)(methyl)amino)-2-ethylimidazo[1,2-a]pyridin-6-yl)pyridin-2-yl)azetidine-3-carboxylic acid (510 mg, 921.23 umol) and azetidine hydrochloride (57.86 mg, 1.01 mmol) in DMF (10 mL) was added HATU (525.42 mg, 1.38 mmol) and DIEA (357.18 mg, 2.76 mmol), the reaction mixture was stirred at 25° C. for 2 h. The mixture was poured into water (100 mL) and extracted with EA (30 mL×2). The organic layer was washed with water (100 mL×2) and brine (100 mL), then dried over $Na_2SO_4$ and concentrated. The residue was purified by Prep-HPLC to afford compound 124, 2-((6-(6-(3-(azetidine-1-carbonyl)azetidin-1-yl)pyridin-3-yl)-2-ethylimidazo[1,2-a]pyridin-3-yl)(methyl)amino)-4-(4-fluorophenyl)thiazole-5-carbonitrile (277 mg, 50.73% yield) as a white solid. $^1$H NMR (400 MHz, DMSO-$d_6$) δ 8.56 (s, 1H), 8.48-8.47 (d, 1H), 8.11-8.07 (t, 2H), 7.95-7.92 (dd, 1H), 7.67 (s, 2H), 7.44-7.40 (t, 2H), 6.48-6.44 (d, 1H), 4.11-4.07 (t, 4H), 3.99-3.95 (t, 2H), 3.89-3.85 (t, 2H), 3.64 (s, 3H), 3.57-3.52 (m, 1H), 2.69-2.64 (dd, 2H), 2.24-2.16 (m, 2H), 1.29-1.25 (t, 3H); MS: m/z=593.3 (M+1, ESI+); HRMS: 593.2245.

5.4.8. Synthesis of Compound 109

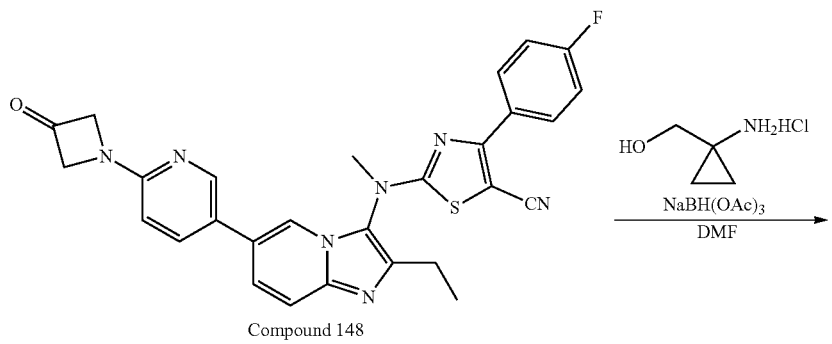

Compound 148

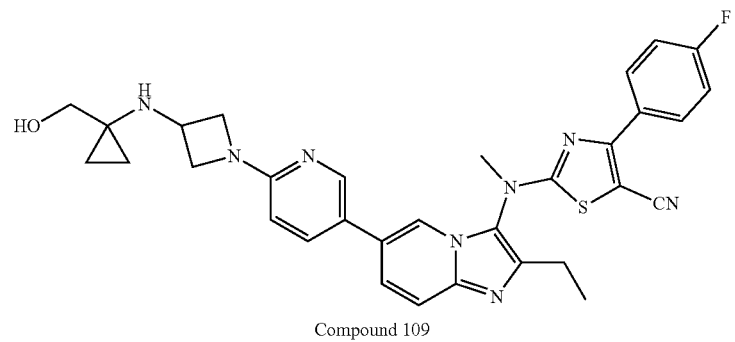

Compound 109

To a solution of compound 148, 2-((2-ethyl-6-(6-(3-oxoazetidin-1-yl)pyridin-3-yl)imidazo[1,2-a]pyridin-3-yl)(methyl)amino)-4-(4-fluorophenyl)thiazole-5-carbonitrile (450 mg, 859.46 umol) and (1-amino cyclopropyl)methanol hydrochloride (159.32 mg, 1.29 mmol) in DCM (20 mL) was added NaBH(OAc)$_3$ (364.31 mg, 1.72 mmol), the reaction mixture was stirred at 25° C. for 16 h. The mixture was poured into water (50 mL), extracted with DCM (10 mL×3). The organic was washed by brine (30 mL), then dried over Na$_2$SO$_4$ and concentrated. The residue was purified by Prep-HPLC to afford compound 109, 2-((2-ethyl-6-(6-(3-((1-(hydroxymethyl)cyclopropyl)amino)azetidin-1-yl)pyridin-3-yl)imidazo[1,2-a]pyridin-3-yl)(methyl)amino)-4-(4-fluorophenyl)thiazole-5-carbonitrile (155 mg, 30.33% yield) as a white solid. $^1$H NMR (400 MHz, DMSO-d$_6$) δ 8.53 (s, 1H), 8.45-8.44 (d, 1H), 8.11-8.07 (t, 2H), 7.91-7.89 (dd, 1H), 7.64 (s, 2H), 7.44-7.40 (t, 2H), 6.43-6.41 (d, 1H), 4.54-4.51 (t, 1H), 4.17-4.13 (t, 2H), 3.83-3.78 (m, 1H), 3.65-3.63 (m, 5H), 3.27-3.26 (d, 2H), 2.86 (bs, 1H), 2.69-2.63 (dd, 2H), 1.28-1.24 (t, 3H), 0.45-0.39 (m, 4H); MS: m/z=595.2 (M+1, ESI+); HRMS: 595.2396.

5.5. Example 4—Synthesis of CH$_2$-Carbonyl-Linked Pyrimidine-Type Compounds Scheme 4

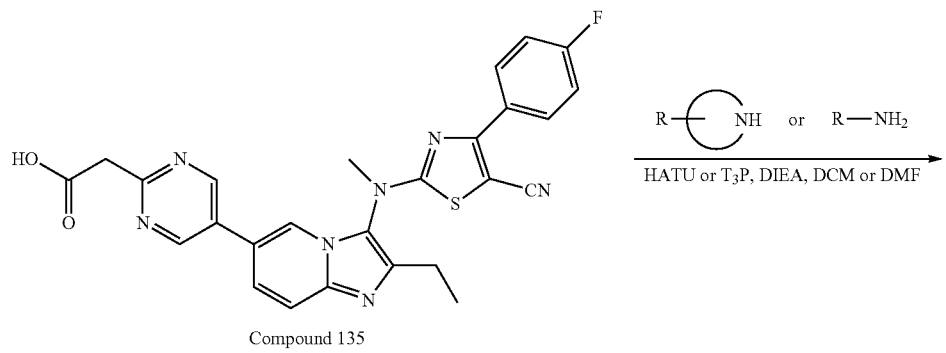

Compound 135

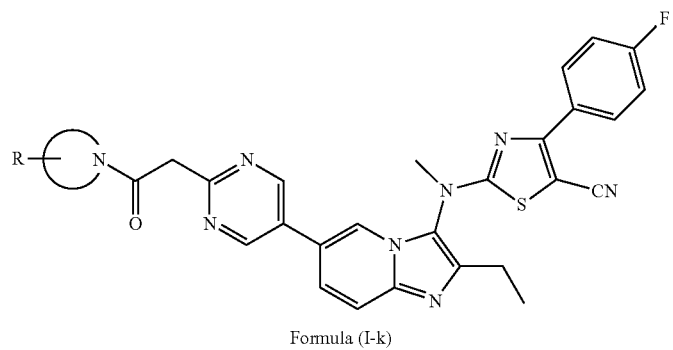

Formula (I-k)

or

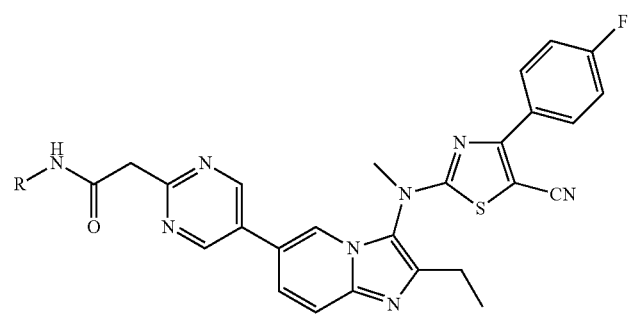

Formula (I-l)

5.5.1. Synthesis of Compound 135

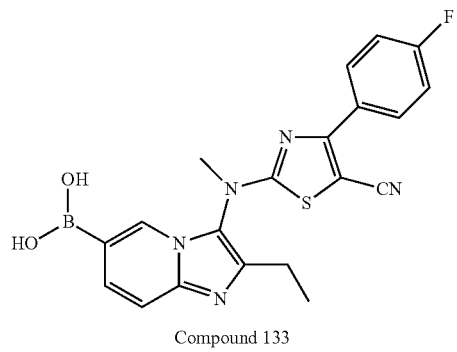

Compound 133

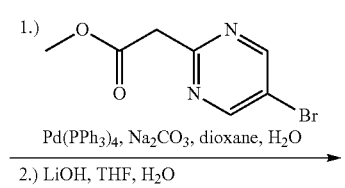

1.) Pd(PPh₃)₄, Na₂CO₃, dioxane, H₂O
2.) LiOH, THF, H₂O

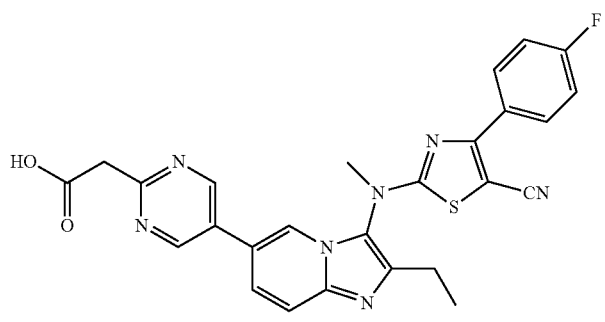

Compound 135

To a solution of compound 133, (3-((5-cyano-4-(4-fluorophenyl)thiazol-2-yl)(methyl)amino)-2-ethylimidazo[1,2-a]pyridin-6-yl)boronic acid (4 g, 9.50 mmol) and methyl 2-(5-bromopyrimidin-2-yl)acetate (2.19 g, 9.50 mmol) in dioxane (40 mL) and H₂O (8 mL) was added Pd(PPh₃)₄ (109.73 mg, 94.95 umol) and Na₂CO; (2.01 g, 18.99 mmol), the reaction mixture was stirred at 100° C. for 5 h under N₂. The reaction mixture was cooled to room temperature and quenched by saturated NH₄Cl (200 mL), extracted with EA (100 mL×3) and the combined organic layers were washed with water (100 mL×3) and brine (100 mL), dried over Na₂SO₄ and concentrated. The residue was purified by column chromatography to afford methyl 2-(5-(3-((5-cyano-4-(4-fluorophenyl)thiazol-2-yl) (methyl)amino)-2-ethylimidazo[1,2-a]pyridin-6-yl)pyrimidin-2-yl)acetate (3 g, 59.89% yield) as a white solid. MS: m/z=528.1 (M+1, ESI+).

To a solution of methyl 2-(5-(3-((5-cyano-4-(4-fluorophenyl)thiazol-2-yl)(methyl)amino)-2-ethyl imidazo[1,2-a]pyridin-6-yl)pyrimidin-2-yl)acetate (3 g, 5.69 mmol) in THF (20 mL) and H₂O (20 mL) was added LiOH (900 mg, 37.58 mmol), the resulting mixture was stirred at 40° C. for 1 h. Cooled to room temperature and the reaction mixture was acidified with 2N HCl to pH to 2, extracted with EA (20 mL×3) and the combined organic layers were washed with water (50 mL×3) and brine (50 mL), dried over Na₂SO₄ and concentrated to afford compound 135, 2-(5-(3-((5-cyano-4-(4-fluorophenyl) thiazol-2-yl)(methyl)amino)-2-ethylimidazo[1,2-a]pyridin-6-yl)pyrimidin-2-yl)acetic acid (2.5 g, 77.89% yield) as a white solid. MS: m/z=514.0 (M+1, ESI+).

5.5.2. Synthesis of Compound 52

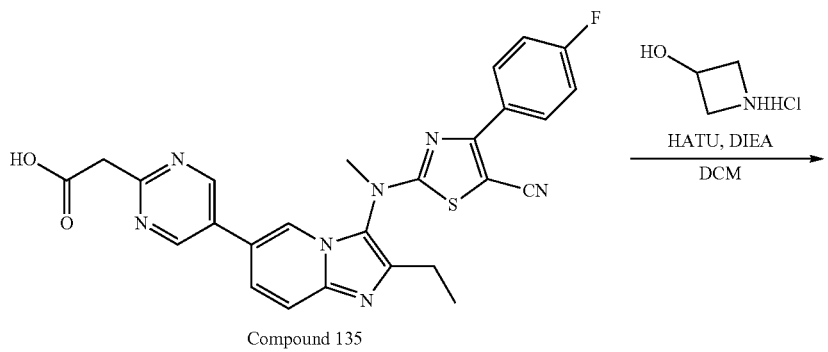

Compound 135

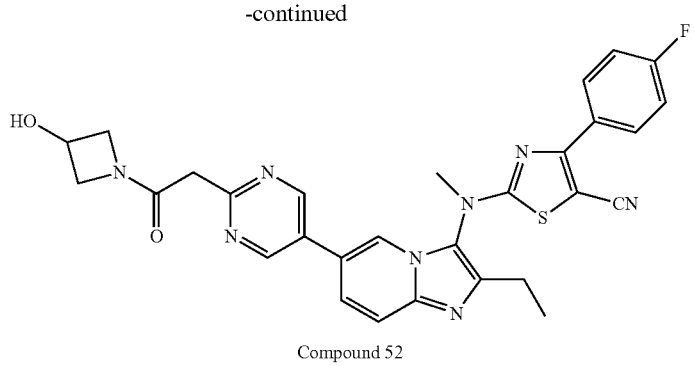

Compound 52

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (100 mg, 194.72 umol) and azetidin-3-ol hydrochloride (21.35 mg, 292.09 umol) in DCM (6 mL) was added HATU (111.06 mg, 292.09 umol) and DIEA (75.50 mg, 584.17 umol), the reaction mixture was stirred at 25° C. for 16 h. The reaction mixture was poured into water (20 mL) and extracted with DCM (10 mL×3). The combined organic layers were dried over Na$_2$SO$_4$ and concentrated under reduced pressure and the residue purified by Prep-HPLC to afford compound 52, 2-((2-ethyl-6-(2-(2-(3-hydroxyazetidin-1-yl)-2-oxoethyl)pyrimidin-5-yl)imidazo[1,2-a]pyridin-3-yl)(methyl)amino)-4-(4-fluorophenyl)thiazole-5-carbonitrile (89 mg, 80.1% yield) as a white solid. $^1$H NMR (400 MHz, DMSO-d$_6$) δ9.15 (s, 2H), 8.89 (s, 1H), 8.10-8.07 (t, 2H), 7.85-7.82 (dd, 1H), 7.78-7.76 (dd, 1H), 7.44-7.40 (t, 2H), 5.73-5.72 (d, 1H), 4.48-4.36 (m, 2H), 4.06-4.02 (dd, 1H), 3.96-3.92 (dd, 1H), 3.79 (s, 2H), 3.64 (s, 3H), 3.61-3.57 (dd, 1H), 2.71-2.66 (dd, 2H), 1.29-1.26 (t, 3H); MS: m/z=569.1 (M+1, ESI+).

5.5.3. Synthesis of Compound 53 Formate

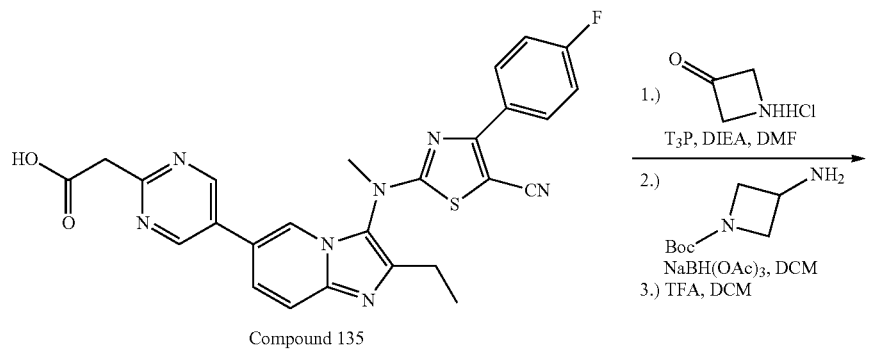

Compound 135

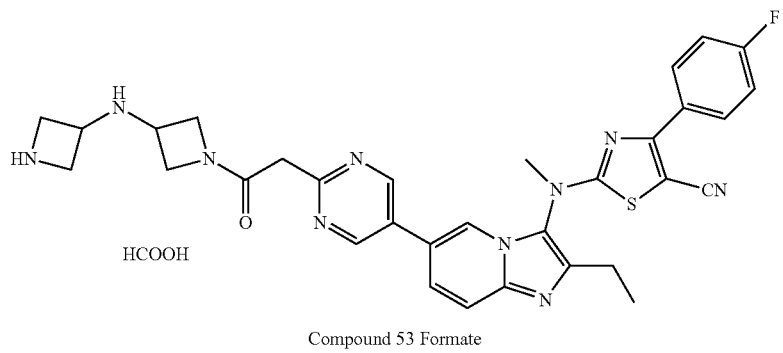

Compound 53 Formate

Step One:

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (800 mg, 1.56 mmol) and azetidin-3-one hydrochloride (132.87 mg, 1.87 mmol) in DMF (20 mL) was added DIEA (603.99 mg, 4.67 mmol) and $T_3P$ (1.49 g, 2.34 mmol, 50% purity), the reaction mixture was stirred at 25° C. for 3 h. The resulting solution was quenched by saturated $NH_4Cl$ (50 mL), extracted with EA (50 mL×2), washed with water (50 mL×2) and brine (50 mL), dried over $Na_2SO_4$ and concentrated. The residue was purified by column chromatography to afford 2-((2-ethyl-6-(2-(2-oxo-2-(3-oxoazetidin-1-yl)ethyl)pyrimidin-5-yl)imidazo[1,2-a]pyridin-3-yl)(methyl)amino)-4-(4-fluorophenyl)thiazole-5-carbonitrile (400 mg, 45.32% yield) as a yellow solid. MS: m/z=567.3 (M+1, ESI+).

Step Two:

To a solution of 2-((2-ethyl-6-(2-(2-oxo-2-(3-oxoazetidin-1-yl)ethyl)pyrimidin-5-yl)imidazo[1,2-a]pyridin-3-yl)(methyl)amino)-4-(4-fluorophenyl)thiazole-5-carbonitrile (400 mg, 705.96 umol) and tert-butyl 3-aminoazetidine-1-carboxylate (121.58 mg, 705.96 umol) in DCM (10 mL) was added $NaBH(OAc)_3$ (448.86 mg, 2.12 mmol) in portions, the reaction mixture was stirred at 25° C. for 24 h. The resulting solution was quenched by saturated $NH_4Cl$ (50 mL), extracted with DCM (50 mL×3), washed with water (50 mL×2) and brine (50 mL), dried over $Na_2SO_4$ and concentrated. The residue was purified by column chromatography to afford tert-butyl 3-((1-(2-(5-(3-((5-cyano-4-(4-fluorophenyl)thiazol-2-yl)(methyl)amino)-2-ethylimidazo[1,2-a]pyridin-6-yl)pyrimidin-2-yl)acetyl) azetidin-3-yl)amino)azetidine-1-carboxylate (180 mg, 35.27% yield) as a yellow solid. MS: m/z=723.6 (M+1, ESI+).

Step Three:

To a suspension of tert-butyl 3-((1-(2-(5-(3-((5-cyano-4-(4-fluorophenyl)thiazol-2-yl)(methyl)amino)-2-ethyl imidazo[1,2-a]pyridin-6-yl)pyrimidin-2-yl)acetyl)azetidin-3-yl)amino)azetidine-1-carboxylate (170 mg, 235.19 umol) in DCM (10 mL) was added TFA (26.82 mg, 235.19 umol). The reaction mixture was stirred at 25° C. for 3 h. The resulting solution was evaporated and the residue was purified by Prep-HPLC to afford compound 53 formate, 2-((6-(2-(2-(3-(azetidin-3-ylamino)azetidin-1-yl)-2-oxoethyl)pyrimidin-5-yl)-2-ethylimidazo[1,2-a]pyridin-3-yl)(methyl)amino)-4-(4-fluorophenyl) thiazole-5-carbonitrile formate (59 mg, 40.29% yield) as a white solid. $^1$H NMR (400 MHz, DMSO-$d_6$) δ 9.15 (s, 2H), 8.91 (s, 1H), 8.73 (s, 1H), 8.62 (s, 1H), 8.10-8.07 (t, 2H), 7.89-7.80 (m, 2H), 7.44-7.40 (t, 2H), 4.35-4.32 (t, 1H), 4.01-3.75 (m, 10H), 3.65-3.55 (m, 6H), 2.73-2.68 (dd, 2H), 1.30-1.26 (t, 3H); MS: m/z=623.2 (M+1, ESI+).

5.5.4. Synthesis of Compound 53

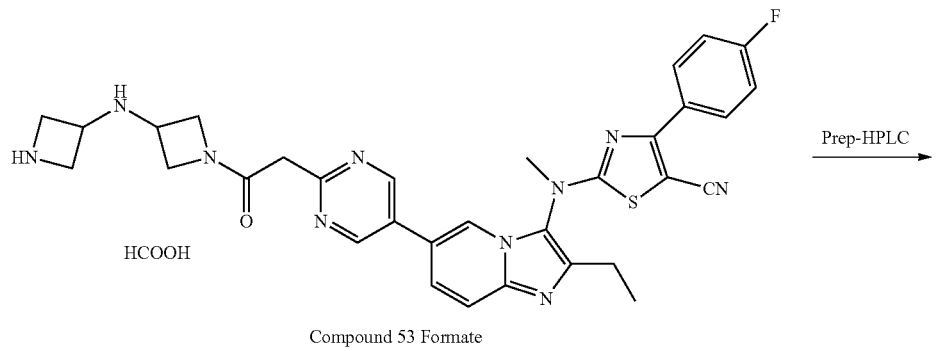

Compound 53 Formate

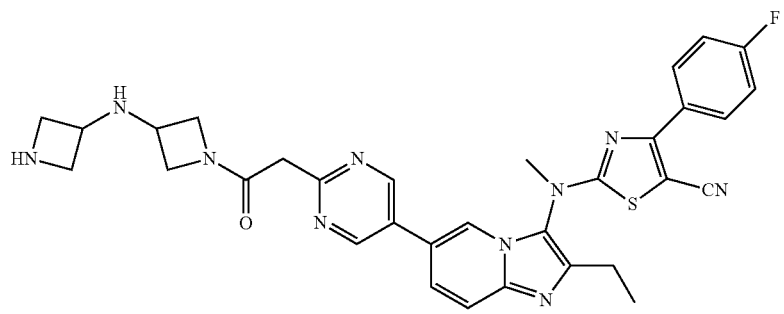

Compound 53

Compound 53 formate, 2-((6-(2-(2-(3-(azetidin-3-ylamino)azetidin-1-yl)-2-oxoethyl)pyrimidin-5-yl)-2-ethyl imidazo[1,2-a]pyridin-3-yl)(methyl)amino)-4-(4-fluorophenyl)thiazole-5-carbonitrile formate (85 mg, 0.127 mmol) was purified by Prep-HPLC to afford compound 53, 2-((6-(2-(2-(3-(azetidin-3-ylamino)azetidin-1-yl)-2-oxoethyl)pyrimidin-5-yl)-2-ethylimidazo[1,2-a]pyridin-3-yl)(methyl)amino)-4-(4-fluoro phenyl)thiazole-5-carbonitrile (6 mg, 7.59% yield) as a white solid. $^1$H NMR (400 MHz, DMSO-$d_6$) δ9.14 (s, 2H), 8.89 (s, 1H), 8.08 (s, 2H), 7.84-7.76 (dd, 2H), 7.43-7.40 (t, 2H), 4.28 (s, 1H), 3.94-3.52 (m, 13H), 3.34 (s, 3H), 2.69-2.68 (d, 2H), 1.29-1.26 (t, 3H); MS: m/z=623.3 (M+1, ESI+).

5.5.5. Synthesis of benzyl azetidin-3-yl(methyl)carbamate

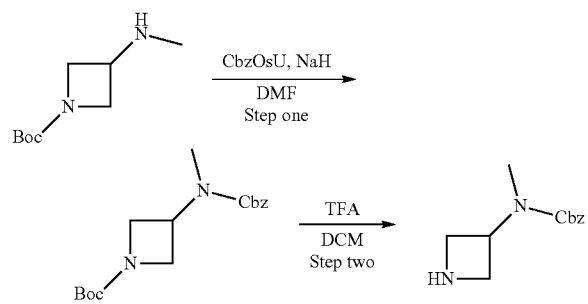

Step One:

To a solution of tert-butyl 3-(methylamino)azetidine-1-carboxylate (2 g, 10.74 mmol) in DMF (20 mL) at 0° C. was added NaH (859.12 mg, 21.48 mmol, 60% purity) in portions and stirred at this temperature for 0.5 h, then CbzOSu (4.01 g, 16.11 mmol) was added to the above solution and stirred at 25° C. for 2 h. The reaction mixture was poured into water (200 mL) and extracted with DCM (50 mL×3). The combined organic layers were washed with water (100 mL×3) and brine (100 mL), dried over Na$_2$SO$_4$ and concentrated under reduce pressure and the residue was purified by column chromatography to afford tert-butyl 3-(((benzyloxy)carbonyl) (methyl)amino) azetidine-1-carboxylate (3.3 g, 10.30 mmol) as a white solid. MS: m/z=265.1 (M−56+1, ESI+).

Step Two:

To a solution of tert-butyl 3-(((benzyloxy)carbonyl)(methyl)amino)azetidine-1-carboxylate (3.3 g, 10.30 mmol) in DCM (25 mL) was added TFA (7.70 g, 67.53 mmol), the reaction mixture was stirred at 25° C. for 2 h. The reaction mixture was evaporated under reduce pressure to afford benzyl azetidin-3-yl(methyl)carbamate (2.12 g, 93.44% yield) as a yellow solid. MS: m/z=221.2 (M+1, ESI+).

5.5.6. Synthesis of Compound 54

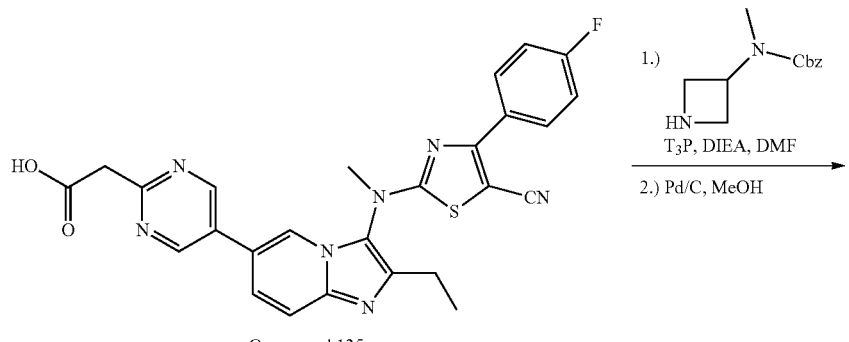

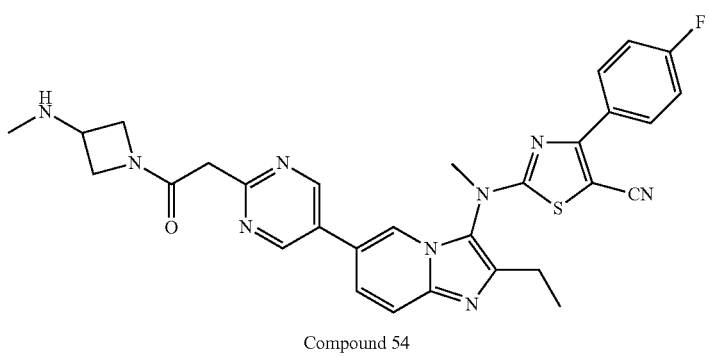

To a solution of benzyl azetidin-3-yl(methyl)carbamate (643.37 mg, 2.92 mmol) and compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (1 g, 1.95 mmol) in DCM (20 mL) was added HATU (1.11 g, 2.92 mmol) and DIEA (754.99 mg, 5.84 mmol), the reaction mixture was stirred at 25° C. for 16 h. The reaction mixture was poured into water (200 mL) and extracted with DCM (50 mL×3). The combined organic layers were washed with water (100 mL×3) and brine (100 mL), dried over Na$_2$SO$_4$ and concentrated under reduce pressure and the residue was purified by column chromatography to afford benzyl (1-(2-(5-(3-((5-cyano-4-(4-fluorophenyl)thiazol-2-yl)(methyl)amino)-2-ethylimidazo[1,2-a]pyridin-6-yl)pyrimidin-2-yl)acetyl)azetidin-3-yl)(methyl)carbamate (1.1 g, 79.13% yield) as a yellow solid. MS: m/z=716.3 (M+1, ESI+)

To a solution of benzyl (1-(2-(5-(3-((5-cyano-4-(4-fluorophenyl)thiazol-2-yl)(methyl)amino)-2-ethylimidazo[1,2-a]pyridin-6-yl)pyrimidin-2-yl)acetyl)azetidin-3-yl)(methyl)carbamate (300.00 mg, 419.11 umol) in MeOH (10 mL) was added Pd/C (300 mg, 10% purity), the reaction mixture was stirred at 25° C. for 16 h under H$_2$. Filtered and the filtrate was evaporated under reduce pressure, the residue was purified by Prep-HPLC to afford compound 54, 2-((2-ethyl-6-(2-(2-(3-(methylamino)azetidin-1-yl)-2-oxoethyl)pyrimidin-5-yl)imidazo[1,2-a]pyridin-3-yl)(methyl)amino)-4-(4-fluorophenyl) thiazole-5-carbonitrile (26 mg, 10.67% yield) as a white solid. $^1$H NMR (400 MHz, DMSO-d$_6$) δ 9.14 (s, 2H), 8.89 (s, 1H), 8.10-8.07 (t, 2H), 7.85-7.82 (dd, 1H), 7.78-7.76 (dd, 1H), 7.44-7.40 (t, 2H), 4.30-4.26 (t, 1H), 3.97-3.92 (m, 1H), 3.88-3.85 (dd, 1H), 3.79-3.77 (d, 2H), 3.64 (s, 3H), 3.55-3.51 (dd, 1H), 3.46-3.32 (m, 1H), 2.71-2.66 (dd, 2H), 2.28 (s, 1H), 2.19 (s, 3H), 1.29-1.26 (t, 3H); MS: m/z=582.2 (M+1, ESI+).

5.5.7. Synthesis of Compound 55

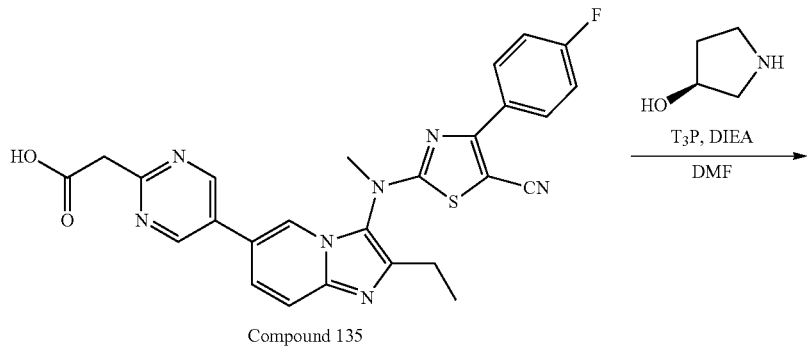

Compound 135

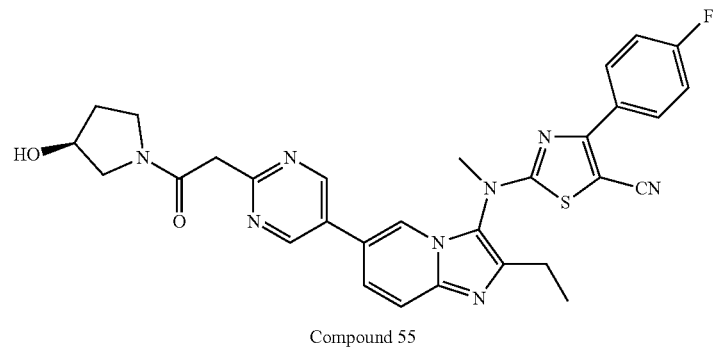

Compound 55

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and (S)-pyrrolidin-3-ol (27.99 mg, 321.30 umol) in DMF (3 mL) was added T$_3$P (139.40 mg, 438.13 umol) and DIEA (113.25 mg, 876.26 umol), the reaction mixture was stirred at 25° C. for 16 h. The reaction mixture was poured into water (200 mL) and extracted with DCM (50 mL×3). The combined organic layers were washed with water (100 mL×3) and brine (100 mL), dried over Na$_2$SO$_4$ and concentrated under reduce pressure and the residue was purified by Prep-HPLC to afford compound 55, (S)-2-((2-ethyl-6-(2-(2-(3-hydroxypyrrolidin-1-yl)-2-oxoethyl)pyrimidin-5-yl)imidazo[1,2-a]pyridin-3-yl)(methyl)amino)-4-(4-fluorophenyl)thiazole-5-carbonitrile (40 mg, 22.96% yield) as a white solid. $^1$H NMR (400 MHz, DMSO-d$_6$) δ 9.15 (s, 2H), 8.90 (s, 1H), 8.10-8.07 (t, 2H), 7.85-7.82 (dd, 1H), 7.78-7.76 (d, 1H), 7.44-7.39 (t, 2H), 5.02-4.93 (dd, 1H), 4.32-4.25 (d, 1H), 4.00-3.94 (m, 2H), 3.64-3.59 (m, 4H), 3.43-3.39 (m, 2H), 3.30-3.23 (m, 1H), 2.71-2.66 (dd, 2H), 2.02-1.72 (m, 2H), 1.29-1.26 (t, 3H); MS: m/z=583.1 (M+1, ESI+).

5.5.8. Synthesis of Compound 56

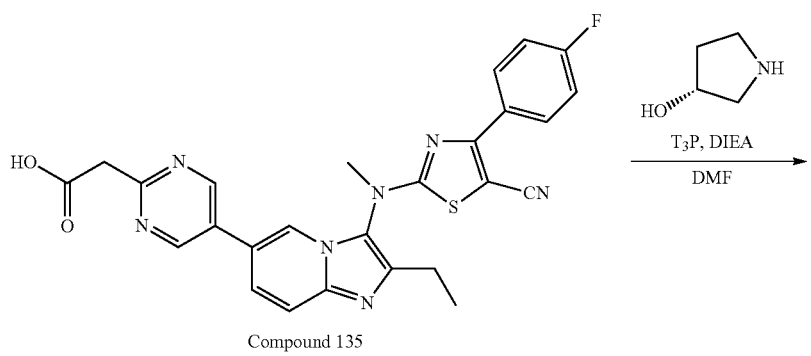

Compound 135

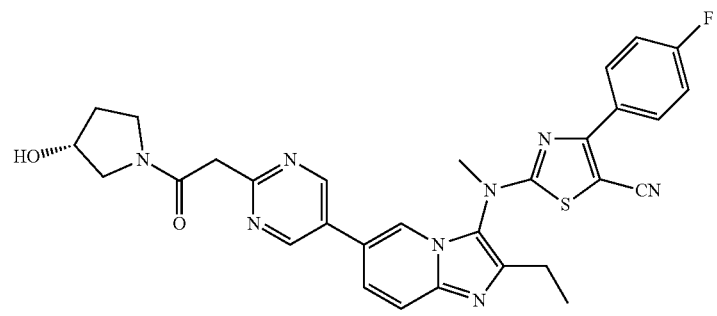

Compound 56

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and (R)-pyrrolidin-3-ol (27.99 mg, 321.30 umol) in DMF (3 mL) was added T₃P (139.40 mg, 438.13 umol) and DIEA (113.25 mg, 876.26 umol), the reaction mixture was stirred at 25° C. for 16 h. The reaction mixture was poured into water (200 mL) and extracted with DCM (50 mL×3). The combined organic layers were washed with water (100 mL×3) and brine (100 mL), dried over Na₂SO₄ and concentrated under reduce pressure and the residue was purified by Prep-HPLC to afford compound 56, (R)-2-((2-ethyl-6-(2-(2-(3-hydroxypyrrolidin-1-yl)-2-oxoethyl)pyrimidin-5-yl)imidazo[1,2-a]pyridin-3-yl)(methyl)amino)-4-(4-fluorophenyl)thiazole-5-carbonitrile (80 mg, 45.92% yield) as a white solid. ¹H NMR (400 MHz, DMSO-d₆) δ 9.15 (s, 2H), 8.90 (s, 1H), 8.10-8.07 (t, 2H), 7.85-7.82 (dd, 1H), 7.78-7.76 (d, 1H), 7.44-7.39 (t, 2H), 5.02-4.93 (dd, 1H), 4.32-4.25 (d, 1H), 4.00-3.94 (m, 2H), 3.65-3.59 (m, 4H), 3.41-3.34 (m, 2H), 3.30-3.23 (m, 1H), 2.72-2.66 (dd, 2H), 2.01-1.72 (m, 2H), 1.30-1.26 (t, 3H); MS: m/z=583.1 (M+1, ESI+).

5.5.9. Synthesis of Compound 57

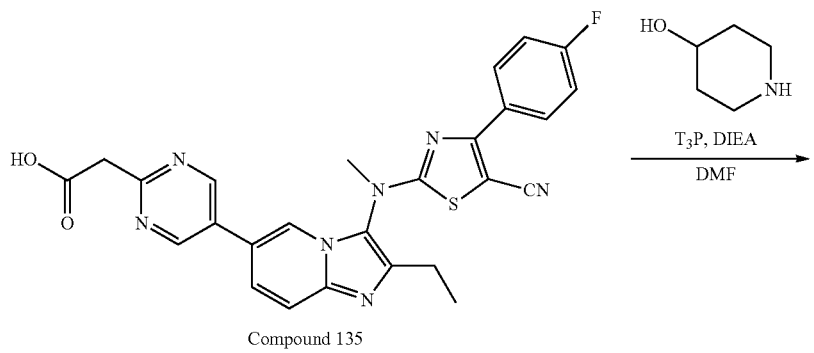

Compound 135

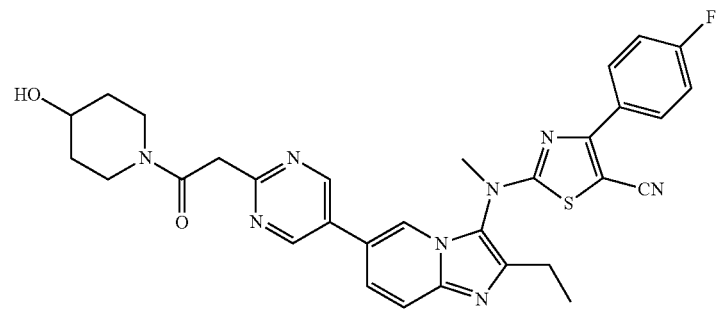

Compound 57

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and piperidin-4-ol (32.50 mg, 321.30 umol) in DMF (3 mL) was added T₃P (139.40 mg, 438.13 umol) and DIEA (113.25 mg, 876.26 umol), the reaction mixture was stirred at 25° C. for 16 h. The reaction mixture was poured into water (200 mL) and extracted with DCM (50 mL×3). The combined organic layers were washed with water (100 mL×3) and brine (100 mL), dried over Na₂SO₄ and concentrated under reduce pressure and the residue was purified by Prep-HPLC to afford compound 57, 2-((2-ethyl-6-(2-(2-(4-hydroxypiperidin-1-yl)-2-oxoethyl)pyrimidin-5-yl)imidazo[1,2-a]pyridin-3-yl)(methyl)amino)-4-(4-fluorophenyl) thiazole-5-carbonitrile (70 mg, 40.04% yield) as a white solid. ¹H NMR (400 MHz, DMSO-d₆) δ 9.16 (s, 2H), 8.90 (s, 1H), 8.10-8.07 (t, 2H), 7.85-7.83 (dd, 1H), 7.78-7.76 (d, 1H), 7.44-7.40 (t, 2H), 4.73-4.72 (d, 1H), 4.05 (s, 2H), 3.91-3.88 (m, 1H), 3.77-3.65 (m, 5H), 3.23-3.18 (t, 1H), 3.05-2.99 (t, 1H), 2.71-2.66 (dd, 2H), 1.70 (s, 2H), 1.29-1.26 (t, 3H); MS: m/z=597.1 (M+1, ESI+).

5.5.10. Synthesis of Compound 58 mg, 486.81 umol) and DIEA (62.92 mg, 486.81 umol), the reaction mixture was stirred at 25° C. for 1 h. The reaction mixture was poured into water (50 mL) and extracted with DCM (10 mL×3). The combined organic layers were washed with water (20 mL×3) and brine (20 mL), dried over Na₂SO₄ and concentrated under reduce pressure and the residue was purified by column chromatography to afford tert-butyl4-(2-(5-(3-((5-cyano-4-(4-fluorophenyl)thiazol-2-yl)(methyl)amino)-2-ethylimidazo[1,2-a] pyridine-6-yl)pyrimidin-2-yl)acetyl)piperazine-1-carboxylate (300 mg, 90.39% yield) as a yellow solid. MS: m/z=682.2 (M+1, ESI+).

Step Two:

To a suspension of tert-butyl 4-(2-(5-(3-((5-cyano-4-(4-fluorophenyl)thiazol-2-yl)(methyl)amino)-2-ethylimidazo[1,2-a]pyridin-6-yl)pyrimidin-2-yl)acetyl)piperazine-1-carboxylate (250 mg, 366.69 umol) in DCM (10 mL) was added 3M HCl in EA (2 mL). The reaction mixture was stirred at 25° C. for 1 h. The resulting solution was evaporated and the residue was purified by Prep-HPLC to afford compound 58, 2-((2-ethyl-6-(2-(2-oxo-2-(piperazin-1-yl)ethyl)pyrimidin-5-yl)imidazo[1,2-a]pyridin-3-yl)(methyl)amino)-4-(4-fluo-

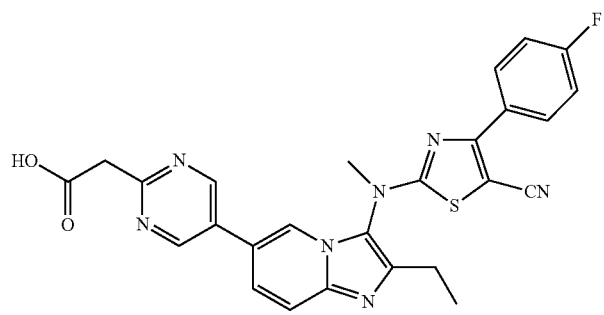

Compound 135

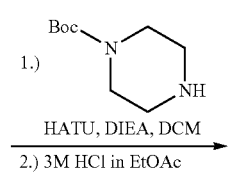

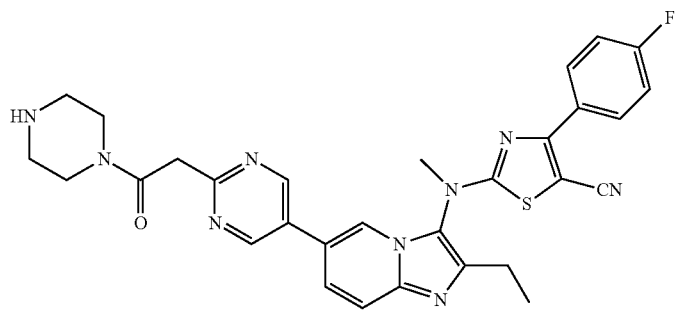

Compound 58

Step One:

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (250 mg, 486.81 umol) and tert-butyl piperazine-1-carboxylate (90.67 mg, 486.81 umol) in DCM (5 mL) was added HATU (185.18 rophenyl)thiazole-5-carbonitrile (96 mg, 45.01% yield) as a white solid. ¹H NMR (400 MHz, DMSO-d₆) δ 9.16 (s, 2H), 8.90 (s, 1H), 8.10-8.07 (t, 2H), 7.85-7.83 (dd, 1H), 7.78-7.76 (d, 1H), 7.44-7.40 (t, 2H), 4.04 (s, 2H), 3.65 (s, 3H), 3.43-3.37 (m, 4H), 2.71-2.61 (m, 7H), 1.29-1.26 (t, 3H); MS: m/z=582.2 (M+1, ESI+).

5.5.11. Synthesis of Compound 59

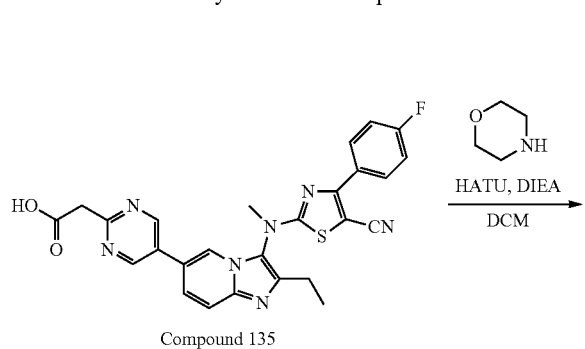

Compound 135

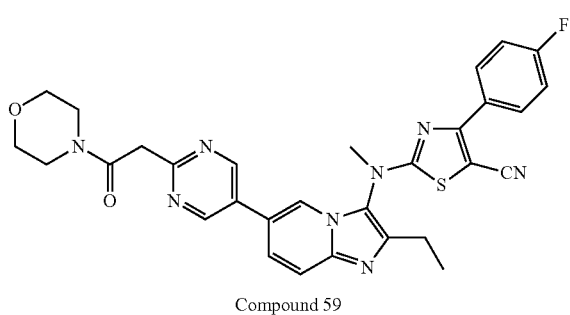

Compound 59

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (140 mg, 272.61 umol) and morpholine (35.62 mg, 408.92 umol) in DCM (5 mL) was added HATU (155.48 mg, 408.92 umol) and DIEA (105.70 mg, 817.84 umol), the reaction mixture was stirred at 25° C. for 16 h. The reaction mixture was poured into water (50 mL) and extracted with DCM (10 mL×3). The combined organic layers were washed with water (20 mL×3) and brine (20 mL), dried over Na₂SO₄ and concentrated under reduce pressure and the residue was purified by Prep-HPLC to afford compound 59, 2-((2-ethyl-6-(2-(2-morpholino-2-oxoethyl)pyrimidin-5-yl)imidazo[1,2-a]pyridin-3-yl)(methyl)amino)-4-(4-fluorophenyl)thiazole-5-carbonitrile (62 mg, 39.11% yield) as a white solid. ¹H NMR (400 MHz, DMSO-d₆) δ 9.16 (s, 2H), 8.90 (s, 1H), 8.09 (s, 2H), 7.85-7.83 (d, 1H), 7.78-7.76 (d, 1H), 7.44-7.40 (t, 2H), 4.08 (s, 2H), 3.65 (s, 3H), 3.57-3.46 (m, 8H), 2.71-2.67 (m, 2H), 1.29-1.26 (t, 3H); MS: m/z=583.1 (M+1, ESI+).

5.5.12. Synthesis of Compound 60

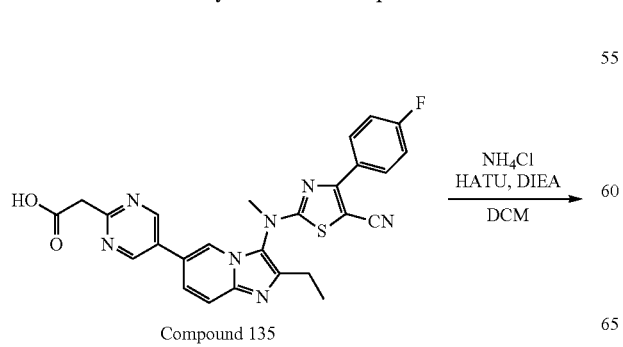

Compound 135

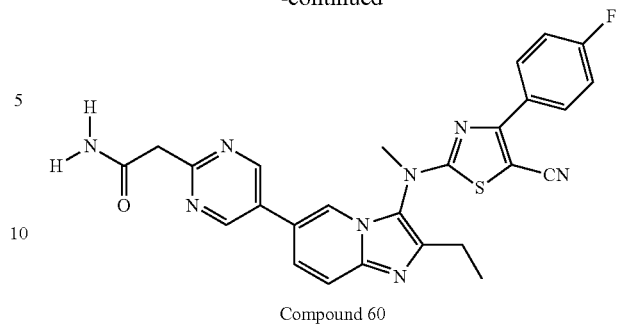

Compound 60

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and NH₄Cl (31.25 mg, 584.17 umol) in DCM (5 mL) was added HATU (166.59 mg, 438.13 umol) and DLEA (113.25 mg, 876.26 umol), the reaction mixture was stirred at 25° C. for 1 h. The reaction mixture was poured into water (50 mL) and extracted with DCM (10 mL×3). The combined organic layers were washed with water (20 mL×3) and brine (20 mL), dried over Na₂SO₄ and concentrated under reduce pressure and the residue was purified by Prep-HPLC to afford compound 60, 2-(5-(3-((5-cyano-4-(4-fluorophenyl)thiazol-2-yl)(methyl)amino)-2-ethylimidazo[1,2-a]pyridin-6-yl)pyrimidin-2-yl)acetamide (50 mg, 33.40% yield) as a white solid. ¹H NMR (400 MHz, DMSO-d₆) δ 9.14 (s, 2H), 8.88 (s, 1H), 8.10-8.07 (t, 2H), 7.84-7.76 (dd, 2H), 7.53 (s, 1H), 7.44-7.39 (t, 2H), 7.04 (s, 1H), 3.78 (s, 2H), 3.65 (s, 3H), 2.72-2.66 (dd, 2H), 1.30-1.26 (t, 3H); MS: m/z=513.1 (M+1, ESI+).

5.5.13. Synthesis of Compound 61

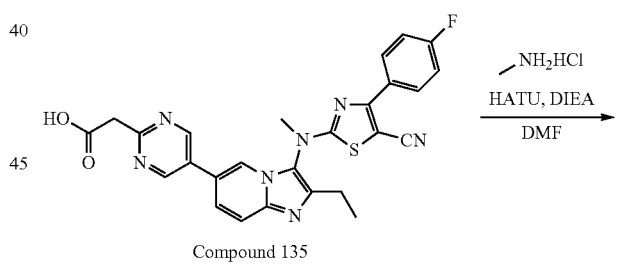

Compound 135

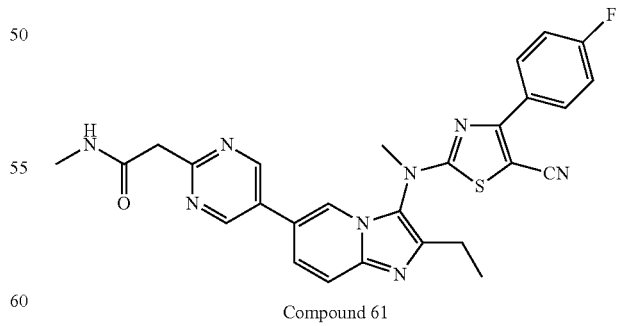

Compound 61

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and methanamine hydrochloride (23.5 mg, 350.87 umol) in DMF (5 mL) was added HATU (165.29 mg, 438.13 umol) and DIEA (151 mg, 1.17 mmol), the reaction mixture was stirred at 25° C. for 16 h. The reaction mixture was poured into water (50 mL) and extracted with DCM (10 mL×3). The combined organic layers were washed with water (20 mL×3) and brine (20 mL), dried over Na$_2$SO$_4$ and concentrated under reduce pressure and the residue was purified by Prep-HPLC to afford compound 61, 2-(5-(3-((5-cyano-4-(4-fluorophenyl)thiazol-2-yl)(methyl)amino)-2-ethylimidazo[1,2-a]pyridin-6-yl)pyrimidin-2-yl)-N-methyl acetamide (35 mg, 22.76% yield) as a white solid. $^1$H NMR (400 MHz, DMSO-d$_6$) δ 9.13 (s, 2H), 8.87 (s, 1H), 8.08-8.02 (m, 3H), 7.84-7.76 (m, 2H), 7.44-7.39 (t, 2H), 3.78 (s, 2H), 3.64 (s, 3H), 2.71-2.66 (dd, 2H), 2.61-2.59 (d, 3H), 1.29-1.26 (t, 3H); MS: m/z=527.3 (M+1, ESI+).

5.5.14. Synthesis of Compound 62

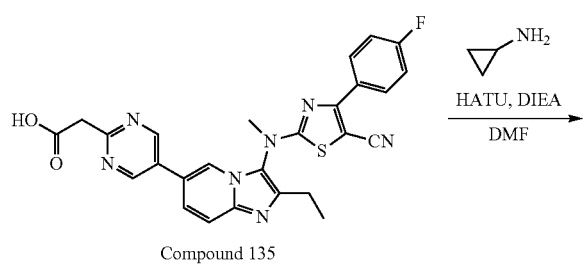

Compound 135

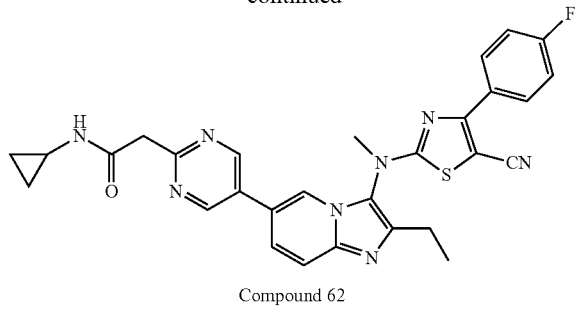

Compound 62

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and cyclopropanamine (20.01 mg, 350.50 umol) in DMF (5 mL) was added HATU (165.29 mg, 438.13 umol) and DIEA (151 mg, 1.17 mmol), the reaction mixture was stirred at 25° C. for 16 h. The reaction mixture was poured into water (50 mL) and extracted with DCM (10 mL×3). The combined organic layers were washed with water (20 mL×3) and brine (20 mL), dried over Na$_2$SO$_4$ and concentrated under reduce pressure and the residue was purified by Prep-HPLC to afford compound 62, 2-(5-(3-((5-cyano-4-(4-fluorophenyl)thiazol-2-yl)(methyl)amino)-2-ethylimidazo[1,2-a]pyridin-6-yl)pyrimidin-2-yl)-N-cyclopropyl acetamide (30 mg, 18.59% yield) as a white solid. $^1$H NMR (400 MHz, DMSO-d$_6$) δ 9.13 (s, 2H), 8.88 (s, 1H), 8.21 (s, 1H), 8.10-8.07 (t, 2H), 7.84-7.76 (m, 2H), 7.44-7.39 (t, 2H), 3.73 (s, 2H), 3.64 (s, 3H), 2.71-2.61 (m, 3H), 1.29-1.26 (t, 3H), 0.63-0.59 (m, 2H), 0.43-0.39 (m, 2H); MS: m/z=553.3 (M+1, ESI+).

5.5.15. Synthesis of Compound 63

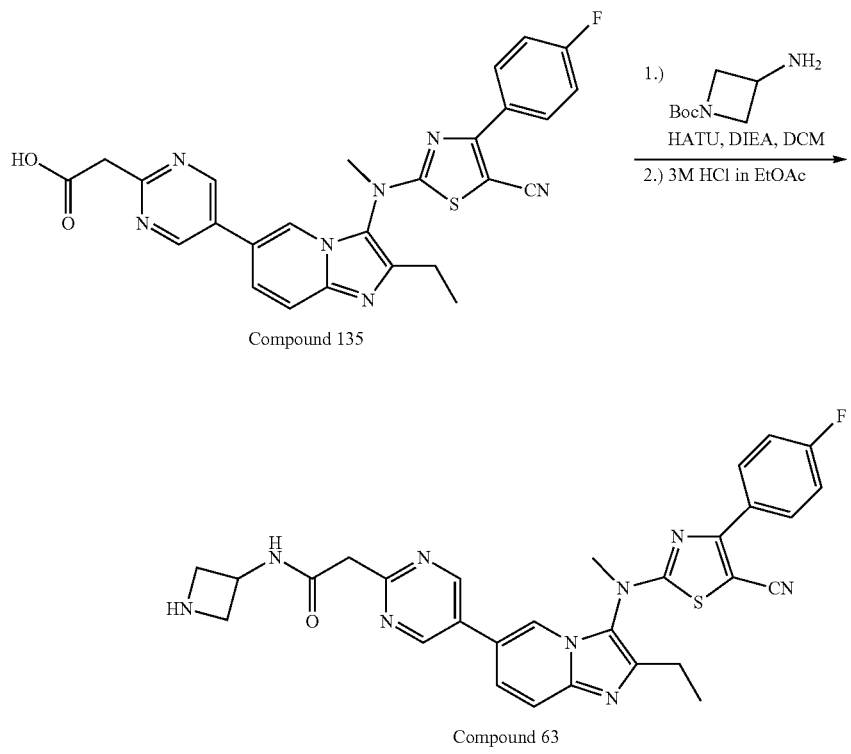

Compound 135

Compound 63

Step One:

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (250 mg, 486.81 umol) and tert-butyl 3-amino azetidine-1-carboxylate (83.84 mg, 486.81 umol) in DCM (5 mL) was added HATU (277.48 mg, 729.78 umol) and DIEA (188.75 mg, 1.46 mmol), the reaction mixture was stirred at 25° C. for 1 h. The reaction mixture was poured into water (50 mL) and extracted with DCM (10 mL×3). The combined organic layers were washed with water (20 mL×3) and brine (20 mL), dried over $Na_2SO_4$ and concentrated under reduce pressure and the residue was purified by column chromatography to afford tert-butyl 3-(2-(5-(3-((5-cyano-4-(4-fluorophenyl)thiazol-2-yl)(methyl)amino)-2-ethyl imidazo[1,2-a]pyridin-6-yl)pyrimidin-2-yl)acetamido)azetidine-1-carboxylate (270 mg, 80.07% yield) as a yellow solid. MS: m/z=668.4 (M+1, ESI+).

Step Two:

To a suspension of tert-butyl 3-(2-(5-(3-((5-cyano-4-(4-fluorophenyl)thiazol-2-yl)(methyl)amino)-2-ethylimidazo[1,2-a]pyridin-6-yl)pyrimidin-2-yl)acetamido)azetidine-1-carboxylate (250 mg, 374.39 umol) in DCM (10 mL) was added 3M HCl in EA (2 mL). The reaction mixture was stirred at 25° C. for 1 h. The resulting solution was evaporated and the residue was purified by Prep-HPLC to afford compound 63, N-(azetidin-3-yl)-2-(5-(3-((5-cyano-4-(4-fluorophenyl)thiazol-2-yl)(methyl)amino)-2-ethylimidazo[1,2-a]pyridin-6-yl)pyrimidin-2-yl)acetamide (47 mg, 22.12% yield) as a white solid. $^1$H NMR (400 MHz, DMSO-$d_6$) δ 9.13 (s, 2H), 8.88 (s, 1H), 8.67-8.65 (d, 1H), 8.10-8.07 (t, 2H), 7.84-7.76 (m, 2H), 7.44-7.39 (t, 2H), 4.51-4.45 (m, 1H), 3.79 (s, 2H), 3.64 (s, 3H), 3.58-3.54 (t, 2H), 3.45-3.41 (t, 2H), 2.71-2.66 (dd, 2H), 1.29-1.26 (t, 3H); MS: m/z=568.4 (M+1, ESI+).

5.5.16. Synthesis of Compound 64

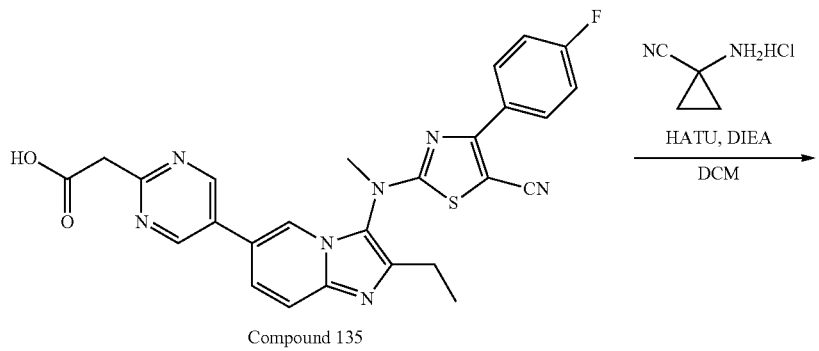

Compound 135

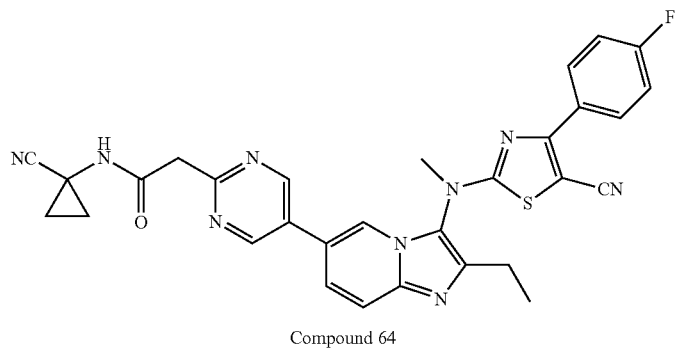

Compound 64

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and 1-aminocyclopropane-1-carbonitrile hydrochloride (69 mg, 584.17 umol) in DCM (5 mL) was added HATU (166.59 mg, 438.13 umol) and DIEA (113.25 mg, 876.26 umol), the reaction mixture was stirred at 25° C. for 1 h. The reaction mixture was poured into water (50 mL) and extracted with DCM (10 mL×3). The combined organic layers were washed with water (20 mL×3) and brine (20 mL), dried over $Na_2SO_4$ and concentrated under reduce pressure and the residue was purified by Prep-HPLC to afford compound 64, 2-(5-(3-((5-cyano-4-(4-fluorophenyl)thiazol-2-yl)(methyl)amino)-2-ethylimidazo[1,2-a]pyridin-6-yl) pyrimidin-2-yl)-N-(1-cyanocyclopropyl)acetamide (42 mg, 24.89% yield) as a white solid. $^1$H NMR (400 MHz, DMSO-$d_6$) δ 9.16 (s, 2H), 9.08 (s, 1H), 8.90 (s, 1H), 8.10-8.07 (t, 2H), 7.86-7.76 (m, 2H), 7.44-7.39 (t, 2H), 3.81 (s, 2H), 3.64 (s, 3H), 2.72-2.66 (dd, 2H), 1.50-1.46 (dd, 2H), 1.29-1.26 (t, 3H), 1.16-1.12 (dd, 2H); MS: m/z=578.1 (M+1, ESI+).

5.5.17. Synthesis of Compound 65

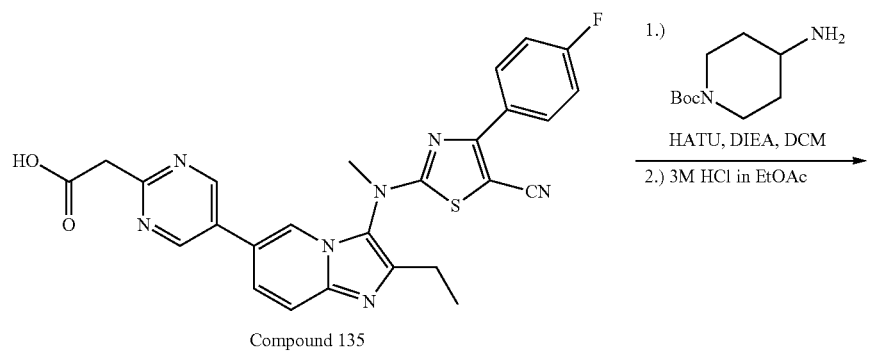

Compound 135

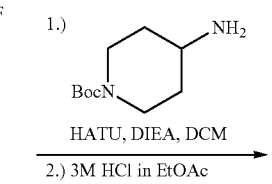

1.) BocN-piperidine-NH$_2$

HATU, DIEA, DCM

2.) 3M HCl in EtOAc

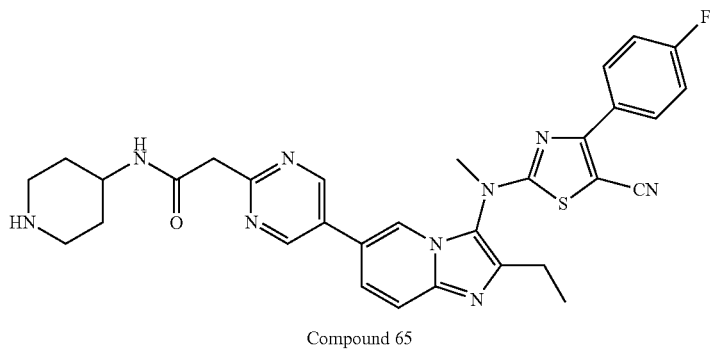

Compound 65

Step One:

To a solution of compound 135, 2-(5-(3-((5-cyano-4-(4-fluorophenyl)thiazol-2-yl)(methyl)amino)-2-ethylimidazo[1,2-a]pyridin-6-yl)pyrimidin-2-yl)acetic acid (150 mg, 292.09 umol) and tert-butyl 4-aminopiperidine-1-carboxylate (87.75 mg, 438.13 umol) in DMF (5 mL) was added HATU (165.29 mg, 438.13 umol) and DIEA (151.00 mg, 1.17 mmol), the reaction mixture was stirred at 25° C. for 16 h. The reaction mixture was poured into water (50 mL) and extracted with DCM (10 mL×3). The combined organic layers were washed with water (20 mL×3) and brine (20 mL), dried over $Na_2SO_4$ and concentrated under reduce pressure and the residue was purified by column chromatography to afford tert-butyl 4-(2-(5-(3-((5-cyano-4-(4-fluorophenyl)thiazol-2-yl)(methyl)amino)-2-ethylimidazo[1,2-a]pyridin-6-yl)pyrimidin-2-yl)acetamido)piperidine-1-carboxylate (100 mg, 49.20% yield) as a yellow solid. MS: m/z=696.3 (M+1, ESI+).

Step Two:

To a suspension of tert-butyl 4-(2-(5-(3-((5-cyano-4-(4-fluorophenyl)thiazol-2-yl)(methyl)amino)-2-ethyl imidazo[1,2-a]pyridin-6-yl)pyrimidin-2-yl)acetamido)piperidine-1-carboxylate (100 mg, 143.88 umol) in DCM (10 mL) was added 3M HCl in EA (2 mL). The reaction mixture was stirred at 25° C. for 3 h. The resulting solution was evaporated and the residue was purified by Prep-HPLC to afford compound 65, 2-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl)acetamide (67 mg, 78.27% yield) as a white solid. $^1$H NMR (400 MHz, DMSO-$d_6$) δ 9.13 (s, 2H), 8.88 (s, 1H), 8.10-8.07 (m, 3H), 7.84-7.75 (m, 2H), 7.44-7.39 (t, 2H), 3.77 (s, 2H), 3.64 (s, 3H), 3.58 (s, 1H), 3.32-3.20 (m, 3H), 2.90-2.87 (d, 2H), 2.71-2.66 (dd, 2H), 2.46-2.40 (t, 2H), 1.69-1.66 (d, 2H), 1.29-1.25 (t, 3H); MS: m/z=596.3 (M+1, ESI+).

5.6. Example 5—Synthesis of Carbonyl-Linked Pyrimidine-Type Compounds
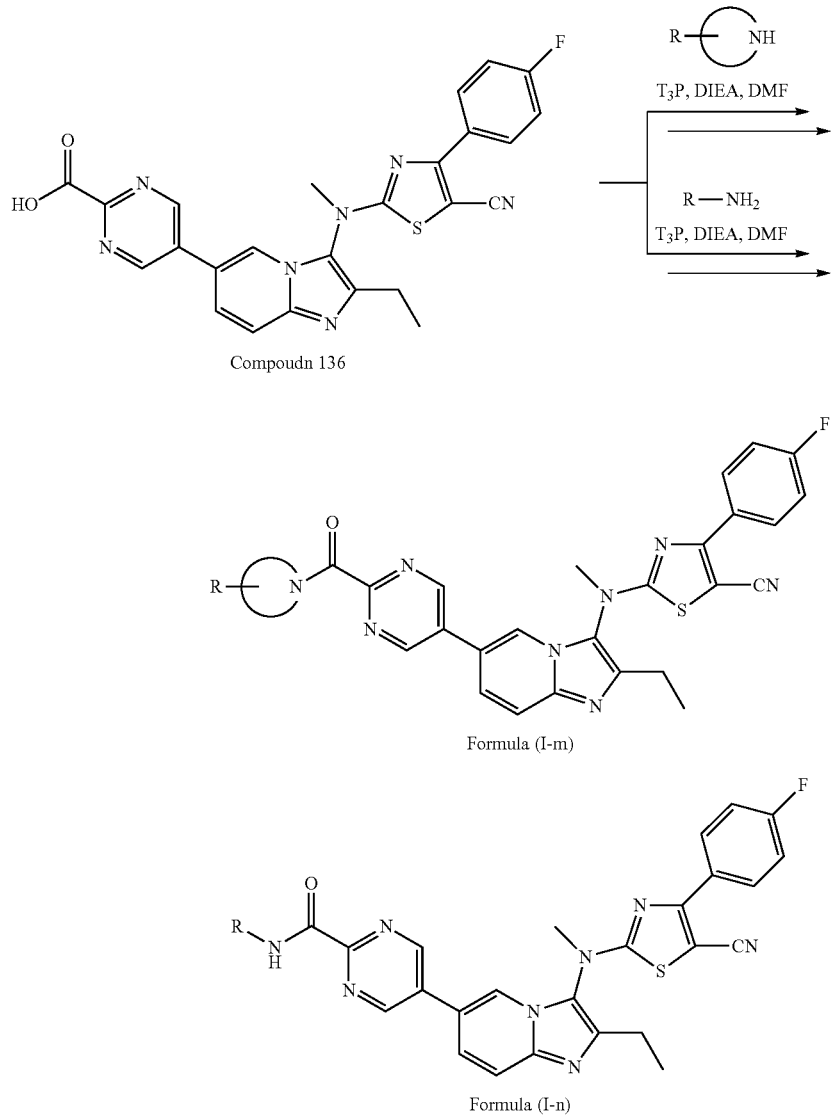
5.6.1 Synthesis of Compound 136
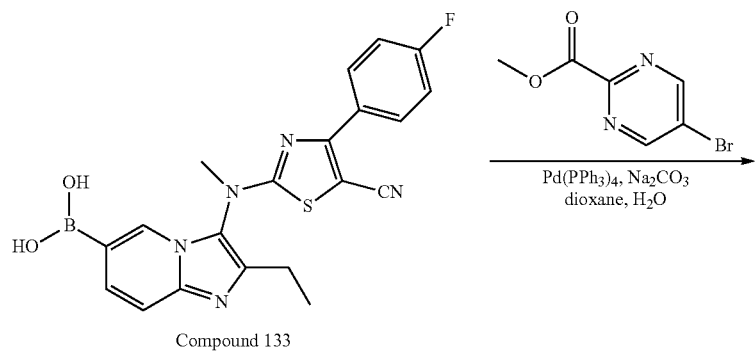

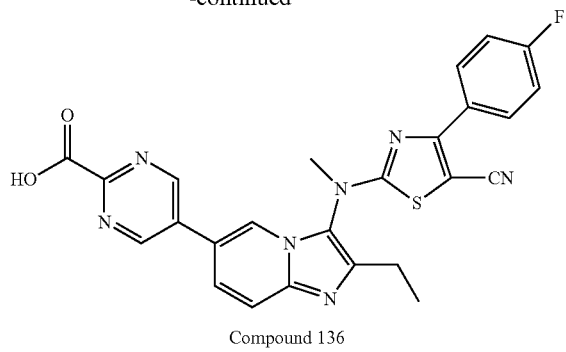

Compound 136

To a solution of compound 133, (3-((5-cyano-4-(4-fluorophenyl)thiazol-2-yl)(methyl)amino)-2-ethylimidazo[1,2-a]pyridin-6-yl)boronic acid (3.1 g, 7.36 mmol) and methyl 5-bromopyrimidine-2-carboxylate (1.60 g, 7.36 mmol) in dioxane/H$_2$O (60 mL/10 mL) was added Na$_2$CO$_3$ (2.34 g, 22.08 mmol) and Pd(PPh$_3$)$_4$ (425.19 mg, 367.95 umol). The reaction mixture was stirred at 100° C. for 3 h under Ar. The resulting solution was poured into water (200 mL) and extracted with EA (50 mL×3). The aqueous layer was acidified with 2N HCl (100 mL) and extracted with EA (50 mL×3). The organic layers were dried over Na$_2$SO$_4$ and concentrated under reduced pressure to afford compound 136, 5-(3-((5-cyano-4-(4-fluorophenyl)thiazol-2-yl)(methyl)amino)-2-ethylimidazo[1,2-a]pyridin-6-yl)pyrimidine-2-carboxylic acid (2.3 g, 62.57% yield) as a yellow solid. MS: m/z=500.0 (M+1, ESI+).

5.6.2. Synthesis of Azetidin-3-one Hydrochloride

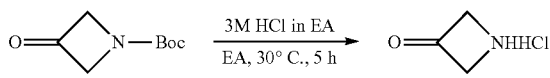

To a solution of tert-butyl 3-oxoazetidine-1-carboxylate (10.00 g, 58.41 mmol) in EA (50 mL) was added 3M ICI in EA (3 M, 58.41 mL). The reaction mixture was stirred at 25° C. for 5 h. The resulting solution was evaporated to afford azetidin-3-one hydrochloride (4.57 g, 72.75% yield) as a light-yellow solid.

5.6.3. Synthesis of Compound 137

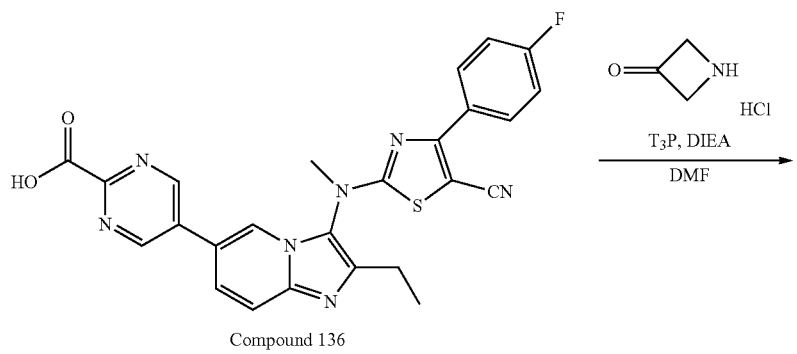

Compound 136

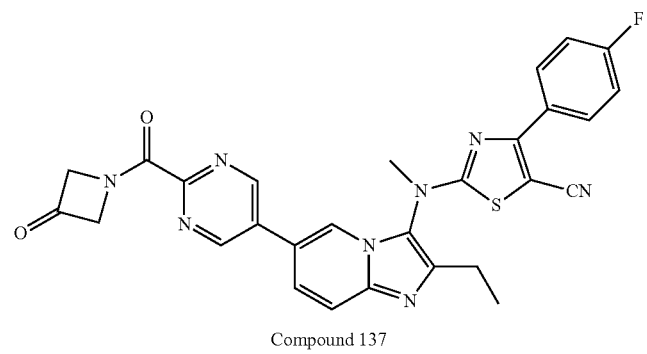

Compound 137

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (750.00 mg, 1.50 mmol) and azetidin-3-one hydrochloride (177.61 mg, 1.65 mmol) in DMF (15 mL) was added DIEA (582.15 mg, 4.50 mmol) and T$_3$P (1.43 g, 2.25 mmol, 50% purity). The reaction mixture was stirred at 25° C. for 2 h. The resulting solution was quenched by saturated NH$_4$Cl (80 mL) and extracted with EA (80 mL×2), the combined organic layers were washed with water (50 mL×2) and brine (50 mL), dried over Na$_2$SO$_4$ and concentrated under reduced pressure. The residue was purified by column chromatography to afford compound 137, 2-((2-ethyl-6-(2-(3-oxoazetidine-1-carbonyl)pyrimidin-5-yl)imidazo[1,2-a]pyridin-3-yl) (methyl)amino)-4-(4-fluorophenyl)thiazole-5-carbonitrile (610 mg, 73.52% yield) as a yellow solid. MS: m/z=553.1 (M+1, ESI+).

5.6.4. Synthesis of Compound 11

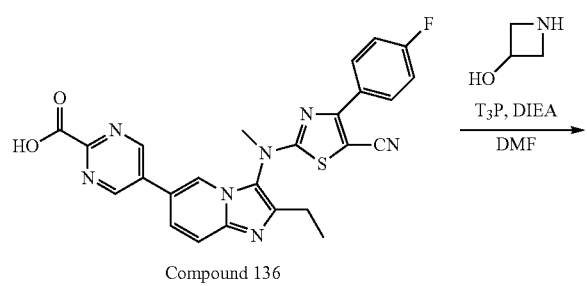

Compound 136

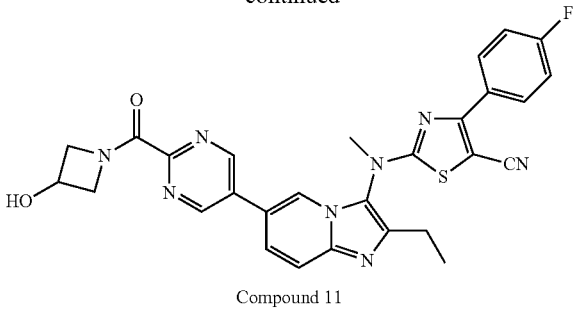

Compound 11

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (1 g, 2.00 mmol) and azetidin-3-ol (146.33 mg, 2.00 mmol) in DMF (20 mL) was added DIEA (776.19 mg, 6.01 mmol) and T$_3$P (1.91 g, 3.00 mmol, 50% purity). The reaction mixture was stirred at 25° C. for 3 h. The resulting solution was quenched by saturated NH$_4$Cl (50 mL) and extracted with EA (50 mL×3), the organic layers were dried over Na$_2$SO$_4$ and concentrated under reduced pressure. The residue was purified by Prep-HPLC to afford compound 11, 2-((2-ethyl-6-(2-(3-hydroxyazetidine-1-carbonyl)pyrimidin-5-yl)imidazo[1,2-a]pyridin-3-yl)(methyl)amino)-4-(4-fluorophenyl)thiazole-5-carbonitrile (400 mg, 36.03% yield) as a white solid. $^1$H NMR (400 MHz, DMSO-d$_6$) δ 9.36 (s, 2H), 9.00 (s, 1H), 8.11-8.08 (t, 2H), 7.92-7.90 (dd, 1H), 7.80-7.78 (dd, 1H), 7.44-7.40 (t, 2H), 5.79-5.78 (d, 1H), 4.59-4.50 (m, 2H), 4.32-4.27 (m, 1H), 4.17-4.14 (dd, 1H), 3.84-3.80 (dd, 1H), 3.66 (s, 3H), 2.72-2.67 (dd, 2H), 1.30-1.26 (m, 3H); MS: m/z=555.1 (M+1, ESI+).

5.6.5. Synthesis of Compound 12

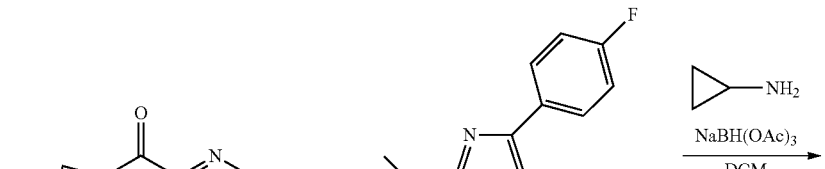

Compound 137

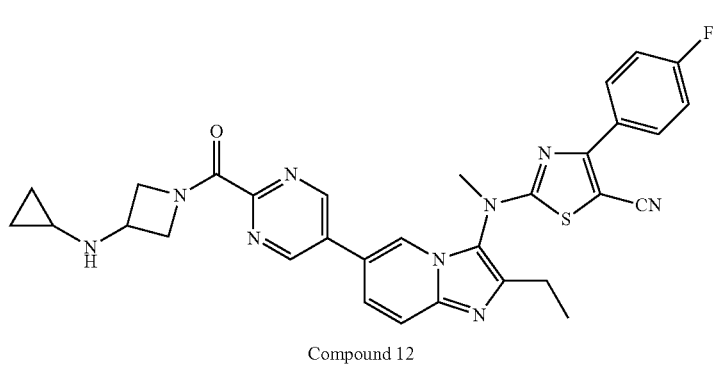

Compound 12

To a solution of compound 137, 2-((2-ethyl-6-(2-(3-oxoazetidine-1-carbonyl)pyrimidin-5-yl)imidazo[1,2-a]pyridin-3-yl)(methyl)amino)-4-(4-fluorophenyl)thiazole-5-carbonitrile (280 mg, 506.71 umol) and cyclopropanamine (37.61 mg, 658.73 umol) in DCM (10 mL) was added NaBH(OAc)$_3$ (214.79 mg, 1.01 mmol). The reaction mixture was stirred at 25° C. for 24 h. The resulting solution was quenched by saturated NH$_4$Cl (50 mL) and extracted with EA (50 mL×2), the combined organic layers were washed with water (50 mL×2) and brine (50 mL), dried over Na$_2$SO$_4$ and concentrated under reduced pressure. The residue was purified by Prep-HPLC to afford compound 12, 2-((6-(2-(3-(cyclopropylamino)azetidine-1-carbonyl)pyrimidin-5-yl)-2-ethylimidazo[1,2-a]pyridin-3-yl)(methyl)amino)-4-(4-fluorophenyl)thiazole-5-carbonitrile (52.6 mg, 17.49% yield) as a white solid. $^1$H NMR (400 MHz, DMSO-d$_6$) δ9.35 (s, 2H), 9.00 (s, 1H), 8.09 (s, 2H), 7.91-7.89 (d, 1H), 7.80-7.77 (d, 1H), 7.43-7.39 (t, 2H), 4.53-4.49 (t, 1H), 4.24-4.14 (m, 2H), 3.81-3.79 (t, 1H), 3.65 (s, 4H), 3.01 (s, 1H), 2.70-2.60 (d, 2H), 2.02 (s, 1H), 1.29-1.26 (t, 3H), 0.35-0.33 (d, 2H), 0.21 (s, 2H); MS: m/z=594.1 (M+1, ESI+).

5.6.6. Synthesis of Compound 13

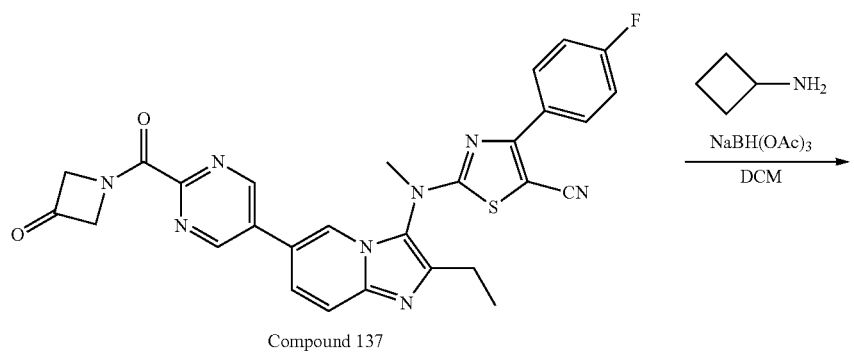

Compound 137

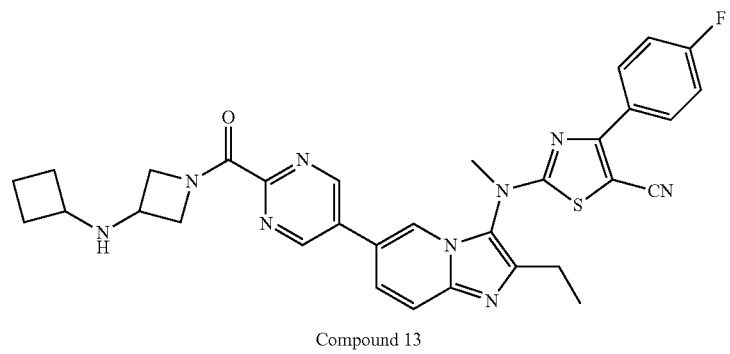

Compound 13

To a solution of compound 137, 2-((2-ethyl-6-(2-(3-oxoazetidine-1-carbonyl)pyrimidin-5-yl)imidazo[1,2-a]pyridin-3-yl)(methyl)amino)-4-(4-fluorophenyl)thiazole-5-carbonitrile (290 mg, 538.44 umol) and cyclobutanamine (49.78 mg, 699.97 umol) in DCM (10 mL) was added NaBH(OAc)$_3$ (228.23 mg, 1.08 mmol). The reaction mixture was stirred at 25° C. for 24 h. The resulting solution was quenched by saturated NH$_4$Cl (50 mL) and extracted with EA (50 mL×2), the combined organic layers were washed with water (50 mL×2) and brine (50 mL), dried over Na$_2$SO$_4$ and concentrated under reduced pressure. The residue was purified by Prep-HPLC to afford compound 13, 2-((6-(2-(3-(cyclobutylamino)azetidine-1-carbonyl)pyrimidin-5-yl)-2-ethylimidazo[1,2-a]pyridin-3-yl)(methyl)amino)-4-(4-fluorophenyl)thiazole-5-carbonitrile (50.4 mg, 15.40% yield) as a white solid. $^1$H NMR (400 MHz, DMSO-d$_6$) δ9.35 (s, 2H), 9.00 (s, 1H), 8.11-8.08 (t, 2H), 7.92-7.89 (dd, 1H), 7.80-7.78 (d, 1H), 7.44-7.40 (t, 2H), 4.49-4.45 (t, 1H), 4.21-4.17 (t, 1H), 4.09-4.05 (m, 1H), 3.76-3.73 (m, 1H), 3.65 (s, 3H), 3.63-3.57 (m, 1H), 3.15-3.09 (m, 1H), 2.72-2.67 (dd, 3H), 2.05-1.98 (m, 2H), 1.70-1.49 (m, 4H), 1.30-1.26 (t, 3H); MS: m/z=608.1 (M+1, ESI+).

5.6.7. Synthesis of Compound 14

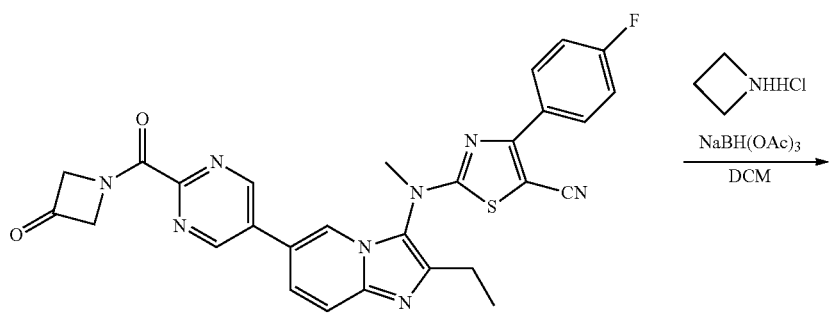

Compound 137

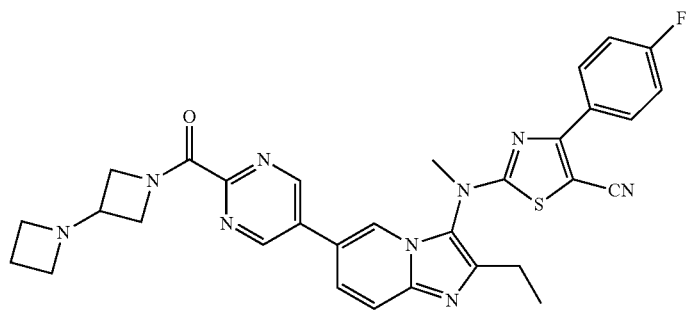

Compound 14

To a solution of compound 137, 2-((2-ethyl-6-(2-(3-oxoazetidine-1-carbonyl)pyrimidin-5-yl)imidazo[1,2-a]pyridin-3-yl)(methyl)amino)-4-(4-fluorophenyl)thiazole-5-carbonitrile (500.00 mg, 904.84 umol) and azetidine hydrochloride (101.58 mg, 1.09 mmol) in DCM (10 mL) was added NaBH(OAc)$_3$ (287.66 mg, 1.36 mmol). The mixture was stirred at 25° C. for 24 h. The resulting solution was quenched by saturated NH$_4$Cl (50 mL) and extracted with EA (50 mL×2), the combined organic layers were washed with water (50 mL×2) and brine (50 mL), dried over Na$_2$SO$_4$ and concentrated under reduced pressure. The residue was purified by Prep-HPLC to afford compound 14, 2-((6-(2-([1,3'-biazetidine]-1'-carbonyl)pyrimidin-5-yl)-2-ethylimidazo[1,2-a]pyridin-3-yl)(methyl)amino)-4-(4-fluorophenyl) thiazole-5-carbonitrile (53 mg, 9.87% yield) as a white solid. $^1$H NMR (400 MHz, DMSO-d$_6$) δ 9.35 (s, 2H), 8.99 (s, 1H), 8.11-8.07 (t, 2H), 7.92-7.89 (dd, 1H), 7.81-7.78 (d, 1H), 7.44-7.40 (t, 2H), 4.39-4.35 (t, 1H), 4.13-4.04 (m, 2H), 3.80-3.76 (dd, 1H), 3.65 (s, 3H), 3.41-3.35 (m, 1H), 3.16-3.12 (t, 4H), 2.72-2.67 (dd, 2H), 2.00-1.93 (m, 2H), 1.30-1.26 (t, 3H); MS: m/z=594.1 (M+1, ESI+).

5.6.8. Synthesis of Compound 15

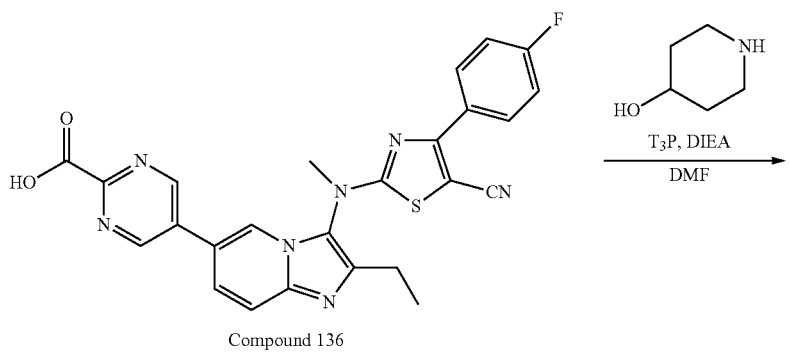

Compound 136

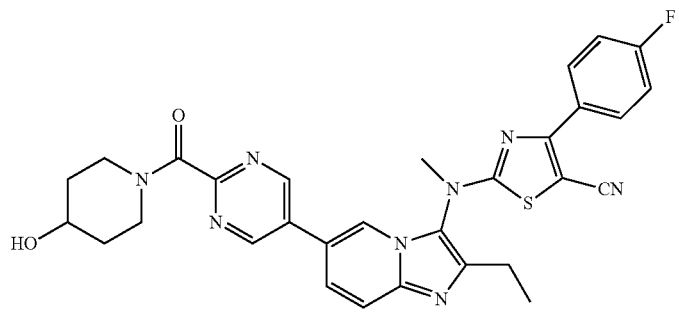

Compound 15

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (260 mg, 520.50 umol) and piperidin-4-ol (52.65 mg, 520.50 umol) in DMF (10 mL) was added T$_3$P (496.84 mg, 780.75 umol, 50% purity) and DIEA (201.81 mg, 1.56 mmol). The reaction mixture was stirred at 25° C. for 3 h. The resulting solution was quenched by saturated NH$_4$Cl (50 mL) and extracted with EA (50 mL×3), the combined organic layers were washed with water (50 mL×3) and brine (50 mL), dried over Na$_2$SO$_4$ and concentrated under reduced pressure. The residue was purified by Prep-HPLC to afford compound 15, 2-((2-ethyl-6-(2-(4-hydroxypiperidine-1-carbonyl)pyrimidin-5-yl)imidazo[1,2-a]pyridin-3-yl)(methyl)amino)-4-(4-fluoro phenyl)thiazole-5-carbonitrile (83 mg, 27.37% yield) as a white solid. $^1$H NMR (400 MHz, DMSO-d$_6$) δ 9.29 (s, 2H), 8.96 (s, 1H), 8.11-8.07 (t, 2H), 7.90-7.87 (dd, 1H), 7.80-7.78 (dd, 1H), 7.44-7.40 (t, 2H), 4.81-4.80 (d, 1H), 4.05-4.00 (m, 1H), 3.77-3.72 (m, 1H), 3.65 (s, 3H), 3.30-3.27 (m, 2H), 3.06-2.99 (m, 1H), 2.72-2.67 (dd, 2H), 1.83-1.81 (m, 1H), 1.69-1.66 (m, 1H), 1.45-1.26 (m, 5H); MS: m/z=583.1 (M+1, ESI+).

5.6.9. Synthesis of Compound 16

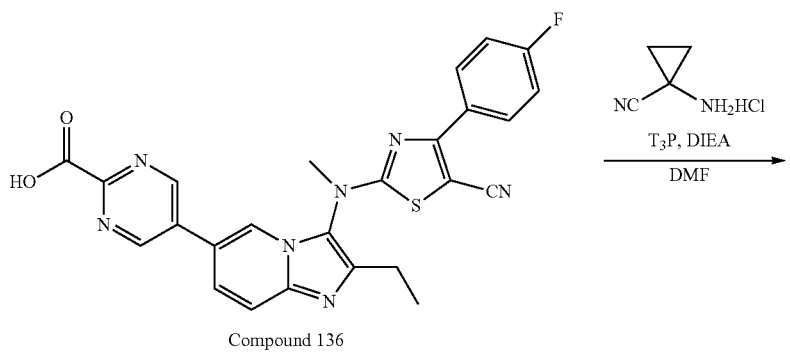

Compound 136

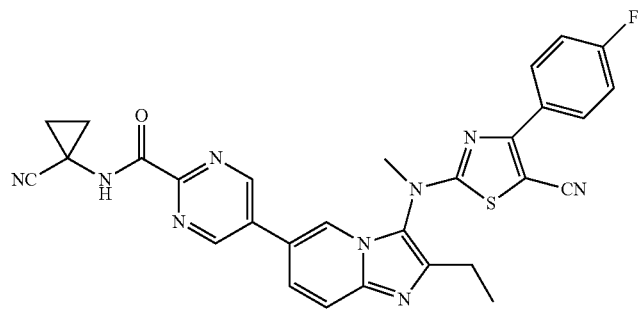

Compound 16

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (130 mg, 260.25 umol) and 1-aminocyclopropane-1-carbonitrile hydrochloride (46.28 mg, 390.38 umol) in DMF (5 mL) was added DIEA (134.54 mg, 1.04 mmol) and T$_3$P (331.23 mg, 520.50 umol, 50% purity). The reaction mixture was stirred at 25° C. for 3 h. The resulting solution was quenched by saturated NH$_4$Cl (50 mL) and extracted with EA (50 mL×3), the combined organic layers were washed with water (50 mL×3) and brine (50 mL), dried over Na$_2$SO$_4$ and concentrated under reduced pressure. The residue was purified by Prep-HPLC to afford compound 16, 5-(3-((5-cyano-4-(4-fluoro phenyl)thiazol-2-yl)(methyl)amino)-2-ethyl imidazo[1,2-a]pyridin-6-yl)-N-(1-cyanocyclopropyl)pyrimidine-2-carboxamide (50.7 mg, 34.57% yield) as a white solid. $^1$H NMR (400 MHz, DMSO-d$_6$) δ 9.85 (s, 1H), 9.38 (s, 2H), 9.00 (s, 1H), 8.09 (s, 2H), 7.93-7.90 (d, 1H), 7.82-7.80 (d, 1H), 7.44-7.40 (t, 2H), 3.66 (s, 3H), 2.72-2.67 (dd, 2H), 1.58 (s, 2H), 1.34-1.26 (m, 5H); MS: m/z=564.1 (M+1, ESI+).

5.6.10. Synthesis of Compound 47

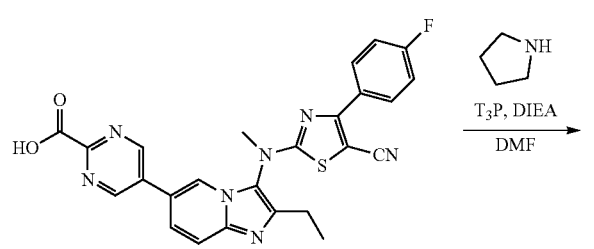

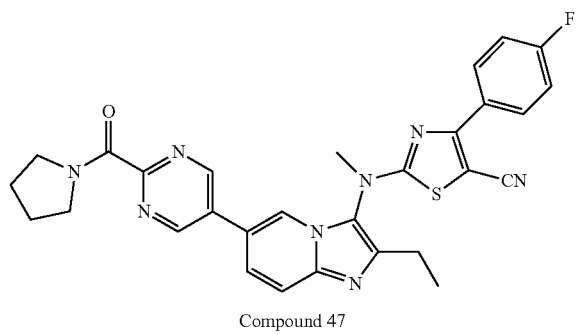

Compound 47

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (200 mg, 400.39 umol) and pyrrolidine (34.17 mg, 480.46 umol) in DMF (10 mL) was added DIEA (155.24 mg, 1.20 mmol) and T$_3$P (382.18 mg, 600.58 umol, 50% purity). The reaction mixture was stirred at 25° C. for 2 h. The resulting solution was quenched by saturated NH$_4$Cl (50 mL) and extracted with EA (50 mL×2), the combined organic layer was washed by water (50 mL×2) and brine (50 mL), dried over Na$_2$SO$_4$ and concentrated. The residue was purified by Prep-HPLC (Waters Xbridge C18 10 um OBD 19*250 mm, A: 10 mmol NH$_4$HCO$_3$ in water; B: CH$_3$CN, 5% to 95%) in NH$_4$HCO$_3$ condition to afford compound 47, 2-((2-ethyl-6-(2-(pyrrolidine-1-carbonyl)pyrimidin-5-yl)imidazo[1,2-a]pyridin-3-yl)(methyl)amino)-4-(4-fluorophenyl)thiazole-5-carbonitrile (70.0 mg, 31.64% yield) as a white solid. $^1$H NMR (400 MHz, DMSO-d$_6$) δ 9.32 (s, 2H), 8.97 (s, 1H), 8.10-8.07 (t, 2H), 7.91-7.88 (dd, 1H), 7.81-7.78 (dd, 1H), 7.44-7.40 (t, 2H), 3.66 (s, 3H), 3.52-3.49 (t, 2H), 3.34-3.31 (m, 2H), 2.72-2.67 (dd, 2H), 1.90-1.82 (m, 4H), 1.30-1.26 (t, 3H); MS: m/z=553.3 (M+1, ESI+).

5.6.11. Synthesis of (5-bromopyrimidin-2-yl)(pyrrolidin-1-yl)methanone

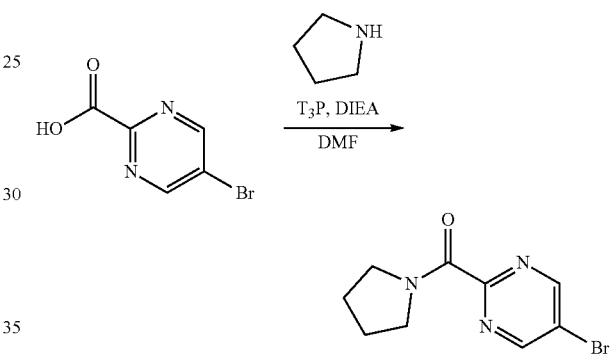

To a solution of 5-bromopyrimidine-2-carboxylic acid (1 g, 4.93 mmol) and pyrrolidine (419 mg, 5.91 mmol) in DMF (15 mL) was added DIEA (1.9 g, 14.79 mmol) and T$_3$P (592 mg, 7.4 mmol, 50% purity). The reaction mixture was stirred at 25° C. for 2 h. The resulting solution was quenched by saturated NH$_4$Cl (150 mL) and extracted with EA (50 mL×2), the combined organic layer was washed by water (50 mL×2) and brine (50 mL), dried over Na$_2$SO$_4$ and concentrated. The residue was purified by Prep-HPLC to afford (5-bromopyrimidin-2-yl)(pyrrolidin-1-yl)methanone (630 mg, 50% yield) as a colorless oil.

5.6.12. Synthesis of Compound 47 Hydrochloride

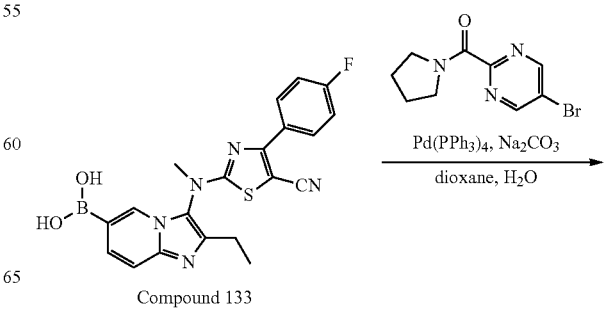

Compound 133

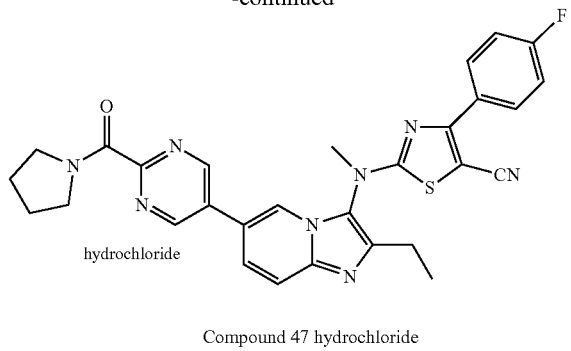

Compound 47 hydrochloride

A mixture of compound 133. (5-bromopyrimidin-2-yl)(pyrrolidin-1-yl)methanone (400 mg, 1.56 mmol), (3-((5-cyano-4-(4-fluorophenyl)thiazol-2-yl)(methyl)amino)-2-ethylimidazo[1,2-a]pyridin-6-yl)boronic acid (985 mg, 2.34 mmol), Pd(PPh$_3$)$_4$ (180 mg, 156 umol) and Na$_2$CO$_3$ (496 mg, 4.68 mmol) was dissolved in dioxane (40 mL) and water (10 mL) and stirred at 80° C. under N$_2$ for 2 h. The mixture was cooled to room temperature, then diluted with water (100 mL), extracted with EA (50 mL×2). The organic layer was dried over Na$_2$SO$_4$ and evaporated, the residue was purified by Prep-HPLC (Waters Xbridge C18 10 um OBD 19*250 mm, A: 0.05% HCl in water; B: CH$_3$CN, 5% to 95%) in HCl condition to afford compound 47 hydrochloride, 2-((2-ethyl-6-(2-(pyrrolidine-1-carbonyl)pyrimidin-5-yl) imidazo[1,2-a]pyridin-3-yl)(methyl)amino)-4-(4-fluorophenyl) thiazole-5-carbonitrile hydrochloride (250 mg, 29% yield) as a brown solid. $^1$H NMR (400 MHz, DMSO-d$_6$) δ 9.38 (s, 2H), 9.31 (s, 1H), 8.46-8.44 (d, 1H), 8.19-8.17 (d, 1H), 8.04-8.01 (t, 2H), 7.42-7.38 (t, 2H), 3.68 (s, 3H), 3.53-3.50 (t, 2H), 3.34-3.31 (t, 2H), 2.90-2.85 (dd, 2H), 1.91-1.83 (m, 4H), 1.37-1.33 (t, 3H); MS: m/z=553.2 (M+1, ESI+).

5.6.13. Synthesis of Compound 48

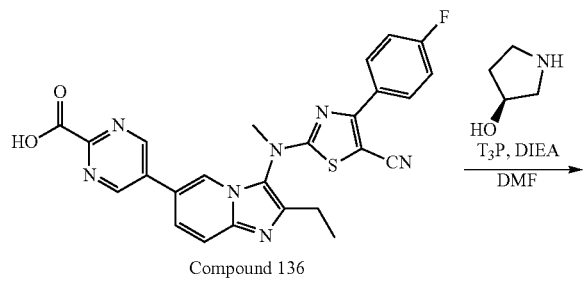

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (200 mg, 400.39 umol) and (S)-pyrrolidin-3-ol (41.86 mg, 480.46 umol) in DMF (10 mL) was added DIEA (155.24 mg, 1.20 mmol) and T$_3$P (382.18 mg, 600.58 umol, 50% purity). The reaction mixture was stirred at 25° C. for 2 h. The resulting solution was quenched by saturated NH$_4$Cl (50 mL) and extracted with EA (50 mL×2), the combined organic layer was washed by water (50 mL×2) and brine (50 mL), dried over Na$_2$SO$_4$ and concentrated. The residue was purified by Prep-HPLC to afford compound 48, (S)-2-((2-ethyl-6-(2-(3-hydroxypyrrolidine-1-carbonyl)pyrimidin-5-yl)imidazo[1,2-a]pyridin-3-yl)(methyl)amino)-4-(4-fluorophenyl) thiazole-5-carbonitrile (71 mg, 31.19% yield) as a white solid. $^1$H NMR (400 MHz, DMSO-d$_6$) δ 9.33 (s, 2H), 8.97 (s, 1H), 8.09 (s, 2H), 7.91-7.89 (d, 1H), 7.81-7.78 (d, 1H), 7.44-7.40 (t, 2H), 5.05-4.99 (dd, 1H), 4.35-4.26 (d, 1H), 3.66 (s, 3H), 3.62-3.38 (m, 4H), 2.72-2.67 (dd, 2H), 2.00-1.76 (m, 2H), 1.30-1.26 (t, 3H); MS: m/z=569.3 (M+1, ESI+).

5.6.14. Synthesis of Compound 49

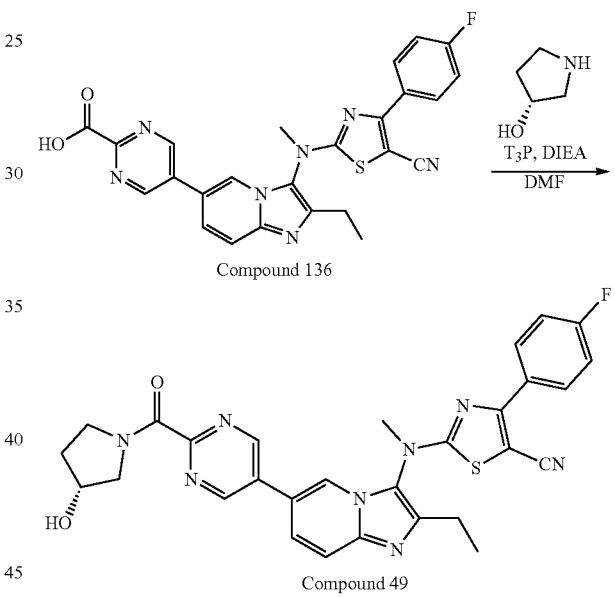

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (200 mg, 400.39 umol) and (R)-pyrrolidin-3-ol (41.86 mg, 480.46 umol) in DMF (10 mL) was added DIEA (155.24 mg, 1.20 mmol) and T$_3$P (382.18 mg, 600.58 umol, 50% purity). The reaction mixture was stirred at 25° C. for 2 h. The resulting solution was quenched by saturated NH$_4$Cl (50 mL) and extracted with EA (50 mL×2), the combined organic layer was washed by water (50 mL×2) and brine (50 mL), dried over Na$_2$SO$_4$ and concentrated. The residue was purified by Prep-HPLC to afford compound 49, (R)-2-((2-ethyl-6-(2-(3-hydroxypyrrolidine-1-carbonyl)pyrimidin-5-yl)imidazo[1,2-a]pyridin-3-yl)(methyl)amino)-4-(4-fluorophenyl) thiazole-5-carbonitrile (62 mg, 27.31% yield) as a white solid. $^1$H NMR (400 MHz, DMSO-d$_6$) δ 9.33 (s, 2H), 8.98 (s, 1H), 8.11-8.08 (t, 2H), 7.91-7.89 (dd, 1H), 7.81-7.78 (d, 1H), 7.44-7.40 (t, 2H), 5.05-4.99 (dd, 1H), 4.35-4.26 (d, 1H), 3.66 (s, 3H), 3.62-3.38 (m, 4H), 2.73-2.67 (dd, 2H), 1.99-1.77 (m, 2H), 1.30-1.27 (t, 3H); MS: m/z=569.3 (M+1, ESI+).

5.6.15. Synthesis of Compound 50

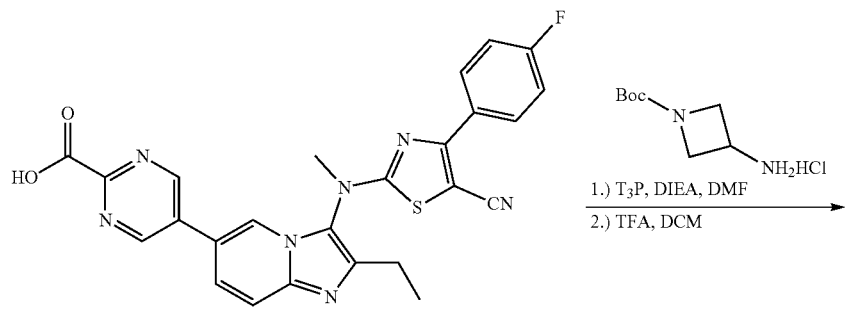

Compound 136

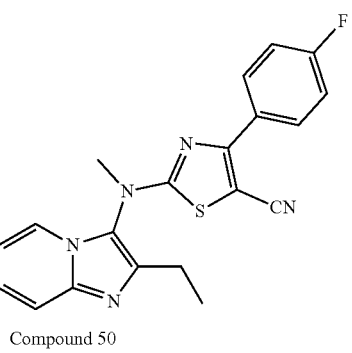

Compound 50

Step One:

To a solution of compound 136, 5-(3-((5-cyano-4-(4-fluorophenyl)thiazol-2-yl)(methyl)amino)-2-ethylimidazo[1,2-a]pyridin-6-yl) pyrimidine-2-carboxylic acid (200 mg, 400.39 umol) and tert-butyl 3-aminoazetidine-1-carboxylate hydrochloride (91.91 mg, 440.43 umol) in DMF (8 mL) was added DIEA (155.24 mg, 1.20 mmol) and T$_3$P (382.18 mg, 600.58 umol, 50% purity). The reaction mixture was stirred at 25° C. for 3 h. The resulting solution was quenched by saturated NH$_4$Cl (50 mL) and extracted with EA (50 mL×2), the combined organic layer was washed by water (50 mL×2) and brine (50 mL), dried over Na$_2$SO$_4$ and concentrated. The residue was purified by column chromatography to afford tert-butyl3-(5-(3-((5-cyano-4-(4-fluorophenyl)thiazol-2-yl)(methyl)amino)-2-ethyl imidazo[1,2-a]pyridin-6-yl)pyrimidine-2-carboxamido)azetidine-1-carboxylate (200 mg, 76.41% yield) as a yellow solid. MS: m/z=654.2 (M+1, ESI+).

Step Two:

To a solution of tert-butyl 3-(5-(3-((5-cyano-4-(4-fluorophenyl)thiazol-2-yl)(methyl)amino)-2-ethyl imidazo[1,2-a]pyridin-6-yl)pyrimidine-2-carboxamido)azetidine-1-carboxylate (190.00 mg, 290.64 umol) in DCM (10 mL) was added TFA (165.69 mg, 1.45 mmol). The mixture was stirred at 25° C. for 2 h. The resulting solution was evaporated and purified by Prep-HPLC to afford compound 50, N-(azetidin-3-yl)-5-(3-((5-cyano-4-(4-fluorophenyl)thiazol-2-yl)(methyl)amino)-2-ethylimidazo[1,2-a]pyridin-6-yl)pyrimidine-2-carboxamide (85 mg, 52.83% yield) as a white solid. $^1$H NMR (400 MHz, DMSO-d$_6$) δ 9.35 (s, 2H), 9.26-9.24 (d, 1H), 8.99 (s, 1H), 8.10-8.07 (t, 2H), 7.91-7.89 (d, 1H), 7.82-7.80 (d, 1H), 7.44-7.39 (t, 2H), 4.75-4.69 (m, 1H), 3.66-3.55 (m, 7H), 2.73-2.67 (dd, 2H), 1.30-1.27 (t, 3H); MS: m/z=554.1 (M+1, ESI+).

5.6.16. Synthesis of Compound 51

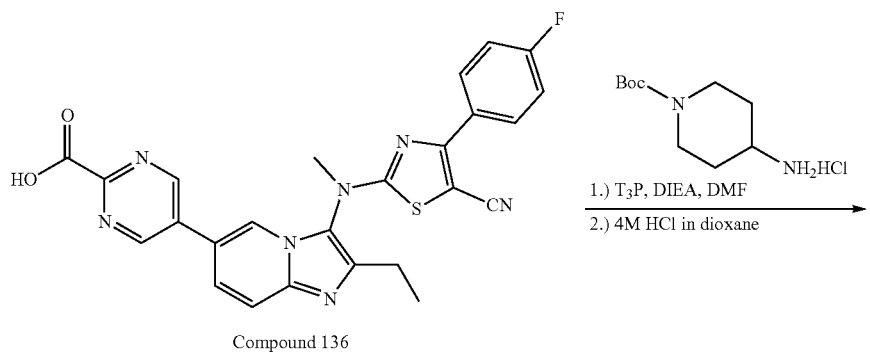

Compound 136

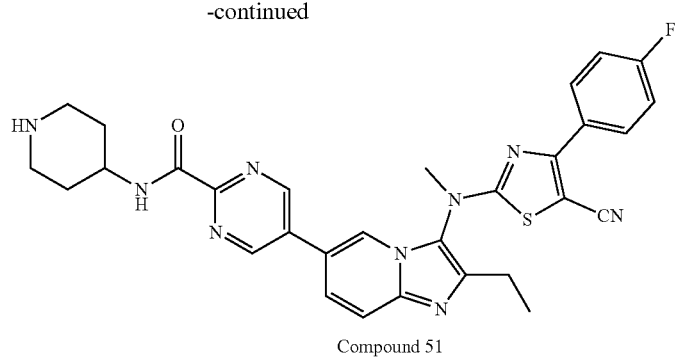

Compound 51

Step One:

To a solution of compound 136, 5-(3-((5-cyano-4-(4-fluorophenyl)thiazol-2-yl)(methyl)amino)-2-ethylimidazo [1,2-a]pyridin-6-yl) pyrimidine-2-carboxylic acid (200 mg, 400.39 umol) and tert-butyl 4-amino piperidine-1-carboxylate hydrochloride (113.74 mg, 480.46 umol) in DMF (8 mL) was added DIEA (155.24 mg, 1.20 mmol) and T$_3$P (382.18 mg, 600.58 umol, 50% purity). The reaction mixture was stirred at 25° C. for 3 h. The resulting solution was quenched by saturated NH$_4$Cl (50 mL) and extracted with EA (50 mL×2), the combined organic layer was washed by water (50 mL×2) and brine (50 mL), dried over Na$_2$SO$_4$ and concentrated. The residue was purified by column chromatography to afford tert-butyl 4-(5-(3-((5-cyano-4-(4-fluorophenyl)thiazol-2-yl)(methyl)amino)-2-ethylimidazo[1,2-a] pyridin-6-yl)pyrimidine-2-carboxamido)piperidine-1-carboxylate (215 mg, 78.76% yield) as a yellow solid. MS: m/z=682.3 (M+1, ESI+).

Step Two:

To a solution of tert-butyl 4-(5-(3-((5-cyano-4-(4-fluorophenyl)thiazol-2-yl)(methyl)amino)-2-ethyl imidazo[1,2-a] pyridin-6-yl)pyrimidine-2-carboxamido)piperidine-1-carboxylate (215 mg, 315.35 umol) in dioxane (5 mL) was added 3M HCl in dioxane (525.58 uL, 1.57 mmol). The mixture was stirred at 25° C. for 5 h. The resulting solution was evaporated and purified by Prep-HPLC to afford compound 51, 5-(3-((5-cyano-4-(4-fluorophenyl)thiazol-2-yl) (methyl)amino)-2-ethylimidazo[1,2-a]pyridin-6-yl)-N-(piperidin-4-yl)pyrimidine-2-carboxamide (65 mg, 35.52% yield) as a white solid. $^1$H NMR (400 MHz, DMSO-d$_6$) δ 9.34 (s, 2H), 8.97 (s, 1H), 8.63-8.61 (d, 1H), 8.10-8.07 (t, 2H), 7.91-7.88 (dd, J H), 7.82-7.80 (d, 1H), 7.44-7.40 (t, 2H), 3.86-3.84 (m, 1H), 3.66 (s, 3H), 2.96-2.93 (d, 2H), 2.73-2.67 (dd, 2H), 2.55-2.51 (t, 3H), 1.75-1.72 (d, 2H), 1.53-1.44 (m, 2H), 1.30-1.26 (t, 3H); MS: m/z=582.3 (M+1, ESI+).

5.7. Example 6—Synthesis of Carbonyl-linked Pyridine-type Compounds

General Scheme 6

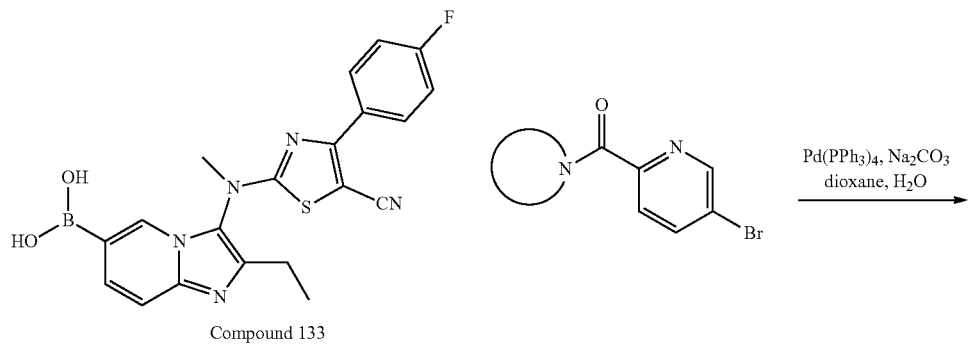

Compound 133

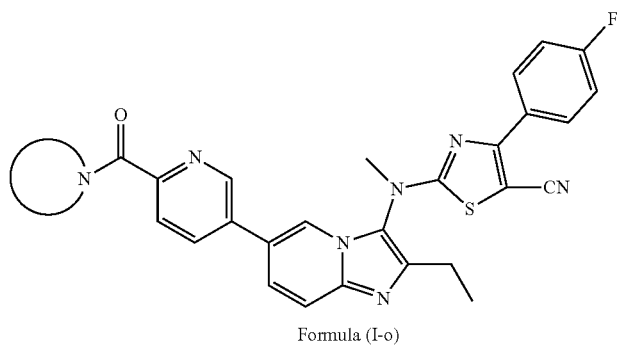

Formula (I-o)

5.7.1. Synthesis of (5-bromopyridin-2-yl)pyrrolidin-1-yl)methanone

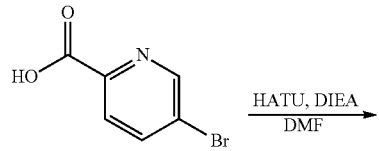

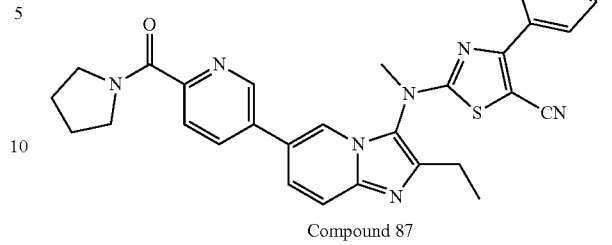

Compound 87

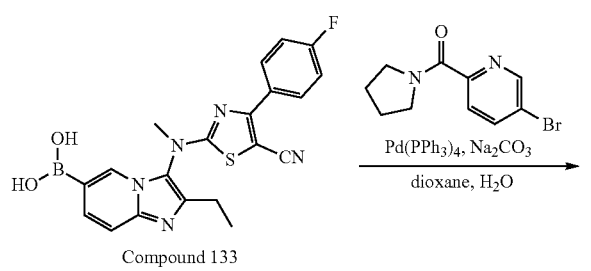

To a solution of 5-bromopicolinic acid (1.5 g, 7.43 mmol) and pyrrolidine (633.74 mg, 8.91 mmol) in DMF (30 mL) was added HATU (4.24 g, 11.14 mmol) and DIEA (2.88 g, 22.28 mmol, 3.88 mL), the reaction mixture was stirred at 25° C. for 2 h. The reaction mixture was quenched by saturated NH₄Cl (300 mL) and extracted with EA (50 mL×3), the organic layer was washed by water (200 mL) and brine (200 mL), then dried over Na₂SO₄ and concentrated. The residue was purified by column chromatography to afford (5-bromopyridin-2-yl)(pyrrolidin-1-yl)methanone (760 mg 40.12% yield) as a yellow oil. MS: m/z=255.0 (M+1, ESI+).

5.7.2. Synthesis of Compound 87

To a mixture of compound 133, (5-bromopyridin-2-yl)(pyrrolidin-1-yl)methanone (200 mg, 783.97 umol) and (3-((5-cyano-4-(4-fluorophenyl)thiazol-2-yl)(methyl)amino)-2-ethylimidazo[1,2-a]pyridin-6-yl)boronic acid (297.23 mg, 705.58 umol) in dioxane (10 mL) and water (2 mL) was added Na₂CO₃ (249.28 mg, 2.35 mmol) and Pd(PPh₃)₄ (45.30 mg, 39.20 umol), the reaction mixture was stirred at 100° C. for 2 h. The reaction mixture was poured into water (100 mL) and extracted with EA (40 mL×3), the organic layer was washed by water (100 mL×2) and brine (100 mL), then dried over Na₂SO₄ and concentrated. The residue was purified by Prep-HPLC to afford compound 87, 2-((2-ethyl-6-(6-(pyrrolidine-1-carbonyl)pyridin-3-yl)imidazo[1,2-a]pyridin-3-yl)(methyl)amino)-4-(4-fluorophenyl)thiazole-5-carbonitrile (110 mg, 25.44% yield) as a white solid. $^1$H NMR (400 MHz, DMSO-$d_6$) δ 9.04-9.03 (d, 1H), 8.88 (s, 1H), 8.34-8.32 (dd, 1H), 8.11-8.08 (t, 2H), 7.86-7.75 (m, 3H), 7.44-7.40 (t, 2H), 3.65-3.64 (m, 5H), 3.53-3.50 (t, 2H), 2.72-2.66 (dd, 2H), 1.85-1.83 (m, 4H), 1.30-1.26 (t, 3H); MS: m/z=552.1 (M+1, ESI+); HRMS: 552.1976.

5.8. Example 7—Synthesis of Piperazine-linked Pyrimidine-type Compounds

General Scheme 7

Route A

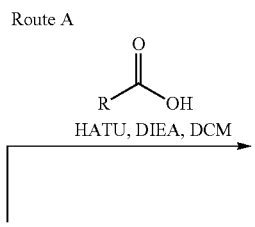

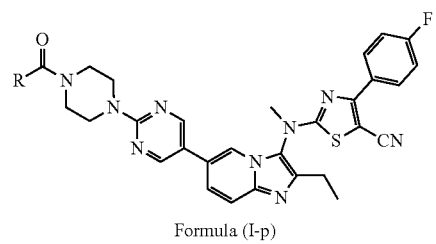

Formula (I-p)

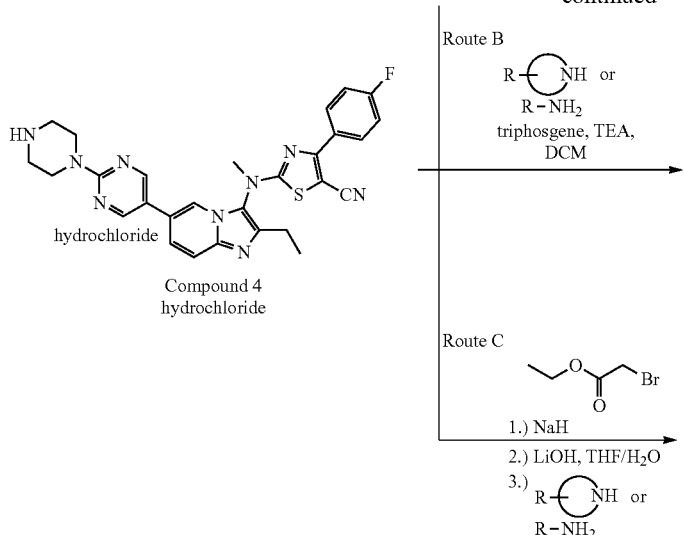

5.8.1. Synthesis of tert-butyl 4-(5-(4,4,5,5-tetramethyl-1,3,2-dioxaborolan-2-yl)pyrimidin-2-yl) piperazine-1-carboxylate

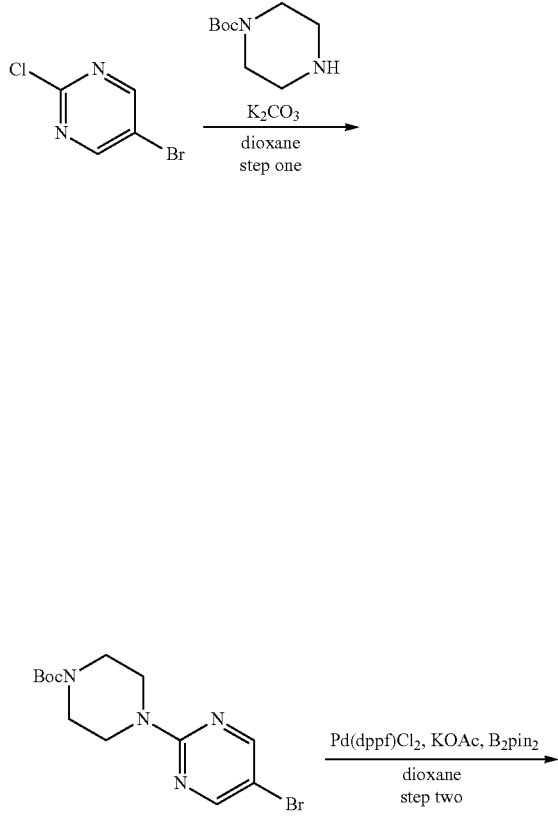

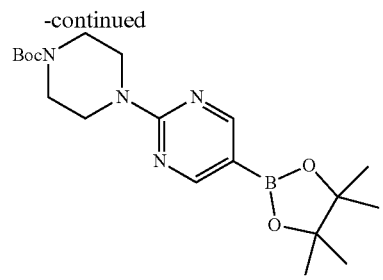

Step One:

To a solution of 5-bromo-2-chloropyrimidine (20 g, 103.40 mmol) and tert-butyl piperazine-1-carboxylate (28.89 g, 155.10 mmol) in dioxane (200 mL) was added $K_2CO_3$ (28.58 g, 206.79 mmol). The mixture was stirred at 110° C. for 4 h. The mixture was poured into water (600 mL) and extracted with EA (600 mL×2). The organic layer was washed with water (300 mL×2) and brine (300 mL×1), then dried over $Na_2SO_4$ and concentrated. The residue was purified by column chromatography to afford tert-butyl 4-(5-bromopyrimidin-2-yl)piperazine-1-carboxylate (27 g, 76.08% yield) as a white solid. $^1$H NMR (400 MHz, DMSO-$d_6$) δ 8.47 (s, 2H), 3.70-3.67 (m, 4H), 3.40-3.38 (m, 4H), 1.42 (s, 9H); MS: m/z=343.1 (M+1, ESI+).

Step Two

To a solution of tert-butyl 4-(5-bromopyrimidin-2-yl)piperazine-1-carboxylate (10 g, 29.14 mmol) and $B_2pin_2$ (8.14 g, 32.05 mmol) in dioxane (300 mL) was added Pd(dppf)Cl$_2$ (2.13 g, 2.91 mmol) and KOAc (11.44 g, 116.54 mmol). The mixture was stirred at 90° C. under $N_2$ for 16 h. The mixture was poured into water (600 mL) and extracted with EA (200 mL×2). The organic layer was washed with water (600 mL×2) and brine (600 mL×1), then dried over $Na_2SO_4$ and concentrated. The residue was purified by column chromatography to afford tert-butyl 4-(5-(4,4,5,5-tetramethyl-1,3,2-dioxaborolan-2-yl)pyrimidin-2-yl)piperazine-1-carboxylate (3.7 g, 32.54% yield) as a yellow solid. MS: m/z=391.1 (M+1, ESI+).

5.8.2. Synthesis of Compound 4 Hydrochloride

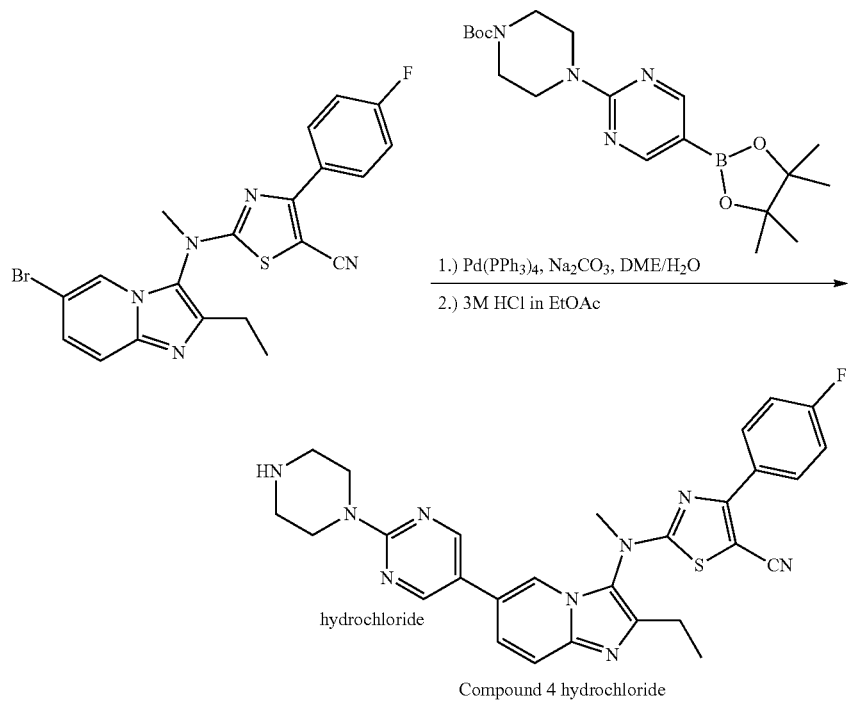

Step One:

To a mixture of 2-((6-bromo-2-ethylimidazo[1,2-a]pyridin-3-yl)(methyl)amino)-4-(4-fluorophenyl) thiazole-5-carbonitrile (800 mg, 1.75 mmol) and tert-butyl 4-(5-(4,4,5,5-tetramethyl-1,3,2-dioxaborolan-2-yl)pyrimidin-2-yl)piperazine-1-carboxylate (821.05 mg, 2.10 mmol) in DME/H$_2$O (16 mL/4 mL) was added Na$_2$CO$_3$ (371.62 mg, 3.51 mmol) and Pd(PPh$_3$)$_4$ (101.29 mg, 87.66 umol). The reaction mixture was stirred at 90° C. under N$_2$ for 1.5 h. The mixture was poured into water (40 mL) and extracted with EA (40 mL×2). The organic layer was washed with water (40 mL×2) and brine (40 mL), then dried over Na$_2$SO$_4$ and concentrated. The residue was purified by column chromatography to afford tert-butyl 4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carboxylate (1 g, 89.16% yield) as a yellow solid. MS: m/z=640.2 (M+1, ESI+).

Step Two:

To a mixture of tert-butyl 4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carboxylate (1.2 g, 1.88 mmol) in EA (10 mL) was added 3M HCl in EA (3 M, 20 mL) and stirred at 25° C. for 3 h. The mixture was filtered and the solid cake was washed with EA, then dried under reduce pressure to afford compound 4 hydrochloride, 2-((2-ethyl-6-(2-(piperazin-1-yl)pyrimidin-5-yl)imidazo[1,2-a]pyridin-3-yl)(methyl)amino)-4-(4-fluoro phenyl)thiazole-5-carbonitrile hydrochloride (1 g, 98.79% yield) as a yellow solid. MS: m/z=540.3 (M+1, ESI+).

5.8.3. Synthesis of Compound 4

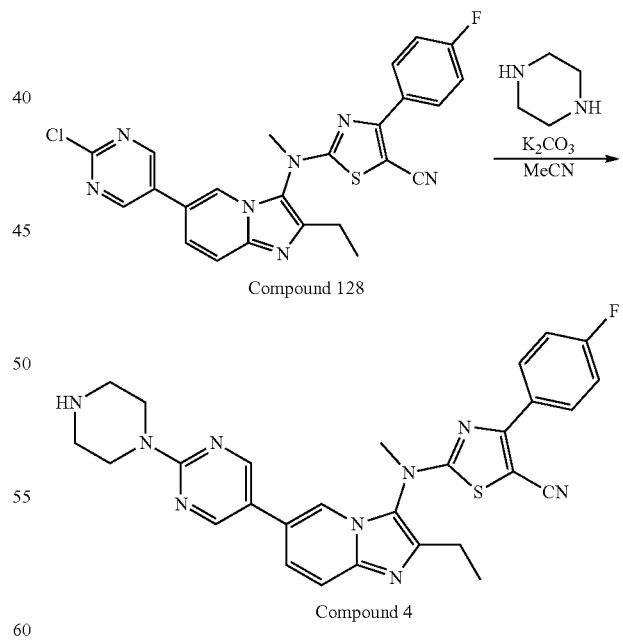

To a solution of compound 128, 2-((6-(2-chloropyrimidin-5-yl)-2-ethylimidazo[1,2-a]pyridin-3-yl)(methyl)amino)-4-(4-fluorophenyl)thiazole-5-carbonitrile (300 mg, 612.3 umol) and piperazine (791.13 mg, 918.5 umol) in MeCN (20 mL) was added K$_2$CO$_3$ (254 mg, 183.7 umol), the reaction mixture was stirred at 80° C. for 2 h. Filtered and concentrated, the residue was purified by Prep-HPLC to afford compound 4, 2-((2-ethyl-6-(2-(piperazin-1-yl)pyrimidin-5-yl)imidazo[1,2-a]pyridin-3-yl)(methyl)amino)-4-(4-fluoro phenyl)thiazole-5-carbonitrile (120 mg, 36.32% yield) as a white solid. ¹H NMR (400 MHz, DMSO-d₆) δ 8.75 (s, 2H), 8.65 (s, 1H), 8.11-8.08 (t, 2H), 7.69 (s, 2H), 7.44-7.39 (t, 2H), 3.71-3.68 (t, 4H), 3.64 (s, 3H), 2.74-2.70 (m, 4H), 2.68-2.64 (q, 2H), 1.29-1.25 (t, 3H); MS: m/z=540.2 (M+1, ESI+).

5.8.4. Synthesis of Compound 5 thiazol-2-yl)(methyl)amino)-2-ethylimidazo[1,2-a] pyridin-6-yl)pyrimidin-2-yl)piperazine-1-carbonyl)-4-hydroxypyrrolidine-1-carboxylate (105 mg, 75.26% yield) which was used for next step without further purification. MS: m/z=753.4 (M+1, ESI+).

Step Two:

To a mixture of tert-butyl (2S,4R)-2-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carbonyl)-4-hydroxy pyrrolidine-1-carboxylate (130 mg, 172.68 umol) in EA (5 mL) was added 3M HCl in EA (3 M, 5 mL)

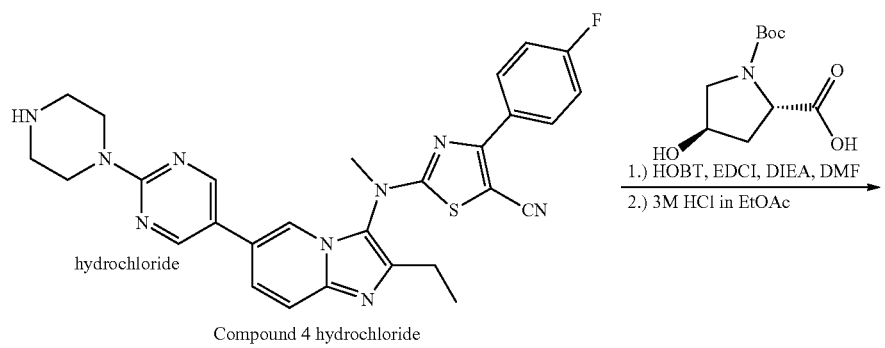

and stirred at 25° C. for 1 h. The reaction mixture was concentrated and purified by Prep-HPLC (Waters Xbridge C18 10 um OBD 19*250 mm, A: 10 mmol NH₄HCO₃ in water; B: CH₃CN, 5% to 95%) in NH₄HCO₃ condition to afford compound 5, 2-((2-ethyl-6-(2-(4-((2S,4R)-4-hydroxypyrrolidine-2-carbonyl)piperazin-1-yl)pyrimidin-5-yl)imidazo[1,2-a]pyridin-3-yl)(methyl)amino)-4-(4-fluoro phenyl)thiazole-5-carbonitrile (51 mg, 45.53% yield) as a white solid. ¹H NMR (400 MHz, DMSO-d₆) δ 8.81 (s, 2H), 8.67 (s, 1H), 8.09 (s, 2H), 7.71 (s, 2H), 7.44-7.40 (t, 2H), 4.70-4.69 (d, 1H), 4.17 (s, 1H), 4.05-4.01 (t, 1H), 3.81-3.45 (m, 13H), 3.07-3.02 (dd, 1H), 2.70-2.64 (q, 2H), 1.86-1.75 (m, 2H), 1.28-1.25 (t, 3H); MS: m/z=653.2 (M+1, ESI+).

Step One:

To a mixture of compound 4 hydrochloride, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile hydrochloride (100 mg, 185.31 umol), (2S,4R)-1-(tert-butoxycarbonyl)-4-hydroxypyrrolidine-2-carboxylic acid (51.42 mg, 222.38 umol), HOBT (37.56 mg, 277.97 umol) and EDCI (53.29 mg, 277.97 umol) in DMF (8 mL) was added DIEA (95.80 mg, 741.25 umol), the reaction mixture was stirred at 25° C. for 6 h. The mixture was poured into water (40 mL) and extracted with EA (40 mL×2). The organic layer was washed with water (40 mL×2) and brine (40 mL), then dried over Na₂SO₄ and concentrated to afford tert-butyl (2S,4R)-2-(4-(5-(3-((5-cyano-4-(4-fluorophenyl)

5.8.5. Synthesis of Compound 5 Hydrochloride

Compound 4 hydrochloride

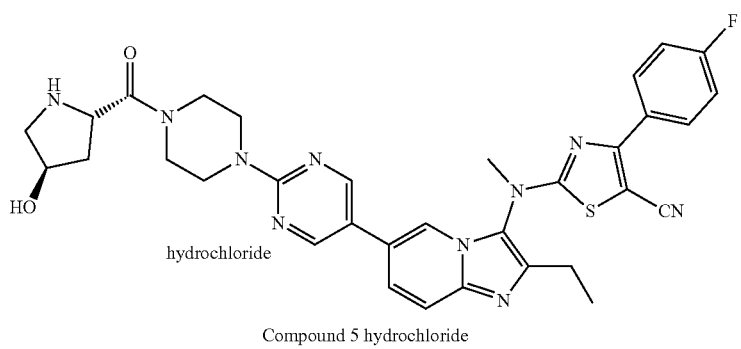

Compound 5 hydrochloride

Step One:

To a mixture of compound 4 hydrochloride, 2-((2-ethyl-6-(2-(piperazin-1-yl)pyrimidin-5-yl)imidazo[1,2-a]pyridin-3-yl)(methyl) amino)-4-(4-fluorophenyl)thiazole-5-carbonitrile hydrochloride (700 mg, 1.30 mmol), (2S,4R)-1-(tert-butoxycarbonyl)-4-hydroxypyrrolidine-2-carboxylic acid (360 mg, 1.56 mmol), HOBT (263 mg, 1.95 mmol) and EDCI (373 mg, 1.95 mmol) in DMF (15 mL) was added DIEA (670 mg, 5.19 mmol), the reaction mixture was stirred at 25° C. for 6 h. The mixture was poured into water (150 mL) and extracted with EA (40 mL×2). The organic layer was washed with water (40 mL×2) and brine (40 mL), then dried over $Na_2SO_4$ and concentrated to afford tert-butyl (2S,4R)-2-(4-(5-(3-((5-cyano-4-(4-fluorophenyl)thiazol-2-yl)(methyl)amino)-2-ethylimidazo[1,2-a] pyridin-6-yl)pyrimidin-2-yl)piperazine-1-carbonyl)-4-hydroxypyrrolidine-1-carboxylate (850 mg, 87% yield) which was used for next step without further purification. MS: m/z=753.4 (M+1, ESI+).

Step Two:

To a mixture of tert-butyl (2S,4R)-2-(4-(5-(3-((5-cyano-4-(4-fluorophenyl)thiazol-2-yl)(methyl) amino)-2-ethylimidazo[1,2-a]pyridin-6-yl)pyrimidin-2-yl)piperazine-1-carbonyl)-4-hydroxy pyrrolidine-1-carboxylate (850 mg, 1.13 mmol) in EA (10 mL) was added 3M HCl in EA (3 M, 5 mL) and stirred at 25° C. for 1 h. The reaction mixture was concentrated and purified by Prep-HPLC (Waters Xbridge C18 10 um OBD 19*250 mm, A: 0.05% HCl in water: B: $CH_3CN$, 5% to 95%) in HCl condition to afford compound 5 hydrochloride, 2-((2-ethyl-6-(2-(4-((2S,4R)-4-hydroxypyrrolidine-2-carbonyl)piperazin-1-yl)pyrimidin-5-yl)imidazo[1,2-a]pyridin-3-yl)(methyl)amino)-4-(4-fluoro phenyl)thiazole-5-carbonitrile hydrochloride (485 mg, 62.3% yield) as a white solid. $^1$H NMR (400 MHz, DMSO-$d_6$) δ 10.53 (s, 1H), 9.15 (s, 1H), 8.93 (s, 2H), 8.69 (s, 1H), 8.44-8.42 (d, 1H), 8.15-8.13 (d, 11H), 8.01 (s, 2H), 7.42-7.38 (t, 2H), 4.77 (s, 1H), 4.44 (s, 1H), 3.90-3.83 (m, 4H), 3.69-3.61 (m, 7H), 3.37-3.34 (m, 1H), 3.13 (s, 1H), 2.92-2.87 (dd, 2H), 2.46-2.41 (m, 1H), 2.01-1.94 (m, 1H), 1.38-1.34 (t, 3H); MS: m/z=653.3 (M+1, ESI+).

5.8.6. Synthesis of Compound 6

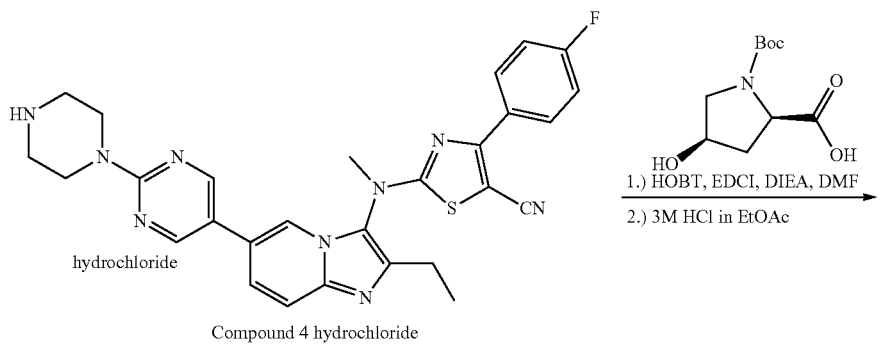

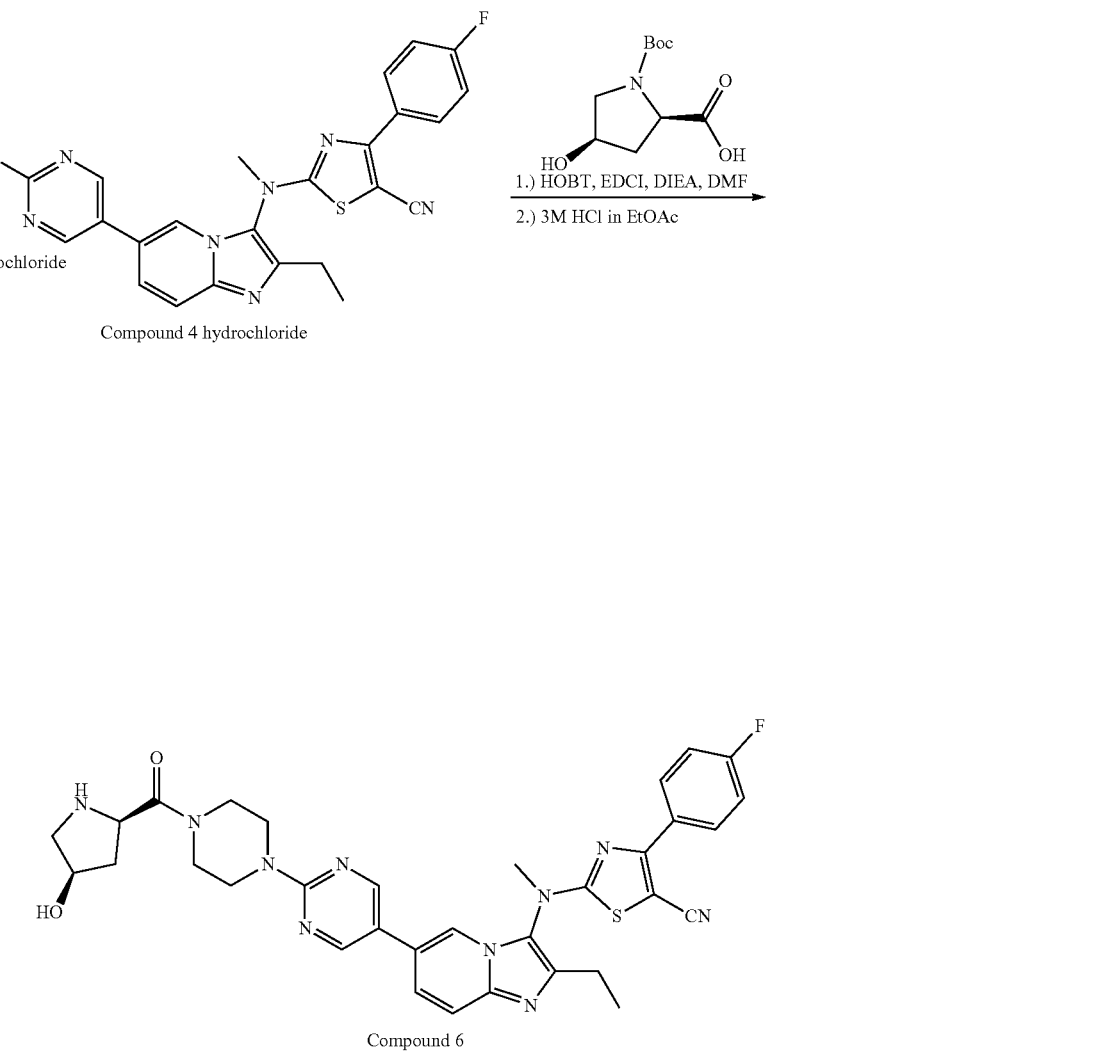

Compound 6

Step One:

To a solution of (2R,4R)-1-(tert-butoxycarbonyl)-4-hydroxypyrrolidine-2-carboxylic acid (72.25 mg, 312.45 umol) in DMF (10 mL) was added DIEA (107.68 mg, 833.20 umol), HOBT (42.22 mg, 312.45 umol) and EDCI (59.83 mg, 312.45 umol). The reaction mixture was stirred at 25° C. for 1 h. Then compound 4 hydrochloride, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile hydrochloride (120 mg, 208.30 umol) was added to the reaction mixture. The resulting mixture was stirred at 25° C. for 16 h. The reaction mixture was poured into water (50 mL) and extracted with EA (30 mL×3). The combined organic layers were dried over Na$_2$SO$_4$ and concentrated under reduced pressure and purified by silica gel column (PE:EA=1:1) to afford tert-butyl (2R,4R)-2-(4-(5-(3-((5-cyano-4-(4-fluorophenyl)thiazol-2-yl) (methyl)amino)-2-ethylimidazo[1,2-a]pyridin-6-yl)pyrimidin-2-yl) piperazine-1-carbonyl)-4-hydroxy pyrrolidine-1-carboxylate (150 mg, crude) as a brown oil. MS: m/z=753.2 (M+1, ESI+).

Step Two:

To a solution of tert-butyl (2R,4R)-2-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carbonyl)-4-hydroxy pyrrolidine-1-carboxylate (150 mg, 199.24 umol) in DCM (5 mL) was added 3M HCl in EA (3 M, 5 mL). The reaction mixture was stirred at 25° C. for 1 h. The excess of solvent was removed under reduced pressure. The residue was purified by Prep-HPLC (Waters Xbridge C18 10 um OBD 19*250 mm, A: 10 mmol NH$_4$HCO$_3$ in water; B: CH$_3$CN, 5% to 95%) in NH$_4$HCO$_3$ condition to afford compound 6, 2-((2-ethyl-6-(2-(4-((2R,4R)-4-hydroxypyrrolidine-2-carbonyl)piperazin-1-yl)pyrimidin-5-yl) imidazo[1,2-a]pyridin-3-yl) (methyl)amino)-4-(4-fluorophenyl)thiazole-5-carbonitrile (15 mg, 11.53% yield) as a white solid. $^1$H NMR (400 MHz, DMSO-d$_6$) δ 8.80 (s, 2H), 8.65 (s, 1H), 8.08 (s, 2H), 7.70 (s, 2H), 7.43-7.39 (t, 2H), 4.55 (s, 1H), 4.41 (s, 1H), 3.81-3.49 (m, 13H), 2.83-2.80 (d, 1H), 2.68-2.56 (m, 3H), 2.24 (s, 1H), 1.47 (s, 1H), 1.28-1.24 (t, 3H); MS: m/z=653.2 (M+1, ESI+).

5.8.7. Synthesis of Compound 6 Hydrochloride

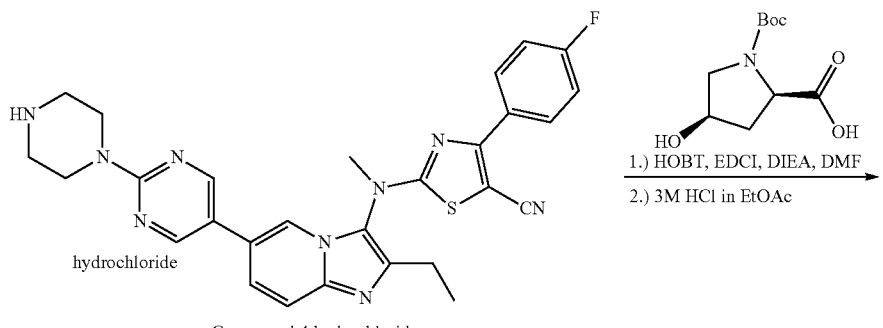

Compound 4 hydrochloride

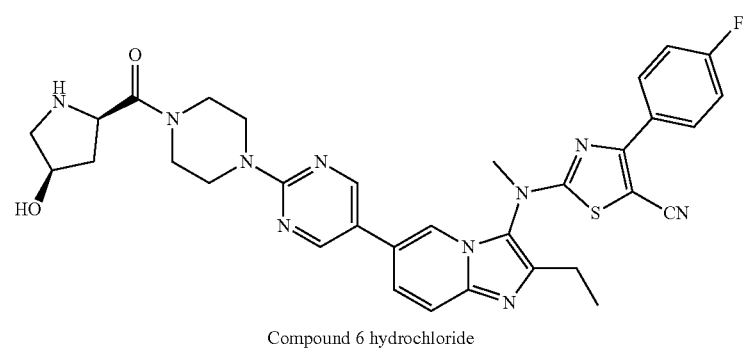

Compound 6 hydrochloride

Step One:

To a solution of (2R,4R)-1-(tert-butoxycarbonyl)-4-hydroxypyrrolidine-2-carboxylic acid (360 mg, 1.56 mmol) in DMF (15 mL) was added DIEA (670 mg, 5.19 mmol), HOBT (263 mg, 1.95 mmol) and EDCI (373 mg, 1.95 mmol). The reaction mixture was stirred at 25° C. for 1 h. Then compound 4 hydrochloride, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile hydrochloride (700 mg, 1.30 mmol) was added to the reaction mixture. The resulting mixture was stirred at 25° C. for 16 h. The reaction mixture was poured into water (150 mL) and extracted with EA (40 mL×3). The combined organic layers were dried over $Na_2SO_4$ and concentrated under reduced pressure and purified by silica gel column (PE:EA=1:1) to afford tert-butyl (2R,4R)-2-(4-(5-(3-((5-cyano-4-(4-fluorophenyl)thiazol-2-yl) (methyl)amino)-2-ethylimidazo[1,2-a]pyridin-6-yl)pyrimidin-2-yl)piperazine-1-carbonyl)-4-hydroxy pyrrolidine-1-carboxylate (400 mg, 39.1% yield) which was used for next step without further purification. MS: m/z=753.2 (M+1, ESI+).

Step Two:

To a solution of tert-butyl (2R,4R)-2-(4-(5-(3-((5-cyano-4-(4-fluorophenyl)thiazol-2-yl)(methyl) amino)-2-ethylimidazo[1,2-a]pyridin-6-yl)pyrimidin-2-yl)piperazine-1-carbonyl)-4-hydroxy pyrrolidine-1-carboxylate (400 mg, 0.53 mmol) in DCM (5 mL) was added 3M HCl in EA (3 M, 5 mL). The reaction mixture was stirred at 25° C. for 1 h. The excess of solvent was removed under reduced pressure. The residue was purified by Prep-HPLC (Waters Xbridge C18 10 um OBD 19*250 mm, A: 0.05% HCl in water; B: $CH_3CN$, 5% to 95%) in HCl condition to afford compound 6 hydrochloride, 2-((2-ethyl-6-(2-(4-((2R,4R)-4-hydroxypyrrolidine-2-carbonyl)piperazin-1-yl)pyrimidin-5-yl) imidazo[1,2-a]pyridin-3-yl) (methyl)amino)-4-(4-fluorophenyl) thiazole-5-carbonitrile (212 mg, 57.9% yield) as a white solid. $^1$H NMR (400 MHz, DMSO-$d_6$) δ 10.29 (s, 1H), 9.54 (s, 1H), 9.09 (s, 1H), 8.90 (s, 2H), 8.53 (s, 1H), 8.37-8.35 (d, 1H), 8.12-8.10 (d, 1H), 8.03-8.00 (t, 2H), 7.42-7.38 (t, 2H), 4.64-4.60 (m, 1H), 4.39 (s, 1H), 4.05-4.03 (t, 1H), 3.95-3.92 (m, 2H), 3.81-3.80 (m, 2H), 3.70-3.53 (m, 6H), 3.19-3.16 (m, 3H), 2.90-2.84 (dd, 2H), 2.66-2.60 (m, 1H), 1.83-1.79 (m, 1H), 1.35-1.31 (t, 3H); MS: m/z=653.3 (M+1, ESI+).

5.8.8. Synthesis of Compound 7

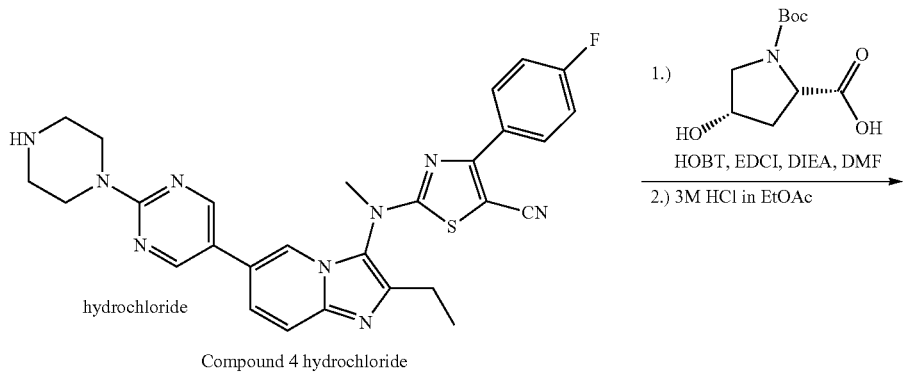

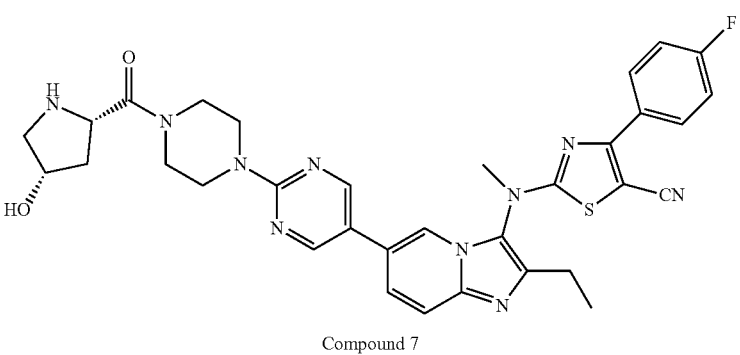

Compound 7

Step One:

To a mixture of compound 4 hydrochloride, 2-((2-ethyl-6-(2-(piperazin-1-yl)pyrimidin-5-yl)imidazo[1,2-a]pyridin-3-yl) (methyl)amino)-4-(4-fluorophenyl)thiazole-5-carbonitrile hydrochloride (150 mg, 260.38 umol) and (2S,4S)-1-(tert-butoxycarbonyl)-4-hydroxypyrrolidine-2-carboxylic acid (60.22 mg, 260.42 umol) in DCM (6 mL) was added DIEA (134.61 mg, 1.04 mmol) and HATU (148.50 mg, 390.56 umol). The resulting mixture was stirred for 1 h at 25° C. The reaction mixture was poured into water (50 mL) and extracted with DCM (10 mL×3). The combined organic layers were dried over $Na_2SO_4$ and concentrated under reduced pressure to afford tert-butyl (2S,4S)-2-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carbonyl)-4-hydroxypyrrolidine-1-carboxylate (150 mg, crude) as a yellow oil. MS: m/z=753.2 (M+1, ESI+).

Step Two:

To a solution of tert-butyl (2S,4S)-2-(4-(5-(3-((5-cyano-4-(4-fluorophenyl)thiazol-2-yl)(methyl)amino)-2-ethyl imidazo[1,2-a]pyridin-6-yl)pyrimidin-2-yl)piperazine-1-carbonyl)-4-hydroxy pyrrolidine-1-carboxylate (150 mg, 199.24 umol) in EA (5 mL) was added 3M HCl in EA (3 M, 5 mL). The reaction mixture was stirred at 25° C. for 1 h. The excess of solvent was removed under reduced pressure. The residue was purified by Prep-HPLC to afford compound 7, 2-((2-ethyl-6-(2-(4-((2S,4S)-4-hydroxypyrrolidine-2-carbonyl) piperazin-1-yl)pyrimidin-5-yl)imidazo[1,2-a] pyridin-3-yl) (methyl)amino)-4-(4-fluorophenyl) thiazole-5-carbonitrile (24 mg, 18.46% yield) as a white solid. $^1$H NMR (400 MHz, DMSO-$d_6$) δ 8.81 (s, 2H), 8.66 (s, 1H), 8.09 (s, 2H), 7.70 (s, 2H), 7.43-7.39 (t, 2H), 4.51 (s, 1H), 4.14 (s, 1H), 3.82-3.50 (m, 13H), 2.83-2.80 (d, 1H), 2.70-2.56 (m, 3H), 2.24 (s, 1H), 1.47 (s, 1H), 1.28-1.25 (t, 3H); MS: m/z=653.2 (M+1, ESI+).

5.8.9. Synthesis of Compound 8

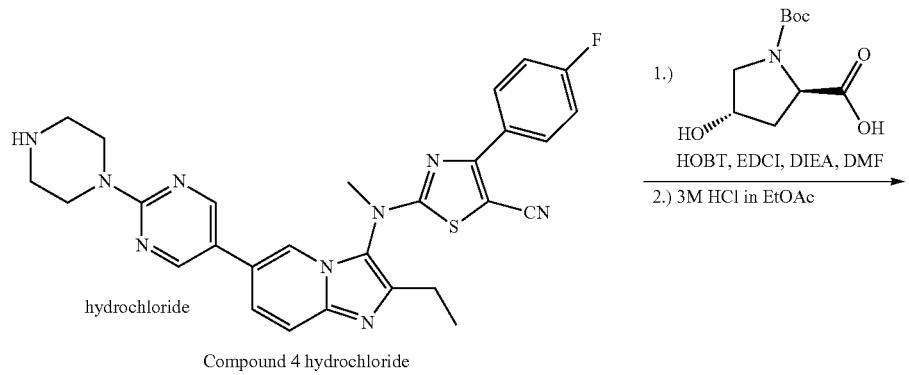

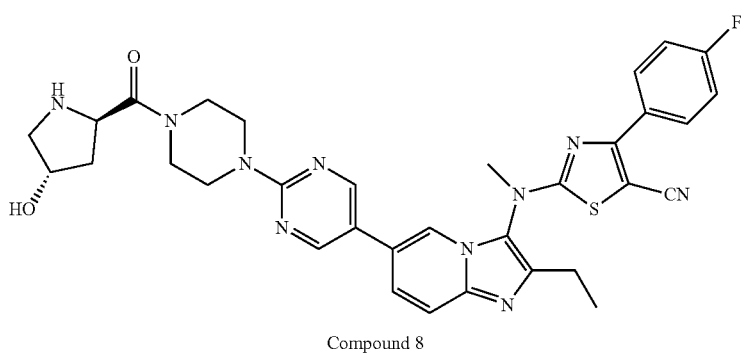

Compound 8

Step One:

To a solution of compound 4 hydrochloride, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile hydrochloride (0.12 g, 208.30 umol) and DIEA (107.69 mg, 833.20 umol) in DCM (5 mL) was added (2R,4S)-1-(tert-butoxycarbonyl)-4-hydroxypyrrolidine-2-carboxylic acid (57.80 mg, 249.96 umol), EDCI (59.90 mg, 312.45 umol) and HOBT (42.22 mg, 312.45 umol). The resulting mixture was stirred at room temperature for 2 h. The reaction mixture was poured into water (50 mL) and extracted with DCM (10 mL×3). The combined organic layers were dried over $Na_2SO_4$ and concentrated under reduced pressure to afford tert-butyl (2R,4S)-2-(4-(5-(3-((5-cyano-4-(4-fluorophenyl)thiazol-2-yl)(methyl)amino)-2-ethyl imidazo[1,2-a]pyridin-6-yl)pyrimidin-2-yl)piperazine-1-carbonyl)-4-hydroxypyrrolidine-1-carboxylate (156 mg, 99.48% yield) as a yellow oil. MS: m/z=753.2 (M+1, ESI+).

Step Two:

To a solution of tert-butyl (2R,4S)-2-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carbonyl)-4-hydroxy pyrrolidine-1-carboxylate (120 mg, 159.39 umol) in DCM (5 mL) was added 3M HCl in EA (3 M, 5 mL). The reaction mixture was stirred at 25° C. for 1 h. The excess of solvent was removed under reduced pressure. The residue was purified by Prep-HPLC to afford compound 8, 2-((2-ethyl-6-(2-(4-((2R,4S)-4-hydroxypyrrolidine-2-carbonyl)piperazin-1-yl)pyrimidin-5-yl) imidazo[1,2-a]pyridin-3-yl)(methyl)amino)-4-(4-fluorophenyl)thiazole-5-carbonitrile (31 mg, 29.80% yield) as a white solid. $^1$H NMR (400 MHz, DMSO-$d_6$) δ 8.81 (s, 2H), 8.67 (s, 1H), 8.11-8.07 (m, 2H), 7.71 (s, 2H), 7.44-7.40 (t, 2H), 4.71-4.70 (d, 1H), 4.18 (s, 1H), 4.06-4.02 (t, 1H), 3.82-3.68 (m, 4H), 3.63-3.49 (m, 8H), 3.07-3.03 (dd, 1H), 2.70-2.64 (q, 2H), 2.56-2.52 (dd, 1H), 1.88-1.75 (m, 2H), 1.28-1.25 (t, 3H); MS: m/z=653.2 (M+1, ESI+).

5.8.10. Synthesis of Compound 9

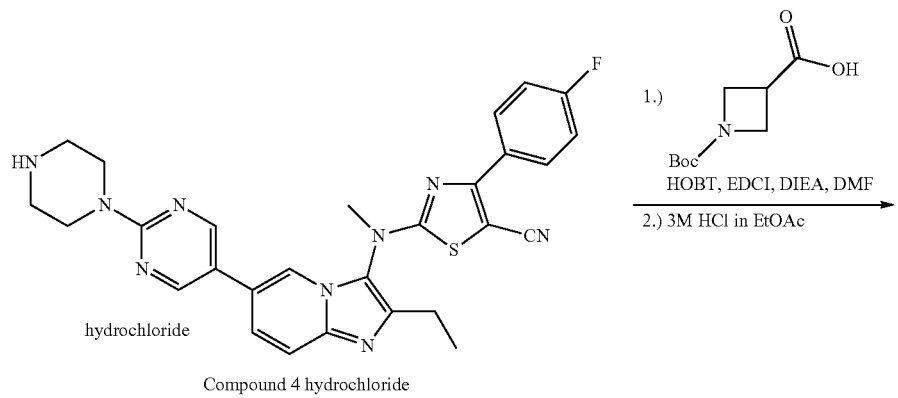

Compound 4 hydrochloride

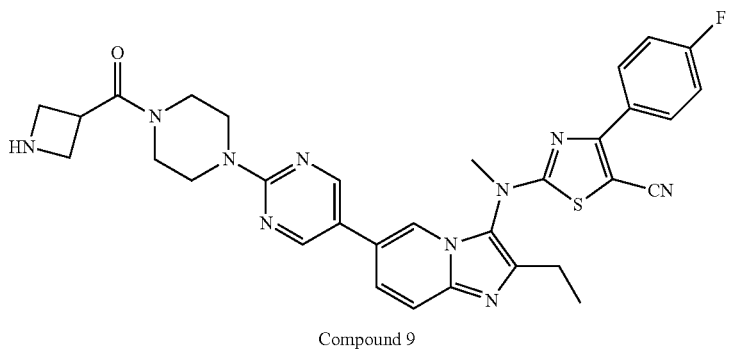

Compound 9

Step One:

To a solution of compound 4 hydrochloride, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile hydrochloride (100 mg, 185.31 umol), 1-(tert-butoxycarbonyl)azetidine-3-carboxylic acid (44.75 mg, 222.38 umol) in DMF (8 mL) was added HOBT (37.56 mg, 277.97 umol), EDCI (53.29 mg, 277.97 umol) and DIEA (95.80 mg, 741.2 umol). The reaction mixture was stirred at 25° C. for 6 h. The reaction mixture was poured into water (40 mL) and extracted with EA (20 mL×2). The organic layers were washed with water (40 mL×2) and brine (40 mL), then dried over $Na_2SO_4$ and concentrated to afford tert-butyl 3-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carbonyl)azetidine-1-carboxylate (100 mg, 74.65% yield) which was used to next step without further purification. MS: m/z=723.3 (M+1, ESI+).

Step Two

To a solution of tert-butyl 3-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carbonyl)azetidine-1-carboxylate (110.00 mg, 152.18 umol) in EA (5 mL) was added 3M HCl in EA (3 M, 5 mL). The reaction mixture was stirred at 25° C. for 1 h. The reaction mixture was concentrated under reduced pressure and the residue was purified by Prep-HPLC to afford compound 9, 2-((6-(2-(4-(azetidine-3-carbonyl)piperazin-1-yl)pyrimidin-5-yl)-2-ethylimidazo[1,2-a]pyridin-3-yl)(methyl)amino)-4-(4-fluorophenyl)thiazole-5-carbonitrile (20 mg, 21.10% yield) as a white solid. $^1$H NMR (400 MHz, DMSO-$d_6$) δ 8.80 (s, 2H), 8.66 (s, 1H), 8.09 (s, 2H), 7.70 (s, 2H), 7.44-7.39 (t, 2H), 3.76-3.63 (m, 11H), 3.52-3.49 (m, 5H), 2.70-2.63 (m, 3H), 1.28-1.25 (t, 3H); MS: m/z=623.2 (M+1, ESI+).

5.8.11. Synthesis of Compound 10

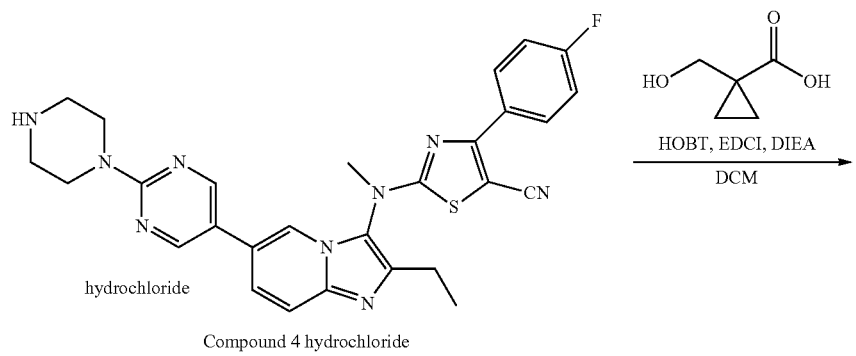

Compound 4 hydrochloride

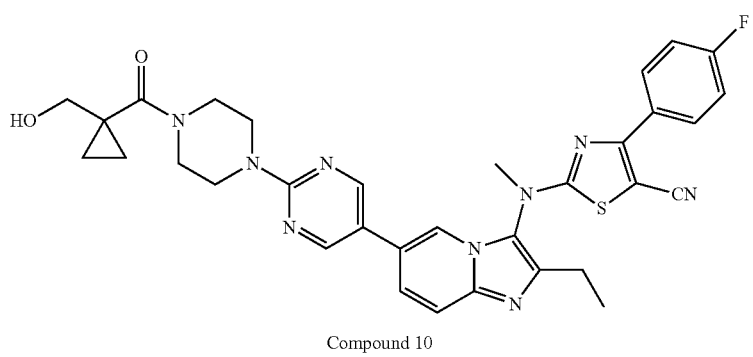

Compound 10

To a solution of compound 4 hydrochloride, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile hydrochloride (100 mg, 173.58 umol) and 1-(hydroxymethyl)cyclopropane-1-carboxylic acid (24.19 mg, 208.30 umol) in DCM (5 mL) was added DIEA (89.74 mg, 694.34 umol), EDCI (49.91 mg, 260.38 umol) and HOBT (35.44 mg, 260.38 umol). The reaction mixture was stirred at 25° C. for 1 h. The reaction mixture was poured into water (40 mL) and extracted with DCM (10 mL×2). The organic layers were washed with water (20 mL×2) and brine (40 mL), then dried over Na$_2$SO$_4$ and concentrated under reduce pressure. The residue was purified by Prep-HPLC to afford compound 10, 2-((2-ethyl-6-(2-(4-(1-(hydroxymethyl) cyclopropane-1-carbonyl)piperazin-1-yl)pyrimidin-5-yl)imidazo[1,2-a]pyridin-3-yl)(methyl)amino)-4-(4-fluorophenyl)thiazole-5-carbonitrile (31 mg, 28.18% yield) as a white solid. $^1$H NMR (400 MHz, DMSO-d$_6$) δ 8.81 (s, 2H), 8.66 (s, 1H), 8.08 (s, 2H), 7.70 (s, 2H), 7.42 (s, 2H), 4.86 (s, 1H), 3.78 (s, 4H), 3.63 (s, 7H), 3.47 (s, 2H), 2.66 (s, 2H), 1.28-1.24 (t, 3H), 0.75-0.70 (d, 4H); MS: m/z=638.1 (M+1, ESI+).

5.8.12. Synthesis of Compound 42

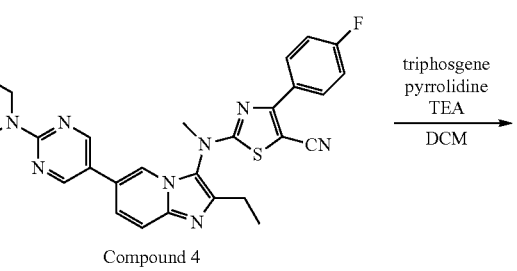

Compound 4

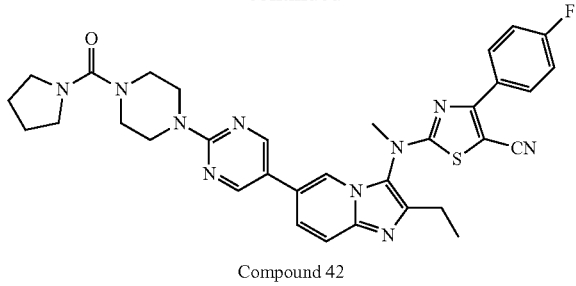

Compound 42

To a mixture of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (200 mg, 370.63 umol) in DCM (10 mL) was added triphosgene (54.99 mg, 185.31 umol) and stirred at 0° C. for 0.5 h, then TEA (112.51 mg, 1.11 mmol) was added and stirred at 0° C. for another 0.5 h. After that, pyrrolidine (52.72 mg, 741.25 umol) was added to the above reaction mixture and stirred at 25° C. for 0.5 h. Added water (50 mL) to the reaction mixture, then extracted with DCM (50 mL×2). The organic layer was washed with water (50 mL) and brine (50 mL), dried over $Na_2SO_4$ and concentrated. The residue was purified by Prep-HPLC to afford compound 42, 2-((2-ethyl-6-(2-(4-(pyrrolidine-1-carbonyl)piperazin-1-yl)pyrimidin-5-yl)imidazo[1,2-a]pyridin-3-yl)(methyl)amino)-4-(4-fluorophenyl)thiazole-5-carbonitrile (35 mg, 14.89% yield) as a white solid. $^1$H NMR (400 MHz, DMSO-$d_6$) δ 8.80 (s, 2H), 8.67 (s, 1H), 8.10-8.07 (t, 2H), 7.71 (s, 2H), 7.44-7.40 (t, 2H), 3.80-3.77 (t, 4H), 3.63 (s, 3H), 3.31-3.28 (m, 4H), 3.25-3.23 (m, 4H), 2.70-2.64 (dd, 2H), 1.77-1.74 (t, 4H), 1.28-1.25 (t, 3H); MS: m/z=637.4 (M+1, ESI+).

5.8.13. Synthesis of Compound 43

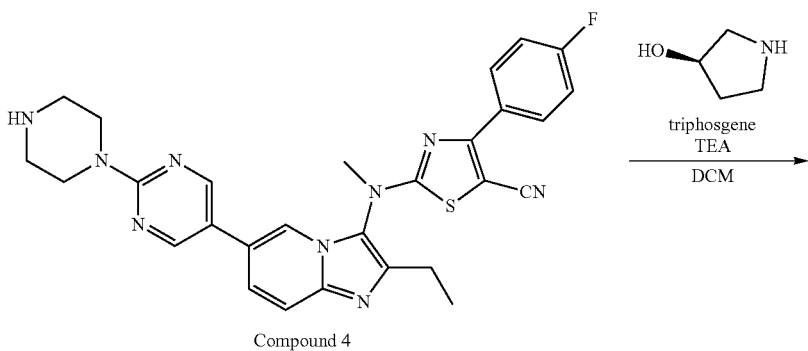

Compound 4

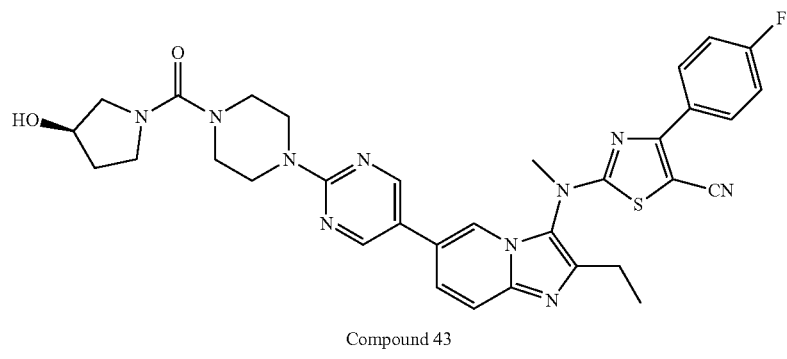

Compound 43

To a mixture of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (200 mg, 370.63 umol) in DCM (10 mL) was added triphosgene (54.99 mg, 185.31 umol) and stirred at 0° C. for 0.5 h, then TEA (112.51 mg, 1.11 mmol) was added and stirred at 0° C. for another 0.5 h. After that, (R)-pyrrolidin-3-ol (64.58 mg, 741.25 umol) was added to the above reaction mixture and stirred at 25° C. for 0.5 h. Added water (50 mL) to the reaction mixture, then extracted with DCM (50 mL×2). The organic layer was washed with water (50 mL) and brine (50 mL), dried over $Na_2SO_4$ and concentrated. The residue was purified by Prep-HPLC (Waters Xbridge C18 10 um OBD 19*250 mm, A: 10 mmol $NH_4HCO_3$ in water; B: $CH_3CN$, 5% to 95%) in $NH_4HCO_3$ condition to afford compound 43, (R)-2-((2-ethyl-6-(2-(4-(3-hydroxypyrrolidine-1-carbonyl)piperazin-1-yl)pyrimidin-5-yl)imidazo[1,2-a]pyridin-3-yl)(methyl)amino)-4-(4-fluorophenyl)thiazole-5-carbonitrile (100 mg, 41.34% yield) as a white solid. $^1$H NMR (400 MHz, DMSO-$d_6$) δ 8.80 (s, 2H), 8.67 (s, 1H), 8.09-8.07 (t, 2H), 7.71 (s, 2H), 7.44-7.40 (t, 2H), 4.92 (s, 1H), 4.22 (s, 1H), 3.83-3.74 (m, 4H), 3.63 (s, 3H), 3.52-3.45 (m, 2H), 3.28-3.18 (m, 5H), 3.13-3.10 (d, 1H), 2.70-2.64 (dd, 2H), 1.82-1.71 (m, 2H), 1.29-1.25 (t, 3H); MS: m/z=653.6 (M+1, ESI+); HRMS: 653.2564.

5.8.14. Synthesis of Compound 43 Hydrochloride

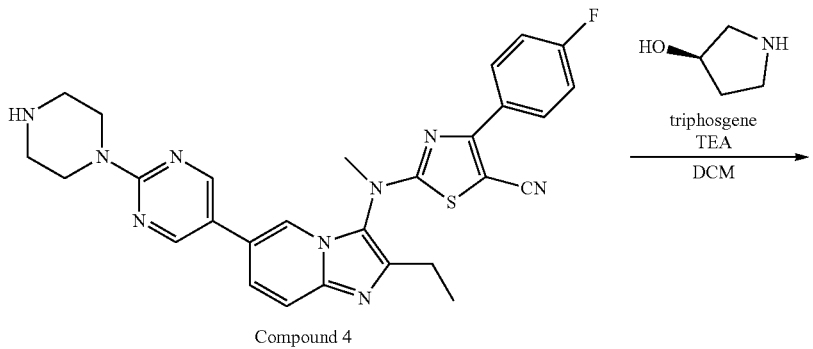

Compound 4

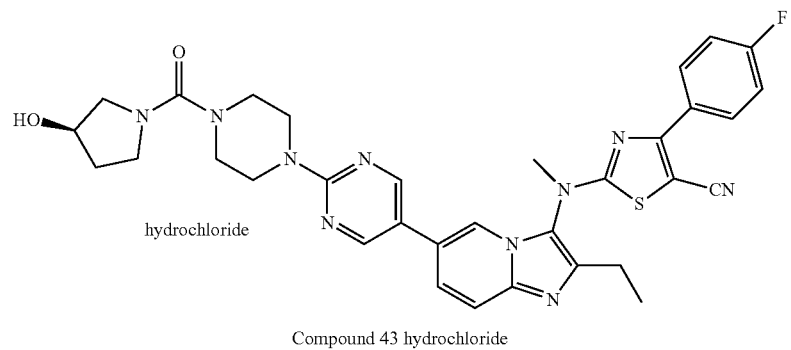

Compound 43 hydrochloride

To a mixture of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (600 mg, 1.11 mmol) in DCM (15 mL) was added triphosgene (165 mg, 556 umol) and stirred at 0° C. for 0.5 h, then TEA (338 mg, 3.33 mmol) was added and stirred at 0° C. for another 0.5 h. After that, (R)-pyrrolidin-3-ol (194 mg, 2.22 mmol) was added to the above reaction mixture and stirred at 25° C. for 0.5 h. Added water (50 mL) to the reaction mixture, then extracted with DCM (50 mL×2). The organic layer was washed with water (50 mL) and brine (50 mL), dried over Na$_2$SO$_4$ and concentrated. The residue was purified by Prep-HPLC (Waters Xbridge C18 10 um OBD 19*250 mm, A: 0.05% HCl in water; B: CH$_3$CN, 5% to 95%) in HCl condition to afford compound 43 hydrochloride, (R)-2-((2-ethyl-6-(2-(4-(3-hydroxypyrrolidine-1-carbonyl) piperazin-1-yl)pyrimidin-5-yl)imidazo[1,2-a]pyridin-3-yl)(methyl)amino)-4-(4-fluorophenyl)thiazole-5-carbonitrile (290 mg, 34.27% yield) as a white solid. $^1$H NMR (400 MHz, DMSO-d$_6$) δ 9.10 (s, 1H), 8.87 (s, 2H), 8.39-8.36 (dd, 2H), 8.13-8.11 (d, 1H), 8.03-7.99 (t, 2H), 7.42-7.38 (t, 2H), 4.22 (s, 1H), 3.87-3.76 (m, 4H), 3.66 (s, 3H), 3.52-3.45 (m, 2H), 3.31-3.18 (m, 5H), 3.13-3.10 (d, 1H), 2.90-2.85 (dd, J1=7.6 Hz, 2H), 1.84-1.71 (m, 2H), 1.35-1.31 (t, 3H); MS: m/z=653.3 (M+1, ESI+).

5.8.15. Synthesis of Compound 44

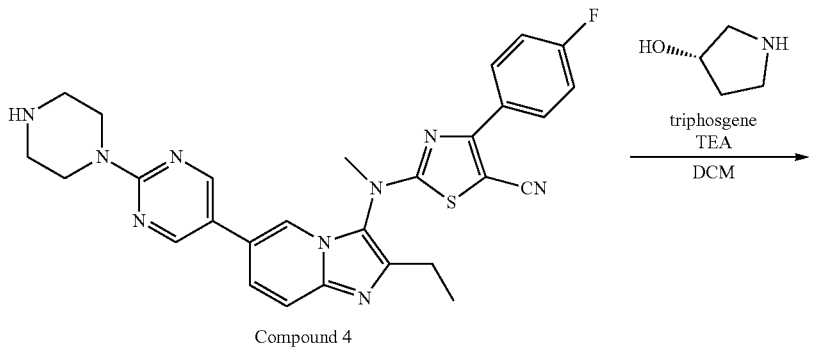

Compound 4

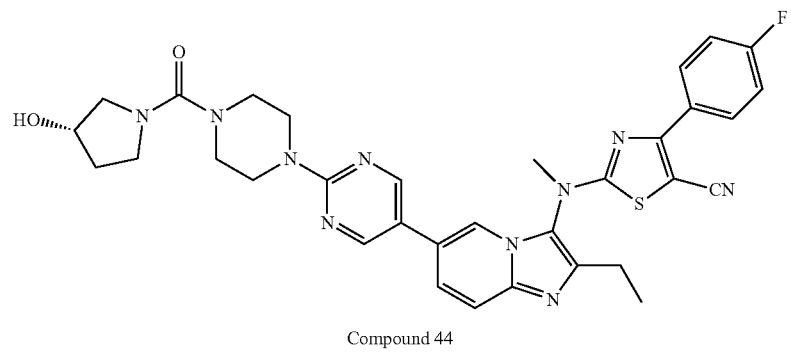

Compound 44

To a mixture of compound 4, 2-((2-ethyl-6-(2-(piperazin-1-yl)pyrimidin-5-yl) imidazo[1,2-a]pyridin-3-yl)(methyl)amino)-4-(4-fluorophenyl)thiazole-5-carbonitrile (200 mg, 370.63 umol) in DCM (10 mL) was added triphosgene (54.99 mg. 185.31 umol) and stirred at 0° C. for 0.5 h, then TEA (112.51 mg, 111 mmol) was added and stirred at 0° C. for another 0.5 h. After that, (3S)-pyrrolidin-3-ol (64 mg, 734.62 umol) was added to the above reaction mixture and stirred at 25° C. for 0.5 h Added water (50 mL) to the reaction mixture, then extracted with DCM (50 mL×2) The organic layer was washed with water (50 mL) and brine (50 mL), dried over Na$_2$SO$_4$ and concentrated. The residue was purified by Prep-HPLC to compound 44, (S)-2-((2-ethyl-6-(2-(4-(3-hydroxypyrrolidine-1-carbonyl)piperazin-1-yl)pyrimidin-5-yl)imidazo[1,2-a]pyridin-3-yl)(methyl)amino)-4-(4-fluorophenvl)thiazole-5-carbonitrile (39 mg, 16.59% yield) as a white solid. $^1$H NMR (400 MHz, DMSO-d$_6$) δ8.80 (s, 2H), 8.67 (s, 1H), 8.10-8.07 (t, 2H), 7.71 (s, 2H). 7.44-7.40 (t, 2H), 4.89-4.88 (d, 1H), 4.22 (s, 1H), 3.84-3.74 (m, 4H), 3.63 (s, 3H), 3.52-3.45 (m, 2H), 3.29-3.18 (m, 5H), 3.12-3.09 (d, 1H). 2.70-2.64 (dd, 2H), 1.80-1.73 (m, 2H), 1.28-1.25 (t, 3H); MS: m/z=653.2 (M+1, ESI+).

5.8.16. Synthesis of Compound 138

2.78 mmol, 60% purity), the reaction mixture was stirred for 30 min at room temperature. Then ethyl 2-bromoacetate (232.11 mg, 1.39 mmol) was added and stirred for 3 h at room temperature. The reaction mixture was quenched with water (200 mL) and extracted with EA (20 mL×3). The combined organic layers were dried over Na$_2$SO$_4$ and concentrated. The residue was purified by column chromatography to afford ethyl 2-(4-(5-(3-((5-cyano-4-(4-fluorophenyl)thiazol-2-yl)(methyl)amino)-2-ethylimidazo[1,2-a]pyridin-6-yl)pyrimidin-2-yl) piperazin-1-yl)acetate (344 mg, 59.33% yield) as a yellow solid. MS: m/z=626.1 (M+1, ESI+).

Step Two:

To a solution of ethyl 2-(4-(5-(3-((5-cyano-4-(4-fluorophenyl)thiazol-2-yl)(methyl)amino)-2-ethyl imidazo[1,2-a]pyridin-6-yl)pyrimidin-2-yl)piperazin-1-yl)acetate (344 mg, 549.77 umol) in THF (5 mL) and H$_2$O (10 mL) was added LiOH (19.75 mg, 824.65 umol). The reaction mixture was stirred for 2 h at room temperature. The reaction mixture was quenched with water (50 mL) and extracted with EA (20 mL×3). The aqueous layer was adjusted to PH 5-6 with 2N

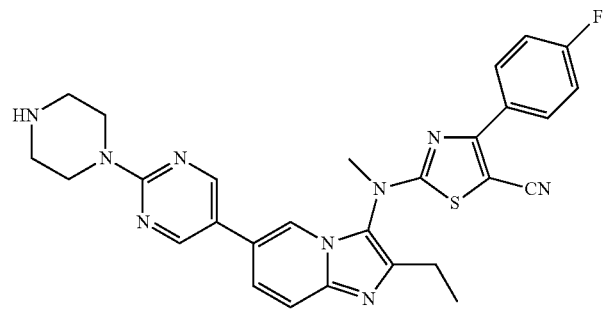

Compound 4

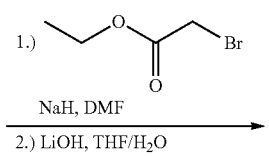

1.) ethyl bromoacetate
NaH, DMF

2.) LiOH, THF/H$_2$O

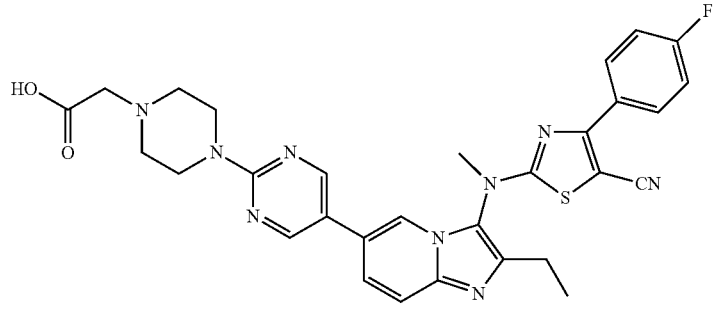

Compound 138

Step One:

To a solution of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (500 mg, 926.56 umol) in DMF (20 mL) was added NaH (111.18 mg, HCl and extracted with DCM (20 mL×3), the combined organic layers were dried over Na$_2$SO$_4$ and concentrated to afford compound 138, 2-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazin-1-yl)acetic acid (300 mg, 91.46% yield). MS: m/z=598.3 (M+1, ESI+).

5.8.17. Synthesis of Compound 45

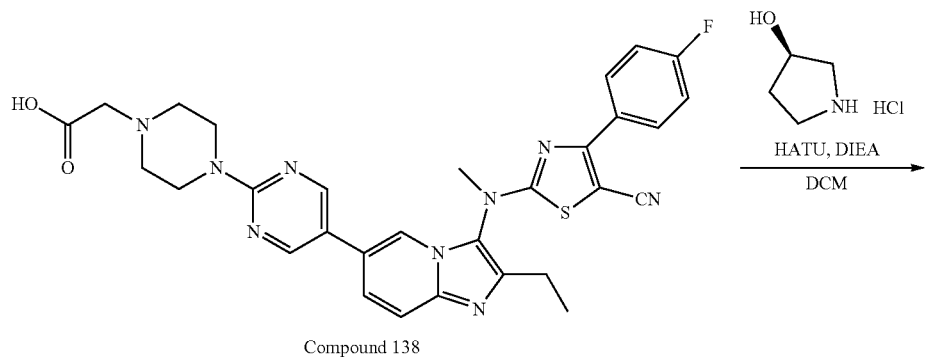

Compound 138

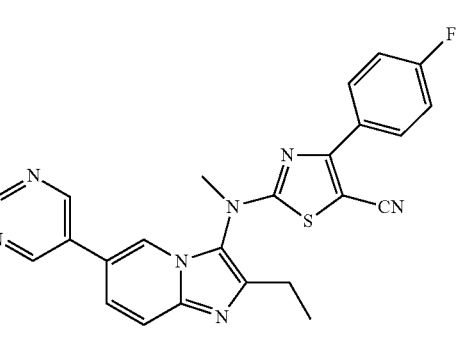

Compound 45

To a solution of compound 138 2-(4-(5-(3-((5-cyano-4-(4-fluorophenyl)thiazol-2-yl)(methyl)amino)-2-ethylimidazo [1,2-a]pyridin-6-yl)pyrimidin-2-yl)piperazin-1-yl)acetic acid (150 mg, 250.98 umol) and (R)-pyrrolidin-3-ol hydrochloride (31.02 mg, 250.98 umol) in DCM (5 mL) was added HATU (286.29 mg, 752.93 umol) and DIEA (162.18 mg, 1.25 mmol), the reaction mixture was stirred at 25° C. for 16 h. The reaction mixture was quenched with water (20 mL) and extracted with DCM (10 mL×3). The combined organic layers were washed with water (20 mL) and brine (20 mL), dried over $Na_2SO_4$ and concentrated. The residue was purified by Prep-HPLC (Waters Xbridge C18 10 um OBD 19*250 mm, A: 10 mmol $NH_4HCO_3$ in water; B: $CH_3CN$, 5% to 95%) in $NH_4HCO_3$ condition to afford compound 45, (R)-2-((2-ethyl-6-(2-(4-(2-(3-hydroxypyrrolidin-1-yl)-2-oxoethyl)piperazin-1-yl)pyrimidin-5-yl)imidazo[1,2-a]pyridin-3-yl)(methyl)amino)-4-(4-fluorophenyl)thiazole-5-carbonitrile (95 mg, 58.53% yield). $^1$H NMR (400 MHz, DMSO-$d_6$) δ 8.77 (s, 2H), 8.65 (s, 1H), 8.10-8.07 (t, 2H), 7.70 (s, 2H), 7.44-7.40 (t, 2H), 4.97-4.88 (dd, 1H), 4.30-4.29 (d, 1H), 3.78 (s, 4H), 3.63 (s, 3H), 3.58-3.52 (m, 2H), 3.28-3.23 (m, 1H), 3.16-3.09 (m, 2H), 2.70-2.64 (dd, 2H), 2.50-2.49 (m, 3H), 1.95-1.68 (m, 2H), 1.28-1.25 (t, 3H); MS: m/z=667.2 (M+1, ESI+).

5.8.18. Synthesis of Compound 45 Hydrochloride

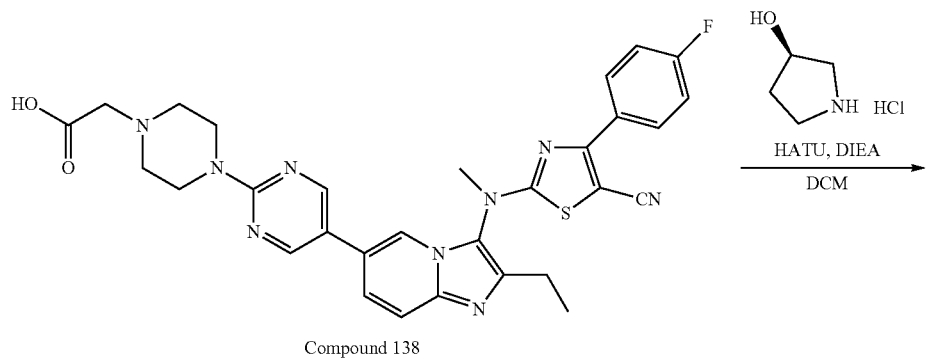

Compound 138

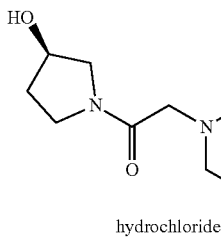 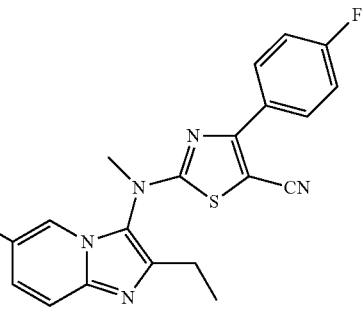

Compound 45 hydrochloride

To a solution of compound 138, 2-(4-(5-(3-((5-cyano-4-(4-fluorophenyl)thiazol-2-yl)(methyl)amino)-2-ethylimidazo [1,2-a]pyridin-6-yl)pyrimidin-2-yl)piperazin-1-yl)acetic acid (1.2 g, 2 mmol) and (R)-pyrrolidin-3-ol hydrochloride (248 mg, 2 mmol) in DCM (20 mL) was added HATU (2.29 g, 6.02 mmol) and DIEA (1.3 g, 10 mmol), the reaction mixture was stirred at 25° C. for 16 h. The reaction mixture was quenched with water (80 mL) and extracted with DCM (10 mL×3). The combined organic layers were washed with water (20 mL) and brine (20 mL), dried over $Na_2SO_4$ and concentrated. The residue was purified by Prep-HPLC (Waters Xbridge C18 10 um OBD 19*250 mm, A: 0.05% HCl in water; B: $CH_3CN$, 5% to 95%) in HCl condition to afford compound 45 hydrochloride, (R)-2-((2-ethyl-6-(2-(4-(2-(3-hydroxypyrrolidin-1-yl)-2-oxoethyl)piperazin-1-yl)pyrimidin-5-yl)imidazo[1,2-a] pyridin-3-yl)(methyl) amino)-4-(4-fluorophenyl)thiazole-5-carbonitrile (270 mg, 17.3% yield). $^1$H NMR (400 MHz, DMSO-$d_6$) δ 10.69 (s, 1H), 9.15 (s, 1H), 8.95 (s, 2H), 8.43-8.41 (d, 1H), 8.14-8.12 (d, 1H), 7.99 (s, 2H), 7.41-7.36 (t, 2H), 4.71-4.68 (m, 2H), 4.38-4.25 (m, 3H), 3.67-3.38 (m, 9H), 3.35-3.25 (m, 5H), 2.90-2.85 (dd, 2H), 1.95-1.81 (m, 2H), 1.36-1.32 (t, 3H); MS: m/z=667.2 (M+1, ESI+).

5.8.19. Synthesis of Compound 46

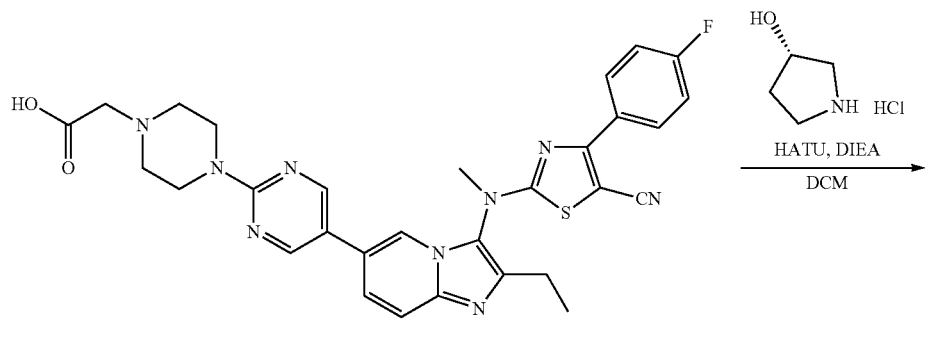

Compound 138

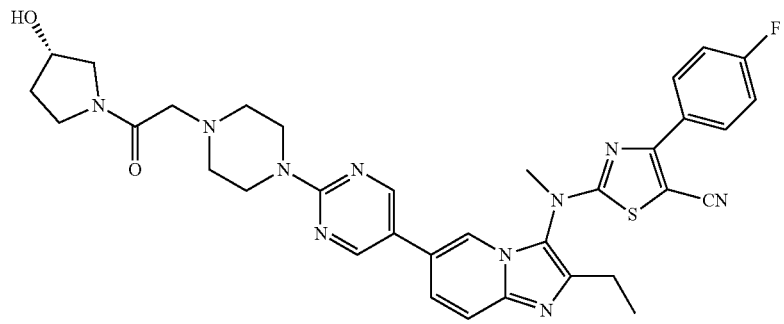

Compound 46

To a solution of compound 138, 2-(4-(5-(3-((5-cyano-4-(4-fluorophenyl)thiazol-2-yl)(methyl)amino)-2-ethylimidazo [1,2-a]pyridin-6-yl)pyrimidin-2-yl)piperazin-1-yl)acetic acid (150 mg, 250.98 umol) and (S)-pyrrolidin-3-ol hydrochloride (46.52 mg, 376.47 umol) in DCM (5 mL) was added HATU (286.29 mg, 752.93 umol) and DIEA (162.18 mg, 1.25 mmol), the reaction mixture was stirred at 25° C. for 16 h. The reaction mixture was quenched with water (20 mL) and extracted with DCM (10 mL×3). The combined organic layers were washed with water (20 mL) and brine (20 mL), dried over Na$_2$SO$_4$ and concentrated. The residue was purified by Prep-HPLC (Waters Xbridge C18 10 um OBD 19*250 mm, A: 10 mmol NH$_4$HCO$_3$ in water; B: CH$_3$CN, 5% to 95%) in NH$_4$HCO$_3$ condition to afford compound 46, (S)-2-((2-ethyl-6-(2-(4-(2-(3-hydroxypyrrolidin-1-yl)-2-oxoethyl)piperazin-1-yl)pyrimidin-5-yl)imidazo [1,2-a]pyridin-3-yl)(methyl)amino)-4-(4-fluorophenyl)thiazole-5-carbonitrile (105 mg, 62.87% yield). 1H NMR (400 MHz, DMSO-d$_6$) δ 8.76 (s, 2H), 8.65 (s, 1H), 8.10-8.07 (t, 2H), 7.70 (s, 2H), 7.44-7.40 (t, 2H), 4.99-4.90 (dd, 1H), 4.30-4.29 (d, 1H), 3.78 (s, 4H), 3.63 (s, 3H), 3.60-3.52 (m, 2H), 3.40-3.36 (m, 2H), 3.29-3.23 (m, 1H), 3.16-3.11 (m, 2H), 2.70-2.64 (dd, 2H), 2.55-2.51 (m, 3H), 1.91-1.71 (m, 2H), 1.28-1.25 (t, 3H); MS: m/z=667.2 (M+1, ESI+).

5.8.20. Synthesis of Compound 46 Hydrochloride

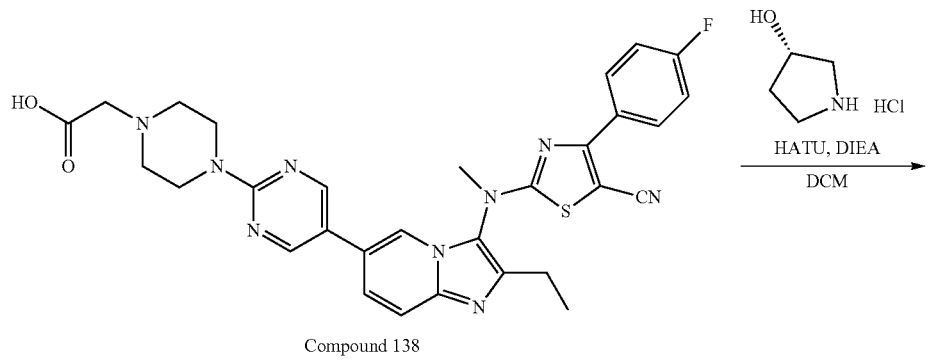

Compound 138

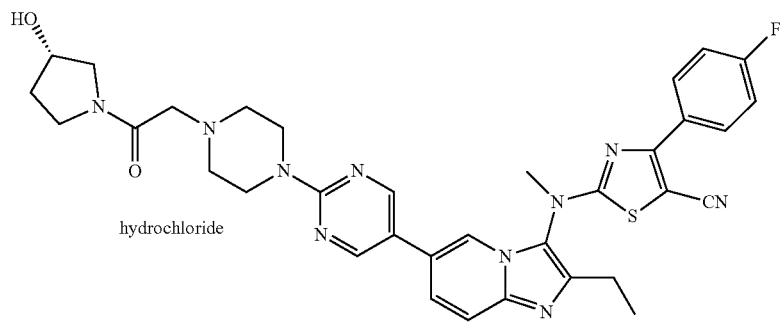

Compound 46 hydrochloride

To a solution of compound 138, 2-(4-(5-(3-((5-cyano-4-(4-fluorophenyl)thiazol-2-yl)(methyl)amino)-2-ethylimidazo [1,2-a]pyridin-6-yl)pyrimidin-2-yl)piperazin-1-yl)acetic acid (1.2 g, 2 mmol) and (S)-pyrrolidin-3-ol hydrochloride (248 mg, 2 mmol) in DCM (20 mL) was added HATU (2.29 g, 6.02 mmol) and DIEA (1.3 g, 10 mmol), the reaction mixture was stirred at 25° C. for 16 h. The reaction mixture was quenched with water (20 mL) and extracted with DCM (10 mL×3). The combined organic layers were washed with water (20 mL) and brine (20 mL), dried over Na$_2$SO$_4$ and concentrated. The residue was purified by Prep-HPLC (Waters Xbridge C18 10 um OBD 19*250 mm, A: 0.05% HCl in water; B: CH$_3$CN, 5% to 95%) in HCl condition to afford compound 46 hydrochloride, (S)-2-((2-ethyl-6-(2-(4-(2-(3-hydroxypyrrolidin-1-yl)-2-oxoethyl)piperazin-1-yl)pyrimidin-5-yl)imidazo[1,2-a]pyridin-3-yl)(methyl) amino)-4-(4-fluorophenyl)thiazole-5-carbonitrile (201 mg, 12.9% yield). $^1$H NMR (400 MHz, DMSO-d$_6$) δ 10.75 (s, 1H), 9.18 (s, 1H), 8.97 (s, 2H), 8.46-8.43 (d, J H), 8.16-8.14 (d, 1H), 8.01 (s, 2H), 7.42-7.38 (t, 2H), 4.73-4.70 (m, 2H), 4.41-4.30 (m, 3H), 3.69-3.39 (m, 9H), 3.37-3.27 (m, 5H), 2.92-2.87 (dd, 2H), 1.94-1.81 (m, 2H), 1.38-1.34 (t, 3H); MS: m/z=667.1 (M+1, ESI+).

5.8.21. Synthesis of Compound 66 Hydrochloride another 0.5 h. After that, tert-butyl 3-aminoazetidine-1-carboxylate (175.53 mg, 1.02 mmol) was added to the above reaction mixture and stirred at 25° C. for 1 h. Added water (50 mL) to the reaction mixture, then extracted with DCM (50 mL×2). The organic layer was washed with water (50 mL) and brine (50 mL), dried over Na$_2$SO$_4$ and concentrated. The residue was purified by column chromatography to afford tert-butyl 3-(4-(5-(3-((5-cyano-4-(4-fluorophenyl)thiazol-2-yl)(methyl)amino)-2-ethylimidazo[1,2-a]pyridin-6-yl)pyrimidin-2-yl) piperazine-1-carboxamido)azetidine-1-carboxylate (600 mg, 79.78% yield) as a yellow solid. MS: m/z=738.2 (M+1, ESI+).

Step Two:

To a solution of tert-butyl 3-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carboxamido)azetidine-1-carboxylate (600 mg, 813.18 umol) in DCM (8 mL) was added TFA (2 g, 17.54 mmol) and stirred at 25° C. for 1 h. The resulting mixture was evaporated under reduce pressure, then the residue was purified by Prep-HPLC (Waters Xbridge C18 10 um OBD 19*250 mm, A: 0.05% HCl in water; B: CH$_3$CN, 5% to 95%) in HCl condition to afford compound 66 hydrochloride, N-(azetidin-3-yl)-4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-

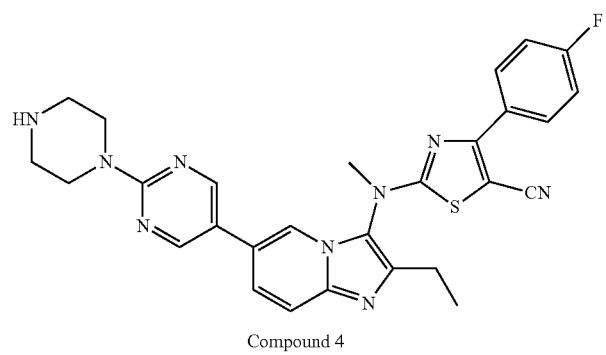

Compound 4

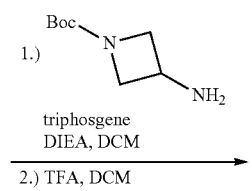

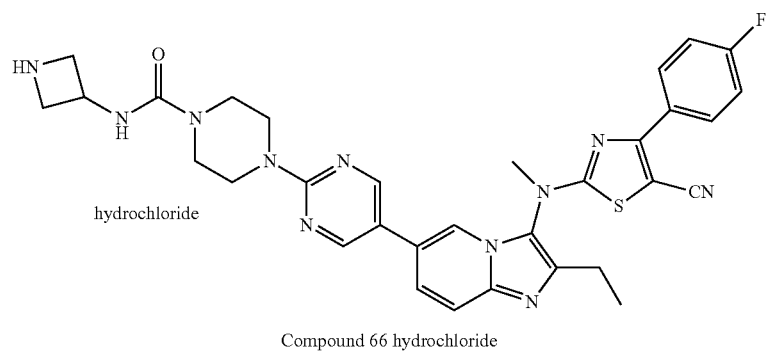

Compound 66 hydrochloride

Step One:

To a mixture of compound 4, 2-((2-ethyl-6-(2-(piperazin-1-yl)pyrimidin-5-yl)imidazo[1,2-a]pyridin-3-yl)(methyl) amino)-4-(4-fluorophenyl) thiazole-5-carbonitrile (550 mg, 1.02 mmol) in DCM (6 mL) was added triphosgene (120.98 mg, 407.69 umol) at 0° C. and stirred for 0.5 h. then DIEA (395.18 mg, 3.06 mmol) was added and stirred at 0° C. for 1-carboxamide hydrochloride (220 mg, 42.42% yield) as a pale yellow solid. $^1$H NMR (400 MHz, DMSO-d$_6$) δ 9.35 (s, 1H), 9.24 (s, 1H), 9.11 (s, 1H), 8.89 (s, 2H), 8.41-8.39 (d, 1H), 8.14-8.12 (d, 1H), 8.01 (s, 2H), 7.64 (s, 1H), 7.42-7.38 (t, 2H), 4.59-4.55 (t, 1H), 4.03-3.98 (m, 4H), 3.80 (s, 4H), 3.67 (s, 3H), 3.46 (s, 4H), 2.91-2.85 (dd, 2H), 1.36-1.32 (t, 3H); MS: m/z=638.2 (M+1, ESI+).

5.8.22. Synthesis of Compound 66 Formate

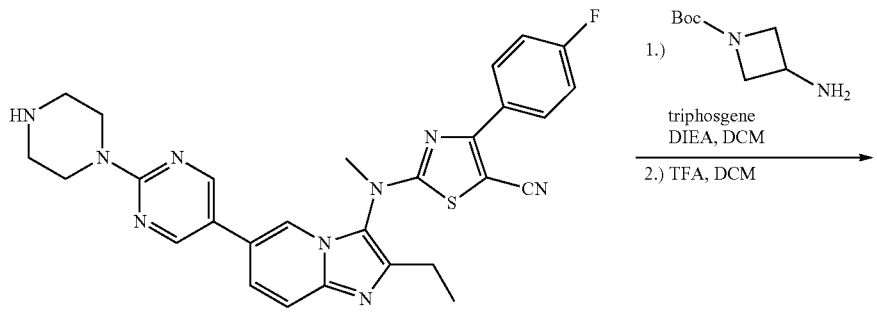

Compound 4

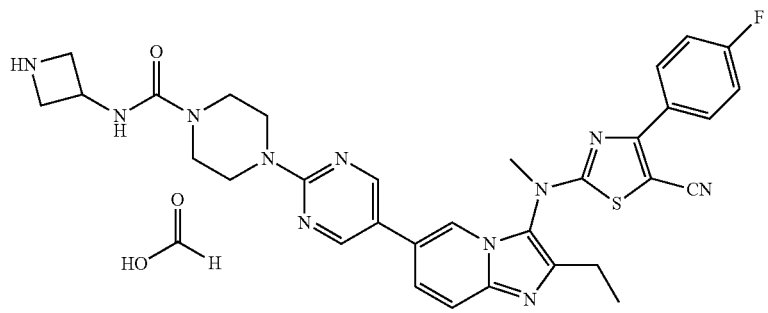

Compound 66 formate

Step One:

To a mixture of compound 4, 2-((2-ethyl-6-(2-(piperazin-1-yl)pyrimidin-5-yl)imidazo[1,2-a]pyridin-3-yl)(methyl)amino)-4-(4-fluorophenyl) thiazole-5-carbonitrile (230 mg, 0.427 mmol) in DCM (6 mL) was added triphosgene (38 mg, 0.128 mmol) at 0° C. and stirred for 0.5 h. then DIEA (165 mg, 1.28 mmol) was added and stirred at 0° C. for another 0.5 h. After that, tert-butyl 3-aminoazetidine-1-carboxylate (73 mg, 0.427 mmol) was added to the above reaction mixture and stirred at 25° C. for 1 h. Added water (50 mL) to the reaction mixture, then extracted with DCM (50 mL×2). The organic layer was washed with water (50 mL) and brine (50 mL), dried over Na$_2$SO$_4$ and concentrated. The residue was purified by column chromatography to afford tert-butyl 3-(4-(5-(3-(((5-cyano-4-(4-fluorophenyl)thiazol-2-yl)(methyl)amino)-2-ethylimidazo[1,2-a]pyridin-6-yl)pyrimidin-2-yl) piperazine-1-carboxamido)azetidine-1-carboxylate (200 mg, 63.7% yield) as a yellow solid. MS: m/z=738.2 (M+1, ESI+).

Step Two:

To a solution of tert-butyl 3-(4-(5-(3-(((5-cyano-4-(4-fluorophenyl)thiazol-2-yl)(methyl)amino)-2-ethylimidazo[1,2-a]pyridin-6-yl)pyrimidin-2-yl)piperazine-1-carboxamido)azetidine-1-carboxylate (200 mg, 271 umol) in DCM (8 mL) was added TFA (666 mg, 90 umol) and stirred at 25° C. for 1 h. The resulting mixture was evaporated under reduce pressure, then the residue was purified by Prep-HPLC (Waters Xbridge C18 10 um OBD 19*250 mm, A: 0.1% FA in water; B: CH$_3$CN, 5% to 95%) in FA condition to afford compound 66 Formate, N-(azetidin-3-yl)-4-(5-(3-(((5-cyano-4-(4-fluorophenyl)thiazol-2-yl)(methyl)amino)-2-ethylimidazo[1,2-a]pyridin-6-yl)pyrimidin-2-yl)piperazine-1-carboxamide formate (150 mg, 81.1% yield) as a pale yellow solid. $^1$H NMR (400 MHz, DMSO-d$_6$) δ 8.80 (s, 2H), 8.66 (s, 1H), 8.42 (s, 1H), 8.11-8.07 (t, 2H), 7.70 (s, 2H), 7.44-7.40 (t, 2H), 4.54-4.48 (m, 1H), 3.93-3.88 (t, 2H), 3.77-3.70 (m, 8H), 3.63 (s, 3H), 3.43-3.40 (m, 4H), 2.70-2.64 (dd, 2H), 1.28-1.25 (t, 3H); MS: m/z=638.2 (M+1, ESI+).

5.8.23. Synthesis of Compound 66

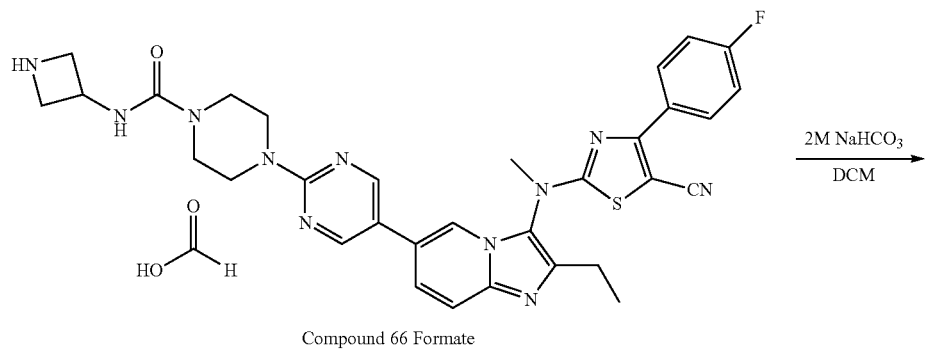

Compound 66 Formate

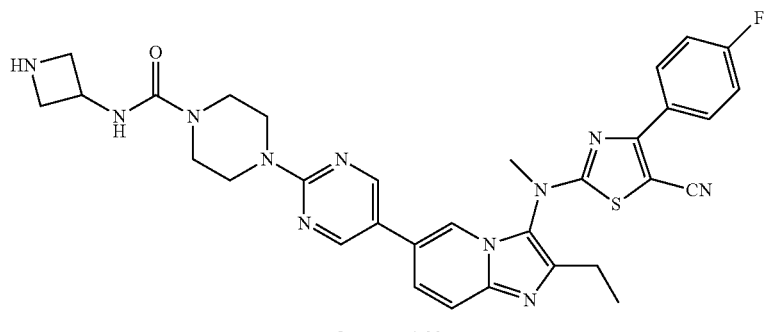

Compound 66

To a mixture of compound 66 formate, N-(azetidin-3-yl)-4-(5-(3-((5-cyano-4-(4-fluorophenyl)thiazol-2-yl)(methyl) amino)-2-ethylimidazo [1,2-a]pyridin-6-yl)pyrimidin-2-yl) piperazine-1-carboxamide formate (120 mg, 0.175 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 66, N-(azetidin-3-yl)-4-(5-(3-((5-cyano-4-(4-fluorophenyl)thiazol-2-yl)(methyl) amino)-2-ethylimidazo [1,2-a]pyridin-6-yl)pyrimidin-2-yl)piperazine-1-carboxamide (75 mg, 66.96% yield) as a yellow solid. $^1$H NMR (400 MHz, DMSO-d$_6$) δ 8.79 (s, 2H), 8.65 (s, 1H), 8.10-8.07 (t, 2H), 7.70 (s, 2H), 7.44-7.39 (t, 2H), 7.08-7.06 (d, J=6.8 Hz, 1H), 3.74-3.51 (m, 13H), 2.70-2.64 (dd, 2H), 1.28-1.25 (t, 3H); MS: m/z=638.3 (M+1, ESI+).

5.8.24. Synthesis of Compound 67 Hydrochloride

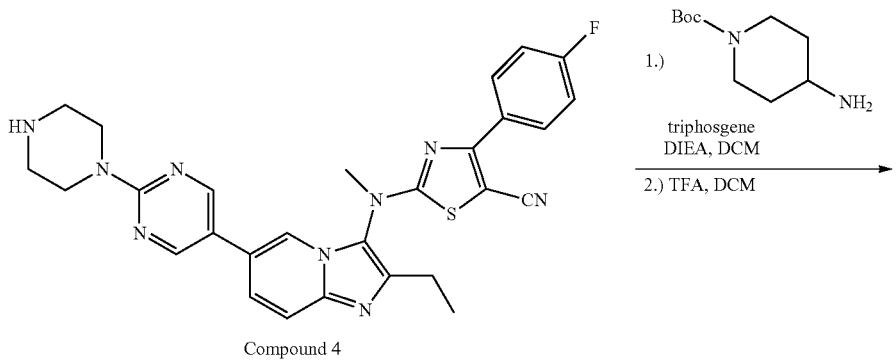

Compound 4

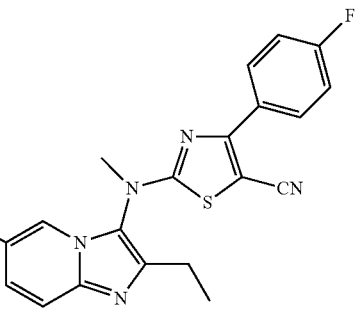

Compound 67 hydrochloride

To a mixture of compound 4, 2-((2-ethyl-6-(2-(piperazin-1-yl)pyrimidin-5-yl)imidazo[1,2-a]pyridin-3-yl)(methyl) amino)-4-(4-fluorophenyl) thiazole-5-carbonitrile (550 mg, 1.02 mmol) in DCM (6 mL) was added triphosgene (120.98 mg, 407.69 umol) at 0° C. and stirred for 0.5 h. then DIEA (395.18 mg, 3.06 mmol) was added and stirred at 0° C. for another 0.5 h. After that, tert-butyl 4-aminopiperidine-1-carboxylate (204.13 mg, 1.02 mmol) was added to the above reaction mixture and stirred at 25° C. for 2 h. Added water (50 mL) to the reaction mixture, then extracted with DCM (50 mL×2). The organic layer was washed with water (50 mL) and brine (50 mL), dried over $Na_2SO_4$ and concentrated. The residue was purified by column chromatography to afford tert-butyl 4-(4-(5-(3-((5-cyano-4-(4-fluorophenyl) thiazol-2-yl)(methyl)amino)-2-ethylimidazo[1,2-a]pyridin-6-yl)pyrimidin-2-yl) piperazine-1-carboxamido)piperidine-1-carboxylate (540 mg, 69.18% yield) as a yellow solid. MS: m/z=766.5 (M+1, ESI+).

Step Two:

To a solution of tert-butyl 4-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carboxamido) piperidine-1-carboxylate (540 mg, 705.05 umol) in DCM (8 mL) was added TFA (2 g, 17.54 mmol) and stirred at 25° C. for 1 h. The resulting mixture was evaporated under reduce pressure, then the residue was purified by Prep-HPLC (Waters Xbridge C18 10 um OBD 19*250 mm, A: 0.05% HCl in water; B: $CH_3CN$, 5% to 95%) in HCl condition to afford compound 67 hydrochloride, 4-(5-(3-((5-cyano-4-(4-fluorophenyl)thiazol-2-yl)(methyl)amino)-2-ethylimidazo[1,2-a] pyridin-6-yl)pyrimidin-2-yl)-N-(piperidin-4-yl) piperazine-1-carboxamide hydrochloride (240 mg, 51.13% yield) as a pale yellow solid. $^1$H NMR (400 MHz, DMSO-$d_6$) δ 9.11 (s, 3H), 8.88 (s, 2H), 8.41-8.39 (d, 1H), 8.14-8.12 (d, 1H), 8.01 (s, 2H), 7.42-7.38 (t, 2H), 6.67 (s, 2H), 3.78-3.67 (m, 8H), 3.43 (s, 4H), 3.25-3.22 (d, 2H), 2.91-2.85 (dd, 2H), 1.89-1.86 (m, 2H), 1.74-1.66 (m, 2H), 1.36-1.33 (t, 3H); MS: m/z=666.4 (M+1, ESI+).

5.8.25. Preparation of Compound 67

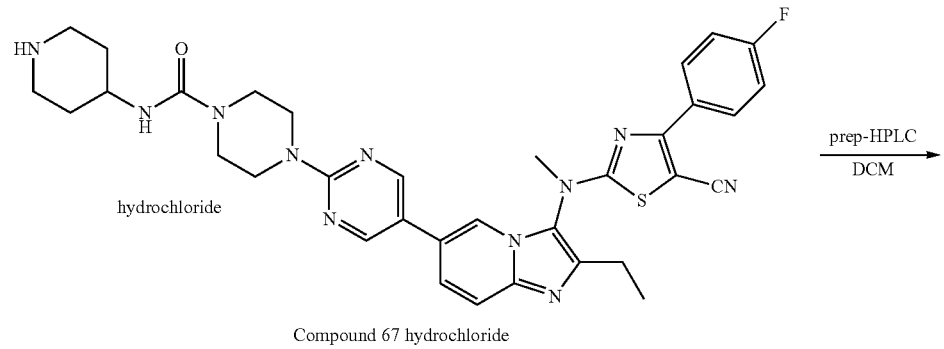

Compound 67 hydrochloride

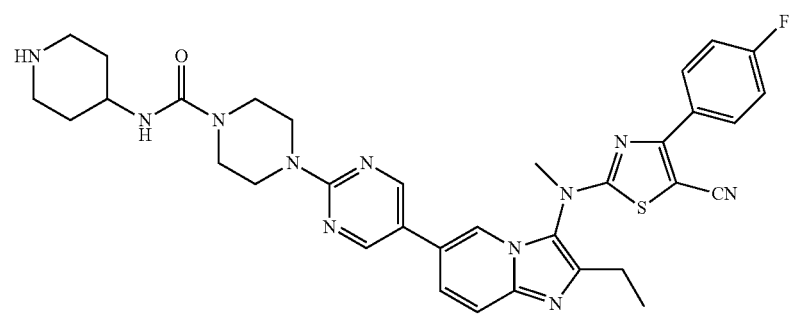

Compound 67

Compound 67 hydrochloride, 4-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl)piperazine-1-carboxamide hydrochloride (180 mg, 0.253 mmol) was purified by Prep-HPLC to afford compound 67, 4-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl)piperazine-1-carboxamide (122 mg, 72.62% yield) as a white solid. $^1$H NMR (400 MHz, DMSO-$d_6$) δ 8.79 (s, 2H), 8.66 (s, 1H), 8.10-8.07 (m, 2H), 7.70 (s, 2H), 7.44-7.40 (t, 2H), 6.30 (d, 2H), 3.75-3.73 (m, 4H), 3.63 (s, 3H), 3.51-3.46 (m, 8H), 2.93-2.90 (d, 2H), 2.70-2.64 (dd, 2H), 2.49-2.42 (m, 2H), 1.68-1.65 (d, 2H), 1.25 (t, 3H); MS: m/z=666.1 (M+1, ESI+).

5.8.26. Synthesis of Compound 67 Formate mL×2). The organic layer was washed with water (50 mL) and brine (50 mL), dried over $Na_2SO_4$ and concentrated. The residue was purified by column chromatography to afford tert-butyl 4-(4-(5-(3-((5-cyano-4-(4-fluorophenyl)thiazol-2-yl)(methyl)amino)-2-ethylimidazo[1,2-a]pyridin-6-yl)pyrimidin-2-yl)piperazine-1-carboxamido)piperidine-1-carboxylate (250 mg, 76.7% yield) as a yellow solid. MS: m/z=766.2 (M+1, ESI+).

Step Two:

To a solution of tert-butyl 4-(4-(5-(3-((5-cyano-4-(4-fluorophenyl)thiazol-2-yl)(methyl)amino)-2-ethylimidazo[1,2-a]pyridin-6-yl) pyrimidin-2-yl)piperazine-1-carboxamido) piperidine-1-carboxylate (250 mg, 326 umol) in DCM (8 mL) was added TFA (95 mg, 978 umol) and stirred at 25° C. for 1 h. The resulting mixture was evaporated under reduce pressure, then the residue was purified by Prep-HPLC (Waters Xbridge C18 10 um OBD 19*250 mm, A: 0.1% FA in

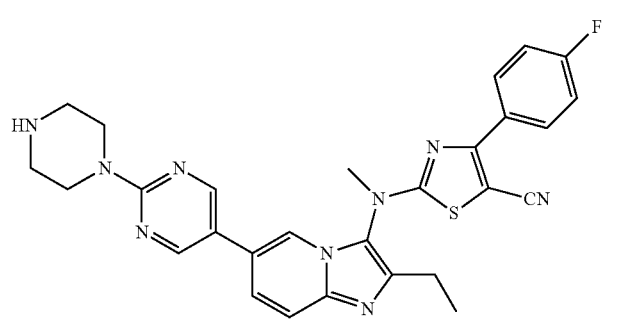

Compound 4

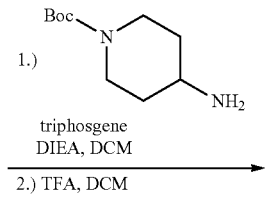

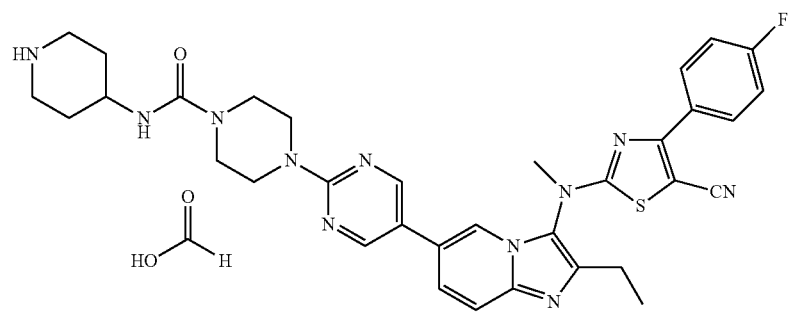

Compound 67 formate

Step One:

To a mixture of compound 4, 2-((2-ethyl-6-(2-(piperazin-1-yl)pyrimidin-5-yl)imidazo[1,2-a]pyridin-3-yl)(methyl)amino)-4-(4-fluorophenyl) thiazole-5-carbonitrile (230 mg, 0.427 mmol) in DCM (6 mL) was added triphosgene (51 mg, 170.5 umol) at 0° C. and stirred for 0.5 h. then DIEA (165 mg, 1.28 mmol) was added and stirred at 0° C. for another 0.5 h. After that, tert-butyl 4-aminopiperidine-1-carboxylate (85 mg, 0.427 mmol) was added to the above reaction mixture and stirred at 25° C. for 1 h. Added water (50 mL) to the reaction mixture, then extracted with DCM (50 water; B: $CH_3CN$, 5% to 95%) in FA condition to afford compound 67 formate, 4-(5-(3-((5-cyano-4-(4-fluorophenyl)thiazol-2-yl) (methyl)amino)-2-ethylimidazo[1,2-a]pyridin-6-yl)pyrimidin-2-yl)-N-(piperidin-4-yl)piperazine-1-carboxamide formate (155 mg, 66.8% yield) as a pale yellow solid. $^1$H NMR (400 MHz, DMSO-$d_6$) δ 8.79 (s, 2H), 8.66 (s, 1H), 8.39 (s, JH), 8.10-8.07 (t, 2H), 7.70 (s, 2H), 7.44-7.40 (t, 2H), 6.50 (s, 1H), 3.74-3.63 (m, 9H), 3.40-3.38 (m, 5H), 3.16 (s, 2H), 2.79-2.64 (m, 4H), 1.83-1.81 (m, 2H), 1.54 (s, 2H), 1.28-1.25 (t, 3H); MS: m/z=666.3 (M+1, ESI+).

5.8.27. Synthesis of Compound 1

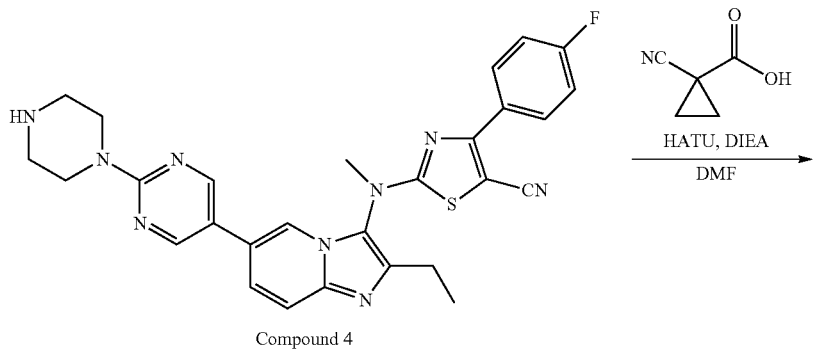

Compound 4

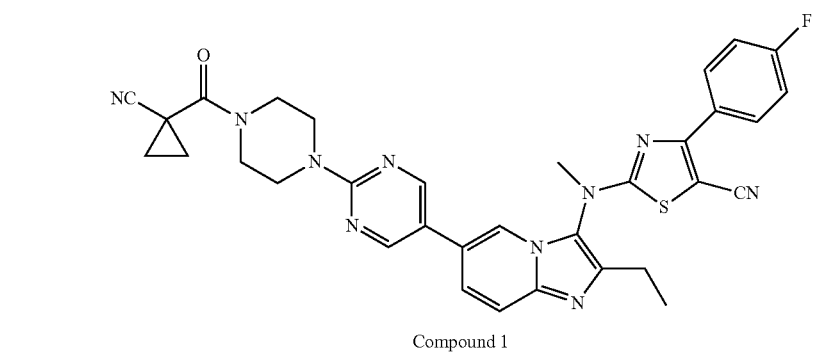

Compound 1

To a solution of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (300 mg, 520.75 umol) and 1-cyanocyclopropane-1-carboxylic acid (57.85 mg, 520.75 umol) in DMF (10 mL) was added HATU (294.70 mg, 781.13 umol) and DIPEA (269.21 mg, 2.08 mmol), the reaction mixture was stirred at 25° C. for 16 h. Added water (50 mL) to the reaction mixture, then extracted with EA (50 mL×2). The organic layer was washed with water (50 mL) and brine (50 mL), dried over $Na_2SO_4$ and concentrated. The residue was purified by Prep-HPLC to afford compound 1, 2-((6-(2-(4-(1-cyanocyclopropane-1-carbonyl)piperazin-1-yl)pyrimidin-5-yl)-2-ethylimidazo[1,2-a]pyridin-3-yl)(methyl)amino)-4-(4-fluorophenyl) thiazole-5-carbonitrile (65 mg, 18.51% yield) as a white solid. $^1$H NMR (400 MHz, DMSO-$d_6$) δ 8.84 (s, 2H), 8.69 (s, 1H), 8.11-8.07 (t, 2H), 7.72-7.71 (dd, 2H), 7.44-7.40 (t, 2H), 3.87-3.63 (m, 10H), 2.95-2.90 (d, 1H), 2.70-2.64 (dd, 2H), 1.64-1.60 (m, 2H), 1.54-1.51 (m, 2H), 1.29-1.25 (t, 3H); MS: m/z=633.5 (M+1, ESI+).

5.8.28. Synthesis of Compound 2

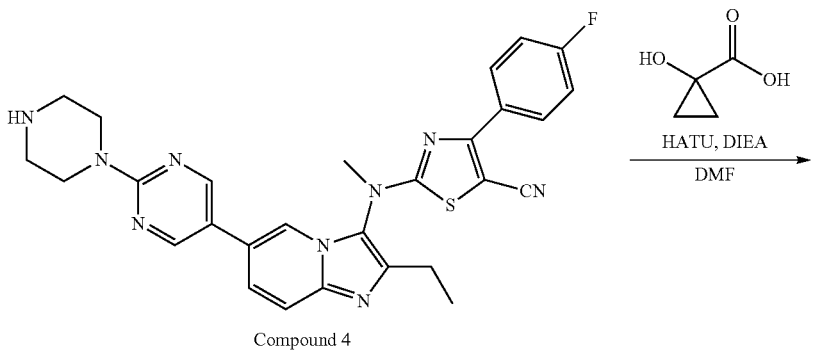

Compound 4

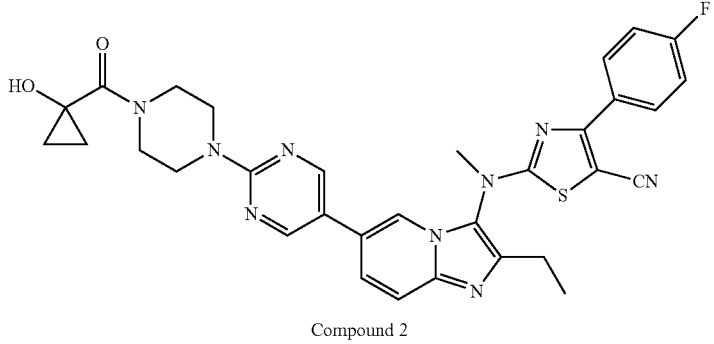

Compound 2

To a solution of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (200 mg, 370.62 umol) and 1-hydroxycyclo propane-1-carboxylic acid (45.40 mg, 444.74 umol) in DMF (10 mL) was added HATU (211.39 mg, 555.93 umol) and DIEA (143.70 mg, 1.11 mmol), the reaction mixture was stirred at 25° C. for 2. The reaction mixture was poured into water (100 mL), extracted with EA (20 mL×3), washed by brine (100 mL) and dried over $Na_2SO_4$. The combined organic layers were concentrated under reduced pressure, the residue was purified by Prep-HPLC to afford compound 2, 2-((2-ethyl-6-(2-(4-(1-hydroxycyclopropane-1-carbonyl)piperazin-1-yl)pyrimidin-5-yl)imidazo[1,2-a]pyridin-3-yl)(methyl)amino)-4-(4-fluorophenyl)thiazole-5-carbonitrile (90 mg, 38.93% yield) as a white solid. $^1$H NMR (400 MHz, DMSO-$d_6$) δ 8.81 (s, 2H), 8.68 (s, 1H), 8.11-8.10 (t, 2H), 7.71 (s, 2H), 7.44-7.40 (t, 2H), 6.40 (s, 1H), 3.81-3.64 (m, 11H), 2.71-2.64 (dd, 2H), 1.29-1.25 (t, 31H), 0.97-0.94 (m, 2H), 0.81-0.78 (m, 2H); MS: m/z=624.2 (M+1, ESI+).

5.8.29. Synthesis of Compound 78 Hydrochloride

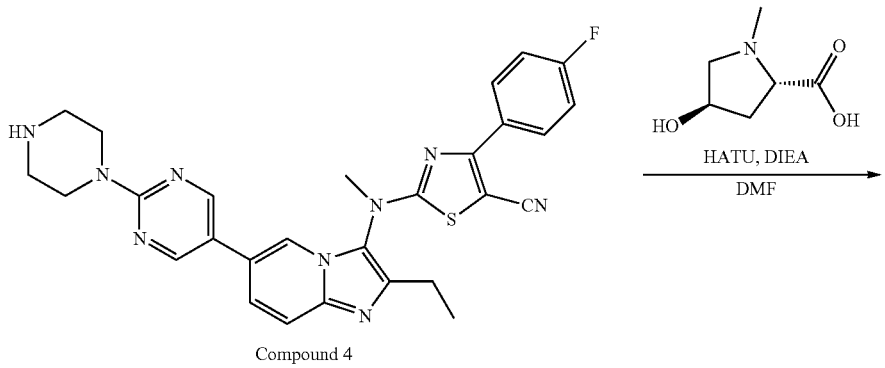

Compound 4

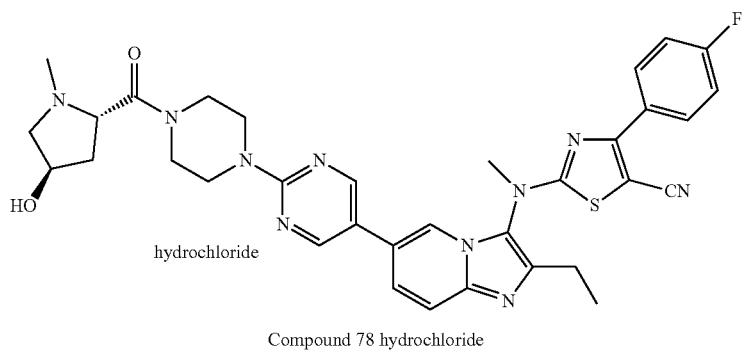

Compound 78 hydrochloride

To a solution of compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (300 mg, 520.75 umol) and (2S,4R)-4-hydroxy-1-methylpyrrolidine-2-carboxylic acid (104.91 mg, 722.72 umol) in DMF (10 mL) was added HATU (314.61 mg, 833.91 umol) and DIPEA (215.55 mg, 1.67 mmol), the reaction mixture was stirred at 25° C. for 16 h. Added water (50 mL) to the reaction mixture, then extracted with EA (50 mL×2). The organic layer was washed with water (50 mL) and brine (50 mL), dried over $Na_2SO_4$ and concentrated. The residue was purified by Prep-HPLC to afford compound 78 hydrochloride, 2-((2-ethyl-6-(2-(4-((2S,4R)-4-hydroxy-1-methylpyrrolidine-2-carbonyl)piperazin-1-yl)pyrimidin-5-yl)imidazo[1,2-a] pyridin-3-yl)(methyl)amino)-4-(4-fluorophenyl)thiazole-5-carbonitrile hydrochloride (100 mg, 25.57% yield) as a pale yellow solid. $^1$H NMR (400 MHz, DMSO-$d_6$) δ 9.75 (s, 1H), 9.12 (s, 1H), 8.92 (s, 2H), 8.42-8.39 (d, 1H), 8.15-8.12 (d, 1H), 8.01 (s, 2H), 7.42-7.38 (t, 2H), 5.04-4.98 (m, 1H), 4.40 (s, 1H), 3.88-3.77 (m, 5H), 3.67-3.56 (m, 7H), 3.08-3.05 (m, 1H), 2.90-2.85 (m, 5H), 2.50-2.45 (m, 1H), 2.09-2.02 (m, 1H), 1.36-1.33 (t, 3H); MS: m/z=667.1 (M+1, ESI+).

5.8.30. Synthesis of Compound 78

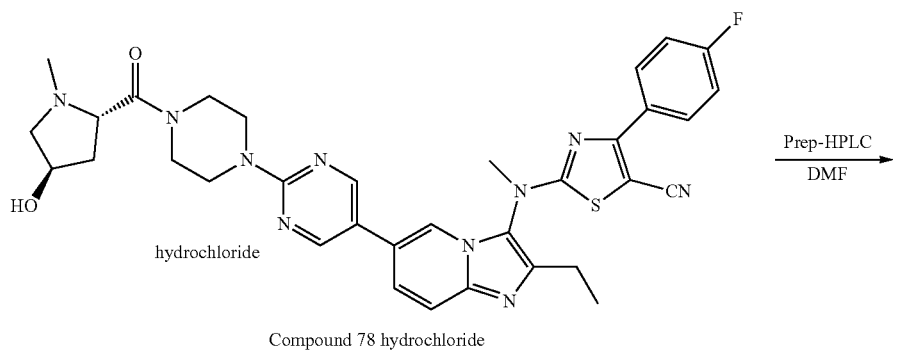

Compound 78 hydrochloride

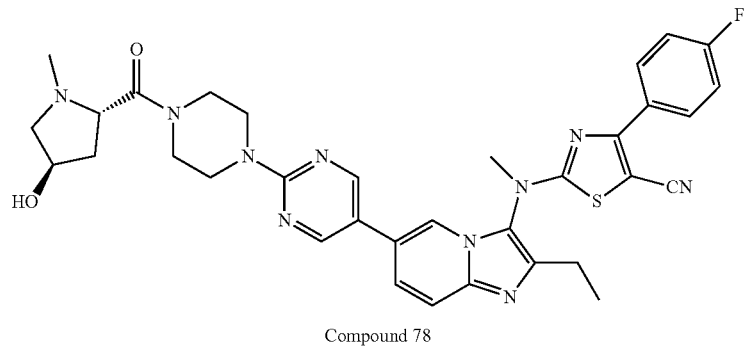

Compound 78

Compound 78 hydrochloride, 2-((2-ethyl-6-(2-(4-((2S, 4R)-4-hydroxy-1-methylpyrrolidine-2-carbonyl)piperazin-1-yl)pyrimidin-5-yl)imidazo[1,2-a]pyridin-3-yl)(methyl) amino)-4-(4-fluorophenyl)thiazole-5-carbonitrile hydrochloride (60 mg, 0.077 mmol) was purified by Prep-HPLC to afford compound 78, 2-((2-ethyl-6-(2-(4-((2S,4R)-4-hydroxy-1-methylpyrrolidine-2-carbonyl)piperazin-1-yl)pyrimidin-5-yl)imidazo [1,2-a]pyridin-3-yl)(methyl) amino)-4-(4-fluorophenyl)thiazole-5-carbonitrile (25 mg, 49.02% yield) as a white solid. $^1$H NMR (400 MHz, DMSO-$d_6$) δ 8.81 (s, 2H), 8.67 (s, 1H), 8.10-8.07 (m, 2H), 7.71 (s, 2H), 7.44-7.40 (t, 2H), 4.89-4.88 (m, 1H), 4.22 (s, 1H), 3.85-3.82 (m, 2H), 3.70-3.60 (m, 8H), 3.48-3.42 (m, 2H), 3.25-3.21 (m, 1H), 2.70-2.64 (dd, 2H), 2.22 (s, 3H), 2.15-2.11 (m, 1H), 2.00-1.95 (m, 1H), 1.89-1.84 (m, 1H), 1.26-1.23 (t, 3H); MS: m/z=667.1 (M+1, ESI+).

5.8.31. Synthesis of Compound 79 Hydrochloride

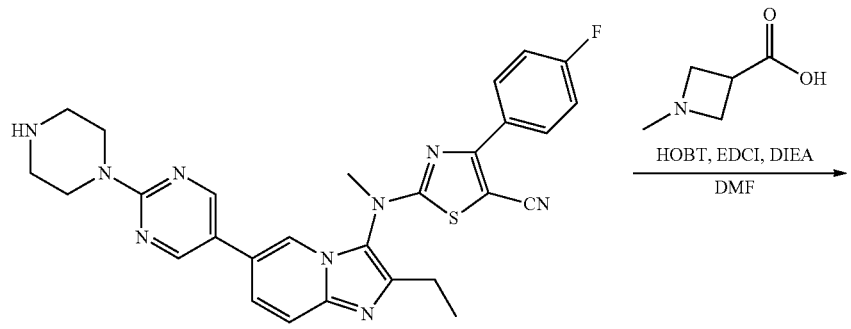

Compound 4

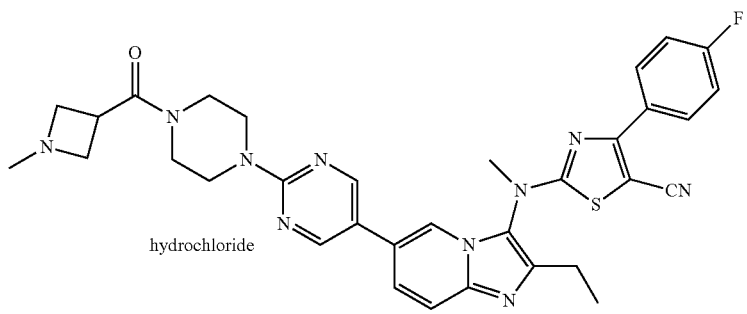

Compound 79 hydrochloride

To a solution of compound 4, 2-(2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (300 mg, 520.75 umol) and 1-methylazetidine-3-carboxylic acid (83.21 mg, 722.72 umol) in DMF (10 mL) was added HOBT (112.68 mg, 833.91 umol), EDCI (159.86 mg, 833.91 umol) and DIPEA (215.55 mg, 1.67 mmol), the reaction mixture was stirred at 25° C. for 16 h. Added water (50 mL) to the reaction mixture, then extracted with EA (50 mL×2). The organic layer was washed with water (50 mL) and brine (50 mL), dried over $Na_2SO_4$ and concentrated. The residue was purified by Prep-HPLC to afford compound 79 hydrochloride, 2-((2-ethyl-6-(2-(4-(1-methylazetidine-3-carbonyl)piperazin-1-yl)pyrimidin-5-yl)imidazo[1,2-a]pyridin-3-yl)(methyl)amino)-4-(4-fluorophenyl)thiazole-5-carbonitrile hydrochloride (210 mg, 56.14% yield) as a pale yellow solid. $^1$H NMR (400 MHz, D20+DMSO-$d_6$) S 9.03 (s, 1H), 8.86 (s, 2H), 8.40-8.37 (d, 1H), 8.14-8.12 (d, 1H), 7.97 (s, 2H), 7.39-7.35 (t, 2H), 4.48-4.41 (m, 2H), 4.07-3.95 (m, 3H), 3.85 (s, 4H), 3.68 (s, 3H), 3.62 (s, 2H), 3.41 (s, 2H), 2.91-2.83 (m, 5H), 1.36-1.32 (t, 3H); MS: m/z=637.3 (M+1, ESI+).

5.8.32. Synthesis of Compound 79

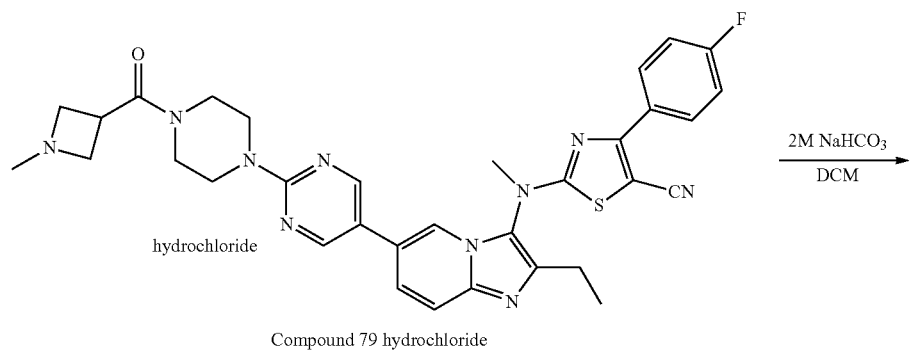

Compound 79 hydrochloride

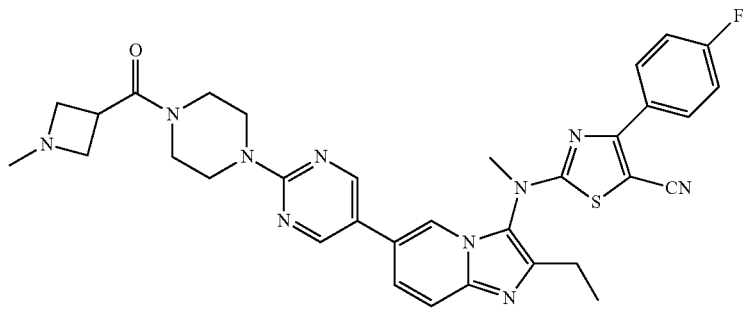

Compound 79

To a mixture of compound 79 hydrochloride, 2-((2-ethyl-6-(2-(4-(1-methylazetidine-3-carbonyl)piperazin-1-yl)pyrimidin-5-yl)imidazo[1,2-a]pyridin-3-yl)(methyl)amino)-4-(4-fluorophenyl)thiazole-5-carbonitrile hydrochloride (130 mg, 0.193 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 79, 2-((2-ethyl-6-(2-(4-(1-methylazetidine-3-carbonyl)piperazin-1-yl)pyrimidin-5-yl)imidazo[1,2-a]pyridin-3-yl)(methyl)amino)-4-(4-fluorophenyl)thiazole-5-carbonitrile (70 mg, 57% yield) as a white solid. $^1$H NMR (400 MHz, DMSO-d$_6$) δ 8.73 (s, 2H), 8.64 (s, 1H), 8.10-8.07 (t, 2H), 7.69 (s, 1H), 7.44-7.40 (t, 2H), 4.18-4.14 (t, 2H), 3.72-3.33 (m, 9H), 2.77-2.64 (m, 4H), 2.26 (s, 3H), 1.28-1.24 (t, 3H); MS: m/z=637.0 (M+1, ESI+).

5.8.33. Synthesis of Compound 82 Hydrochloride

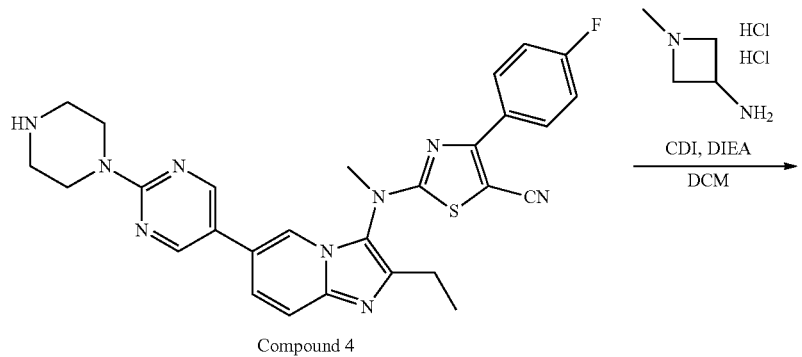

Compound 4

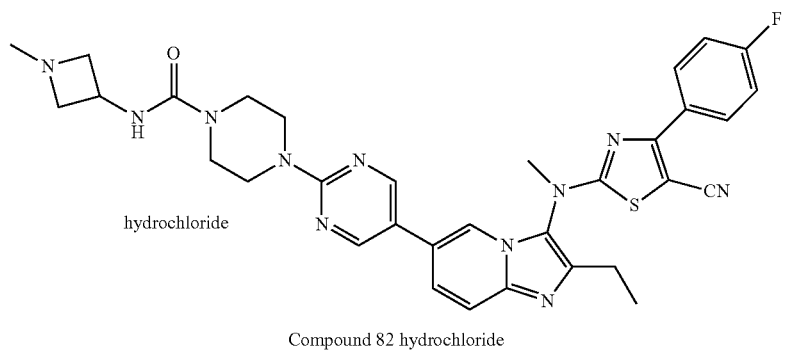

Compound 82 hydrochloride

To a solution of 1-methylazetidin-3-amine 2HCl (176.85 mg, 1.11 mmol) in DMF (10 mL) was added CDI (90.14 mg, 555.94 umol) and DIEA (112.51 mg, 1.11 mmol) and stirred at 25° C. for 3 h. Then compound 4, 2-((2-ethyl-6-(2-(piperazin-1-yl)pyrimidin-5-yl)imidazo[1,2-a]pyridin-3-yl)(methyl)amino)-4-(4-fluorophenyl)thiazole-5-carbonitrile (300 mg, 555.94 umol) was added to the above reaction solution and the reaction mixture was stirred t 25° C. for 16 h. Added water (100 mL) to the reaction mixture, then extracted with EA (30 mL×3). The organic layer was washed with water (100 mL) and brine (100 mL), dried over Na$_2$SO$_4$ and concentrated. The residue was purified by Prep-HPLC to afford compound 82 hydrochloride, 4-(5-(3-((5-cyano-4-(4-fluorophenyl)thiazol-2-yl)(methyl)amino)-2-ethyl imidazo[1,2-a] pyridin-6-yl)pyrimidin-2-yl)-N-(1-methylazetidin-3-yl)piperazine-1-carboxamide hydrochloride (220 mg, 57.50% yield) as a pale yellow solid. $^1$H NMR (400 MHz, D20+DMSO-d$_6$) δ 9.04 (s, 1H), 8.86 (s, 2H), 8.40-8.38 (dd, 1H), 8.15-8.12 (d, 1H), 7.99-7.96 (t, 2H), 7.40-7.35 (t, 2H), 4.61-4.48 (m, 1H), 4.42-4.28 (m, 2H), 4.11-4.04 (m, 2H), 3.82 (s, 4H), 3.68 (s, 3H), 3.47 (s, 4H), 2.93-2.87 (m, 5H), 1.36-1.32 (t, 3H); MS: m/z=652.2 (M+1, ESI+).

5.8.34. Synthesis of Compound 82

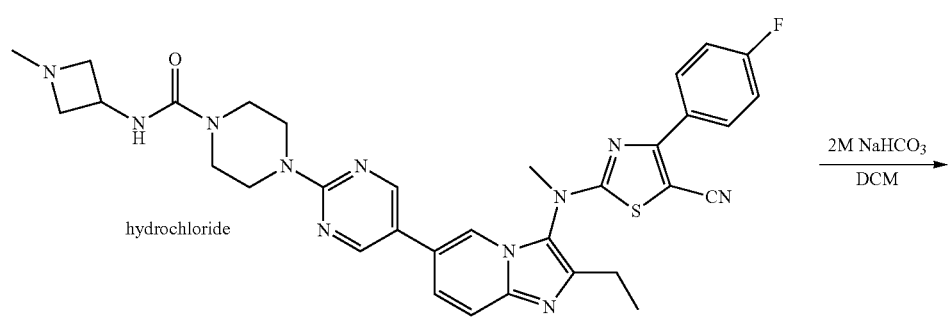

Compound 82 hydrochloride

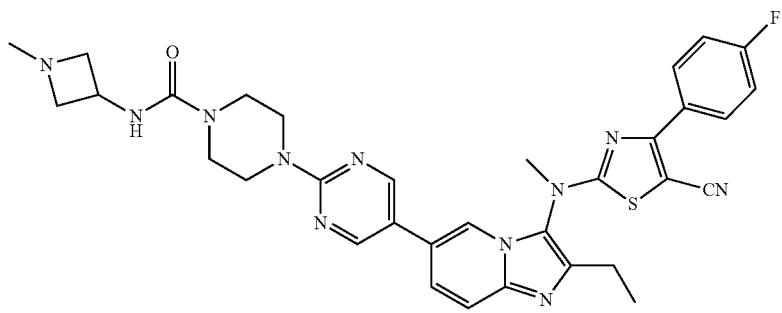

Compound 82

To a mixture of compound 82 hydrochloride, 4-(5-(3-((5-cyano-4-(4-fluorophenyl)thiazol-2-yl)(methyl)amino)-2-ethylimidazo [1,2-a]pyridin-6-yl)pyrimidin-2-yl)-N-(1-methylazetidin-3-yl)piperazine-1-carboxamide hydrochloride (60 mg, 0.078 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 82, 4-(5-(3-((5-cyano-4-(4-fluorophenyl)thiazol-2-yl)(methyl) amino)-2-ethylimidazo[1,2-a]pyridin-6-yl)pyrimidin-2-yl)-N-(1-methylazetidin-3-yl)piperazine-1-carboxamide (8 mg, 15.68% yield) as a white solid. $^1$H NMR (400 MHz, DMSO-d$_6$) δ 8.80 (s, 2H), 8.66 (s, 1H), 8.10-8.07 (t, 2H), 7.70 (s, 2H), 7.44-7.40 (t, 2H), 6.91-6.89 (d, 1H), 4.22-4.17 (m, 1H), 3.76-3.70 (m, 4H), 3.63-3.56 (m, 5H), 3.40-3.38 (m, 4H), 2.97 (s, 2H), 2.70-2.64 (m, 2H), 2.31 (s, 2H), 1.28-1.25 (t, 3H); MS: m/z=652.0 (M+1, ESI+).

5.8.35. Synthesis of (4-(5-bromopyrimidin-2-yl)piperazin-1-yl)(cyclopropyl)methanone

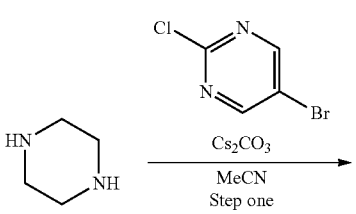

-continued

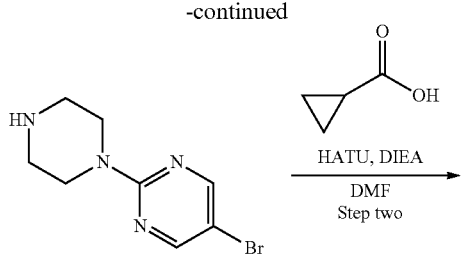

-continued

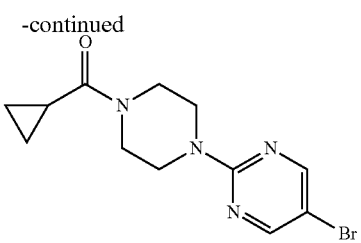

Step One:

To a solution of piperazine (2.67 g, 31.02 mmol) and 5-bromo-2-chloropyrimidine (3 g, 15.51 mmol) in MeCN (30 mL) was added $Cs_2CO_3$ (15.16 g, 46.53 mmol), the reaction mixture was stirred at 80° C. for 2 h. The mixture was filtered and concentrated. The residue was purified by column chromatography to afford 5-bromo-2-piperazin-1-yl-pyrimidine (1.4 g, 37.13% yield) as a yellow solid. MS: m/z=243.1 (M+1, ESI+).

Step Two:

To a solution of cyclopropanecarboxylic acid (389.54 mg, 4.52 mmol) and 5-bromo-2-(piperazin-1-yl)pyrimidine (1 g, 4.11 mmol) in DMF (15 mL) was added HATU (2.35 g, 6.17 mmol) and DIEA (1.59 g, 12.34 mmol), the reaction mixture was stirred at 25° C. for 2 h. The mixture was poured into water (150 mL) and extracted with EA (50 mL×3). The organic layer was washed with water (100 mL×2) and brine (100 mL), then dried over $Na_2SO_4$ and concentrated. The residue was purified by column chromatography to afford (4-(5-bromopyrimidin-2-yl)piperazin-1-yl) (cyclopropyl) methanone (530 mg, 41.41% yield) as a yellow solid. MS: m/z=311.1 (M+1, ESI+).

5.8.36. Synthesis of Compound 110

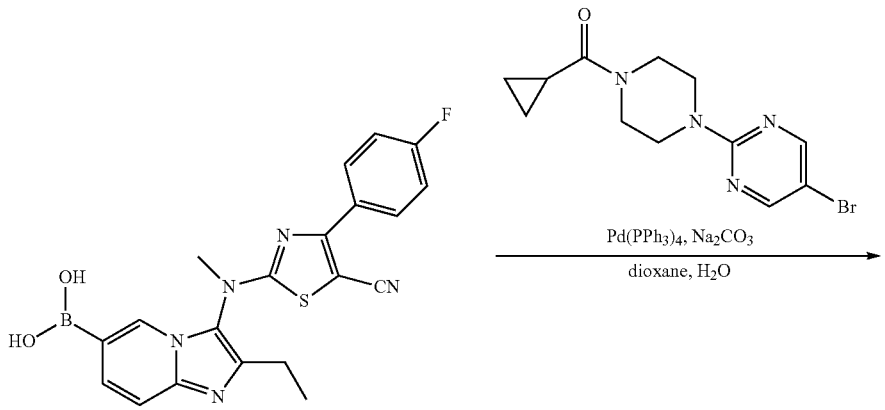

Compound 133

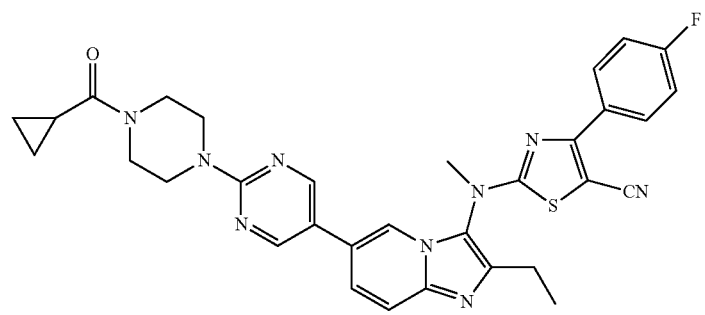

Compound 110

To a mixture of (3-((5-cyano-4-(4-fluorophenyl)thiazol-2-yl)(methyl)amino)-2-ethylimidazo[1,2-a] pyridin-6-yl) boronic acid (406.12 mg, 964.08 umol) and (4-(5-bromopyrimidin-2-yl)piperazin-1-yl)(cyclopropyl)methanone (300 mg, 964.08 umol) in dioxane (10 mL) and water (2 mL) was added $Na_2CO_3$ (306.55 mg, 2.89 mmol) and $Pd(PPh_3)_4$ (557.03 mg, 482.04 umol), the reaction mixture was stirred at 100° C. for 2 h under $N_2$. The mixture was poured into water (60 mL) and extracted with EA (20 mL×2). The organic layer was washed by brine (100 mL), then dried over $Na_2SO_4$ and concentrated. The residue was purified by column chromatography to afford compound 110, 2-((6-(2-(4-(cyclopropanecarbonyl) piperazin-1-yl)pyrimidin-5-yl)-2-ethylimidazo[1,2-a]pyridin-3-yl)(methyl)amino)-4-(4-fluorophenyl) thiazole-5-carbonitrile (154 mg, 26.29% yield) as a white solid. $^1$H NMR (400 MHz, DMSO-$d_6$) δ 8.81 (s, 2H), 8.68 (s, 1H), 8.11-8.08 (t, 2H), 7.71 (s, 2H), 7.44-7.39 (t, 2H), 3.85-3.77 (m, 6H), 3.64 (s, 3H), 3.61-3.56 (m, 2H), 2.71-2.65 (dd, 2H), 2.03-1.99 (m, 1H), 1.29-1.25 (t, 3H), 0.79-0.70 (m, 4H); MS: m/z=608.1 (M+1, ESI+); HRMS: 608.2351.

5.8.37. Synthesis of 1-cyclopropylazetidine-3-carboxylic acid

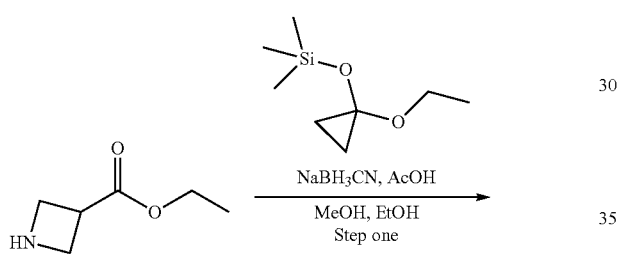

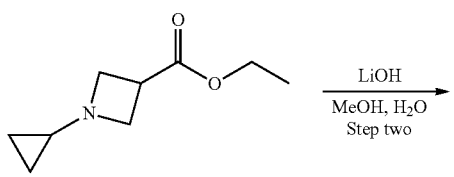

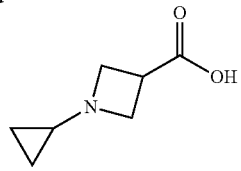

Step One:

To a solution of ethyl azetidine-3-carboxylate (4 g, 30.97 mmol) in MeOH (20 mL) and EtOH (20 mL) was added (1-ethoxycyclopropoxy)trimethylsilane (10.80 g, 61.94 mmol), acetic acid (371.96 mg, 6.19 mmol) and $NaBH_3CN$ (3.89 g, 61.94 mmol), the reaction mixture was stirred at 75° C. for 16 h. The mixture was concentrated, then poured into water (100 mL) and extracted with EA (50 mL×2). The organic layer was washed with water (100 mL) and brine (50 mL), then dried over $Na_2SO_4$ and concentrated. The residue purified by column chromatography to afford ethyl 1-cyclopropylazetidine-3-carboxylate (1.4 g, 26.71% yield) as a yellow oil. $^1$H NMR (400 MHz, CDCl$_3$) δ 4.18 (d, 2H), 3.68-3.56 (m, 2H), 3.53-3.42 (m, 2H), 3.29 (d, 1H), 1.96-1.86 (m, 1H), 1.29 (t, 3H), 0.40 (m, 4H); MS: m/z=169.9 (M+1, ESI+).

Step Two:

To a solution of ethyl 1-cyclopropylazetidine-3-carboxylate (800 mg, 4.73 mmol) in MeOH (10 mL) and water (5 mL) was added LiOH (566.09 mg, 23.64 mmol), the reaction mixture was stirred at 25° C. for 16 h. The mixture was adjusted PH to 5-6 by 2 M HCl and concentrated. The residue was washed with MeOH (5 mL×4). The organic layer was concentrated to afford 1-cyclopropylazetidine-3-carboxylic acid (330 mg, 49.45% yield) as a yellow oil. MS: m/z=142.1 (M+1, ESI+).

5.8.38. Synthesis of Compound 111

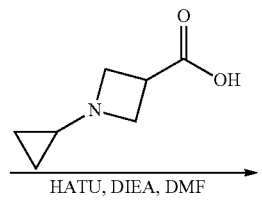

Compound 4

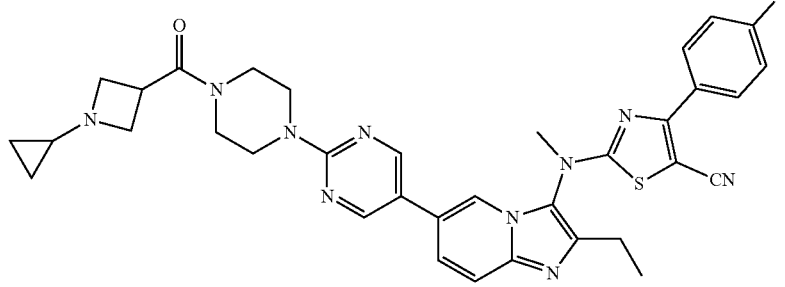

Compound 111

To a solution of 1-cyclopropylazetidine-3-carboxylic acid (156.96 mg, 1.11 mmol) and compound 4, 2-((2-ethyl-6-(2-(piperazin-1-yl)pyrimidin-5-yl)imidazo[1,2-a]pyridin-3-yl)(methyl)amino)-4-(4-fluorophenyl) thiazole-5-carbonitrile (400 mg, 741.25 umol) in DMF (8 mL) was added HATU (422.77 mg, 1.11 mmol) and DIEA (287.40 mg, 2.22 mmol), the reaction mixture was stirred at 25° C. for 2 h. The mixture was poured into water (80 mL) and extracted with EA (30 mL×3). The organic layer was washed with brine (80 mL), then dried over $Na_2SO_4$ and concentrated. The residue was purified by Prep-HPLC to afford compound 111, 2-((6-(2-(4-(1-cyclopropylazetidine-3-carbonyl)piperazin-1-yl)pyrimidin-5-yl)-2-ethylimidazo[1,2-a]pyridin-3-yl)(methyl)amino)-4-(4-fluorophenyl)thiazole-5-carbonitrile (197 mg, 40.10% yield) as a white solid. $^1$H NMR (400 MHz, DMSO-$d_6$) δ 8.80 (s, 2H), 8.67 (s, 1H), 8.11-8.07 (t, 2H), 7.70 (s, 2H), 7.44-7.40 (t, 2H), 3.77-3.74 (t, 4H), 3.63 (s, 3H), 3.54-3.52 (t, 2H), 3.46-3.43 (m, 3H), 3.40-3.32 (m, 2H), 3.27-3.26 (m, 2H), 2.70-2.64 (dd, 2H), 1.81-1.79 (m, 1H), 1.28-1.25 (t, 3H), 0.32-0.28 (m, 2H), 0.19-0.15 (m, 2H); MS: m/z=663.2 (M+1, ESI+); HRMS: 663.2775.

5.9. Example 8—Synthesis of Piperazine-linked Pyridine-type Compounds

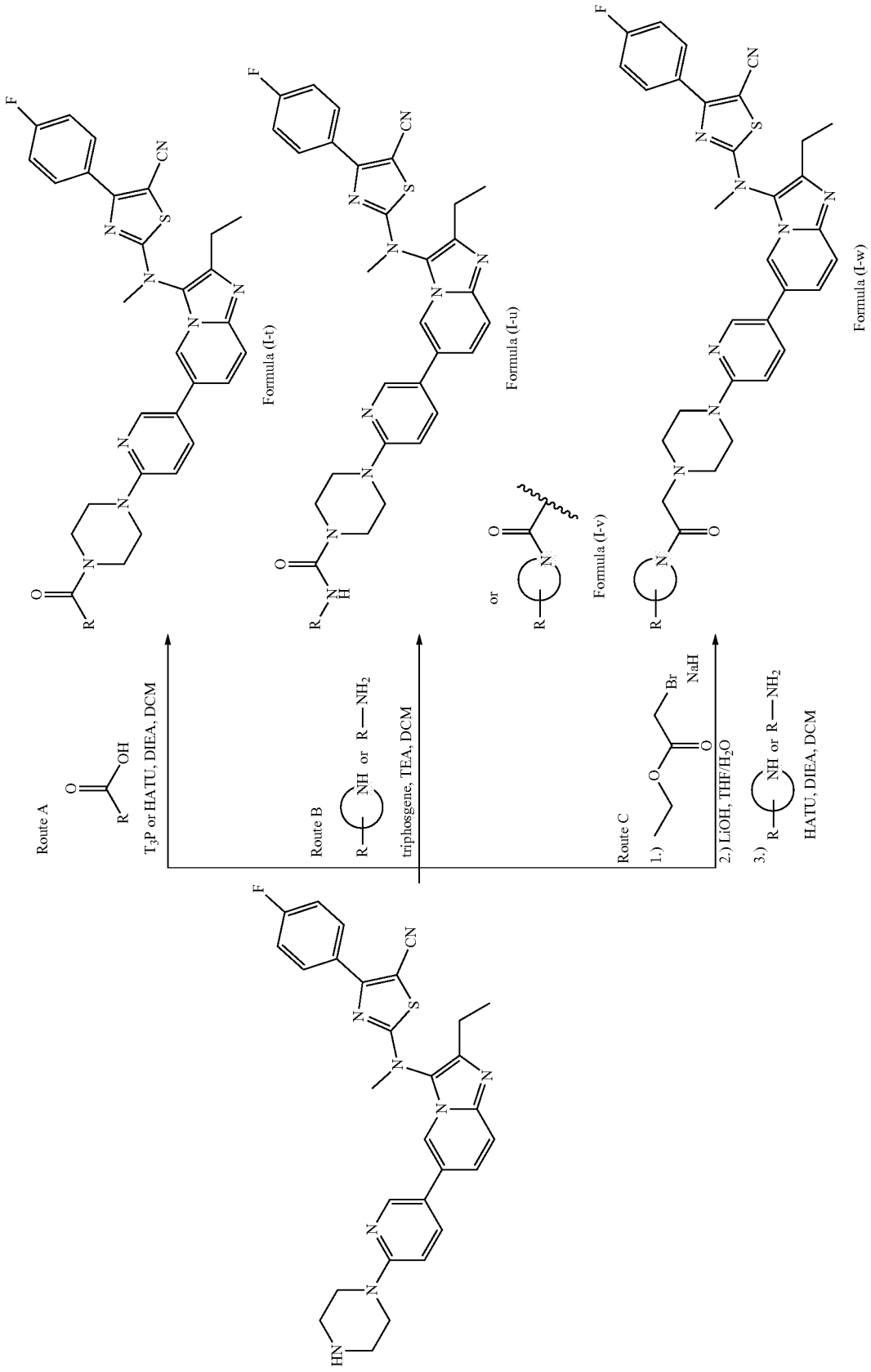

5.9.1. Synthesis of 1-(5-bromopyridin-2-yl)piperazine

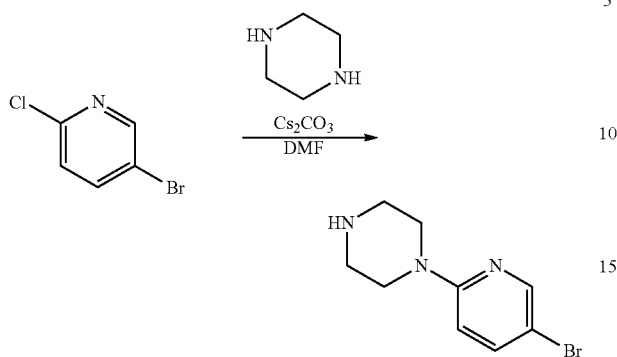

To a mixture of 5-bromo-2-chloropyridine (10 g, 51.96 mmol) and piperazine (89.52 mg, 103.93 mmol) in DMF (10 mL) was added $Cs_2CO_3$ (50.7.9 mg, 155.89 mmol), the reaction mixture was stirred at 120° C. for 3 h. The mixture was quenched by saturated $NH_4Cl$ (100 mL) and extracted with EA (50 mL×3), The organic layer was washed by water (100 mL×2) and brine (100 mL), then dried over $Na_2SO_4$ and concentrated. The residue was purified by column chromatography to afford 1-(5-bromopyridin-2-yl)piperazine (6.4 g, 50.87% yield) as a yellow oil. MS: m/z=243.8 (M+1+2, ESI+).

5.9.2. Synthesis of Compound 139

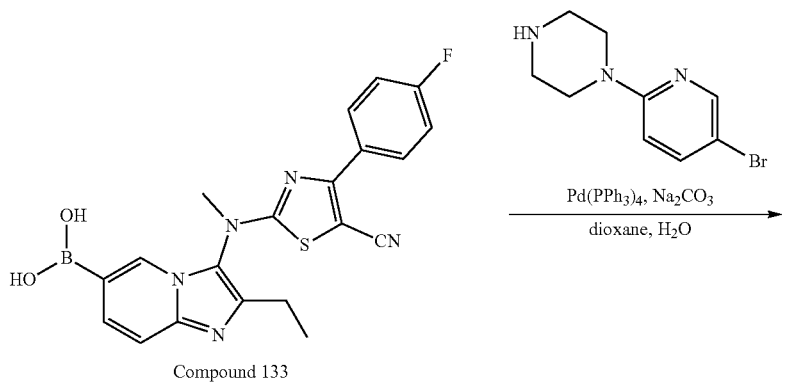

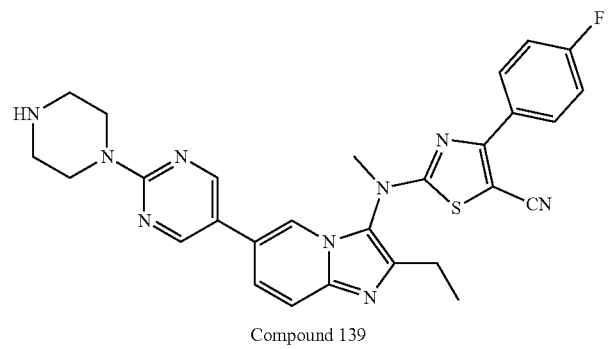

Compound 139

To a mixture of compound 133, (3-((5-cyano-4-(4-fluorophenyl)thiazol-2-yl)(methyl)amino)-2-ethylimidazo[1,2-a]pyridin-6-yl)boronic acid (2 g, 4.75 mmol) and 1-(5-bromopyridin-2-yl)piperazine (1.15 g, 4.75 mmol) in dioxane (20 mL) and water (4 mL) was added Na$_2$CO$_3$ (1.51 g, 14.24 mmol) and Pd(PPh$_3$)$_4$ (548.63 mg, 474.77 umol), the reaction mixture was stirred at 100° C. for 2 h. The mixture was diluted by DCM (100 mL). The organic layer was washed by water (100 mL×2) and brine (100 mL), then dried over Na$_2$SO$_4$ and concentrated. The residue was purified by column chromatography to afford compound 139, 2-((2-ethyl-6-(6-(piperazin-1-yl)pyridin-3-yl)imidazo[1,2-a]pyridin-3-yl) (methyl)amino)-4-(4-fluorophenyl)thiazole-5-carbonitrile (1.8 g, 70.39% yield) as a yellow solid. MS: m/z=539.2 (M+1, ESI+).

h. The mixture was filtered and concentrated, the residue was purified by column chromatography to afford ethyl 2-(4-(5-(3-((5-cyano-4-(4-fluorophenyl) thiazol-2-yl) (methyl)amino)-2-ethylimidazo[1,2-a]pyridin-6-yl)pyridin-2-yl)piperazin-1-yl)acetate (220 mg, 75.87% yield) as a white solid. MS: m/z=625.1 (M+1, ESI+).

Step Two:
To a solution of ethyl 2-(4-(5-(3-((5-cyano-4-(4-fluorophenyl)thiazol-2-yl)(methyl)amino)-2-ethyl imidazo[1,2-a] pyridin-6-yl)pyridin-2-yl)piperazin-1-yl)acetate (220 mg, 352.15 umol) in MeOH (9 mL) and H$_2$O (1 mL) was added LiOH (84.34 mg, 3.52 mmol), the reaction mixture was stirred at 25° C. for 3 h. The reaction mixture was concentrated under reduced pressure and the residue was poured 5.9.3. Synthesis of Compound 149

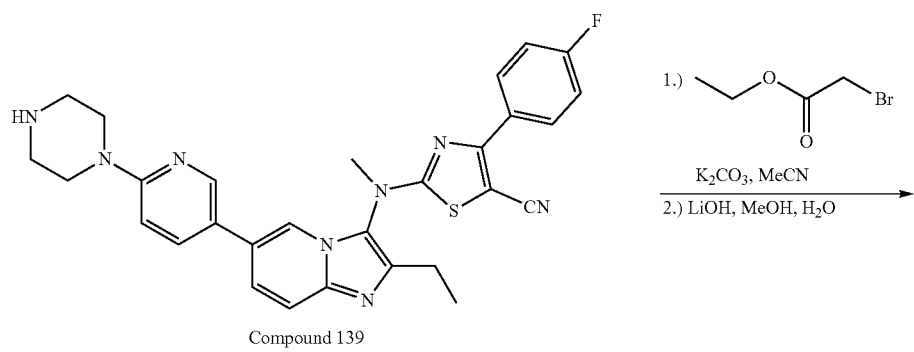

Compound 139

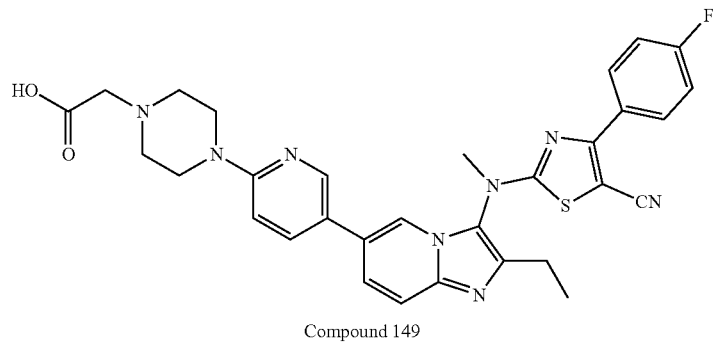

Compound 149

Step One:
To a solution of compound 139, 2-((2-ethyl-6-(6-(piperazin-1-yl)pyridin-3-yl)imidazo[1,2-a]pyridin-3-yl)(methyl) amino)-4-(4-fluorophenyl)thiazole-5-carbonitrile (250 mg, 464.13 umol) and ethyl 2-bromoacetate (93.01 mg, 556.96 umol) in MeCN (10 mL) was added K$_2$CO$_3$ (192.44 mg, 1.39 mmol), the reaction mixture was stirred at 70° C. for 2 into 2N HCl (20 mL) and extracted with EA (10 mL×2), the organic layer was washed by brine (20 mL), then dried over Na$_2$SO$_4$ and concentrated to afford the crude product compound 149, 2-(4-(5-(3-((5-cyano-4-(4-fluorophenyl)thiazol-2-yl)(methyl)amino)-2-ethylimidazo[1,2-a]pyridin-6-yl) pyridin-2-yl)piperazin-1-yl)acetic acid (185 mg, 88.04% yield) as a white solid. MS: m/z=597.2 (M+1, ESI+).

5.9.4. Synthesis of Compound 85

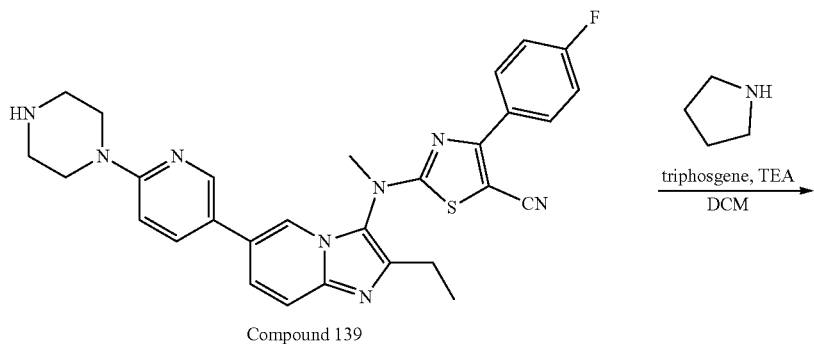

Compound 139

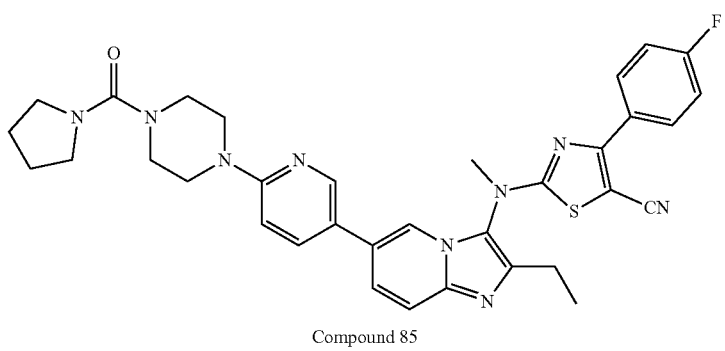

Compound 85

To a solution of compound 139, 2-((2-ethyl-6-(6-(piperazin-1-yl)pyridin-3-yl)imidazo[1,2-a]pyridin-3-yl)(methyl)amino)-4-(4-fluorophenyl)thiazole-5-carbonitrile (250 mg, 464.13 umol) in DCM (10 mL) at 0° C. was added triphosgene (55.09 mg, 185.65 umol), the mixture was stirred at 0° C. for 30 min. Then TEA (234.83 mg, 2.32 mmol) and pyrrolidine (33.01 mg, 464.13 umol) was added. The reaction mixture was stirred at 25° C. for 5 h. The mixture was quenched by water (50 mL) and extracted with DCM (20 mL×3). The organic layer was washed with brine (50 mL), dried over $Na_2SO_4$ and concentrated. The residue was purified by Prep-HPLC to afford compound 85, 2-((2-ethyl-6- (6-(4-(pyrrolidine-1-carbonyl)piperazin-1-yl)pyridin-3-yl) imidazo[1,2-a]pyridin-3-yl)(methyl)amino)-4-(4-fluorophenyl) thiazole-5-carbonitrile (150 mg, 50.83% yield) as a white solid. $^1$H NMR (400 MHz, DMSO-$d_6$) δ 8.59 (s, 1H), 8.55-8.54 (d, 1H), 8.11-8.08 (t, 2H), 7.99-7.96 (m, 1H), 7.72-7.66 (dd, 2H), 7.44-7.40 (t, 2H), 6.93-6.90 (d, 1H), 3.64 (s, 3H), 3.56-3.53 (t, 4H), 3.31-3.25 (m, 8H), 2.69-2.64 (dd, 2H), 1.77-1.74 (t, 4H), 1.29-1.25 (t, 3H); MS: m/z=636.3 (M+1, ESI+); HRMS: 636.2663.

5.9.5. Synthesis of Compound 86 Hydrochloride

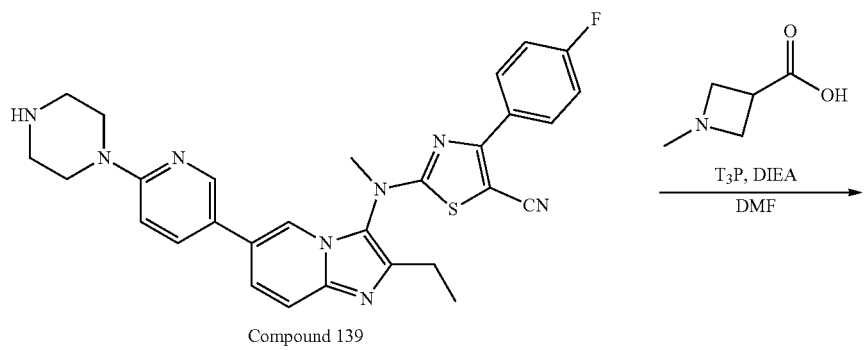

Compound 139

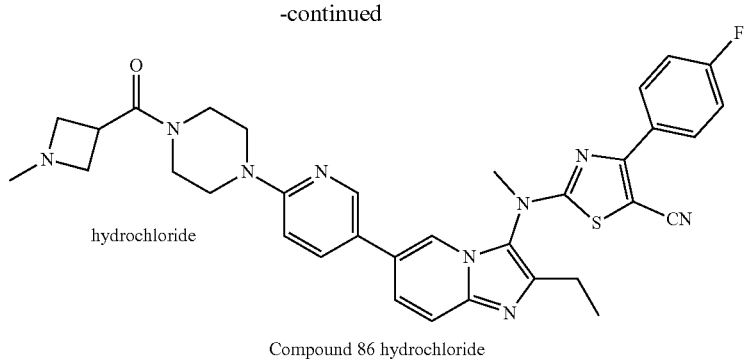

Compound 86 hydrochloride

To a solution of compound 139, 2-((2-ethyl-6-(6-(piperazin-1-yl)pyridin-3-yl)imidazo[1,2-a]pyridin-3-yl)(methyl)amino)-4-(4-fluorophenyl)thiazole-5-carbonitrile (200 mg, 371.31 umol) and 1-methylazetidine-3-carboxylic acid (51.30 mg, 445.57 umol) in DMF (10 mL) was added T$_3$P (354.43 mg, 556.96 umol, 50% purity) and DIEA (143.97 mg, 1.11 mmol), the reaction mixture was stirred at 25° C. for 2 h. The reaction mixture was poured into water (100 mL) and extracted with EA (40 mL×3). The organic layer was washed with brine (100 mL×2), dried over Na$_2$SO$_4$ and concentrated. The residue was purified by Prep-HPLC to afford compound 86 hydrochloride, 2-((2-ethyl-6-(6-(4-(1-methylazetidine-3-carbonyl) piperazin-1-yl)pyridin-3-yl) imidazo[1,2-a] pyridin-3-yl)(methyl)amino)-4-(4-fluorophenyl)thiazole-5-carbonitrile hydrochloride (62 mg, 24.84% yield) as a pale yellow solid. $^1$H NMR (400 MHz, MeOD) δ 8.95 (s, 1H), 8.45 (s, 1H), 8.37-8.31 (t, 2H), 8.09-8.00 (m, 3H), 7.39-7.37 (d, 1H), 7.22-7.18 (t, 2H), 4.59-4.51 (m, 2H), 4.22-4.18 (m, 3H), 3.84-3.79 (m, 6H), 3.75 (s, 3H), 3.68 (s, 2H), 2.99-2.94 (m, 5H), 1.44-1.40 (t, 3H); MS: m/z=636.2 (M+1, ESI+); HRMS: 636.2669.

5.9.6. Synthesis of Compound 86

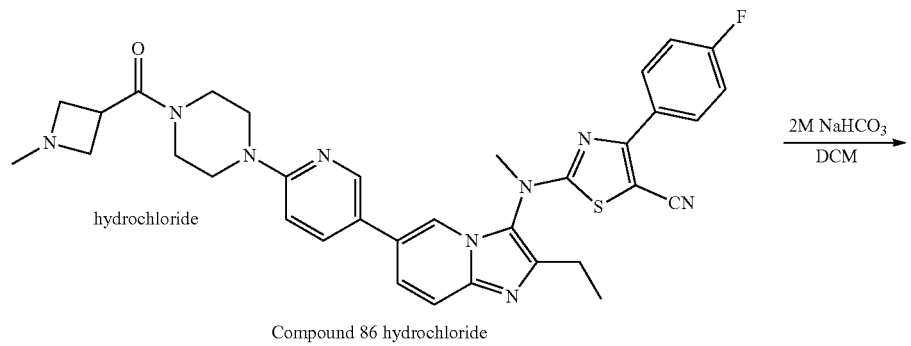

Compound 86 hydrochloride

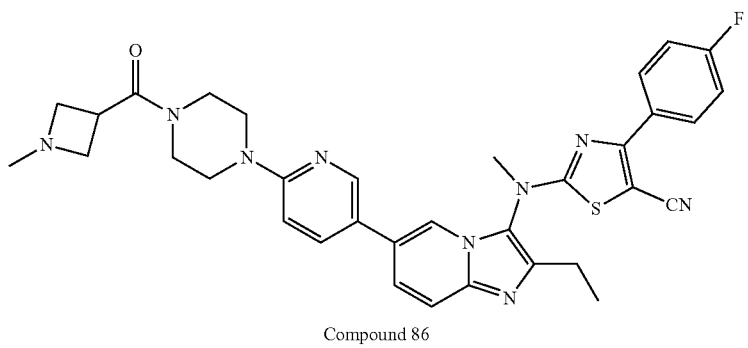

Compound 86

To a mixture of compound 86 hydrochloride, 2-((2-ethyl-6-(6-(4-(1-methylazetidine-carbonyl)piperazin-1-yl)pyridin-3-yl) imidazo[1,2-a]pyridin-3-yl)(methyl)amino)-4-(4-fluorophenyl)thiazole-5-carbonitrile hydrochloride (14 mg, 0.018 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 86, 2-((2-ethyl-6-(6-(4-(1-methylazetidine-3-carbonyl)piperazin-1-yl)pyridin-3-yl) imidazo[1,2-a]pyridin-3-yl)(methyl)amino)-4-(4-fluorophenyl)thiazole-5-carbonitrile (5 mg, 41.67% yield) as a white solid. $^1$H NMR (400 MHz, DMSO-d$_6$) δ 8.59 (s, 1H), 8.55-8.54 (d, 1H), 8.10-8.07 (t, 2H), 8.00-7.97 (m, 1H), 7.72-7.65 (m, 2H), 7.44-7.40 (t, 2H), 6.94-6.92 (d, 1H), 3.63 (s, 3H), 3.53-3.36 (m, 11H), 3.10-3.07 (m, 2H), 2.69-2.63 (m, 2H), 2.16 (s, 3H), 1.28-1.25 (t, 3H); MS: m/z=636.0 (M+1, ESI+).

5.9.7. Synthesis of Compound 91

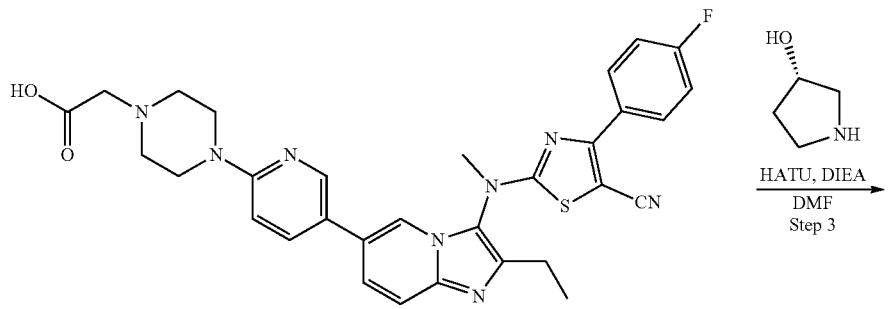

Compound 149

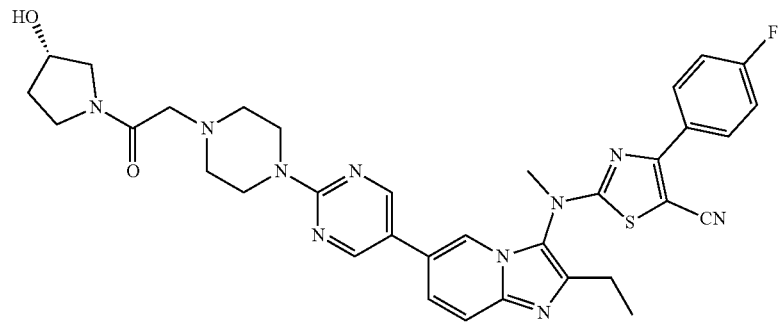

Compound 91

To a solution of compound 149, 2-(4-(5-(3-((5-cyano-4-(4-fluorophenyl)thiazol-2-yl)(methyl)amino)-2-ethylimidazo [1,2-a]pyridin-6-yl)pyridin-2-yl)piperazin-1-yl)acetic acid (185 mg, 310.05 umol) and (S)-pyrrolidin-3-ol (185.87 mg, 1.86 mmol) in DMF (10 mL) was added HATU (175.46 mg, 465.08 umol) and DIEA (120.21 mg, 930.15 umol), the reaction mixture was stirred at 25° C. for 16 h. The mixture was poured into water (100 mL) and extracted with EA (40 mL×2). The organic layer was washed with water (100 mL×2) and brine (100 mL), then dried over $Na_2SO_4$ and concentrated. The residue was purified by Prep-HPLC to afford compound 91, (S)-2-((2-ethyl-6-(6-(4-(2-(3-hydroxypyrrolidin-1-yl)-2-oxoethyl)piperazin-1-yl)pyridin-3-yl) imidazo[1,2-a]pyridin-3-yl)(methyl)amino)-4-(4-fluorophenyl) thiazole-5-carbonitrile (100 mg, 48.44% yield) as a white solid. $^1$H NMR (400 MHz, DMSO-$d_6$) δ 8.58 (s, 1H) 8.53-8.52 (d, 1H), 8.11-8.08 (t, 2H), 7.96-7.93 (dd, 1H), 7.72-7.66 (m, 2H), 7.44-7.39 (t, 2H), 6.91-6.89 (d, 1H), 5.00-4.92 (dd, 1H), 4.31-4.24 (d, 1H), 3.65 (s, 3H), 3.61-3.54 (m, 6H), 3.44-3.34 (m, 1H), 3.31-3.20 (m, 1H), 3.16-3.12 (m, 2H), 2.70-2.65 (dd, 2H), 2.57-2.55 (m, 4H), 1.83-1.73 (m, 2H), 1.29-1.25 (t, 3H); MS: m/z=666.2 (M+1, ESI+); HRMS: 666.2771.

5.9.8. Synthesis of Compound 92

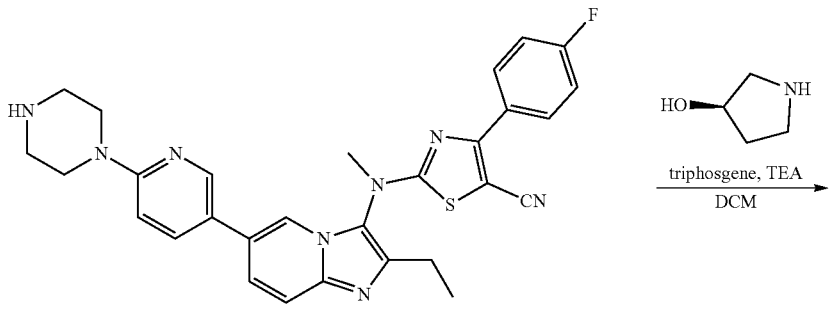

Compound 139

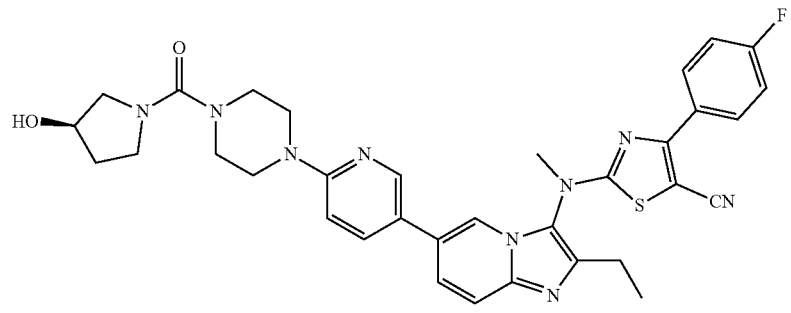

Compound 92

To a suspension of compound 139, 2-((2-ethyl-6-(6-(piperazin-1-yl)pyridin-3-yl)imidazo[1,2-a]pyridin-3-yl)(methyl)amino)-4-(4-fluorophenyl)thiazole-5-carbonitrile (250 mg, 464.13 umol) in DCM (10 mL) at 0° C. was added triphosgene (55.09 mg, 185.65 umol), the reaction mixture was stirred at 0° C. for 30 min. Then TEA (234.83 mg, 2.32 mmol) and (R)-pyrrolidin-3-ol (40.44 mg, 464.13 umol) was added, the reaction mixture was stirred at 25° C. for 5 h. The mixture was quenched by water (50 mL) and extracted with DCM (20 mL×3), the organic layer was washed with brine (50 mL), then dried over Na$_2$SO$_4$ and concentrated. The residue was purified by Prep-HPLC (Waters Xbridge C18 10 um OBD 19*250 mm, A: 10 mmol NH$_4$HCO$_3$ in water; B: CH$_3$CN, 5% to 95%) in NH$_4$HCO$_3$ condition to afford compound 92, (R)-2-((2-ethyl-6-(6-(4-(3-hydroxypyrrolidine-1-carbonyl)piperazin-1-yl)pyridin-3-yl)imidazo[1,2-a]pyridin-3-yl)(methyl)amino)-4-(4-fluorophenyl)thiazole-5-carbonitrile (145 mg, 47.93% yield) as a white solid. $^1$H NMR (400 MHz, DMSO-d$_6$) δ 8.59 (s, 1H), 8.55-8.54 (d, 1H), 8.11-8.07 (t, 2H), 7.99-7.96 (dd, 1H), 7.73-7.65 (m, 2H), 7.44-7.40 (t, 2H), 6.93-6.91 (d, 1H), 4.89 (s, 1H), 4.22 (s, 1H), 3.64 (s, 3H), 3.60-3.45 (m, 6H), 3.30-3.20 (m, 5H), 3.12-3.10 (d, 1H), 2.69-2.64 (dd, 2H), 1.83-1.71 (m, 2H), 1.29-1.25 (t, 3H); MS: m/z=652.2 (M+1, ESI+); HRMS: 652.2617.

5.9.9. Synthesis of Compound 92 Hydrochloride

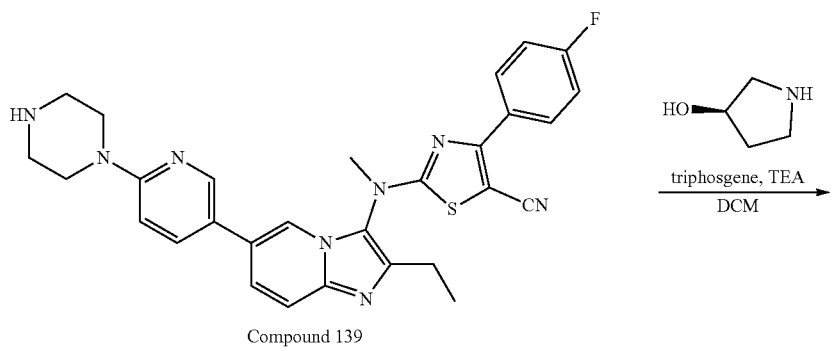

Compound 139

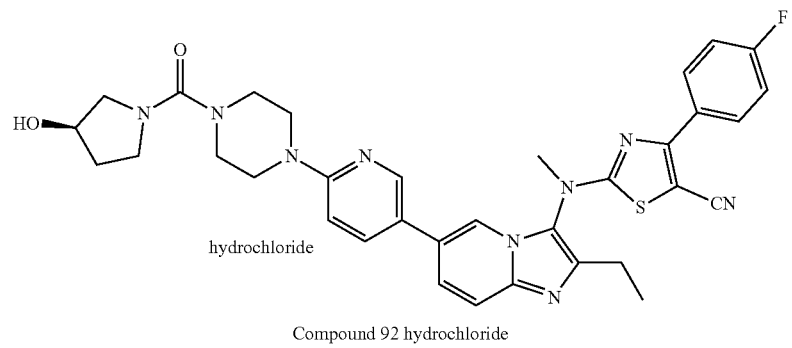

Compound 92 hydrochloride

To a suspension of compound 139, 2-((2-ethyl-6-(6-(piperazin-1-yl)pyridin-3-yl)imidazo[1,2-a]pyridin-3-yl)(methyl) amino)-4-(4-fluorophenyl)thiazole-5-carbonitrile (500 mg, 928 umol) in DCM (10 mL) at 0° C. was added triphosgene (110 mg, 370 umol), the reaction mixture was stirred at 0° C. for 30 min. Then TEA (470 mg, 4.64 mmol) and (R)-pyrrolidin-3-ol (81 mg, 928 umol) was added, the reaction mixture was stirred at 25° C. for 5 h. The mixture was quenched by water (50 mL) and extracted with DCM (20 mL×3), the organic layer was washed with brine (50 mL), then dried over $Na_2SO_4$ and concentrated. The residue was purified by Prep-HPLC (Waters Xbridge C18 10 um OBD 19*250 mm, A: 0.05% HCl in water; B: $CH_3CN$, 5% to 95%) in HCl condition to afford compound 92 hydrochloride, (R)-2-((2-ethyl-6-(6-(4-(3-hydroxypyrrolidine-1-carbonyl)piperazin-1-yl)pyridin-3-yl)imidazo[1,2-a]pyridin-3-yl)(methyl) amino)-4-(4-fluorophenyl)thiazole-5-carbonitrile (205 mg, 29% yield) as a pale yellow solid. $^1$H NMR (400 MHz, DMSO-$d_6$) δ 9.18 (s, 1H), 8.50 (s, 1H), 8.41-8.35 (m, 2H), 8.14-8.12 (dd, J=9.2 Hz, 1H), 8.04-8.00 (t, 2H), 7.42-7.35 (m, 3H), 4.23 (s, 1H), 3.83-3.72 (m, 4H), 3.68 (s, 3H), 3.52-3.45 (m, 2H), 3.41-3.27 (m, 5H), 3.13-3.11 (d, J=10.8 Hz, 1H), 2.91-2.85 (dd, J1=7.2 Hz, J2=14.4 Hz, 2H), 1.85-1.72 (m, 2H), 1.36-1.33 (t, 3H); MS: m/z=652.1 (M+1, ESI+).

5.9.10. Synthesis of Compound 93

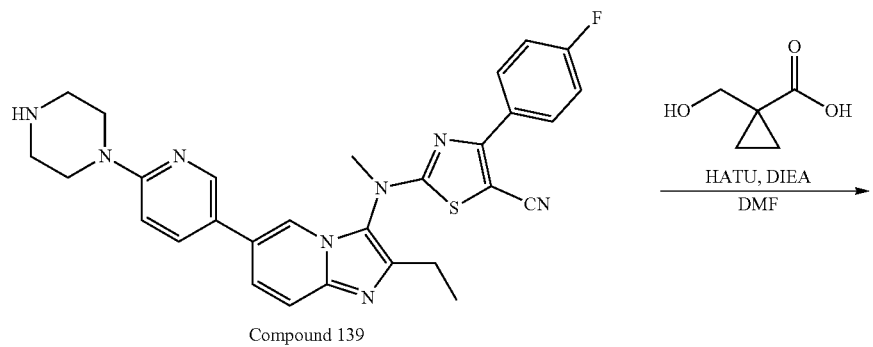

Compound 139

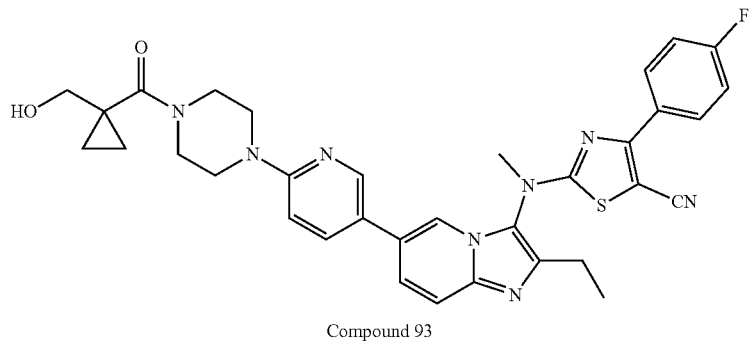

Compound 93

To a solution of compound 139, 2-((2-ethyl-6-(6-(piperazin-1-yl)pyridin-3-yl)imidazo[1,2-a]pyridin-3-yl)(methyl)amino)-4-(4-fluorophenyl)thiazole-5-carbonitrile (250 mg, 464.13 umol) and 1-(hydroxylmethyl) cyclopropane-1-carboxylic acid (64.67 mg, 556.96 umol) in DMF (10 mL) was added HATU (262.65 mg, 696.20 umol) and DIEA (179.95 mg, 1.39 mmol), the reaction mixture was stirred at 25° C. for 2 h. The mixture was poured into water (100 mL) and extracted with EA (40 mL-2). The organic layer was washed with water (100 mL×2) and brine (100 mL), then dried over $Na_2SO_4$ and concentrated. The residue was purified by Prep-HPLC to afford compound 93, 2-((2-ethyl-6-(6-(4-(1-(hydroxylmethyl)cyclopropane-1-carbonyl)piperazin-1-yl)pyridin-3-yl)imidazo[1,2-a]pyridin-3-yl) (methyl)amino)-4-(4-fluorophenyl)thiazole-5-carbonitrile (105 mg, 35.53% yield) as a white solid. $^1$H NMR (400 MHz, DMSO-$d_6$) δ 8.59 (s, 1H), 8.56-8.55 (d, 1H), 8.11-8.07 (t, 2H), 8.00-7.97 (dd, 1H), 7.73-7.66 (m, 2H), 7.44-7.40 (t, 2H), 6.96-6.94 (d, 1H), 4.89-4.86 (t, 1H), 3.64-3.56 (m, 11H), 3.48-3.47 (d, 2H), 2.69-2.64 (dd, 2H), 1.29-1.25 (t, 3H), 0.77-0.69 (m, 4H); MS: m/z=637.2 (M+1, ESI+); HRMS: 637.2510.

5.9.11. Synthesis of Compound 94

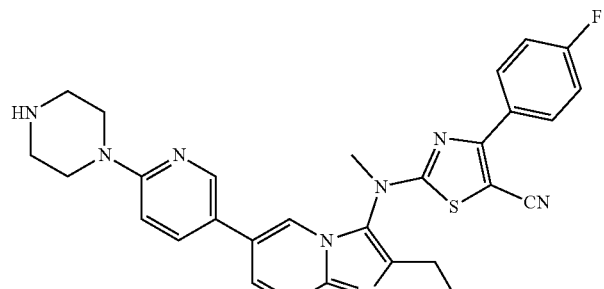

Compound 139

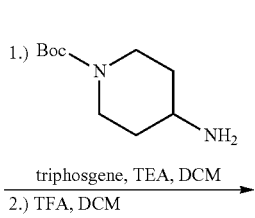

(234.83 mg, 2.32 mmol) was added, the reaction mixture was stirred at 25° C. for 3 h. The mixture was poured into water (100 mL) and extracted with DCM (30 mL×3), the organic layer was washed with brine (100 mL), then dried over $Na_2SO_4$ and concentrated. The residue was purified by column chromatography to afford tert-butyl 4-(4-(5-(3-((5-cyano-4-(4-fluorophenyl)thiazol-2-yl) (methyl)amino)-2-ethylimidazo[1,2-a]pyridin-6-yl)pyridin-2-yl)piperazine-1-carboxamido) piperidine-1-carboxylate (195 mg, 70.42% yield) as a yellow solid. MS: m/z=765.4 (M+1, ESI+).

Step Two:
To a solution of tert-butyl 4-(4-(5-(3-((5-cyano-4-(4-fluorophenyl)thiazol-2-yl)(methyl)amino)-2-ethylimidazo[1,2-a]pyridin-6-yl)pyridin-2-yl)piperazine-1-carboxamido)piperidine-1-carboxylate (195.00 mg, 254.93 umol) in DCM (10 mL) was added TFA (290.67 mg, 2.55 mmol), the reaction mixture was stirred at 25° C. for 5 h. The mixture was concentrated under reduce pressure and the residue was purified by Prep-HPLC to afford compound 94, 4-(5-(3-((5-cyano-4-(4-fluorophenyl)thiazol-2-yl)(methyl)amino)-2-ethylimidazo[1,2-a]pyridin-6-yl)pyridin-2-yl)-N-(piperidin-

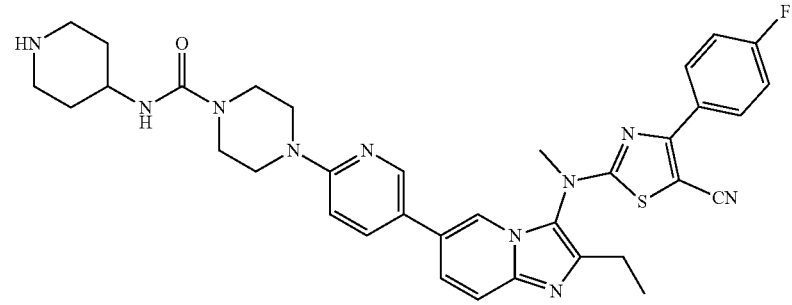

Compound 94

Step One:
To a solution of tert-butyl 4-aminopiperidine-1-carboxylate (102.25 mg, 510.54 umol) in DCM (10 mL) at 0° C. was added triphosgene (55.09 mg, 185.65 umol), the reaction mixture was stirred at 0° C. for 30 min. Then, compound 139, 2-((2-ethyl-6-(6-(piperazin-1-yl)pyridin-3-yl)imidazo[1,2-a]pyridin-3-yl) (methyl)amino)-4-(4-fluorophenyl)thiazole-5-carbonitrile (250 mg, 464.13 umol) and TEA 4-yl)piperazine-1-carboxamide (123 mg, 72.58% yield) as a white solid. $^1$H NMR (400 MHz, DMSO-$d_6$) δ 8.58 (s, 1H), 8.55-8.54 (d, 1H), 8.11-8.07 (t, 2H), 7.98-7.95 (dd, 1H), 7.73-7.66 (m, 2H), 7.44-7.40 (t, 2H), 6.95-6.93 (d, 1H), 6.30-6.29 (d, 1H), 3.64 (s, 3H), 3.52-3.38 (m, 10H), 2.92-2.89 (d, 2H), 2.69-2.64 (dd, 2H), 2.47-2.41 (m, 2H), 1.68-1.65 (d, 2H), 1.32-1.23 (t, 5H); MS: m/z=665.3 (M+1, ESI+); HRMS: 665.2931.

5.9.12. Synthesis of Compound 95

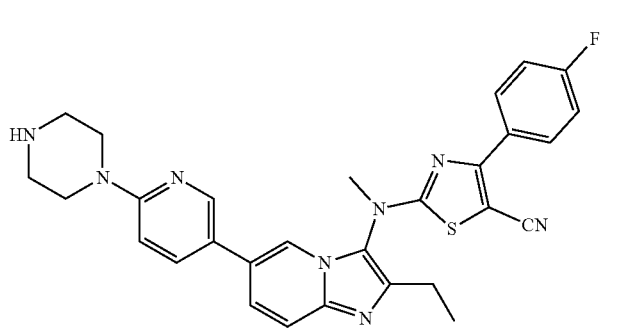
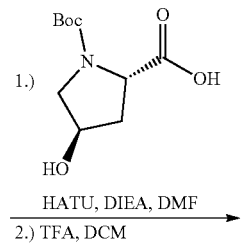

Compound 139

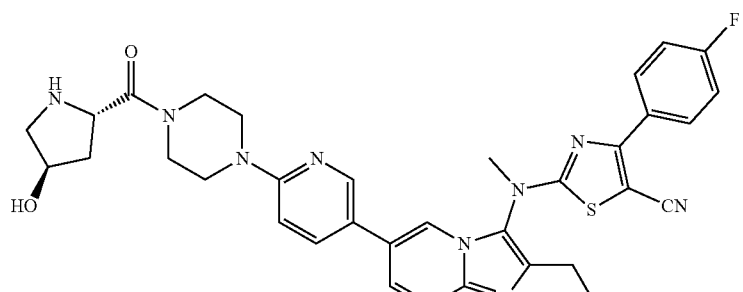

Comopund 95

Step One:

To a solution of compound 139, 2-((2-ethyl-6-(6-(piperazin-1-yl)pyridin-3-yl)imidazo[1,2-a]pyridin-3-yl)(methyl) amino)-4-(4-fluorophenyl)thiazole-5-carbonitrile (250 mg, 464.13 umol) and (2S,4R)-1-(tert-butoxycarbonyl)-4-hydroxypyrrolidine-2-carboxylic acid (128.79 mg, 556.96 umol) in DMF (10 mL) was added HATU (262.65 mg, 696.20 umol) and DIEA (179.95 mg, 1.39 mmol), the reaction mixture was stirred at 25° C. for 2 h. The mixture was poured into water (100 mL) and extracted with EA (40 mL×2). The organic layer was washed with water (100 mL×2) and brine (100 mL), then dried over $Na_2SO_4$ and concentrated. The residue was purified by Prep-HPLC to afford tert-butyl (2S,4R)-2-(4-(5-(3-((5-cyano-4-(4-fluorophenyl)thiazol-2-yl)(methyl)amino)-2-ethylimidazo [1,2-a]pyridin-6-yl)pyridin-2-yl)piperazine-1-carbonyl)-4-hydroxypyrrolidine-1-carboxylate (200 mg, 57.31% yield) as a yellow solid. MS: m/z=752.2 (M+1, ESI+).

Step Two:

To a solution of tert-butyl (2S,4R)-2-(4-(5-(3-((5-cyano-4-(4-fluorophenyl)thiazol-2-yl)(methyl) amino)-2-ethylimidazo[1,2-a]pyridin-6-yl)pyridin-2-yl)piperazine-1-carbonyl)-4-hydroxypyrrolidine-1-carboxylate (200 mg, 266.00 umol) in DCM (5 mL) was added TFA (303.30 mg, 2.66 mmol), the reaction mixture was stirred at 25° C. for 3 h. The mixture was concentrated under reduce pressure and the residue was purified by Prep-HPLC to afford compound 95, 2-((2-ethyl-6-(6-(4-(((2S,4R)-4-hydroxypyrrolidine-2-carbonyl)piperazin-1-yl)pyridin-3-yl)imidazo[1,2-a]pyridin-3-yl) (methyl)amino)-4-(4-fluorophenyl)thiazole-5-carbonitrile (115 mg, 66.33% yield) as a white solid. $^1$H NMR (400 MHz, DMSO-$d_6$) δ 8.60 (s, 1H), 8.56-8.55 (d, 1H), 8.11-8.08 (t, 2H), 8.00-7.97 (dd, 1H), 7.73-7.66 (m, 2H), 7.44-7.39 (t, 2H), 6.96-6.93 (d, 1H), 4.20-4.19 (t, 1H), 4.08-4.04 (t, 1H), 3.65-3.40 (m, 13H), 3.09-3.05 (dd, 1H), 2.70-2.55 (dd, 3H), 1.89-1.77 (m, 2H), 1.29-1.25 (t, 3H); MS: m/z=652.1 (M+1, ESI+); HRMS: 652.2610.

5.9.13. Synthesis of Compound 96 Hydrochloride

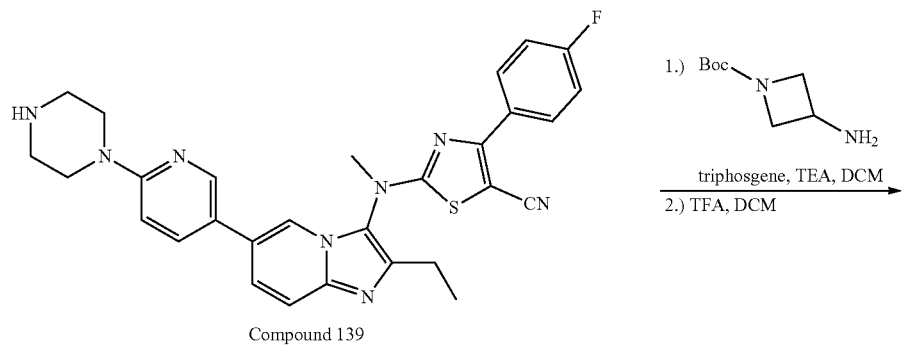

Compound 139

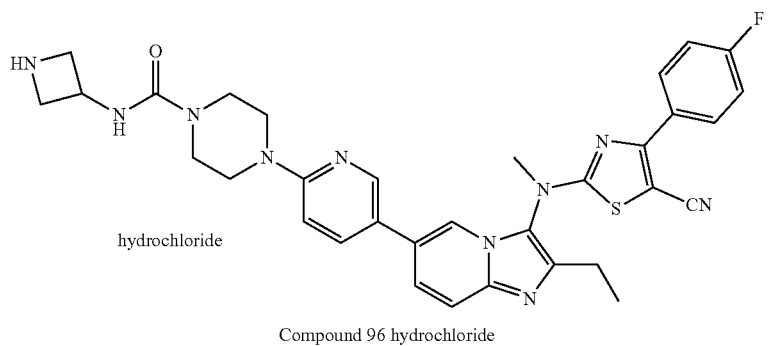

Compound 96 hydrochloride

Step One:

To a suspension of compound 139, 2-((2-ethyl-6-(6-(piperazin-1-yl)pyridin-3-yl)imidazo[1,2-a]pyridin-3-yl)(methyl)amino)-4-(4-fluorophenyl)thiazole-5-carbonitrile (250 mg, 464.13 umol) in DCM (10 mL) at 0° C. was added triphosgene (55.09 mg, 185.65 umol), the reaction mixture was stirred at 0° C. for 30 min. Then TEA (234.83 mg, 2.32 mmol) and tert-butyl 3-aminoazetidine-1-carboxylate (87.93 mg, 510.54 umol) was added, the reaction mixture was stirred at 25° C. for 3 h. The mixture was poured into water (50 mL) and extracted with DCM (20 mL×3), the organic layer was washed with brine (50 mL), then dried over $Na_2SO_4$ and concentrated. The residue was purified by Prep-HPLC to afford tert-butyl 3-(4-(5-(3-(((5-cyano-4-(4-fluorophenyl)thiazol-2-yl)(methyl)amino)-2-ethylimidazo[1,2-a]pyridin-6-yl)pyridin-2-yl)piperazine-1-carboxamido)azetidine-1-carboxylate (190 mg, 55.56% yield) as a yellow solid. MS: m/z=737.4 (M+1, ESI+).

Step Two:

To a solution of tert-butyl 3-(4-(5-(3-(((5-cyano-4-(4-fluorophenyl)thiazol-2-yl)(methyl)amino)-2-ethylimidazo[1,2-a]pyridin-6-yl)pyridin-2-yl)piperazine-1-carboxamido)azetidine-1-carboxylate (190.00 mg, 257.85 umol) in DCM (5 mL) was added TFA (294.00 mg, 2.58 mmol), the reaction mixture was stirred at 25° C. for 5 h. The mixture was concentrated under reduce pressure and the residue was purified by Prep-HPLC to afford compound 96 hydrochloride, N-(azetidin-3-yl)-4-(5-(3-(((5-cyano-4-(4-fluorophenyl)thiazol-2-yl)(methyl)amino)-2-ethylimidazo[1,2-a]pyridin-6-yl)pyridin-2-yl) piperazine-1-carboxamide hydrochloride (125 mg, 72.01% yield) as a yellow solid. $^1$H NMR (400 MHz, DMSO-$d_6$) δ 9.32-9.22 (m, 2H), 9.10 (s, 1H), 8.56-8.55 (d, 1H), 8.37-8.35 (d, 1H), 8.24-8.22 (d, 1H), 8.11-8.08 (d, 1H), 8.04-8.00 (t, 2H), 7.66-7.65 (d, 1H), 7.42-7.38 (t, 2H), 7.23-7.21 (d, 1H), 4.60-4.55 (m, 1H), 4.04-3.99 (dd, 4H), 3.94-3.82 (m, 7H), 3.60-3.51 (m, 4H), 2.90-2.84 (dd, 2H), 1.36-1.32 (t, 3H); MS: m/z=637.3 (M+1, ESI+); HRMS: 637.2620.

5.9.14. Synthesis of Compound 96

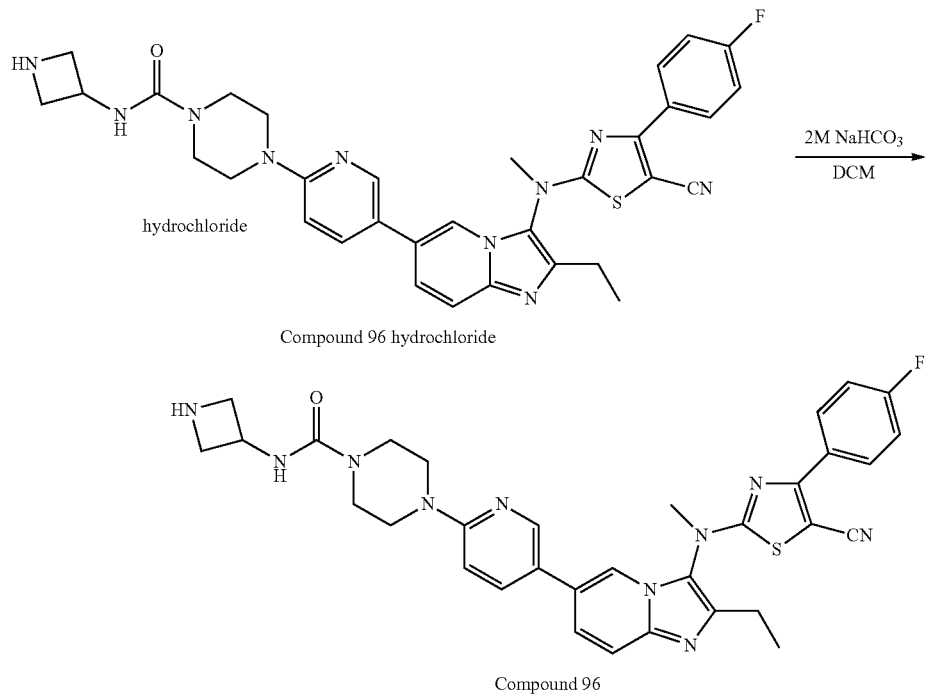

Compound 96 hydrochloride

Compound 96

To a mixture of compound 96 hydrochloride, N-(azetidin-3-yl)-4-(5-(3-((5-cyano-4-(4-fluorophenyl)thiazol-2-yl)(methyl)amino)-2-ethylimidazo[1,2-a]pyridin-6-yl)pyridin-2-yl)piperazine-1-carboxamide hydrochloride (90 mg, 0.120 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 96, N-(azetidin-3-yl)-4-(5-(3-((5-cyano-4-(4-fluorophenyl)thiazol-2-yl)(methyl)amino)-2-ethylimidazo[1,2-a]pyridin-6-yl)pyridin-2-yl)piperazine-1-carboxamide (60 mg, 78.22% yield) as a white solid. $^1$H NMR (400 MHz, DMSO-d$_6$) δ 8.56-8.52 (m, 2H), 8.10-8.07 (t, 2H), 7.98-7.95 (m, 1H), 7.73-7.65 (m, 2H), 7.44-7.39 (t, 2H), 6.96-6.93 (d, 1H), 3.72-3.43 (m, 12H), 2.69-2.64 (m, 3H), 1.28-1.24 (t, 3H); MS: m/z=637.0 (M+1, ESI+).

5.9.15. Synthesis of (4-(5-bromopyridin-2-yl)piperazin-1-yl)cyclopentyl)methanone

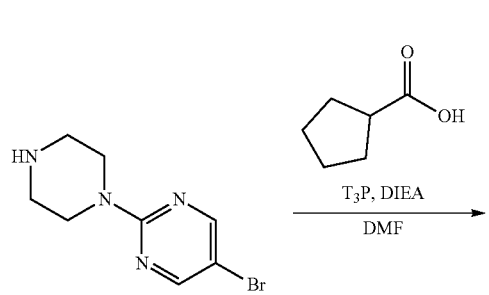

-continued

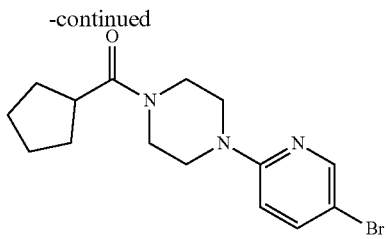

To a solution of cyclopentanecarboxylic acid (450 mg, 3.94 mmol) and 5-bromo-2-(piperazin-1-yl)pyrimidine (954.53 mg, 3.94 mmol) in DMF (10 mL) was added T$_3$P (3.76 g, 5.91 mmol, 50% purity) and DIEA (1.53 g, 11.83 mmol), the reaction mixture was stirred at 25° C. for 2 h. The mixture was poured into water (100 mL) and extracted with EA (40 mL×3). The organic layer was washed with water (100 mL×2) and brine (100 mL), then dried over Na$_2$SO$_4$ and concentrated. The residue was purified by column chromatography to afford (4-(5-bromopyridin-2-yl)piperazin-1-yl)(cyclopentyl)methanone (630 mg, 47.24% yield) as a yellow solid. MS: m/z=338.1 (M+1, ESI+).

5.9.16. Synthesis of Compound 112

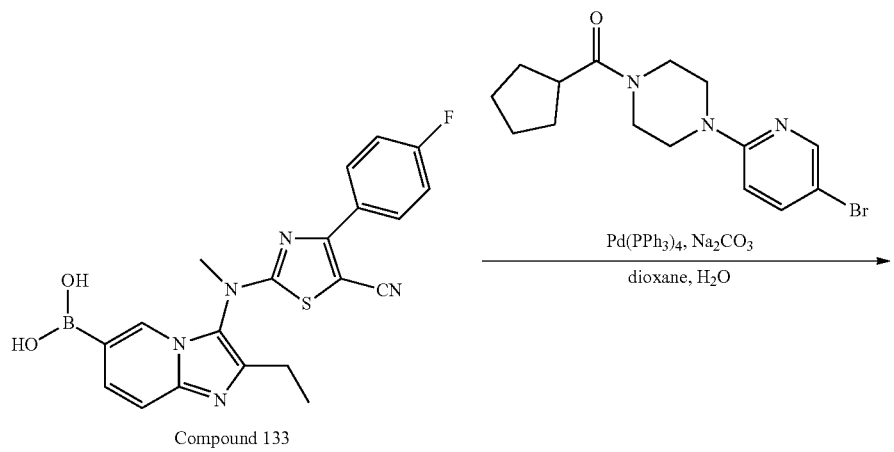

Compound 133

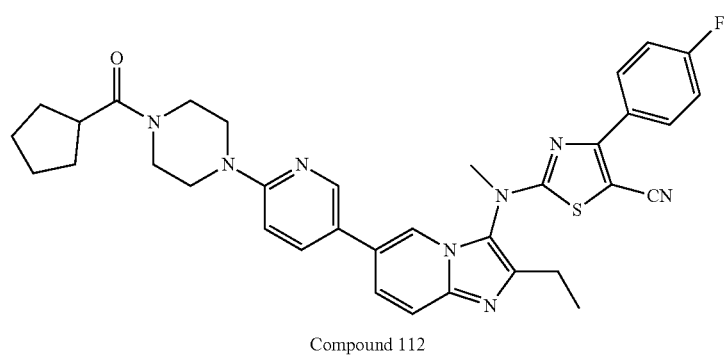

Compound 112

To a mixture of compound 133, (3-((5-cyano-4-(4-fluorophenyl)thiazol-2-yl)(methyl)amino)-2-ethylimidazo[1,2-a]pyridin-6-yl) boronic acid (498.17 mg, 1.18 mmol) and (4-(5-bromopyridin-2-yl)piperazin-1-yl)(cyclopentyl)methanone (400 mg, 1.18 mmol) in dioxane (8 mL) and water (2 mL) was added $Na_2CO_3$ (376.02 mg, 3.55 mmol) and $Pd(PPh_3)_4$ (136.65 mg, 118.26 umol), the reaction mixture was stirred at 100° C. for 2 h under $N_2$. The mixture was poured into water (60 mL) and extracted with EA (20 mL×2). The organic layer was washed by brine (100 mL), then dried over $Na_2SO_4$ and concentrated. The residue was purified by column chromatography to afford compound 112, 2-((6-(6-(4-(cyclopentanecarbonyl)piperazin-1-yl)pyridin-3-yl)-2-ethylimidazo[1,2-a]pyridin-3-yl)(methyl)amino)-4-(4-fluorophenyl)thiazole-5-carbonitrile (160 mg, 21.33% yield) as a white solid. 1H NMR (400 MHz, DMSO-$d_6$) δ 8.60-8.55 (m, 2H), 8.10 (s, 2H), 8.00-7.97 (m, 1H), 7.72-7.66 (dd, 2H), 7.44-7.39 (t, 2H), 6.94-6.92 (d, 1H), 3.65-3.53 (m, 11H), 3.03-2.99 (m, 1H), 2.70-2.64 (dd, 2H), 1.78-1.52 (m, 8H), 1.29-1.25 (t, 3H); MS: m/z=635.2 (M+1, ESI+); HRMS: 635.2710.

5.10. Example 9—Synthesis of Piperidine-linked Pyrimidine-type Compounds
General Scheme 9
Route A
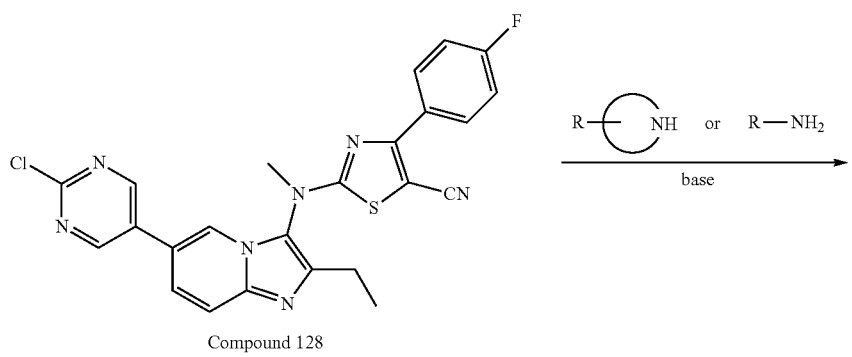
Compound 128
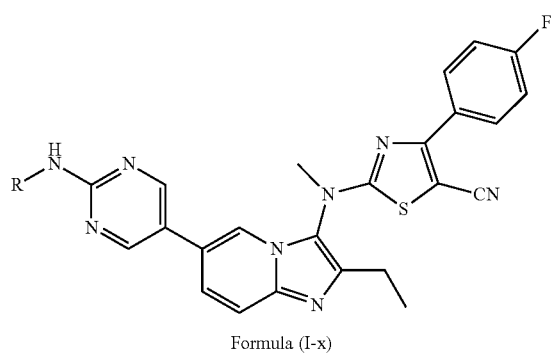
Formula (I-x)
or
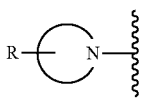
Formula (I-y)
Route B
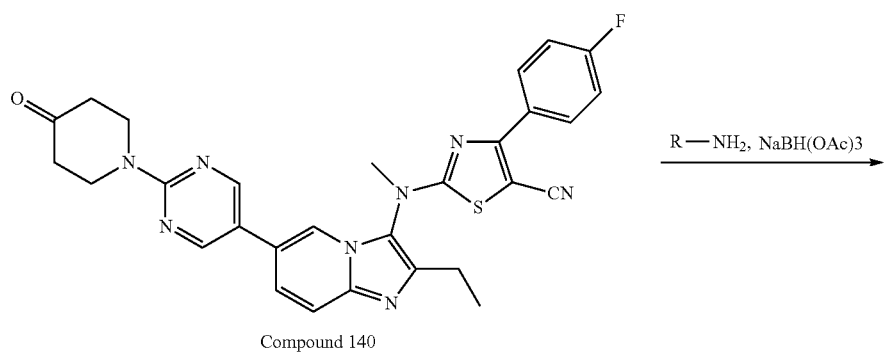
Compound 140

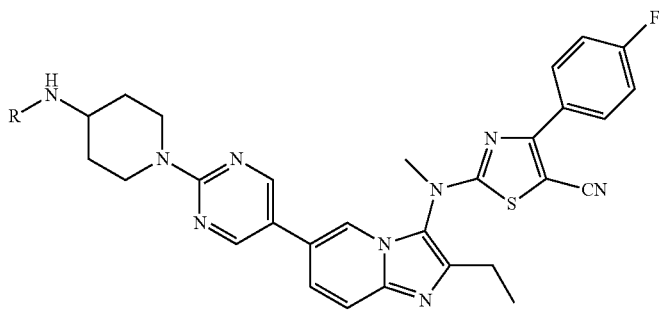
Formula (I-z)
Route C
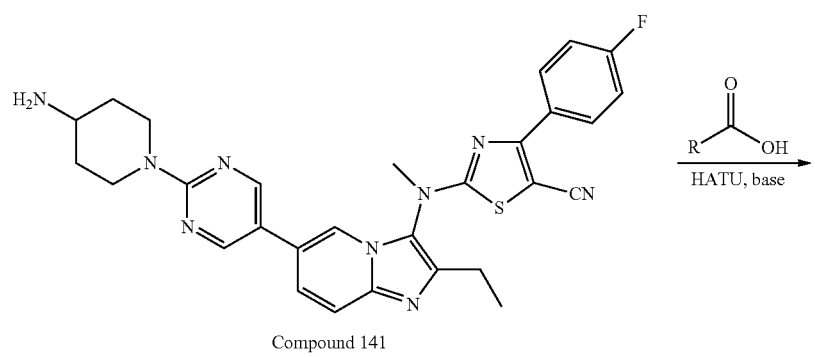
Compound 141
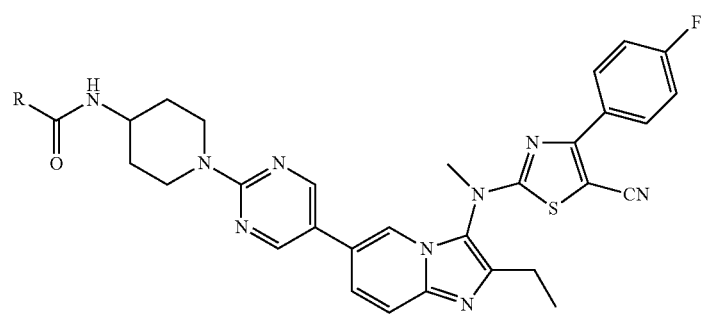
Formula (I-aa)
Route D
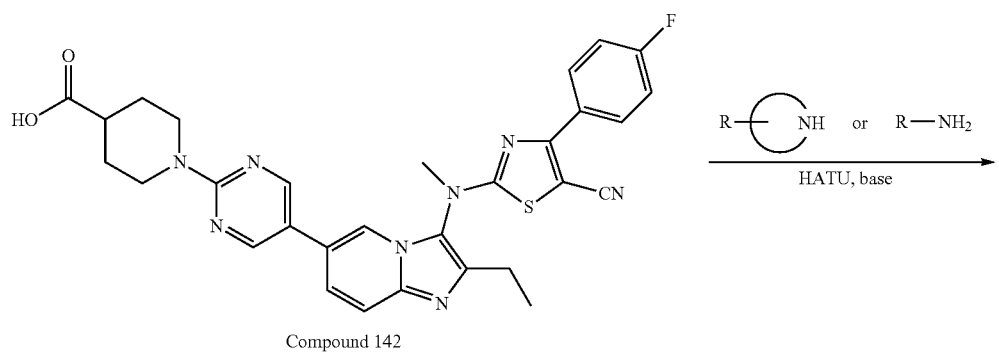
Compound 142

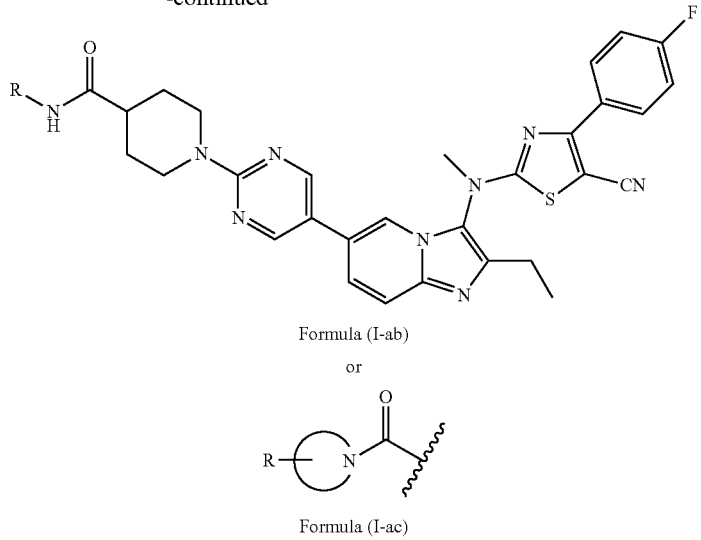

Formula (I-ab)

or

Formula (I-ac)

5.10.1. Synthesis of Compound 140—Method 1

5.10.2. Synthesis of Compound 140—Method 2

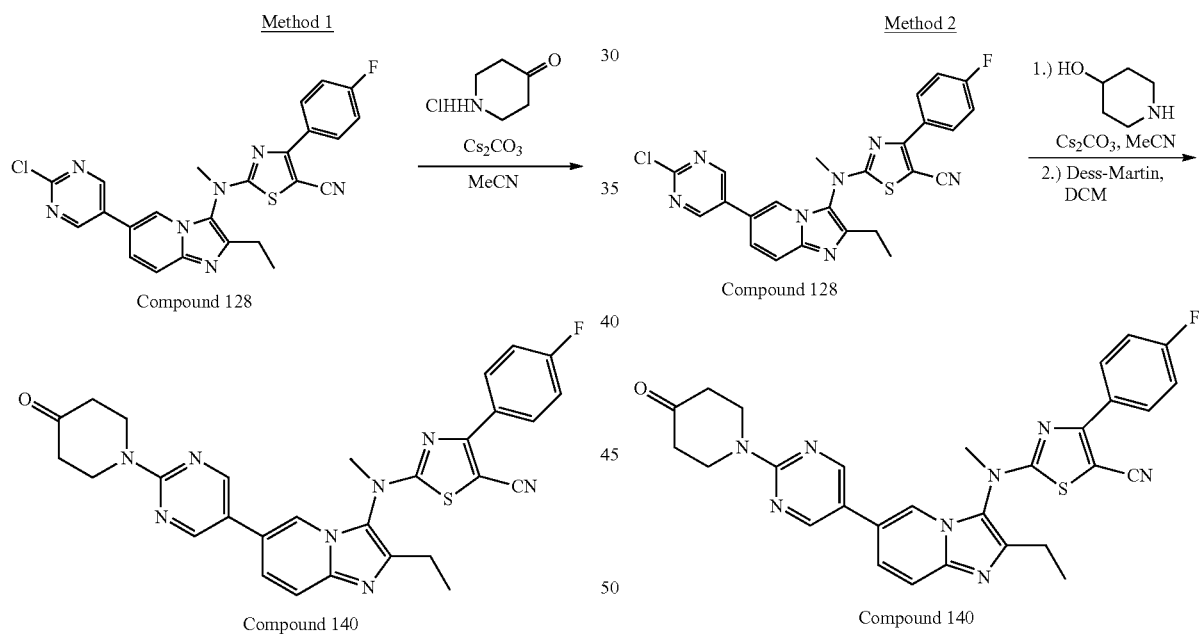

To a solution of compound 128, 2-((6-(2-chloropyrimidin-5-yl)-2-ethylimidazo[1,2-a]pyridin-3-yl)(methyl)amino)-4-(4-fluoro phenyl)thiazole-5-carbonitrile (1 g, 2.04 mmol) and piperidin-4-one hydrochloride (415.12 mg, 3.06 mmol) in MeCN (20 mL) was added $Cs_2CO_3$ (2.66 mg, 8.16 mmol), the reaction mixture was stirred at 80° C. for 16 h. The reaction mixture was concentrated under reduced pressure and the residue was purified by column chromatography to afford compound 140, 2-((2-ethyl-6-(2-(4-oxopiperidin-1-yl)pyrimidin-5-yl)imidazo[1,2-a]pyridin-3-yl)(methyl)amino)-4-(4-fluorophenyl)thiazole-5-carbonitrile (440 mg, 39.01% yield) as a yellow solid. MS: m/z=553. (M+1, ESI+).

Step One:

To a solution of compound 128, 2-((6-(2-chloropyrimidin-5-yl)-2-ethylimidazo[1,2-a]pyridin-3-yl)(methyl)amino)-4-(4-fluorophenyl) thiazole-5-carbonitrile (500 mg, 1.02 mmol) and piperidin-4-ol (150 mg, 1.48 mmol) in MeCN (50 mL) was added $Cs_2CO_3$ (980 mg, 3.01 mmol), the resulting mixture was stirred 70° C. for 16 h. The mixture was concentrated under reduced pressure and the residue was purified by column chromatography to afford 2-((2-ethyl-6-(2-(4-hydroxypiperidin-1-yl)pyrimidin-5-yl) imidazo[1,2-a]pyridin-3-yl)(methyl)amino)-4-(4-fluorophenyl) thiazole-5-carbonitrile (440 mg, 77.74% yield) as a yellow solid. MS: m/z=555.2 (M+1, ESI+).

Step Two:

To a solution of 2-((2-ethyl-6-(2-(4-hydroxypiperidin-1-yl)pyrimidin-5-yl)imidazo[1,2-a]pyridin-3-yl)(methyl)amino)-4-(4-fluorophenyl)thiazole-5-carbonitrile (470 mg, 847.40 umol) in DCM (20 mL) was added Dess-Martin (940 mg, 2.22 mmol) and stirred at 25° C. for 3 h. The reaction mixture was concentrated under reduced pressure and the residue was purified by column chromatography to afford compound 140, 2-((2-ethyl-6-(2-(4-oxopiperidin-1-yl)pyrimidin-5-yl)imidazo[1,2-a] pyridin-3-yl)(methyl)amino)-4-(4-fluorophenyl)thiazole-5-carbonitrile (463 mg, 98.93% yield) as a yellow solid. MS: m/z=553.4 (M+1, ESI+).

5.10.3. Synthesis of Compound 141 Hydrochloride (997.50 mg, 3.06 mmol). The reaction mixture was stirred at 80° C. for 24 h. The reaction mixture was filtered, the filtrate was concentrated under reduced pressure and the residue was purified by Prep-HPLC to afford tert-butyl (1-(5-(3-((5-cyano-4-(4-fluorophenyl)thiazol-2-yl)(methyl)amino)-2-ethylimidazo[1,2-a] pyridine-6-yl)pyrimidin-2-yl)piperidin-4-yl)carbamate (572.1 mg, 85.73% yield) as a yellow solid. MS: m/z=654.2 (M+1, ESI+).

Step Two:

To a solution of tert-butyl (1-(5-(3-((5-cyano-4-(4-fluorophenyl)thiazol-2-yl)(methyl)amino)-2-ethyl imidazo[1,2-a] pyridin-6-yl)pyrimidin-2-yl)piperidin-4-yl)carbamate (572.1 mg, 855.43 umol) in EA (5 mL) was added 3M HCl in EA (3 M, 5 mL), the reaction mixture was stirred at 25°

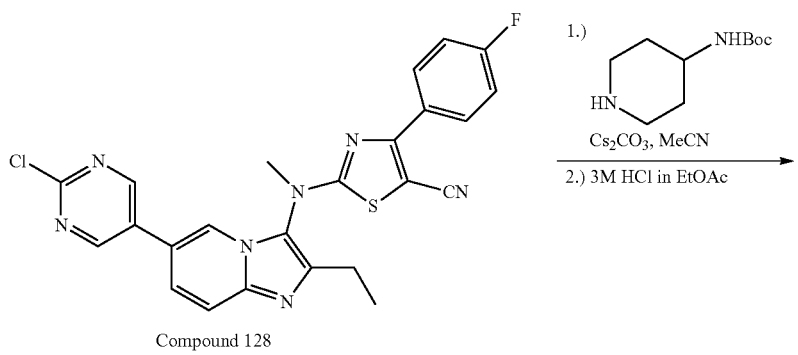

Compound 128

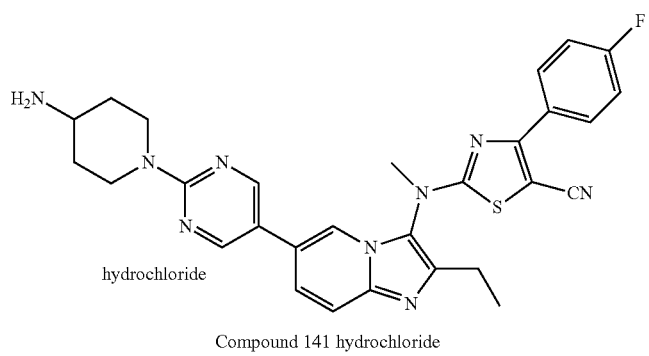

Compound 141 hydrochloride

Step One:

To a solution of compound 128, 2-((6-(2-chloropyrimidin-5-yl)-2-ethylimidazo[1,2-a]pyridin-3-yl)(methyl)amino)-4-(4-fluorophenyl) thiazole-5-carbonitrile (500 mg, 1.02 mmol) and tert-butyl piperidin-4-ylcarbamate (613.15 mg, 3.06 mmol) in MeCN (30 mL) was added Cs₂CO₃

C. for 1 h. The excess of solvent was removed under reduced pressure to afford compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (501.2 mg, 96.82% yield) as a yellow solid. MS: m/z=554.3 (M+1, ESI+).

5.10.4. Synthesis of Compound 142

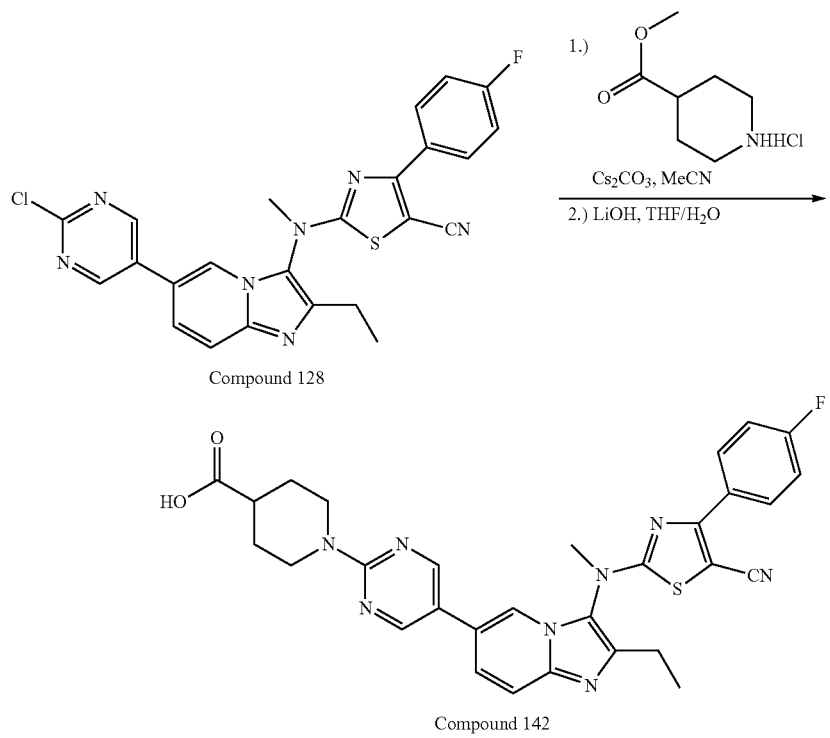

Step One:

To a solution of compound 128, 2-((6-(2-chloropyrimidin-5-yl)-2-ethylimidazo[1,2-a]pyridin-3-yl)(methyl)amino)-4-(4-fluorophenyl) thiazole-5-carbonitrile (700 mg, 1.43 mmol) and methyl piperidine-4-carboxylate hydrochloride (384.99 mg, 2.14 mmol) in MeCN (10 mL) was added $Cs_2CO_3$ (1.40 g, 4.29 mmol), the reaction mixture was stirred at 25° C. for 3 h. The reaction mixture was evaporated under reduce pressure and the residue was purified by column chromatography to afford methyl 1-(5-(3-((5-cyano-4-(4-fluorophenyl)thiazol-2-yl)(methyl)amino)-2-ethylimidazo [1,2-a]pyridin-6-yl) pyrimidin-2-yl)piperidine-4-carboxylate (750 mg, 87.98% yield) as a yellow solid. MS: m/z=597.1 (M+1, ESI+).

Step Two:

To a solution of methyl 1-(5-(3-((5-cyano-4-(4-fluorophenyl)thiazol-2-yl)(methyl)amino)-2-ethyl imidazo[1,2-a]pyridin-6-yl)pyrimidin-2-yl)piperidine-4-carboxylate (750 mg, 1.26 mmol) in THF (10 mL) and $H_2O$ (10 mL) was added LiOH (90.31 mg, 3.77 mmol). The reaction mixture was stirred at 40° C. for 3 h. The reaction mixture was adjusted to pH 5-6 with 2M HCl and extracted with DCM (20 mL×3), the combined organic layers were washed with brine (100 mL), dried over $Na_2SO_4$ and concentrated. The residue was purified by column chromatography to afford compound 142 1-(5-(3-((5-cyano-4-(4-fluorophenyl)thiazol-2-yl)(methyl)amino)-2-ethylimidazo[1,2-a]pyridin-6-yl)pyrimidin-2-yl) piperidine-4-carboxylic acid (600 mg, 81.93% yield) as a yellow solid. MS: m/z=583.3 (M+1, ESI+).

5.10.5. Synthesis of 1-(piperidin-4-ylamino)cyclopropane-1-carbonitrile

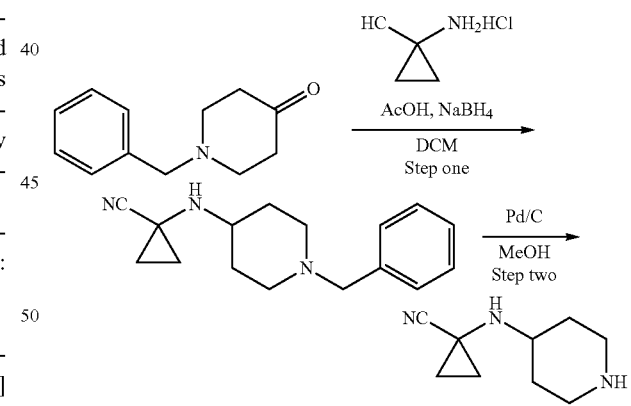

Step One:

To a solution of 1-benzylpiperidin-4-one (1 g, 5.28 mmol) and 1-aminocyclopropane-1-carbonitrile hydrochloride (939.73 mg, 7.93 mmol) in DCM (10 mL) was added AcOH (two drops), the reaction mixture was stirred at 25° C. for 16 h. Then $NaBH_4$ (2.00 g, 52.84 mmol) was added and stirred at 25° C. for 3 h. The reaction mixture was poured into water (50 mL) and extracted with DCM (10 mL×3). The combined organic layers were dried over $Na_2SO_4$ and concentrated under reduced pressure and purified by silica gel column to afford 1-((1-benzylpiperidin-4-yl)amino)cyclo propane-1-carbonitrile (1.05 g, 77.74% yield) as a yellow oil. MS: m/z=256.2 (M+1, ESI+).

Step Two:

To a solution of 1-((1-benzylpiperidin-4-yl)amino)cyclopropane-1-carbonitrile (500 mg, 1.96 mmol) in MeOH (5 mL) was added Pd/C (231.89 mg, 1.96 mmol), the reaction mixture was stirred at 25° C. for 5 h under $H_2$. The reaction mixture was filtered and the filtrate was evaporated under reduce pressure to afford 1-(piperidin-4-ylamino)cyclopropane-1-carbonitrile (600 mg, crude) as a yellow oil which was used for next step without further purification. MS: m/z=166.2 (M+1, ESI+).

5.10.6. Synthesis of Compound 17

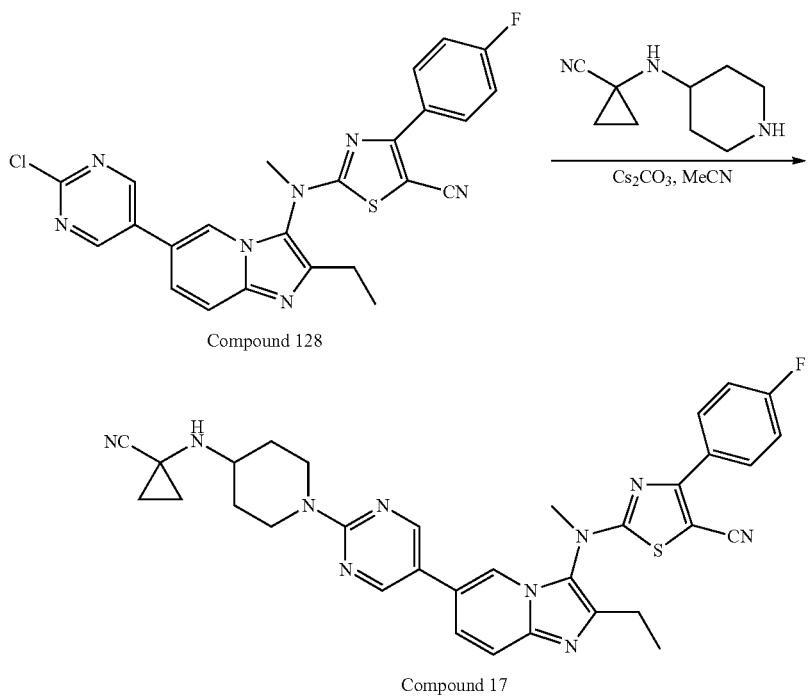

To a solution of compound 128, 2-((6-(2-chloropyrimidin-5-yl)-2-ethylimidazo[1,2-a]pyridin-3-yl)(methyl)amino)-4-(4-fluoro phenyl)thiazole-5-carbonitrile (150 mg, 306.15 umol) and 1-(piperidin-4-ylamino) cyclopropane-1-carbonitrile (101.17 mg, 612.3 umol) in MeCN (10 mL) was added $Cs_2CO_3$ (299.25 mg, 918.45 umol), the reaction mixture was stirred at 25° C. for 3 h. The reaction mixture was filtered, the filtrate was concentrated under reduced pressure and the residue was purified by Prep-HPLC to afford compound 17, 2-((6-(2-(4-((1-cyanocyclopropyl)amino)piperidin-1-yl)pyrimidin-5-yl)-2-ethylimidazo[1,2-a]pyridin-3-yl)(methyl)amino)-4-(4-fluorophenyl)thiazole-5-carbonitrile (42 mg, 22.17% yield) as a white solid. $^1$H NMR (400 MHz, DMSO-$d_6$) δ 8.75 (s, 2H), 8.64 (s, 1H), 8.10-8.07 (t, 2H), 7.69 (s, 2H), 7.44-7.40 (t, 2H), 4.51-4.47 (d, 2H), 3.63 (s, 3H), 3.45 (d, 1H), 3.18-3.12 (t, 2H), 3.04 (s, 1H), 2.70-2.64 (dd, 2H), 1.93-1.89 (dd, 2H), 1.28-1.17 (m, 7H), 0.95-0.92 (m, 2H), MS: m/z=619.4 (M+1, ESI+).

5.10.7. Synthesis of Compound 18

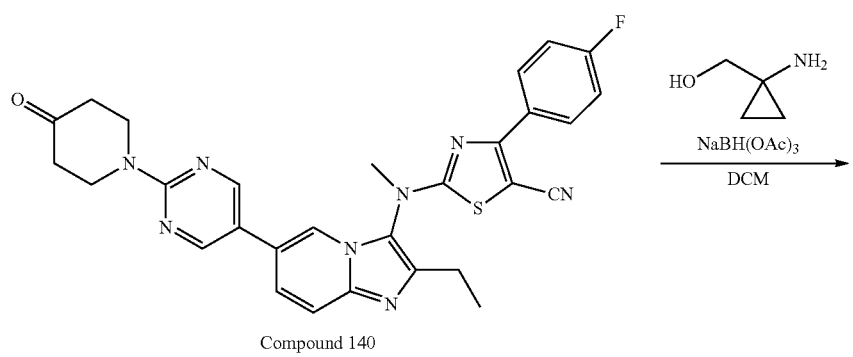

-continued

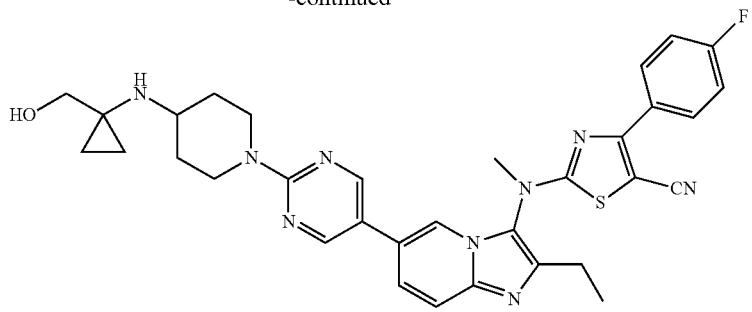

Compound 18

To a solution of compound 140, 2-((2-ethyl-6-(2-(4-oxopiperidin-1-yl)pyrimidin-5-yl)imidazo[1,2-a]pyridin-3-yl)(methyl)amino)-4-(4-fluorophenyl)thiazole-5-carbonitrile (150 mg, 271.43 umol) and (1-amino cyclopropyl) methanol hydrochloride (50.32 mg, 407.15 umol) in DCM (5 mL) was added NaBH(OAc)₃ (115.05 mg, 542.86 umol). The mixture was stirred at 25° C. for 24 h. The resulting solution was quenched by saturated NH₄Cl (30 mL) and extracted with DCM (30 mL×3), the combined organic layers were washed with water (30 mL×2) and brine (30 mL), dried over Na₂SO₄ and concentrated under reduced pressure. The residue was purified by Prep-HPLC to afford compound 18, 2-((2-ethyl-6-(2-(4-((1-(hydroxymethyl)cyclopropyl)amino)piperidin-1-yl)pyrimidin-5-yl)imidazo[1,2-a]pyridin-3-yl) (methyl)amino)-4-(4-fluorophenyl)thiazole-5-carbonitrile (81 mg, 47.84% yield) as a white solid. ¹H NMR (400 MHz, DMSO-d₆) δ 8.74 (s, 2H), 8.64 (s, 1H), 8.11-8.07 (t, 2H), 7.69 (s, 2H), 7.44-7.39 (t, 2H), 4.51-4.48 (t, 3H), 3.63 (s, 3H), 3.36-3.34 (d, 2H), 3.11-3.05 (m, 3H), 2.70-2.64 (dd, 2H), 2.20 (bs, 1H), 1.85-1.82 (d, 2H), 1.29-1.11 (m, 5H), 0.40 (s, 4H); MS: m/z=624.3 (M+1, ESI+).

5.10.8. Synthesis of Compound 19

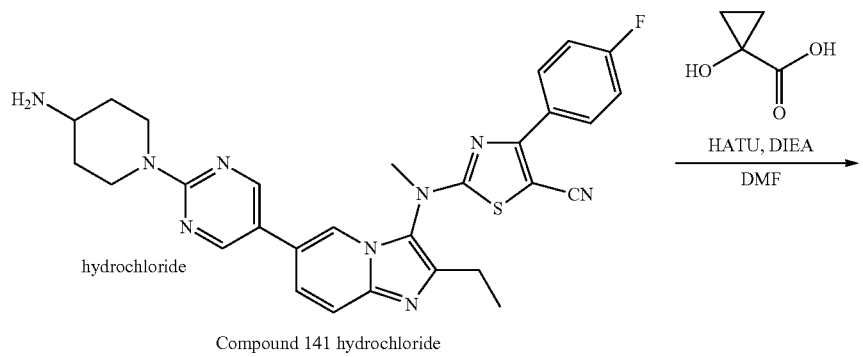

Compound 141 hydrochloride

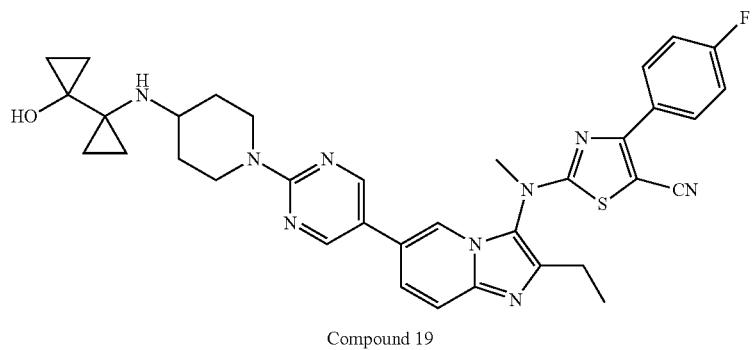

Compound 19

To a solution of compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (250 mg, 423.65 umol) and 1-hydroxycyclopropane-1-carboxylic acid (64.87 mg, 635.47 umol) in DCM (20 mL) was added HATU (241.62 mg, 635.47 umol) and DIEA (164.26 mg, 1.27 mmol), the reaction mixture was stirred at 25° C. for 16 h. The reaction mixture was poured into water (50 mL) and extracted with DCM (10 mL×3). The combined organic layers were dried over $Na_2SO_4$ and concentrated under reduced pressure and purified by Prep-HPLC to afford compound 19, N-(1-(5-(3-((5-cyano-4-(4-fluorophenyl) thiazol-2-yl)(methyl)amino)-2-ethylimidazo[1,2-a]pyridin-6-yl)pyrimidin-2-yl)piperidin-4-yl)-1-hydroxycyclopropane-1-carboxamide (120 mg, 44.46% yield) as a white solid. $^1$H NMR (400 MHz, DMSO-$d_6$) δ 8.77 (s, 2H), 8.65 (s, 1H), 8.11-8.07 (t, 2H), 7.73-7.70 (m, 3H), 7.44-7.40 (t, 2H), 6.17 (s, 1H), 4.68-4.64 (d, 2H), 3.93 (s, 1H), 3.63 (s, 3H), 3.04-2.99 (t, 2H), 2.70-2.64 (dd, 2H), 1.78-1.74 (dd, 2H), 1.53-1.44 (m, 2H), 1.28-1.25 (t, 3H), 1.02-0.99 (dd, 2H), 0.82-0.79 (dd, 2H); MS: m/z=638.3 (M+1, ESI+).

5.10.9. Synthesis of Compound 20

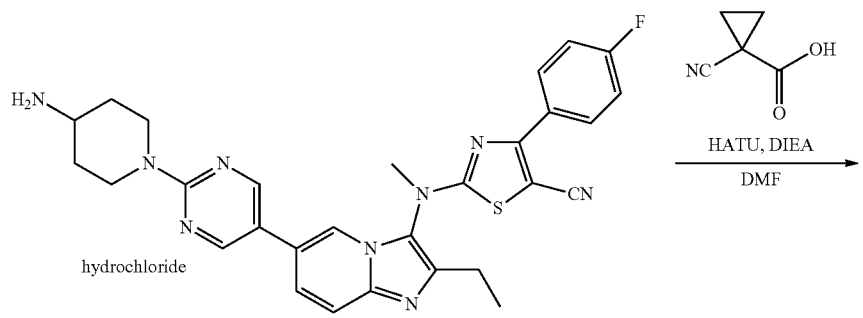

Compound 141 hydrochloride

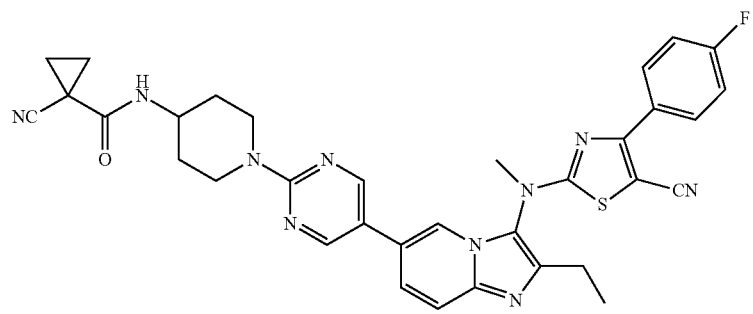

Compound 20

To a solution of compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (250 mg, 423.65 umol), and 1-cyanocyclopropane-1-carboxylic acid (63.54 mg, 571.92 umol) in DCM (20 mL) was added HATU (217.46 mg, 571.92 umol) and DIEA (147.83 mg, 1.14 mmol), the reaction mixture was stirred at 25° C. for 16 h. The reaction mixture was poured into water (50 mL) and extracted with DCM (10 mL×3). The combined organic layers were dried over $Na_2SO_4$ and concentrated under reduced pressure and purified by Prep-HPLC to afford compound 20, 1-cyano-N-(1-(5-(3-((5-cyano-4-(4-fluoro phenyl)thiazol-2-yl)(methyl)amino)-2-ethylimidazo[1,2-a]pyridin-6-yl)pyrimidin-2-yl) piperidin-4-yl) cyclopropane-1-carboxamide (130 mg, 23.38% yield) as a white solid. $^1$H NMR (400 MHz, DMSO-$d_6$) δ8.78 (s, 2H), 8.66 (s, 1H), 8.11-8.07 (t, 2H), 7.97-7.95 (d, 1H), 7.70 (s, 2H), 7.44-7.40 (t, 2H), 4.68-4.64 (d, 2H), 3.92-3.90 (m, 1H), 3.63 (s, 3H), 3.01-2.95 (t, 2H), 2.70-2.64 (dd, 2H), 1.75-1.73 (d, 2H), 1.55-1.46 (m, 6H), 1.28-1.25 (t, 3H); MS: m/z=647.2 (M+1, ESI+).

5.10.10. Synthesis of Compound 68 Formate stirred at 25° C. for 16 h. Then NaBH(OAc)$_3$ (153.41 mg, 723.82 umol) was added to the above solution and stirred at 25° C. for another 3 h. The reaction mixture was concentrated under reduced pressure and the residue was purified by column chromatography to afford tert-butyl3-((1-(5-(3-((5-cyano-4-(4-fluorophenyl)thiazol-2-yl)(methyl)amino)-2-ethylimidazo[1,2-a]pyridin-6-yl) pyrimidin-2-yl)piperidin-4-yl)amino)azetidine-1-carboxylate (145 mg, 56.52% yield) as a yellow solid. MS: m/z=709.3 (M+1, ESI+).

Step Two:

To a solution of tert-butyl 3-((1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)amino) azetidine-1-carboxylate (140 mg, 197.50 umol) in DCM (5 mL) was added TFA (5 mL). The reaction mixture was stirred at 25° C. for 2 h. The reaction mixture was concentrated under reduced pressure and the residue was purified by Prep-HPLC (Waters Xbridge C18 10 um OBD 19*250 mm, A: 0.1% FA in water; B: CH$_3$CN, 5% to 95%) in FA condition to afford compound 68 formate, 2-((6-(2-(4-(azetidin-3-ylamino)piperidin-1-yl)pyrimidin-5-yl)-2-ethylimidazo[1,2-a]pyridin-3-yl)(methyl)amino)-4-(4-fluorophenyl)thiazole-5-carbonitrile formate (75 mg, 58.14% yield) as a

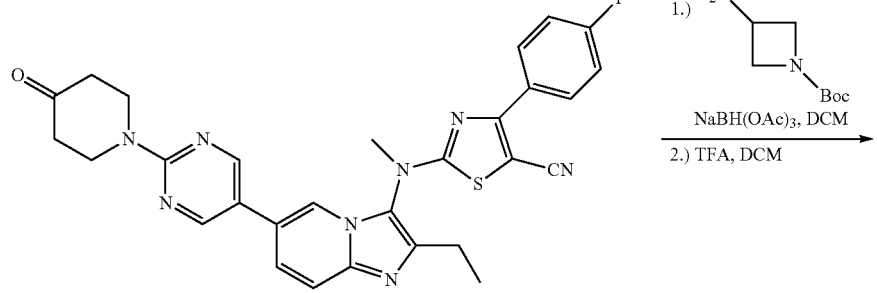

Compound 140

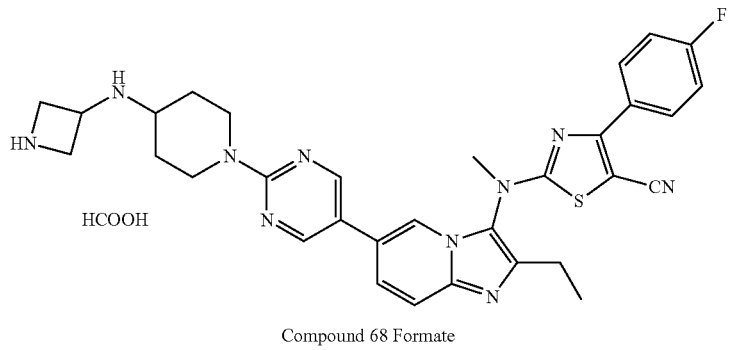

Compound 68 Formate

Step One:

A mixture of compound 140, 2-((2-ethyl-6-(2-(4-oxopiperidin-1-yl)pyrimidin-5-yl)imidazo[1,2-a]pyridin-3-yl)(methyl)amino)-4-(4-fluorophenyl)thiazole-5-carbonitrile (200 mg, 361.91 umol) and tert-butyl 3-aminoazetidine-1-carboxylate (74.80 mg, 434.29 umol) in DCM (5 mL) was white solid. $^1$H NMR (400 MHz, DMSO-$d_6$) δ 8.75 (s, 2H), 8.64 (s, 1H), 8.20 (s, 1H), 8.11-8.07 (t, 2H), 7.69 (s, 2H), 7.44-7.40 (t, 2H), 4.54-4.51 (d, 2H), 4.00 (s, 2H), 3.78-3.63 (m, 7H), 3.06-3.00 (t, 2H), 2.70-2.64 (dd, 3H), 1.77-1.74 (d, 2H), 1.28-1.25 (t, 3H), 1.15-1.13 (d, 2H); MS: m/z=609.2 (M+1, ESI+).

5.10.11. Synthesis of Compound 68 Hydrochloride

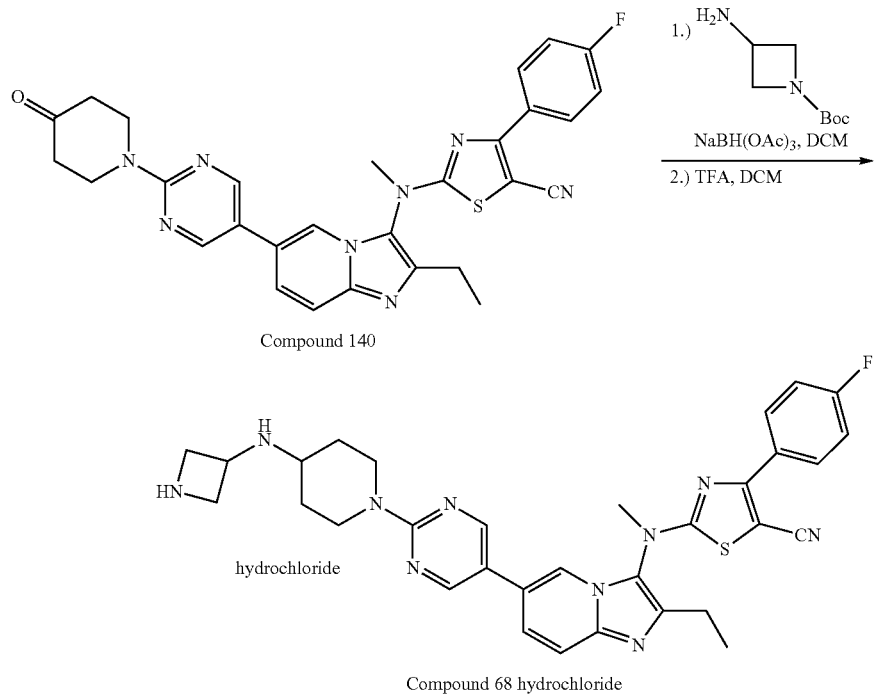

Step One

A mixture of compound 140, 2-((2-ethyl-6-(2-(4-oxopiperidin-1-yl)pyrimidin-5-yl)imidazo[1,2-a]pyridin-3-yl)(methyl)amino)-4-(4-fluorophenyl)thiazole-5-carbonitrile (800 mg, 1.45 mmol) and tert-butyl 3-aminoazetidine-1-carboxylate (74.80 mg, 434.29 umol) in DCM (5 mL) was stirred at 25° C. for 16 h. Then NaBH(OAc)$_3$ (612 mg, 1.74 mmol) was added to the above solution and stirred at 25° C. for another 3 h. The reaction mixture was concentrated under reduced pressure and the residue was purified by column chromatography to afford tert-butyl3-((1-(5-(3-((5-cyano-4-(4-fluorophenyl)thiazol-2-yl)(methyl)amino)-2-ethylimidazo[1,2-a]pyridin-6-yl) pyrimidin-2-yl)piperidin-4-yl)amino)azetidine-1-carboxylate (800 mg, 78.4% yield) as a yellow solid. MS: m/z=709.3 (M+1, ESI+).

Step Two

To a solution of tert-butyl 3-((1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)amino)azetidine-1-carboxylate (800 mg, 1.13 mmol) in DCM (5 mL) was added TFA (5 mL). The reaction mixture was stirred at 25° C. for 2 h. The reaction mixture was concentrated under reduced pressure and the residue was purified by Prep-HPLC (Waters Xbridge C18 10 um OBD 19*250 mm, A: 0.05% HCl in water; B: CH$_3$CN, 5% to 95%) in HCl condition to afford compound 68 HCl, 2-((6-(2-(4-(azetidin-3-ylamino)piperidin-1-yl)pyrimidin-5-yl)-2-ethylimidazo[1,2-a]pyridin-3-yl)(methyl)amino)-4-(4-fluorophenyl)thiazole-5-carbonitrile hydrochloride (125 mg, 15.41% yield) as a white solid. $^1$H NMR (400 MHz, DMSO-d$_6$) δ 8.98 (s, 1H), 8.87 (s, 2H), 8.36-8.34 (d, 1H), 8.11-8.08 (d, 1H), 8.02-7.99 (m, 2H), 7.21-7.17 (t, 2H), 4.90 (s, 2H), 4.64-4.54 (m, 3H), 4.46-4.41 (m, 2H), 3.75 (s, 3H), 3.66-3.60 (m, 1H), 3.23-3.16 (t, 2H), 2.99-2.94 (dd, 2H), 2.24-2.21 (d, 2H), 1.81-1.73 (m, 2H), 1.44-1.40 (t, 3H); MS: m/z=609.2 (M+1, ESI+).

5.10.12. Synthesis of Compound 69 Formate

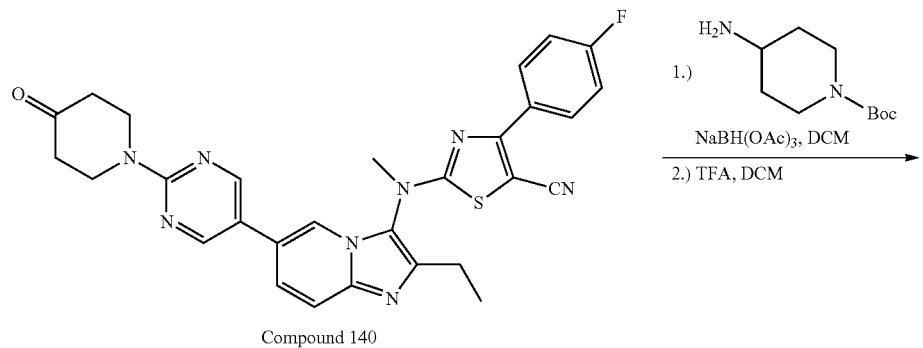

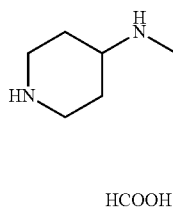
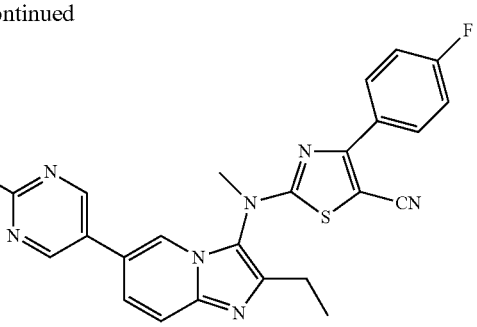

Compound 69 Formate

Step One:

A mixture of compound 140, 2-((2-ethyl-6-(2-(4-oxopiperidin-1-yl)pyrimidin-5-yl)imidazo[1,2-a]pyridin-3-yl)(methyl)amino)-4-(4-fluorophenyl)thiazole-5-carbonitrile (200 mg, 361.91 umol) and tert-butyl4-amino piperidine-1-carboxylate (86.98 mg, 434.29 umol) in DCM (5 mL) was stirred at 25° C. for 16 h. Then NaBH(OAc)₃ (153.41 mg, 723.82 umol) was added to the above solution and stirred at 25° C. for another 3 h. The reaction mixture was concentrated under reduced pressure and the residue was purified by column chromatography to afford tert-butyl 4-((1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)amino)piperidine-1-carboxylate (150 mg, 56.17% yield) as a yellow solid. MS: m/z=737.3 (M+1, ESI+).

Step Two:

To a solution of tert-butyl 4-((1-(5-(3-(((5-cyano-4-(4-fluorophenyl)thiazol-2-yl)(methyl)amino)-2-ethylimidazo[1,2-a]pyridin-6-yl)pyrimidin-2-yl)piperidin-4-yl)amino)piperidine-1-carboxylate (135 mg, 183.20 umol) in DCM (5 mL) was added TFA (5 mL). The reaction mixture was stirred at 25° C. for 2 h. The reaction mixture was concentrated under reduced pressure and the residue was purified by Prep-HPLC (Waters Xbridge C18 10 um OBD 19*250 mm, A: 0.1% FA in water; B: CH₃CN, 5% to 95%) in FA condition to afford compound 69 formate, 2-((2-ethyl-6-(2-(4-(piperidin-4-ylamino) piperidin-1-yl)pyrimidin-5-yl)imidazo[1,2-a]pyridin-3-yl)(methyl)amino)-4-(4-fluorophenyl)thiazole-5-carbonitrile formate (75 mg, 60% yield) as a white solid. ¹H NMR (400 MHz, DMSO-d₆) δ 8.80 (s, 2H), 8.66 (s, 1H), 8.11-8.07 (t, 2H), 7.71 (s, 2H), 7.44-7.40 (t, 2H), 4.75-4.72 (d, 2H), 3.63 (s, 3H), 3.46-3.32 (m, 5H), 3.02-2.89 (m, 5H), 2.70-2.65 (dd, 2H), 2.14-2.05 (m, 4H), 1.69-1.66 (d, 2H), 1.43-1.40 (d, 2H), 1.29-1.25 (t, 3H); MS: m/z=637.3 (M+1, ESI+).

5.10.13. Synthesis of Compound 69 Hydrochloride

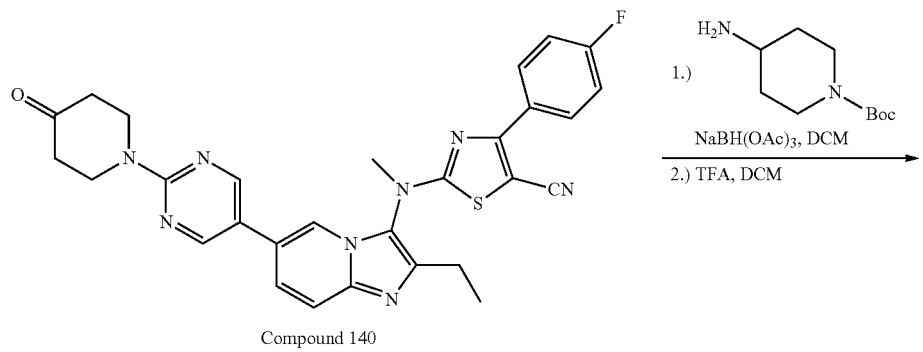

Compound 140

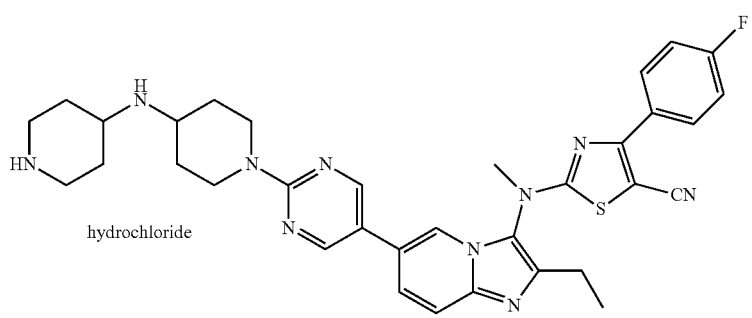

Compound 69 hydrochloride

Step One:

A mixture of 2-((2-ethyl-6-(2-(4-oxopiperidin-1-yl)pyrimidin-5-yl)imidazo[1,2-a]pyridin-3-yl) (methyl)amino)-4-(4-fluorophenyl)thiazole-5-carbonitrile (360 mg, 652 umol) and tert-butyl 4-aminopiperidine-1-carboxylate (156 mg, 782 umol) in DCM (5 mL) was stirred at 25° C. for 16 h. Then NaBH(OAc)$_3$ (207 mg, 978 umol) was added to the above solution and stirred at 25° C. for another 3 h. The reaction mixture was concentrated under reduced pressure and the residue was purified by column chromatography to afford tert-butyl 4-((1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)amino)piperidine-1-carboxylate (320 mg, 66.7% yield) as a yellow solid. MS: m/z=737.3 (M+1, ESI+).

Step Two:

To a solution of tert-butyl 4-((1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)amino) piperidine-1-carboxylate (320 mg, 435 umol) in DCM (5 mL) was added TFA (5 mL). The reaction mixture was stirred at 25° C. for 2 h. The reaction mixture was concentrated under reduced pressure and the residue was purified by Prep-HPLC (Waters Xbridge C18 10 um OBD 19*250 mm, A: 0.05% HCl in water; B: CH$_3$CN, 5% to 95%) in HCl condition to afford 2-((2-ethyl-6-(2-(4-(piperidin-4-ylamino) piperidin-1-yl)pyrimidin-5-yl)imidazo[1,2-a]pyridin-3-yl)(methyl)amino)-4-(4-fluorophenyl) thiazole-5-carbonitrile hydrochloride (250 mg, 77.1% yield) as a white solid. $^1$H NMR (400 MHz, DMSO-d$_6$) δ 9.75 (s, 2H), 9.44 (s, 1H), 9.10-9.05 (m, 2H), 8.87 (s, 2H), 8.40-8.37 (d, 1H), 8.13-8.11 (d, 1H), 8.03-7.99 (t, 2H), 7.42-7.38 (t, 2H), 4.83-4.80 (d, 2H), 3.67 (s, 3H), 3.51 (s, 2H), 3.37-3.34 (d, 2H), 3.03-2.85 (m, 6H), 2.27-2.24 (d, 2H), 2.18-2.15 (d, 2H), 1.97-1.89 (dd, 2H), 1.69-1.61 (dd, 2H), 1.36-1.32 (t, 3H); MS: m/z=637.4 (M+1, ESI+).

5.10.14. Synthesis of Compound 72 Hydrochloride

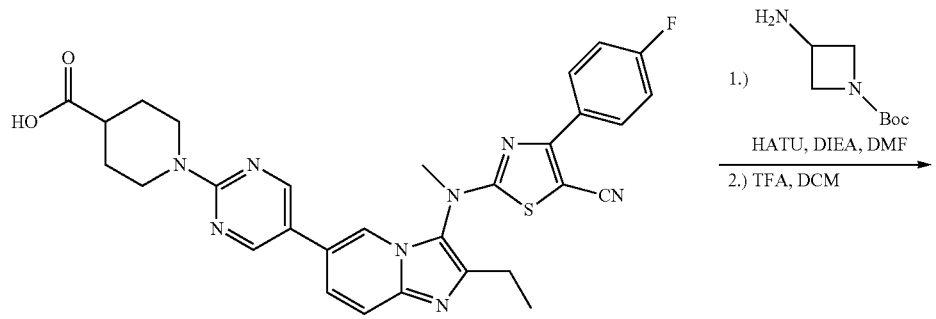

Compound 142

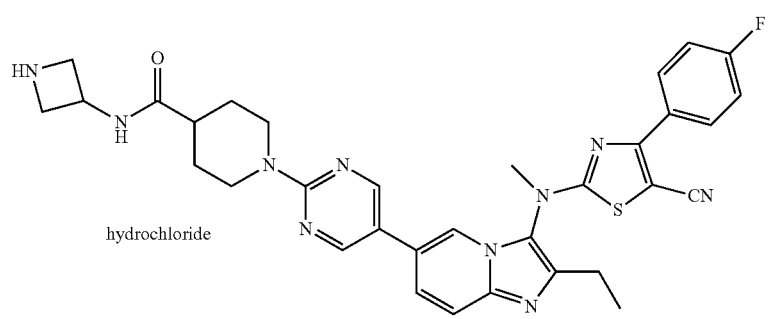

Compound 72 hydrochloride

Step One:

To a solution of compound 142 1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxylic acid (300 mg, 514.89 umol) and tert-butyl 3-aminoazetidine-1-carboxylate (88.68 mg, 514.89 umol) in DMF (10 mL) was added HATU (587.33 mg, 1.54 mmol) and DIEA (332.72 mg, 2.57 mmol), the reaction mixture was stirred at 25° C. for 16 h. The reaction mixture was poured into H$_2$O (100 mL) and extracted with EA (30 mL×3), the combined organic layers were washed with brine (100 mL), dried over Na$_2$SO$_4$ and concentrated. The residue was purified by column chromatography to afford tert-butyl 3-(1-(5-(3-((5-cyano-4-(4-fluorophenyl)thiazol-2-yl)(methyl)amino)-2-ethylimidazo[1,2-a]pyridin-6-yl) pyrimidin-2-yl)piperidine-4-carboxamido)azetidine-1-carboxylate (350 mg, 92.25% yield). MS: m/z=737.4 (M+1, ESI+).

Step Two:

To a solution of tert-butyl 3-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxamido) azetidine-1-carboxylate (350 mg, 474.99 umol) in DCM (10 mL) was added TFA (2 mL) and stirred at 25° C. for 3 h. The reaction mixture was evaporated under reduce pressure and the residue was purified by Prep-HPLC to afford compound 72 hydrochloride, N-(azetidin-3-yl)-1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxamide hydrochloride (160 mg, 52.90% yield) as a pale yellow solid. $^1$H NMR (400 MHz, DMSO-$d_6$) δ 9.55 (s, 1H), 9.42 (s, 1H), 9.12 (s, JH), 8.98-8.97 (d, 1H), 8.87 (s, 2H), 8.42-8.39 (d, 1H), 8.14-8.12 (d, 1H), 8.01 (s, 2H), 7.42-7.38 (t, 2H), 4.71-4.58 (m, 3H), 4.04-3.91 (m, 4H), 3.68 (s, 3H), 3.08-3.02 (t, 2H), 2.91-2.86 (m, 2H), 1.83-1.80 (m, 2H), 1.53-1.45 (m, 2H), 1.37-1.33 (t, 3H); MS: m/z=637.3 (M+1, ESI+).

5.10.15. Synthesis Compound 72

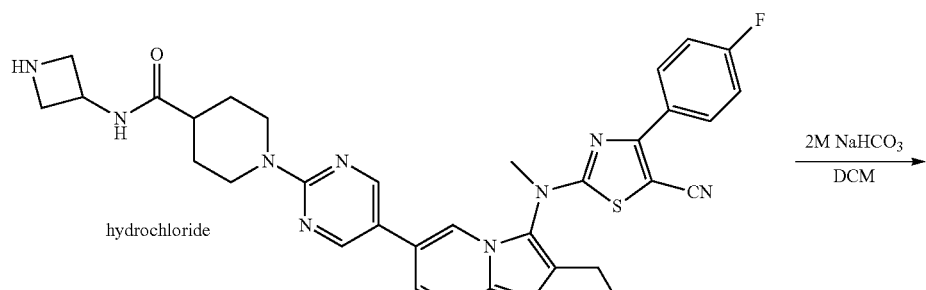

Compound 72 hydrochloride

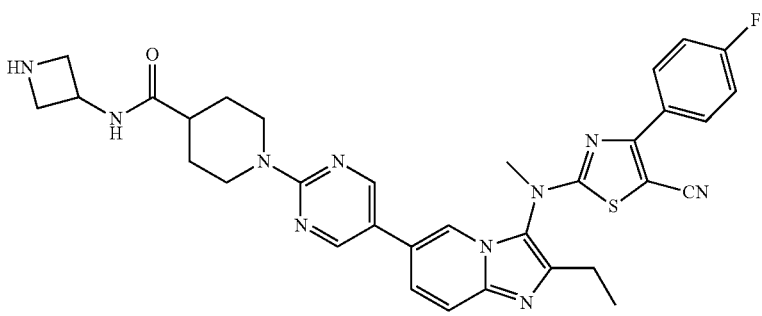

Compound 72

To a mixture of compound 72 hydrochloride. N-(azetidin-3-yl)-1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxamide hydrochloride (120 mg, 0.178 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 72, N-(azetidin-3-yl)-1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxamide (100 mg, 88.5% yield) as a white solid. $^1$H NMR (400 MHz, DMSO-$d_6$) δ 8.76 (s, 2H), 8.64 (s, 1H), 8.55-8.53 (m, 1H), 8.08-8.06 (t, 2H), 7.70 (s, 1H), 7.44-7.40 (t, 2H), 4.70-4.52 (m, 3H), 4.08-4.04 (m, 2H), 3.94-3.88 (m, 2H), 3.63 (s, 31H), 3.03-2.97 (m, 2H), 2.70-2.64 (m, 2H), 1.79-1.76 (m, 2H), 1.51-1.43 (m, 2H), 1.28-1.25 (t, 3H); MS: m/z=609.3 (M+1, ESI+).

5.10.16. Synthesis of Compound 73 Hydrochloride

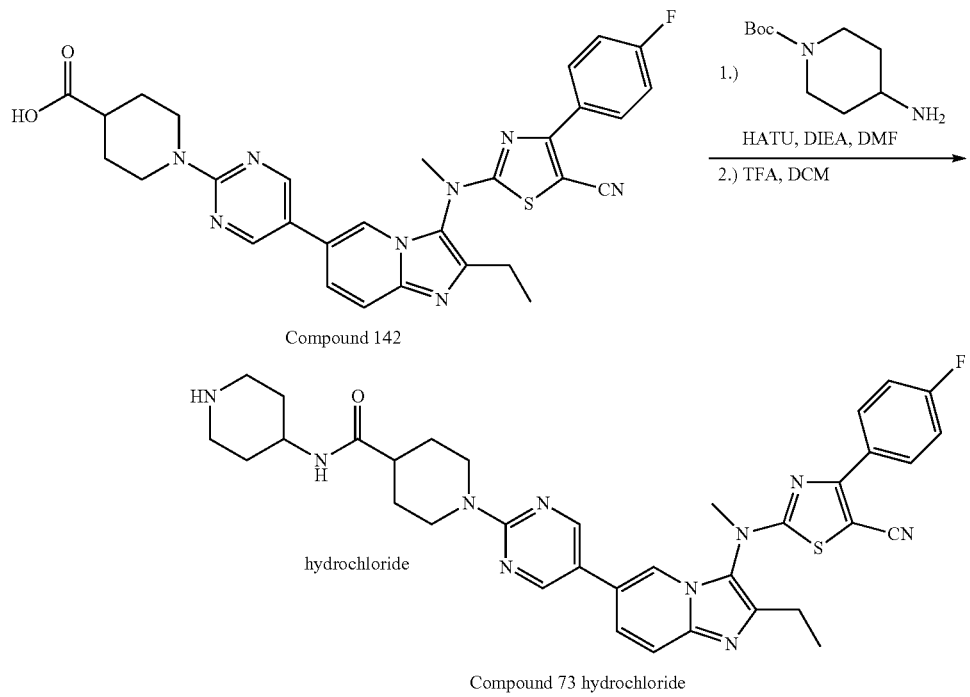

Compound 142

Compound 73 hydrochloride

Step One:

To a solution of compound 142, 1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxylic acid (300 mg, 514.89 umol) and tert-butyl 4-aminopiperidine-1-carboxylate (154.68 mg, 772.33 umol) in DMF (10 mL) was added HATU (587.33 mg, 1.54 mmol) and DIEA (332.72 mg, 2.57 mmol), the reaction mixture was stirred at 25° C. for 16 h. The reaction mixture was poured into H₂O (100 mL) and extracted with EA (30 mL×3), the combined organic layers were washed with brine (100 mL), dried over Na₂SO₄ and concentrated. The residue was purified by column chromatography to afford tert-butyl 4-(1-(5-(3-((5-cyano-4-(4-fluorophenyl)thiazol-2-yl)(methyl)amino)-2-ethylimidazo[1,2-a]pyridin-6-yl) pyrimidin-2-yl)piperidine-4-carboxamido)piperidine-1-carboxylate (300 mg, 76.14% yield). MS: m/z=765.4 (M+1, ESI+).

Step Two:

To a solution of tert-butyl 4-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxamido) piperidine-1-carboxylate (300 mg, 392.20 umol) in DCM (10 mL) was added TFA (2 mL) and stirred at 25° C. for 3 h. The reaction mixture was evaporated under reduce pressure and the residue was purified by Prep-HPLC to afford compound 73 hydrochloride, 1-(5-(3-((5-cyano-4-(4-fluorophenyl)thiazol-2-yl)(methyl)amino)-2-ethylimidazo [1,2-a] pyridin-6-yl)pyrimidin-2-yl)-N-(piperidin-4-yl)piperidine-4-carboxamide hydrochloride (160 mg, 61.37% yield) as a pale yellow solid. ¹H NMR (400 MHz, DMSO-d₆) δ 9.29 (s, 2H), 9.12 (s, 1H), 8.87 (s, 2H), 8.42-8.39 (d, 1H), 8.21-8.19 (d, 1H), 8.14-8.12 (d, 1H), 8.01 (s, 2H), 7.42-7.38 (t, 2H), 4.73-4.70 (d, 2H), 3.80-3.78 (d, 1H), 3.68 (s, 3H), 3.23-2.86 (m, 8H), 1.88-1.45 (m, 9H), 1.37-1.33 (t, 3H); MS: m/z=665.3 (M+1, ESI+)

5.10.17. Preparation of Compound 73

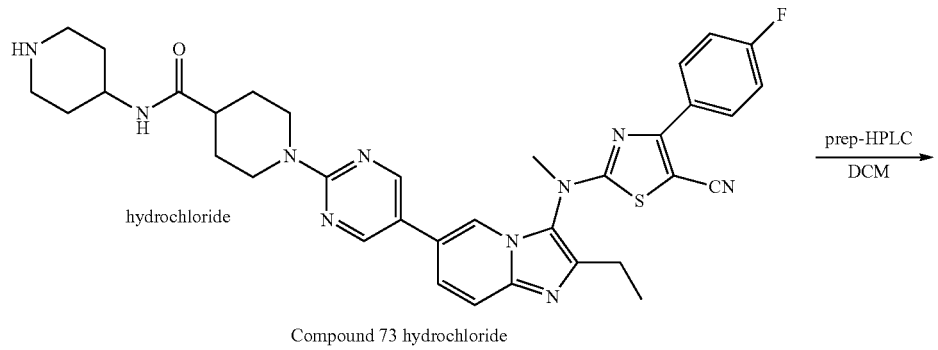

Compound 73 hydrochloride

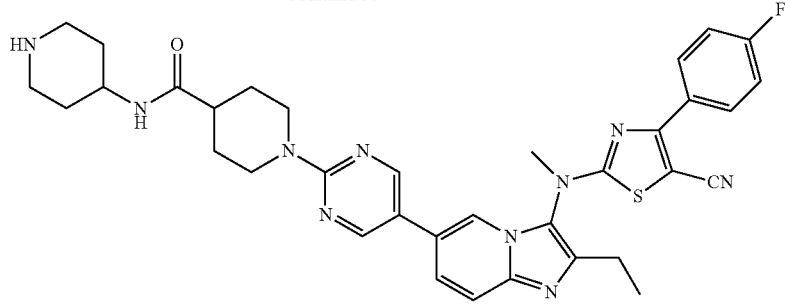

Compound 73

Compound 73 hydrochloride, 1-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl)piperidine-4-carboxamide hydrochloride (120 mg, 0.171 mmol) was purified by Prep-HPLC to afford compound 73, 1-(5-(3-((5-cyano-4-(4-fluorophenyl)thiazol-2-yl)(methyl)amino)-2-ethylimidazo[1,2-a]pyridin-6-yl)pyrimidin-2-yl)-N-(piperidin-4-yl)piperidine-4-carboxamide (70 mg, 61.40% yield) as a white solid. $^1$H NMR (400 MHz, DMSO-$d_6$) δ 8.76 (s, 2H), 8.65 (s, 1H), 8.10-8.07 (t, 2H), 7.73-7.69 (m, 3H), 7.44-7.40 (t, 2H), 4.70-4.67 (d, 2H), 3.63 (s, 3H), 3.58-3.52 (m, 1H), 2.96-2.89 (m, 4H), 2.70-2.64 (dd, 2H), 2.47-2.41 (m, 2H), 1.72-1.69 (d, 2H), 1.64-1.62 (d, 2H), 1.49-1.45 (m, 2H), 1.28-1.18 (m, 7H); MS: m/z=665.1 (M+1, ESI+).

5.10.18. Synthesis of Compound 74 Formate

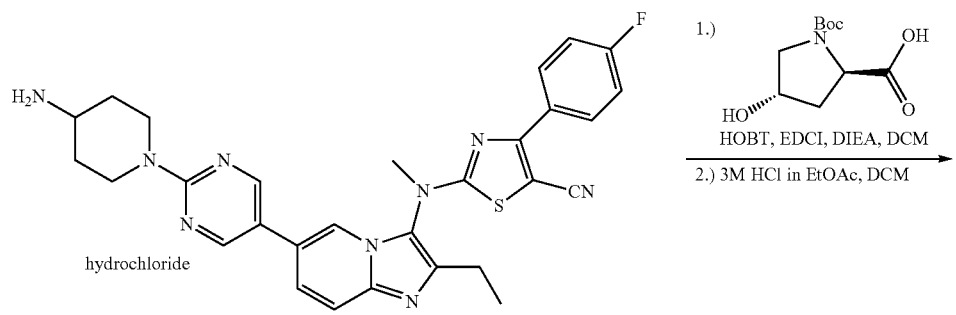

Compound 141 hydrochloride

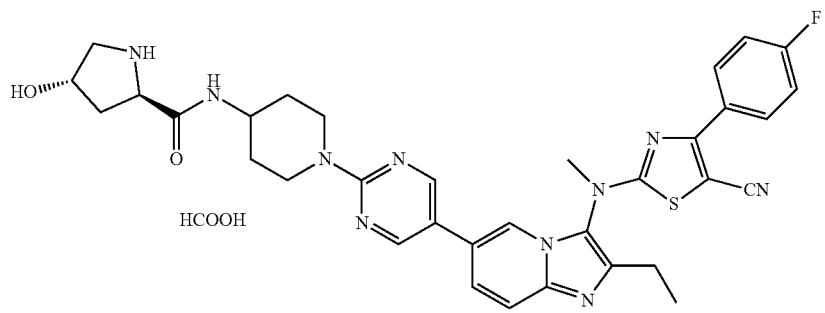

Compound 74 Formate

Step One:
To a solution of compound 141 hydrochloride, 2-((6-(2-(4-aminopiperidin-1-yl)pyrimidin-5-yl)-2-ethylimidazo[1,2-a]pyridin-3-yl)(methyl)amino)-4-(4-fluorophenyl)thiazole-5-carbonitrile hydrochloride (200 mg, 361.24 umol) and (2R,4S)-1-(tert-butoxycarbonyl)-4-hydroxypyrrolidine-2-carboxylic acid (108.59 mg, 469.61 umol) in DMF (10 mL) was added HOBT (73.22 mg, 541.85 umol), EDCI (103.87 mg, 541.85 umol) and TEA (109.66 mg, 1.08 mmol), the reaction mixture was stirred at 25° C. for 16 h. The reaction mixture was poured into $H_2O$ (100 mL) and extracted with EA (30 mL×3), the combined organic layers were washed with brine (100 mL×3), dried over $Na_2SO_4$ and concentrated. The residue was purified by column chromatography to afford tert-butyl (2R,4S)-2-((1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)carbamoyl)-4-hydroxypyrrolidine-1-carboxylate (220 mg, 79.41% yield) as a yellow solid. MS: m/z=767.3 (M+1, ESI+).

Step Two:
To a solution of tert-butyl (2R,4S)-2-((1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)carbamoyl)-4-hydroxy pyrrolidine-1-carboxylate (220 mg, 286.87 umol) in DCM (15 mL) was added 3M HCl in EA (956.25 uL) and stirred at 25° C. for 16 h. The reaction mixture was concentrated and purified by Prep-HPLC to afford compound 73 formate, (2R,4S)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)-4-hydroxypyrrolidine-2-carboxamide formate (103 mg, 53.85% yield) as a white solid. $^1$H NMR (400 MHz, DMSO-$d_6$) δ 8.77 (s, 2H), 8.65 (s, 1H), 8.25 (s, 1H), 8.09 (s, 2H), 7.94 (s, 1H), 7.70 (s, 2H), 7.44-7.40 (t, 2H), 4.57-4.54 (d, 2H), 4.17 (s, 1H), 3.85-3.84 (d, 1H), 3.72-3.68 (t, 1H), 3.63 (s, 3H), 3.13-3.07 (t, 2H), 2.84-2.62 (m, 4H), 1.93 (s, 1H), 1.78-1.75 (d, 2H), 1.67-1.66 (d, 1H), 1.37-1.35 (d, 2H), 1.28-1.24 (t, 3H); MS: m/z=667.5 (M+1, ESI+).

5.10.19. Synthesis of Compound 74

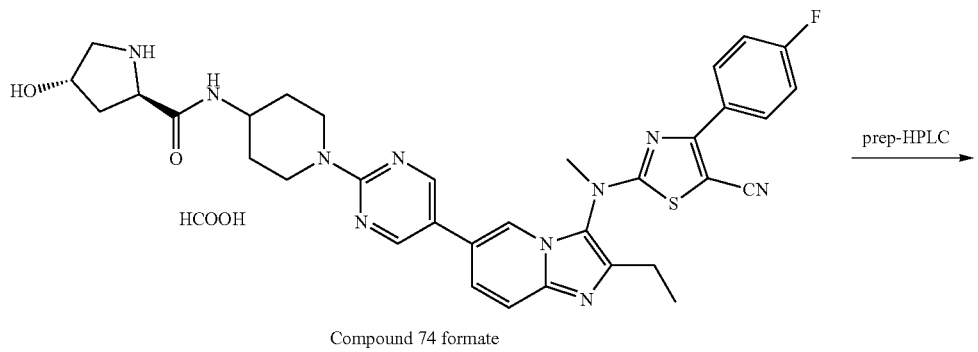

Compound 74 formate

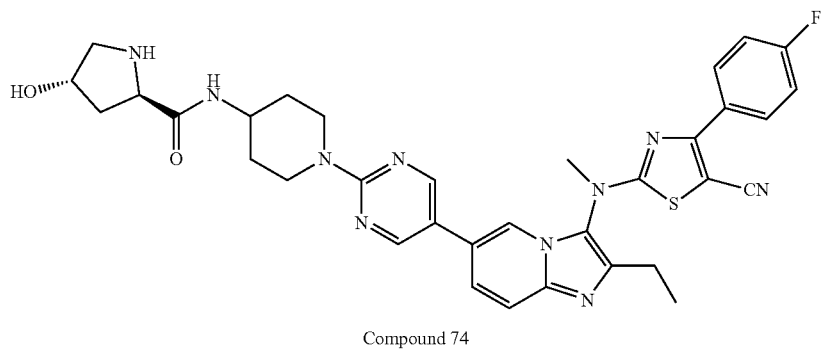

Compound 74

Compound 74 formate, (2R,4S)—N-(1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)-4-hydroxypyrrolidine-2-carboxamide formate (99 mg, 0.139 mmol) was purified by Prep-HPLC to afford compound 74, (2R,4S)—N-(1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)-4-hydroxypyrrolidine-2-carboxamide (56 mg, 60.47% yield) as a white solid. $^1$H NMR (400 MHz, DMSO-$d_6$) δ 8.77 (s, 2H), 8.65 (s, 1H), 8.10-8.01 (m, 3H), 7.70 (s, 2H), 7.44-7.40 (t, 2H), 4.56-4.53 (d, 2H), 4.21 (s, 1H), 3.85-3.74 (m, 2H), 3.63 (s, 3H), 3.15-3.08 (t, 2H), 2.91-2.64 (m, 4H), 1.98-1.77 (m, 4H), 1.38-1.22 (m, 5H); MS: m/z=667.1 (M+1, ESI+).

5.10.20. Synthesis of Compound 75 Formate

EA (30 mL×3), the combined organic layers were washed with brine (100 mL×3), dried over $Na_2SO_4$ and concentrated. The residue was purified by column chromatography to afford tert-butyl (2S,4S)-2-((1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)carbamoyl)-4-hydroxypyrrolidine-1-carboxylate (210 mg, 75.81% yield) as a yellow solid. MS: m/z=767.3 (M+1, ESI+).

Step Two:

To a solution of tert-butyl (2S,4S)-2-((1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)carbamoyl)-4-hydroxy pyrrolidine-1-carboxylate (210 mg, 273.84 umol) in DCM (15 mL) was added 3M HCl in EA (912.78 uL) and stirred at 25° C. for 16 h. The reaction mixture was concentrated and purified by Prep-HPLC to afford compound 75 formate, (2S,4S)—N-(1-(5-(3-((5-

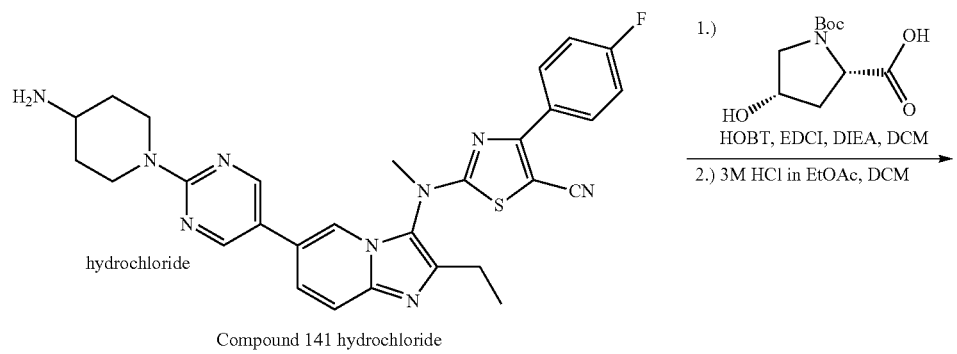

Compound 141 hydrochloride

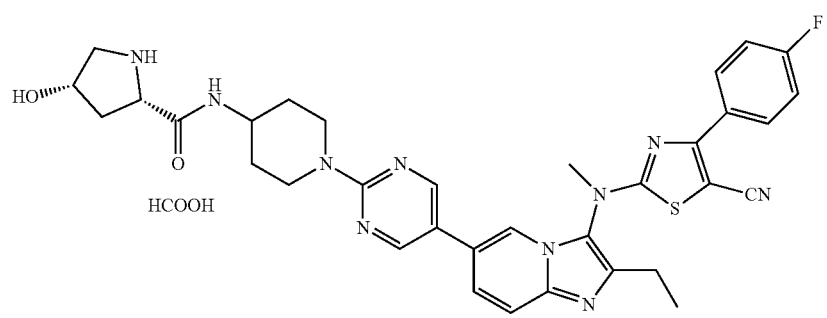

Compound 75 Formate

Step One:

To a solution of compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (200 mg, 361.24 umol) and (2S,4S)-1-(tert-butoxycarbonyl)-4-hydroxypyrrolidine-2-carboxylic acid (108.59 mg, 469.61 umol) in DMF (10 mL) was added HOBT (73.22 mg, 541.85 umol), EDCI (103.87 mg, 541.85 umol) and TEA (109.66 mg, 1.08 mmol), the reaction mixture was stirred at 25° C. for 16 h. The reaction mixture was poured into $H_2O$ (100 mL) and extracted with cyano-4-(4-fluorophenyl)thiazol-2-yl)(methyl)amino)-2-ethylimidazo[1,2-a]pyridin-6-yl)pyrimidin-2-yl)piperidin-4-yl)-4-hydroxypyrrolidine-2-carboxamide formate (57 mg, 29.23% yield) as a white solid. $^1$H NMR (400 MHz, DMSO-$d_6$) δ 8.77 (s, 2H), 8.65 (s, 1H), 8.24 (s, 1H), 8.11-8.07 (t, 2H), 7.94 (s, 1H), 7.70 (s, 2H), 7.44-7.40 (t, 2H), 4.55-4.52 (d, 2H), 4.11 (s, 1H), 3.87-3.86 (d, 1H), 3.63 (s, 3H), 3.53-3.52 (d, 1H), 3.17-3.11 (t, 2H), 2.89-2.87 (t, 1H), 2.70-2.64 (m, 3H), 2.15-2.13 (m, 1H), 1.80-1.77 (d, 2H), 1.60 (s, 1H), 1.41-1.32 (m, 2H), 1.28-1.25 (t, 3H); MS: m/z=667.5 (M+1, ESI+).

5.10.21. Synthesis of Compound 75

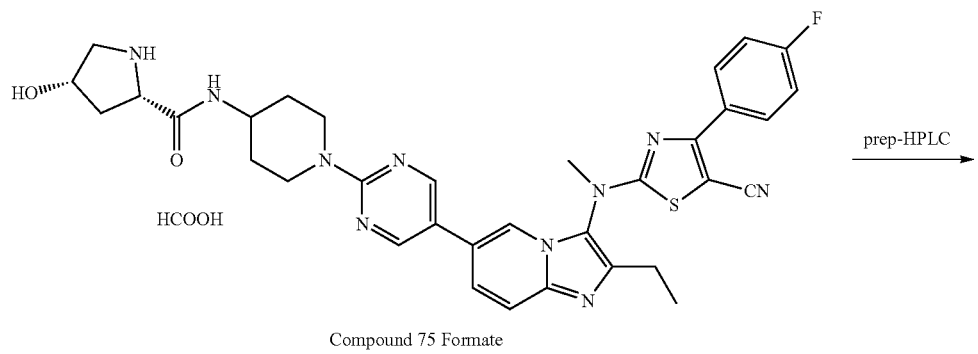

Compound 75 Formate

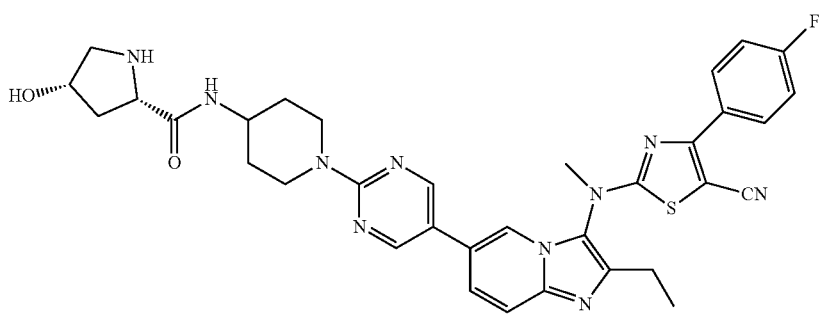

Compound 75

Compound 75 formate, (2S,4S)—N-(1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)-4-hydroxypyrrolidine-2-carboxamide formate (49 mg, 0.069 mmol) was purified by Prep-HPLC to afford compound 75, (2S,4S)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)-4-hydroxypyrrolidine-2-carboxamide (29 mg, 63.31% yield) as a white solid. $^1$H NMR (400 MHz, DMSO-$d_6$) δ 8.77 (s, 2H), 8.65 (s, 1H), 8.10-8.09 (t, 2H), 7.91-7.89 (m, 1H), 7.70 (s, 2H), 7.44-7.40 (t, 2H), 4.67-4.51 (m, 2H), 4.11-4.09 (m, 1H), 3.85-3.74 (m, 1H), 3.63 (s, 3H), 3.50-3.49 (m, 1H), 3.16-3.10 (m, 2H), 2.86-2.63 (m, 4H), 2.14 (s, 1H), 1.80-1.77 (m, 3H), 1.39-1.22 (m, 5H); MS: m/z=667.1 (M+1, ESI+).

5.10.22. Synthesis of Compound 76 Formate

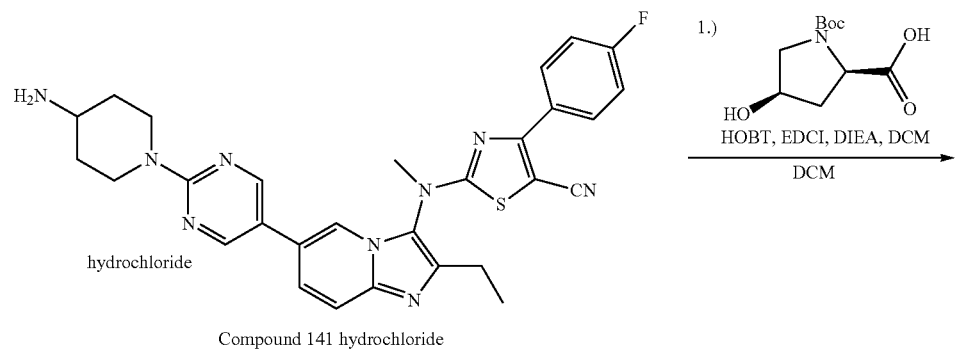

Compound 141 hydrochloride

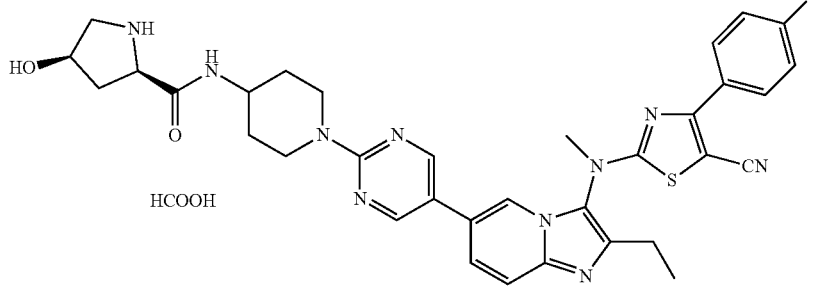

Compound 76 Formate

Step One:

To a solution of compound 141 hydrochloride, 2-((6-(2-(4-aminopiperidin-1-yl)pyrimidin-5-yl)-2-ethylimidazo[1,2-a]pyridin-3-yl)(methyl)amino)-4-(4-fluorophenyl)thiazole-5-carbonitrile hydrochloride (200 mg, 361.24 umol) and (2R,4R)-1-(tert-butoxycarbonyl)-4-hydroxypyrrolidine-2-carboxylic acid (108.59 mg, 469.61 umol) in DMF (10 mL) was added HOBT (73.22 mg, 541.85 umol), EDCI (103.87 mg, 541.85 umol) and TEA (109.66 mg, 1.08 mmol), the reaction mixture was stirred at 25° C. for 16 h. The reaction mixture was poured into H₂O (100 mL) and extracted with EA (30 mL×3), the combined organic layers were washed with brine (100 mL×3), dried over Na₂SO₄ and concentrated. The residue was purified by column chromatography to afford tert-butyl (2R,4R)-2-((1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)carbamoyl)-4-hydroxypyrrolidine-1-carboxylate (210 mg, 75.81% yield) as a yellow solid. MS: m/z=767.3 (M+1, ESI+).

Step Two:

To a solution of tert-butyl (2R,4R)-2-((1-(5-(3-((5-cyano-4-(4-fluorophenyl)thiazol-2-yl)(methyl) amino)-2-ethyl imidazo[1,2-a]pyridin-6-yl)pyrimidin-2-yl)piperidin-4-yl)carbamoyl)-4-hydroxy pyrrolidine-1-carboxylate (210 mg, 273.84 umol) in DCM (15 mL) was added 3M HCl in EA (912.78 uL) and stirred at 25° C. for 16 h. The reaction mixture was concentrated and purified by Prep-HPLC to afford compound 76 formate, (2R,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)-4-hydroxypyrrolidine-2-carboxamide formate (58 mg, 31.77% yield) as a white solid. ¹H NMR (400 MHz, DMSO-d₆) δ 8.77 (s, 2H), 8.66 (s, 1H), 8.32 (s, 1H), 8.11-8.07 (m, 3H), 7.70 (s, 2H), 7.44-7.40 (t, 2H), 4.55-4.52 (d, 2H), 4.16-4.15 (t, 1H), 3.91-3.84 (m, 1H), 3.65-3.64 (m, 4H), 3.18-3.12 (m, 2H), 2.95-2.91 (m, 1H), 2.78-2.74 (m, 1H), 2.70-2.65 (dd, 2H), 2.23-2.16 (m, 1H), 1.81-1.78 (d, 2H), 1.68-1.63 (m, 1H), 1.42-1.32 (m, 2H), 1.29-1.25 (t, 3H); MS: m/z=667.5 (M+1, ESI+).

5.10.23. Synthesis of Compound 76

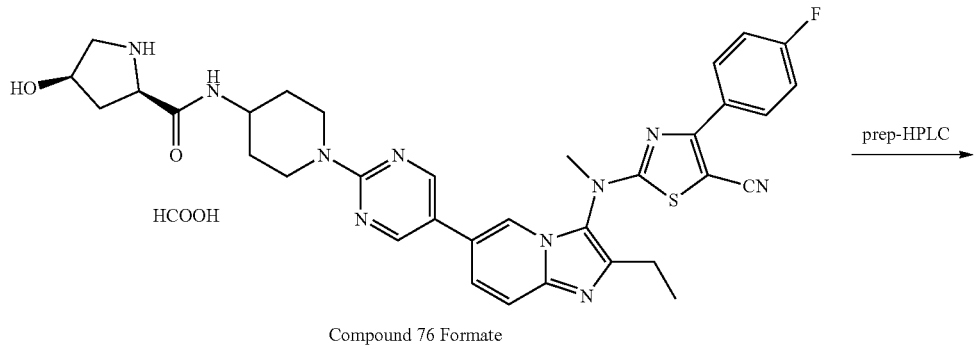

Compound 76 Formate

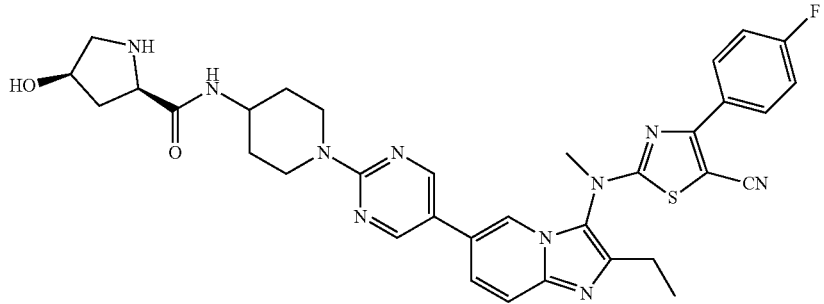

Compound 76

Compound 76 formate (2R,4R)—N-(1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)-4-hydroxypyrrolidine-2-carboxamide formate (51 mg, 0.072 mmol) was purified by Prep-HPLC to afford compound 76, (2R,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-vl) piperidin-4-yl)-4-hydroxypyrrolidine-2-carboxamide (45 mg, 94.34% yield) as a white solid. $^1$H NMR (400 MHz, DMSO-$d_6$) δ 8.77 (s, 2H), 8.65 (s, 1H), 8.10-8.07 (t, 2H), 7.86-7.84 (d, 1H), 7.70 (s, 2H), 7.44-7.40 (t, 2H), 4.61-4.51 (m, 3H), 4.09-4.07 (m, 1H), 3.85-3.74 (m, 1H), 3.63 (s, 3H), 3.13-3.09 (m, 2H), 2.85-2.81 (m, 1H), 2.70-2.60 (m, 3H), 2.14-2.07 (m, 1H), 1.81-1.77 (m, 2H), 1.60-1.54 (m, 1H), 1.40-1.31 (m, 2H), 1.28-1.25 (t, 3H); MS: m/z=667.1 (M+1, ESI+).

5.10.24. Synthesis of Compound 77 Formate mixture was poured into $H_2O$ (100 mL) and extracted with EA (30 mL×3), the combined organic layers were washed with brine (100 mL×3), dried over $Na_2SO_4$ and concentrated. The residue was purified by column chromatography to afford tert-butyl (2S,4R)-2-((1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)carbamoyl)-4-hydroxypyrrolidine-1-carboxylate (200 mg, 72.20% yield) as a yellow solid. MS: m/z=767.3 (M+1, ESI+).

Step Two:

To a solution of tert-butyl (2S,4R)-2-((1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)carbamoyl)-4-hydroxy pyrrolidine-1-carboxylate (180 mg, 234.72 umol) in DCM (15 mL) was added 3M HCl in EA (912.78 uL) and stirred at 25° C. for 16 h. The reaction mixture was concentrated and purified by Prep-HPLC to afford compound 77 formate, (2S,4R)—N-(1-(5-(3-((5-cyano-4-(4-fluorophenyl)thiazol-2-yl)(methyl)amino)-2-

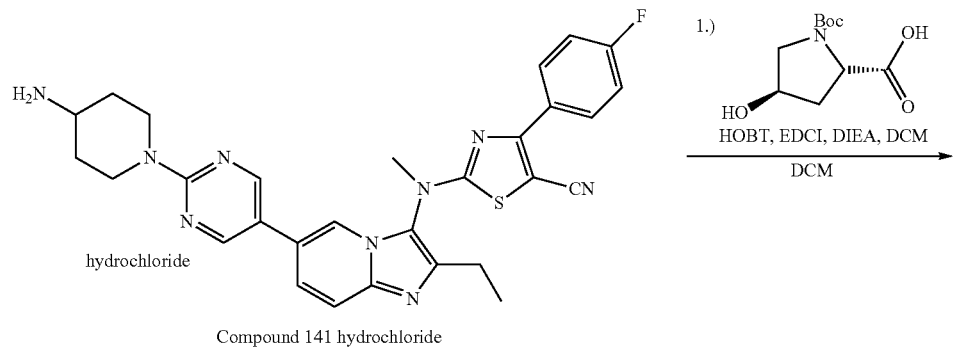

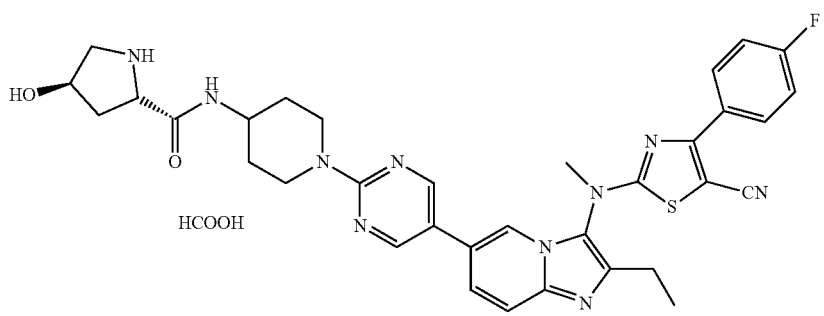

Compound 77 Formate

Step One:

To a solution of compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (200 mg, 361.24 umol) and (2R,4R)-1-(tert-butoxycarbonyl)-4-hydroxypyrrolidine-2-carboxylic acid (108.59 mg, 469.61 umol) in DMF (10 mL) was added HOBT (73.22 mg, 541.85 umol), EDCI (103.87 mg, 541.85 umol) and TEA (109.66 mg, 1.08 mmol), the reaction mixture was stirred at 25° C. for 16 h. The reaction ethylimidazo[1,2-a]pyridin-6-yl)pyrimidin-2-yl)piperidin-4-yl)-4-hydroxypyrrolidine-2-carboxamide formate (92 mg, 58.79% yield) as a white solid. $^1$H NMR (400 MHz, DMSO-$d_6$) δ 8.77 (s, 2H), 8.66 (s, 1H), 8.29 (s, 1H), 8.11-8.07 (m, 3H), 7.70 (s, 2H), 7.44-7.40 (t, 2H), 4.56-4.53 (d, 2H), 4.22 (s, 1H), 3.87-3.81 (m, 2H), 3.63 (s, 3H), 3.15-3.09 (t, 2H), 2.96-2.93 (m, 1H), 2.82-2.79 (m, 1H), 2.70-2.65 (dd, 2H), 2.02-1.97 (m, 1H), 1.80-1.67 (m, 3H), 1.41-1.33 (m, 2H), 1.29-1.25 (t, 3H); MS: m/z=667.2 (M+1, ESI+).

5.10.25. Synthesis of Compound 77

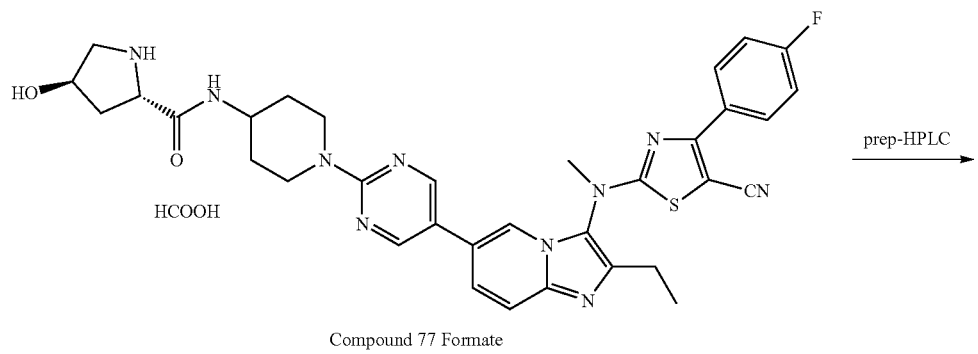

Compound 77 Formate

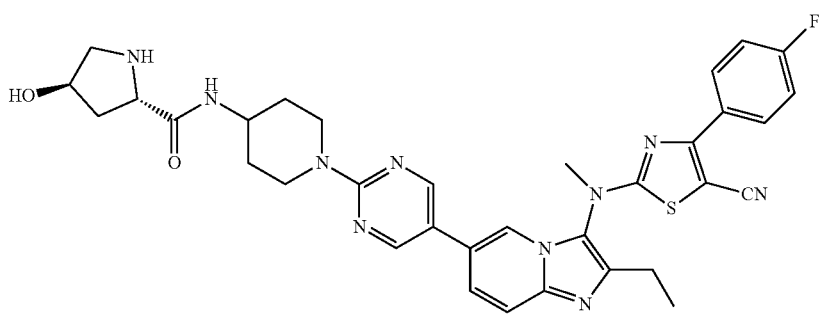

Compound 77

Compound 77 formate, (2S,4R)—N-(1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)-4-hydroxypyrrolidine-2-carboxamide formate (84 mg, 0.118 mmol) was purified by Prep-HPLC to afford compound 77, (2S,4R)—N-(1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)-4-hydroxypyrrolidine-2-carboxamide (75 mg, 95.42% yield) as a white solid. $^1$H NMR (400 MHz, DMSO-$d_6$) δ 8.77 (s, 2H), 8.65 (s, 1H), 8.11-8.07 (t, 2H), 7.88-7.86 (d, 1H), 7.70 (s, 2H), 7.44-7.40 (t, 2H), 4.67-4.54 (m, 31H), 4.15 (s, 1H), 3.85-3.82 (m, 1H), 3.63 (s, 3H), 3.12-3.06 (t, 2H), 2.81-2.64 (m, 4H), 1.90-1.64 (m, 4H), 1.39-1.32 (m, 2H), 1.28-1.25 (t, 3H); MS: m/z=667.2 (M+1, ESI+).

5.10.26. Synthesis of Compound 83 Hydrochloride

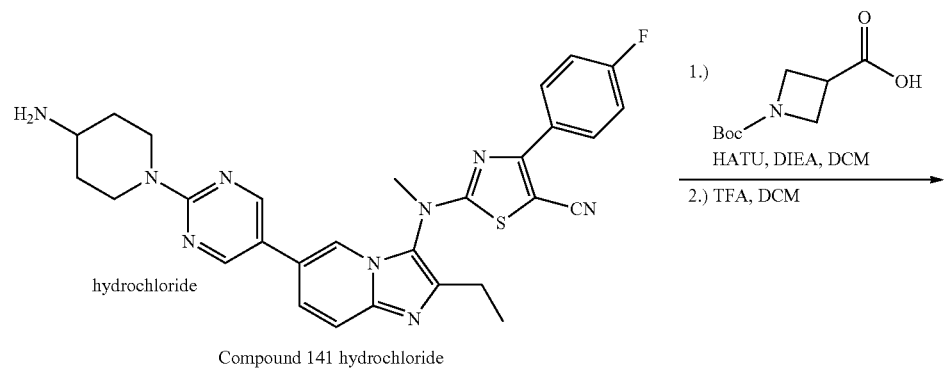

Compound 141 hydrochloride

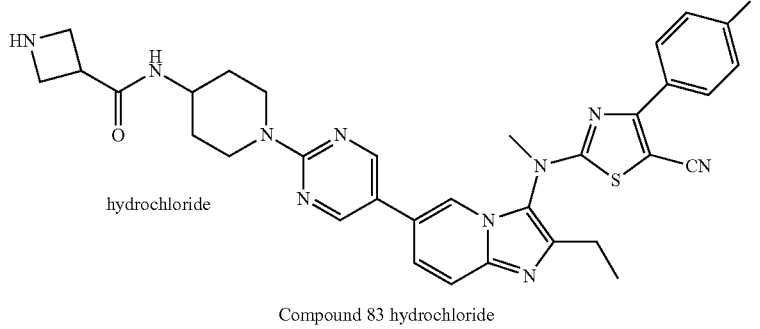

Compound 83 hydrochloride

Step One:

To a solution of compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (300 mg, 508.47 umol) and 1-(tert-butoxycarbonyl) azetidine-3-carboxylic acid (109.03 mg, 541.85 umol) in DCM (10 mL) was added HATU (618.09 mg, 1.63 mmol) and DIEA (350.15 mg, 2.71 mmol), the reaction mixture was stirred at 25° C. for 16 h. The reaction mixture was poured into H₂O (50 mL) and extracted with DCM (20 mL×3), the combined organic layers were washed with brine (50 mL×3), dried over Na₂SO₄ and concentrated. The residue was purified by column chromatography to afford tert-butyl 3-((1-(5-(3-((5-cyano-4-(4-fluorophenyl)thiazol-2-yl)(methyl)amino)-2-ethyl imidazo[1,2-a]pyridine-6-yl)pyrimidin-2-yl)piperidin-4-yl)carbamoyl)azetidine-1-carboxylate (350 mg, 87.66% yield). MS: m/z=737.4 (M+1, ESI+).

Step Two:

To a solution of tert-butyl 3-((1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)carbamoyl)azetidine-1-carboxylate (350 mg, 474.99 umol) in DCM (10 mL) was added TFA (3.08 g, 2.00 mL) and stirred at 25° C. for 3 h. The reaction mixture was concentrated and purified by Prep-HPLC to afford compound 83 hydrochloride, N-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)azetidine-3-carboxamide hydrochloride (160 mg, 50.04% yield) as a pale yellow solid. ¹H NMR (400 MHz, DMSO-$d_6$) δ 9.76 (s, 1H), 9.20 (s, 1H), 9.13 (s, 1H), 8.87 (s, 2H), 8.50-8.48 (d, 1H), 8.42-8.40 (d, 1H), 8.14-8.12 (d, 1H), 8.01 (s, 2H), 7.42-7.38 (t, 2H), 4.55-4.52 (d, 2H), 3.98-3.94 (m, 5H), 3.69-3.61 (m, 4H), 3.28-3.23 (t, 2H), 2.92-2.86 (dd, 2H), 1.84-1.82 (d, 2H), 1.38-1.34 (m, 5H); MS: m/z=637.3 (M+1, ESI+).

5.10.27. Synthesis of Compound 83

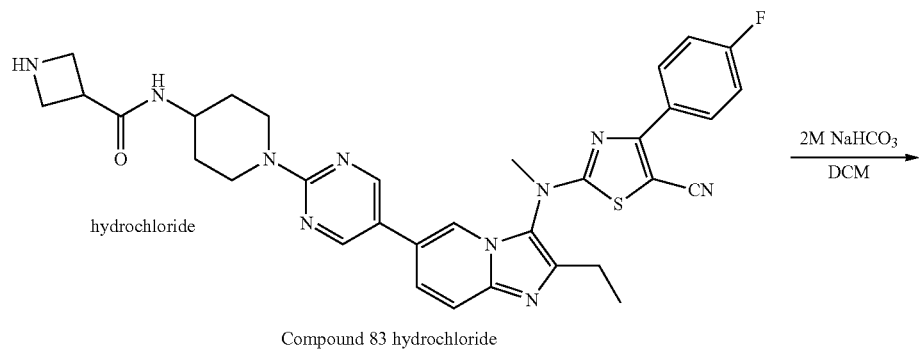

Compound 83 hydrochloride

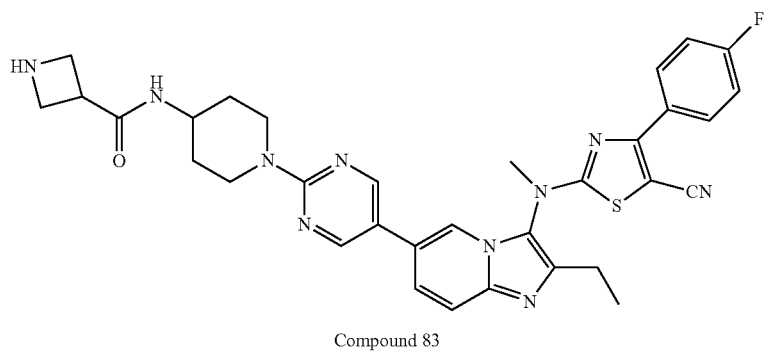

Compound 83

To a mixture of compound 83 hydrochloride, N-(1-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-4-yl)azetidine-3-carboxamide hydrochloride (130 mg, 0.174 mmol) in H$_2$O (3 mL) was added 2 M NaHCO$_3$ (1.05 mL, 2.1 mmol) at 0° C. and stirred for 0.5 h. Then extracted with DCM (5 mL×2). The organic layer was washed with water (5 mL) and brine (5 mL), dried over Na$_2$SO$_4$ and concentrated to afford compound 83, N-(1-(5-(3-((5-cyano-4-(4-fluorophenyl)thiazol-2-yl)(methyl)amino)-2-ethylimidazo[1,2-a]pyridin-6-yl)pyrimidin-2-yl) piperidin-4-yl)azetidine-3-carboxamide (70 mg, 63.6% yield) as a white solid. $^1$H NMR (400 MHz, DMSO-d$_6$) δ 8.76 (s, 2H), 8.65 (s, 1H), 8.10-8.07 (t, 2H), 7.80-7.78 (m, 1H), 7.70 (s, 2H), 7.44-7.40 (t, 2H), 4.55-4.52 (d, 2H), 3.88-3.84 (m, 2H), 3.73-3.69 (t, 1H), 3.63 (s, 3H), 3.54-3.48 (m, 2H), 3.12-3.07 (m, 2H), 2.70-2.64 (m, 2H), 1.81-1.78 (m, 2H), 1.28-1.25 (t, 3H); MS: m/z=637.1 (M+1, ESI+).

5.10.28. Synthesis of Compound 84 Hydrochloride

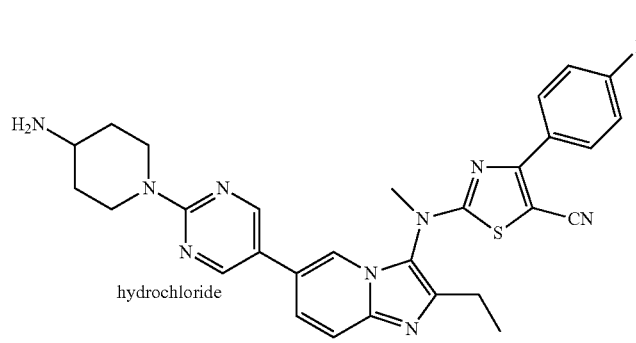

Compound 141 hydrochloride

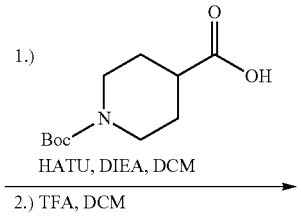

HATU, DIEA, DCM
2.) TFA, DCM

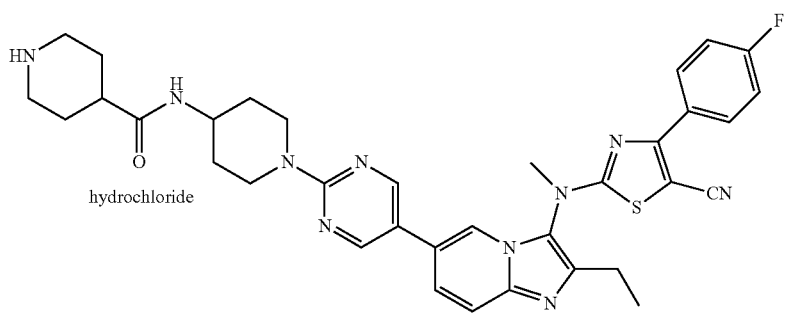

Compound 84 hydrochloride

Step One:
To a solution of compound 141 hydrochloride, 2-((6-(2-(4-aminopiperidin-1-yl)pyrimidin-5-yl)-2-ethylimidazo[1,2-a]pyridin-3-yl) (methyl)amino)-4-(4-fluorophenyl)thiazole-5-carbonitrile hydrochloride (300 mg, 508.47 umol) and 1-(tert-butoxycarbonyl) piperidine-4-carboxylic acid (186.35 mg, 812.78 umol) in DCM (10 mL) was added HATU (618.09 mg, 1.63 mmol) and DIEA (350.15 mg, 2.71 mmol), the reaction mixture was stirred at 25° C. for 16 h. The reaction mixture was poured into H$_2$O (50 mL) and extracted with DCM (20 mL×3), the combined organic layers were washed with brine (50 mL×3), dried over Na$_2$SO$_4$ and concentrated. The residue was purified by column chromatography to afford tert-butyl 4-((1-(5-(3-((5-cyano-4-(4-fluorophenyl)thiazol-2-yl)(methyl)amino)-2-ethyl imidazo[1,2-a] pyridin-6-yl)pyrimidin-2-yl)piperidin-4-yl)carbamoyl)piperidine-1-carboxylate (300 mg, 72.38% yield). MS: m/z=765.3 (M+1, ESI+).

Step Two:
To a solution of tert-butyl 4-((1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)carbamoyl)piperidine-1-carboxylate (300 mg, 392.20 umol) in DCM (10 mL) was added TFA (2.54 g, 1.65 mL) and stirred at 25° C. for 3 h. The reaction mixture was concentrated and purified by Prep-HPLC to afford compound 84 hydrochloride, N-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)piperidine-4-carboxamide hydrochloride (200 mg, 72.72% yield) as a pale yellow solid. $^1$H NMR (400 MHz, DMSO-d$_6$) δ9.40 (s, 1H), 9.12 (s, JH), 9.04 (s, JH), 8.86 (s, 2H), 8.41-8.39 (d, 1H), 8.14-8.09 (m, 2H), 8.01 (s, 2H), 7.42-7.38 (t, 2H), 4.57-4.54 (d, 2H), 3.87 (s, 1H), 3.68 (s, 3H), 3.22-3.16 (m, 4H), 2.91-2.80 (m, 4H), 2.43 (s, 1H), 1.81-1.72 (m, 6H), 1.37-1.33 (m, 5H); MS: m/z=665.4 (M+1, ESI+).

5.10.29. Synthesis of Compound 84

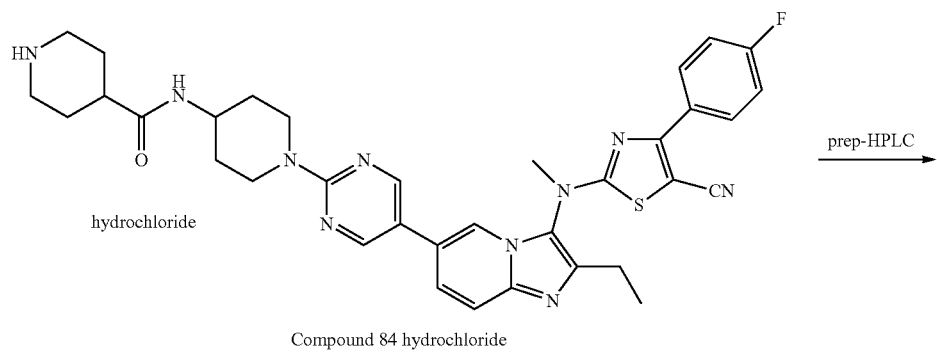

Compound 84 hydrochloride

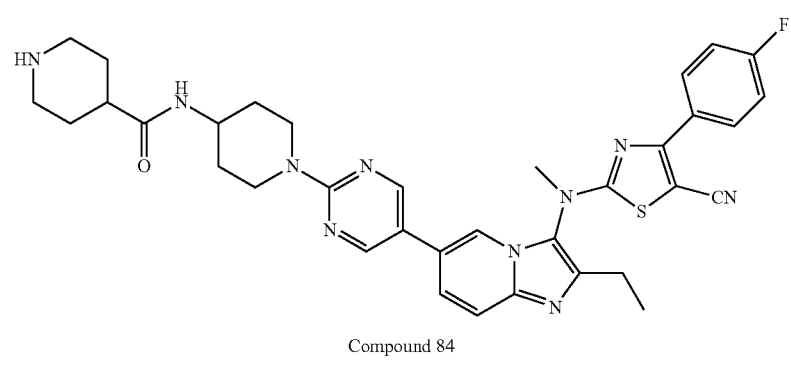

Compound 84

Compound 84 hydrochloride, N-(1-(5-(3-((5-cyano-4-(4-fluorophenyl)thiazol-2-yl)(methyl)amino)-2-ethylimidazo[1,2-a]pyridin-6-yl)pyrimidin-2-vl)piperidin-4-yl)piperidine-4-carboxamide hydrochloride (140 mg, 0.181 mmol) was purified by Prep-HPLC to afford compound 84, N-(1-(5-(3-((5-cyano-4-(4-fluorophenyl)thiazol-2-yl)(methyl)amino)-2-ethylimidazo[1,2-a]pyridin-6-yl)pyrimidin-2-yl)piperidin-4-yl)piperidine-4-carboxamide (110 mg, 91.66% yield) as a white solid. $^1$H NMR (400 MHz, DMSO-$d_6$) δ 8.76 (s, 2H), 8.65 (s, 1H), 8.11-8.07 (t, 2H), 7.70-7.66 (m, 3H), 7.44-7.40 (t, 2H), 4.55-4.52 (d, 2H), 3.84-3.80 (m, 1H), 3.63 (s, 3H), 3.13-3.08 (t, 2H), 2.98-2.95 (d, 2H), 2.70-2.64 (dd, 2H), 2.50-2.45 (m, 2H), 2.19-2.13 (m, 1H), 1.78-1.75 (d, 2H), 1.58-1.41 (m, 4H), 1.33-1.16 (m, 6H); MS: m/z=666.1 (M+1, ESI+).

5.10.30. Synthesis of Compound 107

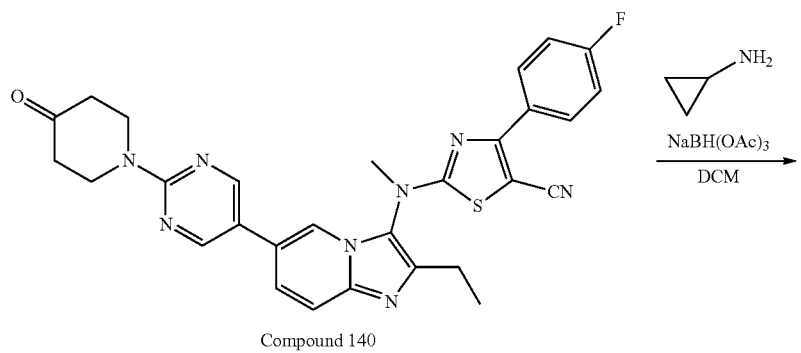

Compound 140

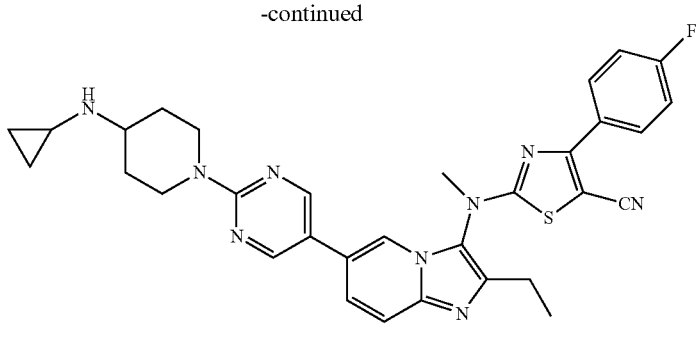

Compound 107

To a solution of compound 140, 2-((2-ethyl-6-(2-(4-oxopiperidin-1-yl)pyrimidin-5-yl)imidazo[1,2-a]pyridin-3-yl)(methyl)amino)-4-(4-fluorophenyl)thiazole-5-carbonitrile (250 mg, 452.39 umol) and cyclopropanamine (38.74 mg, 678.58 umol) in DCM (10 mL) was added NaBH(OAc)$_3$ (191.76 mg, 904.77 umol), the reaction mixture was stirred at 25° C. for 16 h. The mixture was poured into water (30 mL), extracted with DCM (10 mL×3). The organic was washed by brine (30 mL), then dried over Na$_2$SO$_4$ and concentrated. The residue was purified by Prep-HPLC to afford compound 107, 2-((6-(2-(4-(cyclopropylamino)piperidin-1-yl)pyrimidin-5-yl)-2-ethylimidazo[1,2-a]pyridin-3-yl)(methyl)amino)-4-(4-fluorophenyl)thiazole-5-carbonitrile (62 mg, 23.08% yield) as a white solid. 1H NMR (400 MHz, DMSO-d$_6$) δ 8.69 (s, 2H), 8.60 (s, 1H), 8.06-8.03 (t, 2H), 7.64 (s, 2H), 7.39-7.34 (t, 2H), 4.47-4.43 (m, 2H), 3.59 (s, 3H), 3.06-3.01 (t, 2H), 2.73-2.60 (m, 3H), 2.09-2.02 (m, 2H), 1.84-1.81 (d, 2H), 1.24-1.13 (m, 5H), 0.33-0.29 (m, 2H), 0.16-0.13 (m, 2H); MS: m/z=594.1 (M+1, ESI+); HRMS: 594.2558.

5.10.31. Synthesis of Compound 108

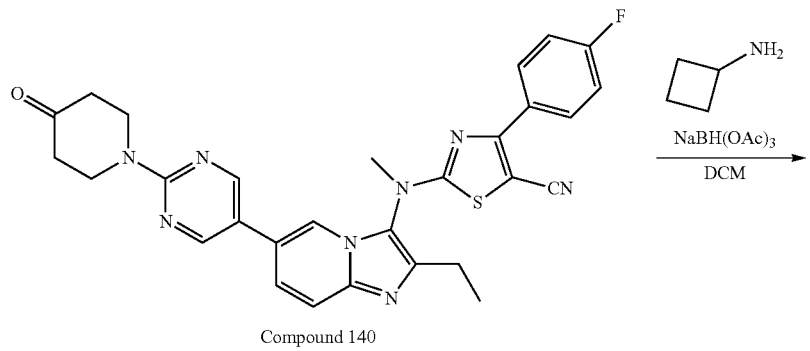

Compound 140

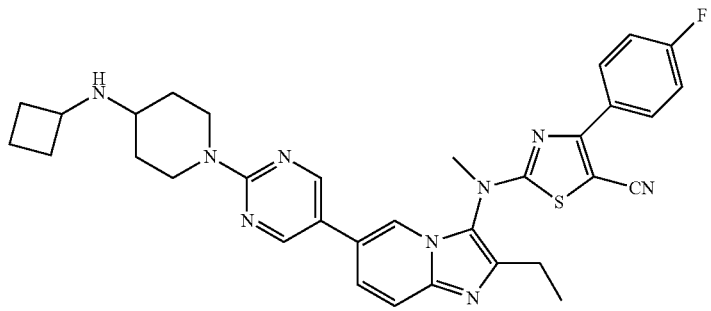

Compound 108

To a solution of compound 140, 2-((2-ethyl-6-(2-(4-oxopiperidin-1-yl)pyrimidin-5-yl)imidazo[1,2-a]pyridin-3-yl) (methyl)amino)-4-(4-fluorophenyl)thiazole-5-carbonitrile (250 mg, 452.39 umol) and cyclobutanamine (48.26 mg, 678.58 umol) in DCM (10 mL) was added NaBH(OAc)$_3$ (191.76 mg, 904.77 umol), the reaction mixture was stirred at 25° C. for 16 h. The mixture was poured into water (30 mL), extracted with DCM (10 mL×3). The organic was washed by brine (30 mL), then dried over Na$_2$SO$_4$ and concentrated. The residue was purified by Prep-HPLC to afford compound 108, 2-((6-(2-(4-(cyclobutylamino)piperidin-1-yl)pyrimidin-5-yl)-2-ethylimidazo[1,2-a]pyridin-3-yl)(methyl)amino)-4-(4-fluorophenyl)thiazole-5-carbonitrile (86 mg, 31.28% yield) as a white solid. $^1$H NMR (400 MHz, DMSO-d$_6$) δ 8.74 (s, 2H), 8.64 (s, 1H), 8.10-8.08 (t, 2H), 7.69 (s, 2H), 7.44-7.39 (t, 2H), 4.50-4.46 (m, 2H), 3.64 (s, 3H), 3.26-3.22 (m, 1H), 3.08-3.03 (t, 2H), 2.70-2.65 (m, 3H), 2.10-2.06 (m, 2H), 1.77-1.50 (m, 6H), 1.29-1.25 (t, 3H), 1.18-1.10 (m, 2H); MS: m/z=608.2 (M+1, ESI+); HRMS: 608.2716.

5.10.32. Synthesis of Compound 115

To a solution of compound 142, 1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxylic acid (400 mg, 686.52 umol) and pyrrolidine (48.83 mg, 686.52 umol) in DMF (8 mL) was added HATU (391.55 mg, 1.03 mmol) and DIEA (266.18 mg, 2.06 mmol), the reaction mixture was stirred at 25° C. for 2 h. The mixture was poured into water (80 mL) and extracted with EA (30 mL×2), the organic layer was washed with brine (50 mL), then dried over Na$_2$SO$_4$ and concentrated. The residue was purified by Prep-HPLC to afford compound 115, 2-((2-ethyl-6-(2-(4-(pyrrolidine-1-carbonyl)piperidin-1-yl)pyrimidin-5-yl)imidazo[1,2-a]pyridin-3-yl)(methyl)amino)-4-(4-fluorophenyl)thiazole-5-carbonitrile (205 mg, 46.97% yield) as a white solid. $^1$H NMR (400 MHz, DMSO-d$_6$) δ 8.76 (s, 2H), 8.65 (s, JH), 8.11-8.07 (t, 2H), 7.69 (s, 2H), 7.44-7.39 (t, 2H), 4.72-4.69 (d, 2H), 3.63 (s, 3H), 3.53-3.49 (t, 2H), 3.27-3.24 (t, 2H), 3.02-2.96 (m, 2H), 2.78-2.64 (m, 3H), 1.91-1.85 (m, 2H), 1.79-1.70 (m, 4H), 1.52-1.42 (m, 2H), 1.29-1.25 (t, 3H); MS: m/z=636.2 (M+1, ESI+); HRMS: 636.2655.

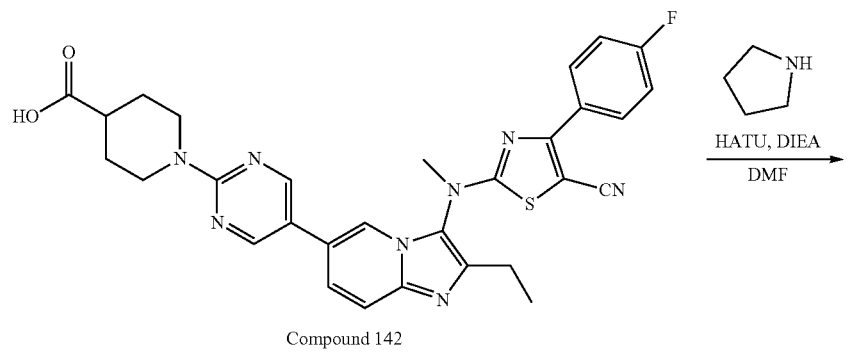

Compound 142

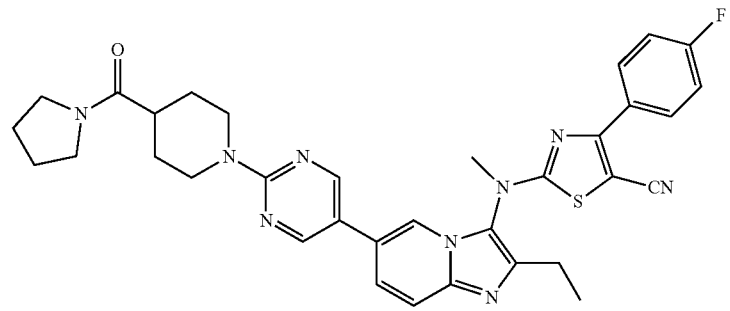

Compound 115

5.10.33. Synthesis of Compound 115 Hydrochloride

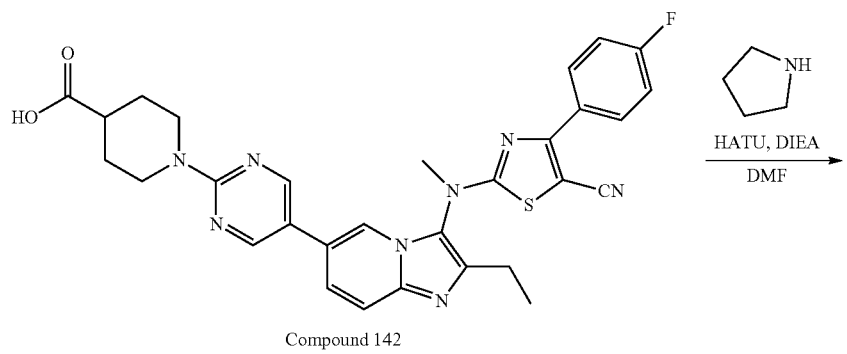

Compound 142

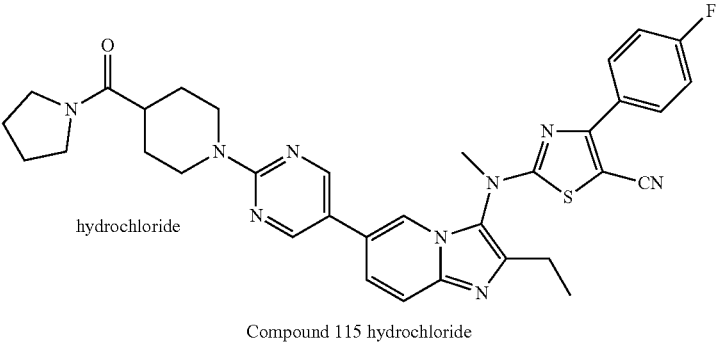

Compound 115 hydrochloride

To a solution of compound 142, 2-((2-ethyl-6-(6-(4-(pyrrolidine-1-carbonyl)piperidin-1-yl)pyridin-3-yl)imidazo[1,2-a]pyridin-3-yl)(methyl)amino)-4-(4-fluorophenyl)thiazole-5-carbonitrile (125 mg, 0.2 mmol) in MeOH (8 mL) was added 2 M HCl (0.6 mL, 1.2 mmol) and stirred at 25° C. for 2 h. The mixture was evaporated under reduced pressure to afford compound 115 hydrochloride, 2-((2-ethyl-6-(6-(4-(pyrrolidine-1-carbonyl) piperidin-1-yl)pyridin-3-yl)imidazo[1,2-a]pyridin-3-yl)(methyl)amino)-4-(4-fluorophenyl)thiazole-5-carbonitrile hydrochloride (140 mg, 95.9% yield) as a pale yellow solid. $^1$H NMR (400 MHz, DMSO-$d_6$) δ 9.06 (s, 1H), 8.83 (s, 2H), 8.35-8.33 (m, 1H), 8.11-8.00 (m, 3H), 7.42-7.38 (t, 2H), 4.74-4.71 (d, 2H), 3.66 (s, 3H), 3.53-3.50 (t, 2H), 3.27-3.23 (t, 2H), 3.06-2.99 (m, 2H), 2.89-2.75 (m, 3H), 1.92-1.72 (m, 6H), 1.52-1.41 (m, 2H), 1.34-1.30 (t, 3H); MS: m/z=636.2 (M+1, ESI+).

5.10.34. Synthesis of Compound 123

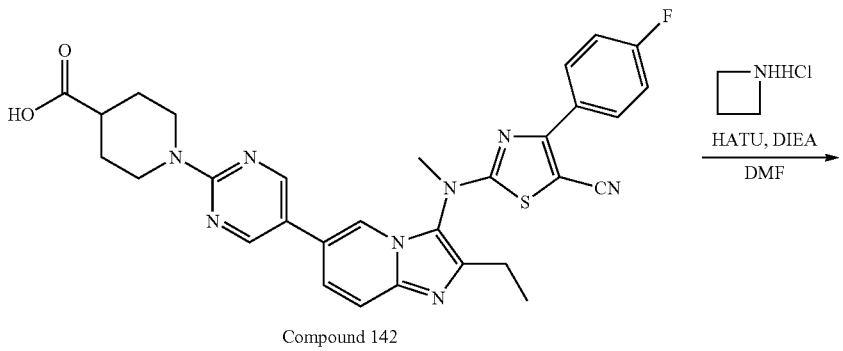

Compound 142

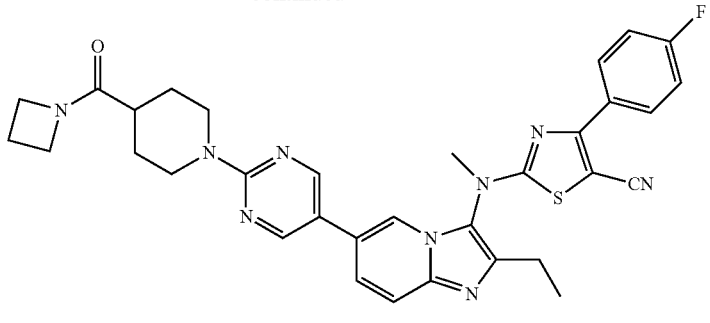

Compound 123

To a solution of compound 142, 1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxylic acid (670 mg, 1.15 mmol) and azetidine hydrochloride (129.10 mg, 1.38 mmol) in DMF (10 mL) was added HATU (650.74 mg, 1.72 mmol) and DIEA (445.85 mg, 3.45 mmol), the reaction mixture was stirred at 25° C. for 2 h. The mixture was poured into water (100 mL) and extracted with EA (40 mL×2), the organic layer was washed with brine (100 mL), then dried over Na$_2$SO$_4$ and concentrated. The residue was purified by Prep-HPLC to afford compound 123, 2-((6-(2-(4-(azetidine-1-carbonyl)piperidin-1-yl)pyrimidin-5-yl)-2-ethylimidazo[1,2-a]pyridin-3-yl)(methyl)amino)-4-(4-fluorophenyl)thiazole-5-carbonitrile (350 mg, 48.96% yield) as a white solid. $^1$H NMR (400 MHz, DMSO-d$_6$) δ 8.75 (s, 2H), 8.65 (s, 1H), 8.11-8.08 (t, 2H), 7.70 (s, 2H), 7.44-7.39 (t, 2H), 4.69-4.66 (d, 2H), 4.21-4.17 (t, 2H), 3.84-3.80 (t, 2H), 3.64 (s, 3H), 3.02-2.95 (m, 2H), 2.70-2.65 (dd, 2H), 2.54-2.49 (m, 1H), 2.22-2.15 (m, 2H), 1.68-1.65 (m, 2H), 1.48-1.37 (m, 2H), 1.29-1.25 (t, 3H); MS: m/z=622.2 (M+1, ESI+); HRMS: 622.2509.

5.10.35. Synthesis of Compound 127

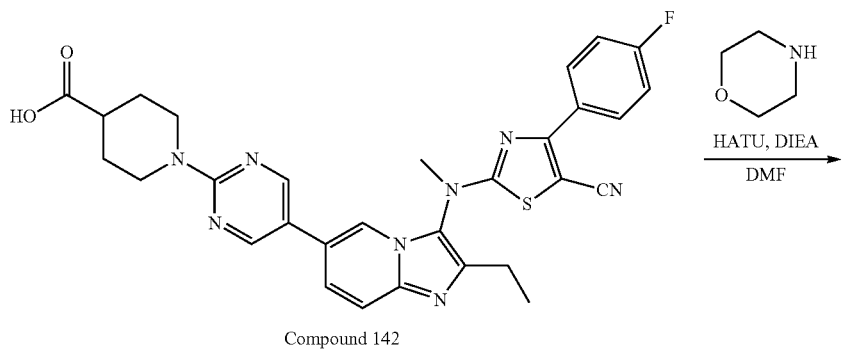

Compound 142

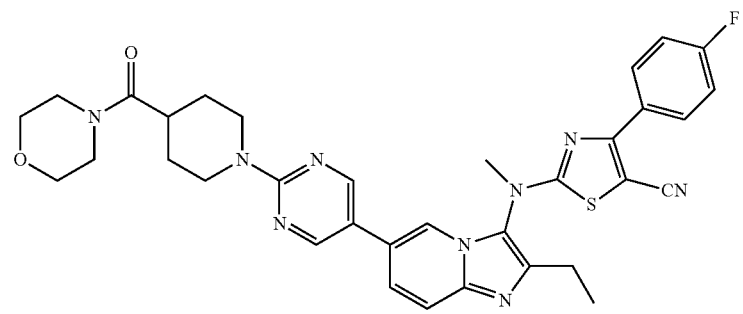

Compound 127

To a solution of compound 142, 1-(5-(3-((5-cyano-4-(4-fluorophenyl)thiazol-2-yl)(methyl)amino)-2-ethylimidazo[1,2-a]pyridin-6-yl)pyrimidin-2-yl)piperidine-4-carboxylic acid (570 mg, 978.29 umol) and morpholine (102.27 mg, 1.17 mmol) in DMF (10 mL) was added HATU (553.62 mg, 1.47 mmol) and DIEA (379.30 mg, 2.93 mmol), the reaction mixture was stirred at 25° C. for 2 h. The mixture was poured into water (100 mL) and extracted with EA (30 mL×2), the organic layer was washed with brine (100 mL), then dried over $Na_2SO_4$ and concentrated. The residue was purified by Prep-HPLC to afford compound 127, 2-((2-ethyl-6-(2-(4-(morpholine-4-carbonyl)piperidin-1-yl)pyrimidin-5-yl)imidazo[1,2-a]pyridin-3-yl)(methyl)amino)-4-(4-fluorophenyl)thiazole-5-carbonitrile (260 mg, 40.78% yield) as a white solid. $^1$H NMR (400 MHz, DMSO-$d_6$) δ 8.76 (s, 2H), 8.65 (s, 1H), 8.11-8.08 (t, 2H), 7.70 (s, 2H), 7.44-7.39 (t, 2H), 4.71-4.68 (d, 2H), 3.64 (s, 3H), 3.58-3.54 (m, 6H), 3.44-3.43 (m, 2H), 3.04-2.93 (m, 3H), 2.71-2.65 (dd, 2H), 1.71-1.68 (m, 2H), 1.54-1.45 (m, 2H), 1.29-1.25 (t, 3H); MS: m/z=652.2 (M+1, ESI+); HRMS: 652.2616.

5.11. Example 10—Synthesis of Piperidine-Linked Pyridine-Type Compounds

General Scheme 10

Route A

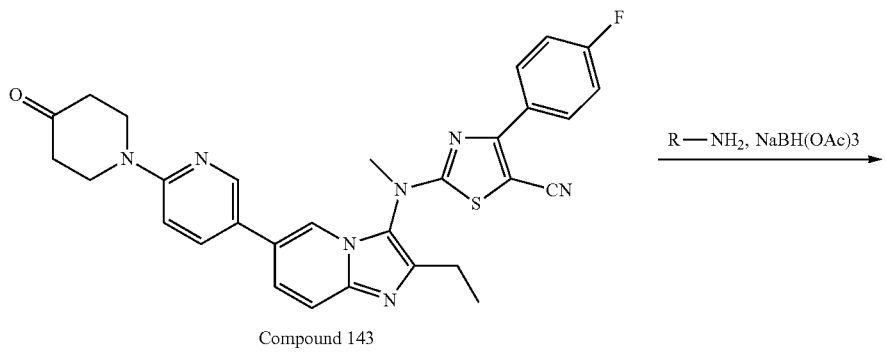

Compound 143

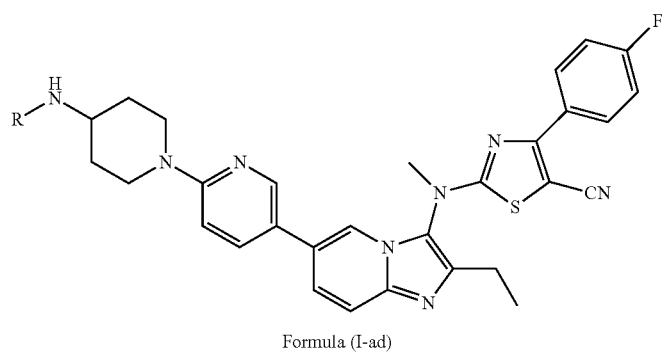

Formula (I-ad)

Route B

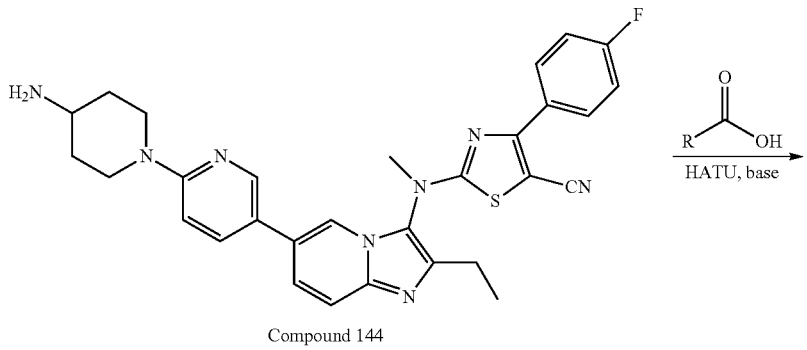

Compound 144

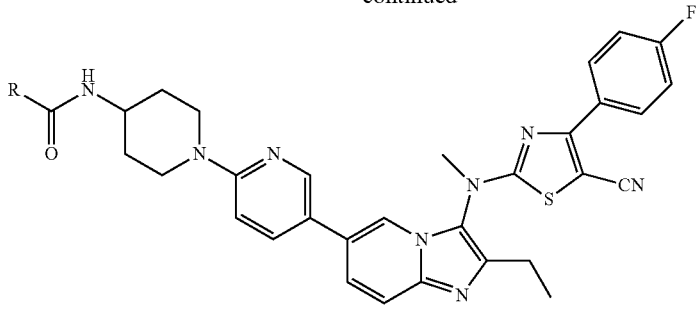

Formula (I-ae)

Route C

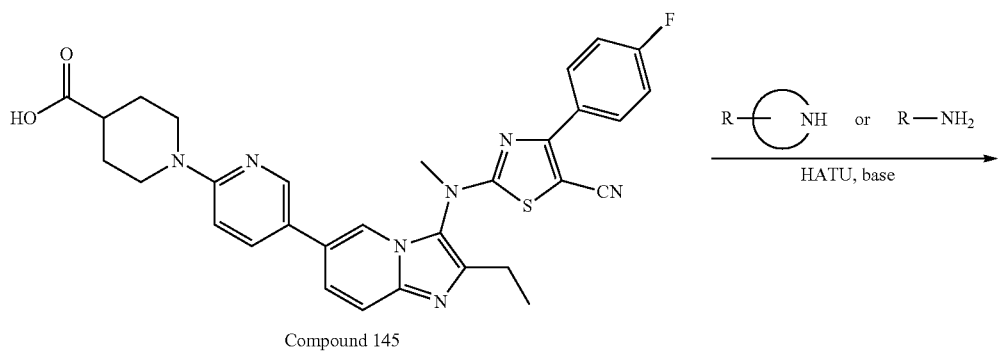

Compound 145

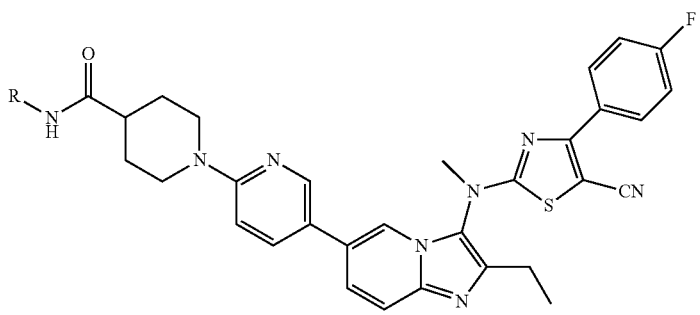

Formula (I-af)

5.11.1. Synthesis of 1-(5-bromopyridin-2-yl)piperidin-4-ol

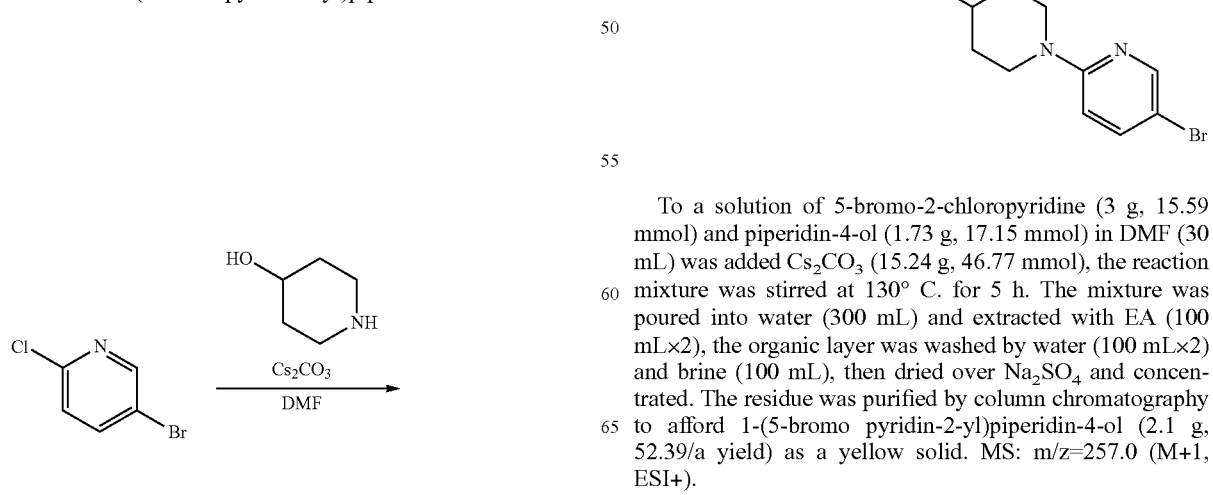

To a solution of 5-bromo-2-chloropyridine (3 g, 15.59 mmol) and piperidin-4-ol (1.73 g, 17.15 mmol) in DMF (30 mL) was added $Cs_2CO_3$ (15.24 g, 46.77 mmol), the reaction mixture was stirred at 130° C. for 5 h. The mixture was poured into water (300 mL) and extracted with EA (100 mL×2), the organic layer was washed by water (100 mL×2) and brine (100 mL), then dried over $Na_2SO_4$ and concentrated. The residue was purified by column chromatography to afford 1-(5-bromo pyridin-2-yl)piperidin-4-ol (2.1 g, 52.39/a yield) as a yellow solid. MS: m/z=257.0 (M+1, ESI+).

5.11.2. Synthesis of Compound 143

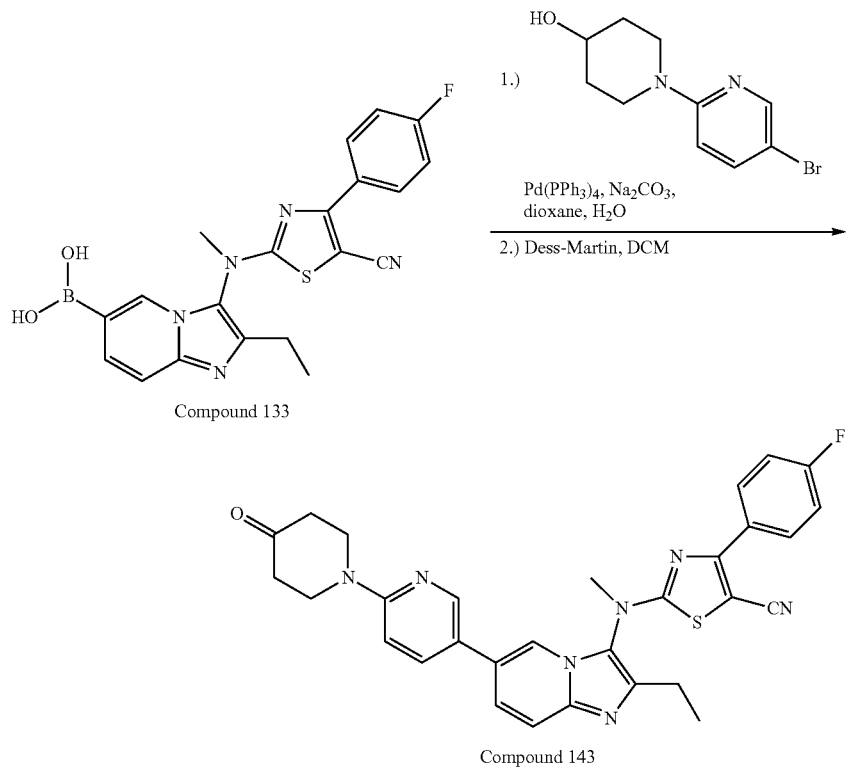

Compound 133

Compound 143

Step One:

To a mixture of 1-(5-bromopyridin-2-yl)piperidin-4-ol (915.57 mg, 3.56 mmol) and compound 133, (3-((5-cyano-4-(4-fluorophenyl)thiazol-2-yl)(methyl)amino)-2-ethylimidazo[1,2-a]pyridin-6-yl)boronic acid (1.5 g, 3.56 mmol) in dioxane (20 mL) and water (4 mL) was added Na$_2$CO$_3$ (1.13 g, 10.68 mmol) and Pd(PPh$_3$)$_4$ (205.74 mg, 178.04 umol), the reaction mixture was stirred at 100° C. for 2 h under N$_2$. The mixture was poured into water (60 mL) and extracted with EA (20 mL×2). The organic layer was washed by brine (100 mL), then dried over Na$_2$SO$_4$ and concentrated. The residue was purified by column chromatography to afford 2-((2-ethyl-6-(6-(4-hydroxypiperidin-1-yl)pyridin-3-yl)imidazo[1,2-a]pyridin-3-yl)(methyl)amino)-4-(4-fluorophenyl)thiazole-5-carbonitrile (1.2 g, 60.87% yield) as a yellow solid. MS: m/z=554.1 (M+1, ESI+).

Step Two:

To a solution of 2-((2-ethyl-6-(6-(4-hydroxypiperidin-1-yl)pyridin-3-yl)imidazo[1,2-a]pyridin-3-yl) (methyl)amino)-4-(4-fluorophenyl)thiazole-5-carbonitrile (1.2 g, 2.17 mmol) in DCM (25 mL) was added Dess-Martin (919.30 mg, 2.17 mmol), the reaction mixture was stirred at 25° C. for 2 h. The mixture was evaporated and purified by column chromatography to afford compound 143, 2-((2-ethyl-6-(6-(4-oxopiperidin-1-yl)pyridin-3-yl)imidazo[1,2-a]pyridin-3-yl)(methyl)amino)-4-(4-fluorophenyl) thiazole-5-carbonitrile (960 mg, 80.29% yield) as a yellow solid. MS: m/z=552.2 (M+1, ESI+).

5.11.3. Synthesis of tert-butyl (1-(5-bromopyridin-2-yl)piperidin-4-yl)carbamate

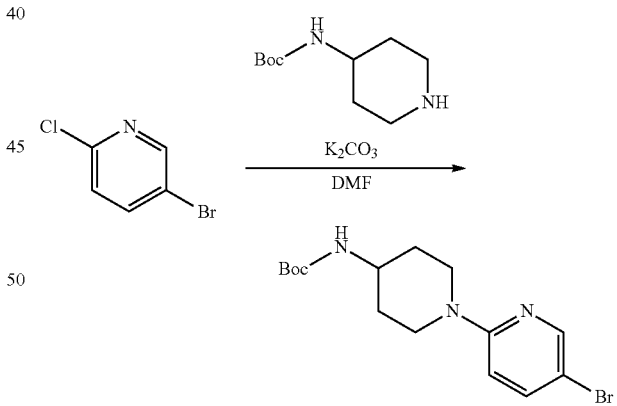

To a mixture of tert-butyl piperidin-4-ylcarbamate (1.77 g, 8.83 mmol) and 5-bromo-2-chloropyridine (1.7 g, 8.83 mmol) in DMF (30 mL) was added K$_2$C03 (3.66 g, 26.50 mmol), the reaction mixture was stirred at 120° C. for 5 h. The mixture was poured into water (300 mL) and extracted with EA (100 mL×2), the organic layer was washed with water (200 mL×2) and brine (200 mL), then dried over Na$_2$SO$_4$ and concentrated. The residue was purified by column chromatography to afford tert-butyl (1-(5-bromopyridin-2-yl)piperidin-4-yl)carbamate (570 mg, 18.11% yield) as a yellow solid. MS: m/z=356.1 (M+1, ESI+).

5.11.4. Synthesis of Compound 144

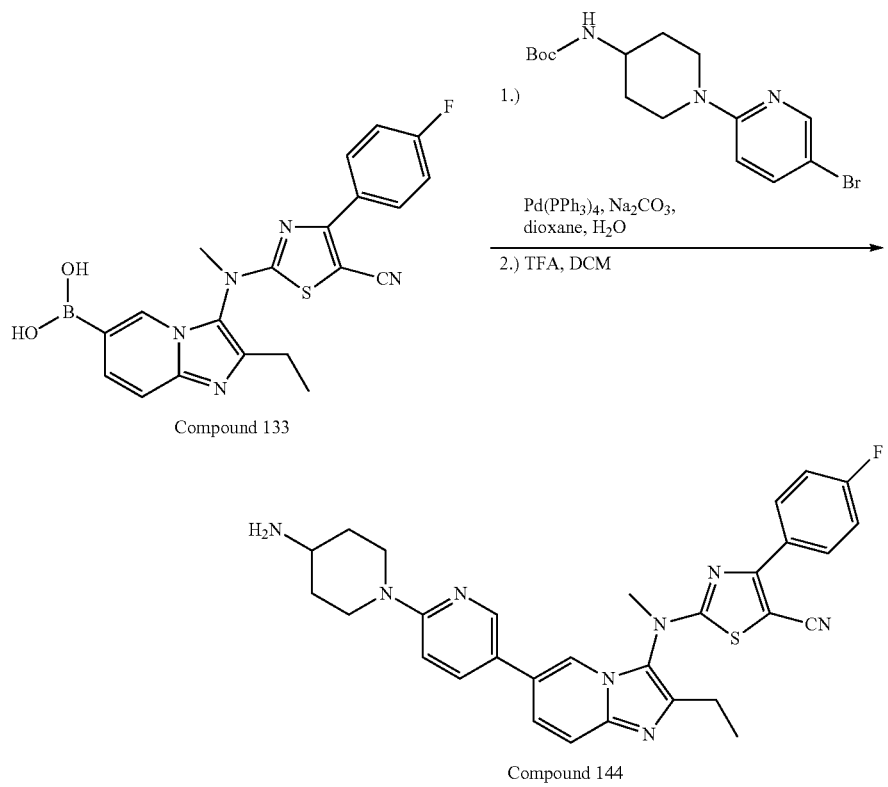

Step One:

To a mixture of compound 133, (3-((5-cyano-4-(4-fluorophenyl)thiazol-2-yl)(methyl)amino)-2-ethylimidazo[1,2-a]pyridin-6-yl)boronic acid (378.38 mg, 898.23 umol) and tert-butyl (1-(5-bromopyridin-2-yl) piperidin-4-yl)carbamate (320 mg, 898.23 umol) in dioxane (10 mL) and water (2 mL) was added Na$_2$CO$_3$ (285.61 mg, 2.69 mmol) and Pd(PPh$_3$)$_4$ (51.90 mg, 44.91 umol), the reaction mixture was stirred at 100° C. for 2 h under N$_2$. The mixture was poured into water (50 mL) and extracted with EA (20 mL×2), the organic layer was washed by brine (30 mL), then dried over Na$_2$SO$_4$ and concentrated. The residue was purified by column chromatography to afford tert-butyl (1-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)carbamate (295 mg, 50.31% yield) as a yellow solid. MS: m/z=653.3 (M+1, ESI+).

Step Two:

To a solution of tert-butyl (1-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)carbamate (295 mg, 451.91 umol) in DCM (5 mL) was added TFA (257.63 mg, 2.26 mmol), the reaction mixture was stirred at 25° C. for 3 h. The mixture was poured into aq.NaHCO$_3$ (50 mL) and extracted with DCM (20 mL×2). The organic layer was washed with water (50 mL×2) and brine (50 mL), then dried over Na$_2$SO$_4$ and concentrated. The residue was purified by column chromatography to afford compound 144, 2-((6-(6-(4-aminopiperidin-1-yl)pyridin-3-yl)-2-ethylimidazo[1,2-a]pyridin-3-yl)(methyl)amino)-4-(4-fluoro phenyl)thiazole-5-carbonitrile (230 mg, 76.46% yield) as a white solid. MS: m/z=553.3 (M+1, ESI+).

5.11.5. Synthesis of methyl 1-(5-bromopyridin-2-yl)piperidine-4-carboxylate

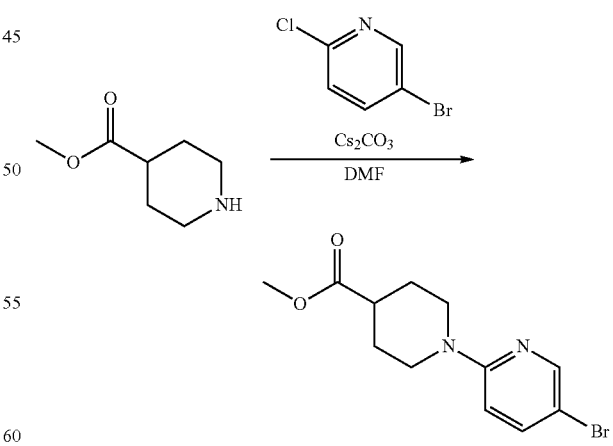

To a solution of methyl piperidine-4-carboxylate (7.44 g, 51.96 mmol) and 5-bromo-2-chloro pyridine (5 g, 25.98 mmol) in DMF (50 mL) was added K$_2$CO$_3$ (10.77 g, 77.95 mmol), the reaction mixture was stirred at 120° C. for 5 h. The mixture was poured into water (500 mL) and extracted with EA (100 mL×3), the organic layer was washed with water (300 mL×2) and brine (300 mL), then dried over Na₂SO₄ and concentrated. The residue was purified by silica gel column to afford methyl 1-(5-bromopyridin-2-yl)piperidine-4-carboxylate (2.6 g, 33.45% yield) as a yellow solid. MS: m/z=299.1 (M+1, ESI+).

5.11.6. Synthesis of Compound 145

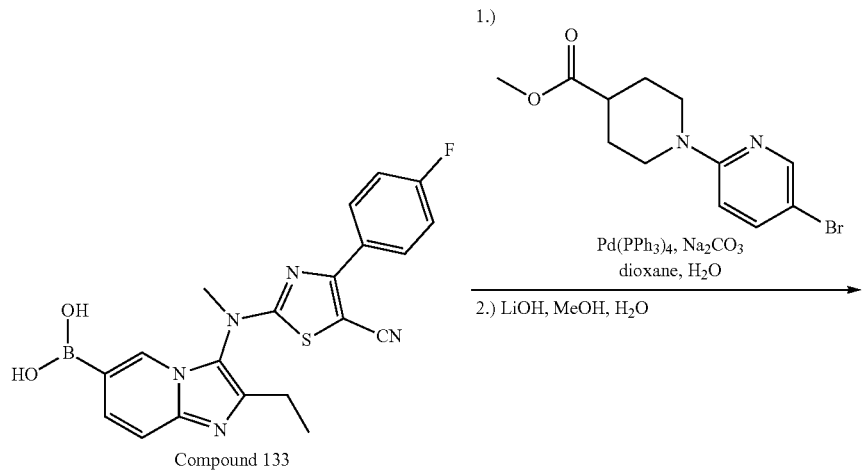

Compound 133

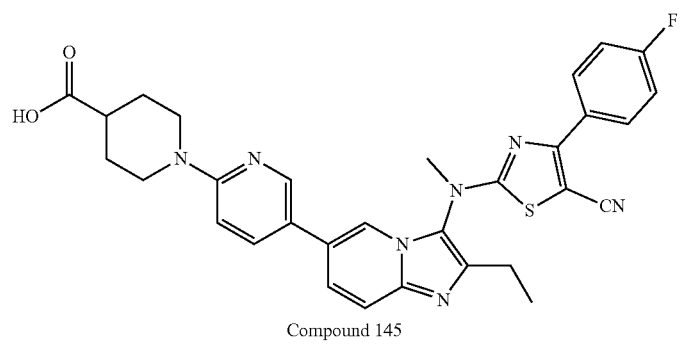

Compound 145

Step One:
To a mixture of compound 133, (3-((5-cyano-4-(4-fluorophenyl)thiazol-2-yl)(methyl)amino)-2-ethylimidazo[1,2-a]pyridin-6-yl) boronic acid (3 g, 7.12 mmol) and methyl 1-(5-bromopyridin-2-yl)piperidine-4-carboxylate (2.34 g, 7.83 mmol) in dioxane (50 mL) and water (10 mL) was added Na₂CO₃ (2.26 g, 21.36 mmol) and Pd(PPh₃)₄ (411.47 mg, 356.08 umol), the reaction mixture was stirred at 100° C. for 2 h under N₂. The mixture was poured into water (100 mL) and extracted with EA (40 mL×2). The organic layer was washed by brine (100 mL), then dried over Na₂SO₄ and concentrated. The residue was purified by column chromatography to afford methyl 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylate (2.7 g, 63.65% yield) as a yellow solid. MS: m/z=596.2 (M+1, ESI+).

Step Two:
To a solution of methyl 1-(5-(3-((5-cyano-4-(4-fluorophenyl)thiazol-2-yl)(methyl)amino)-2-ethyl imidazo[1,2-a]pyridin-6-yl)pyridin-2-yl)piperidine-4-carboxylate (2.7 g, 4.53 mmol) in MeOH (30 mL) and water (10 mL) was added LiOH (542.74 mg, 22.66 mmol), the reaction mixture was stirred at 25° C. for 16 h. The mixture was concentrated and adjusted to pH to 5-6, then poured into water (100 mL) and extracted with EA (40 mL×3). The organic layer was washed with brine (100 mL), then dried over Na₂SO₄ and concentrated to afford compound 145, 1-(5-(3-((5-cyano-4-(4-fluorophenyl) thiazol-2-yl)(methyl)amino)-2-ethylimidazo[1,2-a]pyridin-6-yl)pyridin-2-yl)piperidine-4-carboxylic acid (1.8 g, 68.27% yield) as a yellow solid. MS: m/z=582.1 (M+1, ESI+).

5.11.7. Synthesis of Compound 88

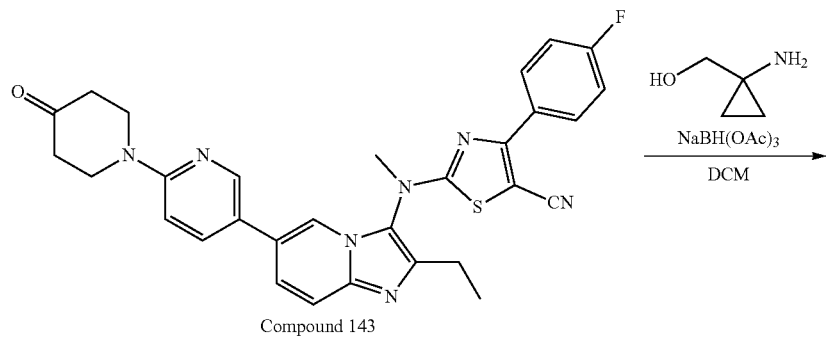

Compound 143

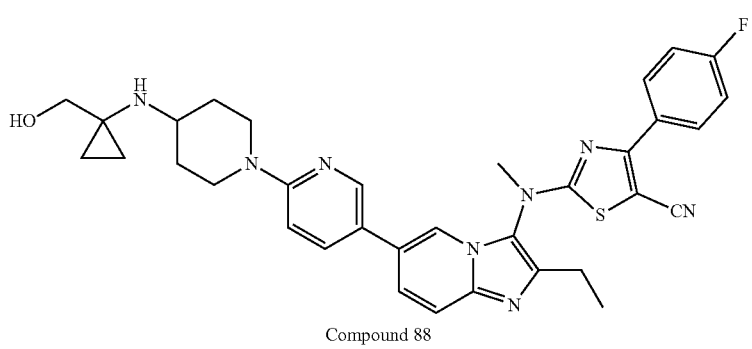

Compound 88

To a solution of compound 143, 2-((2-ethyl-6-(6-(4-oxopiperidin-1-yl)pyridin-3-yl)imidazo[1,2-a]pyridin-3-yl)(methyl)amino)-4-(4-fluorophenyl)thiazole-5-carbonitrile (250 mg, 453.20 umol) and (1-amino cyclopropyl)methanol (43.43 mg, 498.52 umol) in DCM (10 mL) was added NaBH(OAc)$_3$ (115.26 mg, 543.84 umol), the reaction mixture was stirred at 25° C. for 16 h. The mixture was evaporated and purified by Prep-HPLC to afford compound 88 2-((2-ethyl-6-(6-(4-((1-(hydroxymethyl)cyclopropyl)amino) piperidin-1-yl)pyridin-3-yl)imidazo[1,2-a]pyridin-3-yl)(methyl)amino)-4-(4-fluorophenyl)thiazole-5-carbonitrile (139 mg, 49.25% yield) as a white solid. $^1$H NMR (400 MHz, DMSO-d$_6$) δ 8.55 (s, 1H), 8.50 (d, 1H), 8.11-8.08 (t, 2H), 7.92-7.89 (dd, 1H), 7.71-7.65 (m, 2H), 7.44-7.39 (t, 2H), 6.90-6.88 (d, 1H), 4.51-4.48 (t, 1H), 4.21-4.18 (d, 2H), 3.64 (s, 3H), 3.35-3.34 (m, 2H), 3.04-2.91 (m, 3H), 2.69-2.64 (dd, 2H), 2.23 (s, 1H), 1.83-1.81 (d, 2H), 1.29-1.14 (m, 4H), 0.39 (s, 4H); MS: m/z=623.3 (M+1, ESI+); HRMS: 623.2717.

5.11.8. Synthesis of Compound 89 Hydrochloride

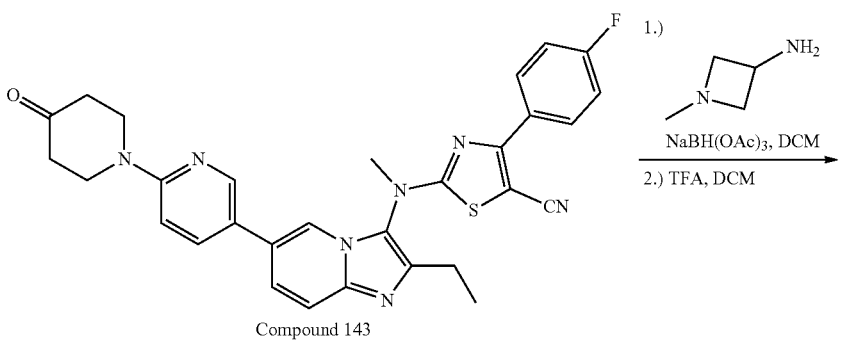

Compound 143

-continued

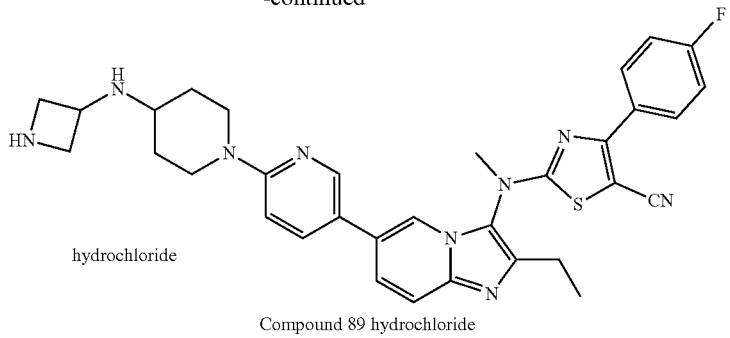

Compound 89 hydrochloride

Step One:

To a suspension of compound 143, 2-((2-ethyl-6-(6-(4-oxopiperidin-1-yl)pyridin-3-yl)imidazo[1,2-a]pyridin-3-yl)(methyl)amino)-4-(4-fluorophenyl)thiazole-5-carbonitrile (250 mg, 453.20 umol) and tert-butyl 3-aminoazetidine-1-carboxylate (78.05 mg, 453.20 umol) in DCM (8 mL) was added NaBH(OAc)$_3$ (115.26 mg, 543.84 umol), the reaction mixture was stirred at 25° C. for 16 h. The mixture was filtered and concentrated. The residue was purified by column chromatography to afford tert-butyl 3-((1-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)amino)azetidine-1-carboxylate (210 mg, 65.46% yield) as a yellow solid. MS: m/z=708.3 (M+1, ESI+).

Step Two:

To a solution of tert-butyl 3-((1-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)amino)azetidine-1-carboxylate (210.00 mg, 296.67 umol) in DCM (5 mL) was added TFA (169.13 mg, 1.48 mmol), the reaction mixture was stirred at 25° C. for 3 h. The mixture was concentrated under reduced pressure and the residue was purified by Prep-HPLC to afford compound 89 hydrochloride, 2-((6-(6-(4-(azetidin-3-ylamino)piperidin-1-yl)pyridin-3-yl)-2-ethylimidazo[1,2-a]pyridin-3-yl)(methyl)amino)-4-(4-fluorophenyl)thiazole-5-carbonitrile hydrochloride (160 mg, 83.72% yield) as a yellow solid. $^1$H NMR (400 MHz, DMSO-d$_6$) δ 11.02 (s, 2H), 10.11-10.10 (d, 1H), 9.31 (s, 1H), 9.22 (s, 1H), 8.48-8.41 (m, 3H), 8.15-8.13 (d, 1H), 8.02 (s, 2H), 7.51-7.49 (d, 1H), 7.43-7.39 (t, 2H), 4.63-4.60 (d, 2H), 4.43-4.35 (m, 3H), 4.17 (s, 2H), 3.70 (s, 3H), 3.50 (s, 1H), 3.27-3.21 (t, 2H), 2.92-2.86 (dd, 2H), 2.17-2.14 (m, 2H), 1.75-1.72 (m, 2H), 1.38-1.34 (t, 3H); MS: m/z=608.3 (M+1, ESI+); HRMS: 608.2712.

5.11.9. Synthesis of Compound 89

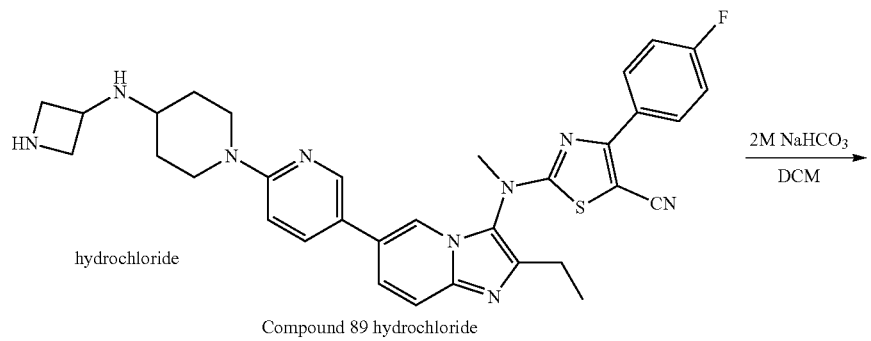

Compound 89 hydrochloride

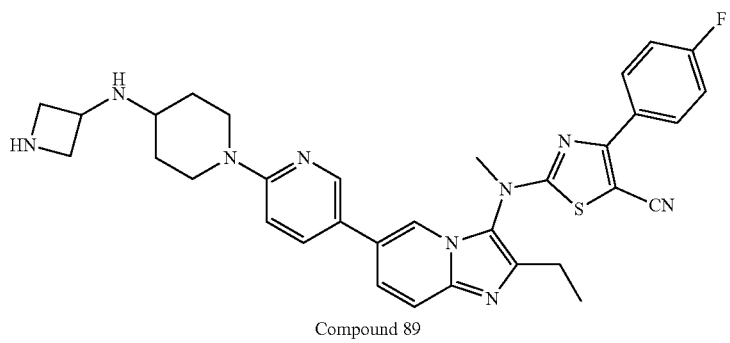

Compound 89

To a mixture of compound 89 hydrochloride, 2-((6-(6-(4-(azetidin-3-ylamino)piperidin-1-yl)pyridin-3-yl)-2-ethyl-imidazo[1,2-a] pyridin-3-yl)(methyl)amino)-4-(4-fluorophenyl)thiazole-5-carbonitrile hydrochloride (90 mg, 0.125 mmol) in H₂O (3 mL) was added 2 M NaHCO₃ (1.05 mL, 2.1 mmol) at 0° C. and stirred for 0.5 h. Then extracted with DCM (5 mL×2). The organic layer was washed with water (5 mL) and brine (5 mL), dried over Na₂SO₄ and concentrated to afford compound 89, 2-((6-(6-(4-(azetidin-3-ylamino) piperidin-1-yl)pyridin-3-yl)-2-ethylimidazo[1,2-a] pyridin-3-yl)(methyl)amino)-4-(4-fluorophenyl) thiazole-5-carbonitrile (80 mg, 81.63% yield) as a white solid. ¹H NMR (400 MHz, DMSO-d₆) δ 8.54-8.49 (m, 2H), 8.10-8.07 (t, 2H), 7.92-7.89 (m, 1H), 7.71-7.65 (m, 2H), 7.44-7.39 (t, 2H), 6.91-6.89 (d, 1H), 4.23-4.20 (m, 2H), 3.76-3.63 (m, 8H), 2.94-2.88 (t, 2H), 2.69-2.63 (m, 4H), 1.74-1.72 (t, 2H), 1.28-1.25 (t, 3H); MS: m/z=609.1 (M+1, ESI+).

5.11.10. Synthesis of Compound 90 mixture was stirred at 25° C. for 16 h. The mixture was filtered and concentrated, the residue was purified by column chromatography to afford tert-butyl 4-((I-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)amino)piperidine-1-carboxylate (215 mg, 64.47% yield) as a yellow solid. MS: m/z=736.3 (M+1, ESI+).

Step Two:

To a solution of tert-butyl 4-((1-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)amino)piperidine-1-carboxylate (215.00 mg, 292.15 umol) in DCM (5 mL) was added TFA (166.56 mg, 1.46 mmol), the reaction mixture was stirred at 25° C. for 3 h. The mixture was concentrated under reduce pressure and the residue was purified by Prep-HPLC to afford compound 90, 2-((2-ethyl-6-(6-(4-(piperidin-4-ylamino)piperidin-1-yl)pyridin-3-yl)imidazo[1,2-a]pyridin-3-yl)(methyl)amino)-4-(4-fluorophenyl)thiazole-5-carbonitrile (135 mg, 72.68% yield) as a

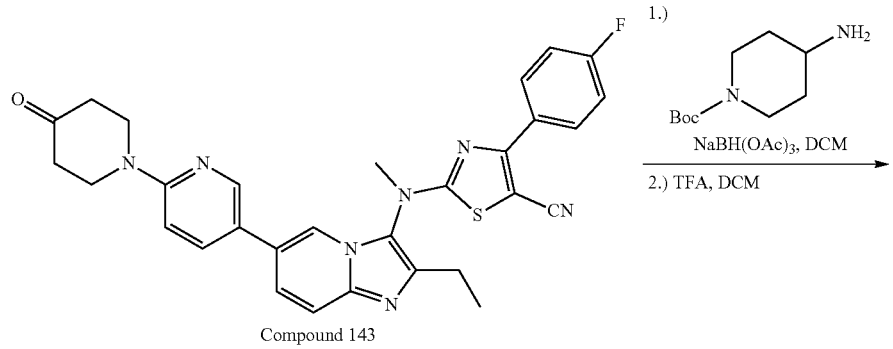

Compound 143

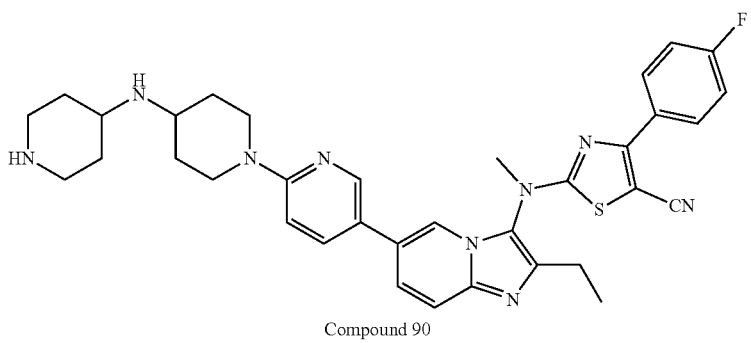

Compound 90

Step One:

To a suspension of compound 143, 2-((2-ethyl-6-(6-(4-oxopiperidin-1-yl)pyridin-3-yl)imidazo[1,2-a]pyridin-3-yl)(methyl)amino)-4-(4-fluorophenyl)thiazole-5-carbonitrile (250 mg, 453.20 umol) and tert-butyl 4-aminopiperidine-1-carboxylate (90.77 mg, 453.20 umol) in DCM (8 mL) was added NaBH(OAc)₃ (115.26 mg, 543.84 umol), the reaction white solid. 1H NMR (400 MHz, DMSO-d₆) δ 8.55-8.49 (m, 2H), 8.11-8.07 (t, 2H), 7.92-7.89 (dd, 1H), 7.71-7.64 (m, 2H), 7.44-7.39 (t, 2H), 6.90-6.88 (d, 1H), 4.23-4.20 (d, 2H), 3.63 (s, 3H), 2.95-2.78 (m, 4H), 2.69-2.64 (dd, 2H), 2.60-2.54 (m, 1H), 2.45-2.39 (t, 2H), 1.82-1.79 (d, 2H), 1.72-1.70 (d, 2H), 1.29-1.16 (t, 3H), 1.24-1.03 (m, 4H); MS: m/z=636.4 (M+1, ESI+); HRMS: 636.3033.

5.11.11. Synthesis of Compound 98

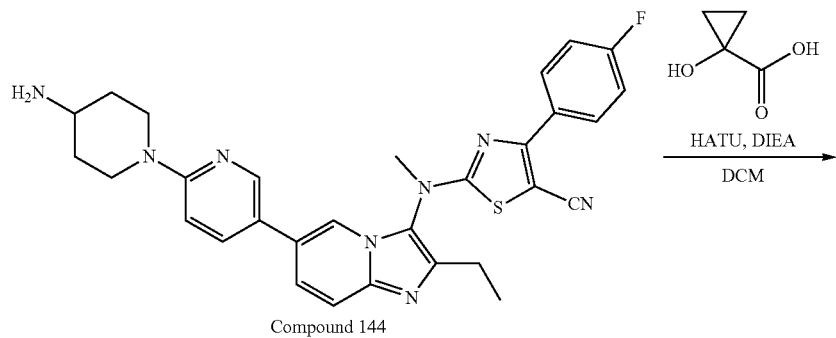

Compound 144

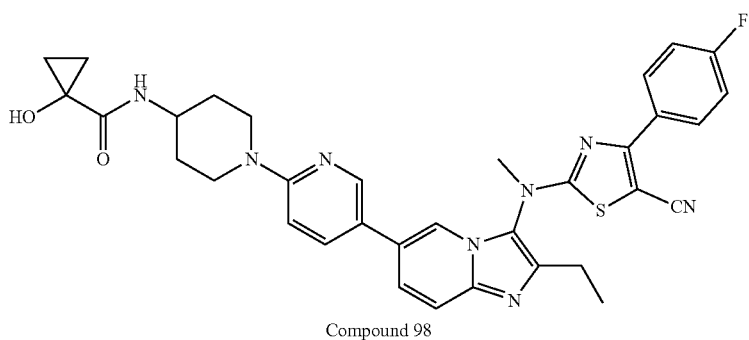

Compound 98

To a solution of compound 144, 2-((6-(6-(4-aminopiperidin-1-yl)pyridin-3-yl)-2-ethylimidazo[1,2-a]pyridin-3-yl)(methyl)amino)-4-(4-fluorophenyl)thiazole-5-carbonitrile (235 mg, 353.02 umol) and 1-hydroxy cyclopropane-1-carboxylic acid (36.04 mg, 353.02 umol) in DMF (5 mL) was added HATU (174.50 mg, 458.93 umol) and DIEA (136.88 mg, 1.06 mmol), the reaction mixture was stirred at 25° C. for 3 h. The mixture was poured into water (50 mL) and extracted with EA (20 mL×2). The organic layer was washed with water (50 mL×2) and brine (50 mL), then dried over Na$_2$SO$_4$ and concentrated. The residue was purified by Prep-HPLC to afford compound 98, N-(1-(5-(3-((5-cyano-4-(4-fluorophenyl)thiazol-2-yl)(methyl)amino)-2-ethylimidazo[1,2-a]pyridin-6-yl)pyridin-2-yl)piperidin-4-yl)-1-hydroxycyclopropane-1-carboxamide (85 mg, 37.81% yield) as a white solid. $^1$H NMR (400 MHz, DMSO-d$_6$) δ 8.57-8.52 (m, 2H), 8.11-8.07 (t, 2H), 7.95-7.92 (dd, 1H), 7.72-7.65 (m, 3H), 7.44-7.40 (t, 2H), 6.94-6.92 (d, 1H), 6.16 (s, 1H), 4.34-4.31 (d, 2H), 3.92-3.86 (m, 1H), 3.64 (s, 3H), 2.95-2.89 (t, 2H), 2.69-2.64 (dd, 2H), 1.76-1.73 (d, 2H), 1.58-1.49 (m, 2H), 1.28-1.25 (t, 3H), 1.02-0.99 (m, 2H), 0.82-0.79 (m, 2H); MS: m/z=637.2 (M+1, ESI+); HRMS: 637.2509.

5.11.12. Synthesis of Compound 113

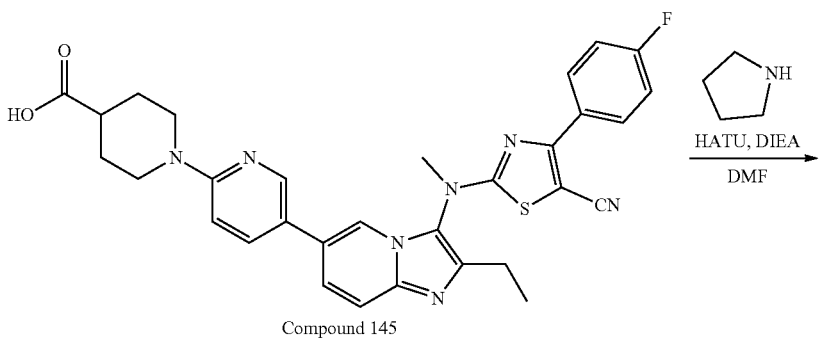

Compound 145

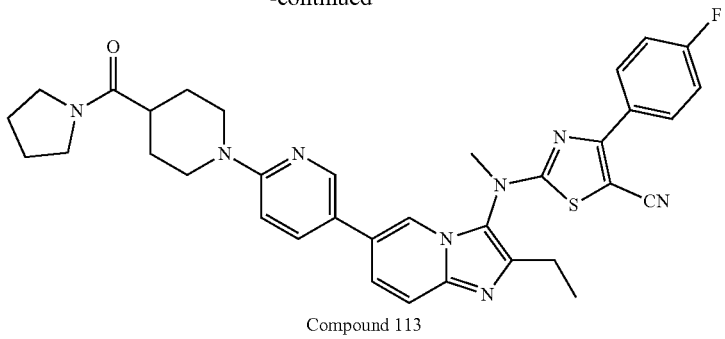

Compound 113

To a solution of pyrrolidine (47.07 mg, 661.90 umol) and compound 145, 1-(5-(3-((5-cyano-4-(4-fluorophenyl) thiazol-2-yl)(methyl)amino)-2-ethylimidazo[1,2-a]pyridin-6-yl)pyridin-2-yl)piperidine-4-carboxylic acid (350 mg, 601.72 umol) in DMF (8 mL) was added HATU (343.19 mg, 902.59 umol) and DIEA (233.30 mg, 1.81 mmol), the reaction mixture was stirred at 25° C. for 2 h. The mixture was poured into water (80 mL) and extracted with EA (30 mL×3). The organic layer was washed with brine (80 mL), then dried over $Na_2SO_4$ and concentrated. The residue was purified by Prep-HPLC (Waters Xbridge C18 10 um OBD 19*250 mm, A: 10 mmol $NH_4HCO_3$ in water; B: $CH_3CN$, 5% to 95%) in $NH_4HCO_3$ condition to afford compound 113, 2-((2-ethyl-6-(6-(4-(pyrrolidine-1-carbonyl)piperidin-1-yl)pyridin-3-yl)imidazo[1,2-a]pyridin-3-yl)(methyl)amino)-4-(4-fluorophenyl)thiazole-5-carbonitrile (193 mg, 50.53% yield) as a white solid. $^1H$ NMR (400 MHz, DMSO-$d_6$) δ 8.57 (s, 1H), 8.51 (d, 1H), 8.11-8.08 (t, 2H), 7.94-7.91 (dd, 1H), 7.72-7.65 (m, 2H), 7.44-7.40 (t, 2H), 6.93-6.90 (d, 1H), 4.39-4.36 (d, 2H), 3.64 (s, 3H), 3.52-3.49 (t, 2H), 3.27-3.24 (t, 2H), 2.94-2.88 (m, 2H), 2.75-2.64 (m, 3H), 1.91-1.84 (m, 2H), 1.79-1.68 (m, 4H), 1.57-1.47 (m, 2H), 1.29-1.25 (t, 3H); MS: m/z=635.3 (M+1, ESI+); HRMS: 635.2703.

5.11.13. Synthesis of Compound 113 Hydrochloride

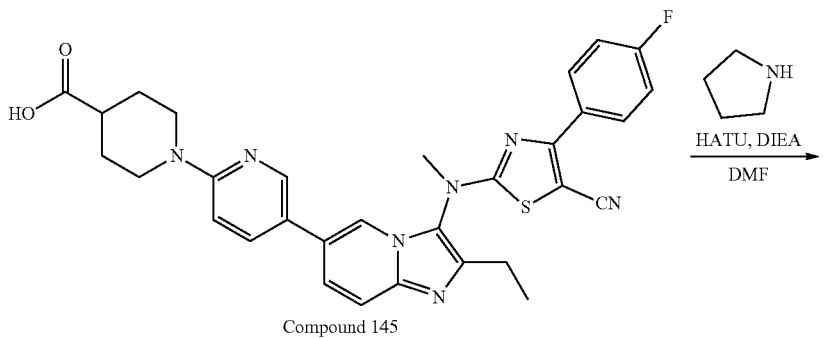

Compound 145

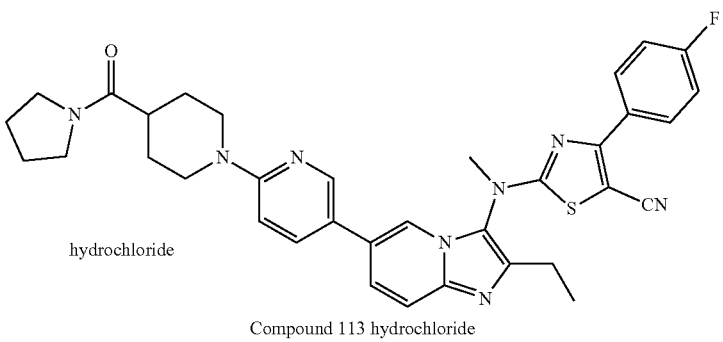

hydrochloride

Compound 113 hydrochloride

To a solution of compound 145, pyrrolidine (67 mg, 945 umol) and 1-(5-(3-((5-cyano-4-(4-fluorophenyl) thiazol-2-yl)(methyl)amino)-2-ethylimidazo[1,2-a]pyridin-6-yl)pyridin-2-yl)piperidine-4-carboxylic acid (500 mg, 860 umol) in DMF (8 mL) was added HATU (490 mg, 1.29 mmol) and DIEA (333 mg, 2.58 mmol), the reaction mixture was stirred at 25° C. for 2 h. The mixture was poured into water (80 mL) and extracted with EA (30 mL×3). The organic layer was washed with brine (80 mL), then dried over Na₂SO₄ and concentrated. The residue was purified by Prep-HPLC (Waters Xbridge C18 10 um OBD 19*250 mm, A: 0.05% HCl in water; B: CH₃CN, 5% to 95%) in HCl condition to afford compound 113 hydrochloride, 2-((2-ethyl-6-(6-(4-(pyrrolidine-1-carbonyl)piperidin-1-yl)pyridin-3-yl)imidazo[1,2-a] pyridin-3-yl)(methyl) amino)-4-(4-fluorophenyl)thiazole-5-carbonitrile hydrochloride (230 mg, 35.93% yield) as a pale yellow solid. ¹H NMR (400 MHz, DMSO-d₆) δ 9.18 (s, 1H), 8.42-8.37 (m, 3H), 8.14-8.12 (d, 1H), 8.04-8.00 (t, 2H), 7.49-7.38 (m, 3H), 4.50-4.47 (d, 2H), 3.68 (s, 3H), 3.54-3.51 (t, 2H), 3.30-3.25 (m, 4H), 2.90-2.83 (m, 3H), 1.91-1.60 (m, 8H), 1.36-1.33 (t, 3H); MS: m/z=635.3 (M+1, ESI+).

5.11.14. Synthesis of Compound 114

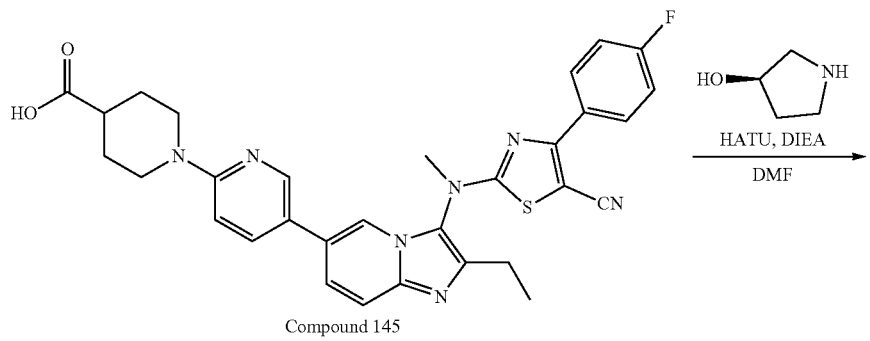

Compound 145

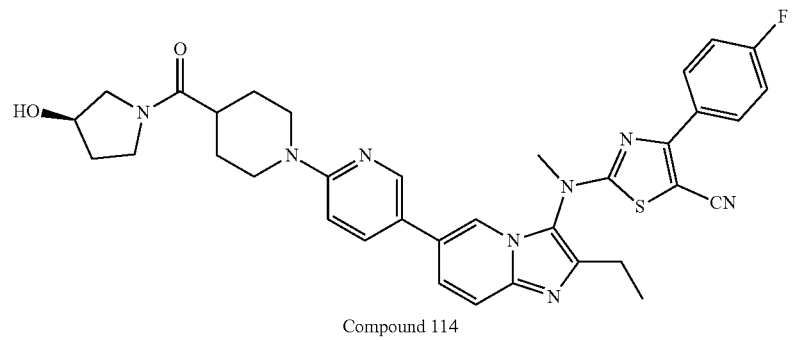

Compound 114

To a solution of compound 145, 1-(5-(3-((5-cyano-4-(4-fluoro phenyl) thiazol-2-yl)(methyl)amino)-2-ethylimidazo [1,2-a]pyridin-6-yl)pyridin-2-yl)piperidine-4-carboxylic acid (400 mg, 687.68 umol) and (R)-pyrrolidin-3-ol (65.90 mg, 756.45 umol) in DMF (8 mL) was added HATU (392.22 mg, 1.03 mmol) and DIEA (266.63 mg, 2.06 mmol), the reaction mixture was stirred at 25° C. for 2 h. The mixture was poured into water (80 mL) and extracted with EA (30 mL×3). The organic layer was washed with brine (80 mL), then dried over $Na_2SO_4$ and concentrated. The residue was purified by Prep-HPLC (Waters Xbridge C18 10 um OBD 19*250 mm, A: 10 mmol $NH_4HCO$; in water; B: $CH_3CN$, 5% to 95%) in $NH_4HCO_3$ condition to afford compound 114, (R)-2-((2-ethyl-6-(6-(4-(3-hydroxypyrrolidine-1-carbonyl)piperidin-1-yl)pyridin-3-yl) imidazo[1,2-a]pyridin-3-yl)(methyl)amino)-4-(4-fluorophenyl)thiazole-5-carbonitrile (223 mg, 49.83% yield) as a white solid. $^1$H NMR (400 MHz, DMSO-$d_6$) δ 8.48-8.47 (m, 2H), 8.10-8.07 (m, 2H), 7.89-7.86 (dd, 1H), 7.67-7.62 (m, 2H), 7.39-7.35 (t, 2H), 6.89-6.86 (d, 1H), 4.86-4.76 (dd, 1H), 4.36-4.24 (m, 3H), 3.64 (s, 3H), 3.61-3.58 (m, 1H), 3.38-3.22 (m, 3H), 2.97-2.91 (m, 2H), 2.76-2.63 (m, 3H), 1.98-1.69 (m, 4H), 1.61-1.51 (m, 2H) 1.29-1.25 (t, 3H); MS: m/z=651.2 (M+1, ESI+); HRMS: 651.2653.

5.11.15. Synthesis of Compound 114 Hydrochloride

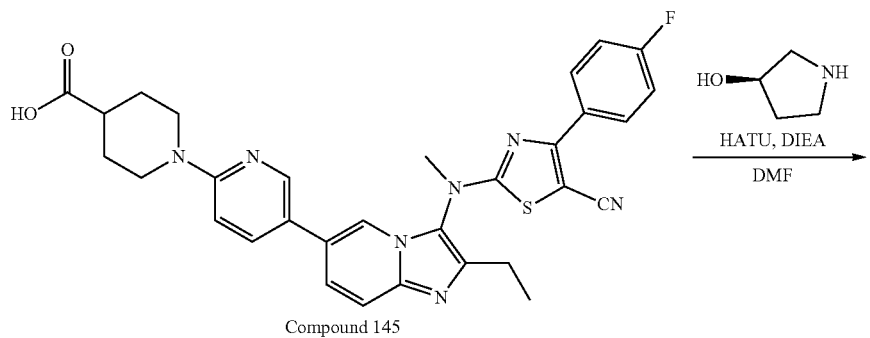

Compound 145

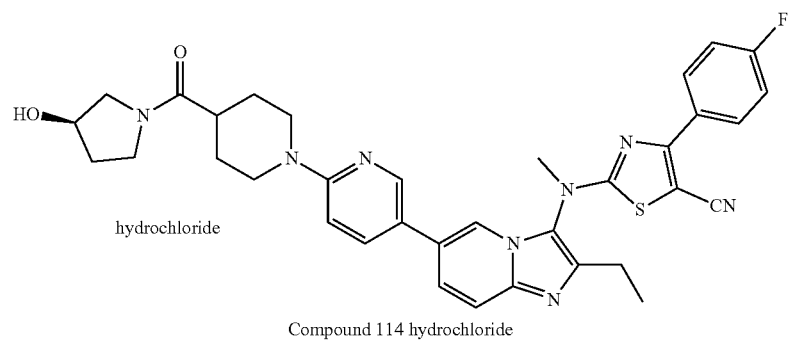

Compound 114 hydrochloride

To a solution of compound 145, (R)-pyrrolidin-3-ol (82 mg, 945 umol) and 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (500 mg, 860 umol) in DMF (8 mL) was added HATU (490 mg, 1.29 mmol) and DIEA (333 mg, 2.58 mmol), the reaction mixture was stirred at 25° C. for 2 h. The mixture was poured into water (80 mL) and extracted with EA (30 mL×3). The organic layer was washed with brine (80 mL), then dried over $Na_2SO_4$ and concentrated. The residue was purified by Prep-HPLC (Waters Xbridge C18 10 um OBD 19*250 mm, A: 0.05% HCl in water; B. $CH_3CN$, 5% to 95%) in HCl condition to afford compound 114 hydrochloride, (R)-2-((2-ethyl-6-(6-(4-(3-hydroxypyrrolidine-1-carbonyl)piperidin-1-yl)pyridin-3-yl)imidazo [1,2-a] pyridin-3-yl)(methyl)amino)-4-(4-fluorophenyl)thiazole-5-carbonitrile hydrochloride (205 mg, 31.34% yield) as a pale yellow solid. $^1$H NMR (400 MHz, DMSO-$d_6$) δ 9.10 (s, 1H), 8.46 (s, 1H), 8.35-8.24 (m, 2H), 8.10-8.07 (d, 1H), 8.04-8.01 (t, 2H), 7.42-7.31 (m, 3H), 4.46-4.16 (m, 4H), 3.67-3.58 (m, 5H), 3.41-3.16 (m, 5H), 2.89-2.76 (m, 3H), 1.97-1.54 (m, 6H), 1.35-1.33 (t, 3H); MS: m/z=651.2 (M+1, ESI+).

5.11.16. Synthesis of Compound 118 mg, 1.55 mmol), the reaction mixture was stirred at 25° C. for 2 h. The mixture was poured into water (50 mL) and extracted with EA (20 mL×3). The organic layer was washed with water (50 mL×2) and brine (50 mL), then dried over $Na_2SO_4$ and concentrated. The residue was purified by silica gel column to afford tert-butyl 4-(1-(5-(3-((5-cyano-4-(4-fluorophenyl)thiazol-2-yl)(methyl)amino)-2-ethylimidazo [1,2-a]pyridin-6-yl)pyridin-2-yl) piperidine-4-carbonyl)piperazine-1-carboxylate (280 mg, 72.39% yield) as a yellow solid. MS: m/z=750.1 (M+1, ESI+).

Step Two:

To a solution of tert-butyl 4-(1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carbonyl)piperazine-1-carboxylate (280 mg, 373.38 umol) in DCM (5 mL) was added TFA (212.87 mg, 1.87 mmol), the reaction mixture was stirred at 25° C. for 5 h. The mixture was concentrated and purified by Prep-HPLC to afford compound 118, 2-((2-ethyl-6-(6-(4-(piperazine-1-carbonyl)piperidin-1-yl)pyridin-3-yl)imidazo[1,2-a]pyridin-3-yl)(methyl)amino)-4-(4-fluorophenyl)thiazole-5-carbonitrile

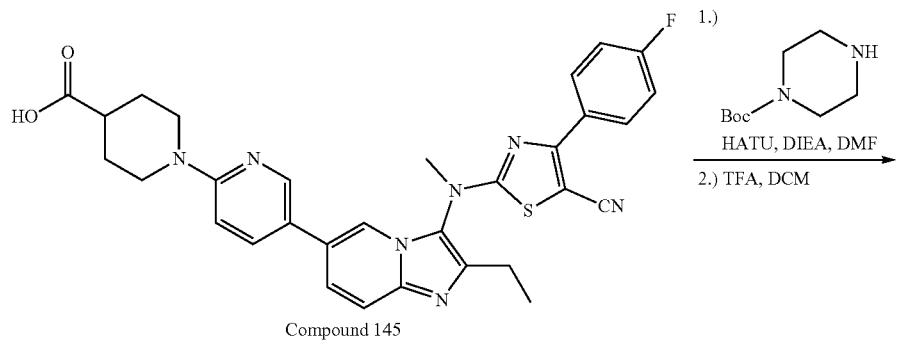

Compound 145

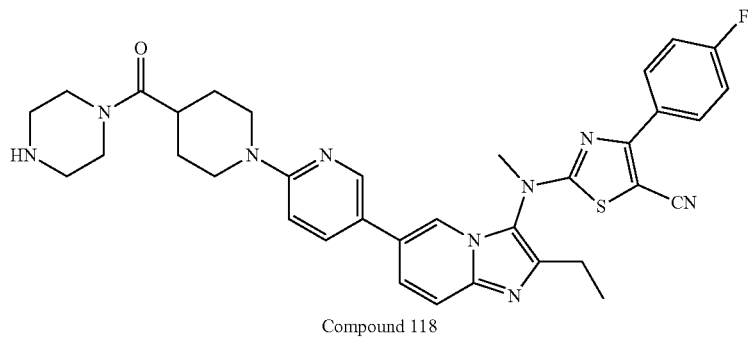

Compound 118

Step One:

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (300 mg, 515.76 umol) and tert-butyl piperazine-1-carboxylate (105.67 mg, 567.34 umol) in DMF (5 mL) was added HATU (294.16 mg, 773.65 umol) and DIEA (199.98

(172 mg, 70.89% yield) as a white solid. $^1$H NMR (400 MHz, DMSO-$d_6$) δ 8.57 (s, 1H), 8.51 (d, 1H), 8.11-8.08 (t, 2H), 7.94-7.91 (dd, 1H), 7.71-7.65 (m, 2H), 7.44-7.39 (t, 2H), 6.92-6.90 (d, 1H), 4.37-4.33 (d, 2H), 3.64 (s, 3H), 3.45-3.44 (m, 2H), 3.36-3.34 (m, 2H), 2.95-2.87 (m, 3H), 2.70-2.60 (m, 6H), 1.66-1.52 (m, 4H), 1.29-1.25 (t, 3H); MS: m/z=650.3 (M+1, ESI+); HRMS: 650.2822.

5.11.17. Synthesis of Compound 119

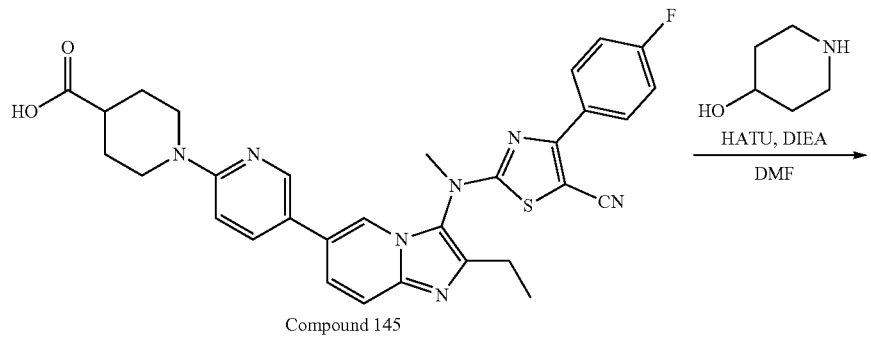

Compound 145

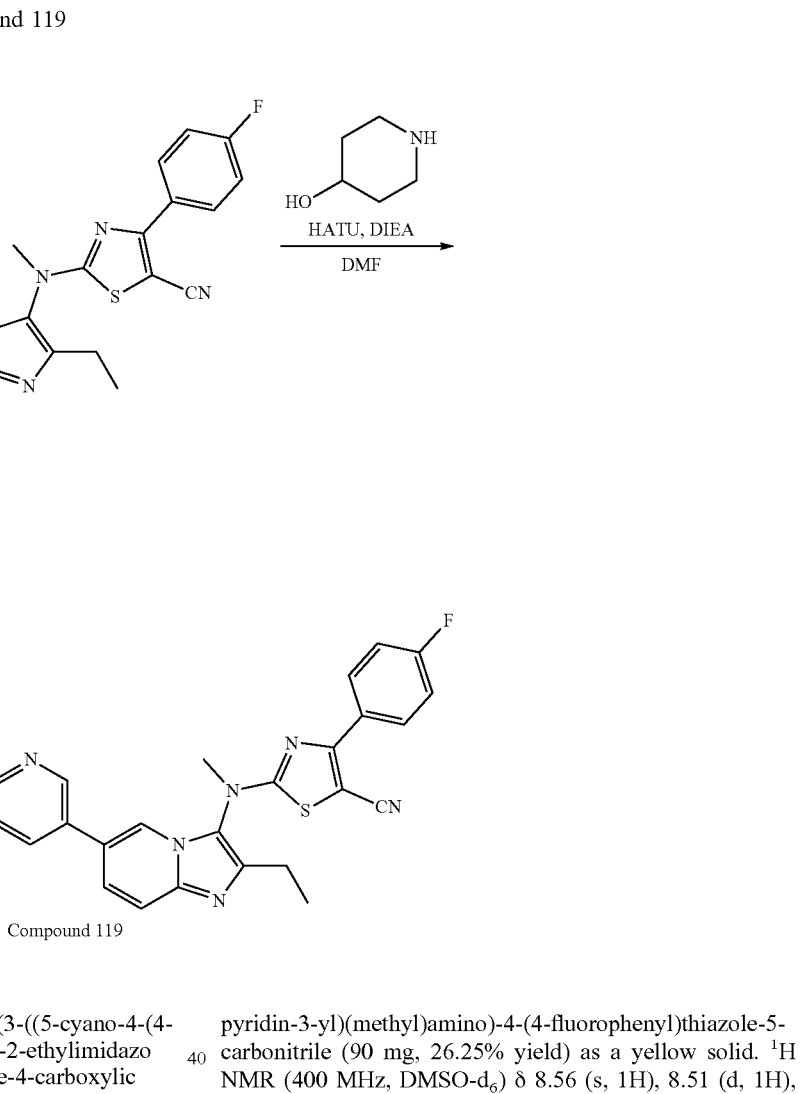

Compound 119

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (300 mg, 515.76 umol) and piperidin-4-ol (62.60 mg, 618.92 umol) in DMF (5 mL) was added HATU (291.87 mg, 773.65 umol) and DIEA (199.98 mg, 1.55 mmol), the reaction mixture was stirred at 25° C. for 2 h. The mixture was poured into water (50 mL) and extracted with EA (20 mL×3). The organic layer was washed with water (50 mL×2) and brine (50 mL), then dried over $Na_2SO_4$ and concentrated. The residue was purified by silica gel column to afford compound 119, 2-((2-ethyl-6-(6-(4-(4-hydroxypiperidine-1-carbonyl) piperidin-1-yl)pyridin-3-yl)imidazo[1,2-a]pyridin-3-yl)(methyl)amino)-4-(4-fluorophenyl)thiazole-5-carbonitrile (90 mg, 26.25% yield) as a yellow solid. $^1$H NMR (400 MHz, DMSO-$d_6$) δ 8.56 (s, 1H), 8.51 (d, 1H), 8.11-8.07 (t, 2H), 7.94-7.91 (dd, 1H), 7.71-7.65 (m, 2H), 7.44-7.39 (t, 2H), 6.92-6.90 (d, 1H), 4.74-4.73 (d, 1H), 4.36-4.33 (d, 2H), 3.91-3.78 (m, 2H), 3.71-3.64 (m, 1H), 3.63 (s, 3H), 3.24-3.19 (m, 1H), 2.99-2.90 (m, 4H), 2.69-2.64 (dd, 2H), 1.77-1.75 (m, 1H), 1.65-1.62 (m, 3H), 1.56-1.50 (m, 2H), 1.35-1.20 (m, 6H); MS: m/z=665.2 (M+1, ESI+); HRMS: 665.2819.

5.11.18. Synthesis of Compound 120

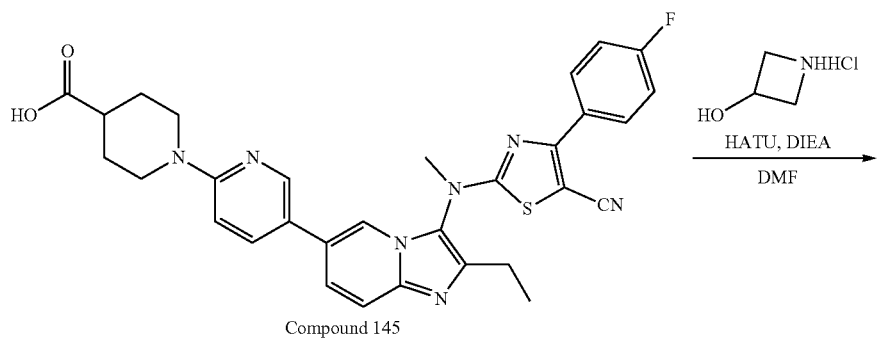

Compound 145

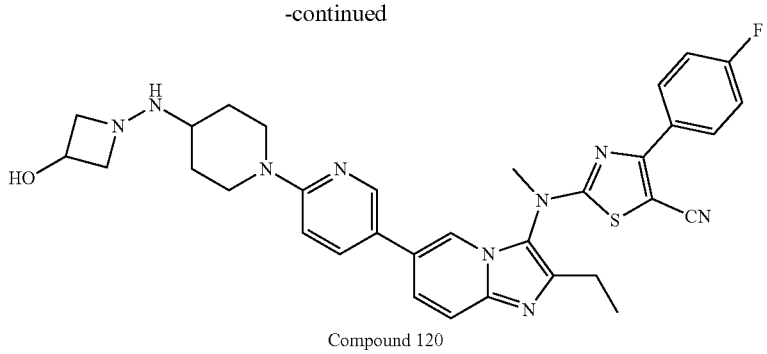

Compound 120

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (300 mg, 515.76 umol) and azetidin-3-ol hydrochloride (45.24 mg, 618.92 umol) in DMF (10 mL) was added HATU (291.87 mg, 773.65 umol) and DIEA (199.98 mg, 1.55 mmol), the reaction mixture was stirred at 25° C. for 2 h. The mixture was poured into water (100 mL) and extracted with EA (30 mL×3). The organic layer was washed with water (100 mL×2) and brine (100 mL), then dried over Na$_2$SO$_4$ and concentrated. The residue was purified by silica gel column to afford compound 120, 2-((2-ethyl-6-(6-(4-(3-hydroxyazetidine-1-carbonyl)piperidin-1-yl)pyridin-3-yl)imidazo[1,2-a]pyridin-3-yl)(methyl)amino)-4-(4-fluorophenyl) thiazole-5-carbonitrile (120 mg, 36.54% yield) as a white solid. $^1$H NMR (400 MHz, DMSO-d$_6$) δ 8.56 (s, 1H), 8.51 (d, 1H), 8.11-8.07 (t, 2H), 7.93-7.91 (dd, 1H), 7.71-7.64 (m, 2H), 7.44-7.39 (t, 2H), 6.92-6.90 (d, 1H), 5.71-5.69 (d, 1H), 4.46-4.33 (m, 4H), 4.01-3.99 (m, 1H), 3.97-3.88 (m, 1H), 3.63 (s, 3H), 3.56-3.52 (m, 1H), 2.93-2.87 (m, 2H), 2.69-2.63 (dd, 2H), 1.65-1.62 (m, 2H), 1.51-1.45 (m, 2H), 1.28-1.24 (t, 3H); MS: m/z=637.2 (M+1, ESI+); HRMS: 637.2505.

5.11.19. Synthesis of Compound 121

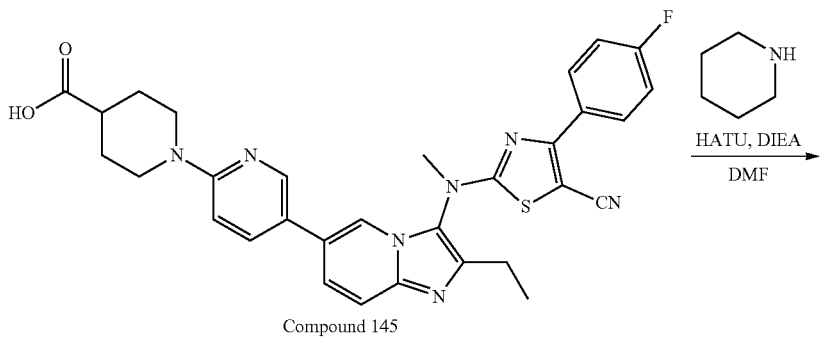

Compound 145

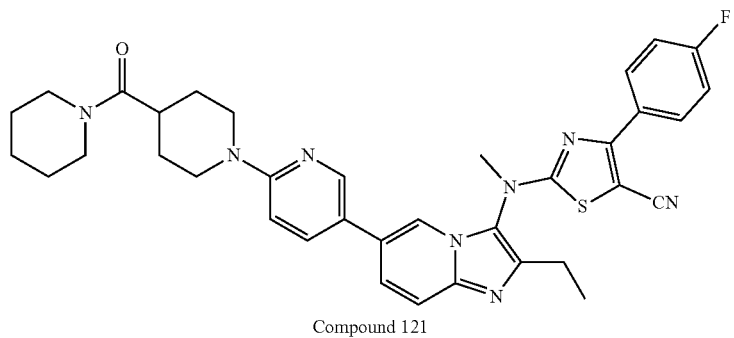

Compound 121

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (500 mg, 859.61 umol) and piperidine (87.83 mg, 1.03 mmol) in DMF (10 mL) was added HATU (486.46 mg, 1.29 mmol) and DIEA (333.29 mg, 2.58 mmol), the reaction mixture was stirred at 25° C. for 2 h. The mixture was poured into water (100 mL) and extracted with EA (30 mL×3). The organic layer was washed with water (100 mL×2) and brine (100 mL), then dried over $Na_2SO_4$ and concentrated. The residue was purified by Prep-HPLC (Waters Xbridge C18 10 um OBD 19*250 mm, A: 10 mmol $NH_4HCO_3$ in water; B: $CH_3CN$, 5% to 95%) in $NH_4HCO_3$ condition to afford compound 121, 2-((2-ethyl-6-(6-(4-(piperidine-1-carbonyl)piperidin-1-yl) pyridin-3-yl)imidazo[1,2-a]pyridin-3-yl)(methyl)amino)-4-(4-fluorophenyl)thiazole-5-carbonitrile (200 mg, 35.86% yield) as a white solid. $^1$H NMR (400 MHz, DMSO-$d_6$) δ 8.57 (s, 1H), 8.52-8.51 (d, 1H), 8.11-8.08 (t, 2H), 7.94-7.91 (dd, 1H), 7.69-7.65 (m, 2H), 7.44-7.39 (t, 2H), 6.92-6.89 (d, 1H), 4.37-4.33 (d, 2H), 3.64 (s, 3H), 3.48-3.41 (m, 4H), 2.96-2.90 (m, 3H), 2.70-2.64 (dd, 2H), 1.65-1.50 (m, 8H), 1.41-1.40 (m, 2H), 1.29-1.25 (t, 3H), MS: m/z=649.2 (M+1, ESI+); HRMS: 649.2870.

5.11.20. Synthesis of Compound 121 Hydrochloride

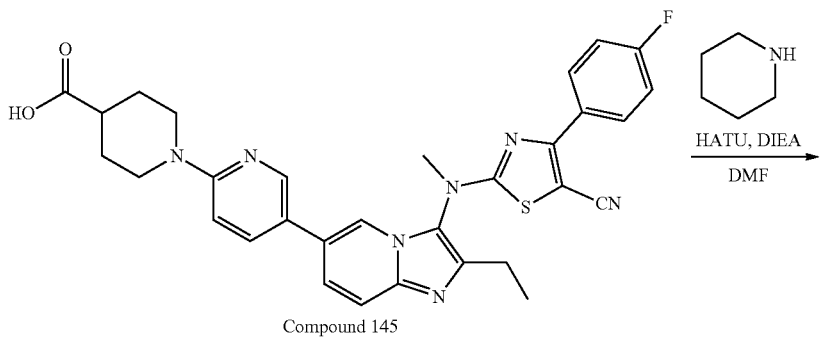

Compound 145

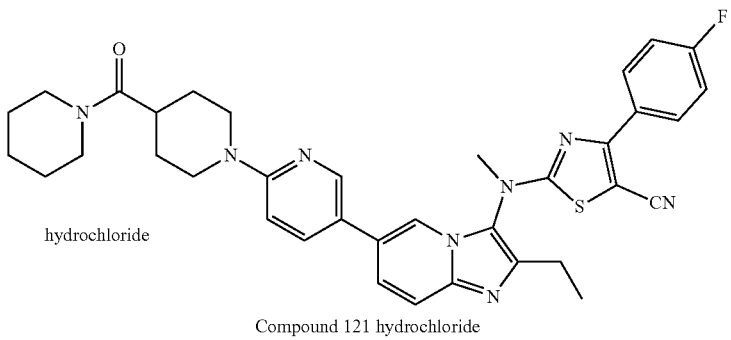

Compound 121 hydrochloride

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (500 mg, 859.61 umol) and piperidine (87.83 mg, 1.03 mmol) in DMF (10 mL) was added HATU (486.46 mg, 1.29 mmol) and DIEA (333.29 mg, 2.58 mmol), the reaction mixture was stirred at 25° C. for 2 h. The mixture was poured into water (100 mL) and extracted with EA (30 mL×3). The organic layer was washed with water (100 mL×2) and brine (100 mL), then dried over $Na_2SO_4$ and concentrated. The residue was purified by Prep-HPLC (Waters Xbridge C18 10 um OBD 19*250 mm, A: 0.05% HCl in water; B: $CH_3CN$, 5% to 95%) in HCl condition to afford compound 121 hydrochloride, 2-((2-ethyl-6-(6-(4-(piperidine-1-carbonyl)piperidin-1-yl) pyridin-3-yl)imidazo[1,2-a]pyridin-3-yl)(methyl)amino)-4-(4-fluorophenyl)thiazole-5-carbonitrile hydrochloride (170 mg, 26.07% yield) as a white solid. $^1$H NMR (400 MHz, DMSO-d6) δ 9.11 (s, 1H), 8.45 (s, 1H), 8.35-8.25 (m, 2H), 8.10-8.00 (m, 3H), 7.42-7.32 (m, 3H), 4.44-4.41 (d, 2H), 3.67 (s, 3H), 3.50-3.40 (m, 4H), 3.25-3.19 (t, 2H), 3.06-3.01 (m, 1H), 2.89-2.83 (m, 2H), 1.76-1.40 (m, 10H), 1.35-1.31 (t, 3H); MS: m/z=649.4 (M+1, ESI+).

5.11.21. Synthesis of Compound 122

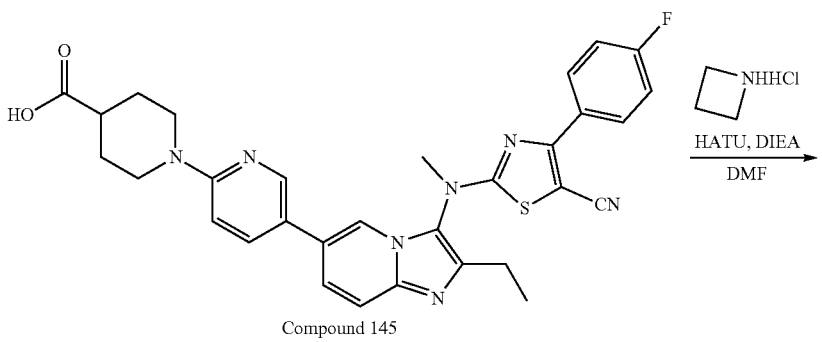

Compound 145

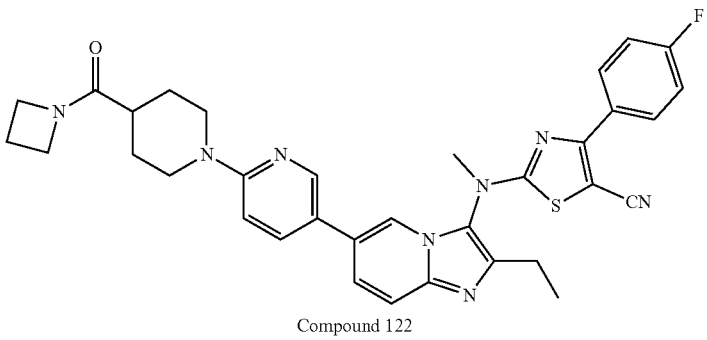

Compound 122

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (500 mg, 859.61 umol) and azetidine hydrochloride (96.50 mg, 1.03 mmol) in DMF (10 mL) was added HATU (486.46 mg, 1.29 mmol) and DIEA (333.29 mg, 2.58 mmol), the reaction mixture was stirred at 25° C. for 2 h. The mixture was poured into water (100 mL) and extracted with EA (30 mL×3). The organic layer was washed with water (100 mL×2) and brine (100 mL), then dried over $Na_2SO_4$ and concentrated. The residue was purified by silica gel column to afford compound 122, 2-((6-(6-(4-(azetidine-1-carbonyl)piperidin-1-yl)pyridin-3-yl)-2-ethylimidazo[1,2-a]pyridin-3-yl)(methyl)amino)-4-(4-fluorophenyl)thiazole-5-carbonitrile (110 mg, 20.61% yield) as a white solid. $^1$H NMR (400 MHz, DMSO-$d_6$) δ 8.58 (s, 1H), 8.52-8.51 (d, 1H), 8.12-8.08 (t, 2H), 7.93-7.91 (dd, 1H), 7.72-7.66 (m, 2H), 7.44-7.39 (t, 2H), 6.92-6.89 (d, 1H), 4.37-4.34 (d, 2H), 4.20-4.16 (t, 2H), 3.84-3.80 (t, 2H), 3.65 (s, 3H), 2.93-2.87 (t, 2H), 2.70-2.65 (dd, 2H), 2.49-2.45 (m, 1H), 2.22-2.15 (m, 2H), 1.65-1.63 (m, 2H), 1.53-1.43 (m, 2H), 1.30-1.26 (t, 3H); MS: m/z=621.2 (M+1, ESI+); HRMS: 621.2560.

5.11.22. Synthesis of Compound 126

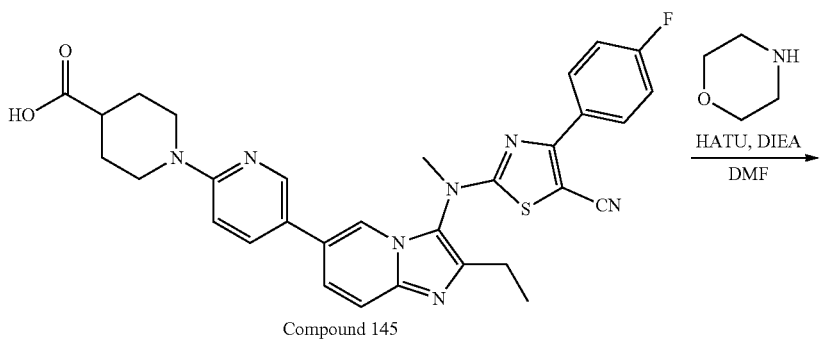

Compound 145

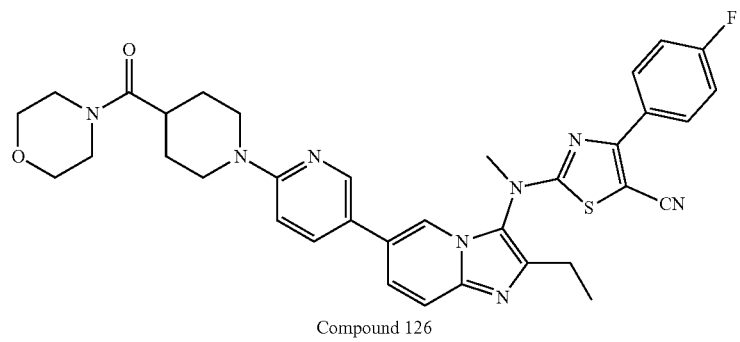

Compound 126

To a solution of compound 145, 1-(5-(3-((5-cyano-4-(4-fluorophenyl)thiazol-2-yl)(methyl)amino)-2-ethylimidazo[1,2-a]pyridin-6-yl)pyridin-2-yl)piperidine-4-carboxylic acid (500 mg, 859.61 umol) and morpholine (82.38 mg, 945.57 umol) in DMF (10 mL) was added HATU (490.27 mg, 1.29 mmol) and DIEA (333.29 mg, 2.58 mmol), the reaction mixture was stirred at 25° C. for 2 h. The mixture was poured into water (100 mL) and extracted with EA (30 mL×2), the organic layer was washed with brine (100 mL), then dried over $Na_2SO_4$ and concentrated. The residue was purified by Prep-HPLC to afford compound 126, 2-((2-ethyl-6-(6-(4-(morpholine-4-carbonyl)piperidin-1-yl)pyridin-3-yl)imidazo[1,2-a]pyridin-3-yl)(methyl)amino)-4-(4-fluorophenyl)thiazole-5-carbonitrile (272 mg, 48.62% yield) as a white solid. $^1$H NMR (400 MHz, DMSO-$d_6$) δ 8.58 (s, 1H), 8.52-8.51 (d, 1H), 8.11-8.08 (t, 2H), 7.94-7.91 (dd, 1H), 7.72-7.66 (m, 2H), 7.44-7.40 (t, 2H), 6.93-6.91 (d, 1H), 4.37-4.34 (d, 2H), 3.64 (s, 3H), 3.58-3.53 (m, 6H), 3.44-3.43 (m, 2H), 2.95-2.89 (m, 3H), 2.70-2.64 (dd, 2H), 1.68-1.65 (m, 2H), 1.59-1.49 (m, 2H), 1.29-1.25 (t, 3H); MS: m/z=651.2 (M+1, ESI+); HRMS: 651.2662.

5.12. Example 11—Synthesis of Reverse Piperidine-Linked Pyrimidine-Type Compounds

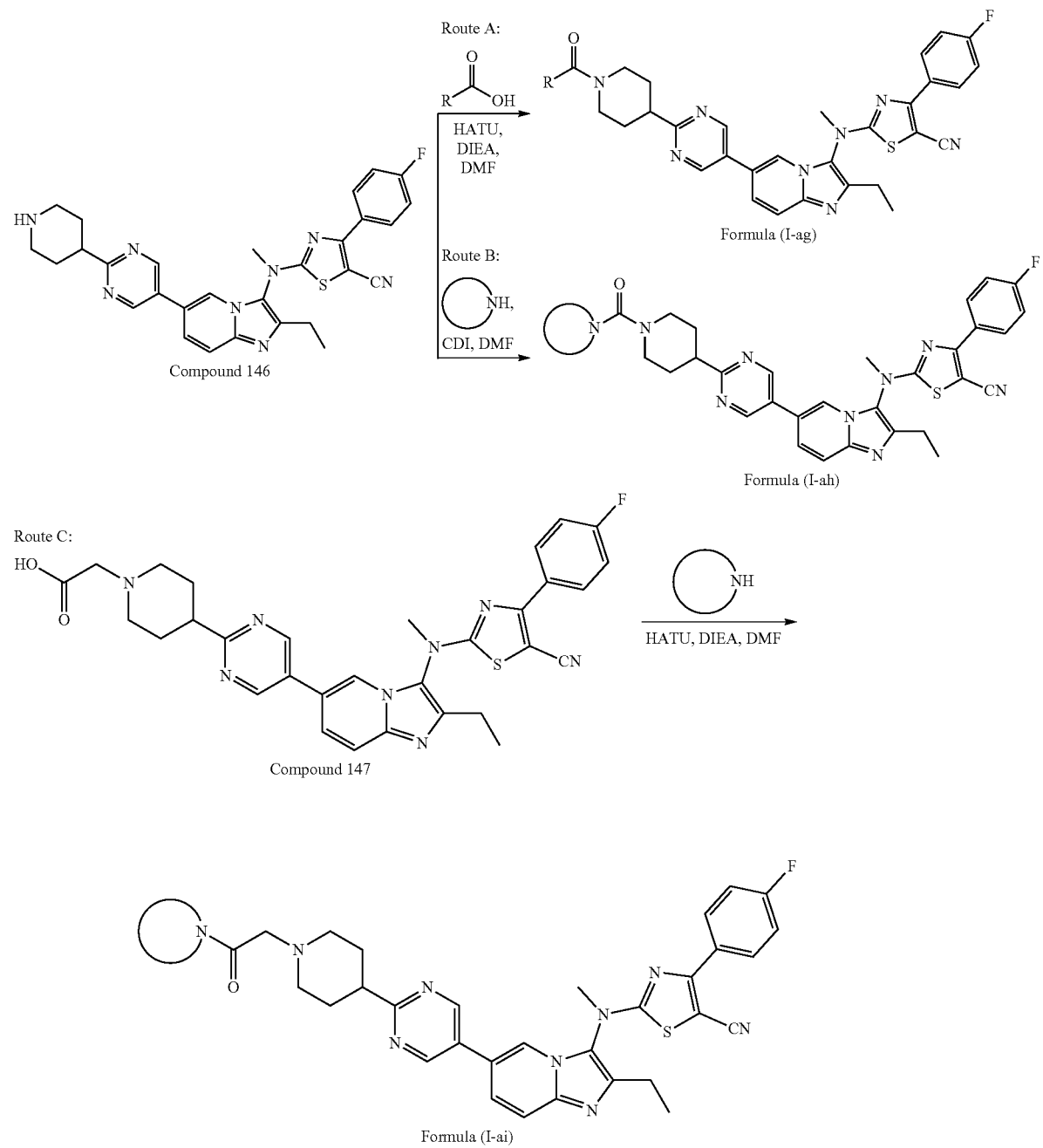

5.12.1. Synthesis of tert-butyl 4-(5-bromopyrimidin-2-yl)piperidine-1-carboxylate

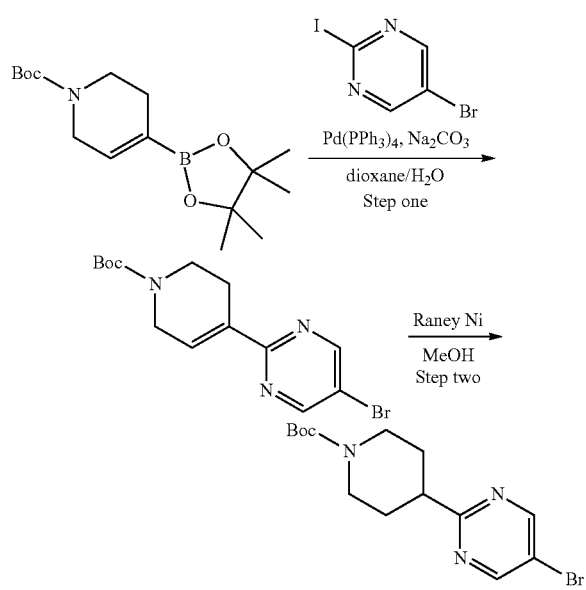

Step One:

To a solution of tert-butyl 4-(4,4,5,5-tetramethyl-1,3,2-dioxaborolan-2-yl)-3,6-dihydropyridine-1(2H)-carboxylate (20 g, 64.68 mmol) and 5-bromo-2-iodopyrimidine (27.64 g, 97.02 mmol) in dioxane (100 mL) and H$_2$O (20 mL) was added Na$_2$CO$_3$ (20.57 g, 194.04 mmol) and Pd(PPh$_3$)$_4$ (3.74 g, 3.23 mmol), the reaction mixture was stirred at 80° C. for 16 h. The mixture was poured into water (300 mL) and extracted with EA (100 mL×2). The organic layer was washed with water (300 mL×2) and brine (300 mL-1), then dried over Na$_2$SO$_4$ and concentrated. The residue was purified by column chromatography to afford tert-butyl 4-(5-bromopyrimidin-2-yl)-3,6-dihydropyridine-1(2H)-carboxylate (10 g, 45.44% yield) as a white solid. MS: m/z=340.2 (M+1, ESI+).

Step Two:

To a solution of tert-butyl 4-(5-bromopyrimidin-2-yl)-3,6-dihydropyridine-1(2H)-carboxylate (8 g, 23.51 mmol) in MeOH (80 mL) was added Raney Ni (1.38 g, 23.51 mmol). The reaction mixture was stirred at 25° C. for 16 h under H$_2$. Filtered and the filtrate was concentrated under reduce pressure. The residue was purified by column chromatography to afford tert-butyl 4-(5-bromopyrimidin-2-yl)piperidine-1-carboxylate (1.6 g, 19.88% yield) as a colorless oil. MS: m/z=342.3 (M+1, ESI+).

5.12.2. Synthesis of Compound 146

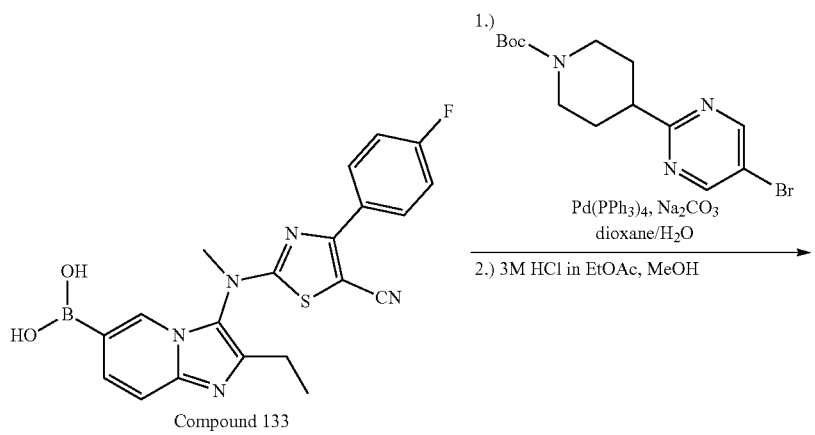

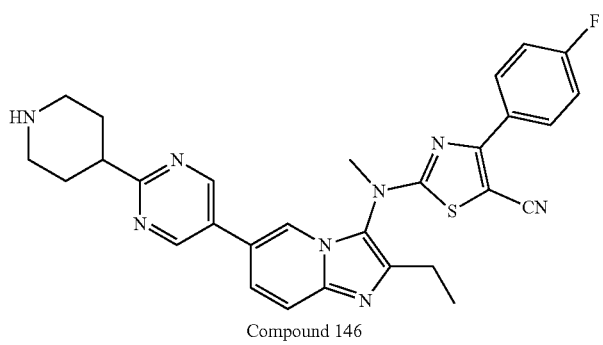

Compound 146

Step One:

To a solution of compound 133, (3-((5-cyano-4-(4-fluorophenyl)thiazol-2-yl)(methyl)amino)-2-ethylimidazo[1,2-a]pyridin-6-yl)boronic acid (2.26 g, 5.36 mmol) and tert-butyl 4-(5-bromopyrimidin-2-yl)piperidine-1-carboxylate (2.2 g, 6.43 mmol) in dioxane (20 mL) and H₂O (5 mL) was added Na₂CO₃ (1.70 g, 16.07 mmol) and Pd(PPh₃)₄ (309.52 mg, 267.85 umol), the reaction mixture was stirred at 80° C. for 16 h. The mixture was poured into water (200 mL) and extracted with EA (80 mL×2). The organic layer was washed with water (200 mL×2) and brine (200 mL×1), then dried over Na₂SO₄ and concentrated. The residue was purified by column chromatography to afford tert-butyl 4-(5-(3-((5-cyano-4-(4-fluorophenyl)thiazol-2-yl)(methyl)amino)-2-ethylimidazo[1,2-a]pyridin-6-yl) pyrimidin-2-yl)piperidine-1-carboxylate (2.3 g, 67.22% yield) as a white solid. MS: m/z=639.2 (M+1, ESI+).

Step Two:

To a solution of tert-butyl 4-(5-(3-((5-cyano-4-(4-fluorophenyl)thiazol-2-yl)(methyl)amino)-2-ethyl imidazo[1,2-a]pyridin-6-yl)pyrimidin-2-yl)piperidine-1-carboxylate (1 g, 1.57 mmol) in MeOH (10 mL) was added 3M HCl in EA (5.2 mL, 15.7 mmol) and the mixture was stirred at 25° C. for 16 h. The solution was adjusted to pH 8 with aq.NaHCO₃ and extracted with EA (20 mL×2). The organic layer was washed with water (40 mL×2) and brine (40 mL×1), then dried over Na₂SO₄ and concentrated. The residue was purified by column chromatography to compound 146, afford 2-((2-ethyl-6-(2-(piperidin-4-yl)pyrimidin-5-yl)imidazo[1,2-a]pyridin-3-yl)(methyl)amino)-4-(4-fluorophenyl) thiazole-5-carbonitrile (810 mg, 96.06% yield) as a yellow solid. MS: m/z=539.2 (M+1, ESI+).

5.12.3. Synthesis of Compound 147

Step One:

To a solution of compound 146, 2-((2-ethyl-6-(2-(piperidin-4-yl)pyrimidin-5-yl)imidazo[1,2-a]pyridin-3-yl)(methyl)amino)-4-(4-fluorophenyl)thiazole-5-carbonitrile (800 mg, 1.49 mmol) and ethyl 2-bromoacetate (744.10 mg, 4.46 mmol) in MeCN (10 mL) was added K₂CO₃ (153.95 mg, 1.11 mmol), the reaction mixture was stirred at 60° C. for 2 h. The reaction mixture was concentrated under reduced pressure and the residue was purified by column chromatography to afford ethyl 2-(4-(5-(3-((5-cyano-4-(4-fluorophenyl)thiazol-2-yl)(methyl)amino)-2-ethylimidazo[1,2-a]pyridin-6-yl) pyrimidin-2-yl)piperidin-1-yl)acetate (920 mg, crude) as yellow solid. MS: m/z=625.2 (M+1, ESI+).

Step Two:

To a solution of ethyl 2-(4-(5-(3-((5-cyano-4-(4-fluorophenyl)thiazol-2-yl)(methyl)amino)-2-ethyl imidazo[1,2-a]pyridin-6-yl)pyrimidin-2-yl)piperidin-1-yl)acetate (920 mg, 1.47 mmol) in THF (5 mL) and H₂O (5 mL) was added LiOH (176.34 mg, 7.36 mmol), the reaction mixture was stirred at 25° C. for 16 h. The mixture was concentrated under reduce pressure and the residue was purified by Prep-HPLC to afford compound 147, 2-(4-(5-(3-((5-cyano-4-(4-fluorophenyl)thiazol-2-yl)(methyl)amino)-2-ethylimidazo[1,2-a]pyridin-6-yl)pyrimidin-2-yl)piperidin-1-yl)acetic acid (750 mg, 85.35% yield) as a yellow solid. m/z=597.0 (M+1, ESI+).

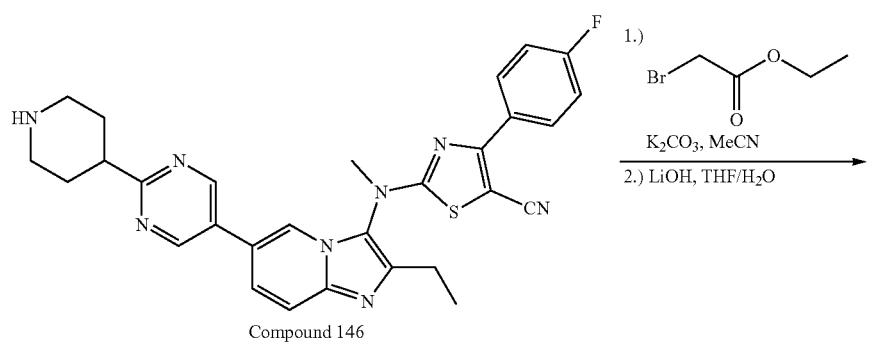

5.12.4. Synthesis of Compound 99

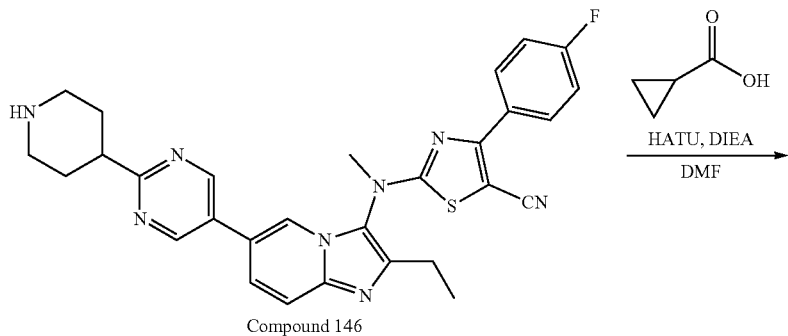

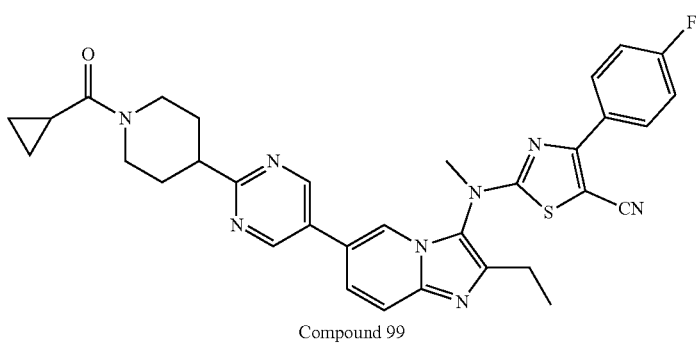

Compound 99

To a solution of compound 146, 2-((2-ethyl-6-(2-(piperidin-4-yl)pyrimidin-5-yl)imidazo[1,2-a]pyridin-3-yl)(methyl)amino)-4-(4-fluorophenyl)thiazole-5-carbonitrile (500 mg, 928 umol) and cyclopropanecarboxylic acid (159.83 mg, 1.86 mmol) in DMF (10 mL) was added HATU (420.25 mg, 1.11 mmol) and DIEA (360 mg, 2.79 mmol). The reaction mixture was stirred at 25° C. for 16 h. The mixture was poured into water (100 mL) and extracted with EA (40 mL×2). The organic layer was washed with water (100 mL-2) and brine (100 mL), then dried over $Na_2SO_4$ and concentrated. The residue was purified by Prep-HPLC to afford compound 99, 2-((6-(2-(1-(cyclopropanecarbonyl)piperidin-4-yl)pyrimidin-5-yl)-2-ethylimidazo[1,2-a]pyridin-3-yl)(methyl)amino)-4-(4-fluorophenyl)thiazole-5-carbonitrile (170 mg, 30.19% yield) as a white solid. $^1$H NMR (400 MHz, DMSO-$d_6$) δ 9.15 (s, 2H), 8.87 (s, 1H), 8.11-8.07 (t, 2H), 7.84-7.75 (m, 2H), 7.44-7.39 (t, 2H), 4.44-4.32 (m, 2H), 3.65 (s, 3H), 3.21-3.13 (m, 2H), 2.77-2.66 (m, 3H), 2.04-1.95 (m, 3H), 1.77-1.59 (m, 2H), 1.30-1.26 (t, 3H), 0.75-0.67 (m, 4H); MS: m/z=607.3 (M+1, ESI+); HRMS: 607.2404.

5.12.5. Synthesis of Compound 100

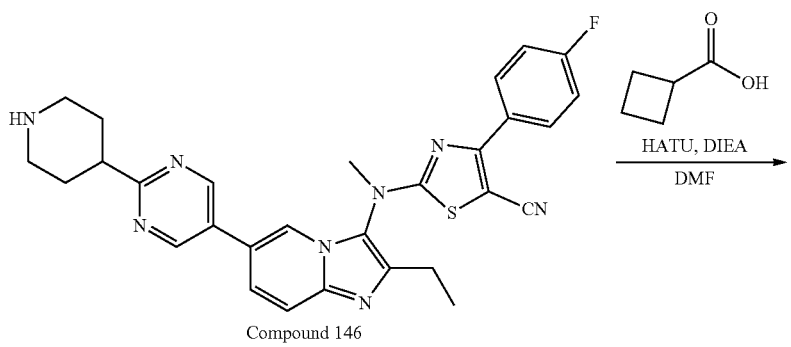

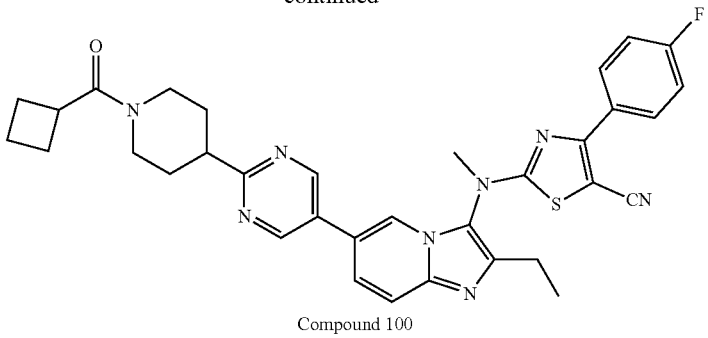

Compound 100

To a solution of compound 146, 2-((2-ethyl-6-(2-(piperidin-4-yl)pyrimidin-5-yl)imidazo[1,2-a]pyridin-3-yl)(methyl)amino)-4-(4-fluorophenyl)thiazole-5-carbonitrile (500 mg, 928 umol) and cyclobutanecarboxylic acid (185.87 mg, 1.86 mmol) in DMF (10 mL) was added HATU (420.25 mg, 1.11 mmol) and DIEA (360 mg, 2.79 mmol). The reaction mixture was stirred at 25° C. for 16 h. The mixture was poured into water (100 mL) and extracted with EA (40 mL×2). The organic layer was washed with water (100 mL×2) and brine (100 mL), then dried over Na$_2$SO$_4$ and concentrated. The residue was purified by Prep-HPLC to afford compound 100, 2-((6-(2-(1-(cyclobutanecarbonyl)piperidin-4-yl)pyrimidin-5-yl)-2-ethylimidazo[1,2-a]pyridin-3-yl)(methyl)amino)-4-(4-fluorophenyl)thiazole-5-carbonitrile (180 mg, 31.24% yield) as a white solid. $^1$H NMR (400 MHz, DMSO-d$_6$) δ 9.14 (s, 2H), 8.87 (s, 1H), 8.10-8.07 (t, 2H), 7.83-7.75 (m, 2H), 7.44-7.39 (t, 2H), 4.44-4.41 (d, 1H), 3.79-3.75 (d, 1H), 3.65 (s, 3H), 3.38-3.34 (m, 1H), 3.15-3.06 (m, 2H), 2.76-2.66 (m, 3H), 2.19-2.04 (m, 4H), 1.98-1.85 (m, 3H), 1.76-1.56 (m, 3H), 1.30-1.26 (t, 3H); MS: m/z=621.3 (M+1, ESI+); HRMS: 621.2561.

5.12.6. Synthesis of Compound 101

(300 mg, 557 umol) in DMF (5 mL) was added CDI (135.46 mg, 835.44 umol), the reaction was stirred at room temperature for 1 h and azetidine hydrochloride (156.32 mg, 1.67 mmol) was added into the above solution. The reaction mixture was stirred at 65° C. for 16 h. The mixture was poured into water (50 mL) and extracted with EA (20 mL×2). The organic layer was washed with water (50 mL: 2) and brine (50 mL), then dried over Na$_2$SO$_4$ and concentrated. The residue was purified by Prep-HPLC to afford compound 101, 2-((6-(2-(1-(azetidine-1-carbonyl)piperidin-4-yl)pyrimidin-5-yl)-2-ethylimidazo[1,2-a]pyridin-3-yl)(methyl)amino)-4-(4-fluorophenyl)thiazole-5-carbonitrile (62 mg, 17.90% yield) as a white solid. $^1$H NMR (400 MHz, DMSO-d$_6$) δ 9.14 (s, 2H), 8.86 (s, 1H), 8.10-8.07 (t, 2H), 7.83-7.75 (m, 2H), 7.44-7.39 (t, 2H), 3.90-3.79 (m, 3H), 3.64-3.61 (m, 4H), 3.08-3.01 (m, 1H), 2.90-2.82 (m, 2H), 2.74-2.66 (m, 5H), 2.17-2.09 (m, 1H), 1.94-1.91 (d, 2H), 1.80-1.64 (m, 2H), 1.29-1.25 (t, 3H); MS: m/z=622.3 (M+1, ESI+); HRMS: 622.2509.

5.12.7. Synthesis of Compound 102

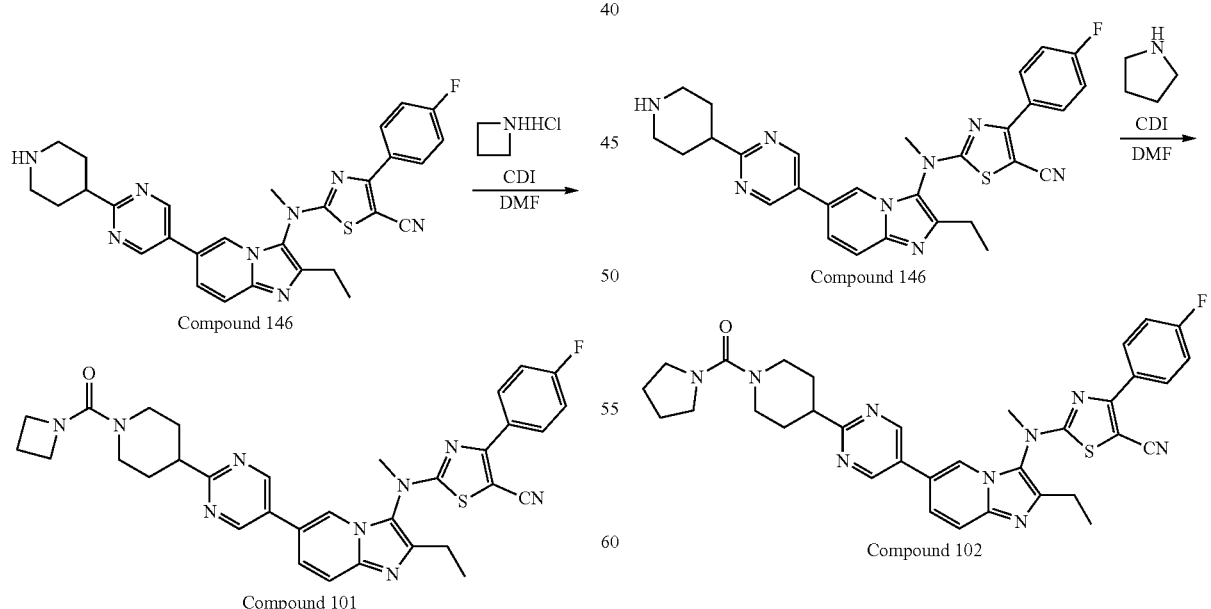

To a solution of compound 146, 2-((2-ethyl-6-(2-(piperidin-4-yl)pyrimidin-5-yl)imidazo[1,2-a]pyridin-3-yl)(methyl)amino)-4-(4-fluorophenyl)thiazole-5-carbonitrile (300 mg, 557 umol) in DMF (10 mL) was added CDI (135.46 mg, 835.44 umol), the reaction was stirred at room temperature for 1 h and pyrrolidine (118.83 mg, 1.67 mmol) was added into the above solution. The reaction mixture was stirred at 80° C. for 16 h. The mixture was poured into water (100 mL) and extracted with EA (30 mL-2). The organic layer was washed with water (100 mL×2) and brine (100 mL), then dried over Na$_2$SO$_4$ and concentrated. The residue was purified by Prep-HPLC to afford compound 102, 2-((2-ethyl-6-(2-(1-(pyrrolidine-1-carbonyl)piperidin-4-yl)pyrimidin-5-yl)imidazo[1,2-a]pyridin-3-yl)(methyl)amino)-4-(4-fluorophenyl)thiazole-5-carbonitrile (68 mg, 19.20% yield) as a white solid. $^1$H NMR (400 MHz, DMSO-d$_6$) δ 9.14 (s, 2H), 8.86 (s, 1H), 8.10-8.07 (t, 2H), 7.83-7.75 (m, 2H), 7.44-7.39 (t, 2H), 3.75-3.72 (d, 2H), 3.64 (s, 3H), 3.28-3.25 (t, 4H), 3.08-3.02 (m, 1H), 2.87-2.82 (t, 2H), 2.71-2.66 (dd, 2H), 1.95-1.92 (d, 2H), 1.79-1.70 (m, 6H), 1.29-1.25 (t, 3H); MS: m/z=636.4 (M+1, ESI+); HRMS: 636.2662.

5.12.8. Synthesis of Compound 103

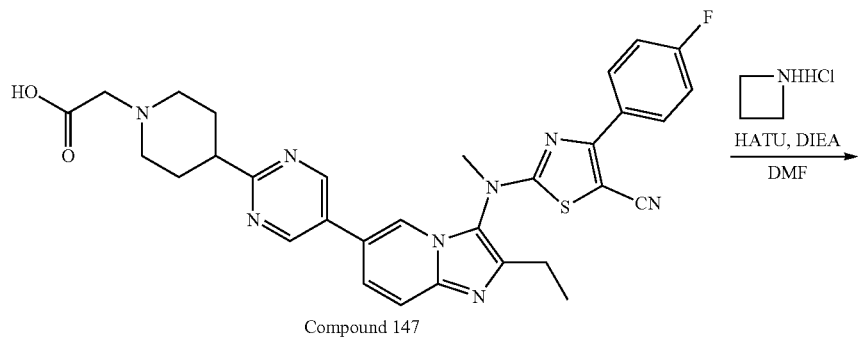

Compound 147

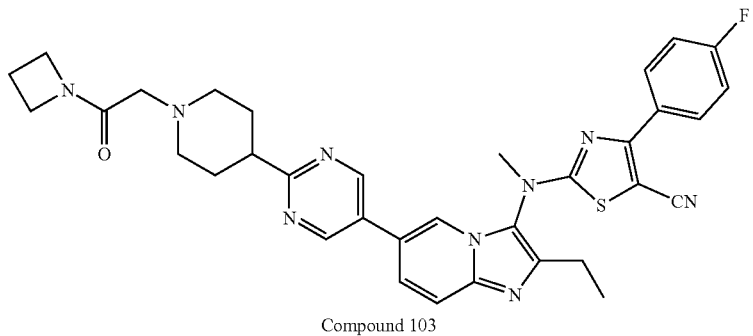

Compound 103

To a solution of compound 147, 2-(4-(5-(3-((5-cyano-4-(4-fluorophenyl)thiazol-2-yl)(methyl)amino)-2-ethylimidazo [1,2-a]pyridin-6-yl)pyrimidin-2-yl)piperidin-1-yl)acetic acid (150 mg, 251.39 umol) and azetidine hydrochloride (28.71 mg, 306.84 umol) in DMF (5 mL) was added HATU (189.69 mg, 502.78 umol) and DIEA (98 mg, 755 umol). The reaction mixture was stirred at 25° C. for 16 h. The mixture was poured into water (50 mL) and extracted with EA (20 mL×2). The organic layer was washed with water (50 mL×2) and brine (50 mL), then dried over $Na_2SO_4$ and concentrated. The residue was purified by Prep-HPLC to afford compound 103, 2-((6-(2-(1-(2-(azetidin-1-yl)-2-oxoethyl)piperidin-4-yl)pyrimidin-5-yl)-2-ethylimidazo[1,2-a]pyridin-3-yl)(methyl)amino)-4-(4-fluorophenyl)thiazole-5-carbonitrile (62 mg, 38.75% yield) as a white solid. $^1$H NMR (400 MHz, DMSO-$d_6$) δ 9.13 (s, 2H), 8.86 (s, 1H), 8.10-8.07 (t, 2H), 7.83-7.75 (m, 2H), 7.44-7.39 (t, 2H), 4.21-4.17 (t, 2H), 3.86-3.83 (t, 2H), 3.64 (s, 3H), 2.96-2.79 (m, 5H), 2.72-2.66 (dd, 2H), 2.22-2.14 (m, 4H), 1.93-1.81 (m, 4H), 1.29-1.25 (t, 3H); MS: m/z=636.1 (M+1, ESI+); HRMS: 636.2666.

5.12.9. Synthesis of Compound 104

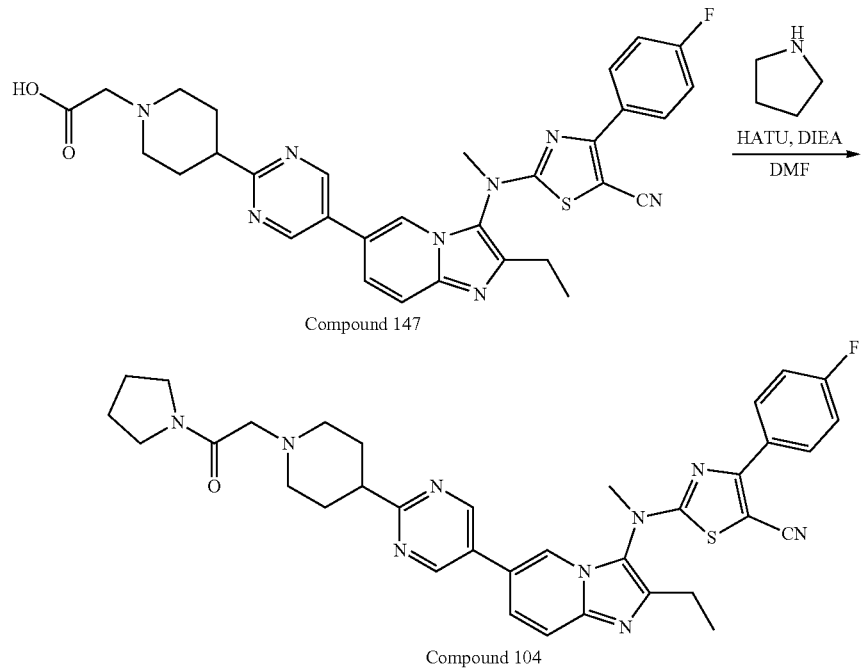

Compound 147

Compound 104

To a solution of compound 147, 2-(4-(5-(3-((5-cyano-4-(4-fluorophenyl)thiazol-2-yl)(methyl)amino)-2-ethylimidazo [1,2-a]pyridin-6-yl)pyrimidin-2-yl)piperidin-1-yl)acetic acid (300 mg, 502.78 umol) and pyrrolidine (107.28 mg, 1.51 mmol) in DMF (5 mL) was added HATU (379.37 mg, 1.01 mmol) and DIEA (196 mg, 1.51 mmol). The reaction mixture was stirred at 25° C. for 16 h. The mixture was poured into water (50 mL) and extracted with EA (20 mL×2). The organic layer was washed with water (50 mL×2) and brine (50 mL), then dried over $Na_2SO_4$ and concentrated. The residue was purified by Prep-HPLC to afford compound 104, 2-((2-ethyl-6-(2-(1-(2-oxo-2-(pyrrolidin-1-yl)ethyl)piperidin-4-yl)pyrimidin-5-yl)imidazo[1,2-a]pyridin-3-yl)(methyl)amino)-4-(4-fluorophenyl)thiazole-5-carbonitrile (90 mg, 27.55% yield) as a white solid. $^1$H NMR (400 MHz, DMSO-$d_6$) δ 9.13 (s, 2H), 8.86 (s, 1H), 8.10-8.07 (t, 2H), 7.83-7.75 (m, 2H), 7.44-7.39 (t, 2H), 3.64 (s, 3H), 3.50-3.46 (t, 2H), 3.29-3.26 (t, 2H), 3.11 (s, 2H), 2.96-2.86 (m, 31H), 2.70-2.66 (dd, 2H), 2.22 (s, 2H), 1.93-1.71 (m, 8H), 1.29-1.26 (t, 3H); MS: m/z=650.2 (M+1, ESI+); HRMS: 650.2820.

5.13. Example 12—Activity of Exemplary Compounds in hATX/ENPP2 Biochemical Assays This example describes the biochemical data ($IC_{50\ value}$ ranges) of the compounds described in the present disclosure from hATX/ENPP2 assays using 16:0-LPC as the substrate. The subject compounds were compared to compound GPLG-1690 as a reference compound. GPLG-1690 (Ziritaxestat) is a known compound of the following structure:

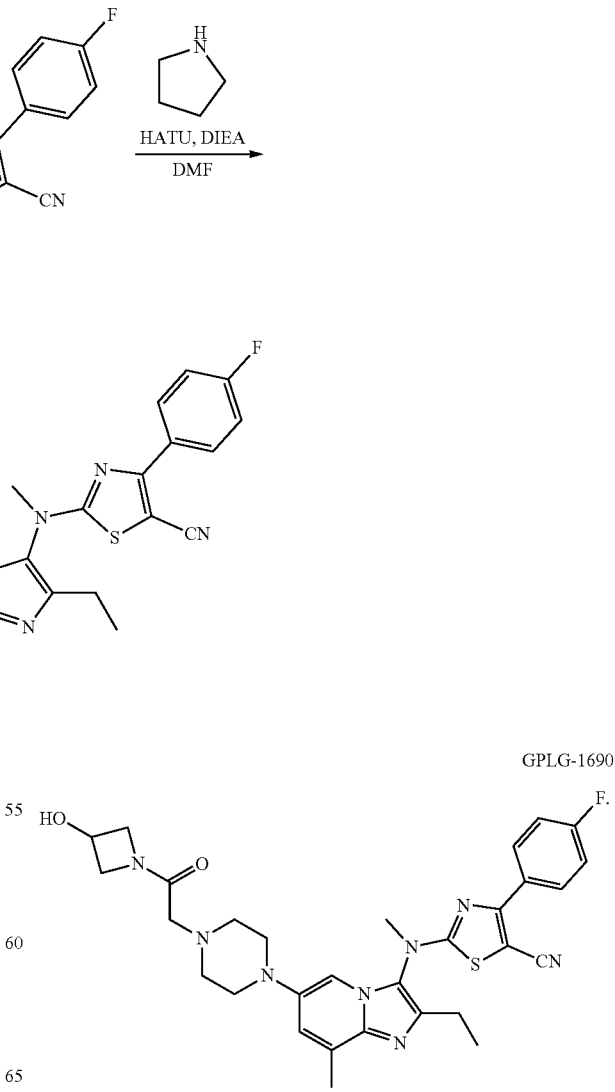

GPLG-1690

Experimental Procedures 20 nL of a dilution series (a total of 12 concentrations) of compound, starting from 10 mM highest concentration, 1/3 dilution, is transferred to the wells by Echo®550 Liquid Handler.

hENPP2 is used at a final concentration of 2.5 nM. The enzyme is diluted in 50 mM Tris-HCl pH 8.0, 140 mM NaCl, 5 mM $CaCl_2$, 0.01% Triton X-100 in a total volume of 5 μL. The aqueous solution of enzyme is added to the wells and incubated with different concentrations of the compounds at room temperature for 15 min. The reaction is started by the addition of 5 μL of 80 μM LPC (16:0) and 10 μL of the detection mixture containing 200 μM Amplex Red, 10 U/mL choline oxidase and 4 U/mL HRP.

Fluorescence at 590 nm was measured kinetically with excitation at 530 nm. The slope of the curve (from 60 to 70 min of the reaction time) was used to calculate the compounds' $IC_{50}$ values.

Data

The $IC_{50}$ values of reference compound GPLG-1690; and exemplary compounds 1-115 and 118-127 from hATX/ENPP2 assays are listed in Table 2 below. hATX/ENPP2 $IC_{50}$ (nM) ranges: (A) refers to $IC_{50} \leq 20$ nM; (B) refers to $20 < IC_{50} \leq 200$ nM; and (C) refers to $IC_{50} > 200$ nM.

TABLE 2

Activity of exemplary compounds in hATX/ENPP2 assays

| Cmpd No. | hATX/ENPP2 $IC_{50}$ (nM) |
|---|---|
| GPLG-1690 (reference) | B |
| 1 | A |
| 2 | A |
| 3 | B |
| 4 | B |
| 5 | A |
| 6 | A |
| 7 | A |
| 8 | A |
| 9 | A |
| 10 | A |
| 11 | B |
| 12 | B |
| 13 | C |
| 14 | B |
| 15 | B |
| 16 | B |
| 17 | B |
| 18 | A |
| 19 | A |
| 20 | B |
| 21 | B |
| 22 | C |
| 23 | B |
| 24 | B |
| 25 | B |
| 26 | B |
| 27 | B |
| 28 | B |
| 29 | B |
| 30 | B |
| 31 | B |
| 32 | A |
| 33 | A |
| 34 | C |
| 35 | B |
| 36 | B |
| 37 | B |
| 38 (formate salt) | C |
| 39 | B |
| 40 | C |
| 41 | B |
| 42 | A |
| 43 | A |

TABLE 2-continued

Activity of exemplary compounds in hATX/ENPP2 assays

| Cmpd No. | hATX/ENPP2 $IC_{50}$ (nM) |
|---|---|
| 44 | A |
| 45 | A |
| 46 | A |
| 47 | B |
| 48 | B |
| 49 | B |
| 50 | B |
| 51 | B |
| 52 | B |
| 53 | B |
| 54 | B |
| 55 | B |
| 56 | B |
| 57 | B |
| 58 | B |
| 59 | B |
| 60 | B |
| 61 | B |
| 62 | B |
| 63 | C |
| 64 | B |
| 65 | B |
| 66 (hydrochloride salt) | A |
| 67 | B |
| 68 (formate salt) | A |
| 69 (formate salt) | A |
| 70 (hydrochloride salt) | B |
| 71 (hydrochloride salt) | B |
| 72 (hydrochloride salt) | A |
| 73 | A |
| 74 | A |
| 75 | A |
| 76 | A |
| 77 | A |
| 78 | A |
| 79 (hydrochloride salt) | A |
| 80 (hydrochloride salt) | B |
| 81 (hydrochloride salt) | B |
| 82 (hydrochloride salt) | A |
| 83 (hydrochloride salt) | A |
| 84 | A |
| 85 | B |
| 86 | B |
| 87 | B |
| 88 | A |
| 89 (hydrochloride salt) | A |
| 90 | A |
| 91 | A |
| 92 | A |
| 93 | A |
| 94 | B |
| 95 | A |
| 96 (hydrochloride salt) | B |
| 97 | B |
| 98 | A |
| 99 | B |
| 100 | B |
| 101 | B |
| 102 | B |
| 103 | B |
| 104 | B |
| 105 | B |
| 106 | B |
| 107 | B |
| 108 | B |
| 109 | B |
| 110 | B |
| 111 | B |
| 112 | B |
| 113 | A |
| 114 | A |
| 115 | A |
| 118 | A |
| 119 | A |
| 120 | A |

TABLE 2-continued

Activity of exemplary compounds in hATX/ENPP2 assays

| Cmpd No. | hATX/ENPP2 IC$_{50}$ (nM) |
|---|---|
| 121 | B |
| 122 | A |
| 123 | A |
| 124 | B |
| 125 | B |
| 126 | A |
| 127 | A |

As seen above, the majority of the subject compounds show better or comparative activity to the reference compound GPLG-1690 in hATX/ENPP2 assays.

5.14. Example 13—Inhibitory Activity of Exemplary Compounds in LPA Assays

Autotaxin (ATX) plays an important role in lysophosphatidic acid (LPA) signaling. An in vitro LPA assay was conducted to determine IC$_{50}$ values of the test compounds on reduction of LPA 18:2 level in rat or mouse plasma. This example describes the assay data (IC$_{50}$ value ranges) of exemplary compounds from LPA assays using mouse and rat plasma. Compound GPLG-1690 was assayed as a reference compound.

Experimental Procedures

The 10 mM DMSO stock solutions of test compounds and 4-fold serial dilutions of the test compounds were prepared at various concentrations. The diluted solutions of the compounds were diluted with 1×PBS (pH 7.5) buffer. 38 μL of rat or mouse plasma samples were mixed with 2 μL of the diluted solutions of the compounds or 2% DMSO solutions in 96-well plate (final 0.1% DMSO). After incubating for 2 hr at 37° C., 120 μL MeOH containing IS (250 ng/mL of LPA 17:0) was added to each well. Mixture was vortexed for 1 min, and then centrifuged for 30 min (4000 rpm, 4° C.). 100 μL supernatant was transferred to a 96-well plate containing 100 μL pure water and the plate was shaken for 10 min. 5 μL supernatant was injected into LC-MS/MS system. No calibration curve will be prepared for LPA 18:2 and all quantifications were performed based on peak area ratios (LPA 18:2/LPA 17:0). For each concentration of compound LPA data were expressed as percentage of reduction (% reduction) using the formula.

100−[((LPA ratio-LPA ratio in control sample after 0 hr incubation)/(LPA ratio in control sample after 2 hr incubation—LPA ratio in control sample after 0 hr incubation))*100].

Data

The IC$_{50}$ values of reference compound GPLG-1690 and various subject compounds from LPA assays in mouse and rat plasma are listed in Table 3 below. IC$_{50}$ (nM) ranges: (A) refers to IC$_{50}$≤200 nM; (B) refers to 200<IC$_{50}$≤800 nM; and (C) refers to IC$_{50}$>800 nM.

TABLE 3

Inhibitory Activity of exemplary compounds in LPA Assays

| Cmpd No. | Mouse plasma, LPA IC$_{50}$ | Rat plasma, LPA IC$_{50}$ |
|---|---|---|
| GPLG-1690 (reference) | C | C |
| 10 | B | A |
| 30 | B | B |
| 42 | B | B |
| 43 | A | A |
| 44 | B | B |
| 45 (hydrochloride salt) | B | A |
| 46 (hydrochloride salt) | B | B |
| 79 (hydrochloride salt) | B | A |
| 85 | B | A |
| 86 (hydrochloride salt) | C | B |
| 87 | B | B |
| 92 | A | B |
| 93 | B | A |
| 109 | B | A |
| 113 | C | A |
| 114 | B | B |
| 115 | B | A |
| 118 | B | A |
| 119 | B | B |
| 120 | B | B |
| 121 | B | A |
| 121 | B | A |
| 123 | B | B |
| 124 | B | B |
| 125 | B | A |
| 126 | B | A |
| 127 | B | A |

As seen above, the majority of the subject compounds show better inhibitory activity as compared to the reference compound GPLG-1690 in LPA assays.

5.15. Example 14—Pharmacokinetic Data

This example describes the pharmacokinetic (PK) data obtained for various compounds of the present disclosure, from studies using mice. The following PK parameters were calculated:

Bioavailability (F %) were calculated using the linear/log trapezoidal rule

Peak plasma concentrations (C$_{max}$ (ng/mL)) were taken directly from the plasma concentration vs. time profiles for the PO group Area under the curve e.g., the area under the concentration curve from time 0 to infinity (AUC$_{0-inf}$(ng*h/mL)).

Experimental Procedures

After intravenous (IV) and oral (PO) administration at 2 mg/kg and 10 mg/kg to male C57BL/6 mice, respectively, the blood samples were collected at the designed sampling time points. All blood samples were transferred into pre-chilled commercial polyethylene microcentrifuge tubes containing K$_2$-EDTA as an anticoagulant. Samples were processed for plasma by centrifugation. Plasma samples was transferred into polypropylene tubes pre-chilled on dry ice and then quickly frozen over dry ice and kept at −70±10° C. until LC-MS/MS analysis. Mice plasma samples were analyzed using qualified bioanalytical methods based on protein precipitation followed by LC-MS/MS analysis. Individual plasma concentration data of each compound was subjected to noncompartmental pharmacokinetic analysis using Phoenix WinNonlin™. Nominal doses were used for pharmacokinetic parameters calculation.

Data

The PK parameters of various subject compounds are listed in Table 4 below.

TABLE 4

Mouse PK study of exemplary compounds

| Cmpd No. | F % $C_{max}$ (ng/mL) $AUC_{0-inf}$ (ng*h/mL) |
|---|---|
| 1 | F %: 56.5 |
|  | $C_{max}$: 3034 |
|  | $AUC_{0-inf}$: 27236 |
| 2 | F %: 61.0 |
|  | $C_{max}$: 4070 |
|  | $AUC_{0-inf}$: 35115 |
| 10 | F %: 28.0 |
|  | $C_{max}$: 4951 |
|  | $AUC_{0-inf}$: 26691 |
| 30 | F %: 42 |
|  | $C_{max}$: 4312 |
|  | $AUC_{0-inf}$: 21714 |
| 43 | F %: 39.5 |
|  | $C_{max}$: 5166 |
|  | $AUC_{0-inf}$: 31028 |
| 44 | F %: 33.4 |
|  | $C_{max}$: 4727 |
|  | $AUC_{0-inf}$: 25035 |
| 47 | F %: 62.3 |
|  | $C_{max}$: 4763 |
|  | $AUC_{0-inf}$: 42329 |
| 92 | F %: 25 |
|  | $C_{max}$: 4264 |
|  | $AUC_{0-inf}$: 22842 |
| 113 | F %: 44.7 |
|  | $Cm_{ax}$: 6528 |
|  | $AUC_{0-inf}$: 40493 |
| 114 | F %: 28.4 |
|  | $C_{max}$: 7042 |
|  | $AUC_{0-inf}$: 37962 |
| 115 | F %: 48.5 |
|  | $C_{max}$: 3985 |
|  | $AUC_{0-inf}$: 37146 |
| 119 | F %: 33.06 |
|  | $C_{max}$: 7682 |
|  | $AUC_{0-inf}$: 57122 |
| 120 | F %: 40.82 |
|  | $C_{max}$: 8468 |
|  | $AUC_{0-inf}$: 50455 |
| 122 | F %: 57.8 |
|  | $C_{max}$: 7000 |
|  | $AUC_{0-inf}$: 47658 |
| 123 | F %: 55.7 |
|  | $C_{max}$: 7753 |
|  | $AUC_{0-inf}$: 60965 |
| 124 | F %: 40.0 |
|  | $C_{max}$: 3823 |
|  | $AUC_{0-inf}$: 13126 |
| 115 | F %: 38.8 |
|  | $C_{max}$: 10233 |
|  | $AUC_{0-inf}$: 34069 |
| 126 | F %: 59.2 |
|  | $C_{max}$: 5582 |
|  | $AUC_{0-inf}$: 38287 |

EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are herein incorporated by reference in their entirety, for all purposes.

The invention claimed is:

1. A compound of formula (I):

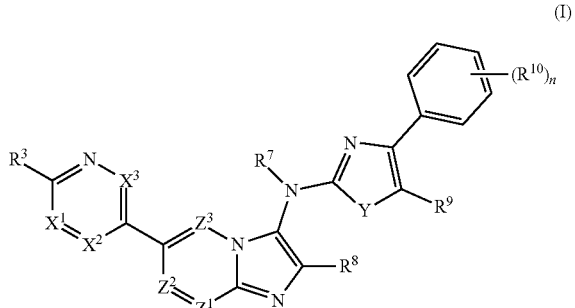

or a pharmaceutically acceptable salt or isomer thereof, wherein:

$X^1$, $X^2$, and $X^3$ are independently selected from C—$R^1$ and N;

$Z^1$, $Z^2$, and $Z^3$ are independently selected from C—$R^1$ and N;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^3$ is selected from optionally substituted $R^4$—C(O)—($C_1$-$C_3$)alkyl-, $R^4$C(O)—, optionally substituted monocyclic or bicyclic carbocycle, optionally substituted monocyclic or bicyclic heterocycle, $R^5R^6$HC—, and $R^5R^6$N—;

$R^4$ is selected from $H_2$N—, HO—, $R^5R^6$N—, optionally substituted ($C_1$-$C_{10}$)alkyl-, optionally substituted ($C_1$-$C_{10}$)alkoxy-, optionally substituted monocyclic or bicyclic carbocycle, optionally substituted monocyclic or bicyclic heterocycle, optionally substituted cycloalkyl-($C_1$-$C_6$)alkylene-, and optionally substituted heterocycle-($C_1$-$C_6$)alkylene-;

$R^5$ and $R^6$ are independently selected from H—, $H_2$N—, HO—, optionally substituted ($C_1$-$C_{10}$)alkyl-, optionally substituted monocyclic or bicyclic carbocycle, optionally substituted monocyclic or bicyclic heterocycle, optionally substituted $R^4$C(O)—($C_1$-$C_{10}$)alkyl-, $R^4$C(O)—, $R^4$—, and substituted amino; or $R^5$ and $R^6$ together with the nitrogen or carbon atom to which they are attached are cyclically linked to form an optionally substituted carbocycle or an optionally substituted heterocycle;

$R^7$ is selected from H—, and optionally substituted ($C_1$-$C_6$)alkyl-;

$R^8$ is selected from —H, -halogen, and optionally substituted —($C_1$-$C_6$)alkyl;

$R^9$ and each $R^{10}$ are independently selected from —H, -halogen, —CN, —OH, optionally substituted —($C_1$-$C_6$)alkoxy, —$NH_2$, substituted amino, optionally substituted —($C_1$-$C_6$)alkyl-$NH_2$ and optionally substituted —($C_1$-$C_6$)alkyl; and n is 0, 1, 2, 3, 4, or 5;

with the proviso that:

a) when i) $X^1$, $X^2$, and $X^3$ are C—H, or $X^1$ and $X^2$ are C—H and $X^3$ is C—$CH_3$ or N, ii) $R^3$ is $R^4$-C(O)—($C_1$-$C_3$)alkyl-, and iii) $R^4$ is $R^5R^6$N—:

$R^5$ and $R^6$ are independently selected from H—, $H_2N$—, HO—, optionally substituted $(C_1-C_{10})$alkyl-, optionally substituted monocyclic or bicyclic carbocycle, optionally substituted monocyclic or bicyclic heterocycle, optionally substituted $R^4C(O)$—$(C_1-C_{10})$alkyl-, $R^4C(O)$—, $R^4$-, and substituted amino; or $R^5$ and $R^6$ together with the nitrogen atom to which they are attached are cyclically linked to form an unsubstituted heterocycle;

b) when i) $X^1$ is C—F and $X^2$ and $X^3$ are C—H, ii) $R^3$ is $R^4$-C(O)-$(C_1-C_3)$alkyl- or $R^4$-C(O)—, and iii) $R^4$ is $R^5R^6N$—:

$R^5$ and $R^6$ are independently selected from H—, $H_2N$—, HO—, optionally substituted $(C_1-C_{10})$alkyl-, optionally substituted monocyclic or bicyclic carbocycle, optionally substituted monocyclic or bicyclic heterocycle, optionally substituted $R^4C(O)$-$(C_1-C_{10})$alkyl-, $R^4C(O)$—, $R^4$-, and substituted amino; or $R^5$ and $R^6$ together with the nitrogen atom to which they are attached are cyclically linked to form an unsubstituted heterocycle; and c) when i) $X^1$ and $X^3$ are C—H and $X^2$ is N and, ii) $R^3$ is $R^4$-C(O)-$(C_1-C_3)$alkyl-, $R^4$-C(O)—, or $R^5R^6N$—, wherein iii) $R^4$ is $R^5R^6N$—:

$R^5$ and $R^6$ are independently selected from H—, $H_2N$—, HO—, optionally substituted $(C_1-C_{10})$alkyl-, optionally substituted monocyclic or bicyclic carbocycle, optionally substituted monocyclic or bicyclic heterocycle, optionally substituted $R^4C(O)$-$(C_1-C_{10})$alkyl-, $R^4C(O)$—, $R^4$-, and substituted amino; or $R^5$ and $R^6$ together with the nitrogen atom to which they are attached are cyclically linked to form an unsubstituted heterocycle;

wherein:
when one of $R^5$ and $R^6$ is H—:
the other one of $R^5$ and $R^6$ is independently selected from $H_2N$—, HO—, unsubstituted $(C_1-C_{10})$alkyl-, optionally substituted monocyclic or bicyclic carbocycle, optionally substituted monocyclic heterocycle, optionally substituted $R^4C(O)$-$(C_1-C_{10})$alkyl-, $R^4C(O)$—, $R^4$-, and substituted amino.

2. The compound of claim 1, wherein the compound is of formula (Ia):

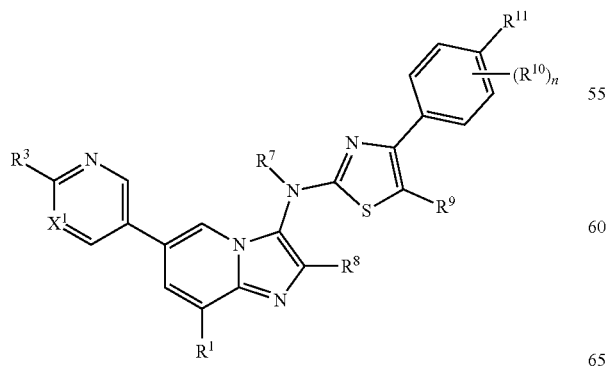

(Ia)

wherein:

$R^1$ is selected from —H, -halogen, optionally substituted —$(C_1-C_6)$alkyl and optionally substituted —$(C_1-C_6)$alkoxy;

$R^3$ is selected from $R^4C(O)$—, $R^4C(O)CH_2$—, $R^5R^6N$—, and $R^5R^6HC$—;

$R^{11}$ is selected from —H, -halogen, —CN, —OH, optionally substituted —$(C_1-C_6)$alkoxy, —$NH_2$, —$NR^5R^6$, —$CH_2NH_2$ and optionally substituted —$(C_1-C_6)$alkyl; and n is 0, 1, 2, or 3.

3. The compound of claim 2, wherein $X^1$ is N.

4. The compound of claim 2, wherein $X^1$ is C—H.

5. The compound of claim 1, wherein $R^7$ is optionally substituted $(C_1-C_6)$alkyl-.

6. The compound of claim 1, wherein $R^8$ is optionally substituted —$(C_1-C_6)$alkyl.

7. The compound of claim 1, wherein $R^9$ is —CN.

8. The compound of claim 2, wherein $R^{11}$ is -halogen.

9. The compound of claim 1, wherein the compound is of formula (Ib):

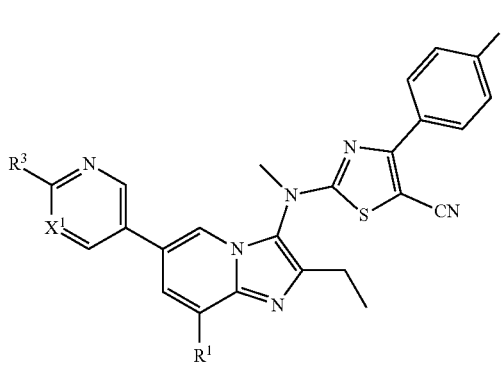

(Ib)

wherein:

$X^1$ is C—H or N; and $R^1$ is —H, -halogen, or optionally substituted —$(C_1-C_6)$alkyl and optionally substituted —$(C_1-C_6)$alkoxy.

10. The compound of claim 1, wherein:

a) $R^3$ is $R^4$ 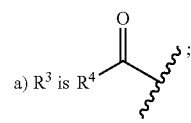;

b)

$R^3$ is 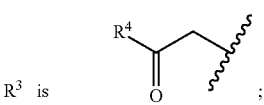;

c)

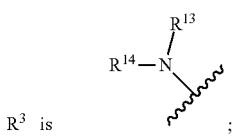

R³ is d)

R³ is that is an optionally substituted monocyclic or bicyclic (C₂-C₉)heterocycle-; or e)

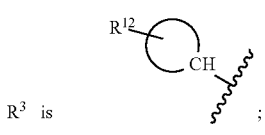

R³ is that is an optionally substituted monocyclic or bicyclic (C₃-C₈)carbocycle-, or an optionally substituted monocyclic or bicyclic (C₂-C₉)heterocycle-;
wherein:
- R⁴ is selected from HO—, H₂N—, R¹⁵R¹⁶N—, optionally substituted (C₁-C₅)alkyl-, optionally substituted monocyclic or bicyclic carbocycle, and optionally substituted monocyclic or bicyclic heterocycle;
- R¹² is selected from —H, —NH₂, —OH, —CH₂C(O)R⁴, —C(O)R⁴, —CHR¹⁵R¹⁶, —NR¹⁵R¹⁶, optionally substituted —(C₁-C₅)alkyl, optionally substituted monocyclic or bicyclic —(C₃-C₈)carbocycle, and an optionally substituted monocyclic or bicyclic —(C₂-C₉)heterocycle; and
- R¹³ and R¹⁴ are independently selected from —H, —CH₂C(O)R¹⁷, —CH₂R¹⁷, —C(O)R¹⁷, —R¹⁸C(O)R¹⁷, —CH₂R¹⁸C(O)R¹⁷, optionally substituted —(C₁-C₅)alkyl, optionally substituted monocyclic or bicyclic —(C₃-C₈)carbocycle, and an optionally substituted monocyclic or bicyclic —(C₂-C₉)heterocycle, wherein R¹⁷ and R¹⁸ are independently selected from optionally substituted —(C₁-C₅)alkyl, optionally substituted monocyclic or bicyclic —(C₃-C₈)carbocycle, and an optionally substituted monocyclic or bicyclic —(C₂-C₉)heterocycle; and
- R¹⁵ and R¹⁶ are independently selected from H—, optionally substituted (C₂-C₅)heterocycloalkyl-C(O)—, optionally substituted (C₃-C₆) cycloalkyl-C(O)—, optionally substituted (C₁-C₅)alkyl-, optionally substituted 3- to 10-membered saturated monocyclic heterocycle or carbocycle, and optionally substituted 3- to 10-membered saturated bicyclic heterocycle or carbocycle, wherein the optional substituents are selected from hydroxy, HOCH₂—, cyano, halogen, substituted amino, and (C₁-C₅)alkyl; or R¹⁵ and R¹⁶ are cyclically linked to form a 3- to 6-membered monocyclic saturated heterocycle, optionally substituted with hydroxy, HOCH₂—, cyano, halogen, substituted amino, or (C₁-C₅)alkyl.

11. The compound of claim 10, wherein:
R³ is

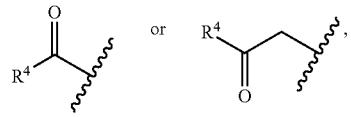

R⁴ is selected from R³², R³²HN—, R³²N(R³³)—, and R³²HN—R³⁶—;

R³² and R³³ are independently selected from H—, optionally substituted (C₁-C₃)alkyl, optionally substituted cycloalkyl, and optionally substituted saturated heterocycle;

R³⁶ is selected from optionally substituted (C₁-C₃)alkyl, optionally substituted cycloalkyl, and optionally substituted saturated heterocycle; and the optional substituents of the R³², R³³ and R³⁶ groups are independently selected from —CN, —OH, —CH₂OH, —(C₁-C₃)alkyl, —(C₁-C₃)alkoxy, —(C₃-C₆)cycloalkyl, (C₂-C₅)heterocycloalkyl, and —N(R³⁷)R³⁸, wherein R³⁷ and R³⁸ are independently selected from H, (C₁-C₃)alkyl, (C₃-C₆)cycloalkyl, and (C₂-C₅)heterocycloalkyl.

12. The compound of claim 11, wherein R⁴ is selected from:

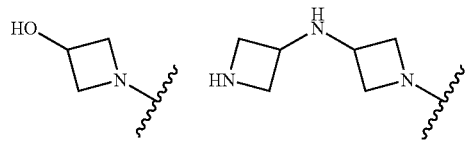

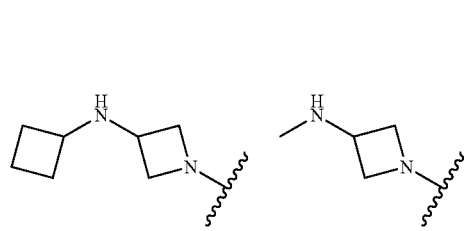

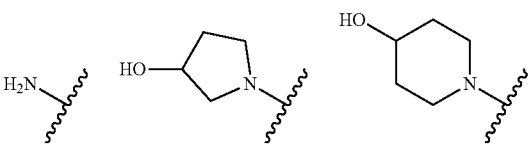

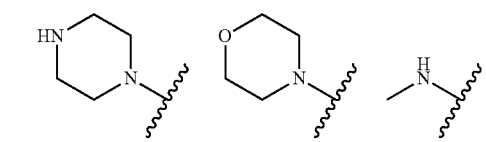

-continued
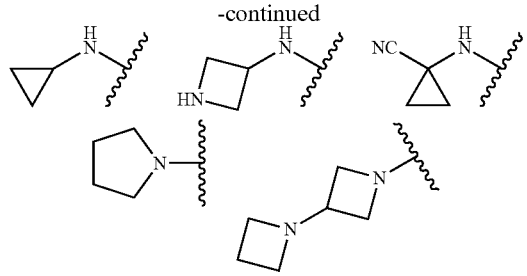
-continued
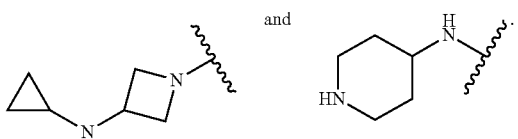
13. The compound of claim 12, wherein the compound is selected from:
Compound 11
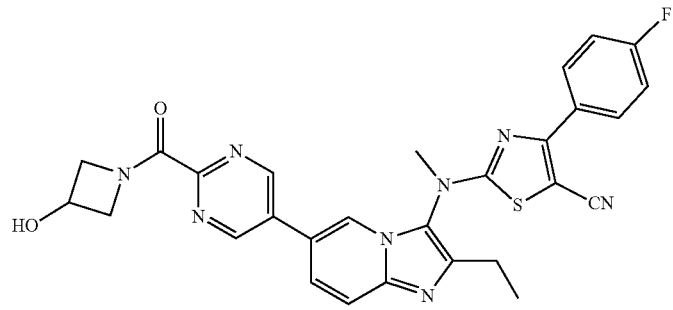
Compound 12
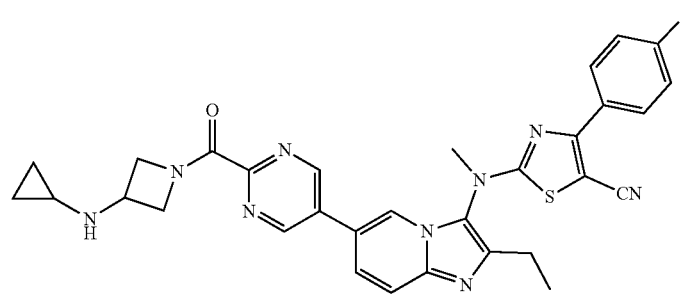
Compound 13
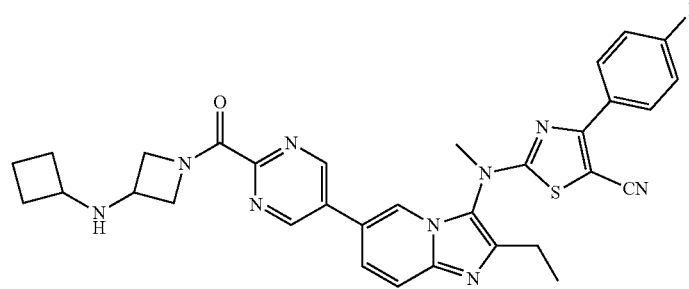
Compound 14
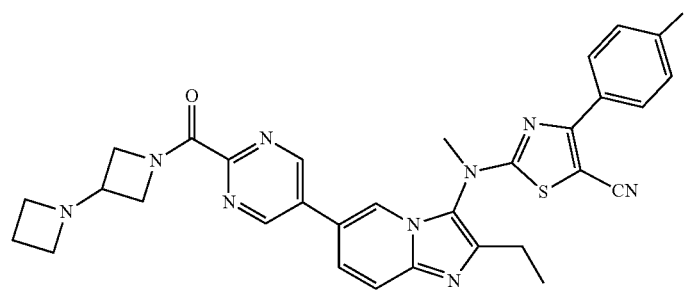

-continued
Compound 15
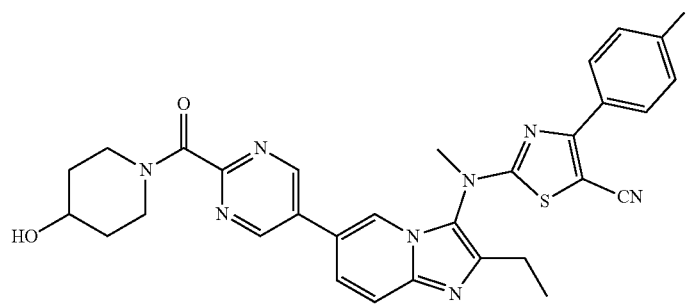
Compound 16
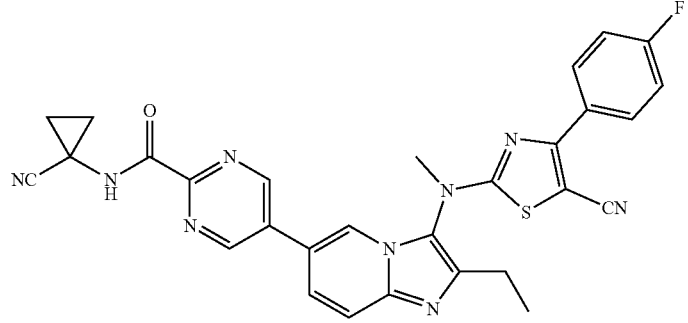
Compound 47
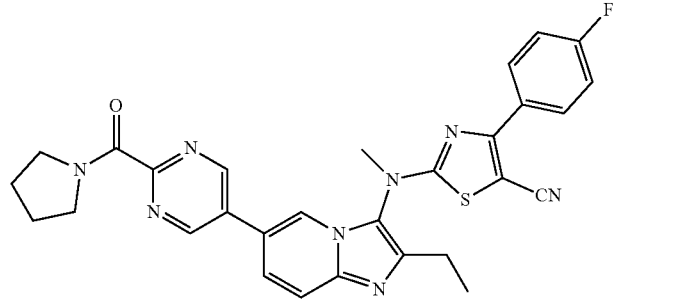
Compound 48
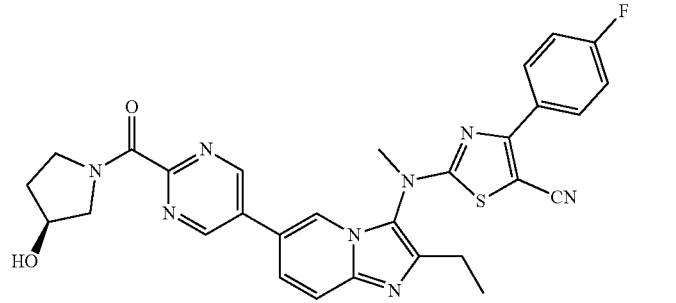
Compound 49
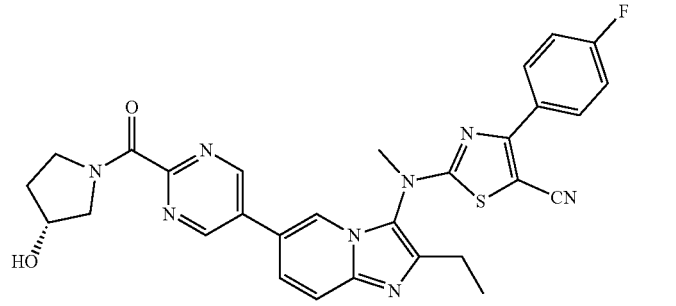

-continued
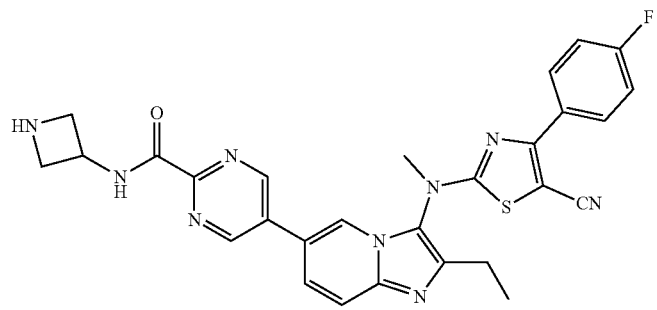
Compound 50
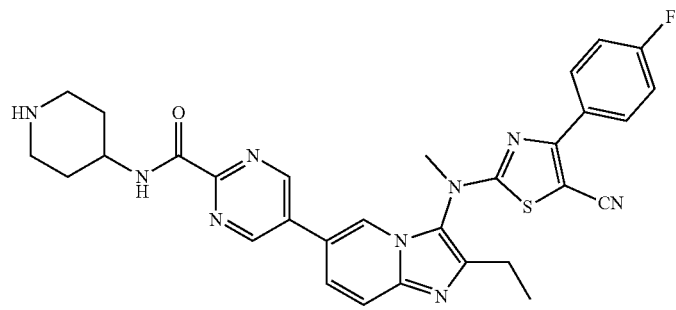
Compound 51
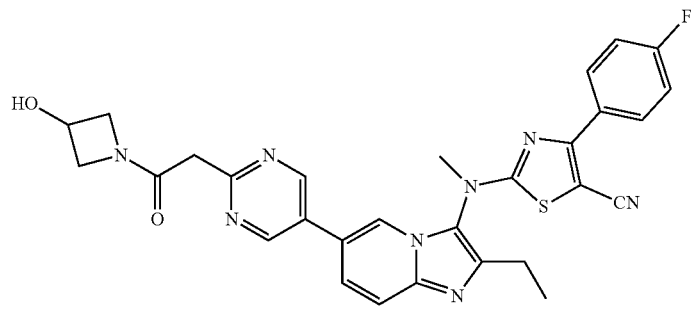
Compound 52
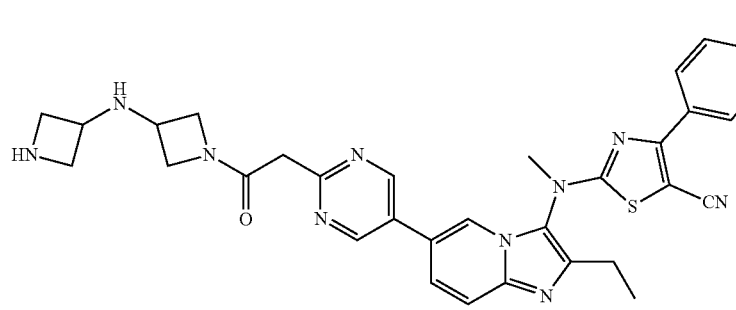
Compound 53
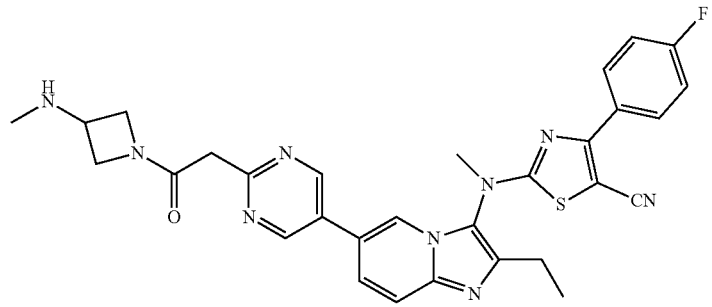
Compound 54

-continued
Compound 55
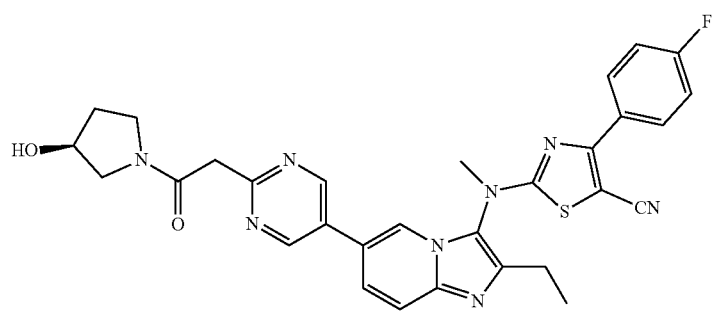
Compound 56
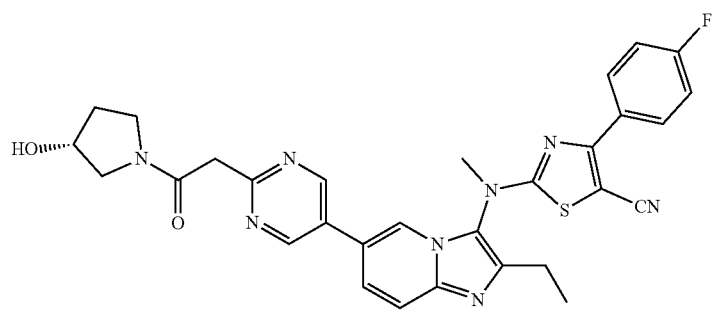
Compound 57
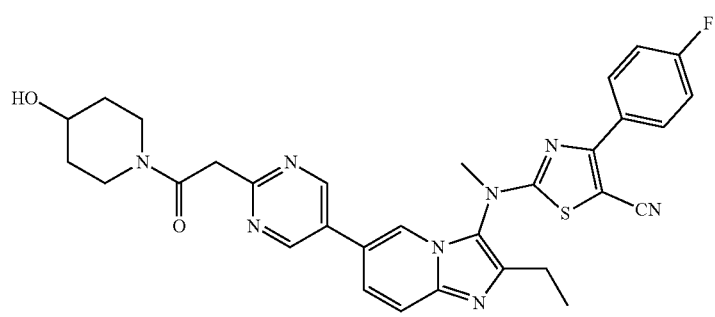
Compound 58
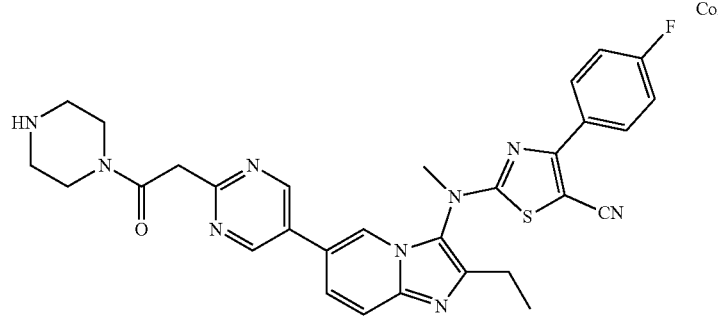
Compound 59
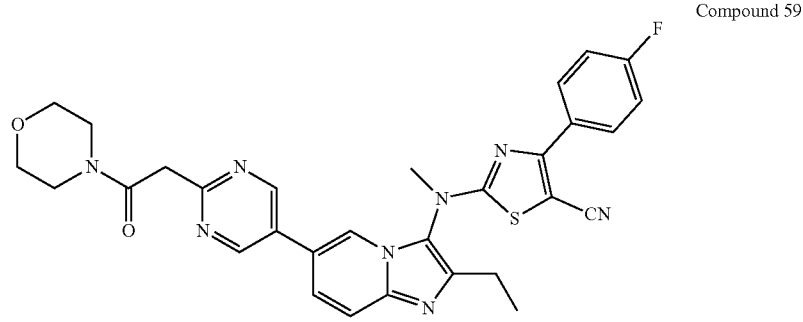

Compound 60
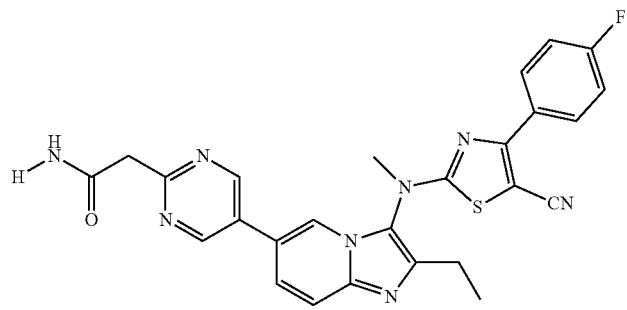
Compound 61
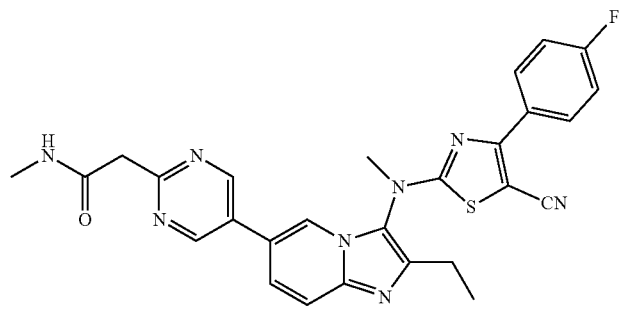
Compound 62
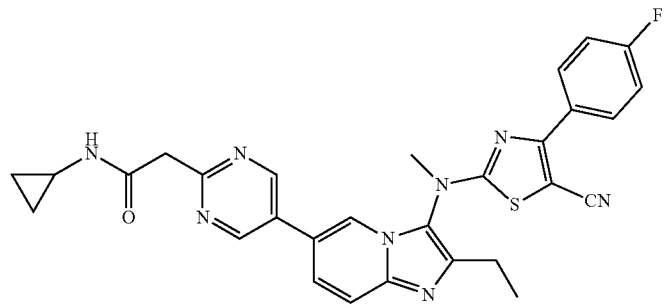
Compound 63
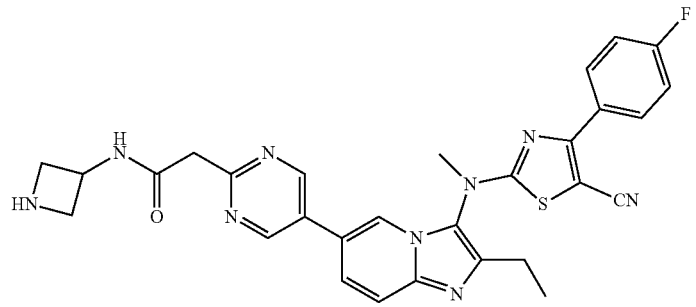
Compound 64
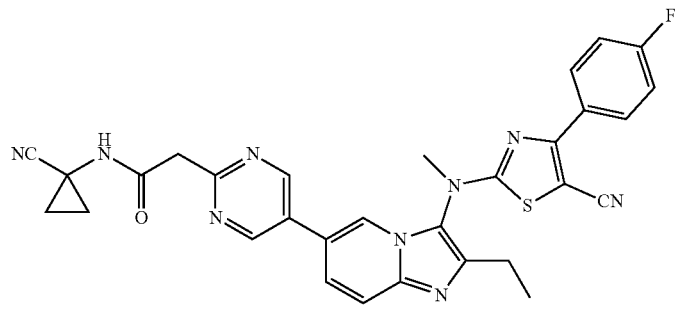

-continued

Compound 65

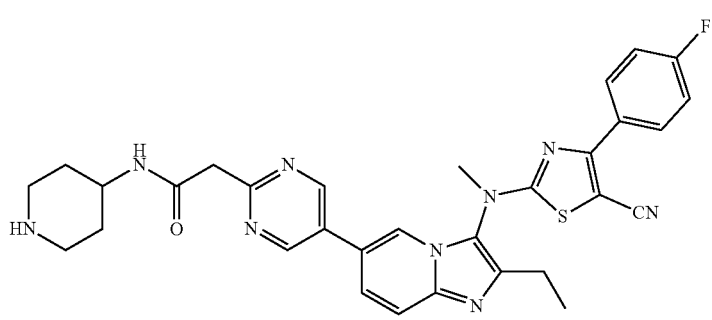

and

Compound 87

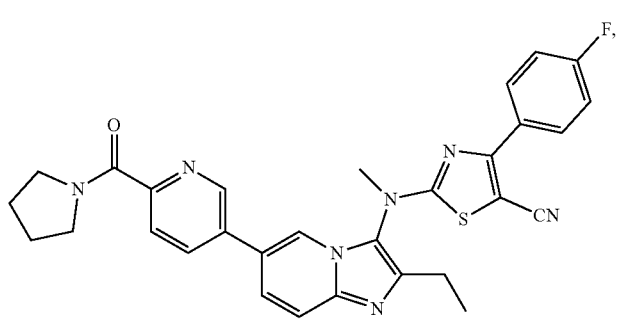

or a pharmaceutically acceptable salt thereof.

14. The compound of claim 10, wherein:
R$^3$ is

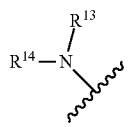

R$^{14}$ is selected from R$^{34}$—, R$^{34}$CH$_2$—, R$^{34}$C(O)R$^{35}$—, and R$^{34}$C(O)R$^{35}$CH$_2$—;

each R$^{34}$ and R$^{35}$ are independently selected from optionally substituted —(C$_1$-C$_3$)alkyl, optionally substituted cycloalkyl, and optionally substituted saturated heterocycle;

the optional substituents of the R$^{34}$ and R$^{35}$ groups are independently selected from —CN, —OH, —CH$_2$OH, —(C$_1$-C$_3$)alkyl, —(C$_1$-C$_3$)alkoxy, and —(C$_1$-C$_3$)alkyl; and R$^{13}$ is —H.

15. The compound of claim 14, wherein R$^{14}$ is selected from:

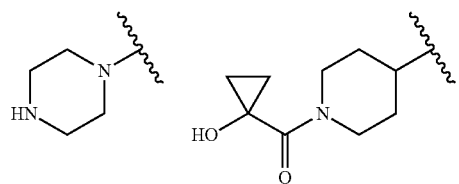

-continued

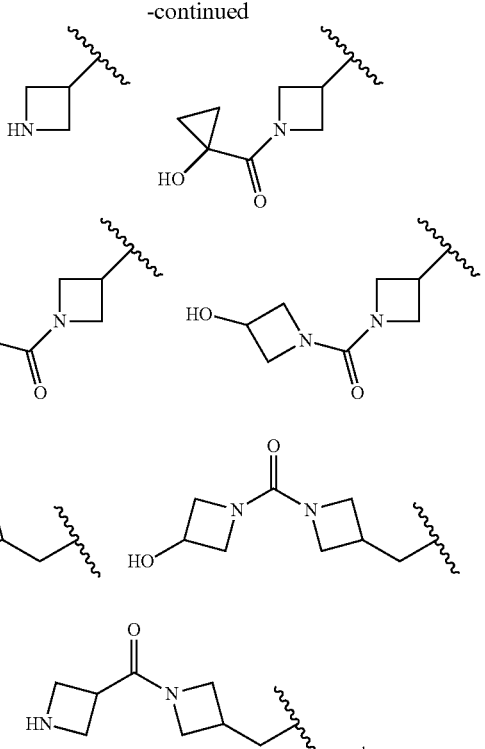

and

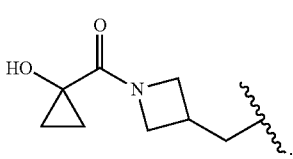

16. The compound of claim 15, wherein the compound is selected from:
Compound 21
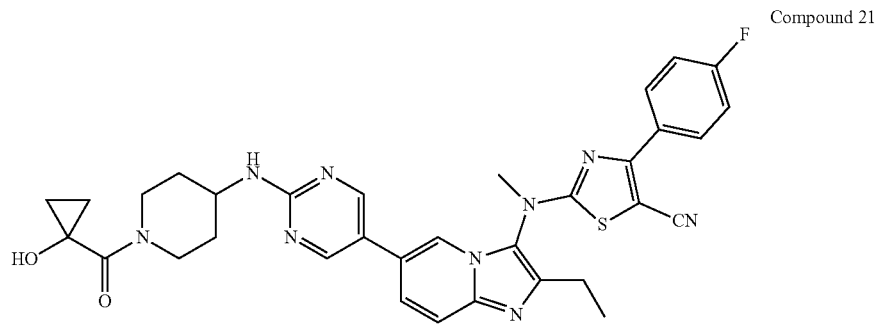
Compound 22
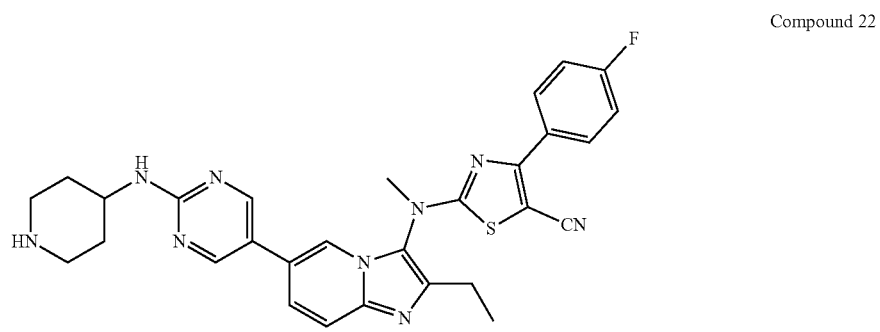
Compound 34
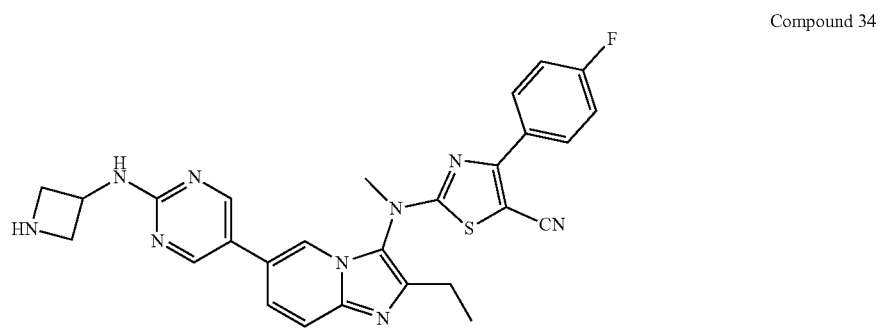
Compound 35
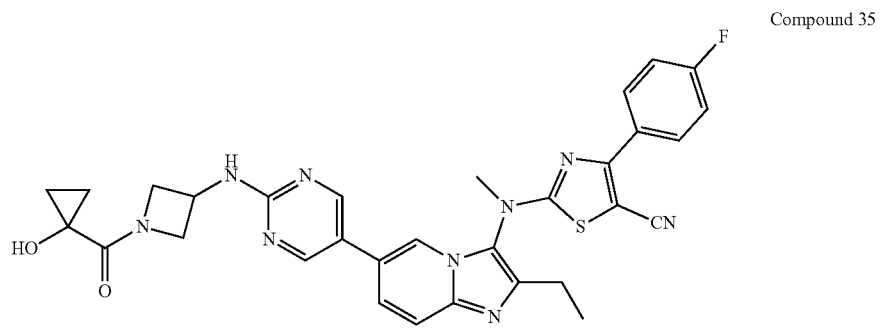
Compound 36
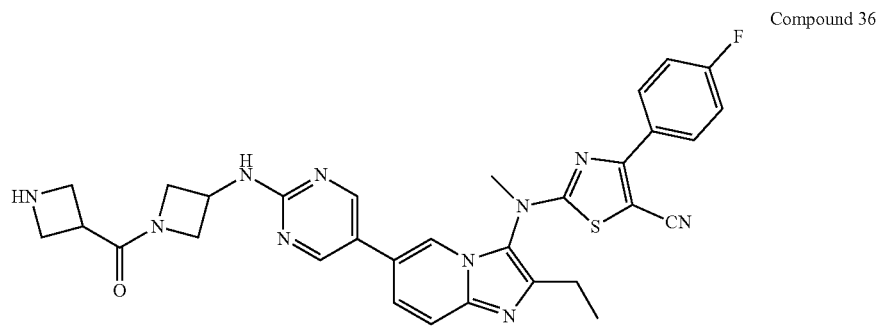

Compound 37
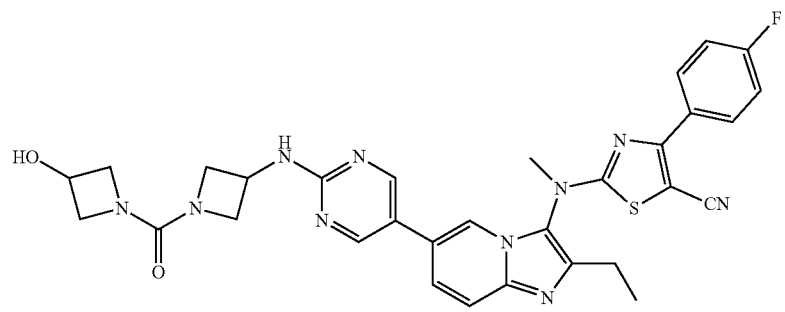
Compound 38
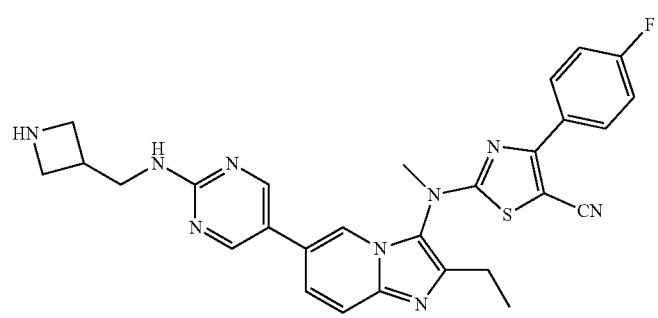
Compound 39
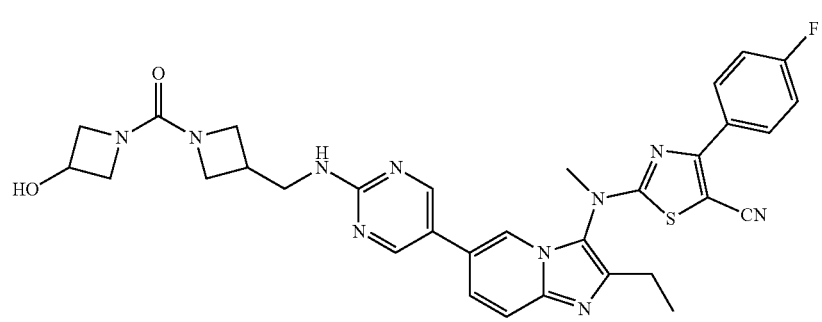
Compound 40
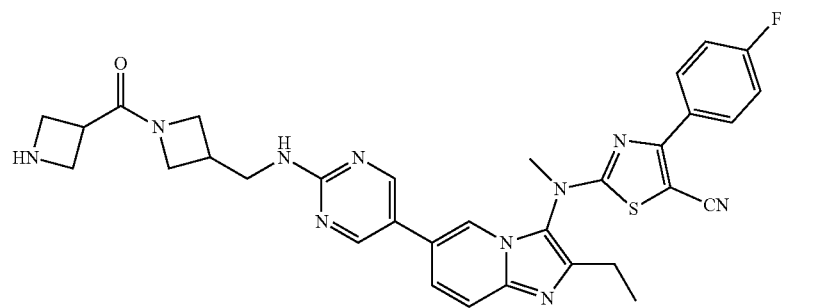
and Compound 41

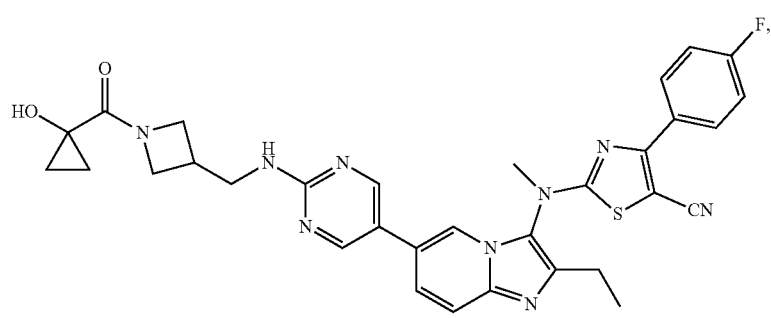

or a pharmaceutically acceptable salt thereof.

17. The compound of claim 10, wherein $R^3$ is

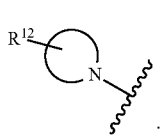

18. The compound of claim 17, wherein $R^3$ is selected from:

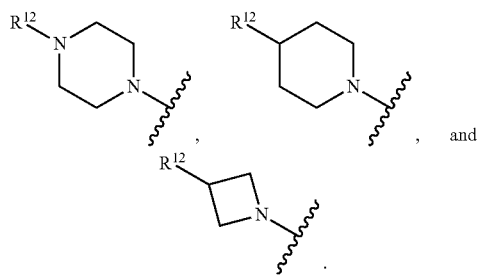

19. The compound of claim 17, wherein:
$R^{12}$ is selected from H—, $H_2N$—, $R^{31}$—C(O)—, $R^{31}$—C(O)$CH_2$—, $R^{31}$—NHC(O)—, $R^{31}$—C(O)NH—, $R^{31}$—NH—, $R^{31}$—N(CH$_3$)C(O)—, $R^{31}$—C(O)N(CH$_3$)—, $R^{31}$—N(CH$_3$)—, and $R^{31}$—O—;
$R^{31}$ is selected from optionally substituted cycloalkyl, and optionally substituted saturated heterocycle; and
the optional substituents of the $R^{31}$ group are selected from NC—, HO—, HOCH$_2$—, (C$_1$-C$_3$)alkoxy-, substituted (C$_1$-C$_3$)alkyl-, (C$_3$-C$_6$)cycloalkyl-, and (C$_2$-C$_5$) heterocycloalkyl-.

20. The compound of claim 17, wherein $R^{12}$ is selected from:

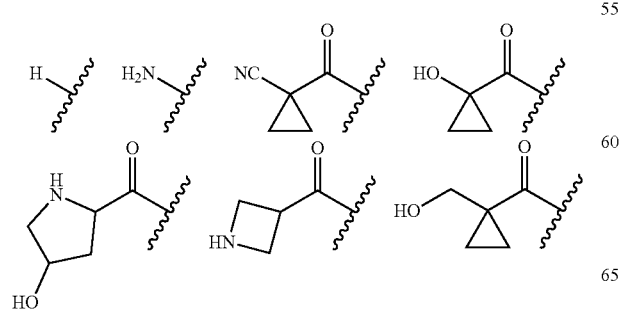

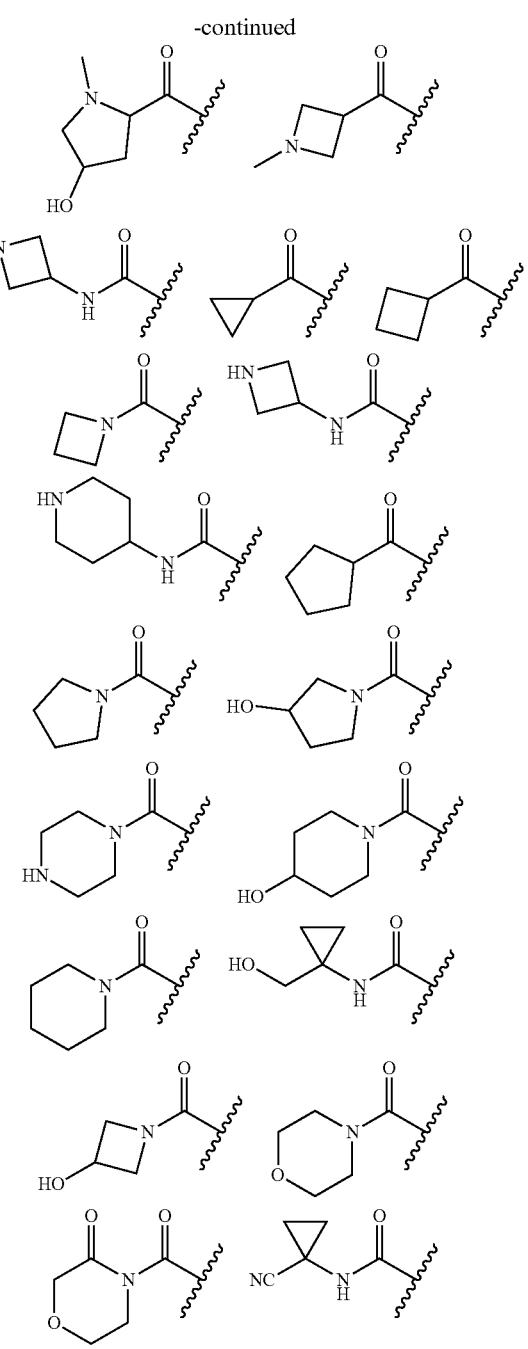

473
-continued
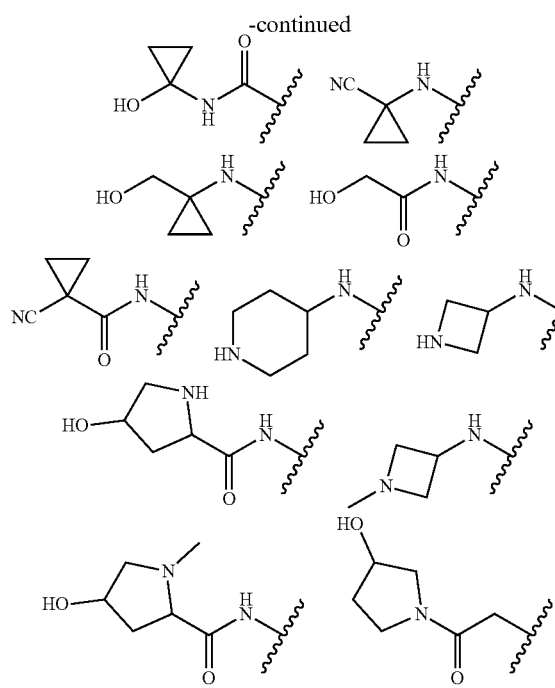
474
-continued
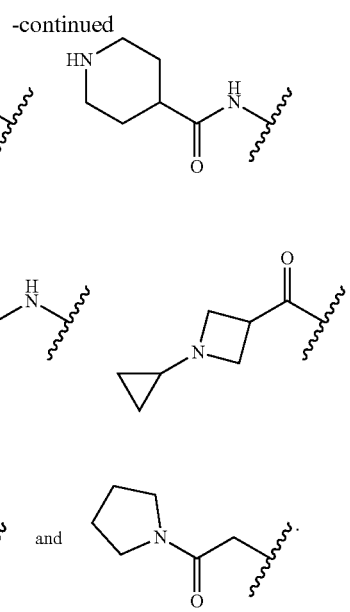
21. The compound of claim 17, wherein the compound is selected from:
Comound 1
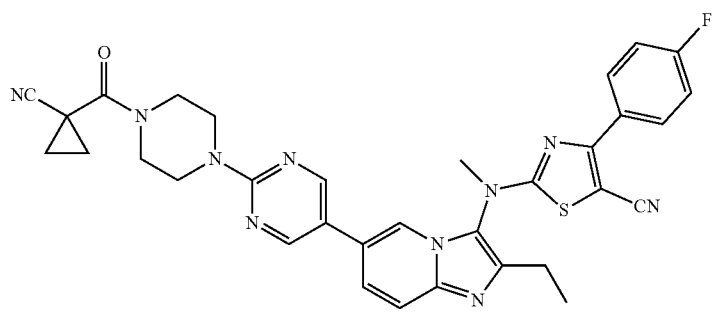
Compound 2
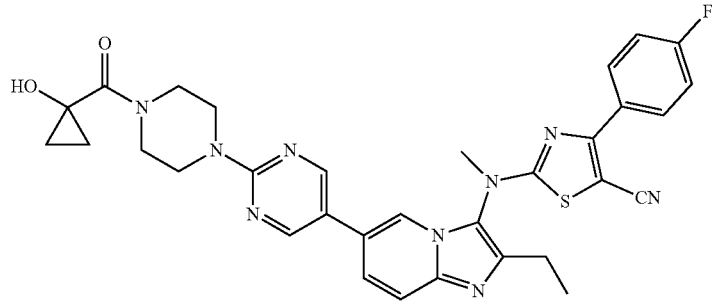
Compound 3
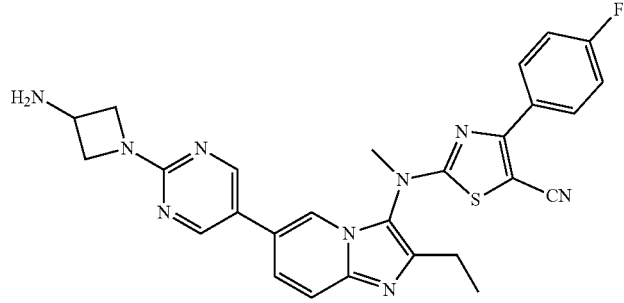

-continued
Compound 4
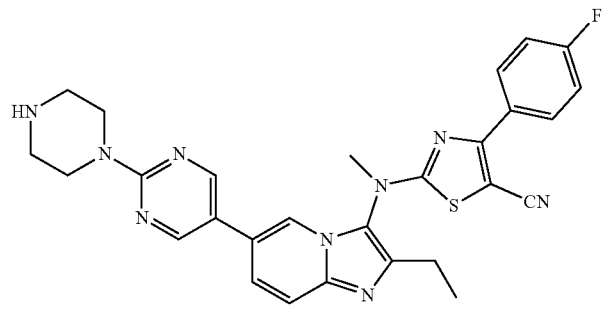
Compound 5
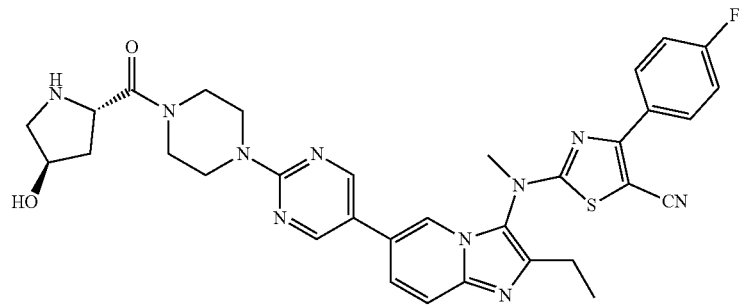
Compound 6
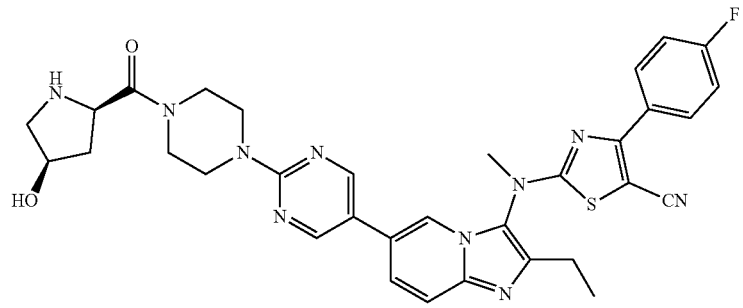
Compound 7
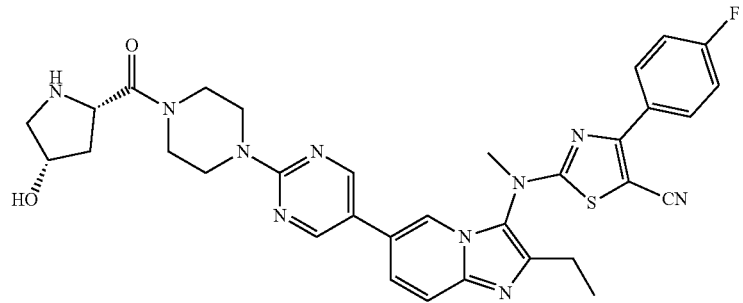
Compound 8
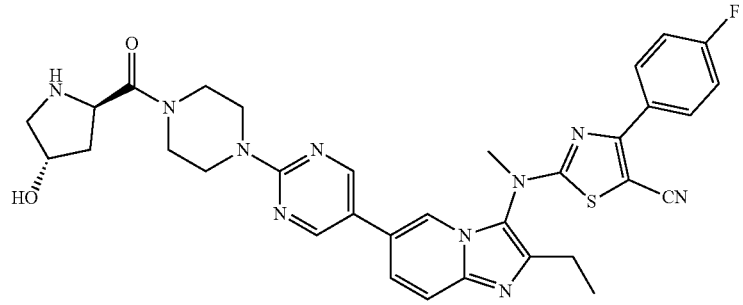

-continued
Compound 9
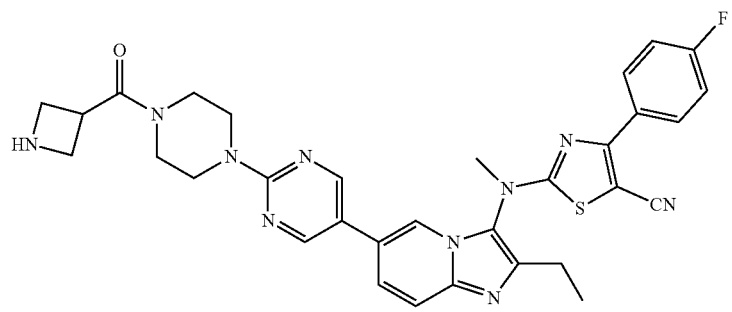
Compound 10
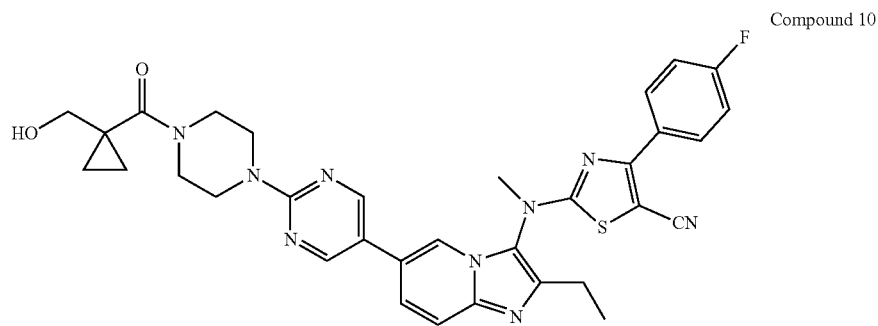
Compound 17
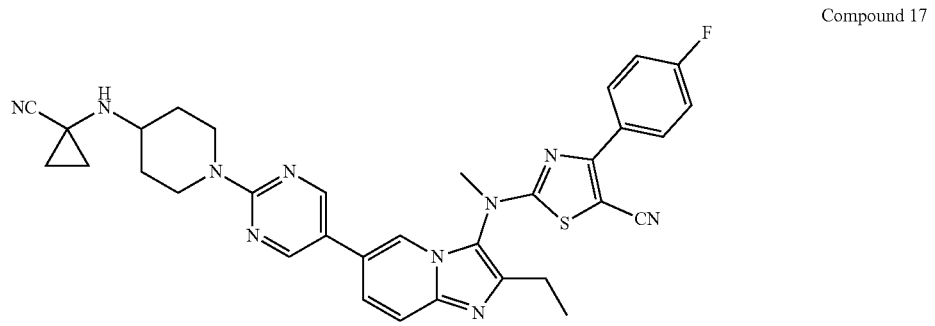
Compound 18
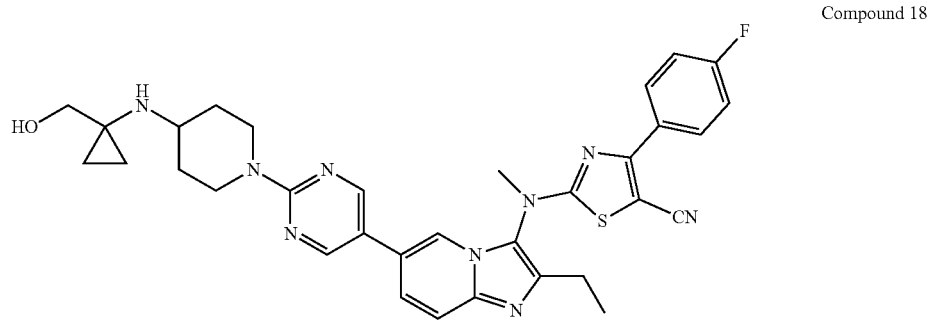
Compound 19
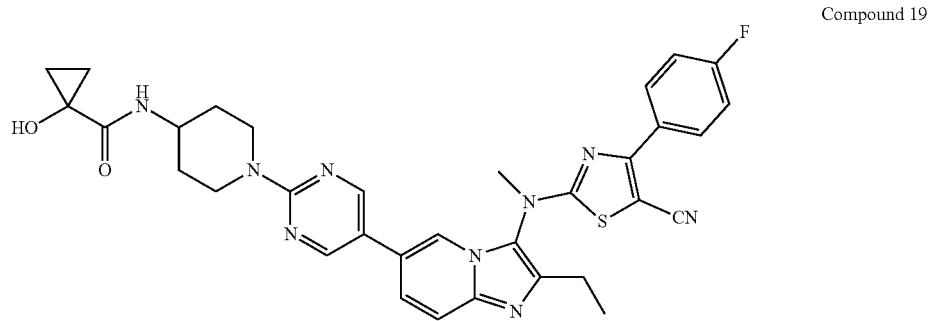

-continued
Compound 20
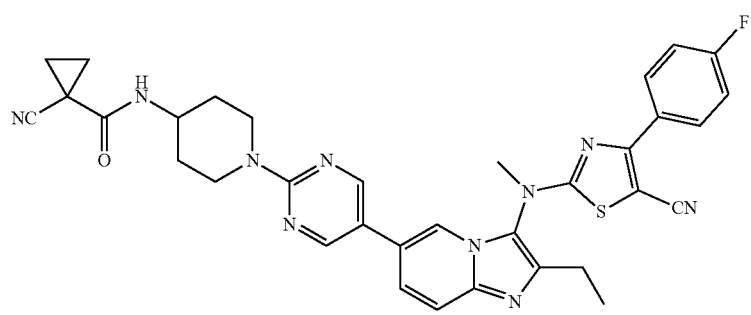
Compound 23
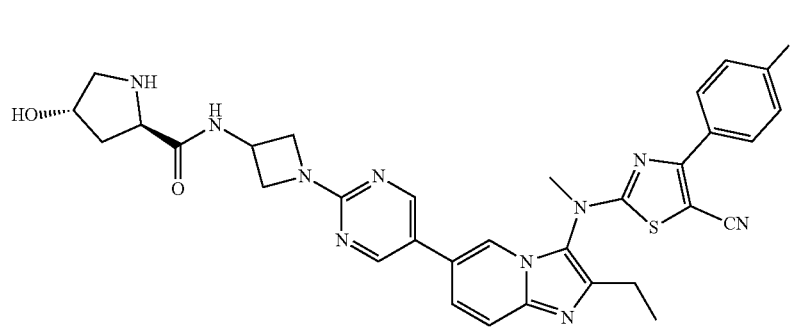
Compound 24
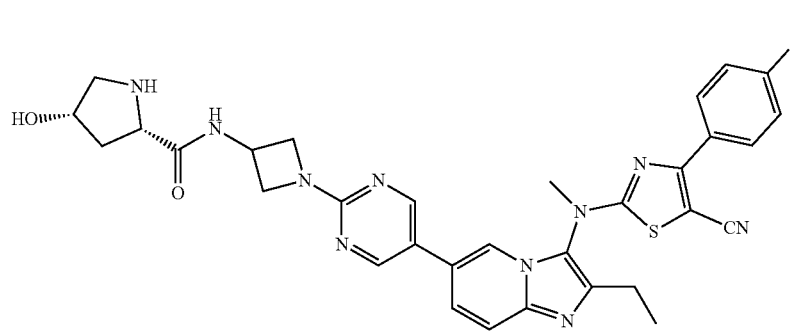
Compound 25
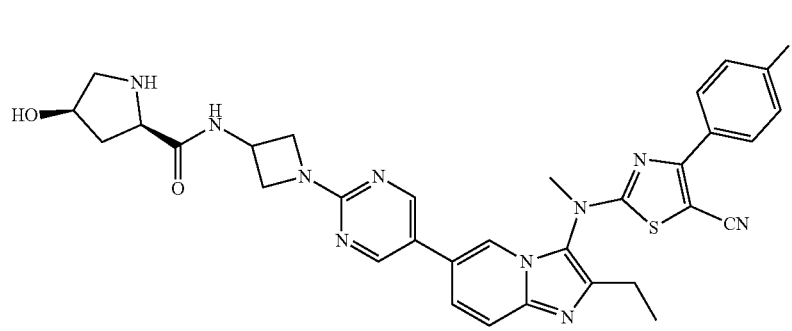
Compound 26
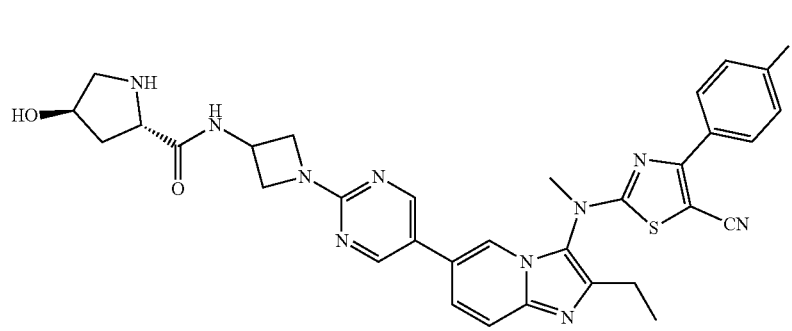

-continued
Compound 27
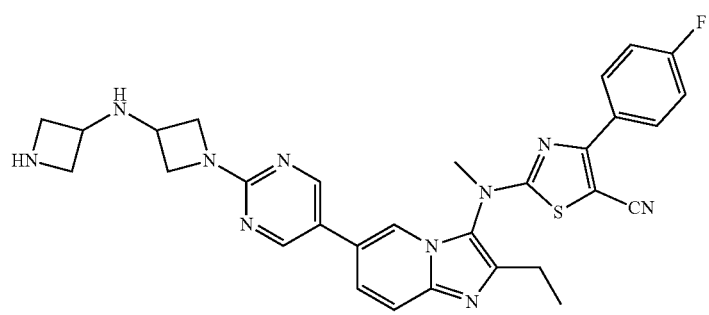
Compound 28
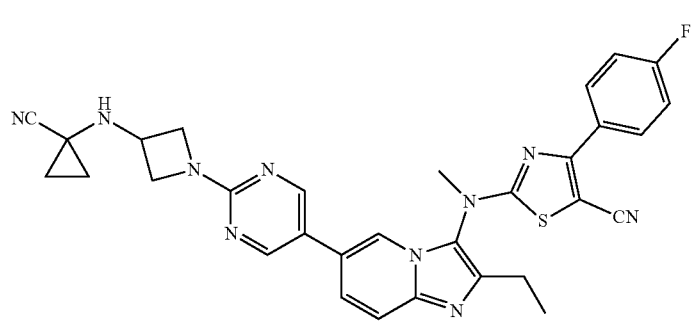
Compound 29
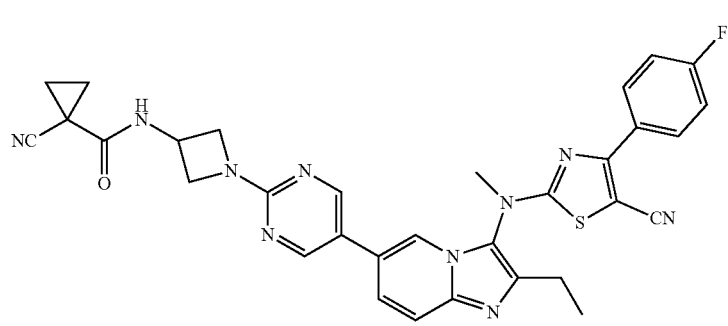
Compound 30
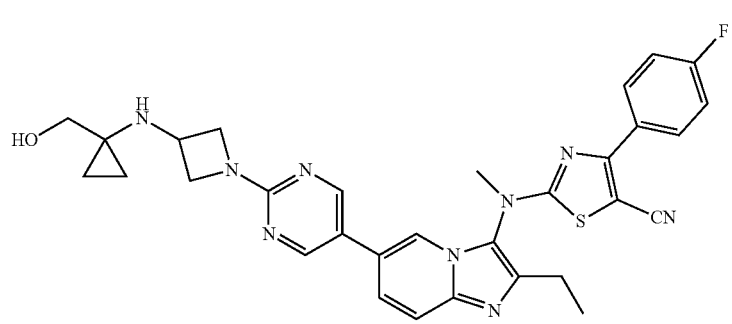
Compound 31
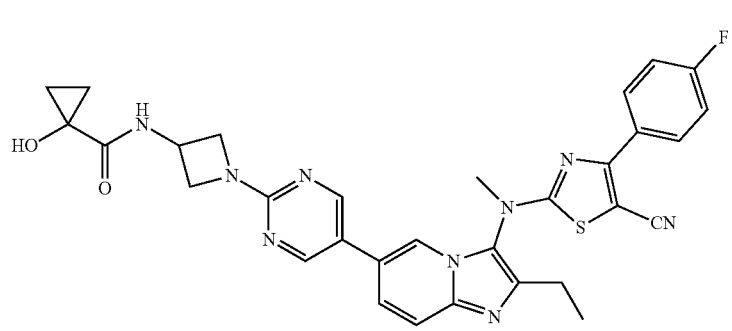

-continued
Compound 32
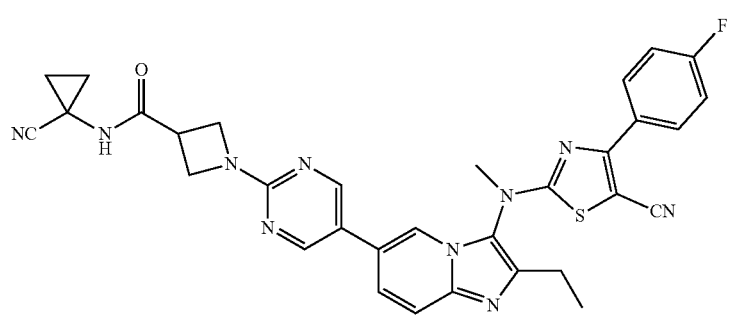
Compound 33
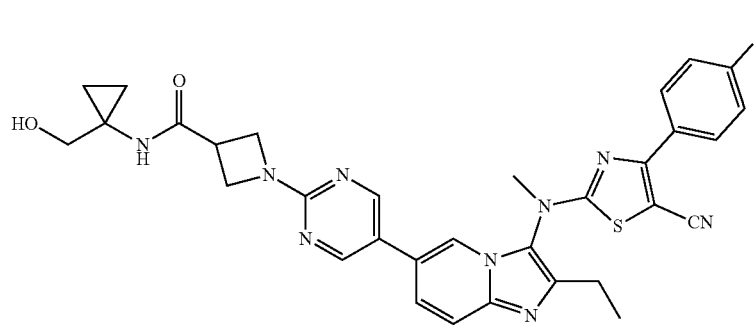
Compound 42
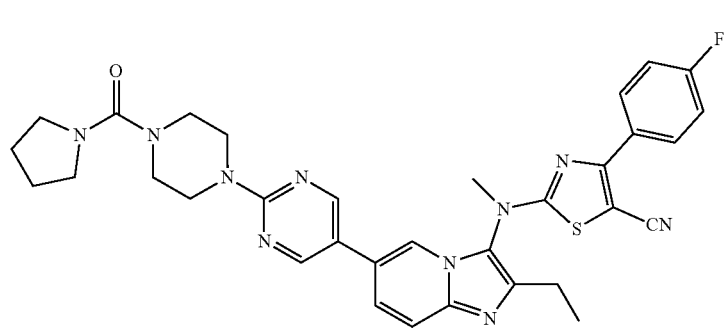
Compound 43
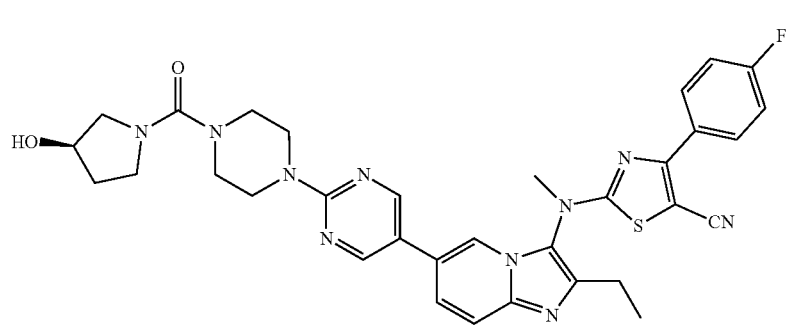
Compound 44
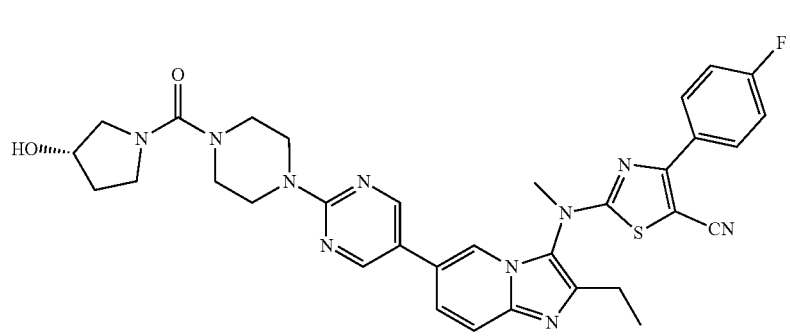

-continued
Compound 45
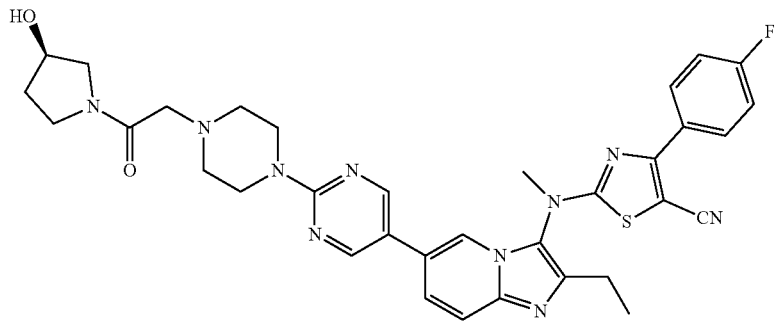
Compound 46
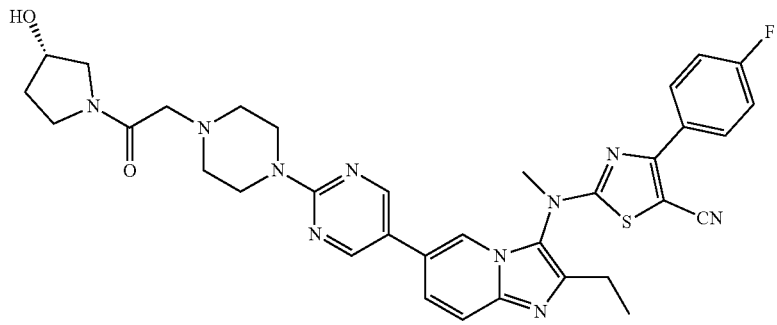
Compound 66
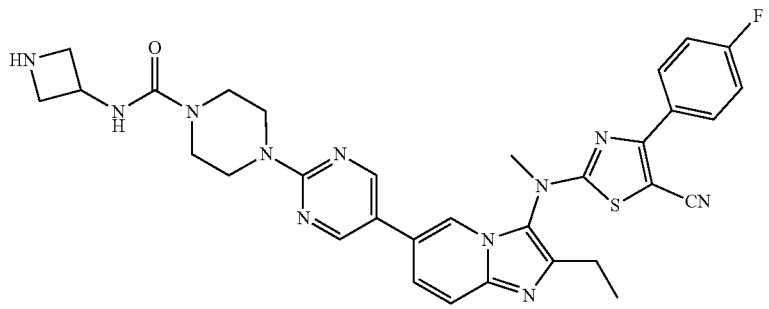
Compound 67
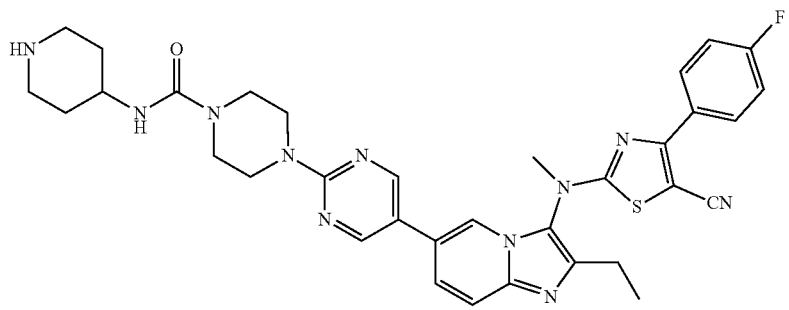
Compound 68
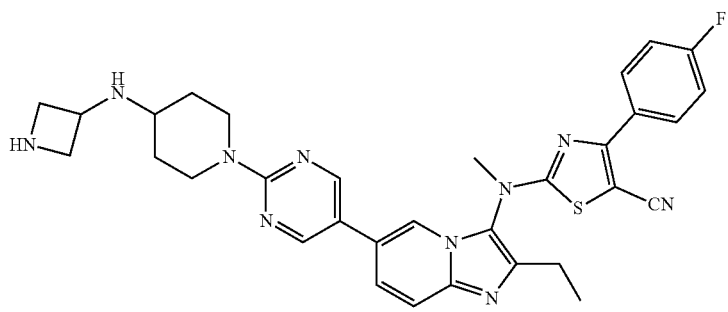

-continued
Compound 69
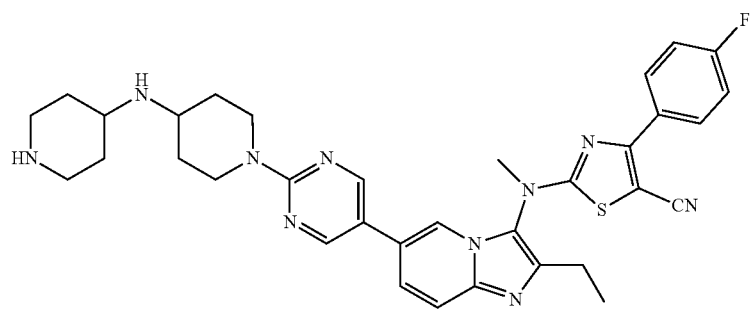
Compound 70
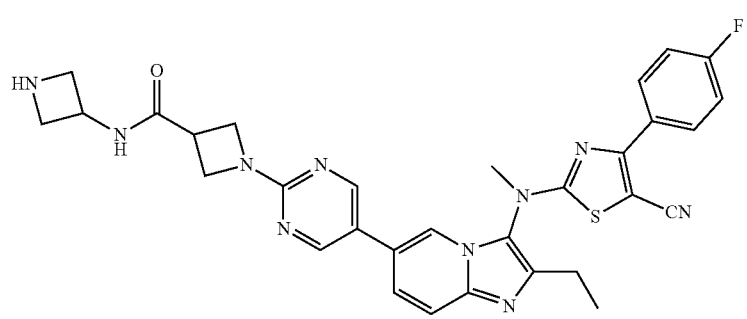
Compound 71
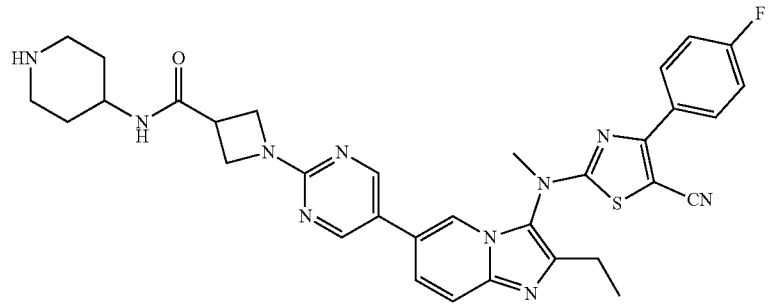
Compound 72
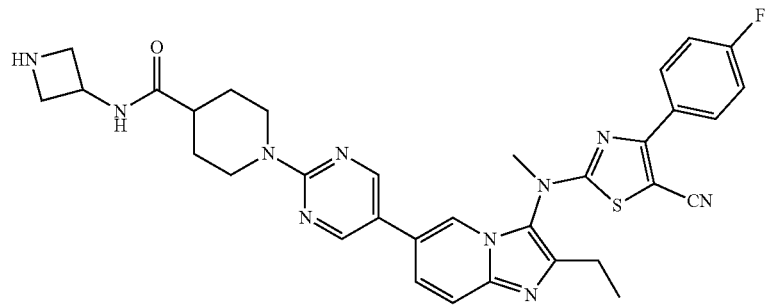
Compound 73
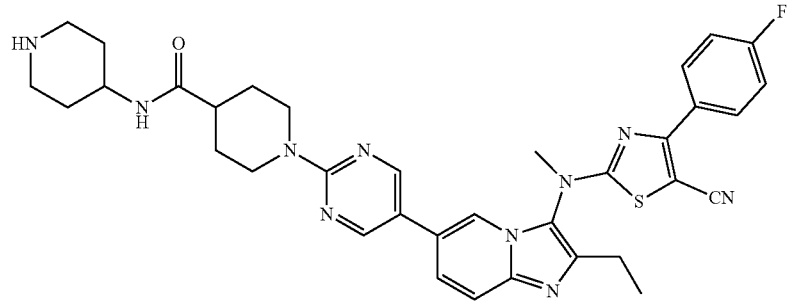

-continued
Compound 74
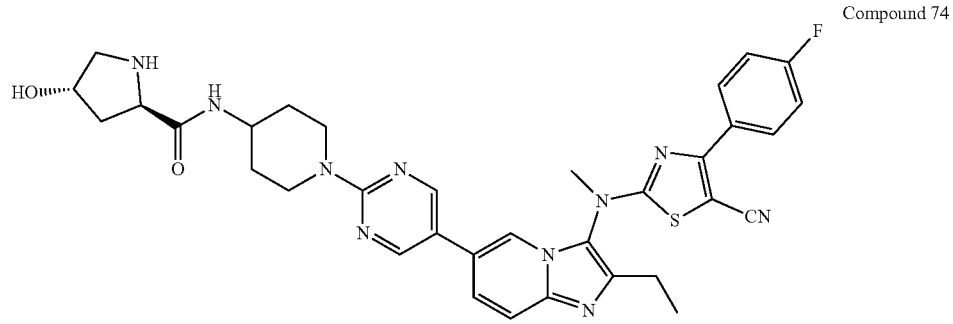
Compound 75
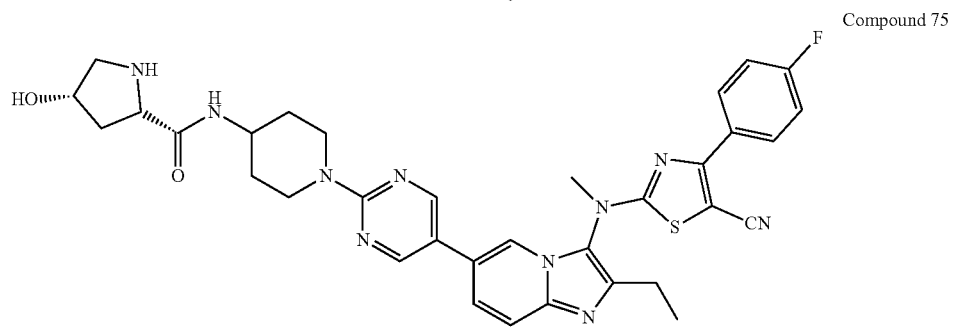
Compound 76
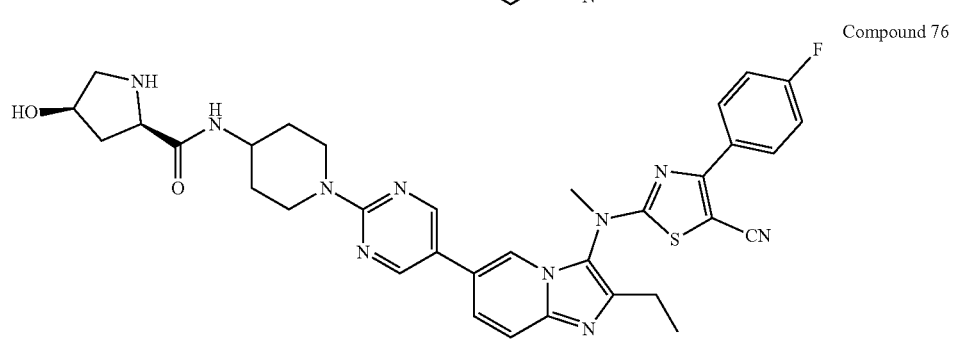
Compound 77
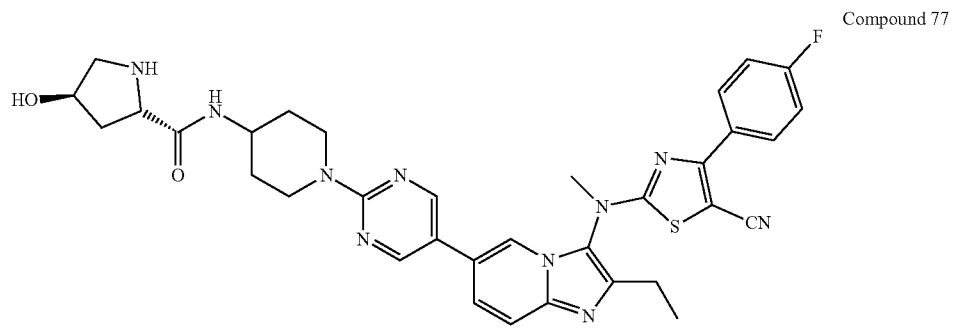
Compound 78
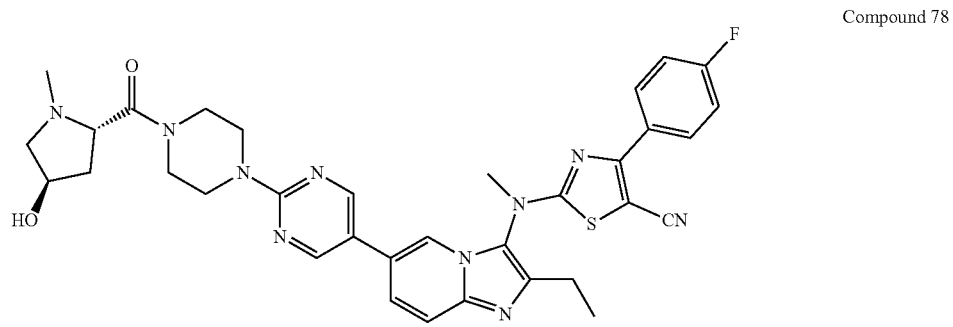

Compound 79
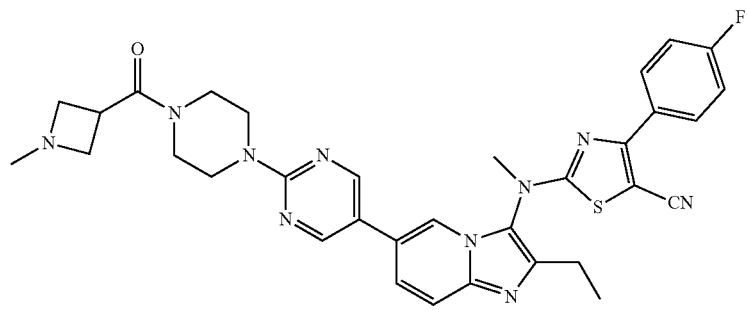
Compound 80
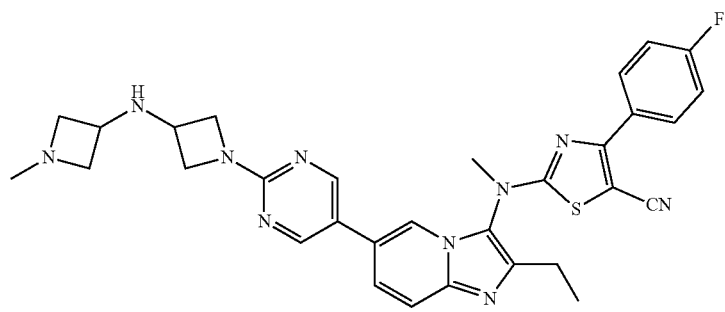
Compound 81
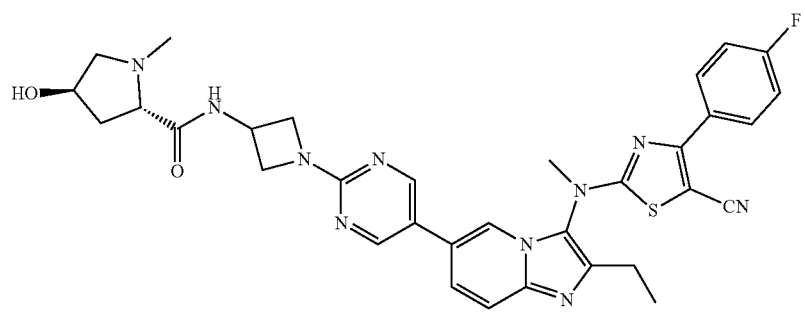
Compound 82
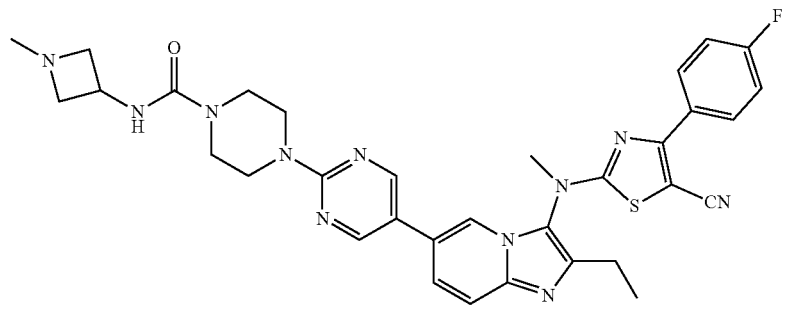
Compound 83
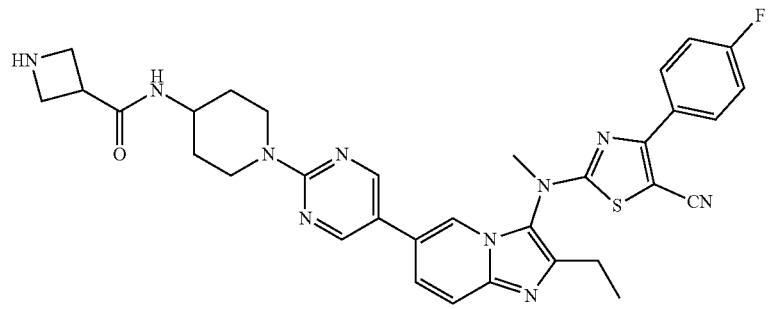

-continued
Compound 84
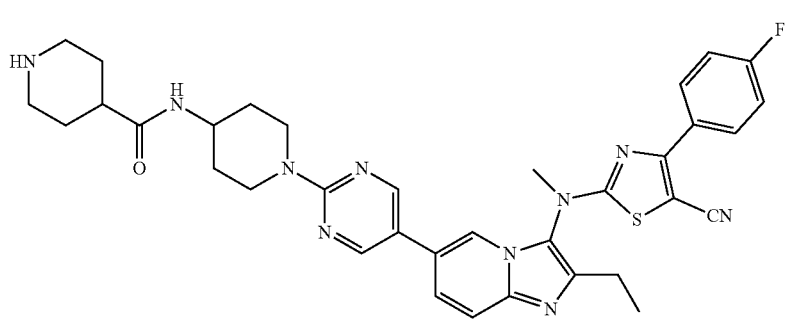
Compound 85
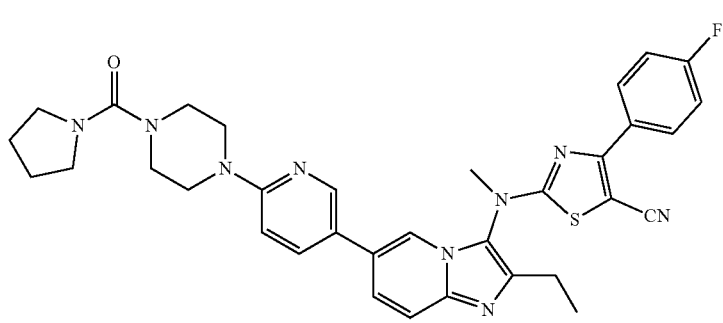
Compound 86
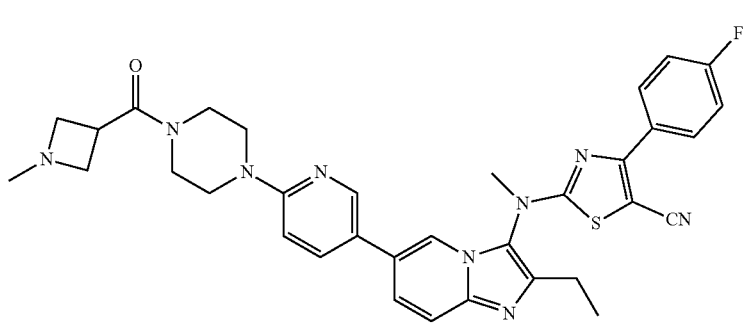
Compound 88
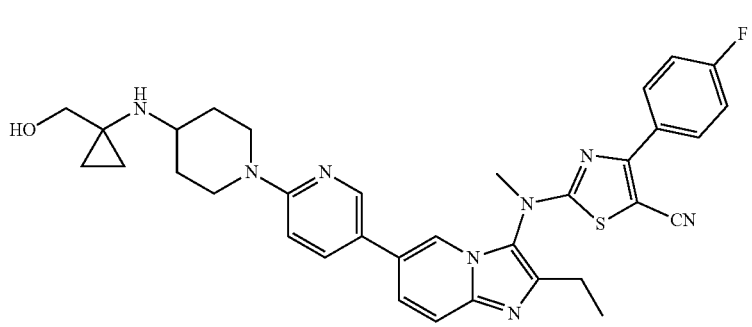
Compound 89
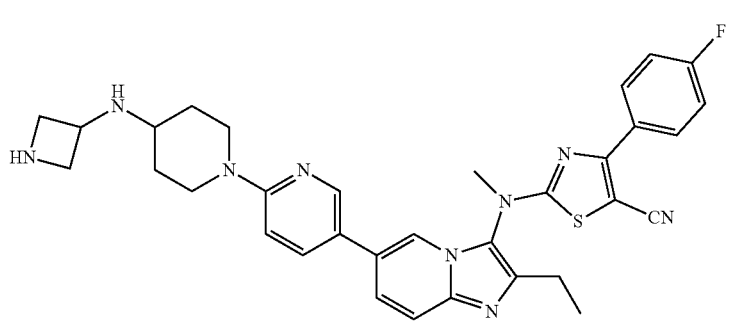

-continued
Compound 90
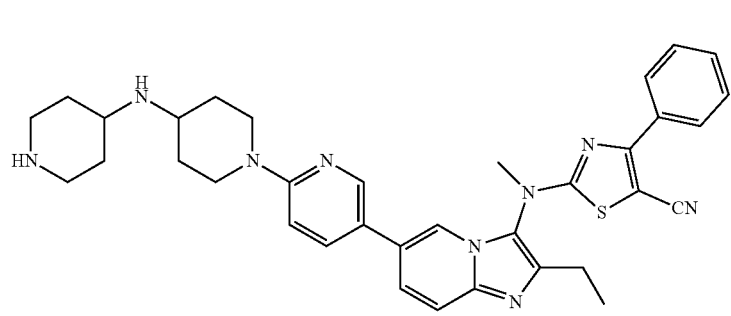
Compound 91
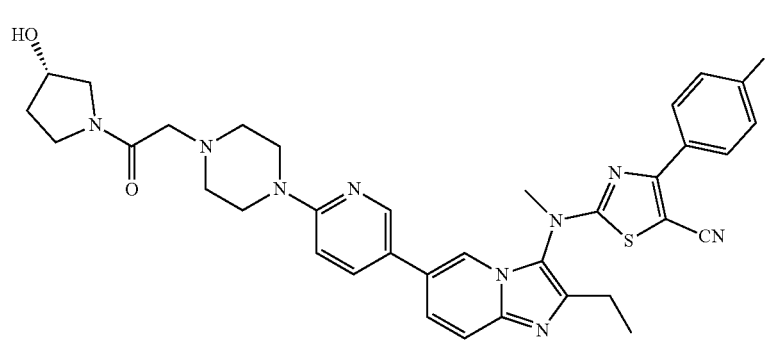
Compound 92
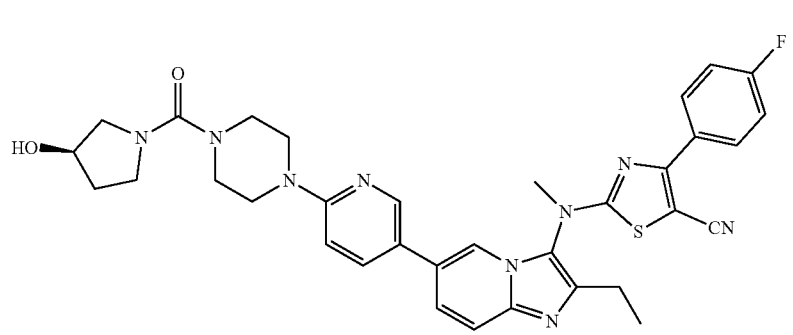
Compound 93
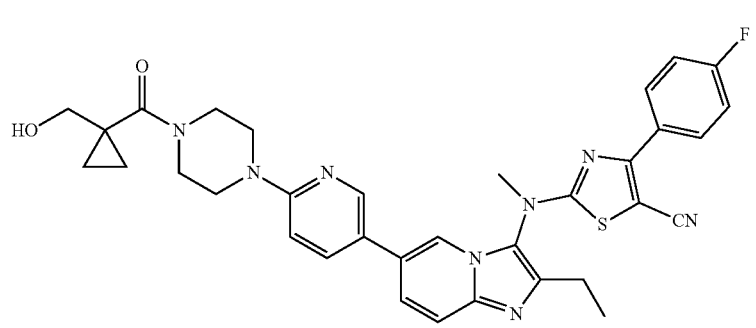
Compound 94
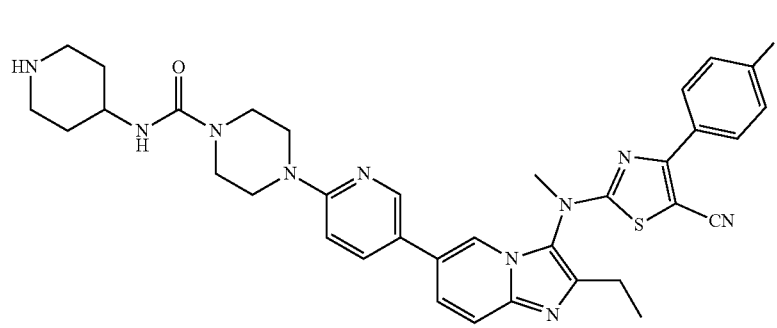

Compound 95
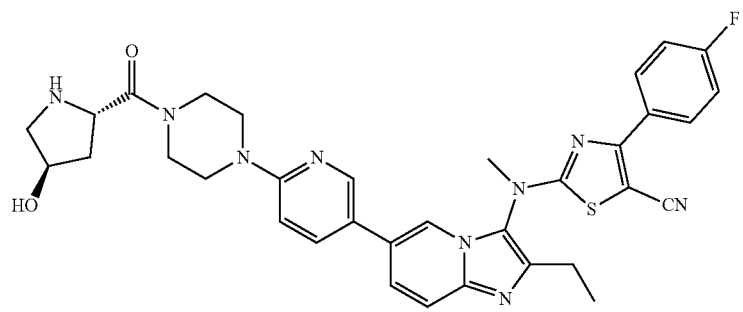
Compound 96
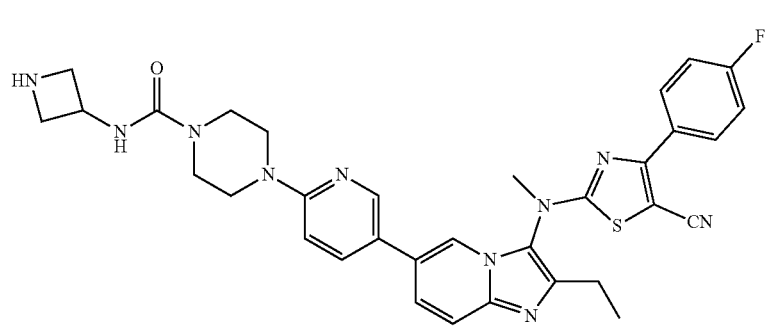
Compound 97
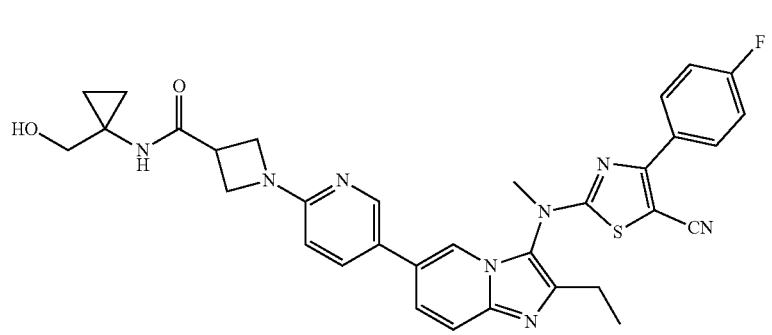
Compound 98
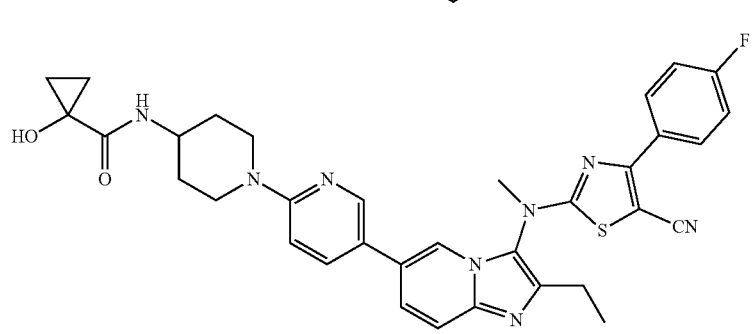
Compound 105
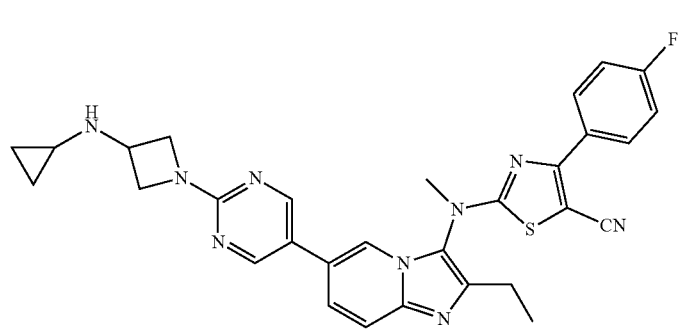

-continued
Compound 106
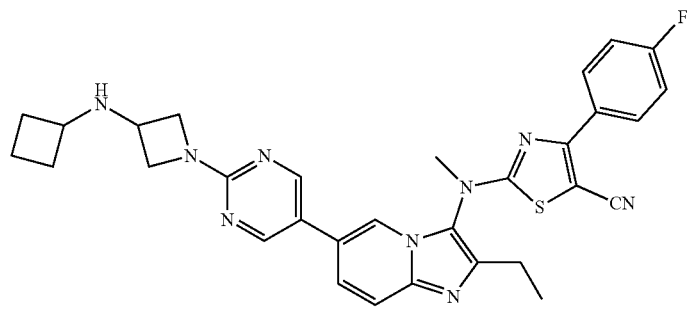
Compound 107
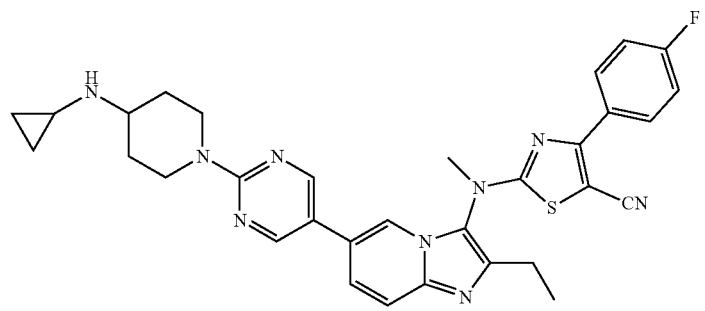
Compound 108
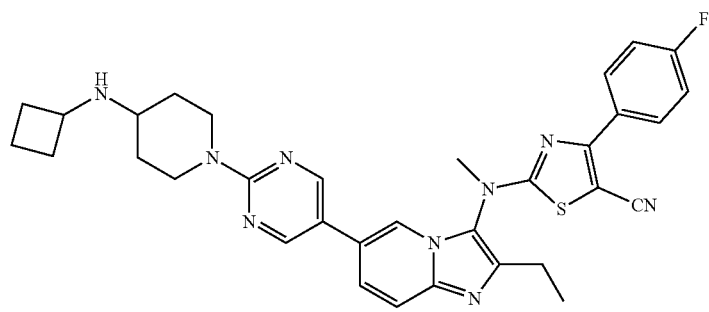
Compound 109
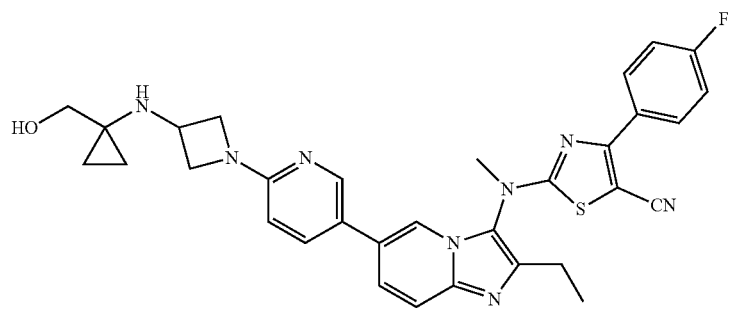
Compound 110
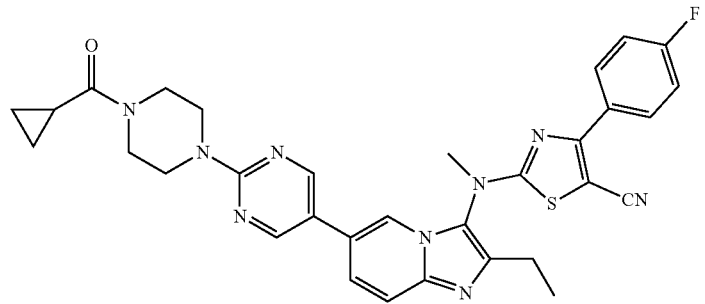

-continued
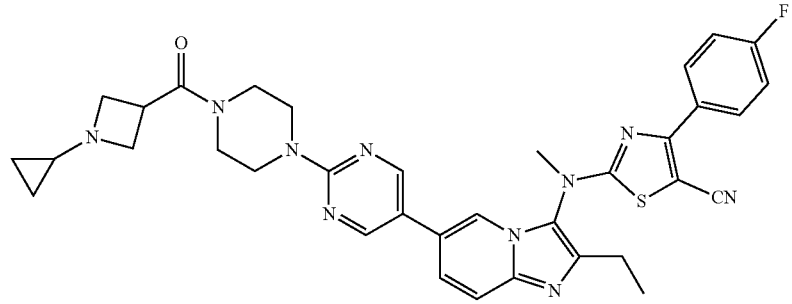
Compound 111
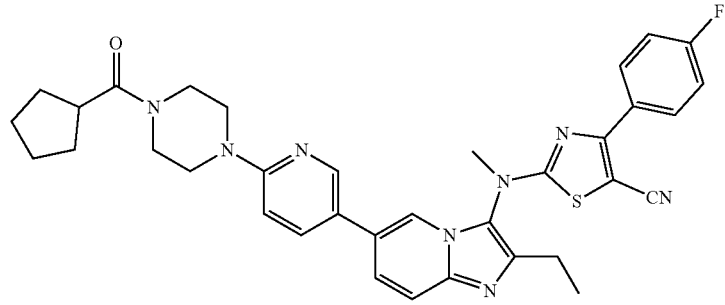
Compound 112
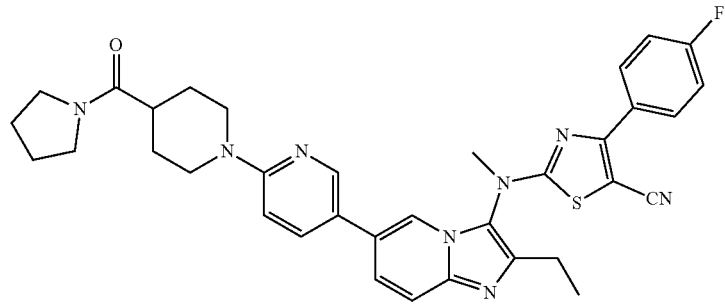
Compound 113
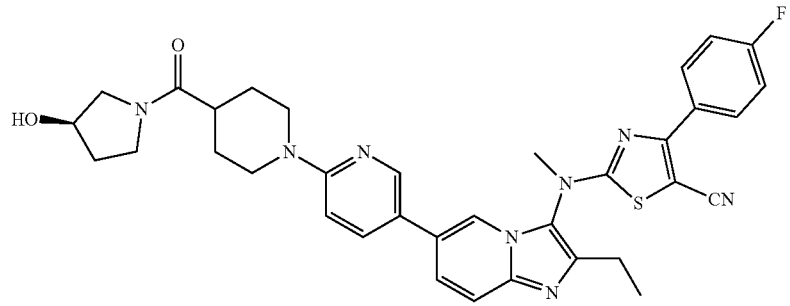
Compound 114
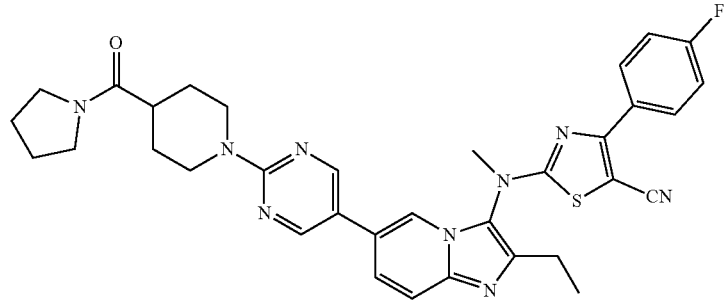
Compound 115

Compound 118
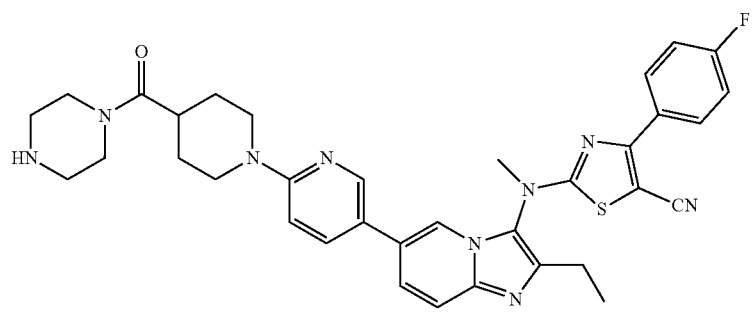
Compound 119
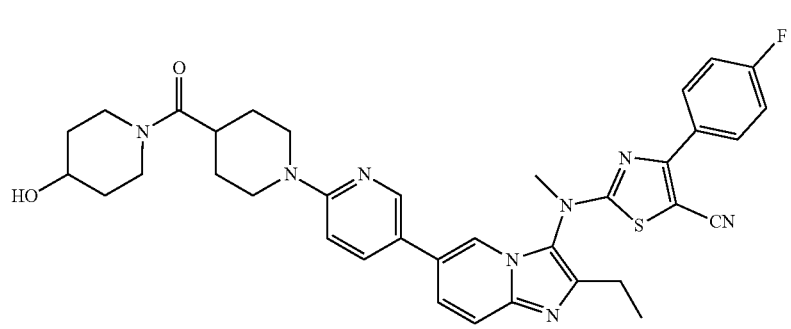
Compound 120
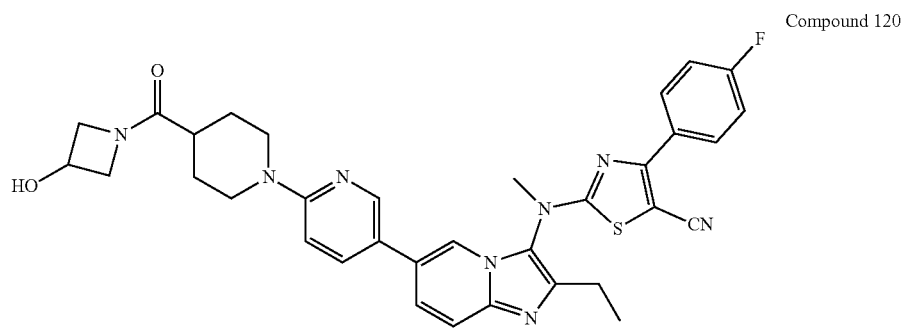
Compound 121
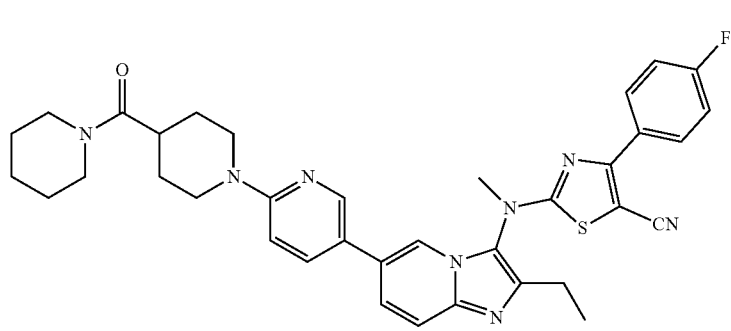
Compound 122
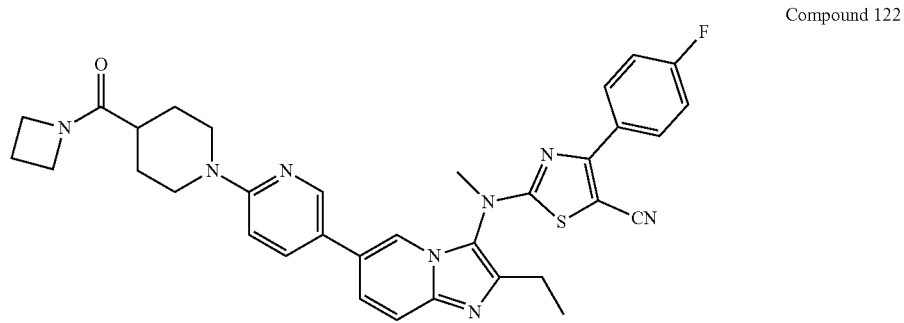

Compound 123
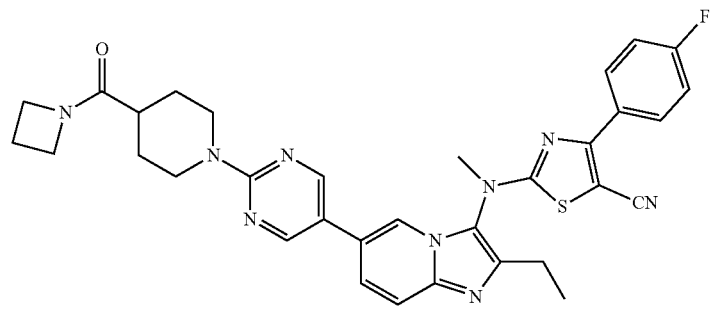
Compound 124
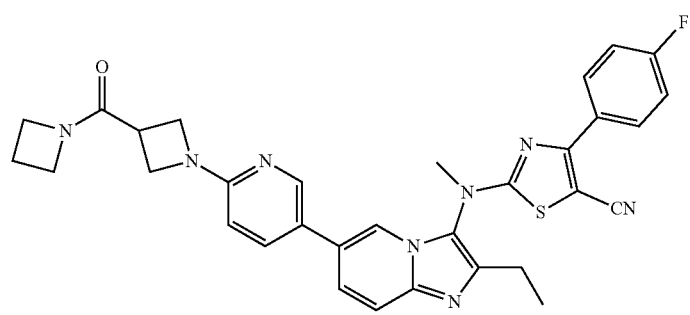
Compound 125
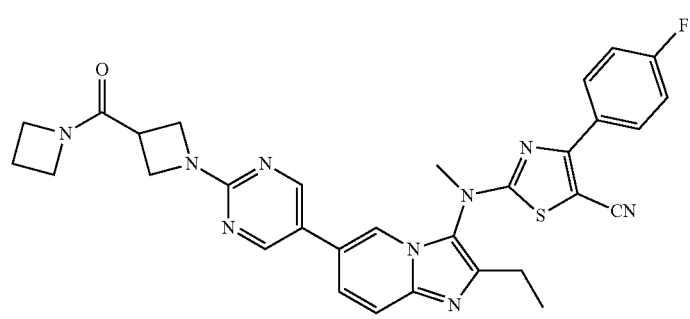
Compound 126
and
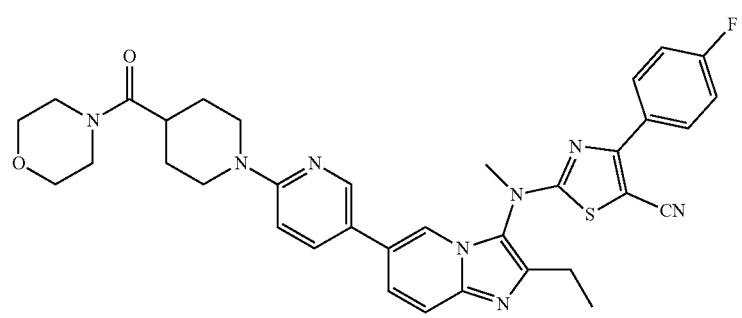

Compound 127 or a pharmaceutically acceptable salt thereof.

22. The compound of claim 1, wherein the compound is of formula (Ie):

(Ie)

wherein:

X$^1$ and X$^4$ are independently N or C—R$^1$;

R$^1$ is selected from H, halogen, optionally substituted —(C$_1$-C$_6$)alkyl, and optionally substituted —(C$_1$-C$_6$)alkoxy; and R$^{31}$ is selected from optionally substituted (C$_2$-C$_5$)heterocycloalkyl, and optionally substituted (C$_3$-C$_7$)cycloalkyl-;

R$^{11}$ is selected from —H, -halogen, —CN, —OH, optionally substituted —(C$_1$-C$_6$)alkoxy, —NH$_2$, —NR$^5$R$^6$, —CH$_2$NH$_2$ and optionally substituted —(C$_1$-C$_6$)alkyl; and n is 0, 1, 2, or 3.

23. The compound of claim 22, wherein the optional substituents of the R$^{31}$ group are selected from NC—, HO—, HOCH$_2$—, (C$_1$-C$_3$)alkyl- (e.g., H$_3$C—), (C$_1$-C$_3$) alkoxy-, substituted (C$_1$-C$_3$)alkyl-, and (C$_3$-C$_6$)cycloalkyl- (e.g., cyclopropyl).

24. The compound of claim 22, wherein the compound is of formula (If):

(If)

wherein:

X$^1$ and X$^4$ are independently N or CH;

R$^{41}$ is H—, or HO—; and q is 0, 1 or 2; wherein when q is 0 or 1, X$^5$ is CH$_2$; and when q is 2, X$^5$ is NH, 0, or CH(OH).

25. The compound of claim 17, wherein the compound is of formula (Ic):

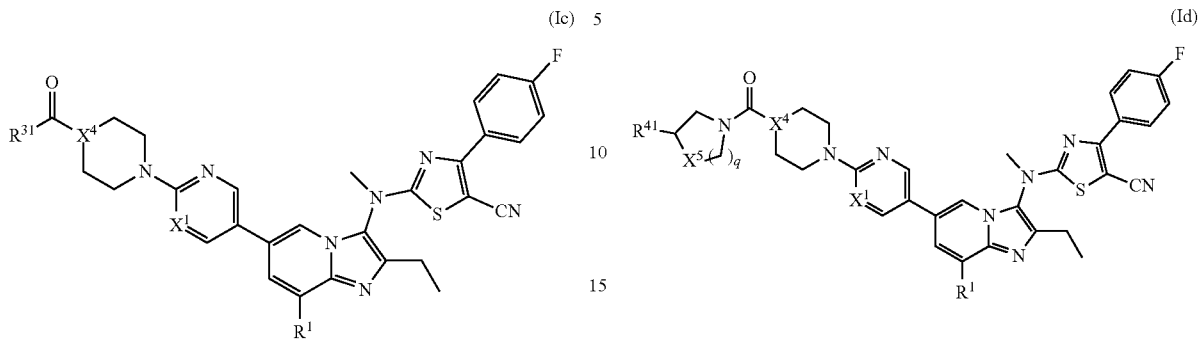

wherein:
$X^1$ and $X^4$ are independently N or C—$R^1$;
$R^1$ is selected from H, halogen, optionally substituted —($C_1$-$C_6$)alkyl, and optionally substituted —($C_1$-$C_6$)alkoxy; and
$R^{31}$ is selected from optionally substituted ($C_2$-$C_5$)heterocycloalkyl, and optionally substituted ($C_3$-$C_7$)cycloalkyl-.

26. The compound of claim 25, wherein the compound is of formula (Id):

wherein:
$X^1$ and $X^4$ are independently N or CH;
$R^{41}$ is H—, or HO—; and
q is 0, 1 or 2; wherein
when q is 0 or 1, $X^5$ is $CH_2$; and
when q is 2, $X^5$ is NH, O, or CH(OH).

27. The compound of claim 26, wherein the compound is selected from:

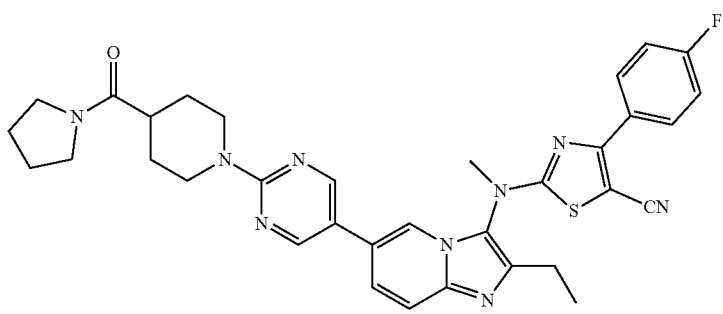

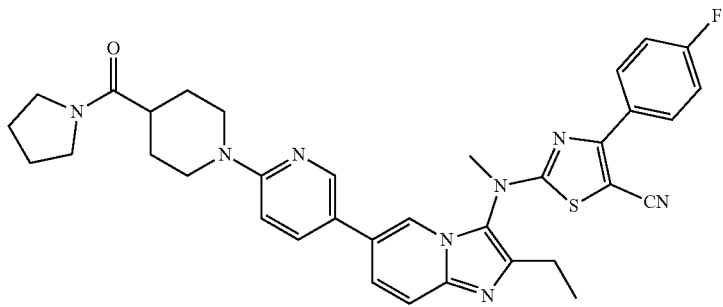

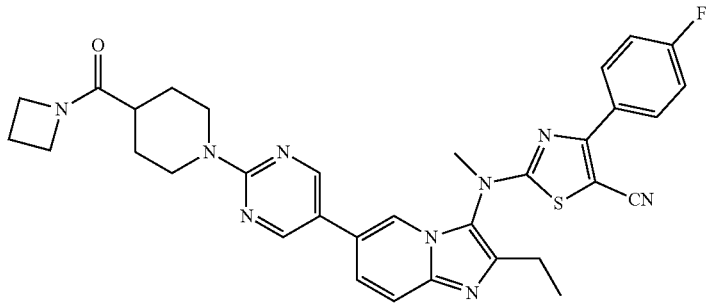

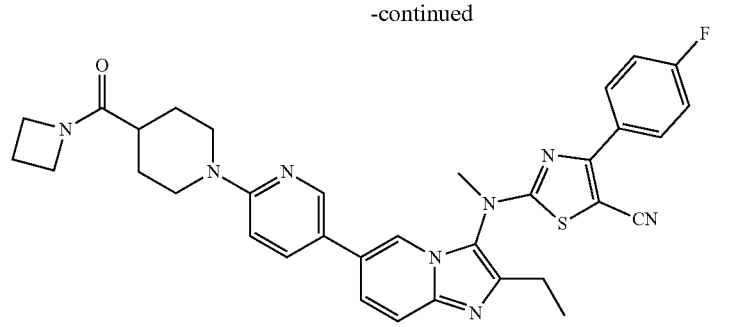
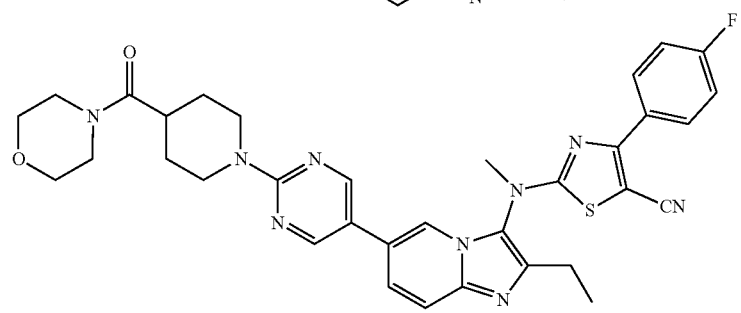
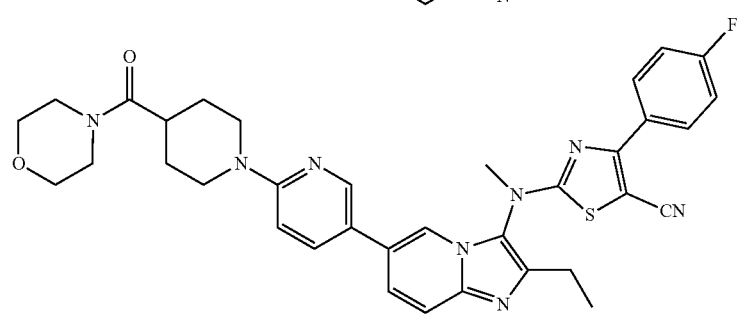
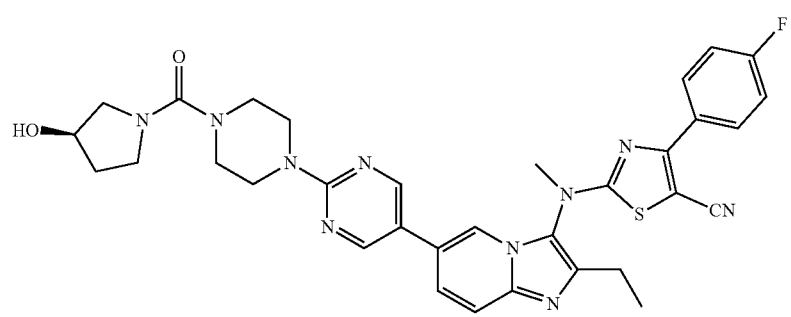
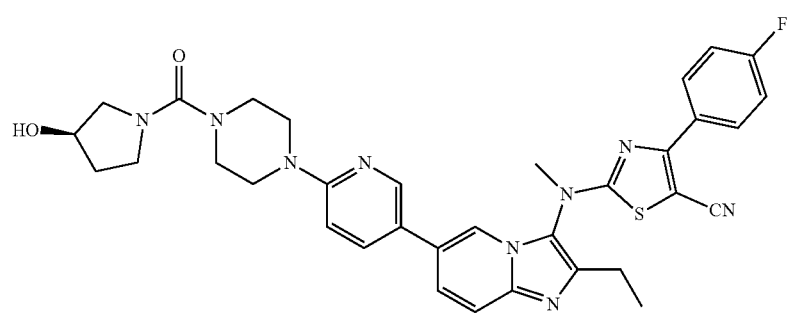

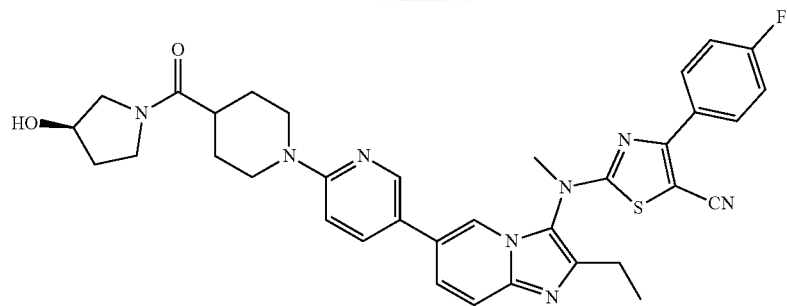
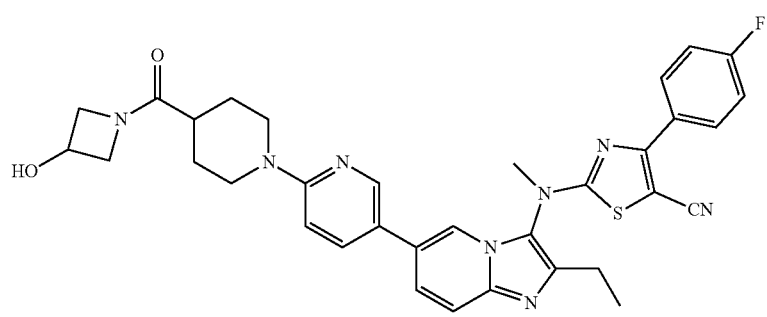
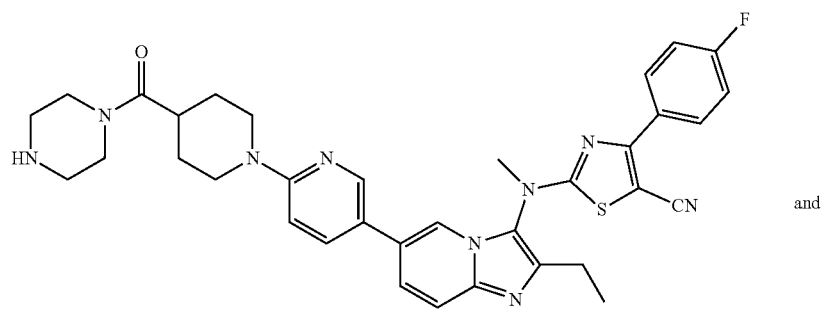
and

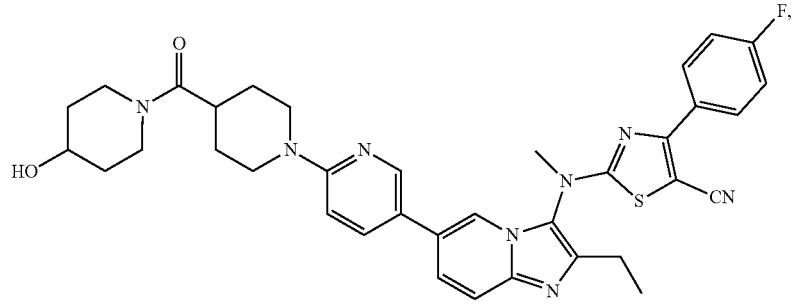

or a pharmaceutically acceptable salt thereof.

28. The compound of claim 10, wherein $R^3$ is

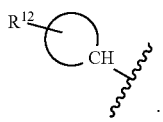

29. The compound of claim 28, wherein $R^3$ is

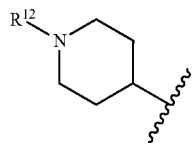

30. The compound of claim 28, wherein:

$R^{12}$ is selected from H—, $R^{31}$—C(O)—, $R^{31}$—C(O)CH$_2$—, $R^{31}$—NHC(O)—, $R^{31}$—C(O)NH—, $R^{31}$—N(CH$_3$)C(O)—, and $R^{31}$—C(O)N(CH$_3$)—;

$R^{31}$ is selected from optionally substituted (C$_1$-C$_3$)alkyl-, optionally substituted cycloalkyl-, and optionally substituted saturated heterocycle; and the optional substituents of the $R^{31}$ group are selected from NC—, HO—, HOCH$_2$—, (C$_1$-C$_3$)alkyl-, (C$_1$-C$_3$) alkoxy- and substituted (C$_1$-C$_3$)alkyl-.

31. The compound of claim 28, wherein $R^{12}$ is selected from:

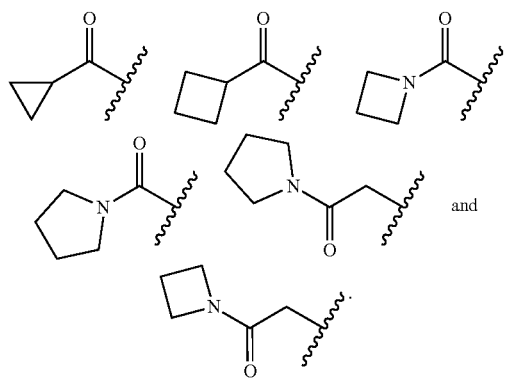

and

32. The compound of claim 28, wherein the compound is selected from:

Compound 99

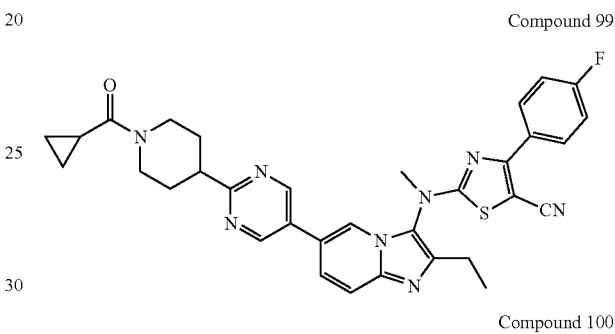

Compound 100

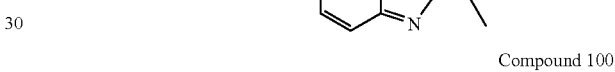

Compound 101

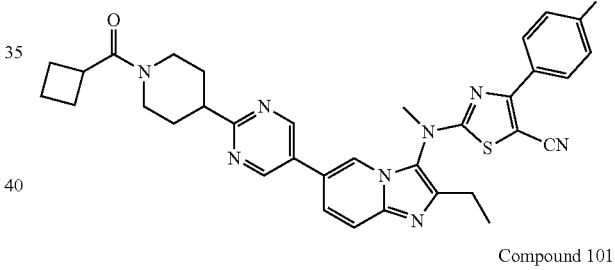

Compound 102

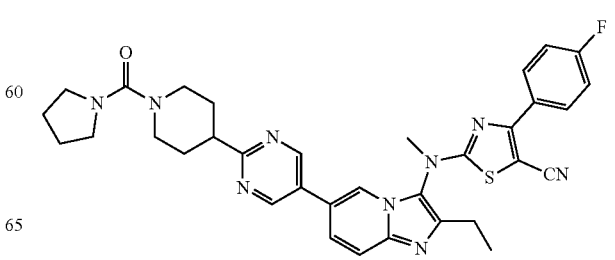

Compound 103

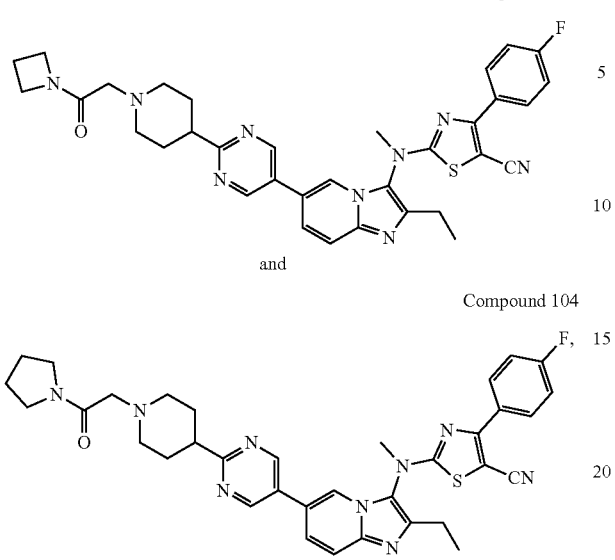

and

Compound 104

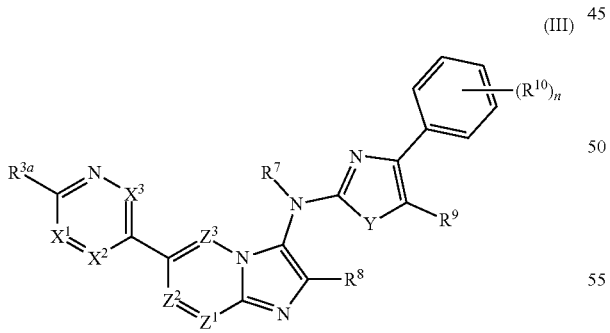

or a pharmaceutically acceptable salt thereof.

33. A pharmaceutical composition comprising:
a compound or a pharmaceutically acceptable salt thereof according to claim 1; and
a pharmaceutically acceptable excipient.

34. A method of inhibiting autotaxin, the method comprising contacting a biological system comprising autotaxin with an effective amount of a compound or a pharmaceutically acceptable salt thereof according to claim 1 to inhibit autotaxin.

35. A method of inhibiting autotaxin in a subject in need thereof, comprising administering to the subject a therapeutically effective amount of a compound or a pharmaceutically acceptable salt thereof according to claim 1.

36. A method of treating liver fibrosis in a subject in need thereof, comprising administering to the subject a therapeutically effective amount of a compound or a pharmaceutically acceptable salt thereof according to claim 1.

37. A compound of formula (III):

(III)

or a pharmaceutically acceptable salt or isomer thereof, wherein:

$X^1$, $X^2$, and $X^3$ are independently selected from C—$R^1$ and N;

$Z^1$, $Z^2$, and $Z^3$ are independently selected from C—$R^1$ and N;

each $R^1$ is independently selected from —H, -halogen, optionally substituted —($C_1$-$C_6$)alkyl and optionally substituted —($C_1$-$C_6$)alkoxy;

Y is selected from S, O, and N—$R^2$, wherein $R^2$ is selected from —H, and optionally substituted —($C_1$-$C_6$)alkyl;

$R^{3a}$ is selected from optionally substituted $R^4$—C(O)—($C_1$-$C_3$)alkyl-, $R^4$C(O)—, halogen, optionally substituted monocyclic or bicyclic carbocycle, optionally substituted monocyclic or bicyclic heterocycle, $R^5R^6$HC—, and $R^5R^6$N—;

$R^4$ is selected from $H_2N$—, HO—, $R^5R^6N$—, optionally substituted ($C_1$-$C_{10}$)alkyl-, optionally substituted ($C_1$-$C_{10}$)alkoxy-, optionally substituted monocyclic or bicyclic carbocycle, optionally substituted monocyclic or bicyclic heterocycle, optionally substituted cycloalkyl-($C_1$-$C_6$)alkylene-, and optionally substituted heterocycle-($C_1$-$C_6$)alkylene-;

$R^5$ and $R^6$ are independently selected from H—, $H_2N$—, HO—, optionally substituted ($C_1$-$C_{10}$)alkyl-, optionally substituted monocyclic or bicyclic carbocycle, optionally substituted monocyclic or bicyclic heterocycle, optionally substituted $R^4$C(O)—($C_1$-$C_{10}$)alkyl-, $R^4$C(O)—, $R^4$-, and substituted amino;

or $R^5$ and $R^6$ together with the nitrogen or carbon atom to which they are attached are cyclically linked to form an optionally substituted carbocycle or an optionally substituted heterocycle;

$R^7$ is selected from H—, and optionally substituted ($C_1$-$C_6$)alkyl-;

$R^8$ is selected from —H, -halogen, and optionally substituted —($C_1$-$C_6$)alkyl;

$R^9$ and each $R^{10}$ are independently selected from —H, -halogen, —CN, —OH, optionally substituted —($C_1$-$C_6$)alkoxy, —$NH_2$, substituted amino, optionally substituted —($C_1$-$C_6$)alkyl-$NH_2$ and optionally substituted —($C_1$-$C_6$)alkyl; and n is 0, 1, 2, 3, 4, or 5;

with the proviso that:

a) when i) $X^1$, $X^2$, and $X^3$ are C—H, or $X^1$ and $X^2$ are C—H and $X^3$ is C—$CH_3$ or N, ii) $R^3$ is $R^4$- C(O)—($C_1$-$C_3$)alkyl-, and iii) $R^4$ is $R^5R^6N$—:

$R^5$ and $R^6$ are independently selected from H—, $H_2N$—, HO—, optionally substituted ($C_1$-$C_{10}$)alkyl-, optionally substituted monocyclic or bicyclic carbocycle, optionally substituted monocyclic or bicyclic heterocycle, optionally substituted $R^4$C(O)—($C_1$-$C_{10}$)alkyl-, $R^4$C(O)—, $R^4$-, and substituted amino; or $R^5$ and $R^6$ together with the nitrogen atom to which they are attached are cyclically linked to form an unsubstituted heterocycle;

b) when i) $X^1$ is C—F and $X^2$ and $X^3$ are C—H, ii) $R^3$ is $R^4$-C(O)-($C_1$-$C_3$)alkyl- or $R^4$-C(O)—, and $R^4$ is $R^5R^6N$—:

$R^5$ and $R^6$ are independently selected from H—, $H_2N$—, HO—, optionally substituted ($C_1$-$C_{10}$)alkyl-, optionally substituted monocyclic or bicyclic carbocycle, optionally substituted monocyclic or bicyclic heterocycle, optionally substituted $R^4$C(O)-($C_1$-$C_{10}$)alkyl-, $R^4$C(O)—, $R^4$-,and substituted amino; or $R^5$ and $R^6$ together with the nitrogen atom to which they are attached are cyclically linked to form an unsubstituted heterocycle; and c) when i) $X^1$ and $X^3$ are C—H and $X^2$ is N and, ii) $R^3$ is $R^4$-C(O)-($C_1$-$C_3$)alkyl-, $R^4$-C(O)—, or $R^5R^6N$—, wherein iii) $R^4$ is $R^5R^6N$—:

$R^5$ and $R^6$ are independently selected from H—, $H_2N$—, HO—, optionally substituted ($C_1$-$C_{10}$)alkyl-, optionally substituted monocyclic or bicyclic carbocycle, optionally substituted monocyclic or bicyclic heterocycle, optionally substituted R⁴C(O)-(C₁-C₁₀)alkyl-, R⁴C(O)—, R⁴-, and substituted amino; or R⁵ and R⁶ together with the nitrogen atom to which they are attached are cyclically linked to form an unsubstituted heterocycle;

wherein:

when one of R⁵ and R⁶ is H—:

the other one of R⁵ and R⁶ is independently selected from H₂N—, HO—, unsubstituted (C₁-C₁₀)alkyl-, optionally substituted monocyclic or bicyclic carbocycle, optionally substituted monocyclic heterocycle, optionally substituted R⁴C(O)-(C₁-C₁₀)alkyl-, R⁴C(O)—, R⁴-, and substituted amino.

38. The compound of claim 37, wherein the compound is:

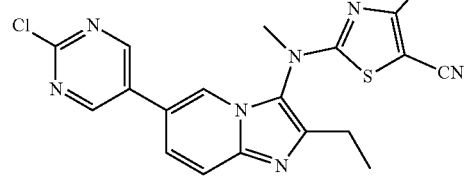

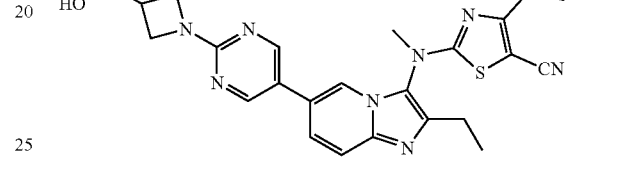

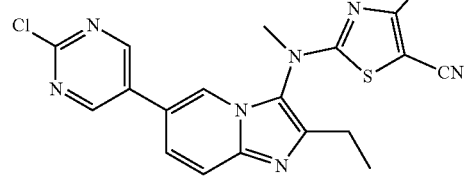

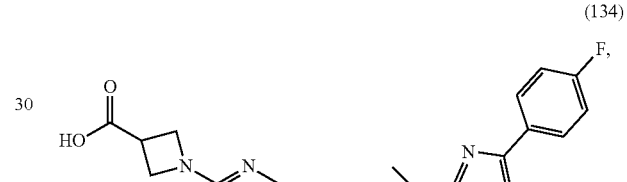


521
-continued
(137)
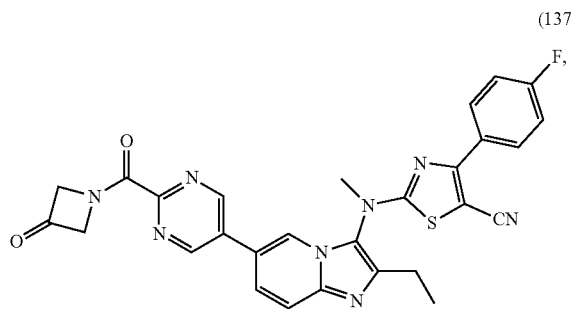
(138)
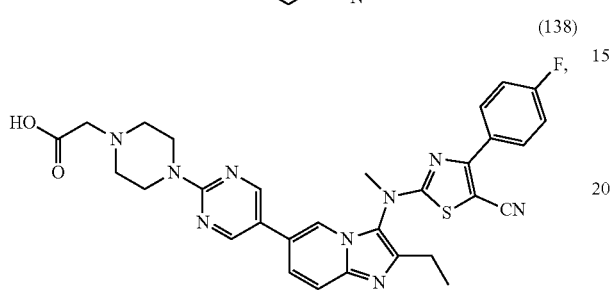
(139)
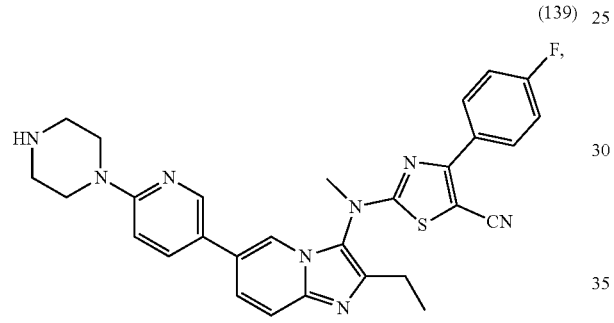
(140)
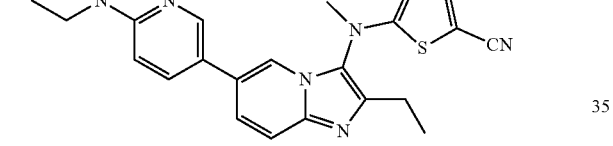
(141)
522
-continued
(142)
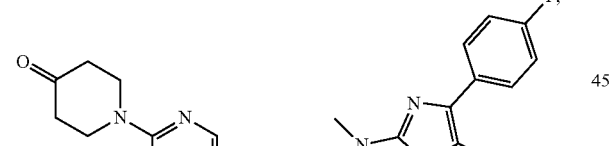
(143)
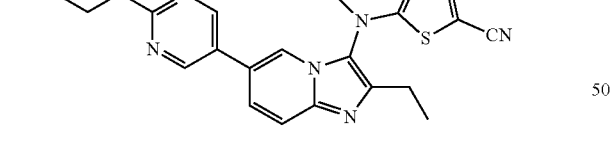
(144)
(145)
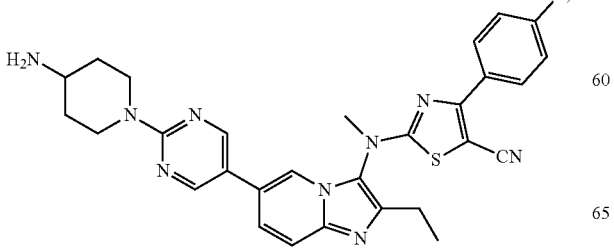
(146)

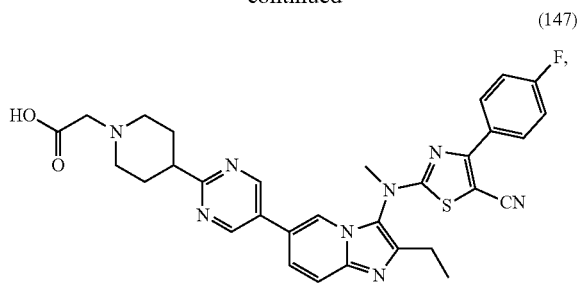

(147)

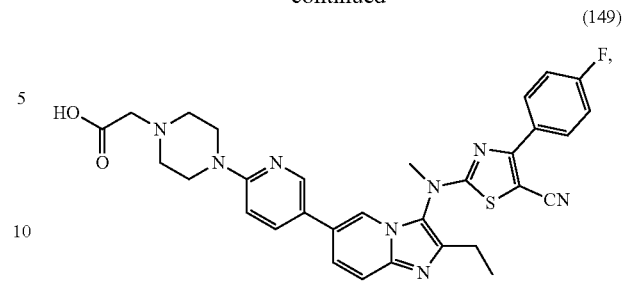

(149)

or a pharmaceutically acceptable salt thereof.

39. The compound of claim 21, wherein the compound is

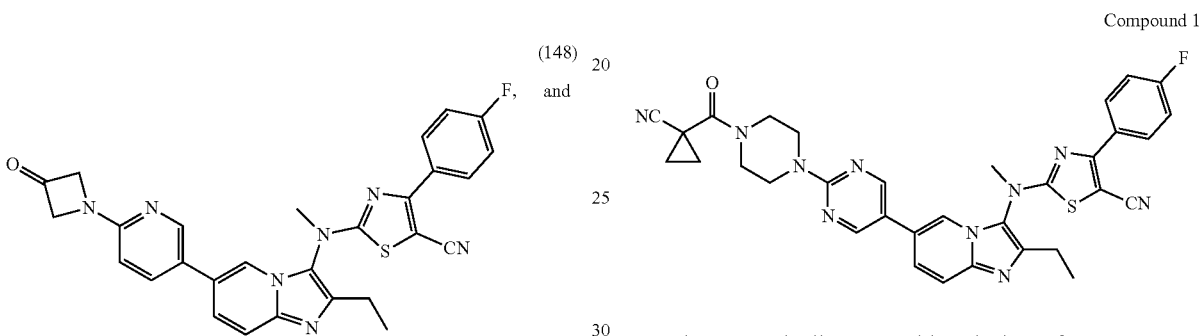

Compound 1

(148) and or a pharmaceutically acceptable salt thereof.

40. The compound of claim 21, wherein the compound is

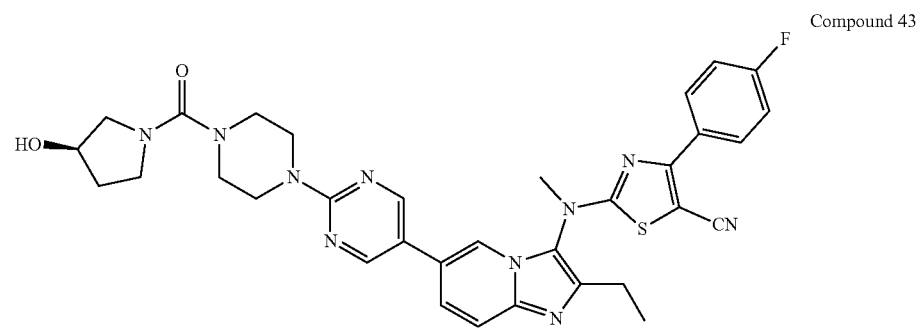 [SMILES: CCc1nc2ccc(-c3cnc(N4CCN(C(=O)N5CC[C@@H](O)C5)CC4)nc3)cn2c1N(C)c1nc(-c2ccc(F)cc2)c(C#N)s1]

Compound 43 or a pharmaceutically acceptable salt thereof.

41. The compound of claim 21, wherein the compound is

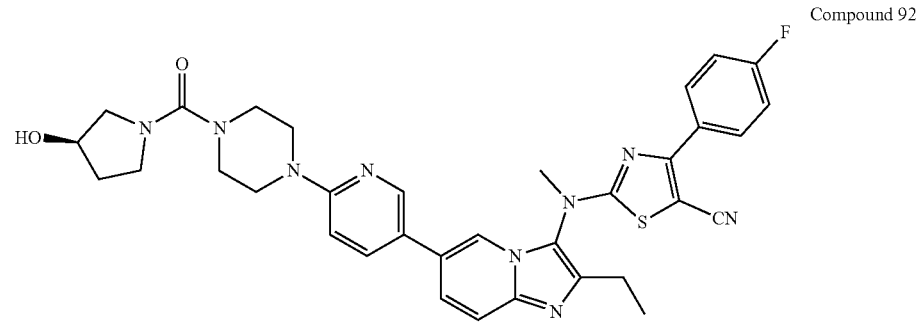 [SMILES: CCc1nc2ccc(-c3ccc(N4CCN(C(=O)N5CC[C@@H](O)C5)CC4)nc3)cn2c1N(C)c1nc(-c2ccc(F)cc2)c(C#N)s1]

Compound 92 or a pharmaceutically acceptable salt thereof.

42. The compound of claim 21, wherein the compound is

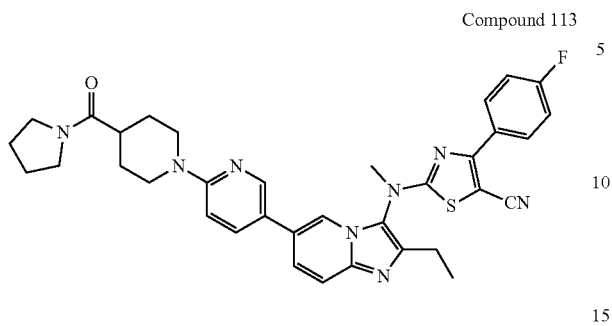

Compound 113 or a pharmaceutically acceptable salt thereof.

43. The compound of claim 21, wherein the compound is

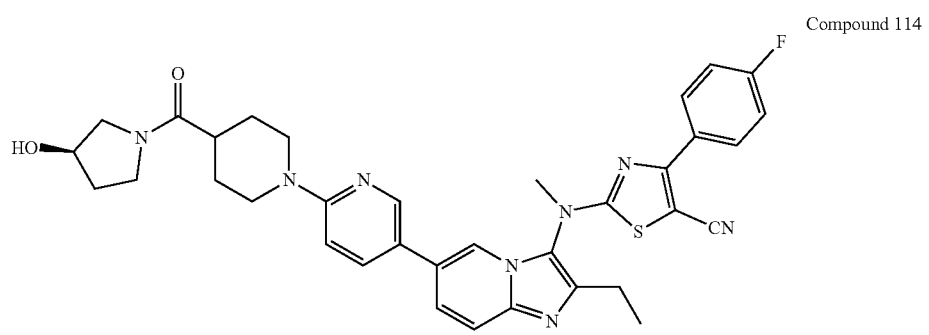 [SMILES: CCc1nc2ccc(-c3ccc(N4CCC(C(=O)N5CC[C@@H](O)C5)CC4)nc3)cn2c1N(C)c1nc(-c2ccc(F)cc2)c(C#N)s1]

Compound 114 or a pharmaceutically acceptable salt thereof.

44. The compound of claim 21, wherein the compound is

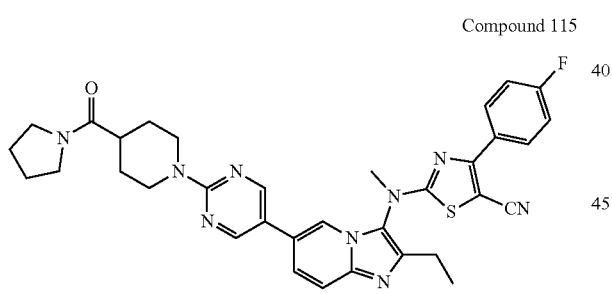

Compound 115 or a pharmaceutically acceptable salt thereof.

45. The compound of claim 21, wherein the compound is

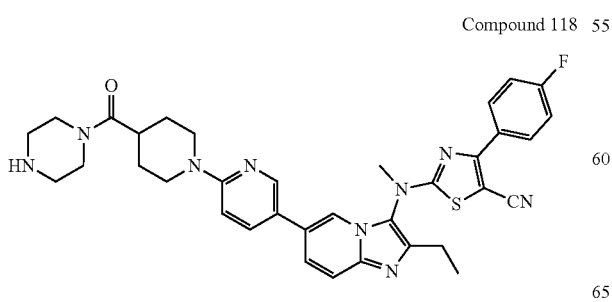

Compound 118 or a pharmaceutically acceptable salt thereof.

46. The compound of claim 21, wherein the compound is

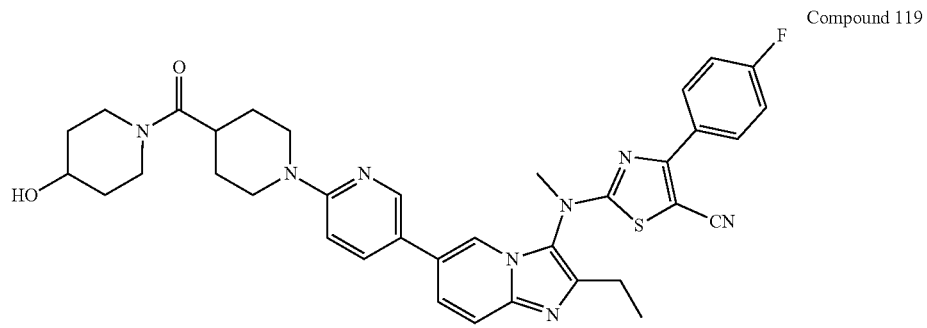 [SMILES: CCc1nc2ccc(-c3ccc(N4CCC(C(=O)N5CCC(O)CC5)CC4)nc3)cn2c1N(C)c1nc(-c2ccc(F)cc2)c(C#N)s1]
Compound 119 or a pharmaceutically acceptable salt thereof.

47. The compound of claim 21, wherein the compound is

Compound 120

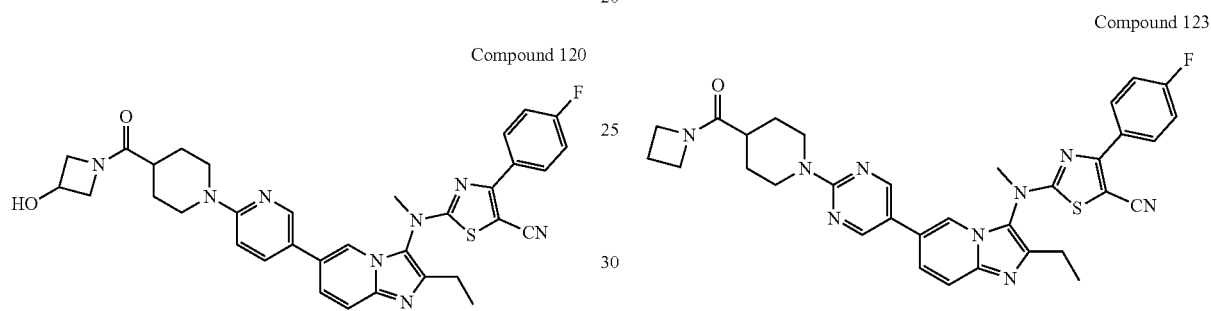

or a pharmaceutically acceptable salt thereof.

48. The compound of claim 21, wherein the compound is

Compound 122

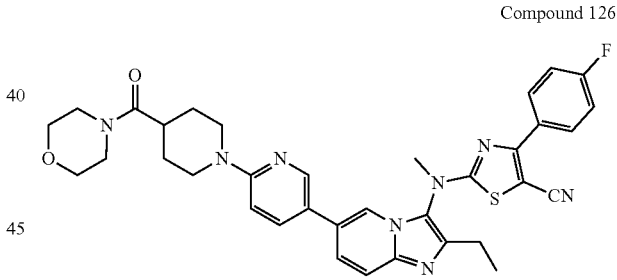

or a pharmaceutically acceptable salt thereof.

49. The compound of claim 21, wherein the compound is

Compound 123 or a pharmaceutically acceptable salt thereof.

50. The compound of claim 21, wherein the compound is

Compound 126

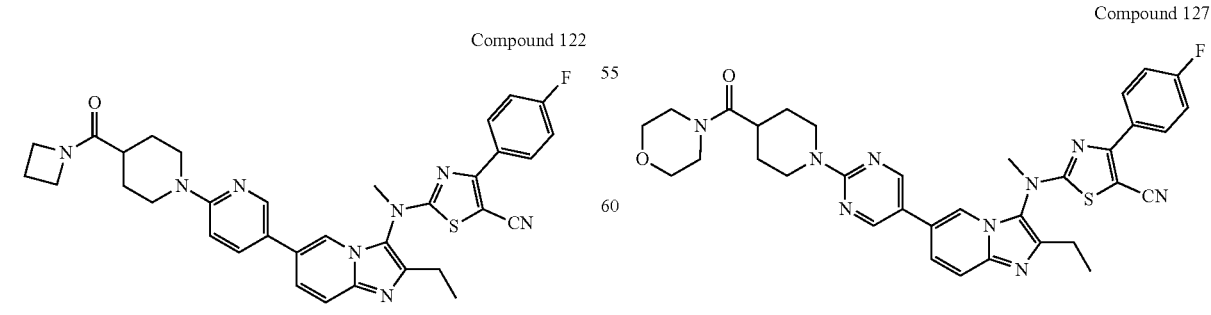

or a pharmaceutically acceptable salt thereof.

51. The compound of claim 21, wherein the compound is

Compound 127 or a pharmaceutically acceptable salt thereof.

* * * * *